US012533603B2

(12) United States Patent
Andrews et al.

(10) Patent No.: US 12,533,603 B2
(45) Date of Patent: Jan. 27, 2026

(54) DISPOSABLE FOR A SPRAY DRYING SYSTEM

(71) Applicant: Velico Medical, Inc., Beverly, MA (US)

(72) Inventors: Robert R. Andrews, Norfolk, MA (US); Herman E. Snyder, W. Lafayette, IN (US); William J. Merritt, Danvers, MA (US); Evan P. Ordway, Salem, MA (US); Clair Strohl, Emmaus, PA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 19/043,116

(22) Filed: Jan. 31, 2025

(65) Prior Publication Data

US 2025/0276255 A1 Sep. 4, 2025

Related U.S. Application Data

(63) Continuation of application No. 18/467,102, filed on Sep. 14, 2023, now Pat. No. 12,246,266, which is a (Continued)

(51) Int. Cl.
*B01D 1/18* (2006.01)
*C12N 5/078* (2010.01)
(Continued)

(52) U.S. Cl.
CPC ............. *B01D 1/18* (2013.01); *C12N 5/0634* (2013.01); *F26B 3/12* (2013.01); *F26B 21/004* (2013.01); *F26B 25/06* (2013.01)

(58) Field of Classification Search
CPC .......... F26B 3/12; F26B 21/004; F26B 25/06; B01D 1/18; C12N 5/0634; C12N 5/064
(Continued)

(56) References Cited

U.S. PATENT DOCUMENTS 2,362,025 A 11/1944 Price
2,411,152 A 11/1946 Folsom
(Continued)

FOREIGN PATENT DOCUMENTS

AU 2010234607 10/2010
BR 112020002403 B1 12/2024
(Continued)

OTHER PUBLICATIONS

Lea, et al. "The Reaction between Proteins and Reducing Sugars in the "Dry" State" Department of Pathology, University of Cambridge; Jun. 5, 1950; pp. 626-629.
(Continued)

*Primary Examiner* — Stephen M Gravini
(74) *Attorney, Agent, or Firm* — Antoinette G Giugliano; Antoinette G Giugliano PC

(57) ABSTRACT

The present invention includes a spray drying disposable device for use in a spray drying system. The disposable has a spray drying head and a plasma drying chamber. The head has a spray dry nozzle assembly in fluid communication with the plasma source and the pressurized aerosol gas source. The pressurized gas flows in a vortex pattern that atomizes plasma droplets in the chamber. The head also includes a plenum has uniform air pressure of the drying gas. A baffle plate forms the floor of the plenum having drying gas jets that supply drying gas to the chamber. The atomized plasma droplets evaporate in the presence of the drying gas emitted from the jets to obtain dried plasma particles and humid air. A capture filter captures the dried plasma particles and allows the humid air to pass. The humid air passes through the gas outlet and the exhaust port.

15 Claims, 139 Drawing Sheets

Related U.S. Application Data continuation-in-part of application No. 17/945,124, filed on Sep. 15, 2022, now Pat. No. 11,841,189.

(51) Int. Cl.
*F26B 3/12* (2006.01)
*F26B 21/00* (2006.01)
*F26B 25/06* (2006.01)

(58) Field of Classification Search
USPC ........................................................ 424/46
See application file for complete search history.

(56) References Cited

U.S. PATENT DOCUMENTS

| | | | | |
|---|---|---|---|---|
| 2,528,476 | A | 10/1950 | Roos et al. | |
| 2,575,175 | A | 11/1951 | Kronisch | |
| 3,228,838 | A | 1/1966 | Rinfret et al. | |
| 3,230,689 | A | 1/1966 | Hussmann | |
| 3,449,124 | A | 6/1969 | Lipner | |
| 3,507,278 | A | 4/1970 | Werding | |
| 3,644,128 | A | 2/1972 | Lipner | |
| 3,654,705 | A | 4/1972 | Smith et al. | |
| 3,693,886 | A | 9/1972 | Conrad | |
| 3,735,792 | A | 5/1973 | Asizawa et al. | |
| 3,945,574 | A | 3/1976 | Polnauer | |
| 4,187,617 | A | 2/1980 | Becker, Jr. et al. | |
| 4,251,510 | A | 2/1981 | Tankersley | |
| 4,347,259 | A | 8/1982 | Suzuki et al. | |
| 4,358,901 | A | 11/1982 | Takabatake et al. | |
| 4,376,010 | A | 3/1983 | Gauvin | |
| 4,378,346 | A | 3/1983 | Tankersley | |
| 4,380,491 | A | 4/1983 | Joy | |
| 4,422,900 | A | 12/1983 | Bordelon | |
| 4,597,868 | A | 7/1986 | Watanabe | |
| 4,600,613 | A | 7/1986 | Yoshida | |
| 4,645,482 | A | 2/1987 | Yoshida | |
| 4,705,612 | A | 11/1987 | Shimomura et al. | |
| 4,725,355 | A | 2/1988 | Yamamoto et al. | |
| 4,735,832 | A | 4/1988 | Ishikawa et al. | |
| 4,743,375 | A | 5/1988 | Seita et al. | |
| 4,774,019 | A | 9/1988 | Watanabe et al. | |
| 4,787,154 | A | 11/1988 | Titus | |
| 4,845,132 | A | 7/1989 | Masuoka et al. | |
| 4,861,632 | A | 8/1989 | Caggiano | |
| 4,966,699 | A | 10/1990 | Sasaki et al. | |
| 5,096,537 | A | 3/1992 | Bergquist et al. | |
| 5,139,529 | A | 8/1992 | Seita et al. | |
| 5,145,706 | A | 9/1992 | Hagi et al. | |
| 5,167,763 | A | 12/1992 | Sakamoto | |
| 5,181,415 | A | 1/1993 | Esvan et al. | |
| 5,227,017 | A | 7/1993 | Tanaka | |
| 5,244,578 | A | 9/1993 | Ohnishi et al. | |
| 5,252,221 | A | 10/1993 | van Dommelen | |
| 5,254,248 | A | 10/1993 | Nakamura | |
| 5,257,983 | A | 11/1993 | Garyantes et al. | |
| 5,267,646 | A | 12/1993 | Inoue et al. | |
| 5,279,738 | A | 1/1994 | Seita et al. | |
| 5,309,649 | A | 5/1994 | Bergmann et al. | |
| 5,372,811 | A | 12/1994 | Yoder | |
| 5,447,077 | A | 9/1995 | Lautenschlager | |
| 5,499,768 | A | 3/1996 | Tanaka | |
| 5,522,156 | A | 6/1996 | Ware | |
| 5,523,004 | A | 6/1996 | Tanokura et al. | |
| 5,529,821 | A | 6/1996 | Ishikawa et al. | |
| 5,547,576 | A | 8/1996 | Onishi et al. | |
| 5,562,919 | A | 10/1996 | Doty et al. | |
| 5,567,238 | A | 10/1996 | Long, Jr. | |
| 5,575,999 | A | 11/1996 | Yoder | |
| 5,581,903 | A | 12/1996 | Botich | |
| 5,582,794 | A | 12/1996 | Hagiwara et al. | |
| 5,610,170 | A | 3/1997 | Inoue et al. | |
| 5,615,493 | A * | 4/1997 | Funder ...................... | F26B 3/08 34/583 |
| 5,624,530 | A | 4/1997 | Sadykhov | |
| 5,647,142 | A | 7/1997 | Andersen et al. | |
| 5,657,555 | A | 8/1997 | Milojevic | |
| 5,680,712 | A | 10/1997 | Kiyokawa | |
| 5,727,333 | A | 3/1998 | Folan | |
| 5,924,216 | A | 7/1999 | Takahashi | |
| 5,993,804 | A | 11/1999 | Read et al. | |
| 6,004,576 | A | 12/1999 | Weaver et al. | |
| 6,060,323 | A | 5/2000 | Jina | |
| D430,939 | S | 9/2000 | Zukor et al. | |
| 6,128,830 | A | 10/2000 | Bettcher | |
| 6,148,536 | A | 11/2000 | Lijima | |
| 6,151,798 | A * | 11/2000 | Petersen .................. | B01D 1/18 34/304 |
| 6,197,289 | B1 | 3/2001 | Wirt et al. | |
| 6,223,455 | B1 | 5/2001 | Chickering | |
| 6,284,282 | B1 | 9/2001 | Maa et al. | |
| 6,299,906 | B1 | 10/2001 | Bausch et al. | |
| 6,308,434 | B1 | 10/2001 | Chickering, III et al. | |
| 6,308,826 | B1 | 10/2001 | Merrell | |
| 6,345,452 | B1 | 2/2002 | Feuilloley et al. | |
| 6,463,675 | B1 | 10/2002 | Hansen et al. | |
| 6,523,276 | B1 | 2/2003 | Meldrum | |
| 6,526,774 | B1 | 3/2003 | Lu et al. | |
| 6,560,897 | B2 | 5/2003 | Chickering, III et al. | |
| 6,569,447 | B2 | 5/2003 | Kisic et al. | |
| 6,582,654 | B1 | 6/2003 | Kral et al. | |
| 6,723,497 | B2 | 4/2004 | Wolkers et al. | |
| 6,762,336 | B1 | 7/2004 | Macphee et al. | |
| 6,883,248 | B2 | 4/2005 | Ko | |
| 6,893,412 | B2 | 5/2005 | Saito et al. | |
| 7,005,857 | B2 | 2/2006 | Stiene et al. | |
| 7,007,406 | B2 | 3/2006 | Wang et al. | |
| 7,074,582 | B2 | 7/2006 | Fischer et al. | |
| 7,089,681 | B2 | 8/2006 | Herbert et al. | |
| 7,094,378 | B1 | 8/2006 | Goodrich, Jr. et al. | |
| 7,297,716 | B2 | 11/2007 | Shanbrom | |
| 7,361,306 | B2 | 4/2008 | Bole | |
| 7,363,726 | B2 | 4/2008 | Wang | |
| 7,367,137 | B2 * | 5/2008 | Jonsson .................. | D06F 73/02 34/265 |
| 7,399,637 | B2 | 7/2008 | Wright et al. | |
| 7,419,682 | B2 | 9/2008 | Campbell et al. | |
| 7,527,805 | B2 | 5/2009 | Crenshaw et al. | |
| 7,648,699 | B2 | 1/2010 | Goodrich et al. | |
| 7,931,919 | B2 | 4/2011 | Bakaltcheva et al. | |
| 7,993,310 | B2 | 8/2011 | Rosiello | |
| 8,322,046 | B2 | 12/2012 | Wang et al. | |
| 8,398,732 | B2 | 3/2013 | Turok et al. | |
| 8,407,912 | B2 | 4/2013 | Hubbard et al. | |
| 8,434,242 | B2 | 5/2013 | Hubbard et al. | |
| 8,449,520 | B2 | 5/2013 | Pepper et al. | |
| 8,469,202 | B2 | 6/2013 | Rosiello | |
| 8,518,452 | B2 | 8/2013 | Bjornstrup et al. | |
| 8,533,971 | B2 | 9/2013 | Hubbard et al. | |
| 8,533,972 | B2 | 9/2013 | Hubbard et al. | |
| 8,595,950 | B2 | 12/2013 | Hubbard et al. | |
| 8,601,712 | B2 | 12/2013 | Hubbard et al. | |
| 8,726,532 | B2 * | 5/2014 | Hogan .................. | F26B 17/104 15/345 |
| 8,793,896 | B2 | 8/2014 | Patel | |
| 8,968,879 | B2 | 3/2015 | Inaba et al. | |
| 9,440,011 | B2 | 9/2016 | Van Waeg et al. | |
| 9,453,676 | B2 | 9/2016 | Robinson | |
| 9,545,379 | B2 | 1/2017 | Liu et al. | |
| 9,551,527 | B2 | 1/2017 | Beetz | |
| 9,561,184 | B2 | 2/2017 | Khan et al. | |
| 9,561,893 | B2 | 2/2017 | Root et al. | |
| 9,808,065 | B2 * | 11/2017 | Moloney ................ | A45D 20/50 |
| 9,863,699 | B2 | 1/2018 | Corbin, III et al. | |
| 9,863,701 | B2 | 1/2018 | Robinson | |
| 9,867,782 | B2 | 1/2018 | Fischer et al. | |
| 9,915,473 | B2 | 3/2018 | Ilan | |
| 10,022,478 | B2 | 7/2018 | Anzai et al. | |
| 10,041,730 | B2 | 8/2018 | Diener | |
| 10,251,911 | B2 | 4/2019 | DaCorta et al. | |
| 10,279,359 | B2 | 5/2019 | Ackerman | |
| 10,376,614 | B2 | 8/2019 | Kohama | |
| 10,376,809 | B2 | 8/2019 | Nielsen | |
| 10,377,520 | B2 | 8/2019 | Root et al. | |

(56) References Cited

U.S. PATENT DOCUMENTS

| | | | |
|---|---|---|---|
| 10,391,518 | B2 | 8/2019 | Kim |
| 10,539,367 | B2 | 1/2020 | Corbin, III et al. |
| 10,793,327 | B2 | 10/2020 | Weimer et al. |
| 10,806,665 | B2 | 10/2020 | Murto |
| 10,843,100 | B2 | 11/2020 | Khan et al. |
| 10,960,023 | B2 | 3/2021 | DaCorta et al. |
| 10,969,171 | B2 | 4/2021 | Corbin, III et al. |
| 11,052,045 | B2 | 7/2021 | Liu et al. |
| 11,090,622 | B2 | 8/2021 | Beetz |
| 11,187,460 | B2 | 11/2021 | Ge |
| 11,213,488 | B2 | 1/2022 | Fischer et al. |
| 11,428,467 | B2 | 8/2022 | Kim |
| 11,806,431 | B2 | 11/2023 | Liu |
| 11,841,189 | B1 * | 12/2023 | Andrews ................... F26B 3/14 |
| 11,913,722 | B1 | 2/2024 | Andrews |
| 11,913,723 | B1 | 2/2024 | Andrews |
| 11,975,274 | B2 | 5/2024 | Liu |
| 11,998,861 | B2 | 6/2024 | Andrews |
| 12,064,518 | B2 * | 8/2024 | Liu ...................... A61K 9/1617 |
| 12,092,397 | B2 | 9/2024 | Andrews |
| 12,104,851 | B2 | 10/2024 | Garcfa |
| 12,225,914 | B1 * | 2/2025 | Porter ................... F26B 25/063 |
| 12,246,266 | B2 * | 3/2025 | Andrews ................. F26B 25/06 |
| 12,253,308 | B1 | 3/2025 | Andrews |
| 12,274,955 | B2 | 4/2025 | Andrews |
| 12,303,807 | B2 | 5/2025 | Luthe |
| 12,337,260 | B2 | 6/2025 | Meehan |
| 2002/0056206 | A1 | 5/2002 | Pace |
| 2002/0122803 | A1 | 9/2002 | Kisic et al. |
| 2002/0182195 | A1 | 12/2002 | Marguerre et al. |
| 2003/0037459 | A1 | 2/2003 | Chickering, II et al. |
| 2003/0099633 | A1 | 5/2003 | Campbell et al. |
| 2003/0103962 | A1 | 6/2003 | Campbell et al. |
| 2003/0143518 | A1 | 7/2003 | Luck et al. |
| 2003/0163931 | A1 | 9/2003 | Beyerinck |
| 2003/0180283 | A1 | 9/2003 | Batycky |
| 2003/0186004 | A1 | 10/2003 | Koslow |
| 2003/0190314 | A1 | 10/2003 | Campbell et al. |
| 2003/0209245 | A1 | 11/2003 | Poole et al. |
| 2004/0058309 | A1 | 3/2004 | Washizu |
| 2004/0086420 | A1 | 5/2004 | MacPhee |
| 2004/0110871 | A1 | 6/2004 | Perrut et al. |
| 2004/0146565 | A1 | 7/2004 | Strohbehn et al. |
| 2004/0175296 | A1 | 9/2004 | Opalsky et al. |
| 2004/0202660 | A1 | 10/2004 | Campbell et al. |
| 2004/0247628 | A1 | 12/2004 | Lintz et al. |
| 2005/0142208 | A1 | 6/2005 | Yoo |
| 2005/0170068 | A1 | 8/2005 | Roodink et al. |
| 2005/0186183 | A1 | 8/2005 | DeAngelo et al. |
| 2005/0271674 | A1 | 12/2005 | Campbell et al. |
| 2006/0045907 | A1 | 3/2006 | Campbell et al. |
| 2006/0088642 | A1 | 4/2006 | Boersen et al. |
| 2006/0130768 | A1 | 6/2006 | Crenshaw et al. |
| 2006/0216687 | A1 | 9/2006 | Alves-Filho et al. |
| 2006/0222980 | A1 | 10/2006 | Makino et al. |
| 2007/0014806 | A1 | 1/2007 | Marguerre et al. |
| 2007/0084244 | A1 | 4/2007 | Rosenflanz et al. |
| 2007/0166389 | A1 | 7/2007 | Bakaltcheva |
| 2008/0058469 | A1 | 3/2008 | Abe et al. |
| 2008/0060213 | A1 | 3/2008 | Gehrmann et al. |
| 2008/0119818 | A1 | 5/2008 | Bakaltcheva et al. |
| 2008/0138340 | A1 | 6/2008 | Campbell et al. |
| 2008/0145444 | A1 | 6/2008 | Merchant et al. |
| 2008/0145834 | A1 | 6/2008 | Ho |
| 2008/0213263 | A1 | 9/2008 | Campbell et al. |
| 2008/0234653 | A1 | 9/2008 | McCarthy et al. |
| 2008/0317640 | A1 | 12/2008 | Mayer |
| 2009/0092678 | A1 | 4/2009 | Marguerre et al. |
| 2009/0113753 | A1 | 5/2009 | Pepper et al. |
| 2009/0145783 | A1 | 6/2009 | Forker |
| 2009/0155410 | A1 | 6/2009 | Crenshaw et al. |
| 2009/0223080 | A1 | 9/2009 | McCarthy |
| 2010/0011610 | A1 | 1/2010 | Bittorf |
| 2010/0108183 | A1 | 5/2010 | Rosiello |
| 2010/0215667 | A1 | 8/2010 | Campbell et al. |
| 2010/0233671 | A1 | 9/2010 | Bakaltcheva |
| 2010/0273141 | A1 | 10/2010 | Bakaltcheva |
| 2011/0142885 | A1 | 6/2011 | Haley et al. |
| 2011/0282325 | A1 | 11/2011 | Gregory |
| 2012/0027867 | A1 | 2/2012 | Fischer et al. |
| 2012/0103536 | A1 * | 5/2012 | Hubbard, Jr. ............ B01D 1/18<br>159/48.1 |
| 2012/0167405 | A1 | 7/2012 | Hubbard, Jr. |
| 2012/0222326 | A1 | 9/2012 | Hubbard et al. |
| 2013/0000774 | A1 | 1/2013 | Rosiello |
| 2013/0048225 | A1 | 2/2013 | Hubbard et al. |
| 2013/0056158 | A1 | 3/2013 | Hubbard et al. |
| 2013/0126101 | A1 | 5/2013 | Hubbard, Jr. et al. |
| 2013/0129817 | A1 | 5/2013 | Consigny |
| 2013/0209985 | A1 | 8/2013 | Hoke |
| 2013/0243877 | A1 | 9/2013 | Haley |
| 2013/0264288 | A1 | 10/2013 | Hlavinka et al. |
| 2014/0083627 | A1 | 3/2014 | Khan et al. |
| 2014/0083628 | A1 | 3/2014 | Khan et al. |
| 2014/0088768 | A1 | 3/2014 | Haley et al. |
| 2014/0221873 | A1 | 8/2014 | Hayakawa et al. |
| 2014/0230266 | A1 | 8/2014 | Luy et al. |
| 2015/0099866 | A1 | 4/2015 | Kelleher |
| 2015/0158652 | A1 | 6/2015 | Root et al. |
| 2015/0354894 | A1 | 12/2015 | Corbin, III et al. |
| 2016/0015863 | A1 | 1/2016 | Gupta et al. |
| 2016/0082043 | A1 | 3/2016 | Khan et al. |
| 2016/0082044 | A1 | 3/2016 | Liu |
| 2016/0084572 | A1 | 3/2016 | Khan et al. |
| 2016/0113965 | A1 | 4/2016 | DaCorta et al. |
| 2016/0223255 | A1 | 8/2016 | Beetz |
| 2016/0362307 | A1 | 12/2016 | Shiner |
| 2017/0100339 | A1 | 4/2017 | Liu et al. |
| 2017/0113824 | A1 | 4/2017 | Root et al. |
| 2017/0203871 | A1 | 7/2017 | Murto et al. |
| 2017/0259186 | A1 | 9/2017 | Khan et al. |
| 2017/0367322 | A1 | 12/2017 | Liu et al. |
| 2018/0128544 | A1 | 5/2018 | Corbin et al. |
| 2018/0153811 | A1 | 6/2018 | Fischer et al. |
| 2018/0207654 | A1 | 7/2018 | Phua |
| 2018/0229150 | A1 | 8/2018 | Sorensen |
| 2019/0106254 | A1 | 4/2019 | Weimer et al. |
| 2019/0223671 | A1 | 7/2019 | Tomasiak |
| 2019/0241300 | A1 | 8/2019 | Root et al. |
| 2019/0255455 | A9 | 8/2019 | Sorensen |
| 2019/0298765 | A1 | 10/2019 | DaCorta et al. |
| 2020/0022691 | A1 | 1/2020 | Pollack |
| 2020/0298137 | A9 | 9/2020 | Khan |
| 2021/0069607 | A1 | 3/2021 | Khan et al. |
| 2021/0213057 | A1 | 7/2021 | DaCorta et al. |
| 2021/0290545 | A1 | 9/2021 | Liu et al. |
| 2022/0040110 | A1 | 2/2022 | Liu et al. |
| 2022/0106357 | A1 | 4/2022 | Patatanyan |
| 2023/0172849 | A1 | 6/2023 | Zeki |
| 2024/0091156 | A1 | 3/2024 | Andrews |
| 2024/0091666 | A1 | 3/2024 | Meehan |
| 2024/0109000 | A1 | 4/2024 | Liu |
| 2024/0131062 | A1 | 4/2024 | Popovsky |
| 2024/0131236 | A1 * | 4/2024 | LaRocque ........... A61M 1/0272 |
| 2024/0131446 | A1 * | 4/2024 | Andrews ................. F26B 21/10 |
| 2024/0159462 | A1 | 5/2024 | Andrews |
| 2024/0191943 | A1 * | 6/2024 | Andrews ................ A61K 35/16 |
| 2025/0099868 | A1 | 3/2025 | Meehan |

FOREIGN PATENT DOCUMENTS

| | | | |
|---|---|---|---|
| CA | 1182411 | A | 2/1985 |
| CA | 2065582 | A1 | 10/1992 |
| CA | 2 472 028 | | 8/2003 |
| CA | 2757961 | | 10/2010 |
| CA | 2816090 | A1 | 5/2012 |
| CH | 622683 | A5 | 4/1981 |
| CN | 1315139 | A | 10/2001 |
| CN | 102206273 | A | 10/2011 |
| CN | 108005711 | A | 5/2018 |
| CN | 111789867 | B | 1/2022 |
| DE | 3507278 | | 9/1986 |
| EP | 0058903 | A1 | 9/1982 |
| EP | 0408801 | A1 | 1/1991 |

(56) References Cited

FOREIGN PATENT DOCUMENTS

| | | | | |
|---|---|---|---|---|
| EP | 1050220 | A1 | 8/2000 | |
| EP | 2745922 | A2 | 6/2014 | |
| EP | 2745923 | A2 | 6/2014 | |
| EP | 2416790 | | 5/2018 | |
| EP | 3151662 | B1 | 10/2020 | |
| GB | 573500 | | 11/1945 | |
| GB | 886533 | | 10/1962 | |
| GB | 964367 | | 7/1964 | |
| GB | 975786 | | 11/1964 | |
| GB | 1188168 | | 4/1970 | |
| GB | 2003042 | A | 3/1979 | |
| HK | 1167098 | | 8/2012 | |
| JP | 56011903 | | 2/1981 | |
| JP | 63218201 | | 9/1988 | |
| JP | 01011618 | | 1/1989 | |
| JP | 03131302 | | 6/1991 | |
| JP | 03181301 | | 8/1991 | |
| JP | 5245301 | | 9/1993 | |
| JP | 525910 | | 10/1993 | |
| JP | H10182124 | A | 7/1998 | |
| JP | 3219828 | B2 | 10/2001 | |
| JP | 2002009037 | | 1/2002 | |
| JP | 2005191275 | A | 7/2005 | |
| JP | 2007216158 | A | 8/2007 | |
| JP | 6336419 | | 6/2018 | |
| KR | 911657 | B1 | 8/2009 | |
| KR | 2022079809 | A | 6/2022 | |
| MX | 2011010633 | | 1/2012 | |
| WO | WO1996015849 | A1 | 5/1996 | |
| WO | WO1996018312 | A1 | 6/1996 | |
| WO | WO1997038578 | A1 | 10/1997 | |
| WO | WO1999007236 | A1 | 2/1999 | |
| WO | WO1999007390 | A1 | 2/1999 | |
| WO | WO2000056166 | A1 | 9/2000 | |
| WO | WO2001072141 | A2 | 10/2001 | |
| WO | WO2002078741 | A2 | 10/2002 | |
| WO | WO2002078742 | A2 | 10/2002 | |
| WO | WO2002083157 | A1 | 10/2002 | |
| WO | WO2002092213 | A1 | 11/2002 | |
| WO | WO2003030654 | A1 | 4/2003 | |
| WO | WO2003030918 | A1 | 4/2003 | |
| WO | WO-03037303 | A | 5/2003 | |
| WO | WO2003063607 | A1 | 8/2003 | |
| WO | WO2004075988 | A2 | 9/2004 | |
| WO | WO2004078187 | A1 | 9/2004 | |
| WO | WO2005079755 | A2 | 9/2005 | |
| WO | WO2007036227 | A1 | 4/2007 | |
| WO | WO-2008080167 | A2 | 7/2008 | |
| WO | WO2008122288 | A1 | 10/2008 | |
| WO | WO2008143769 | A1 | 11/2008 | |
| WO | WO2010111132 | A2 | 9/2010 | |
| WO | WO2010113632 | A1 | 10/2010 | |
| WO | WO2010117976 | A1 | 10/2010 | |
| WO | WO2011075614 | A2 | 6/2011 | |
| WO | WO2012058575 | A3 | 5/2012 | |
| WO | WO2013141050 | A1 | 9/2013 | |
| WO | WO2016036807 | A1 | 3/2016 | |
| WO | WO2016208675 | A1 | 12/2016 | |
| WO | WO2019074886 | A1 | 4/2019 | |
| WO | WO-2020065413 | A1 | 4/2020 | |
| WO | WO2020111132 | A1 | 6/2020 | |
| WO | WO2024059759 | A1 | 3/2024 | |
| WO | WO2024059762 | A1 | 3/2024 | |
| WO | WO2024059763 | A1 | 3/2024 | |
| WO | WO-2024059764 | A1 * | 3/2024 | ............... B01D 1/18 |
| WO | WO2024059765 | A1 | 3/2024 | |
| WO | WO2024059766 | A1 | 3/2024 | |
| WO | WO2024059767 | A1 | 3/2024 | |
| WO | WO2024059768 | A1 | 3/2024 | |
| WO | WO2024059769 | A1 | 3/2024 | |
| WO | WO2024059770 | | 3/2024 | |
| WO | WO-2024059770 | A1 * | 3/2024 | ............. A61K 35/16 |
| WO | WO2024059771 | A1 | 3/2024 | |
| WO | WO2024059772 | A1 | 3/2024 | |
| WO | WO2024059774 | A1 | 3/2024 | |
| WO | WO-2024119151 | A1 | 6/2024 | |

OTHER PUBLICATIONS

Carpenter, et al. "Rational Design of Stable Lyophilized Protein Formulations: Theory and Practice" Kluwer Academic/Plenum Publishers; 2002; pp. 109-133.

Schmid "Spray drying of protein precipitates and Evaluation of the Nano Spray Dryer B-90" PhD Thesis; 2011; 125 pages.

Shuja, et al. "Development and Testing of Low-Volume Hyperoncotic, Hyperosmotic Spray-Dried Plasma for the treatment of Trauma-Associated Coagulopathy" The Journal of Trauma; Mar. 2011; vol. 70; No. 3; pp. 664-671.

Bakaltcheva; et al. "Freeze-dried whole plasma: Evaluating sucrose, trehalose, sorbitol, mannitol and glycine as stabilizers" Thrombosis Research; 2007; vol. 120; pp. 105-116.

European Search Report, EP Application No. 14154366, mailed Aug. 29, 2014, pp. 1-3.

European Search Opinion, EP Application No. 14154366, mailed Aug. 29, 2014, pp. 1-3.

International Search Report and Written Opinion, PCT/US2010/049176, mailed Nov. 4, 2010, pp. 1-10.

International Search Report and Written Opinion, PCT/US2011/058358, mailed Jul. 4, 2012, pp. 1-9.

Answer, Affirmative Defenses, Counterclaims, Cross-Claims and Jury Demand, *Entegrion, Inc.* vs *Velico Medical, Inc.*, dated Dec. 3, 2012, pp. 1-47.

Civil Action Cover Sheet; *Entegrion, Inc.* vs *Velico Medical, Inc.*, dated Oct. 19, 2012, pp. 1-2.

Complaint including Exhibit A, B, and C; *Entegrion, Inc.* vs *Velico Medical, Inc.*, dated Oct. 19, 2012, pp. 1-29.

Mini Spray Dryer B-290—Application Note; www.buchi.com; Mar. 30, 2008, entire document; 1 page.

Nano Spray Dryer B-90; www.buchi.com; Jul. 18, 2011, entire document, 12 pages.

Mini Spray Dryer System Configuration; www.buchi.com; Jan. 8, 2007, entire document, 1 page.

Quick Operation Guide; Mini Spray Dryer B-290; www.buchi.com; Sep. 16, 2004, pp. 15-53.

Process Parameters; www.buchi.com; Nov. 21, 2008, pp. 1-2.

Training Papers Spray Drying; Version B; www.buchi.com; 19 pages; Oct. 29, 2002.

Mini Spray Dryer B-290; www.buchi.com; May 10, 2007, pp. 1-8.

Fischer M., et al., "Stability of African swine fever virus on spiked spray-dried porcine plasma," *Transboundary and Emerging Diseases*, 68(5): 2806-2811 (2021).

International Preliminary Report on Patentability, PCT/US2011/058358, mailed Apr. 30, 2013, pp. 1-7.

Edwards et al., The Preparation and Use of Dried Plasma for Transfusion; British Medical journal; vol. 1, No. 4131; Mar. 9, 1940; pp. 377-381.

Blazquez, E., et al., "Biosafety steps in the manufacturing process of spray-dried plasma: a review with emphasis on the use of ultraviolet irradiation as a redundant biosafety procedure," *Porcine Health Management*, 6(16): p. 78 refs. (2020), 9 pages.

Blazquez, E., et al., "Effect of spray-drying and ultraviolet C radiation as biosafety steps for CSFV and ASFV inactivation in porcine plasma," *PLoS One*, 16(4) (2021), entire document, 11 pages.

Entegrion's Reply to Counterclaims; *Entegrion, Inc.* vs *Velico Medical, Inc*; Dated: Jan. 14, 2013, entire document, 22 pages.

Entegrion's Motion to Dismiss Counts I, II, V, VI and XI of Velico Medical, Inc's Counterclaims and Memorandum in Support of Entegrion's Motion to Dismiss Counts I, II, V, VI, and XI of Velico Medical, Inc.'S Counterclaims; *Entegrion, Inc.* vs *Velico Medical, Inc*; Dated: Jan. 14, 2013, entire document, 3 pages.

International Preliminary Report on Patentability, PCT/US2010/049176, mailed Feb. 18, 2014, pp. 1-9.

Pusateri, Anthony E."Dried plasma: state of the science and recent developments" *Transfusion* 56: S128-S139 (Apr. 2016).

(56) References Cited

OTHER PUBLICATIONS

Pusateri, Anthony E."Comprehensive US government program for dried plasma development" *Transfusion* 56: S16-S23 (2016).
Popovsky, Mark A. "Spray-dried plasma: A post-traumatic blood "bridge" for life-saving resuscitation" *Transfusion*. 2021;61:S294-S300 (2021).
Flaumenhaft, Elissa J. et al., "Retention of Coagulation Factors and Storage of Freeze-Dried Plasma," *Military Med*. 186 (S1):400-407 (2021).
Parr, Ashely, "Coagulation Activity of Freeze-Dried Plasma is similar to that of Fresh Frozen Plasma" (May 16, 2018) entire document, 14 pages.
Peng, Henry T. "Ex vivo hemostatic and immune-inflammatory profiles of freeze-dried plasma" Transfusion 61: S119-S130 (2021).
Larry J. Dumont, et al., "The bioequivalence of frozen plasma prepared from whole blood held overnight at room temperature compared to fresh-frozen plasma prepared within eight hours of collection," *Transfusion* 55: 480 (2015) , entire document, 9 pages.
Blazquez, E., et al., "Combined effects of spray-drying conditions and postdrying storage time and temperature on *Salmonella choleraesuis* and *Salmonella typhimurium* survival when inoculated in liquid porcine plasma," *Letters in Applied Microbiology*, 67(2): 205-211 (2018).
S. Suessner, et al., "Comparison of several complement and coagulation factor concentrations in different plasma products." *Transfusion Medicine and Hemotherapy*, 41 (supplement 1) Abstract No. PBK-V02: p. 36 (2014), 3 pages.
Cancelas, J. A., "A Phase 1, Single-Center, Partial Double-blind, Randomized, Controlled (Versus Fresh Frozen Plasma [FFP] in Cohort 3 Only) Clinical Study of the Safety of Ascending Doses of Autologous Freeze Dried Plasma (FDP) in Healthy Volunteers," Falls Church, VA: The Surgeon General, Department of the Army (2018), p. 1-128.
Polo, J., et al., "Neutralizing antibodies against porcine circovirus type 2 in liquid pooled plasma contribute to the biosafety of commercially manufactured spray-dried porcine plasma," *Journal of Animal Science*, 91(5): 2192-2198 (2013).
Blazquez, E., et al., "UV-C irradiation is able to inactivate pathogens found in commercially collected porcine plasma as demonstrated by swine bioassay," *Veterinary Microbiology*, 239 (2019) , entire document, 2 pages.
Blazquez, E., et al., "Evaluation of the effectiveness of the SurePure Turbulator ultraviolet-C irradiation equipment on inactivation of different enveloped and non-enveloped viruses inoculated in commercially collected liquid animal plasma," PLoS One, 14(2) (2019), entire document, 17 pages.
Shen, E., et al., "Commercially produced spray-dried porcine plasma contains increased concentrations of porcine circovirus type 2 DNA but does not transmit porcine circovirus type 2 when fed to naïve pigs," *Journal of Animal Science*, 89(6): 1930-1938 (2011).
Pujols, J., and Segales, J., "Survivability of porcine epidemic diarrhea virus (PEDV) in bovine plasma submitted to spray drying processing and held at different time by temperature storage conditions," *Veterinary Microbiology*, 174(3/4): 427-432 (2014).
Blazquez, E., et al., "Evaluation of ultraviolet-C and spray-drying processes as two independent inactivation steps on enterotoxigenic *Escherichia coli* K88 and K99 strains inoculated in fresh unconcentrated porcine plasma," *Letters in Applied Microbiology*, 67(5): 442-448 (2018).
Pujols, J., et al., "No transmission of hepatitis E virus in pigs fed diets containing commercial spray-dried porcine plasma: a retrospective study of samples from several swine trials," *Virology Journal*, 11: p. 232 (2014), 8 pages.
Foddai, A., et al., "Probability of introducing porcine epidemic diarrhea virus into Danish pig herds by imported spray-dried porcine plasma," *Porcine Health Management*, 1: p. 18 (2015), 11 pages.
Gerber, P. F., et al., "The spray-drying process is sufficient to inactivate infectious porcine epidemic diarrhea virus in plasma," *Veterinary Microbiology*, 174(1/2): 86-92 (2014).
Patterson, A. R., et al., "Efficacy of experimentally produced spray-dried plasma on infectivity of porcine circovirus type 2," *Journal of Animal Science*, 88(12: 4078-4085 (2010).
Pujols, J., et al., "Commercial spray-dried porcine plasma does not transmit porcine circovirus type 2 in weaned pigs challenged with porcine reproductive and respiratory syndrome virus," *Veterinary Journal*, 190(2): 16-20 (2011).
Blazquez, E., et al., "Ultraviolet (UV-C) inactivation of Enterococcus faecium, *Salmonella choleraesuis* and *Salmonella typhimurium* in porcine plasma," *PLoS One*, 12(4) (2017), 11 pages.
Polo, J., et al., "Ultraviolet Light (UV) Inactivation of Porcine Parvovirus in Liquid Plasma and Effect of UV Irradiated Spray Dried Porcine Plasma on Performance of Weaned Pigs," *PLoS One*, 10(7) (2015), 12 pages.
Pujols, J., et al., "Lack of transmission of porcine circovirus type 2 to weanling pigs by feeding them spray-dried porcine plasma," *Veterinary Record*, 163(18): 536-538 (2008).
Opriessnig, T., et al., "Porcine Epidemic Diarrhea Virus RNA Present in Commercial Spray-Dried Porcine Plasma Is Not Infectious to Naïve Pigs," *PLoS One*, 9(8) (2014), 10 pages.
Polo, J., et al., "Efficacy of spray-drying to reduce infectivity of pseudorabies and porcine reproductive and respiratory syndrome (PRRS) viruses and seroconversion in pigs fed diets containing spray-dried animal plasma," *Journal of Animal Science*, 83(8): 1933-1938 (2005).
Perez-Bosque, A., et al., "Spray dried plasma as an alternative to antibiotics in piglet feeds, mode of action and biosafety," *Porcine Health Management*, 2: p. 16 (2016) 10 pages.
Moreto, M., et al., "Dietary supplementation with spray-dried porcine plasma has prebiotic effects on gut microbiota in mice," *Scientific Reports*, 10(1): p. 2926 (2020), 13 pages.
Hulst, M. M., et al., "Study on inactivation of porcine epidemic diarrhoea virus, porcine sapelovirus 1 and adenovirus in the production and storage of laboratory spray-dried porcine plasma," *Journal of Applied Microbiology*, 126(6): 1931-1943 (2019).
Pasick, J., et al., "Investigation into the Role of Potentially Contaminated Feed as a Source of the First-Detected Outbreaks of Porcine Epidemic Diarrhea in Canada," *Transboundary and Emerging Diseases*, 61(5): 397-410 (2014).
Duffy, M. A., et al., "Impact of dietary spray-dried bovine plasma addition on pigs infected with porcine epidemic diarrhea virus," *Translational Animal Science*, 2(4): 349-357 (2018).
Cottingim, K. M., et al., "Ultraviolet irradiation of spray-dried porcine plasma does not affect the growth performance of nursery pigs when compared with nonirradiated bovine plasma," *Journal of Animal Science*, 95(7): 3120-3128 (2017).
Gebhardt, J. T., et al., "Determining the impact of commercial feed additives as potential porcine epidemic diarrhea virus mitigation strategies as determined by polymerase chain reaction analysis and bioassay," *Translational Animal Science*, 3(1): 28-37 (2019).
Champagne C. P., et al., "Effect of bovine colostrum, cheese whey, and spray-dried porcine plasma on the in vitro growth of probiotic bacteria and *Escherichia coli*," *Canadian Journal of Microbiology*, 60(5): 287-295 (2014).
Perez-Bosque, A., et al., "The Anti-Inflammatory Effect of Spray-Dried Plasma Is Mediated by a Reduction in Mucosal Lymphocyte Activation and Infiltration in a Mouse Model of Intestinal Inflammation," *Nutrients*, 8(10) (2016), p. 1-13.
Prabhu, B., et al., "Effects of spray-dried animal plasma on the growth performance of weaned piglets—A review," *Journal of Animal Physiology and Animal Nutrition*, 105(4): 699-714 (2021).
Santos, D., et al., "Spray Drying: An Overview," *Biomaterials*, (2017) , p. 1-29.
USAMRMC military plasma article "Advanced Development Products," (Second Edition). U.S. Army Medical Research and Materiel Command (2017), p. 521-529.
GovTribe, "Definitive Contract H9222216C0081", [online], [retrieved on Mar. 20, 2020], Retrieved from https://govtribe.com/award/federal-contract-award/definitive-contract-h9222216c0081, entire document, 3 pages.

(56) References Cited

OTHER PUBLICATIONS

Noorman, F. et al. "Lyophilized Plasma, an Alternative to 4 degrees C Stored Thawed Plasma for the Early Treatment of Trauma Patients with (Massive) Blood Loss in Military Theatre," *Transfusion* 55A (2012), p. 1-2.
Bux, J., et al., "Quality of freeze-dried (lyophilized) quarantined single-donor plasma," *Transfusion*, 53: 3203-3209 (2013).
Noorman, F., "Comparison of a single Spray dried plasma product with standard Sanquin and MBB frozen, thawed (coldstored) plasma," (Final Report). Utrecht, Netherlands: Military Blood Bank (2021), p. 1-7.
Sailliol, A., et al., "The evolving role of lyophilized plasma in remote damage control resuscitation in the French Armed Forces Health Service," *Transfusion*, 53: 65S-71S (2013).
Zaza, M., et al. "Dried Plasma," *Damage Control Resuscitation: Identification and Treatment of Life-Threatening Hemorrhage*, 145-162 (2019).
Wataha, K., et al., "Spray-dried plasma and fresh frozen plasma modulate permeability and inflammation in vitro in vascular endothelial cells," *Transfusion*, 53: 80S-90S (2013).
Wang, H.H., et al., "Effect of gallbladder hypomotility on cholesterol crystallization and growth in CCK-deficient mice," *Biochim Biophys Acta*, 1801(2): 138-146 (2010).
Gadeela, N., et al., "The Impact of Circulating Cholesterol Crystals on Vasomotor Function. Implications for No-Reflow Phenomenon," *J Am Coll Cardiol Int*, 4: 521- 529 (2011).
Abela, G.S., et al., "The Effect of Ethanol on Cholesterol Crystals During Tissue Preparation for Scanning Electron Microscopy," *J Am Coll Cardiol* 1: 93 (2012), 1 page.
Li, H., et al., "Synthesis of β-cyclodextrin conjugated superparamagnetic iron oxide nanoparticles for selective binding and detection of cholesterol crystals," *Chem Commun*, 48(28): 3385-3387 (2012).
Elizabeth, A., et al., "Growth and micro-topographical studies of gel grown cholesterol crystals," *Bull Mater Sci*, 24(4): 431-434 (2001).
Kroll, M.H., et al., "Effect of Lyophilization on Results of Five Enzymatic Methods for Cholesterol," *Clin Chem*, 35(7): 1523-1526 (1989).
Mughal, M.M., et al., "Symptomatic and asymptomatic carotid artery plaque," *Expert Rev Cardiovasc Ther*, 9(10): 1315-1330 (2011).
Morales, J., and Gonzalez, E., "Cholesterol Crystal Embolization," *Blood Purif*, 24: 431-432 (2006).
Walton, T.J., et al., "Systemic cholesterol crystal embolisation with pulmonary involvement: a fatal combination after coronary angiography," *Postgrad Med J*, 78: 288-289 (2002).
Oe, K., et al., "Late Onset of Cholesterol Crystal Embolism after Thrombolysis for Cerebral Infarction," *Inter Med*, 49: 833-836 (2010).
Warren, B. A., and Vales, O., "The ultrastructure of the stages of atheroembolic occlusion of renal arteries," *Br J Exp Pathol*, 54(5): 469-478 (1973).
Warren B. A., Vales, O., "Electron microscopy of the sequence of events in the atheroembolic occlusion of cerebral arteries in an animal model," *Br J Exp Pathol*, 56(3):205-215 (1975).
Warren, B. A., and Vales, O., "The ultrastructure of the reaction of arterial walls to cholesterol crystals in atheroembolism," *Br J Exp Pathol*, 57(1), 67-77 (1976).
Steiner, T.J., et al., "Cholesterol crystal embolization in rat brain: a model for atheroembolic cerebral infarction," *Stroke*, 11: 184-189 (1980).
Nozari A., et al., "Microemboli may link spreading depression, migraine aura, and patent foramen ovale," *Ann Neurol*, 67(2):221-229 (2010).
Duewell, P., et al., "NLRP3 inflammasomes are required for atherogenesis and activated by cholesterol crystals," *Nature*, 464,7293: 1357-1361 (2010).
Samstadt, E. O., et al., "Cholesterol crystals induce complement-dependent inflammasome activation and cytokine release," *J Immunol*, 192(67): 2837-2845 (2014).
Grebe, A., and Latz, E., "Cholesterol Crystals and Inflammation," *Curr Rheumatol Rep*, 15: 313 (2013) 7 pages.
Sheedy, F., et al., "CD36 coordinates NLRP3 inflammasome activation by facilitating intracellular nucleation of soluble ligands into particulate ligands in sterile inflammation," *Nat Immunol*, 14: 812-820 (2013).
Ness, M. V., et al., "Neutrophils Contain Cholesterol Crystals in Transfusion-Related Acute Lung Injury (TRALI)," *Am J Clin Pathol*, 140(2): 170-176 (2013).
Sheffield, W. P., et al., "Retention of hemostatic and immunological properties of frozen plasma and Covid-19 convalescent apheresis fresh-frozen plasma produced and freeze-dried in Canada," *Transfusion*, 62: 418-428 (2021).
Garrigue, D., et al., "French lyophilized plasma versus fresh frozen plasma for the initial management of trauma-induced coagulopathy: a randomized open-label trial," *J Thrombosis and Haemostasis*, 16:481-489 (2017).
Van, P. Y., et al., "Lyophilized Plasma Reconstituted With Ascorbic Acid Suppresses Inflammation and Oxidative DNA Damage," *J Trauma*, 71(1) :20-24 (2011).
Medical Countermeasures, "BARDA continues partnership with Velico Medical for development of their FrontlineODP spray-dry plasma system to prepare for a radiological or nuclear emergency," [online], [retrieved on Sep. 20, 2021], Retrieved from https:/www.medicalcountermeasure.gov/newsroom/2021/velico-medical/ entire document, 20 pages.
Burnouf, T., et al., "Assessment of complement activation during membrane-based plasmapheresis procedures," *J Clin Apheresis*, 19: 142-147 (2004).
Ohta, R., et al., "Serum concentrations of complement anaphylatoxins and proinflammatory mediators in patients with 2009 H1N1 influenza," *Microbiology and Immunology*, 55: 191-198 (2011).
"French Lyophilised Plasma (FLYP)," Ministry of Defence, Armed Forces Health Service, Jean Julliard Armed Forces Blood Transfusion Service (Technical Notice and Summary of Product Characteristics) (2013), 2 pages.
Arun, R., "Freeze Dried Plasma Role in Emergency Resuscitation", Tirupati, India: Sri Venkateswara Institute of Medical Sciences, https://www.ist./net.in/transmedcon2016.presentations/99.%20Freeze%20Dried%20Plasma-Role%20Emergency%20Resuscitation.pdf, downloaded on Jan. 16, 2021, entire document, 51 pages.
Pusateri, A.E., and Weiskopf, R.B. "Dried Plasma for Trauma Resuscitation," *Trauma Induced Coagulopathy*, 705-718 (2021).
Sunde, G.A., "Prehospital Plasma / TXA experience—FDP in Norwegian HEMS," Norway: Norsk Luftambulanse (2014), p. 1-24.
Acker, J. P., et al., "Quality Assessment of Established and Emerging Blood Components for Transfusion," *Journal of Blood Transfusion*, (2016) p. 1-29.
Warr, M., "Lyoplas reconstitution English," Deutsches Rotes Kreuz, [Youtube], [retrieved on Jan. 9, 2022], Retrieved from https://www.youtube.com/watch?v=PdydStBygtk. Entire document.
"LyoPlas N—w A freeze-dried single donor plasma," Brochure, DRK-Blutspendedienst West, Hagen, Germany: Deutsches Rotes Kreuz (May 2012), entire document, 14 pages.
Mew, I., "Reconstituting Lyoplas (Freeze dried FFP)", [Youtube], [retrieved on Jan. 9, 2022], Retrieved from https://www.youtube.com/watch?v=RxpQDMwVK8Y.), entire document, 9 pages.
Cancelas, J. A., et al., "Characterization and first-in-human clinical dose-escalation safety evaluation of a next-gen human freeze-dried plasma," *Transfusion*, 62: 406-417 (2021).
"Mirasol Pathogen Reduction Technology System", TerumoBCT (2012), entire document, 13 pages.
Terumo BCT, "Terumo BCT Awarded $1.9 Million from the United States Government to Support Development of Freeze-Dried Plasma," [online], [retrieved on Mar. 20, 2020], Retrieved from https://www.terumobet.com/Pages/News/Press%20Releases/Terumo_BCT_Awarded_$1-9_Million_from_the_United_States_Government_to Support_Development_of_Freeze-Dried_Plasma.aspx., entire document, 2 pages.
Spinella, P. C., "Zero preventable deaths after traumatic injury: an achievable goal," *J Trauma Acute Care Surg*, 82:S2-S8 (2017).
Davis, J. S., et al., "An analysis of prehospital deaths: who can we save?," *J Trauma Acute Care Surg*, 77:213-218 (2014).

(56) References Cited

OTHER PUBLICATIONS

Shackelford, S. A., et al., "Association of prehospital blood product transfusion during medical evacuation of combat casualties in Afghanistan with acute and 30-day survival," *JAMA*, 318:1581-1591 (2017).
Gurney, J. M., and Spinella, P. C., "Blood transfusion management in the severely bleeding military patient," *Curr Opin Anesthesiol*, 31:207-214 (2018).
Moore, E. E., et al., "Plasma first in the field for postinjury hemorrhagic shock," *Shock*, 41(Suppl 1):35-38 (2014).
Maegele, M., et al., "Red-blood-cell to plasma ratios transfused during massive transfusion are associated with mortality in severe multiple injury: a retrospective analysis from the trauma registry of the deutsche Gesellshaft fur Unfallchirugerie," *Vox Sang*, 95:112-119 (2008).
Holcomb, J. B., et al., "Prehospital transfusion of plasma and red blood cells in trauma patients," *Prehosp Emerg Care*, 19:1-9 (2015).
Holcomb, J. B., et al., "The prospective, observational, multicenter major trauma transfusion (PROMMTT) study: comparative effectiveness of a time-varying treatment with competing risks," *JAMA Surg*, 148:127-136 (2013).
Holcomb, J. B., et al., "Damage control resuscitation: directly addressing the early coagulopathy of trauma," *J Trauma Acute Care Surg*, 62:307-310 (2007).
Holcomb, J. B., et al., "Transfusion of plasma, platelets, and red blood cells in a 1:1:1 vs 1:1:2 ratio and mortality in patients with severe trauma: the PROPPR randomized clinical trial," *JAMA*, 313:471-482 (2015).
Sperry, J. L., et al., "Prehospital plasma during air medical transport in trauma patients at risk for hemorrhagic shock," *N Engl J Med*, 379:315-326 (2018).
Zink, K. A., et al., "A high ratio of plasma and platelets to packed red blood cells in the first 6 hours of massive transfusion improves outcomes in a large multicenter study," *Am J Surg*, 197:565-570 (2009).
Saillol, A., et al., "The evolving role of lyophilized plasma in remote damage control resuscitation in the French armed forces health service," *Transfusion*, 53(Suppl 1): S129-S39 (2013).
Nuguyen, C., et al., "Use of French lyophilized plasma transfusion in severe trauma patients is associated with an early plasma transfusion and early transfusion ratio improvement," *J Trauma Acute Care Surg*, 84:780-785 (2018).
Shlaifer, A., et al., "Prehospital administration of freeze-dried plasma, is it the solution for trauma casualties?," *J Trauma Acute Care Surg*, 83:675-682 (2017).
Shlaifer, A., et al., "The impact of prehospital administration of freeze-dried plasma on casualty outcome," *J Trauma Acute Care Surg*, 86:108-115 (2019).
Bjerkvig, C.K., et al., ""Blood failure" time to view blood as an organ: how oxygen debt contributes to blood failure and its implications for remote damage control resuscitation," *Transfusion*, 56(Suppl 2):S182-S189 (2016).
White, N. J., et al., "Hemorrhagic blood failure: oxygen debt, coagulopathy, and endothelial damage," *J Trauma Acute Care Surg*, 82(6S Suppl 1):S41-S49 (2017).
Aird, W. C., "Endothelium and haemostasis," *Hamostaseologie*, 35:11-16 (2015).
Esmon, C. T., "Inflammation and the activated protein C anticoagulant pathway," *Semin Thromb Hemost*, 32(Suppl 1):49-60 (2006).
Tuma, M., et al., "Trauma and endothelial glycocalyx: the microcirculation helmet?," *Shock*, 46:352-357 (2016).
Kozar, R. A., and Pati, S., "Syndecan-1 restitution by plasma after hemorrhagic shock," *J Trauma Acute Care Surg*, 78(6 Suppl 1):S83-S86 (2015).
Rahbar, E., et al., "Endothelial glycocalyx shedding and vascular permeability in severely injured trauma patients," *J Transl Med*, 13:117 (2015), entire document, 7 pages.
Johansson, P. I., et al., "Traumatic Endotheliopathy: a prospective observational Study of 424 severely injured patients," *Ann Surg*, 265:597-603 (2017).
Wu, F., et al., "miR-19b targets pulmonary endothelial syndecan-1 following hemorrhagic shock," *Sci Rep*, 10:15811 (2020), 10 pages.
Johansson, P. I., et al., "Shock induced endotheliopathy (Shine) in acute critical illness—a unifying pathophysiologic mechanism," *Crit Care*, 21:25 (2017), 7 pages.
Spronk, H. M., et al., "New insights into modulation of thrombin formation," *Curr Atheroscler Rep*, 15:363 (2013), 9 pages.
Dunbar, N. M., and Chandler, W. L., "Thrombin generation in trauma patients," *Transfusion*, 49:2652-2660 (2009).
Chandler, W. L., "Procoagulant activity in trauma patients," *Am J Clin Pathol*, 134:90-96 (2010).
Cardenas, J. C., et al., "Measuring thrombin generation as a tool for predicting hemostatic potential and transfusion requirements following trauma," *J Trauma Acute Care Surg*, 77:839-845 (2014).
Rourke, C., et al., "Fibrinogen levels during trauma hemorrhage, response to replacement therapy, and association with patient outcomes," *J Thromb Haemost*, 10:1342-1351 (2012).
Raza, I., et al., "The incidence and magnitude of fibrinolytic activation in trauma patients," *J Thromb Haemost*, 11:307-314 (2013).
Hayakawa, M., et al., "Disseminated intravascular coagulation at an early phase of trauma is associated with consumption coagulopathy and excessive fibrinolysis both by plasmin and neutrophil elastase," *Surgery*, 149:221-230 (2011).
Kaplan, A. P., and Ghebrehiwet, B., "The plasma bradykinin-forming pathways and its interrelationships with complement," *Mol Immunol*, 47:2161-2169 (2010).
Omar, M. N., Mann, K. G., "Inactivation of factor Va by plasmin," *J Biol Chem*, 262:9750-9755 (1987).
Marcos-Contreras, O. A., et al., "Hyperfibrinolysis increases blood-brain barrier permeability by a plasmin- and bradykinin-dependent mechanism," *Blood*, 128:2423-2434 (2016).
Chapman, M. P., et al., "Overwhelming tPA release, not PAI-1 degradation, is responsible for hyperfibrinolysis in severely injured trauma patients," *J Trauma Acute Care Surg*, 80:16-25 (2016).
Cardenas, J. C., et al., "Elevated tissue plasminogen activator and reduced plasminogen activator inhibitor promote hyperfibrinolysis in trauma patients," *Shock*, 41:514-521 (2014).
Moore, H. B., et al., "Acute fibrinolysis shutdown after injury occurs frequently and increases mortality: a multicenter evaluation of 2,540 severely injured patients," *J Am Coll Surg*, 222:347-355 (2016).
Shakur, H., et al., "Effects of tranexamic acid on death, vascular occlusive events, and blood transfusion in trauma patients with significant haemorrhage (Crash-2): a randomised, placebo-controlled trial," *Lancet*, 376:23-32 (2010).
Peng, Z., et al., "Fresh frozen plasma lessens pulmonary endothelial inflammation and hyperpermeability after hemorrhagic shock and is associated with loss of syndecan 1," *Shock*, 40:195-202 (2013).
Diebel, L. N., "Microfluidics: a high-throughput system for the assessment of the endotheliopathy of trauma and the effect of timing of plasma administration on ameliorating shock-associated endothelial dysfunction," *J Trauma Acute Care Surg*, 84:575-582 (2018).
Yu, Q., et al., "Identification of fibrinogen as a key anti-apoptotic factor in human fresh frozen plasma for protecting endothelial cells in vitro," *Shock*, 53:646-652 (2020).
Wu, F., and Kozar, R. A., "Fibrinogen protects against barrier dysfunction through maintaining cell surface syndecan-1 in vitro," *Shock*, 51:740-744 (2019).
Wu, F., et al., "Fibrinogen activates PAK1/Cofilin signaling pathway to protect endothelial barrier integrity," *Shock*, 55:660-665 (2020).
Lopez, E., et al., "Antithrombin III contributes to the protective effects of fresh frozen plasma following hemorrhagic shock by preventing syndecan-1 shedding and endothelial barrier disruption," *Shock*, 53:156-163 (2020).
Deng, X., et al., "Adiponectin in fresh frozen plasma contributes to restoration of vascular barrier function after hemorrhagic shock," *Shock*, 45:50-54 (2016).
Rizoli, S. B., et al., "Clotting factor deficiency in early trauma-associated coagulopathy," *J Trauma*, 71(5 Suppl 1):S427-S434 (2011).

(56) References Cited

OTHER PUBLICATIONS

Pati, S., et al., "Lyophilized plasma attenuates vascular permeability, inflammation and lung injury in hemorrhagic shock," *PLoS One*, 13:e0192363 (2018) , entire document, 13 pages.
Reineccius, G., "Flavor encapsulation, Chapter 7. Spray-drying of food flavors," United Kingdom: Taylor and Francis, 55-66 (1989).
"Considerations for the Development of Dried Plasma Products Intended for Transfusion", (Final Report). Food and Drug Administration (2019), entire document, 9 pages.
Liu, Q. P., et al., "Single-donor spray-dried plasma," *Transfusion*, 59:707-723 (2019).
Meledeo, M. A., et al., "Spray-dried plasma deficient in high-molecular weight multimers of von Willebrand factor retains hemostatic properties," *Transfusion*, 59:714-722 (2019).
Buckley, L., and Gonzales, R., "Challenges to producing novel therapies-dried plasma for use in trauma and critical care," *Transfusion*, 59:837-845 (2019).
Bercovitz, R., et al., "Microfluidic analysis of thrombus formation in reconstituted whole blood samples comparing spray-dried plasma versus fresh-frozen plasma," *Vox Sang*, 116:540-546 (2020).
Spinella, P. C., et al., "All plasma products are not created equal: characterizing differences between plasma products," *J Trauma Acute Care Surg*, 78:S18-S25 (2015).
Bomey, N., "Hurricane Maria halts crucial drug manufacturing in Puerto Rico, may cause shortages," USA Today, [online], [retrieved on Oct. 20, 2017] Retrieved from https://www.usatoday.com/story/money/2017/09/22/hurricane-maria-pharmaceutical.industry-puerto-rico/692752001/ (2017), entire document, 9 pages.
Robinson, R. A., "Barda Strategic Plan 2011-2016", Washington, D.C.: Biomedical Advanced Research and Development Authority. (2016), entire document, 20 pages.
Pusateri A.E., "Dried Plasma Development Update," Defense Health Agency (2015) , entire document, 58 pages.
Downes, K. A., et al., "Serial measurement of clotting factors in thawed plasma stored for 5 days," *Transfusion*, 41: 570-570 (2001).
Runkel, S., et al., "The impact of whole blood processing and freezing conditions on the quality of therapeutic plasma prepared from whole blood," *Transfusion*, 55: 796-804 (2015).
Kelley, D., "Update on Plasma and Cryoprecipitate Transfusion," (Issue 1). *Institute for Transfusion Medicine* (2004) , entire document, 2 pages.
Parsons, J. C., "Coagulation Hereditary bleeding disorders von Willebrand disease," [online], [retrieved on May 12, 2015], Retrieved from https://www.pathologyoutlines.com/topic/coagulationvonwillebranddisease.html, entire document, 5 pages.
ARUP Consult, "Von Willebrand Disease Testing," [online], [retrieved on May 12, 2015], Retrieved from https://arupconsult.com/sites/default/files/von_Willebrand_Disease_Testing_Algorithm.pdf, entire document, 1 page.
Heger, A., et al., "Biochemical quality of the pharmaceutically licensed plasma OctaplasLG® after implementation of a novel prion protein (PrPSc) removal technology and reduction of the solvent/detergent (S/D) process time," *Vox Sanguinis*, 97: 219-225 (2009).
Pusateri, A. E., et al., "Use of Dried Plasma in Prehospital and Austere Environments," *Anesthesiology*, 136: 327-335 (2022).
Pusateri, A. E., "Dried plasma: state of the science and recent developments," *Transfusion*, 56: S128-S139 (2016).
Chaffin, J., "Liquid Plasma," [online], [retrieved on Nov. 2, 2021], Retrieved from https:www.bbguy.org/education/glossary/gll04/, entire document, 2 pages.
Chaffin, J., "Thawed Plasma," [online], [retrieved on Nov. 2, 2021], Retrieved from https:www.bbguy.org/education/glossary/glt04/, entire document, 2 pages.
Barrows, E., "Freeze-dried Plasma the Trail Back to the Battlefield," *Defense AT&L Technology Transition*, pp. 16-19 (Sep.-Oct. 2006).
Martinaud, C., et al., "French Dried Plasma Program: Update on prehospital and emergency unit use for massive hemorrhage management," *French Military Blood Institute* (Jun. 27, 2017), entire document, 34 pages.
Martinaud, C., et al., "In Vitro Hemostatic Properties of French Lyophilized Plasma," *Anesthesiology*, 117: 339-346 (2012).
Sicard, B., et al., "Lyophilized Plasma in Out-of-Hospital Resuscitation: Risk Benefit Balance," *Ann Emerg Med*, S141:357 (2017).
Jost, D., et al., "Pre-hospital Administration of Lyophilized Plasma for Post-traumatic Coagulopathy Treatment (PREHO-PLYO)," [online], [retrieved on Apr. 25, 2022], Retrieved from https://clinicaltrials.gov/ct2/show/study/NCT02736812, entire document, 9 pages.
News 4 WOAI San Antonio, "Freeze-dried plasma saves special ops soldiers", [Youtube], [retrieved on Apr. 25, 2022], Retrieved from https://www.youtube.com/watch?y=rstOJiwnwkw, entire document, 6 pages.
Lee, T., et al., "The use of lyophilized plasma in a severe multi-injury pig model," *Transfusion*, 53: 72S-79S (2013).
Holcomb, J.B., et al., "Increased Plasma and Platelet to Red Blood Cell Ratios Improves Outcome in 466 Massively Transfused Civilian Trauma Patients," *Ann Surg*, 3: 447-458 (2008).
Gatnau, R., "Spray dried porcine plasma as a source of protein and immunoglobins for weanling pigs." Unpublished master's thesis, Iowa State University, Ames, Iowa. (1990), entire document, 95 pages.
Murad, M.H., et al., "The effect of plasma transfusion on morbidity and mortality: a systematic review and meta-analysis," *Transfusion*, 50(6): 1370-1383 (2010).
Buchi Mini Spray Dryer B-191; www.buchi.com; Dec. 19, 2000, entire document, 28 pages.
DSS "Powdered Blood? Synthetic Blood Trials Show Promising Result" https://www.discoveryscientificsolutions.com/item/73 (downloaded Dec. 22, 2022) , entire document, 9 pages.
Hamilton GJ "Lyophilized plasma with ascorbic acid decreases inflammation in hemorrhagic shock." J Trauma, 71 (2):292-7 (2011), 7 pages.
Hawksworth, J.S. et al., Evaluation of lyophilized platelets as an infusible hemostatic agent in experimental non-compressible hemorrhage in swine, Journal of Thrombosis and Haemostasis, Oct. 2009, vol. 7, No. 10, pp. 1663-1671, 9 pages.
Solheim B G et al., Improved Preservation of Coagulation Factors After Pre-Storage Leukocyte Depletion of Whole Blood; Transfus Apher Sci., Oct. 2003. 29(2): pp. 133-139, 7 pages.
Goto et al., Characterization of the Unique Mechanism Mediating the Shear-dependent Binding of Soluble von Willebrand Factor to Platelets, The Journal of Biological Chemistry, vol. 270, No. 40, Oct. 6, 1995, pp. 23352-23361, 1995, 10 pages.
Horn, R.G., Addition of a polarizing microscope to the Weissenberg Rheogoniometer, 1979 American Institute of Physics, Rev. Sci. Instrum. 50(50, May 1979, pp. 659-661, 4 pages.
Moake, et al., Involvement of Large Plasma von Willebrand Factor (vWF) Multimers and Unusually Large vWF Forms Derived from Endothelial Cells in Shear Stress-induced Platelet Aggregation, The American Society for Clinical Investigation, Inc., vol. 78, Dec. 1986, pp. 1456-1461, 7 pages.
Shuja et al., Development and Testing of Freeze-Dried Plasma for the Treatment of Trauma-Associated Coagulopathy, The Journal of Trauma Injury, Infection and Critical Care, Presented at the 38th Annual Meeting of the Western Trauma Association, Feb. 24-Mar. 1, 2008, vol. 65, pp. 975-985, 11 pages.
CardianBCT, Inc "Mirasol Pathogen Reduction Technology", PN 306690-148, retrieved online Apr. 4, 2023 <URL: http://eurolambda.sk/shared/files/mirasol_plasma.pdf>, 2 pages. (Year: 2009).
Terumo BCT, Inc "Mirasol Pathogen Reduction Technology System", PN 306690232, retrieved online Apr. 4, 2023 <URL: https://www.terumopenpol.com/wp-content/uploads/2019/12/306690232-1.pdf>, 7 pages. (Year: 2012).
Heger, Andrea "Frozen and Freeze-dried solvent/detergent treated plasma: Tow different pharmaceutical formations with comparable quality" *Transfusion* (62): pp. 2621-2630 (Sep. 11, 2022) , 10 pages.
Highlights of Prescribing Information https://octaplasusa.com/wp-content/uploads/2021/03/20210202_pil_952_US_25.pdf Downloaded Apr. 11, 2023; Octapharma USA Inc, (Feb. 2021) pp. 1-9.
Operation Manual; Mini Spray Dryer B-290; Version G; www.buchi.com; Feb. 8, 2007, pp. 1-57.

(56) References Cited

OTHER PUBLICATIONS

Bulut, S. et al., "Effects of Combined Shear and Thermal Forces on Destruction of *Microbacterium lacticum" Appl Environ Microbiol*, vol. 65, No. 10, pp. 4464-4469 (Oct. 1999) , 6 pages.
International Search Report and Written Opinion, Application No. PCT/US2023/074261 pp. 1-17 (Dec. 4, 2023).
Booth, Garrett S. et al., Spray: Single-Donor Plasma Product for Room Temperature Storage, *Transfusion*: 52: 828-833 (Apr. 2012) 6 pages.
Dickey et al., "Use of Dried Plasma in Prehospital Battlefield Resuscitation Apr. 2011", Defense Technical Information Center, Aug. 8, 2011, accessible online at: https://apps.dtic.mil/sti/citations/AD1034120 (8 pages) (Aug. 8, 2011) , 18 pages.
Butler, Frank K. "Fluid Resuscitation in Tactical Combat Casualty Care: Yesterday and Today", Wilderness & Environmental Medicine, vol. 28, Issue 2, S74-S81, Jun. 2017, DOI: https:/doi.org/10.1016/j.wem.2016.12.007 (8 pages).
WayBack Machine archive of https://apps.dtic.mil/sti/citations/AD1034120, WayBack Machine, Nov. 29, 2020 (2 pages).
Semantic Scholar Web page concerning Dickey et al. "Use of Dried Plasma in Prehospital Battlefield Resuscitation", accessed by Examiner Dec. 14, 2023, U R L: https://www.semanticscholar.org/paper/Use-of -Dried-Plasma-in-Prehospital-Battlefield-Dickey/b87005a2c 7 cd54f022b 1728a80de07 df3a 7f8e40 (3 pages).
International Search Report and Written Opinion, Application No. PCT/US2023/074274 pp. 1-16 (Jan. 18, 2024).
International Search Report and Written Opinion, Application No. PCT/US2023/074266, pp. 1-11 (Dec. 21, 2023).
International Search Report and Written Opinion, Application No. PCT/US2023/074265, pp. 1-17 (Feb. 6, 2024).
International Search Report and Written Opinion, Application No. PCT/US2023/074264, pp. 1-13 (Feb. 6, 2024).
International Search Report and Written Opinion, Application No. PCT/US2023/074267, pp. 1-12 (Feb. 6, 2024).
International Search Report and Written Opinion, Application No. PCT/US2023/074268, pp. 1-23 (Feb. 9, 2024).
International Search Report and Written Opinion, Application No. PCT/US2023/074269, pp. 1-16 (Feb. 9, 2024).
International Search Report and Written Opinion, Application No. PCT/US2023/074277, pp. 1-13 (Feb. 9, 2024).
International Search Report and Written Opinion, Application No. PCT/US2023/074270, pp. 1-21 (Mar. 5, 2024).
International Search Report and Written Opinion, Application No. PCT/US2023/074272, pp. 1-15 (Feb. 9, 2024).
International Search Report and Written Opinion, Application No. PCT/US2023/074273, pp. 1-16 (Mar. 1, 2024).
International Search Report and Written Opinion, Application No. PCT/US2023/074275, pp. 1-16 (Mar. 1, 2024).
International Preliminary Report on Patentability PCT Application No. PCT/US2023/074267 pp. 1-9 (Mar. 27, 2025).
International Preliminary Report on Patentability PCT Application No. PCT/US2023/074261 pp. 1-11 (Mar. 27, 2025).
International Preliminary Report on Patentability PCT Application No. PCT/US2023/074264 pp. 1-11 (Mar. 27, 2025).
International Preliminary Report on Patentability PCT Application No. PCT/US2023/074265 pp. 1-12 (Mar. 27, 2025).
International Preliminary Report on Patentability PCT Application No. PCT/US2023/074266 pp. 1-8 (Mar. 27, 2025).
International Preliminary Report on Patentability PCT Application No. PCT/US2023/074268 pp. 1-19 (Mar. 27, 2025).
International Preliminary Report on Patentability PCT Application No. PCT/US2023/074269 pp. 1-13 (Mar. 27, 2025).
International Preliminary Report on Patentability PCT Application No. PCT/US2023/074270 pp. 1-15 (Mar. 27, 2025).
International Preliminary Report on Patentability PCT Application No. PCT/US2023/074272 pp. 1-11 (Mar. 27, 2025).
International Preliminary Report on Patentability PCT Application No. PCT/US2023/074273 pp. 1-13 (Mar. 27, 2025).
International Preliminary Report on Patentability PCT Application No. PCT/US2023/074274 pp. 1-12 (Mar. 27, 2025).
International Preliminary Report on Patentability PCT Application No. PCT/US2023/074275 pp. 1-15 (Mar. 27, 2025).
International Preliminary Report on Patentability PCT Application No. PCT/US2023/074277 pp. 1-10 (Mar. 27, 2025).
Qu W, Wang Z, Hunt C, et al. Platelet-Rich Plasma for Wound Care in the Medicare Population Rockville (MD): Agency for Healthcare Research and Quality (US); Sep. 17, 2020. Appendix H.

* cited by examiner

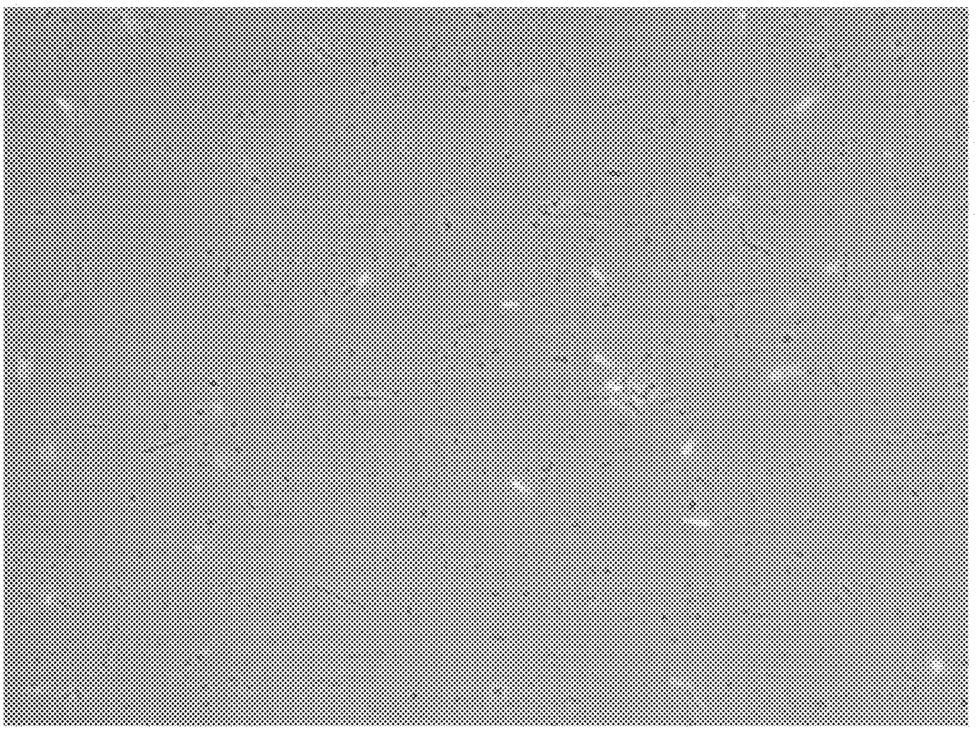
Freeze Dried plasma sample #1 at 100x
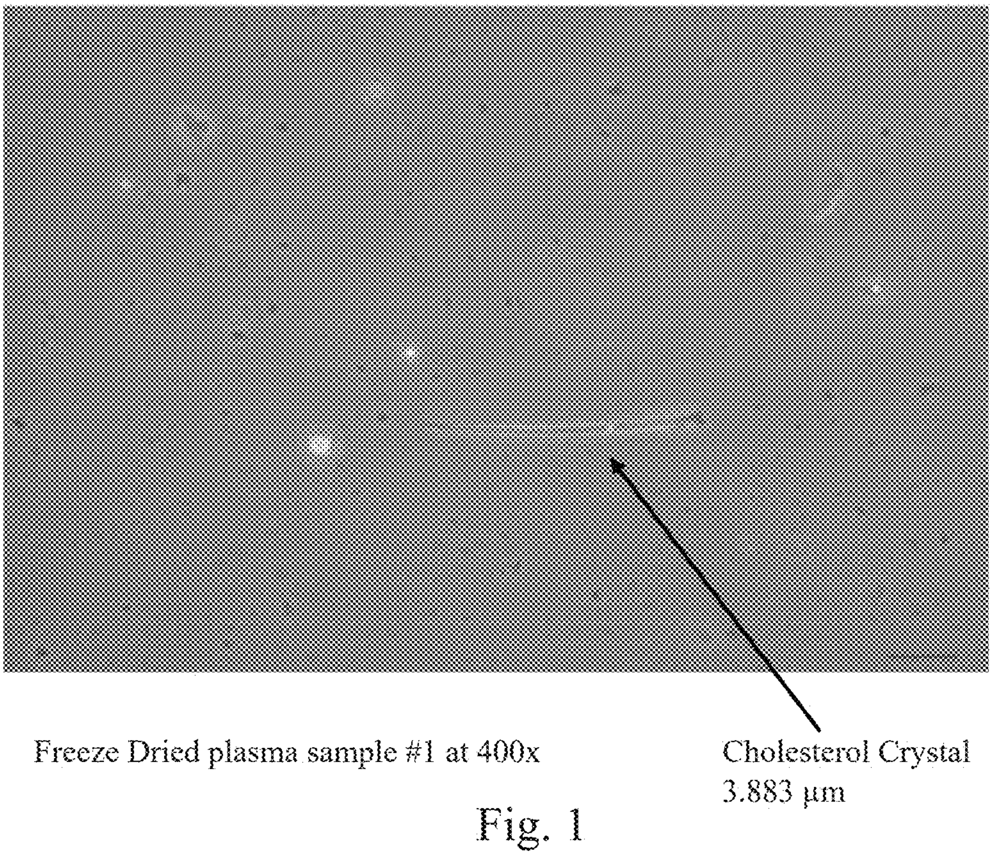
Freeze Dried plasma sample #1 at 400x
Cholesterol Crystal 3.883 μm
Fig. 1

The length of the cholesterol needles is 1-3 µm

SEM images Run #3.

SEM images for Run #7.

Thromboelastography (TEG): Rebuilt WB and Simulated Resuscitation

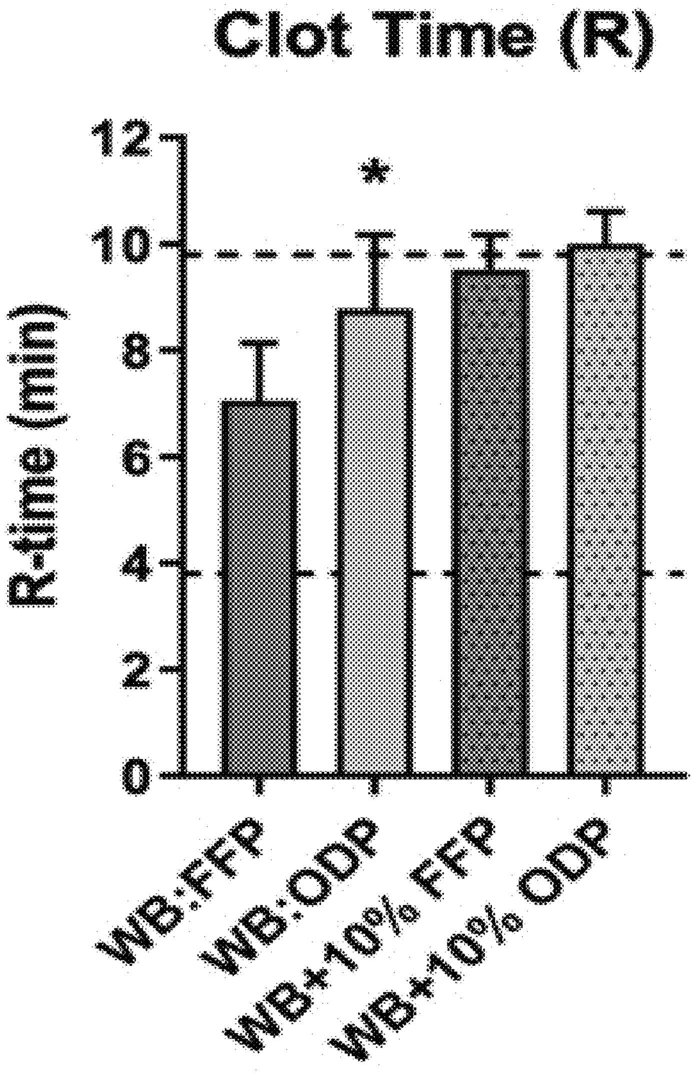

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 9A

Thromboelastography (TEG): Rebuilt WB and Simulated Resuscitation

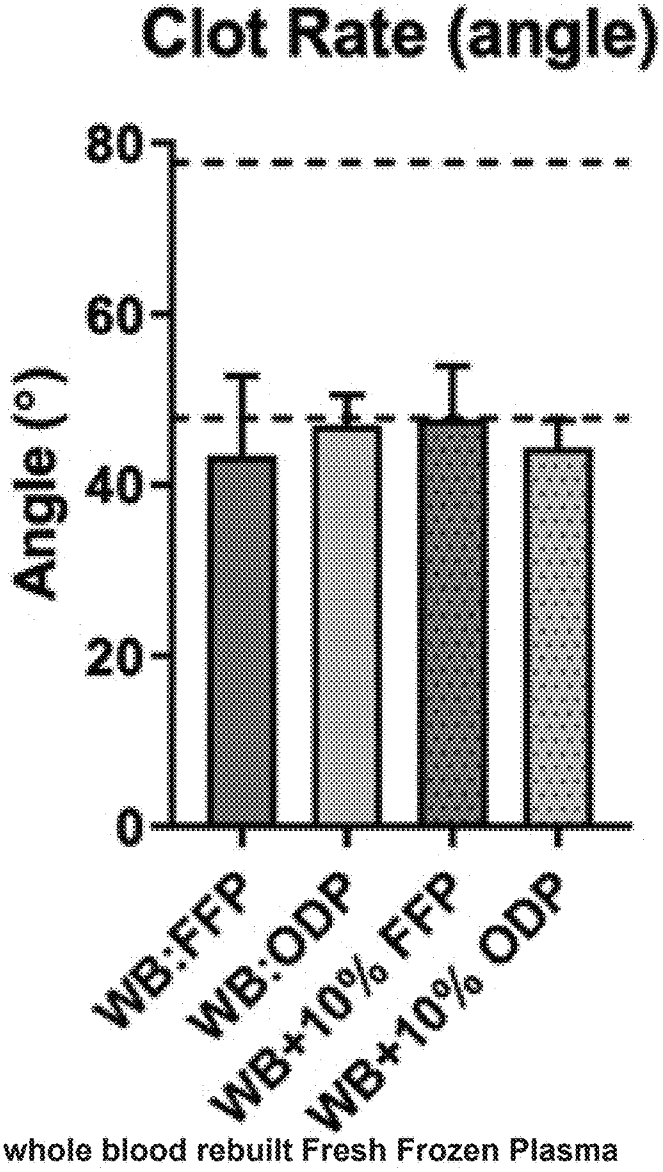

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 9B

Thromboelastography (TEG): Rebuilt WB and Simulated Resuscitation

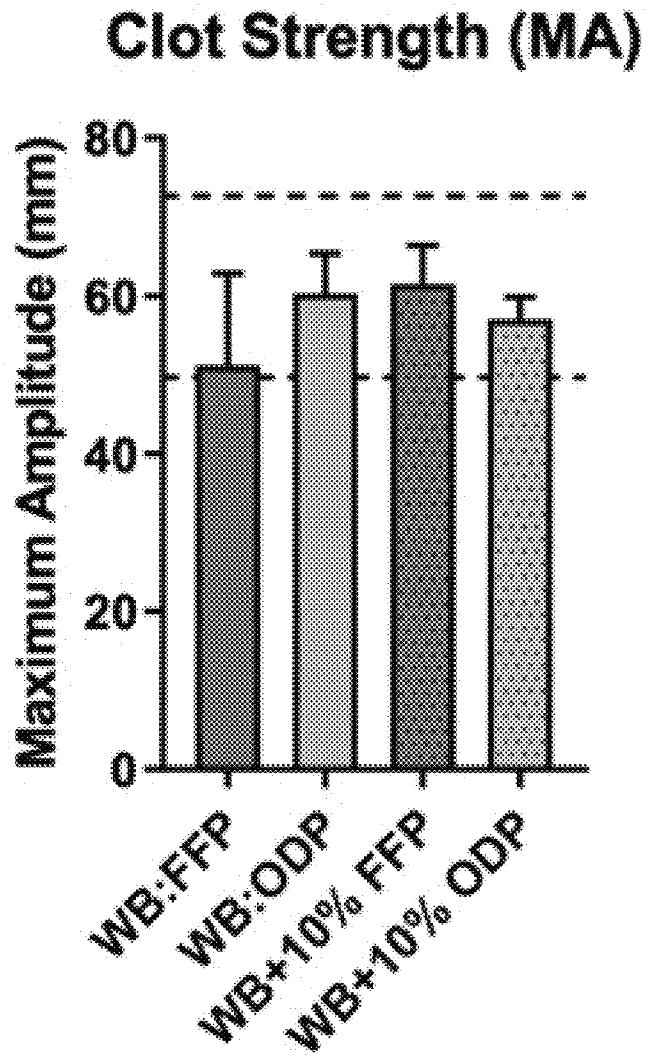

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 9C

Thromboelastography (TEG): Rebuilt WB and Simulated Resuscitation

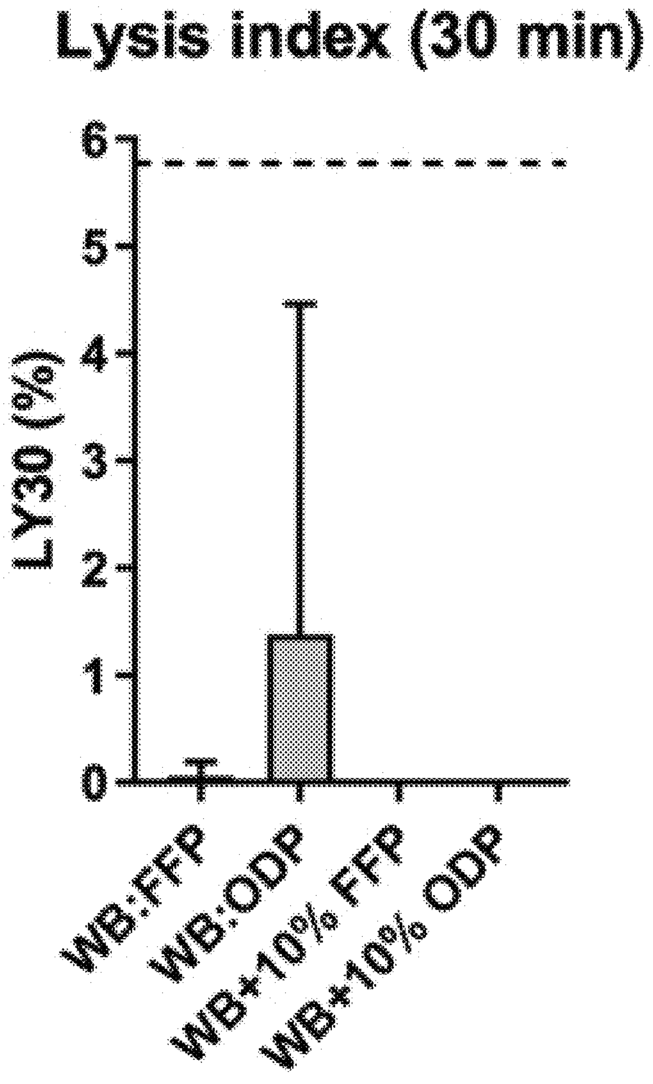

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 9D

Thromboelastography (TEG): Rebuilt WB and Simulated Resuscitation

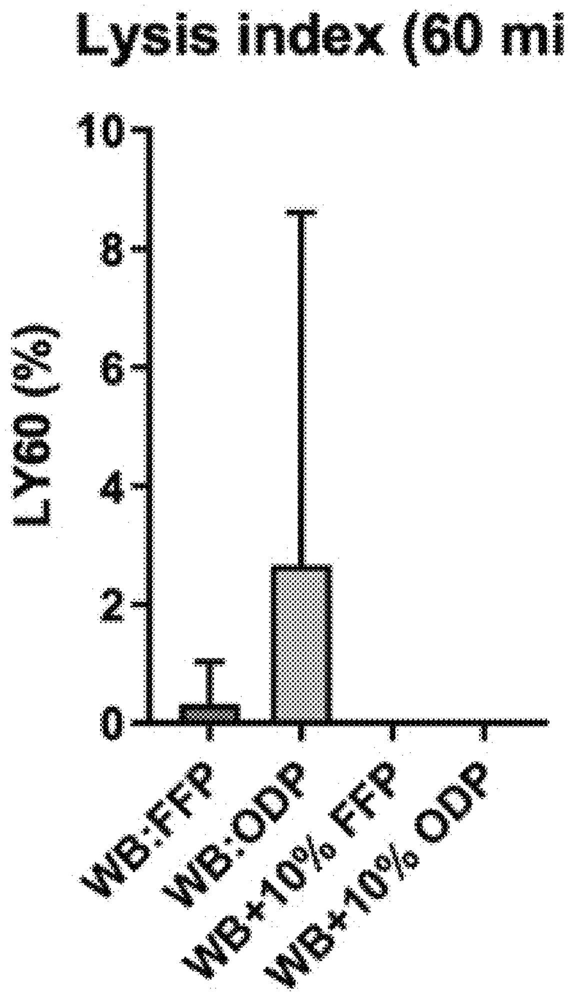

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 9E

Thromboelastography (TEG): Plasma Only

FFP = Fresh Frozen Plasma
ODP – Spray dried plasma unit of the present invention
WB+10% FFP = whole blood resuscitated with 2 units of FFP
WB+10% ODP = whole blood resuscitated with 2 units of ODP
Reference ranges are shown by dotted lines.

Thromboelastography (TEG): Plasma Only

FFP = Fresh Frozen Plasma
ODP – Spray dried plasma unit of the present invention
WB+10% FFP = whole blood resuscitated with 2 units of FFP
WB+10% ODP = whole blood resuscitated with 2 units of ODP
Reference ranges are shown by dotted lines.

Thromboelastography (TEG): Plasma Only

FFP = Fresh Frozen Plasma
ODP – Spray dried plasma unit of the present invention
WB+10% FFP = whole blood resuscitated with 2 units of FFP
WB+10% ODP = whole blood resuscitated with 2 units of ODP
Reference ranges are shown by dotted lines.

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

FFP - Fresh Frozen Plasma
ODP - spray dried plasma unit of the present invention Platelet Adhesion Bioflux Study

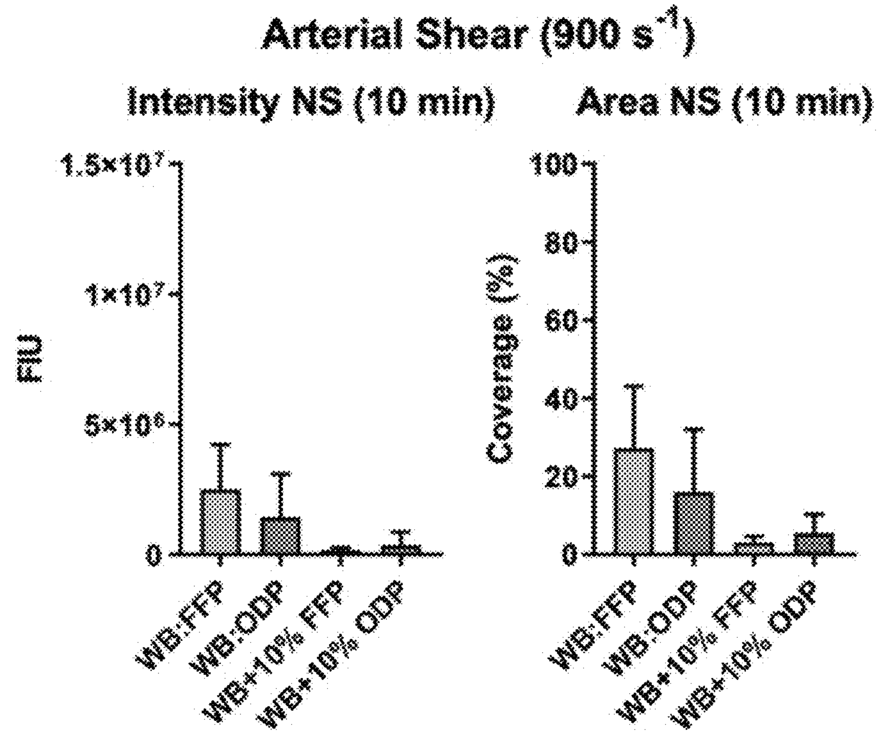

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 13A

Platelet Adhesion Bioflux Study

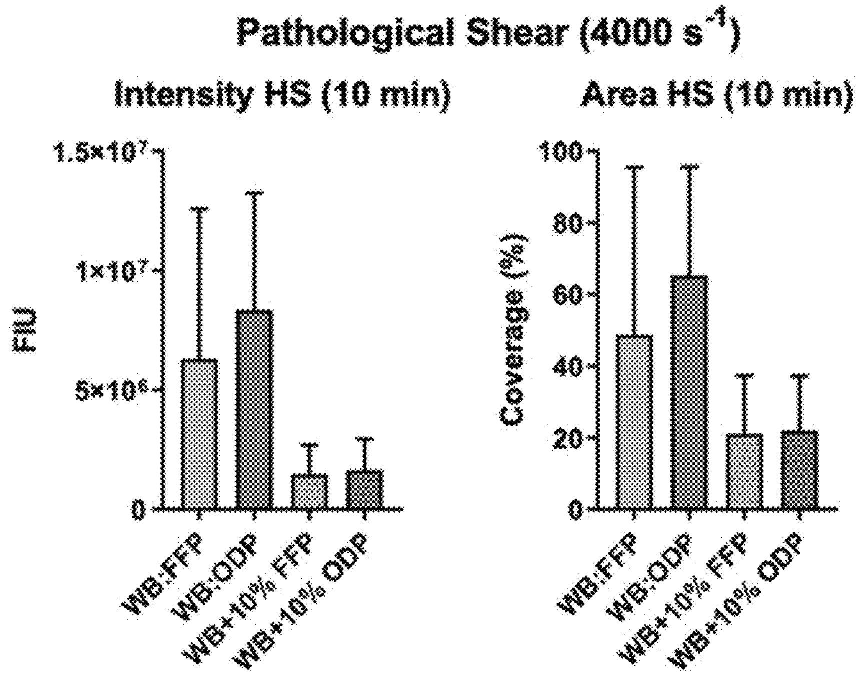

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
Reference ranges are shown by dotted lines.

Fig. 13B

CAT Thrombin Generation Assay

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
*p<0.05;p<0.01; *p<0.001.

CAT Thrombin Generation Assay

WB:FFP = whole blood rebuilt Fresh Frozen Plasma
WB:ODP _ whole blood rebuilt with ODP, spray dried plasma unit of the present invention
WB+10% FFP = whole blood resuscitated with 2 units of FFP
WB+10% ODP = whole blood resuscitated with 2 units of ODP, , spray dried plasma unit of the present invention
*p<0.05;p<0.01; *p<0.001

Flow Cytometry: Residual Cell Matter

FFP - Fresh Frozen Plasma
ODP - Spray dried plasma unit of the present invention
WBCs – White Blood Cells
RBCs – Red Blood Cells Lane
13 Type 2B vWD Control
14 Healthy Control
15 CP (naïve FFP)
16 CP/PreT
17 SpDP
18 SpDP/PreT C3a vs. pH C5a vs. pH Computation Flow Domain Drying gas flow- Surface Of Constant Velocity (15 m/s) Inside Plenum

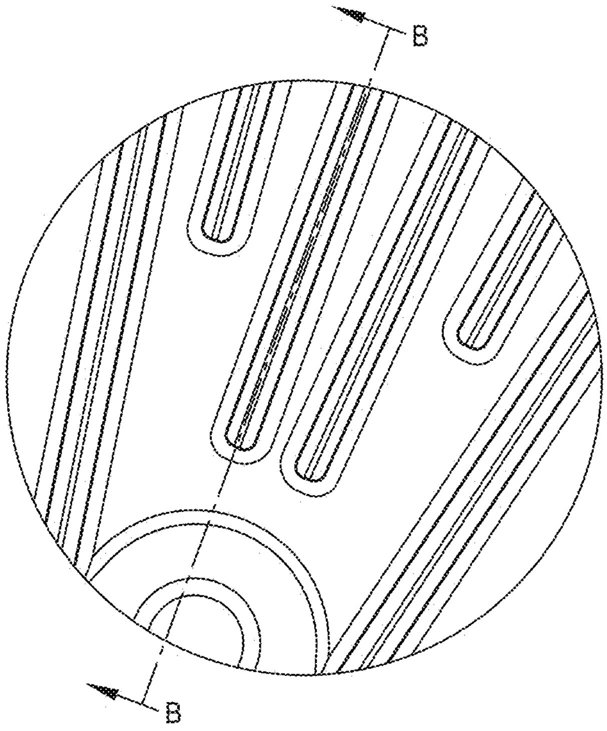
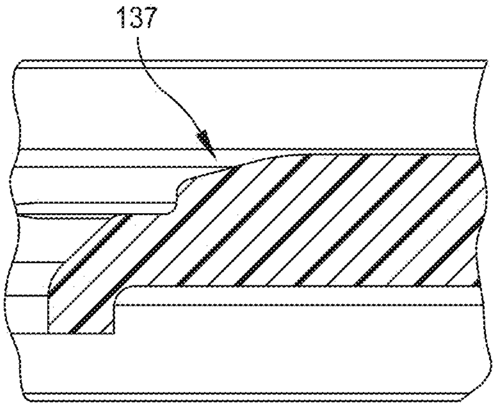
FIG. 43La
(CONTINUED)

Drying Gas Flow Jets Into Drying Chamber Showing
Uniform Jet Penetration And Drying Gas Distribution
Surface Of Constant Velocity (25 M/S) Inside Chamber

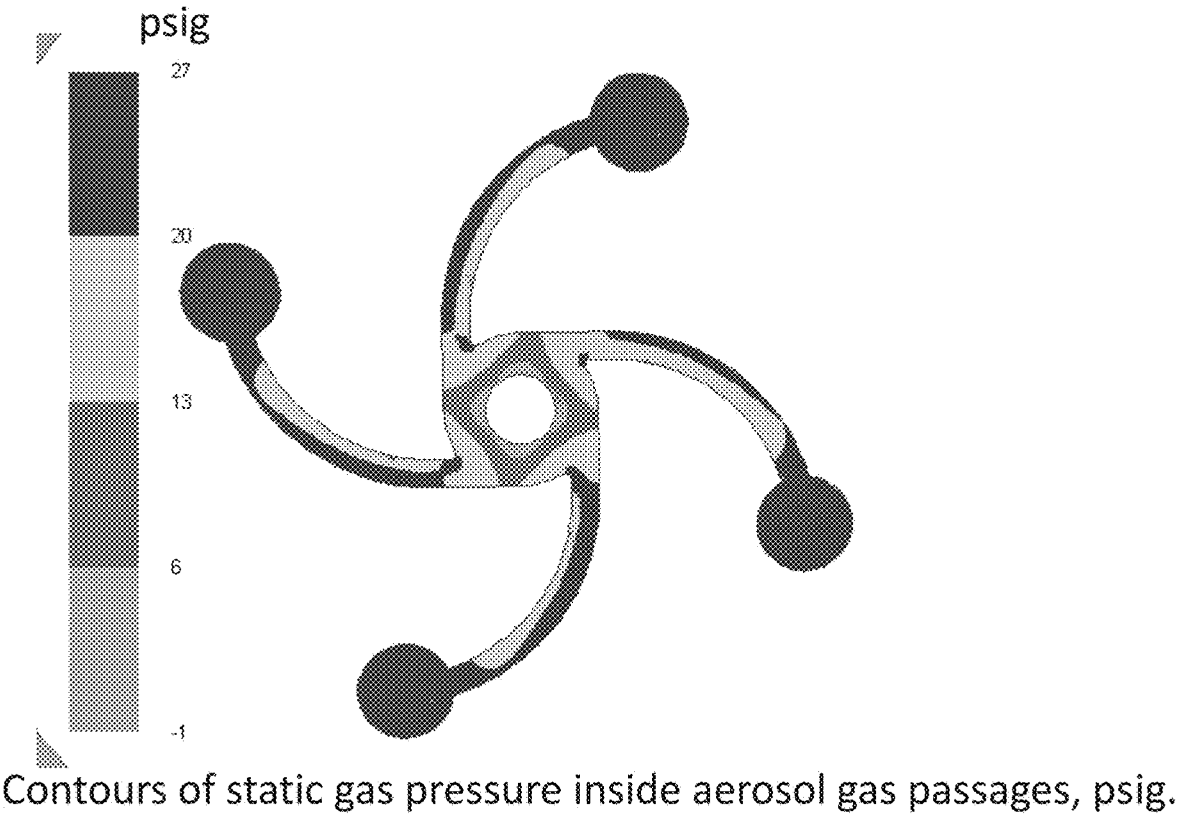
Contours of static gas pressure inside aerosol gas passages, psig.
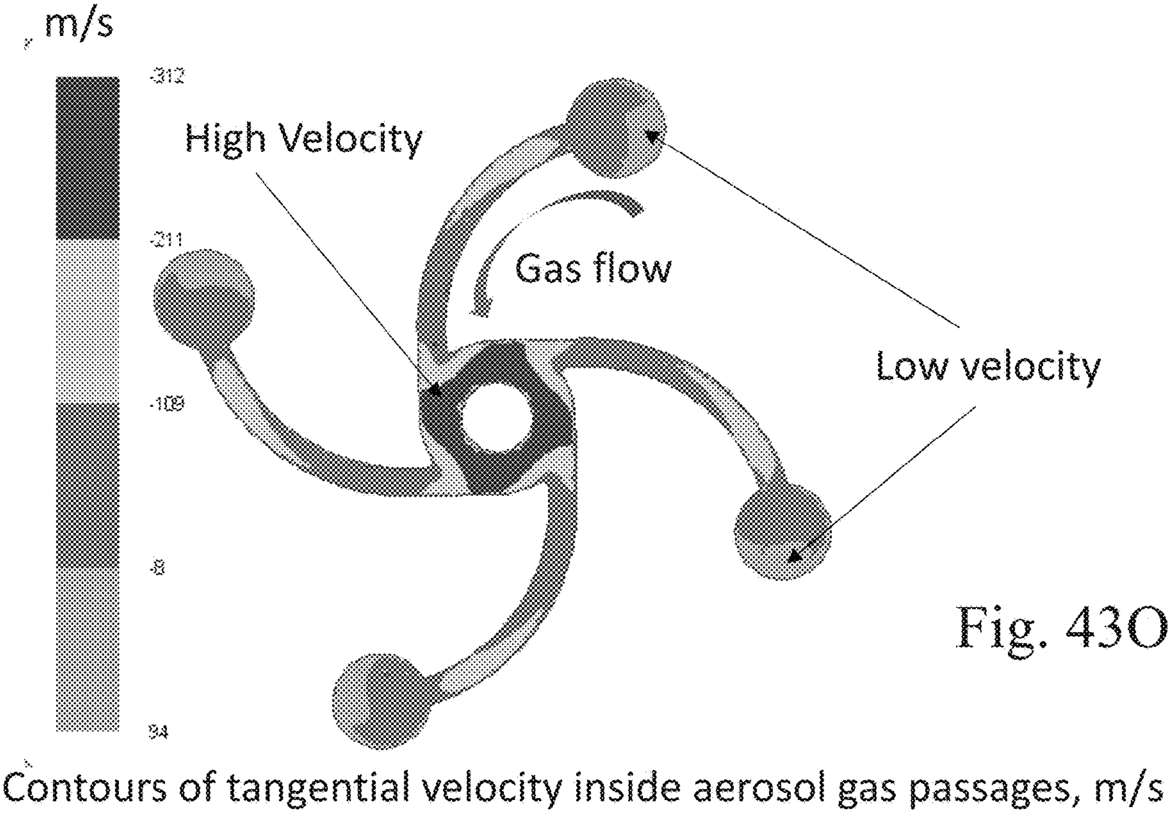
Fig. 43O
Contours of tangential velocity inside aerosol gas passages, m/s Velocity magnitude vectors inside aerosol gas passages, m/s During evaporation droplets experience wet bulb temperatures AM - AIR MANIFOLD
B - TRANSFER BAG
CN - CONNECTOR
DPT - DIFFERENTIAL PRESSURE TRANSDUCER
F - FILTER
FS - FLOW SENSOR
H - HEATER
MFC - MASS FLOW CONTROLLER
OS - SENSOR
P - PERISTALIC PUMP
PP - PNEUMATIC PISTON
PR - PRESSURE REGULATOR
PRV - PRESSURE RELIEF VALVE / RUPTURE DISK
PT - PRESSURE TRANSDUCER
PV - VALVE (ARROW DOWN IS FAIL CLOSED, ARROW UP IS FAIL OPEN)
S - SCALE
SS - SOLENOID
TC - THERMOCOUPLE
TS - THERMOCOUPLE SENSOR
TT - TEMPERATURE TRANSDUCER
☐ - DUPLICATION OF SAME NAME
⬚ - COMPONENTS IMPLEMENTED AS ONE PART

| | |
|---|---|
| DONOR PRETREATED PLASMA LINE | LINES C, I |
| DRYING AIR LINE | LINES B, E, G |
| PRESSURIZED AEROSOL AIR LINE | LINES A, D, H |
| DISPOSABLE DEFLATION LINE | LINE F |
| DISPOSABLE EXHAUST LINE | LINE J |
| HOUSING EXHAUST LINE | LINE K |
| LEAK DETECTION LINE | LINE L |

FIG. 46C
(CONTINUED)

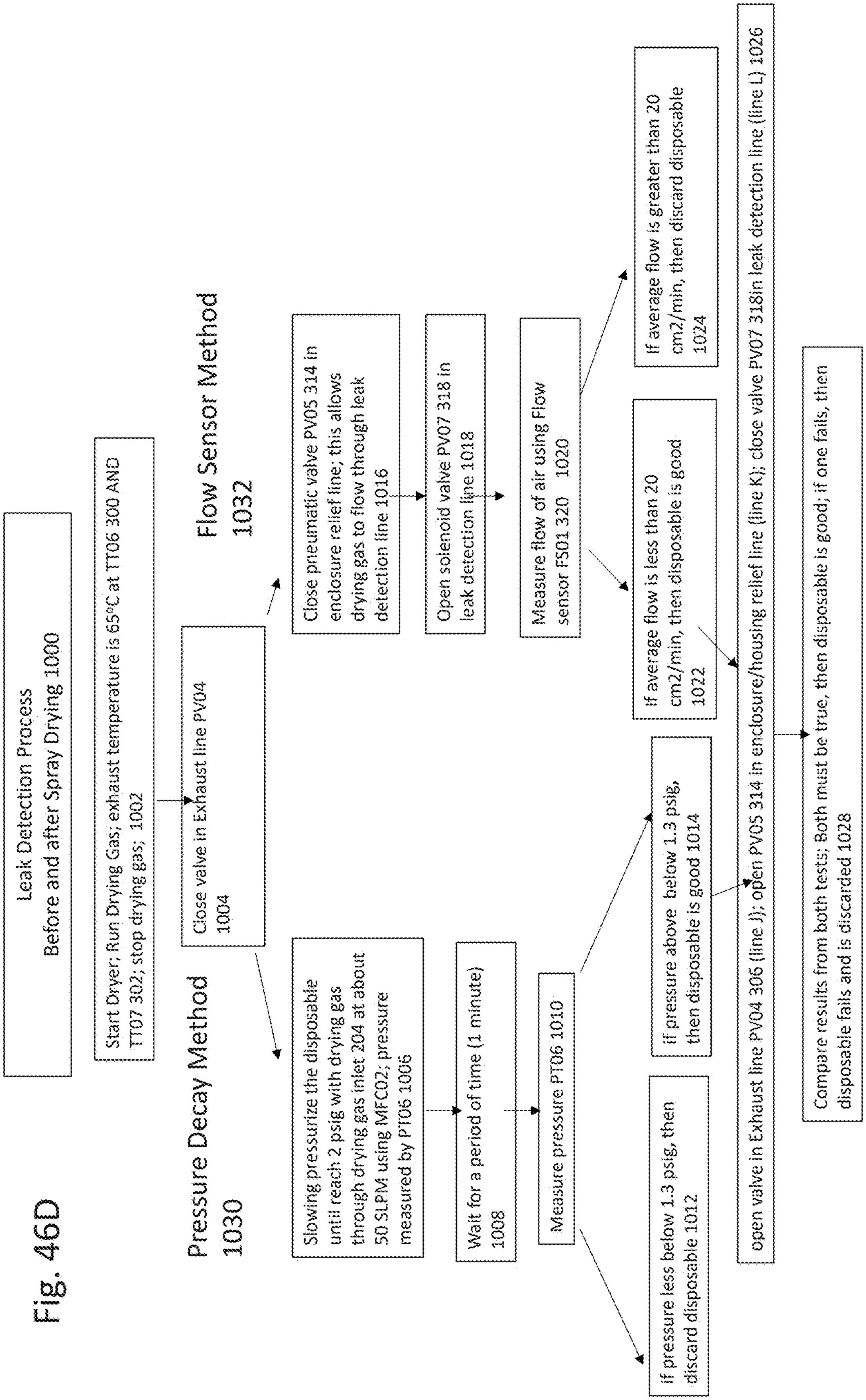
Fig. 46D
Leak Detection Process
Before and after Spray Drying 1000
Start Dryer; Run Drying Gas; exhaust temperature is 65°C at TT06 300 AND TT07 302; stop drying gas; 1002
Close valve in Exhaust line PV04 1004
Pressure Decay Method 1030
Flow Sensor Method 1032
Slowing pressurize the disposable until reach 2 psig with drying gas through drying gas inlet 204 at about 50 SLPM using MFC02; pressure measured by PT06 1006
Wait for a period of time (1 minute) 1008
Measure pressure PT06 1010
if pressure less below 1.3 psig, then discard disposable 1012
if pressure above below 1.3 psig, then disposable is good 1014
Close pneumatic valve PV05 314 in enclosure relief line; this allows drying gas to flow through leak detection line 1016
Open solenoid valve PV07 318 in leak detection line 1018
Measure flow of air using Flow sensor FS01 320 1020
If average flow is less than 20 cm2/min, then disposable is good 1022
If average flow is greater than 20 cm2/min, then discard disposable 1024
open valve in Exhaust line PV04 306 (line J); open PV05 314 in enclosure/housing relief line (line K); close valve PV07 318in leak detection line (line L) 1026
Compare results from both tests; Both must be true, then disposable is good; if one fails, then disposable fails and is discarded 1028

AM - AIR MANIFOLD
CN - CONNECTOR
CV - CHECK VALVE
EM -ELECTRIC MOTOR
FS - FLOW SENSOR
FR - FLOW RESTRICTOR
PP -PNEUMATIC PISTON
PR - PRESSURE REGULATOR
PT - PRESSURE TRANSDUCER
PV - VALVE (ARROW DOWN IS FAIL CLOSED, ARROW UP IS FAIL OPEN
SC - SPEED CONTROLLER
SR - SENSOR
VG - VACUUM GENERATOR
□ - DUPLICATION OF SAME NAME
⬚ - COMPONENTS IMPLEMENTED AS ONE PART

AIR LINE LINE A
EXTRACTION VACUUM LINE LINE B
EXTRACTION PISTON LINE LINES C, D
IMPACTOR LINE LINES E, F, G, H, N, O, T, U
CUTTING LINE LINES I, J, P, Q, V, W
SEALING LINE LINES K, L, M, R, S, X, Y

FIG. 49B
(CONTINUED)

Liquid flow existing nozzle assembly

DISPOSABLE FOR A SPRAY DRYING SYSTEM

RELATED APPLICATION(S)

This application is a continuation of U.S. application Ser. No. 18/467,102, entitled, “Disposable For A Spray Drying System” by Robert R. Andrews et al., filed Sep. 14, 2023, which is a continuation-in-part of U.S. application Ser. No. 17/945,124, entitled, “Disposable For A Spray Drying System” by Robert R. Andrews et al., filed Sep. 15, 2022.

The entire teachings of the above application(s) are incorporated herein by reference.

GOVERNMENT SUPPORT

This invention was made with Government support under contract Nos. HHSO100201200005C and 75A50121C00059 awarded by the Biomedical Advanced Research and Development Authority (BARDA). The Government has certain rights in the invention.

BACKGROUND OF THE INVENTION

The spray drying process, in general, is a well-known technology to dry a variety of liquid compositions for applications including cosmetics, animal feed, pharmaceuticals and others. Unfortunately, until the present invention, spray drying of blood plasma for transfusion has not been commercially feasible and generally spray drying has been an industrial or laboratory specialty involving complex, difficult to operate and often large machinery for manufacturing cosmetics, pharmaceuticals, animal feed and the like. Often, the aforementioned devices and methods have suffered from being impractical for use by a wide range of operators with little training or for aseptically manufacturing end products for human or animal medical use. These apparatuses are intended for use by highly skilled, experienced operators and not intended for use in environments or with personnel associated with the manufacture of human plasma for transfusion in blood centers and elsewhere.

With respect to plasma, transfused human blood plasma is often crucial to bleeding control and wound treatment in trauma victims and in surgery. Unfortunately, plasma is not readily available in many circumstances world-wide including battlefield, first responder, and rural settings remote from large hospitals, and in the second and third world.

The principal reason human plasma is not available as widely as needed is that in general blood plasma could only be stored frozen for long periods or as a liquid for very short periods. Accordingly, if a large amount of plasma is needed (e.g., such as in a mass casualty event), it may not be available in such quantities, or if plasma is needed in an emergency, it may not be available in time since it has to be thawed which can take 30-45 minutes or more.

The spray drying plasma process involves drying liquid plasma, a biological component, into a dried powder plasma. Maintaining the integrity of the plasma drying chamber of the disposable during spray drying and of the plasma unit assists in preventing a breach of the biological component and its exposure to pathogens.

Hence, a need exists to increase safety for a plasma spray drying system, the disposable and its dried plasma product. A need exists for a disposable for a spray dryer for use by a wide range of operators with little training or for aseptically manufacturing end products for human or animal medical use. A further need exists to design a spray drying system in which the spray drying plasma chamber and related components aseptically provides a dried plasma unit. Yet a further need exists for a spray drying system that provides a dried plasma unit from the spray dry chamber of a disposable used in the system to maintain system integrity. A further need exists for dried plasma to be readily available and able to rehydrate in a few minutes.

SUMMARY OF THE INVENTION

The present invention relates to a spray drying disposable device that has a spray drying head and a drying chamber. The spray drying disposable device is for use in a spray drying system that has a drying gas source, a plasma source and a pressurized aerosol gas source. In an embodiment, spray drying disposable device dries a single unit of donor plasma into a single unit of dried plasma. If desired, pooled plasma can also be prepared using the apparatus and process of the present invention.

The spray drying system of the present invention includes for example the spray drying disposable device and a spray drying apparatus. The spray drying system has a drying gas source that provides a drying gas, a plasma source that provides a plasma and a pressurized aerosol gas source that provides a pressurized aerosol gas.

The spray drying head includes a spray dry nozzle assembly in fluid communication with the plasma source and the pressurized aerosol gas source, wherein the pressurized aerosol gas flows in a vortex pattern, wherein, when in use, the pressurized aerosol gas atomizes the plasma entering the drying chamber to obtain atomized plasma droplets. The spray drying head also includes a plenum having a drying gas inlet in communication with the drying gas source, wherein, when in use, the drying gas resides in the plenum with uniform air pressure, wherein the plenum supports the nozzle assembly. The spray drying head further includes a baffle plate forming the floor of the plenum having one or more drying gas jets, wherein drying gas jet provides drying gas to the drying chamber.

The drying chamber of the spray drying disposable device is attached to the baffle plate in which atomized plasma droplets evaporate in the presence of the drying gas emitted from the one or more drying gas jets to thereby obtain dried plasma particles and humid air. The drying chamber further includes a capture filter, residing in the drying chamber, wherein the capture filter captures the dried plasma particles and allows the humid air to pass. The drying chamber also includes a gas outlet, wherein the gas outlet is attached to the exhaust port of the spray drying system during operation, wherein the humid air flows through the gas outlet.

In an embodiment, the spray dry nozzle assembly includes a cannula. The cannula, in an aspect, has an inner diameter in a range between about 0.010 inches and about 0.040 inches and an outer diameter between about 0.030 inches and about 0.060 inches.

In another embodiment, the spray drying disposable device further includes a vortex generator in communication with the pressurized aerosol gas. In an aspect, the vortex generator has a plurality of channels and a plurality of pads to create the vortex pattern of pressurized aerosol gas. The plurality of channels and the plurality of pads can be curved and/or the plurality of channels are curved and the plurality of pads have one or more curved edges.

In yet another embodiment, the nozzle assembly has an opening with a diameter. At this opening, the cannula emits the plasma and the pressurized aerosol gas. The nozzle opening has an inner surface. The cannula has an inner diameter and an outer diameter, and an outer surface. The opening emits pressurized aerosol gas in a vortex pattern. In particular, the vortex pattern of pressurized aerosol gas flows through the outer surface of the cannula and the inner surface of the opening. In an embodiment, the distance between the outer surface of the cannula and the inner surface of the opening is between about 0.015 inches and about 0.091 inches. In an aspect, the nozzle assembly extends past the plane defined by baffle plate into the plasma drying chamber.

In an embodiment, the drying gas inlet receives the drying gas source through a deflector that directs the drying gas to the inner side wall of the plenum. The drying gas inlet receives the drying gas source through a deflector that comprises a 90 degree elbow.

In yet another aspect, the plenum of the spray drying head further includes a baffle filter (e.g., 0.2 micron filter), through which the drying gas flows. In an embodiment, the baffle plate comprises one or more ribs on which the baffle filter rests. The baffle plate, in an aspect, has one or more channels of air flow communicating with the one or more drying gas jet. The one or more channels define one or more pie shaped air channels communicating with the one or more drying gas jet.

In an embodiment, the drying chamber of spray drying disposable device has a section that, after sealing and separation, becomes the dried plasma unit product. As such, this section further includes at least one or more ports for injecting reconstitution fluid or transferring the reconstituted plasma to a recipient, a slot for hanging the dried plasma unit, and a label. Along these lines, the drying chamber includes cut and seal locations that form the walls of the dried plasma unit.

In an embodiment, the drying chamber of spray drying disposable device has a separator at the capture filter, wherein the separator separates the capture filter from the inner wall of the spray drying chamber.

In yet another embodiment, the spray drying disposable device includes a locating arrangement for aligning the spray drying disposable device with the spray drying system.

The present invention includes methods of making spray dried plasma using the spray drying disposable device and spray drying system described herein and storing the spray dried plasma unit. The present invention further includes kits and systems having the spray drying disposable device and spray dried plasma unit described herein.

Advantageously, the present invention involves a spray drying system that has an easy-to-use spray dryer and a disposable that includes a drying chamber within it. A further advantage of the spray drying disposable is that, once the spray drying is completed, it converts into the spray dried plasma product that can be used in the field. The dried plasma of the present invention enables simplified storage, transport, and use options (e.g., refrigerated/ambient temperature storage) as compared to frozen plasma, the current standard for plasma. The present invention overcomes the inadequacies of the previous spray drying systems and permits the rapid, aseptic manufacture of small or single unit quantities of a wide range of materials by minimally trained operators of a wide range of statures. The applications of the present invention are wide and include dried human blood plasma. In particular, the present invention provides a process for moving the plasma into desired compartments of the disposable and sealing the disposable at certain locations to create a packaged, ready to use container for the dried material. The present invention is advantageously applicable to the aseptic manufacture of products for use in medicine such as pharmaceuticals or dried blood plasma. This plasma unit is rehydrated with sterile water and ready to use in minutes, providing easy and quick access to plasma.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a black and white photograph showing phase contrast microscopy at 100× and 400× magnification of cholesterol crystals in freeze-dried plasma known as LYOPLAS™ plasma.

FIG. 9A is a bar graph showing results of Clot Time (R) in minutes from a Thromboelastography TEG study with Rebuilt WB and Simulated Resuscitation (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 9B is a bar graph showing results of Clot Rate (angle) in degrees from a Thromboelastography TEG study with Rebuilt WB and Simulated Resuscitation (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 9C is a bar graph showing results of Clot Strength (MA) in Maximum Amplitude (mm) from a Thromboelastography TEG study with Rebuilt WB and Simulated Resuscitation (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 9D is a bar graph showing results of Lysis index (30 minutes) in LY30 in percentage (%) from a Thromboelastography TEG study with Rebuilt WB and Simulated Resuscitation (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 9E is a bar graph showing results of Lysis index (60 minutes) in LY60 in percentage (%) from a Thromboelastography TEG study with Rebuilt WB and Simulated Resuscitation (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 13A is two bar graphs showing results of from a platelet adhesion Bioflux study showing arterial shear at $900^{s-1}$ of intensity NS (10 minutes) in Fluorescence Intensity Units (FIU) and Area NS (10 minutes) coverage in percentage (%). (abbreviations: NS=Normal Shear conditions; WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 13B includes two bar graphs showing results of from a platelet adhesion Bioflux study showing pathological shear at 4000 $s^{-1}$ of intensity HS (10 minutes) in Fluorescence Intensity Units (FIU) and Area HS (10 minutes) coverage in percentage (%). (abbreviations: HS=High Shear conditions; WB:FFP=whole blood (WB) rebuilt with Fresh Frozen Plasma (FFP); WB:ODP—whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 43Ia is schematic showing a bottom view nozzle cap of FIG. 43I with the cannular residing within the cap opening.

FIG. 43Ib schematic showing three possible vortex generator flow patterns that could be used with the nozzle cap insert of FIG. 43I.

FIG. 43Ic is a schematic showing a cross-sectional view of nozzle cap insert of FIG. 43H residing within nozzle cap of FIG. 43I.

FIG. 43Ka is a model representation showing the modeled drying gas flow within the plenum chamber using a constant velocity magnitude surface of 15 m/s.

FIG. 43La is a schematic showing a cut out section of the rib design of the baffle plate shown in FIG. 43L and a cut out section of another variation of the baffle plate rib design. FIG. 43La also shows a cross section of one of the ribs.

FIG. 43Ma is a model representation showing uniform jet penetration and drying gas distribution at constant velocity of 25 m/s and hence results in a circumferentially uniform introduction of the drying gas around the spray plume.

FIG. 43Na is a model representation displaying the gas velocity magnitude contours within the disposable's center plane indicating the drying jet penetration into the drying chamber and the effect of baffle plate flow channels and interaction with the high velocity spray plume which act to pull the drying gas jets radially inward to assist in the desired rapid mixing of the droplets and gas flows.

FIG. 43O is a model representation showing the gas pressure flow (psig) (top) and tangential velocity flow (m/s) (bottom) of the vortex generated in the nozzle insert and cap assembly.

FIG. 43Sa is a line graph temperature in ° C. and time (seconds) of a plasma droplet as it becomes a particle in the model. Once the evaporation is complete, the protein encased in a solid particle is more tolerant of elevated temperature as it equilibrates with the dryer outlet temperature. In this case, evaporation occurs in less than fractions of a second (e.g., 0.01 to 0.05 seconds).

FIG. 46D is a flow chart showing the steps of the leak detection method employing the spray dryer and spray drying disposable.

FIG. 46I is a line graph showing the slope employing the method for detecting integrity of filters and showing that the baffle filter has failed intact by measuring Pressure (psig), elapsed time (min) and pressure rate of change (psi/min).

FIG. 48L is a schematic showing a side view of the impactor, separator and sealer of the finishing apparatus shown in FIG. 48D.

FIG. 49A is a schematic showing a front view of the spray dry plasma unit obtained from the spray drying disposable device after processed by the finishing apparatus.

Figure 49A:
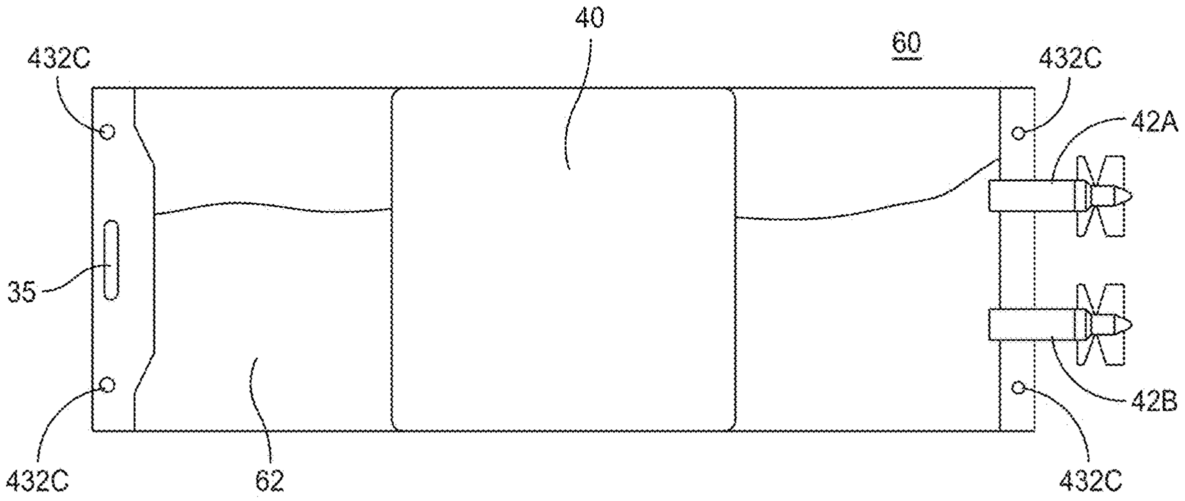
Figure 49B:
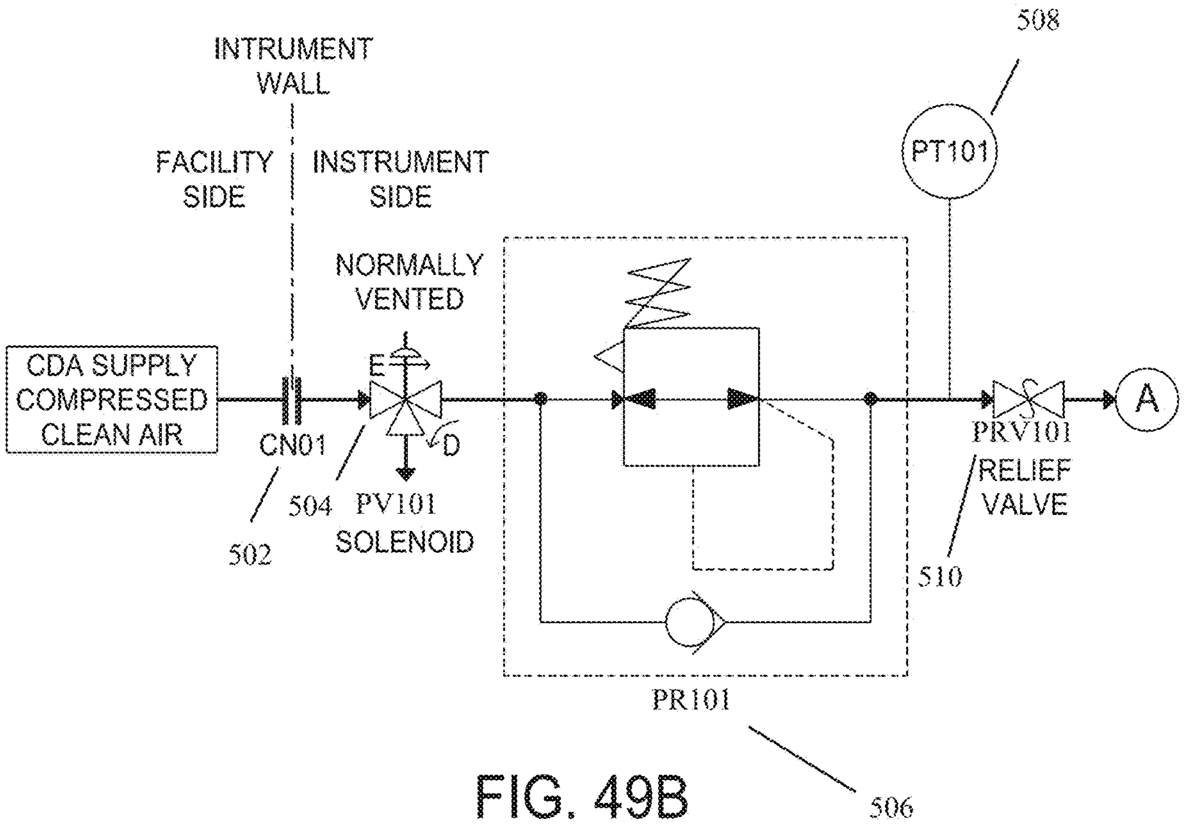
Figure 49B:
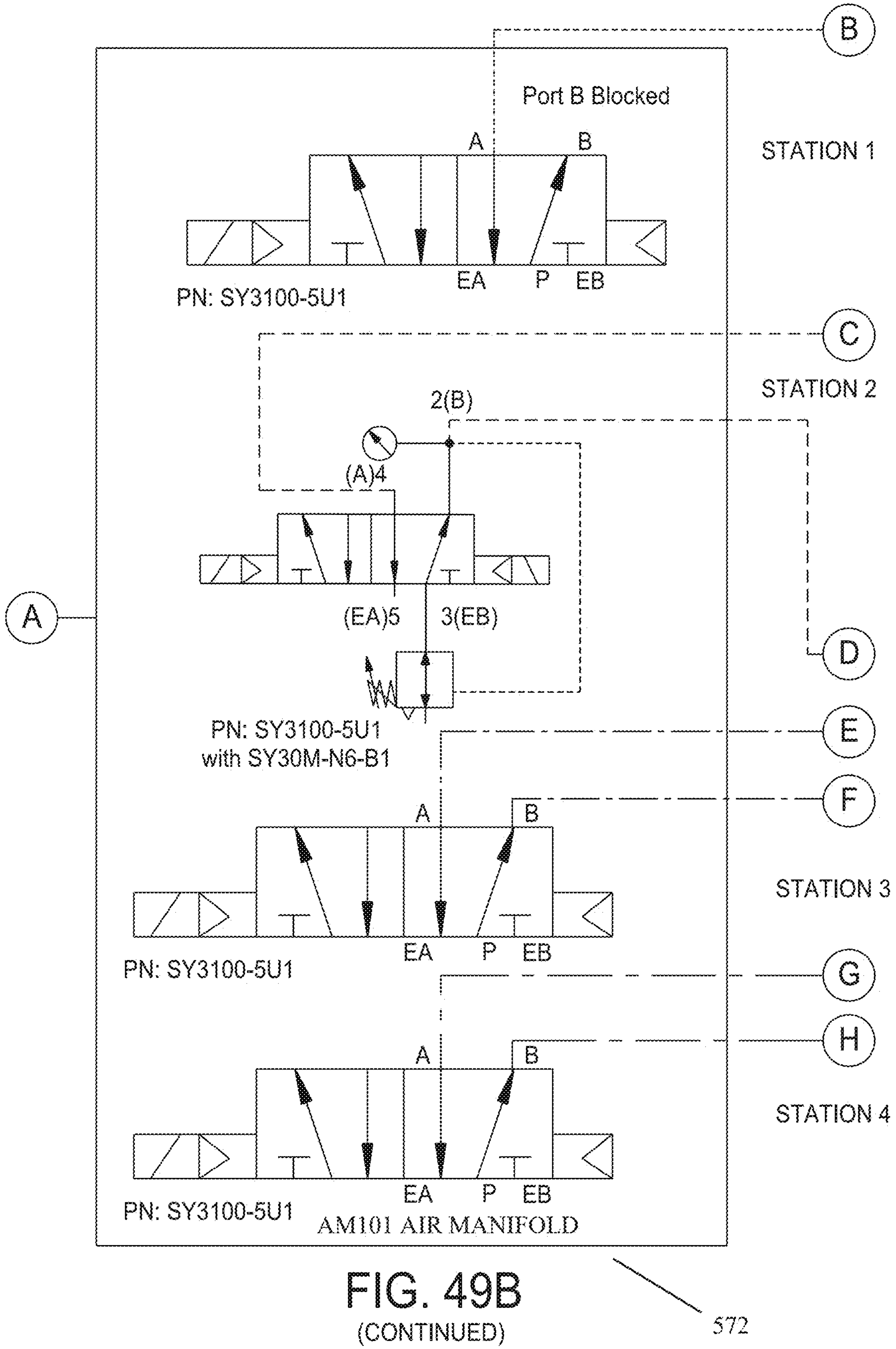
Figure 49B:
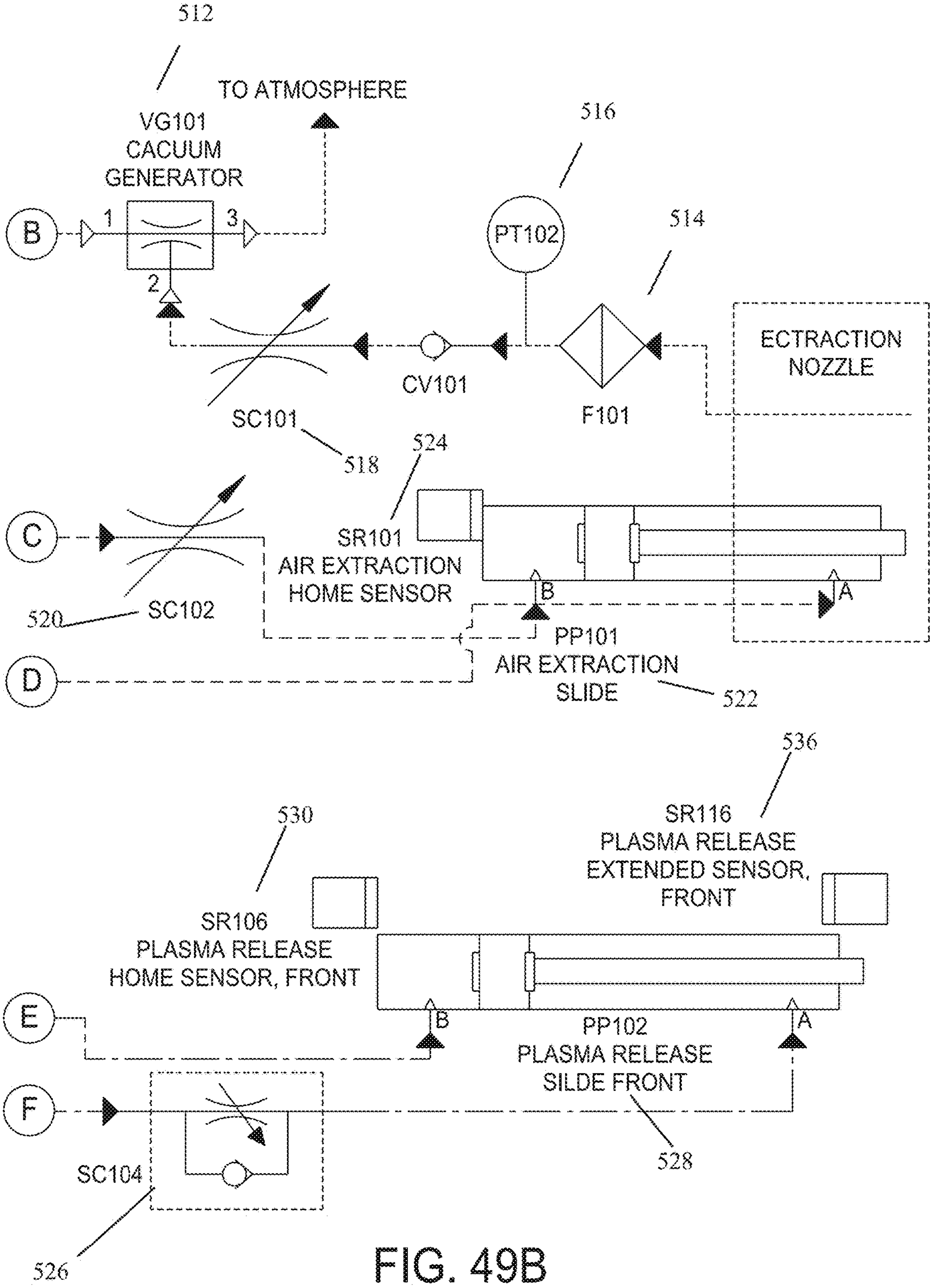
Figure 49B:
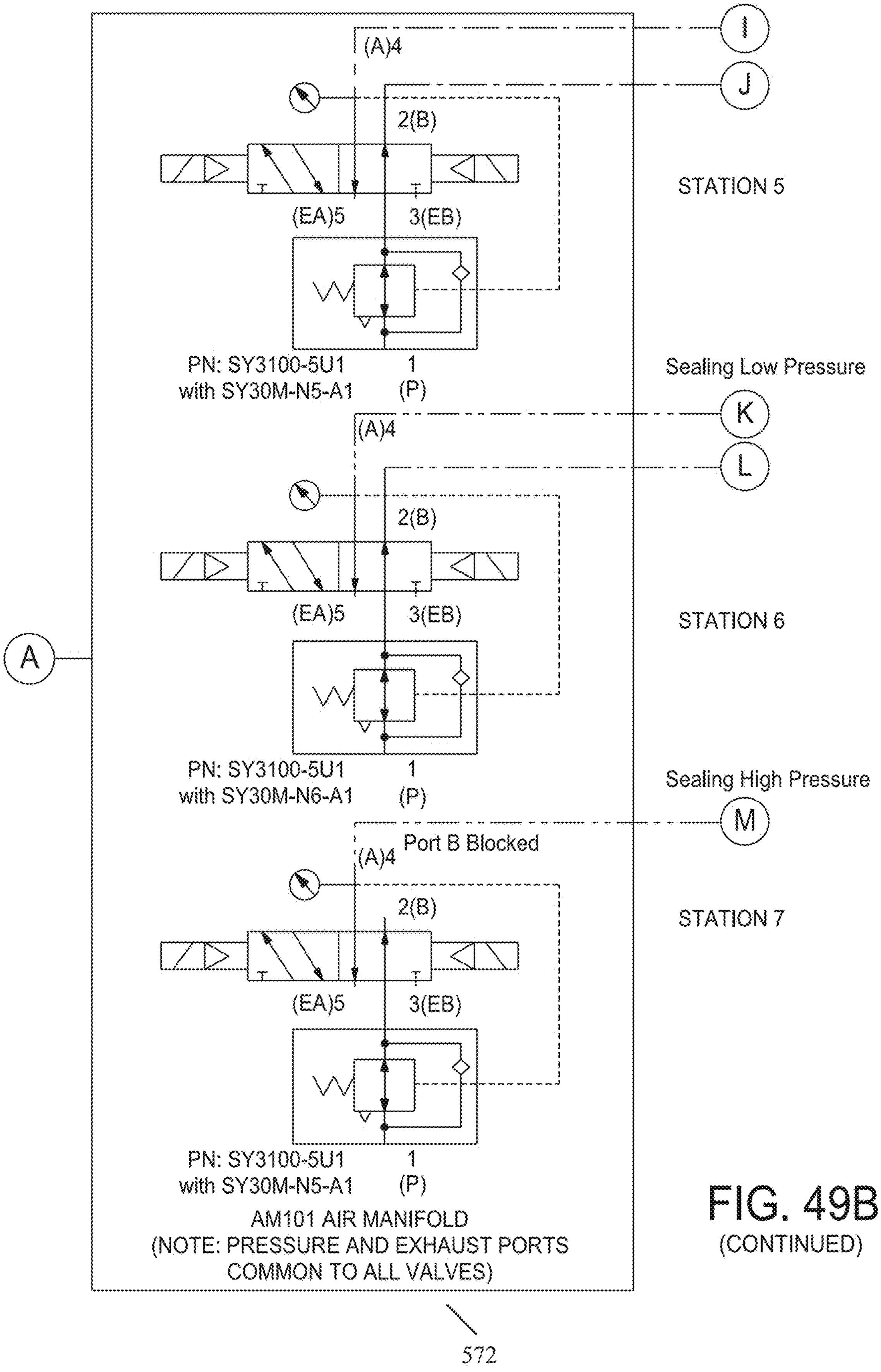
Figure 49B:
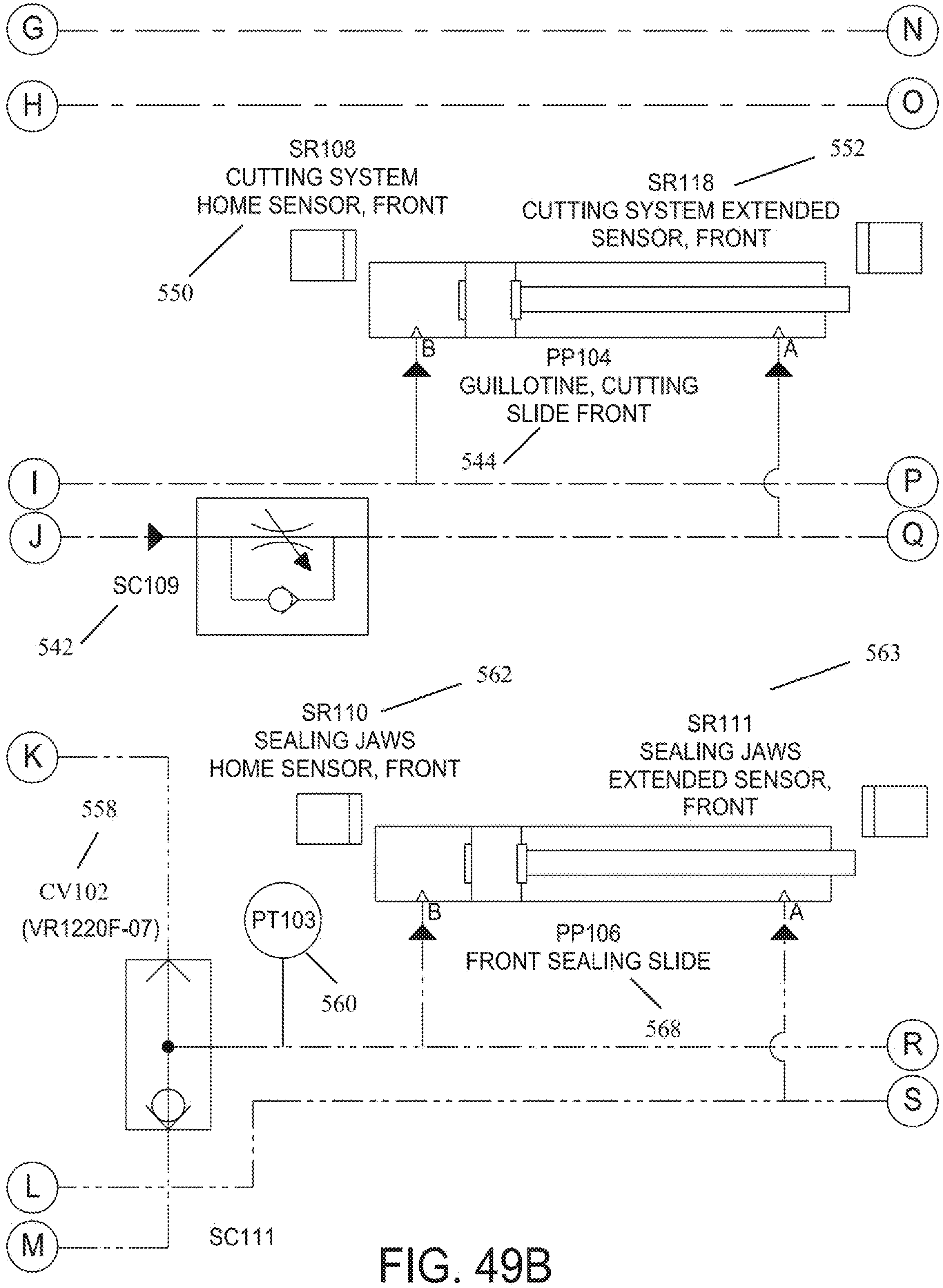
Figure 49B:
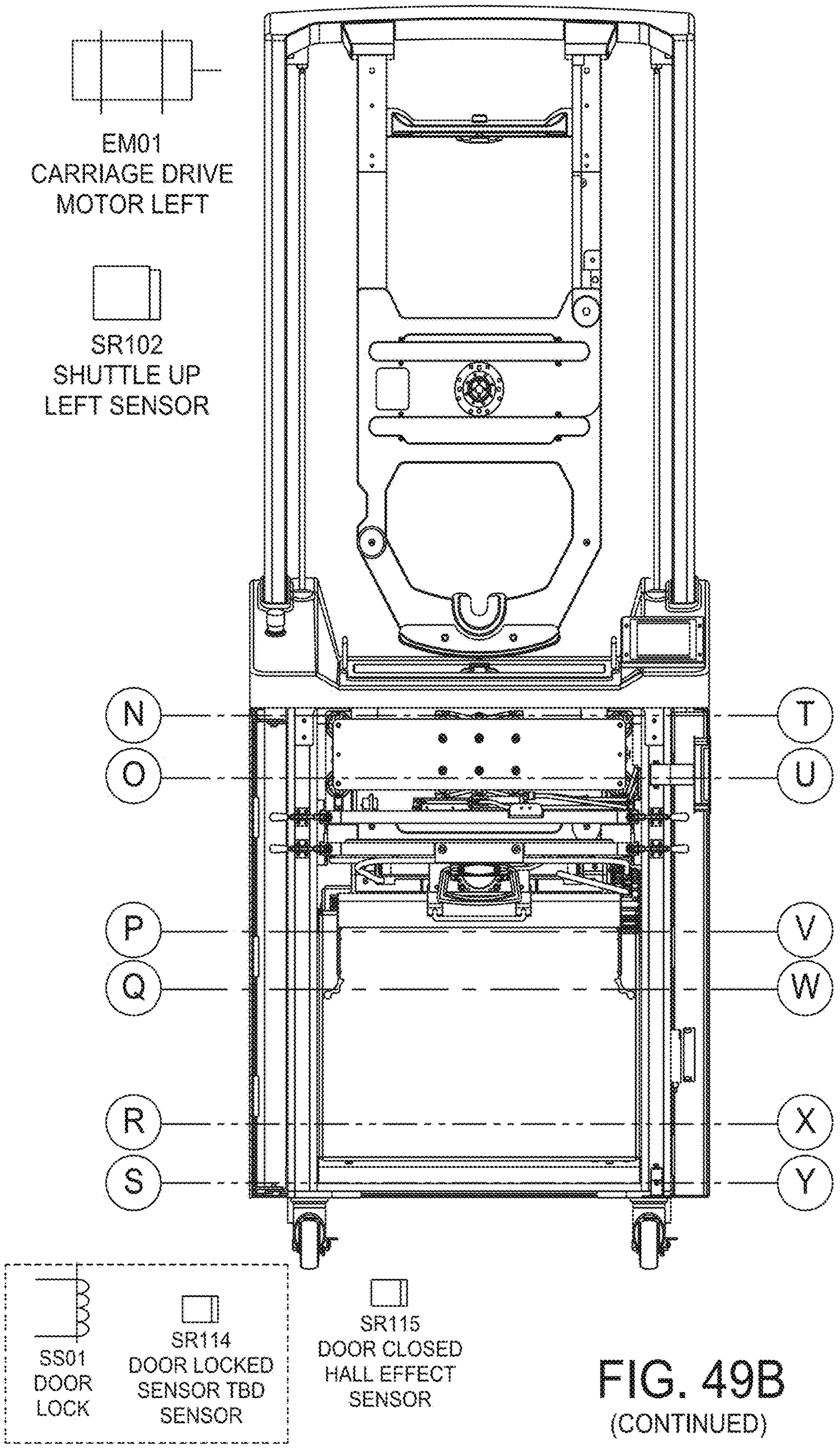
Figure 49B:
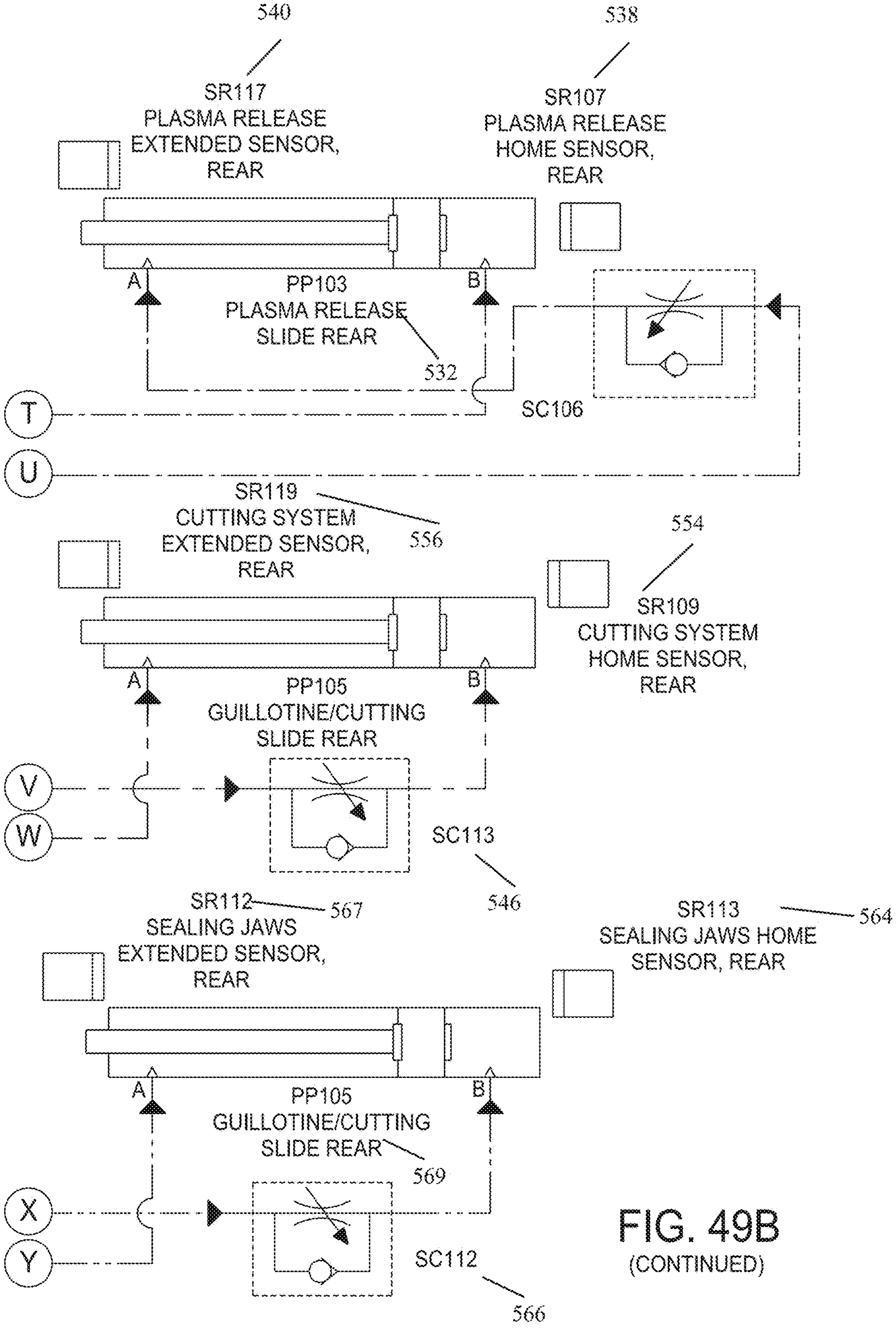
Figure 49B:
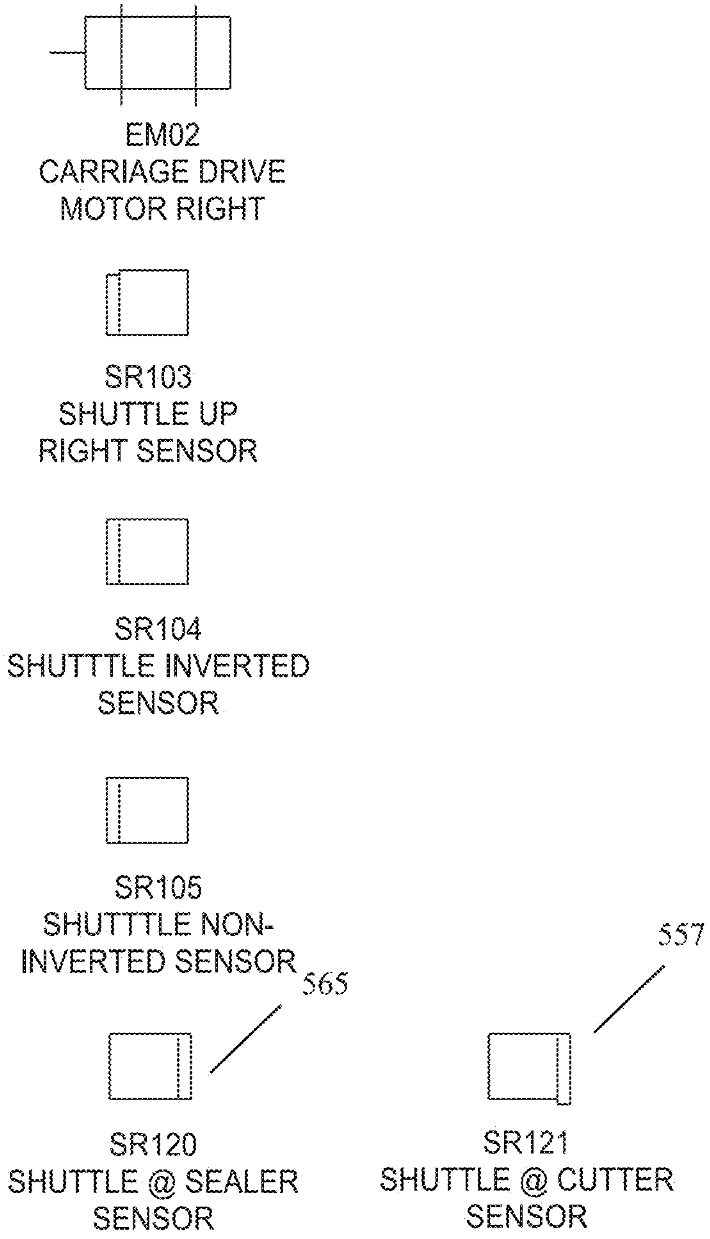
Figure 49B:
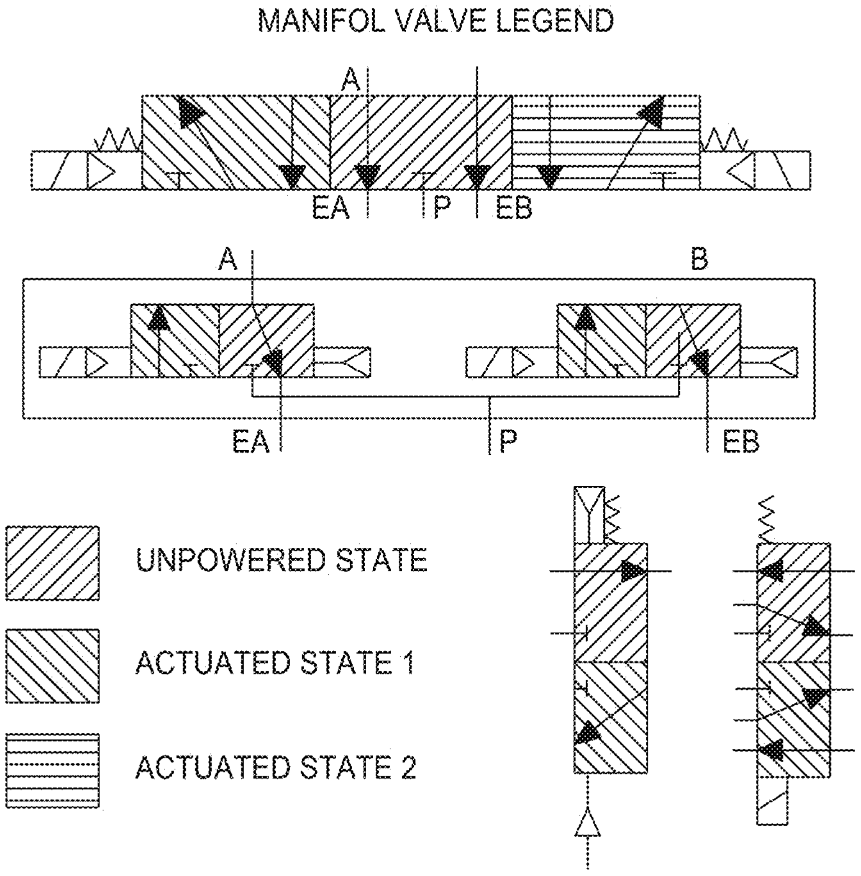
Figure 50:
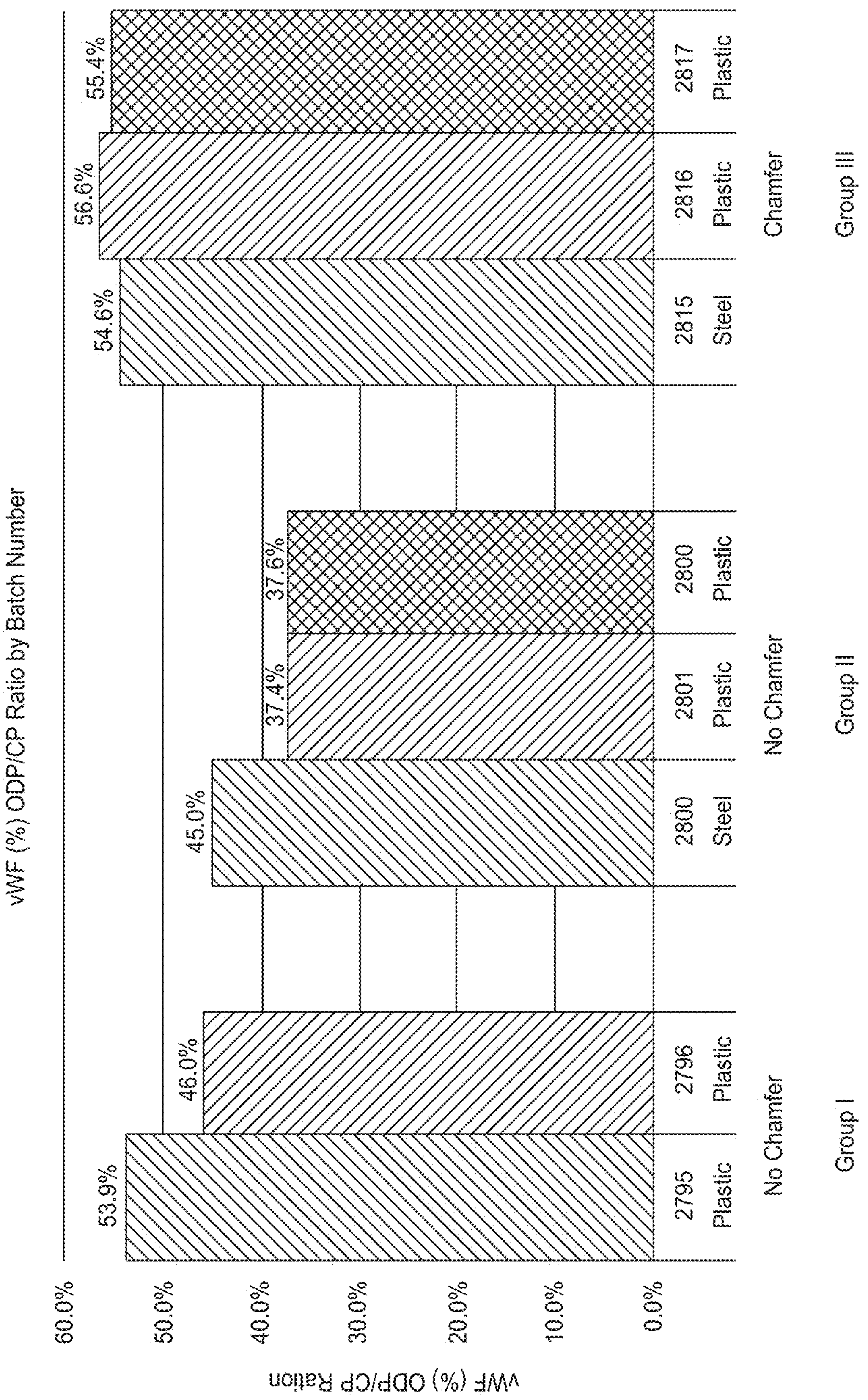

FIG. 49B is a schematic showing the architecture of finisher 400'. Abbreviations included are: AM—Air Manifold, CN—Connector, CV—Check Valve, EM—Electric Motor, FS—Flow Sensor, FR—Flow Restrictor, PP—Pneumatic Piston, PR—Pressure Regulator, PT—Pressure Transducer, PV—Valve Arrow (Down Is Fail Closed, Arrow Up Is Fail Open), SC—Speed Controller, SR—Sensor, and VG—Vacuum Generator FIG. 50 is a bar graph comparing vWF % ratio of reconstituted plasma (to a never dried control aliquot) that was dried using disposable devices with composite nozzle assembly without a chamfer, with a chamfer and a benchmark stainless-steel nozzle.

Figure 51A:
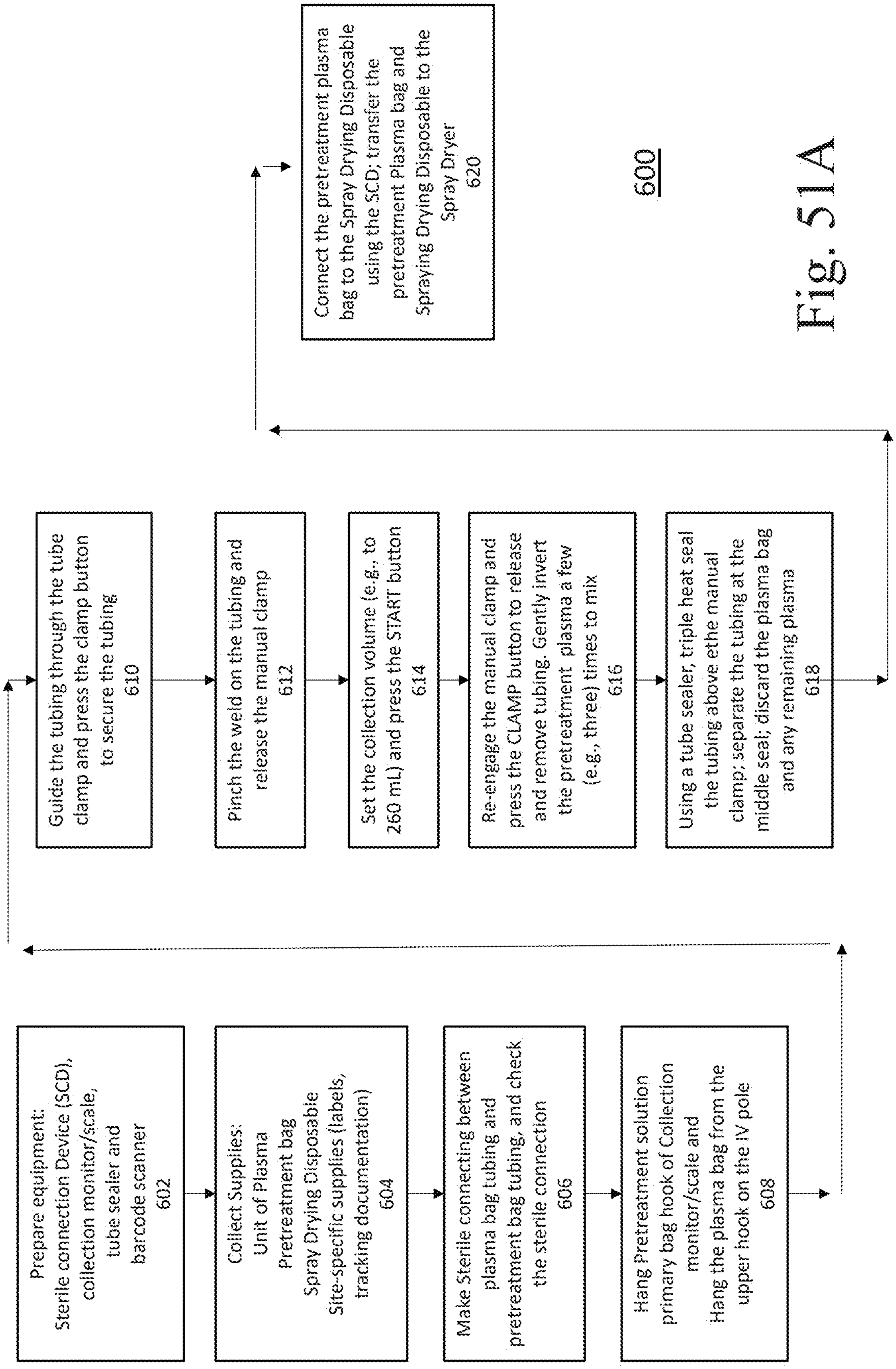

FIG. 51A is a flow chart showing the steps of the pretreatment methodology.

Figure 51B:
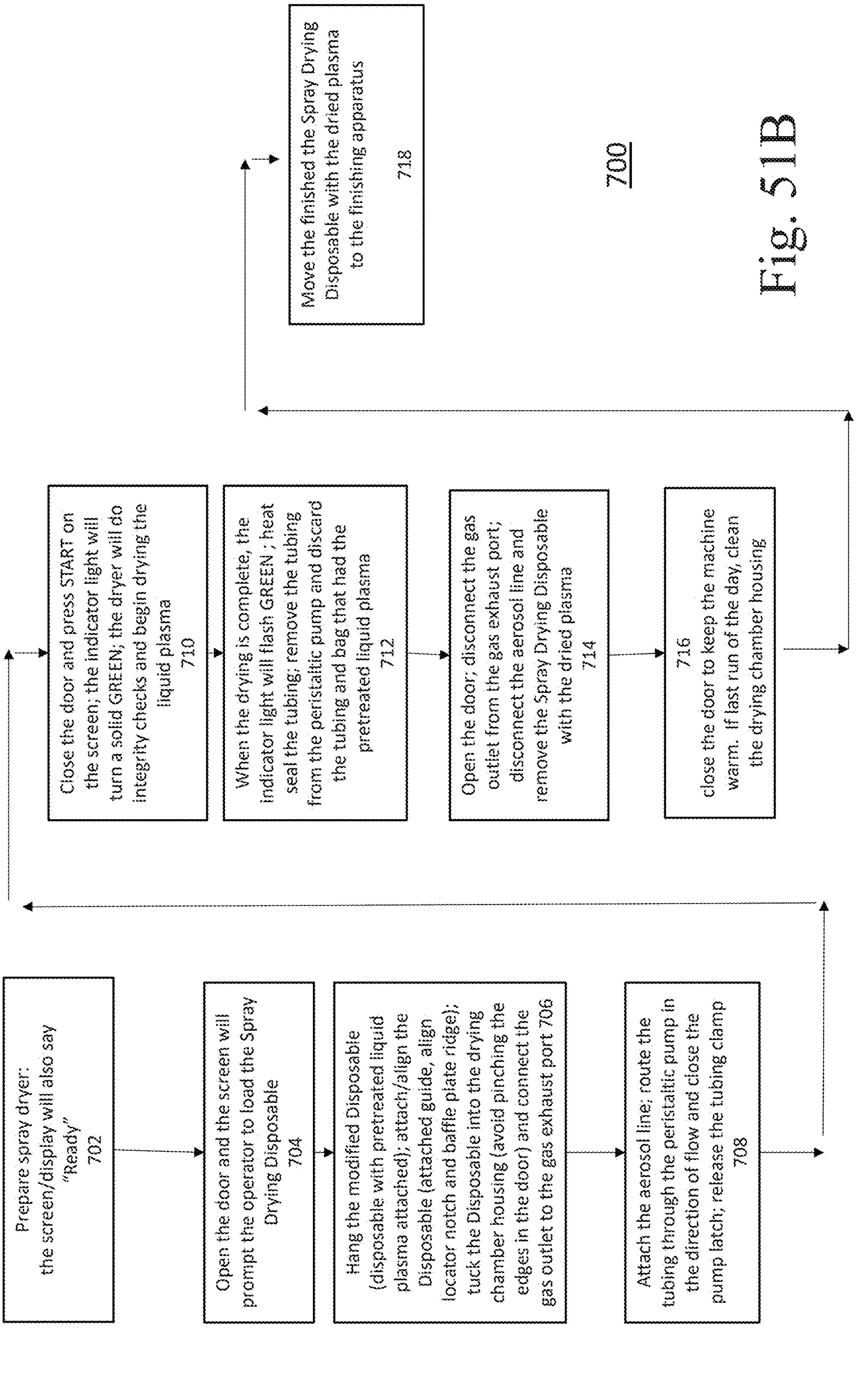

FIG. 51B is a flow chart showing the steps of the spray drying methodology employing the spray dryer and spray drying disposable.

Figure 51C:
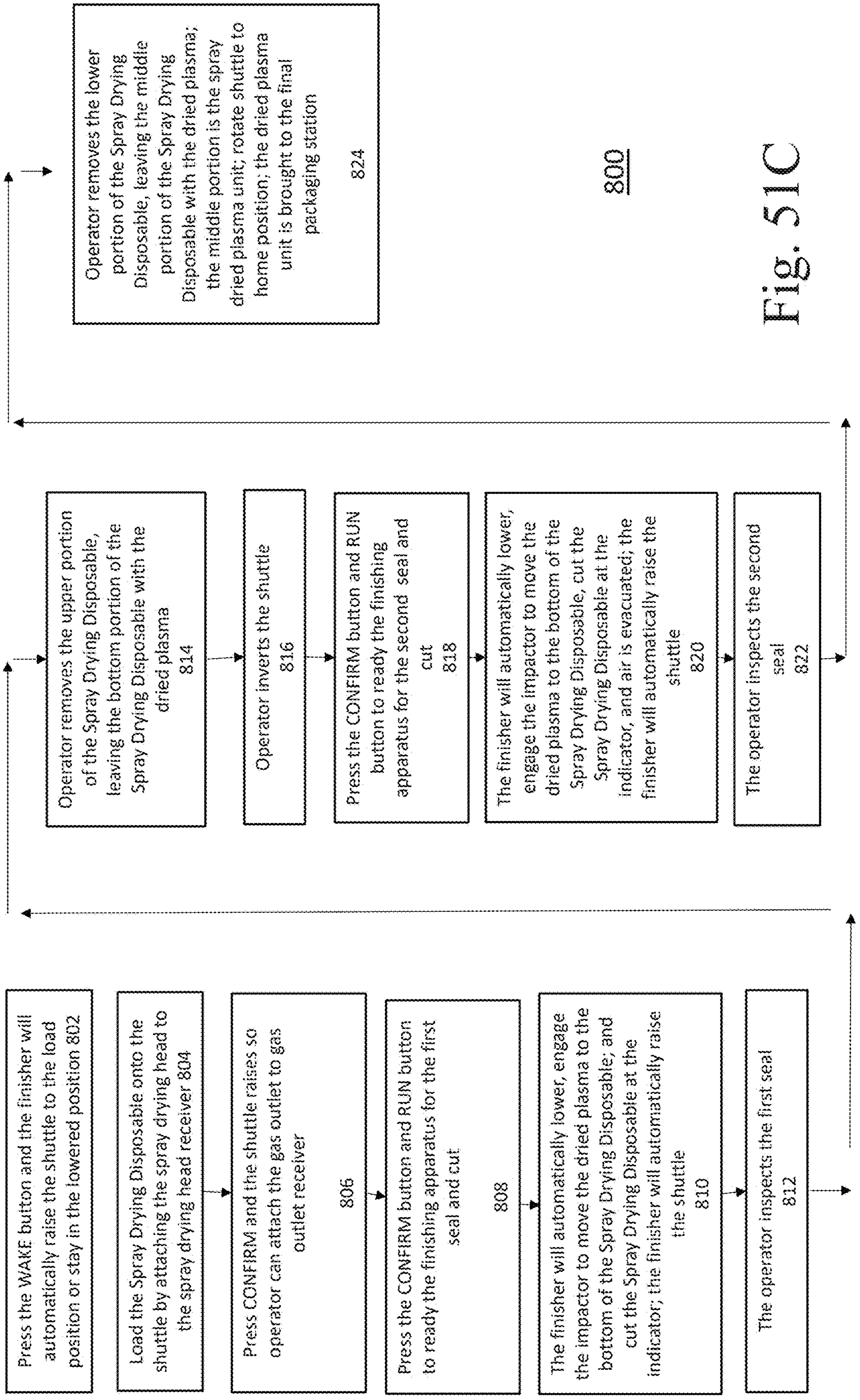

FIG. 51C is a flow chart showing the steps of the finishing methodology employing the finisher and spray drying disposable to create a dried plasma unit.

Figure 51D:
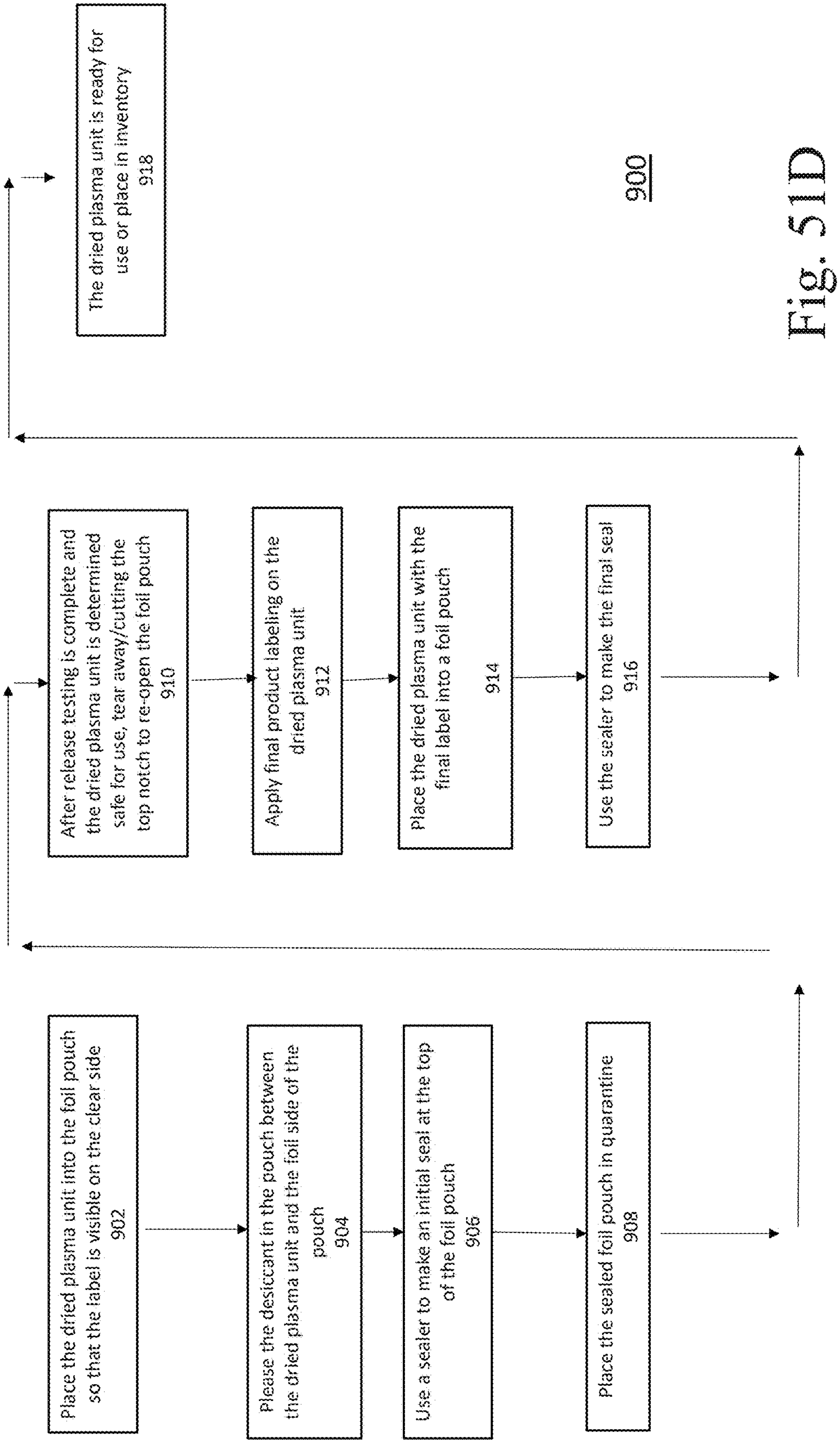

FIG. 51D is a flow chart showing the steps of the storage methodology once the spray dried unit is made.

Figure 52:
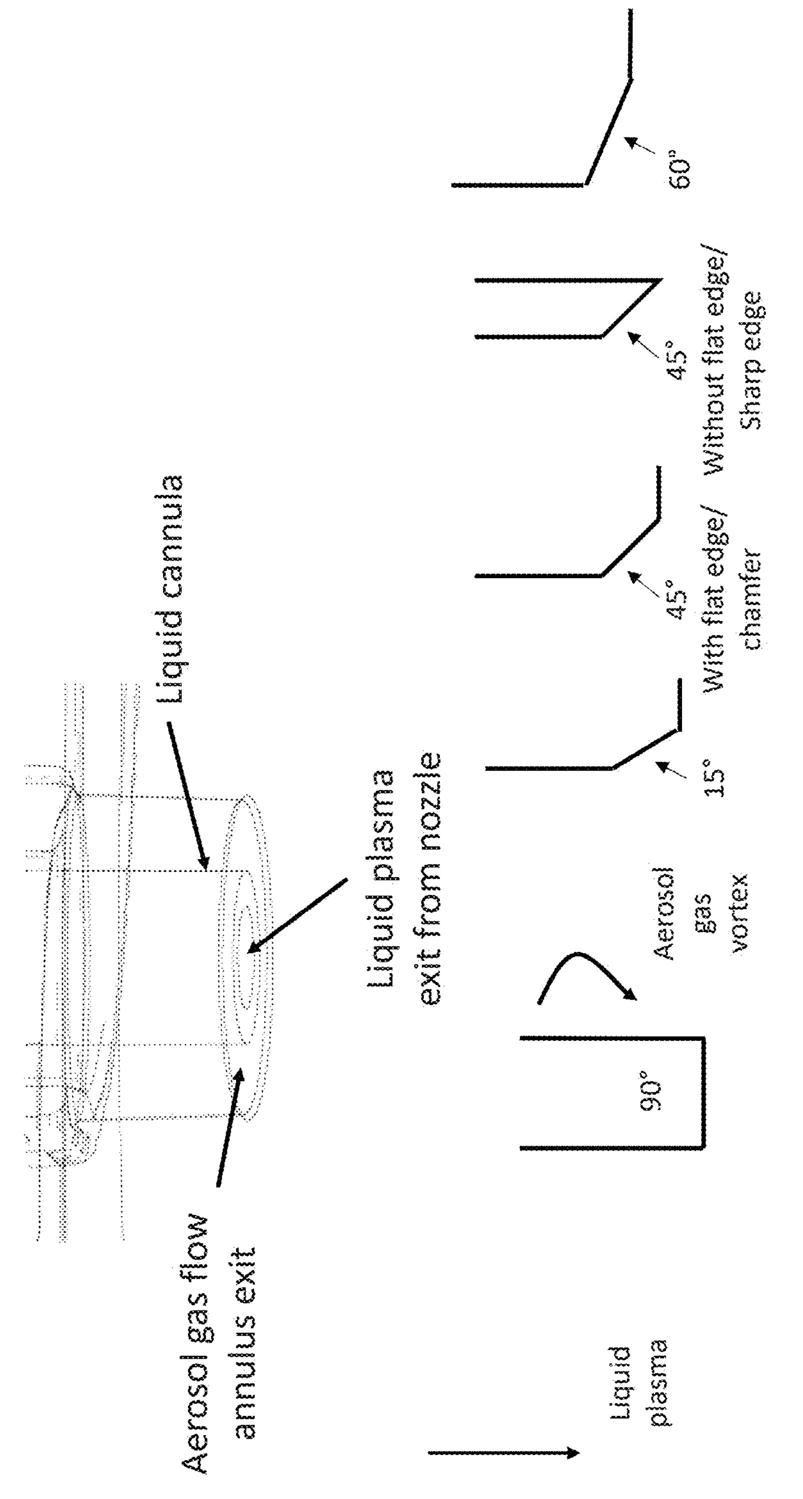

FIG. 52 is a schematic showing the geometry of the cannula to show sheer on vWF protein when exiting the cannula. The curved arrow shows the aerosol gas vortex direction within the annulus. In order to show the amount sheer impact on the liquid plasma at the exit area of the cannula, the figure shows the cannula edges at 15, 90, 45 (with chamfer and sharp edges) and 60 degrees and shows how the sheering contact of the cannula is reduced by the angled edge.

Figure 53A:
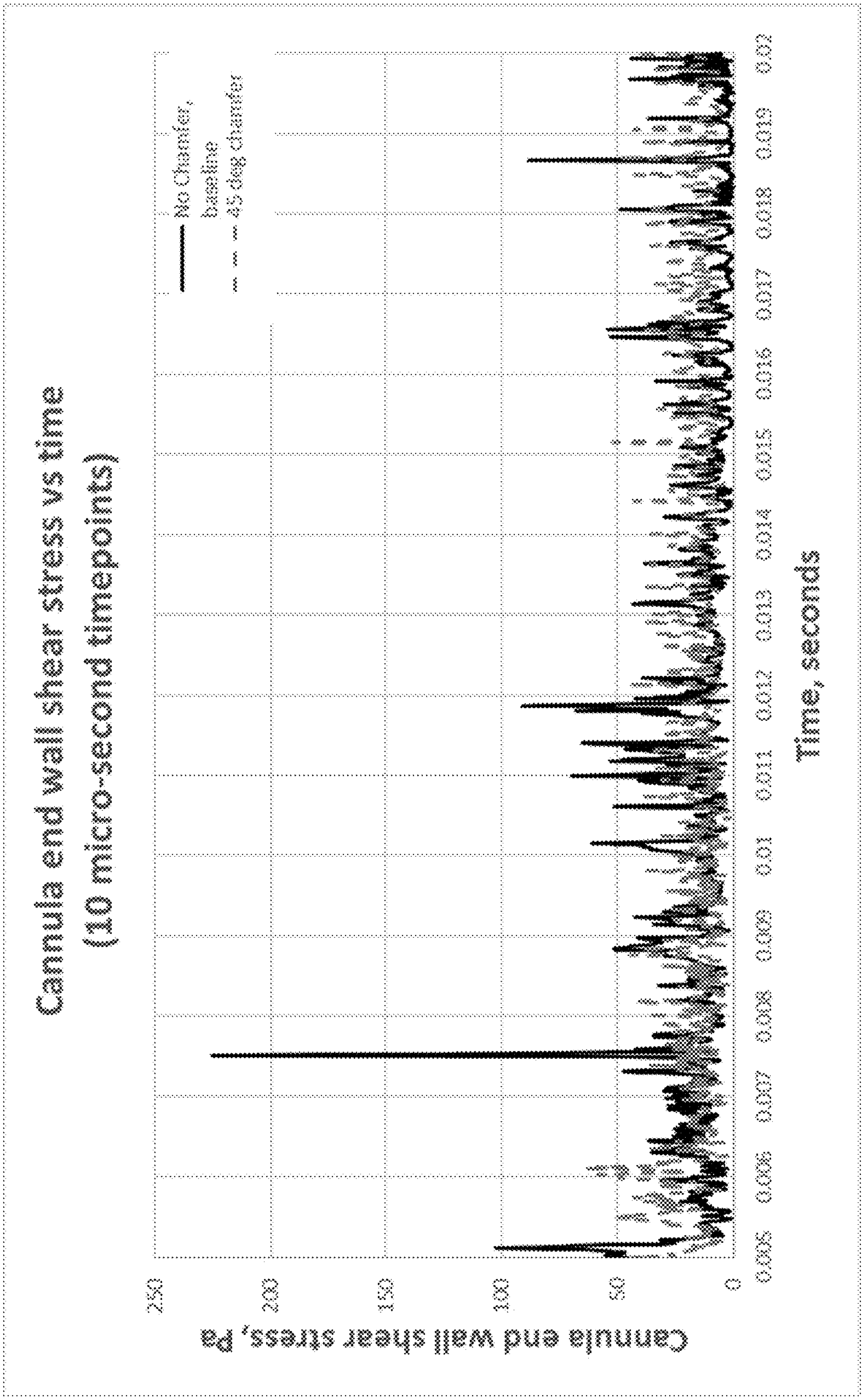

FIG. 53A is a line graph showing time in seconds and cannula end wall shear stress in Pa at 10 micro-second timepoints for a cannula with no chamber and a cannula with a 45 deg chamfer.

Figure 53B:
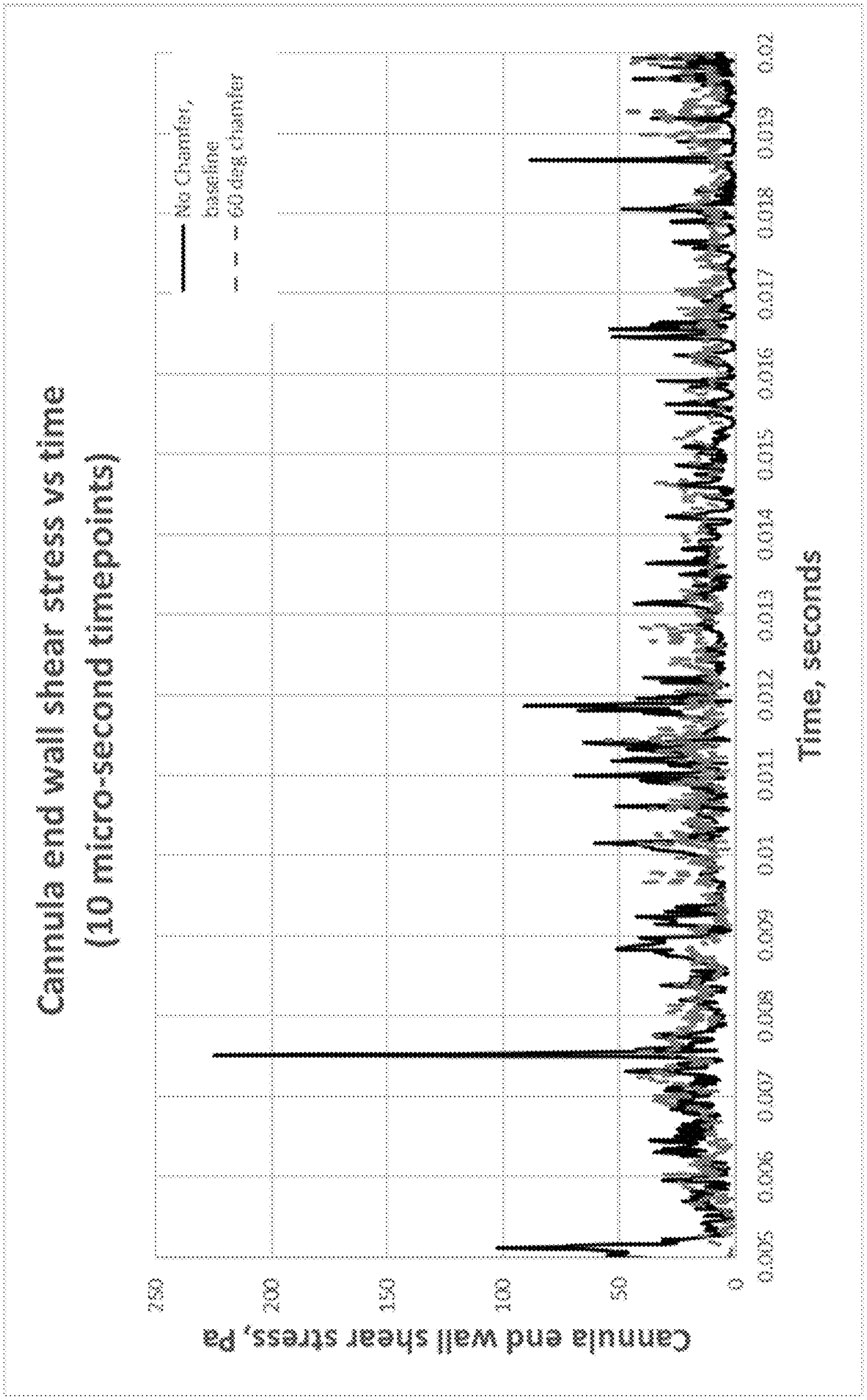

FIG. 53B is a line graph showing time in seconds and cannula end wall shear stress in Pa at 10 micro-second timepoints for a cannula with no chamber and a cannula with a 60 deg chamfer.

DETAILED DESCRIPTION OF THE INVENTION

A description of preferred embodiments of the invention follows.

The present invention relates to the components and system for using a spray drying disposable device. The spray drying system include a spray drying apparatus (hereinafter referred to as "drying apparatus," "machine," "spray dryer" or "dryer"), a spray drying finishing apparatus (hereinafter referred to as "finishing apparatus" "seal and separator," or "finisher") and a spray drying disposable device (hereinafter referred to as "disposable device" or "disposable"). The present invention includes a system that allows the spray drying disposable device having a liquid atomization nozzle and drying chamber that efficiently dries liquids including liquid human or animal blood plasma while protecting the active components such as plasma proteins. The spray drying disposable device is installed in the spray dryer that controls plasma flow, pressurized aerosol gas flow, drying gas flow, temperatures, pressures, etc. within the disposable. Once the spray drying process is complete, the disposable having dried plasma powder is aligned and processed by a spray drying finishing apparatus in which a portion of the disposable is sealed and separated to become the dried plasma unit. Moreover, the invention advantageously provides apparatuses for carrying out functions of spray drying and finishing products including dried human blood plasma.

The spray drying disposable of the present invention has compact drying chamber producing dried powder (<2% residual moisture) with a high powder production rate. The disposable is small, readily handled, and easy to use drying chamber with high performance. The drying systems of the present invention are a significant improvement providing a removable, disposable drying chamber for spray drying suitable for small batch size processing, such as individual blood units.

Certain older disposable drying chambers of the Applicant were quite long, being between 58" and 66" or more in length, to allow enough time (flight path) for the plasma to be dried to an acceptable residual moisture level. See Applicant's U.S. Pat. Nos. 8,533,971, 8,595,950, 8,434,242, 8,601,712, 8,533,972, and 10843100. However, their length made those prior art disposables unacceptable in practice for use because they were difficult and inefficient to handle during installation in the spray dryer instrument. The shorter disposable of the present invention, as further described herein, is more easily handled than these prior art disposables which required reaching and stooping distances for users of over 6' and under 5' respectively. The shorter disposable makes the spray drying of human blood plasma practical in real world applications by real world people. Also, the disposable drying chamber of the present invention is a removable, disposable drying chamber that preserves quality and integrity of the plasma while improving processing time and product quality at reduced cost.

Several challenges were overcome to shorten the drying chamber of the present invention. For example, drying any product to a given degree of dryness involves exposing the material to be dried with enough heat energy to obtain the desired drying level while maintaining the functionality of the substance being dried. However, shortening the drying chamber also reduces the drying pathway.

The disposable drying chamber of the present invention is improved by:

- Plasma being more efficiently manufactured;
- Being considerably shorter;
- Being readily usable by persons of a wide range of statures;
- Drying material in less time;
- Reducing the inlet air temperature;
- Achieving a nozzle assembly and drying environment to obtain rapid mixing of the atomized droplets with the drying gas and rapid evaporation;
- Achieving a lower level of residual dryness e.g., less than 2.5% residual moisture; and
- Utilizing a specially designed, cost-efficient composite spray drying nozzle, as further described herein.

Overview of Spray Dry Disposable

In particular, disposable 100 has two general areas, the spray drying head 2 and the plasma drying chamber 28.

Spray Drying Head Overview

Figure 42A:
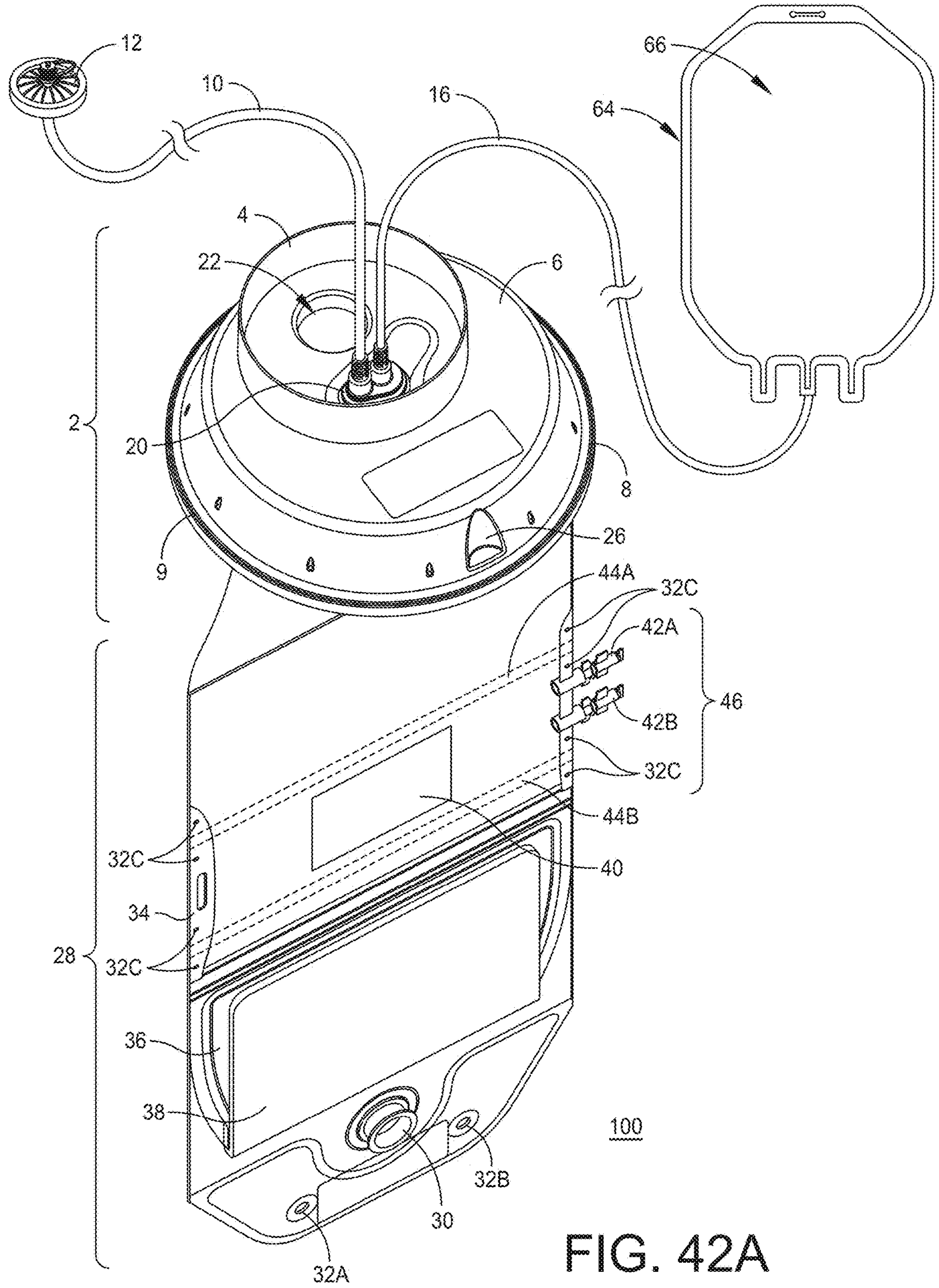
FIG. 42A is a schematic showing a perspective view of the spray drying disposable device, which includes the liquid plasma bag, spray drying head and spray drying chamber, wherein the disposable has alignment elements which allow it to align with a spray drying apparatus and a finishing apparatus.
Figure 43A:
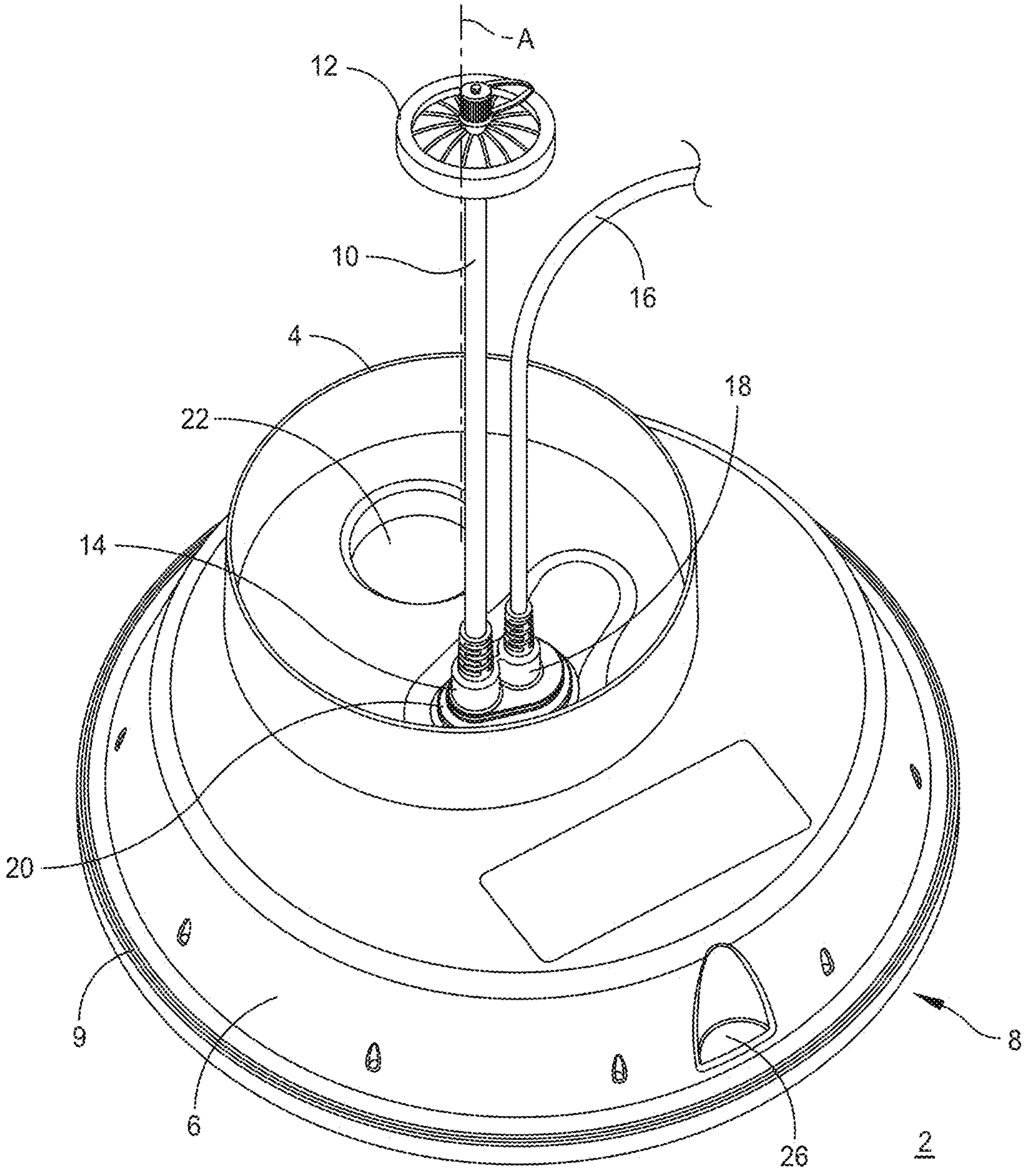
FIG. 43A is a schematic showing a perspective view of the spray drying head of the spray drying disposable device shown in FIG. 42A.

Spray drying head 2 of disposable 100 that has guide 4 that is offset as positioned on plenum 6, and baffle plate 8 having ridge 9 (FIGS. 42A and 43A). Plenum 6 has guide 4 on top of spray drying head 2. Within guide 4 is spray dry nozzle assembly 20 which has plasma flow inlet 18 connected to the liquid plasma via plasma tube 16 and pressurized aerosol gas inlet 14 connect to the pressurized gas via aerosol tube 10 and aerosol filter 12. Additionally, drying gas inlet port 22 is shown and is in communication with the drying gas source (not shown) which may be a source of air, nitrogen or other drying gas. Optionally, drying gas inlet port 22 may be covered by a removable cover such as a self-adhesive paper label or similar. This cover should be removed just prior to installation of disposable 100 into the spray dryer 200. The drying case source can optionally be in communication with a moisture reducing drying system. In one embodiment, the drying gas source is an Atlas-Copco SF 22+ compressor (Atlas Copco Nacka Municipality, Sweden) in conjunction with an Atlas-Copco CD45 desiccant drying system supplying clean dry air (CDA) to the spray dryer and heats air to the appropriate temperature for spray drying. In an embodiment, the drying gas flows through a filter from the CDA and, for example, is a Millipore Series 3000 0.2 micron filter CTGB71TP3 from Millipore Sigma of Danvers MA USA. The CDA supply is used, in an embodiment, for the supply for the drying gas and for the pressurized gas. In certain embodiments spray drying nozzle assembly 20 includes a "manifold" that coordinates the plasma and aerosol lines. When the plasma source, pressurized gas source, and drying gas source combine, the liquid plasma droplets are formed and dried into dried plasma (e.g., a fine, amorphous plasma powder). Plenum 6 has a notch, which is a locator referred to herein as locator 26 or a second locator, as further described herein.

Figure 45A:
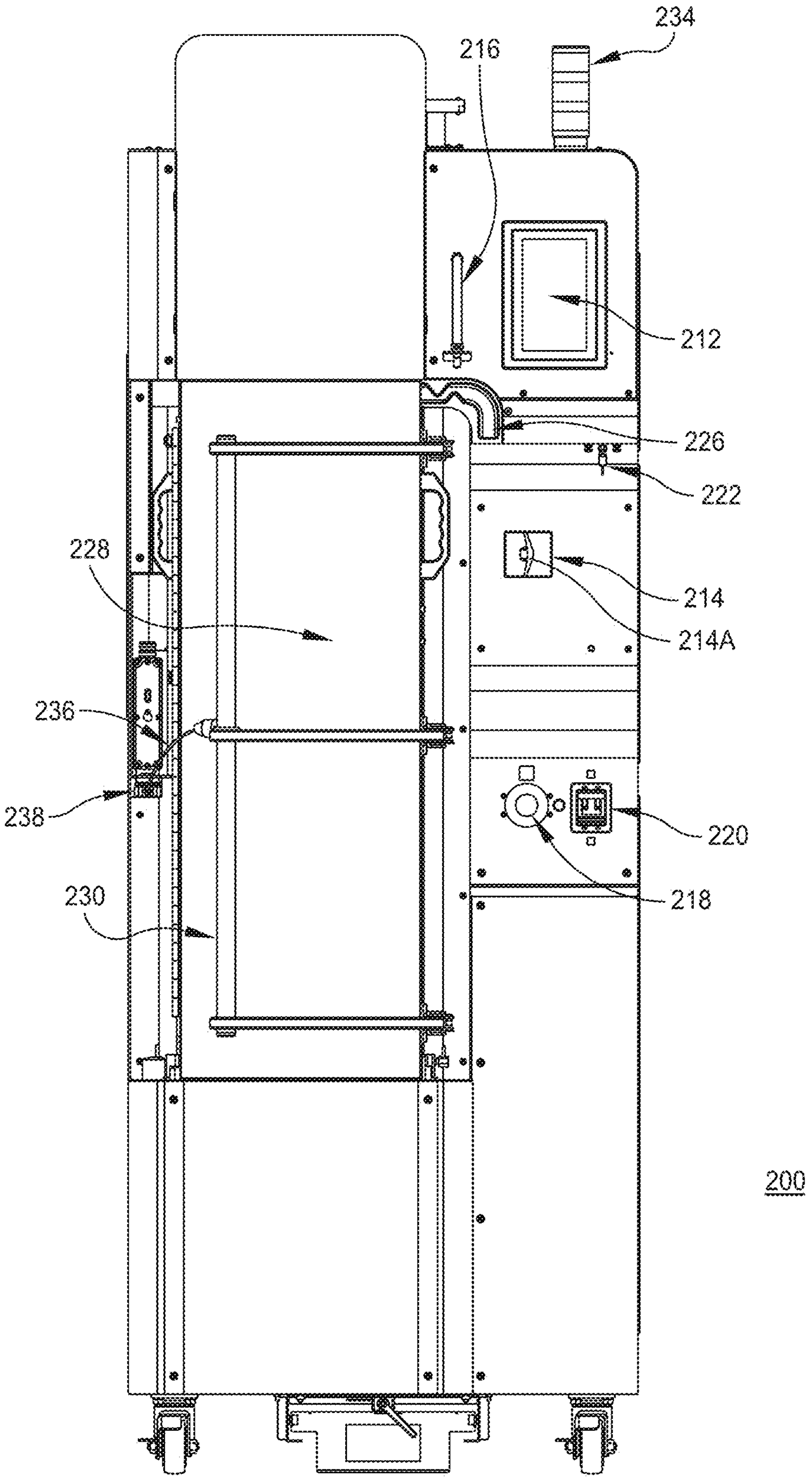
FIG. 45A is a schematic showing a front view of the spray drying apparatus with the door closed.
Figure 45B:
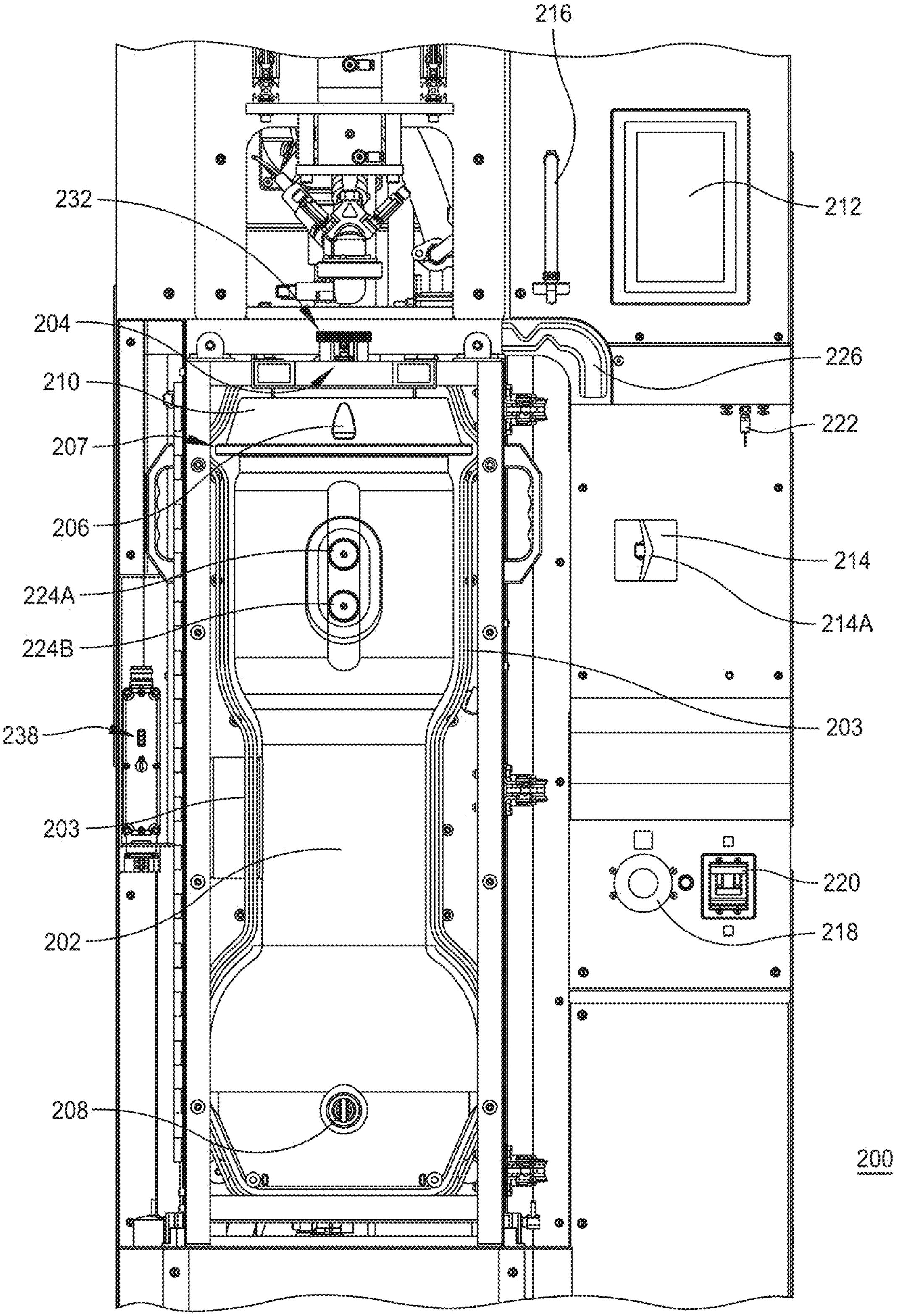
FIG. 45B is a drawing of a partial front view of the spray drying apparatus without the door to reveal the drying chamber housing having alignment elements that allow for alignment with the spray drying disposable device.
Figure 45C:
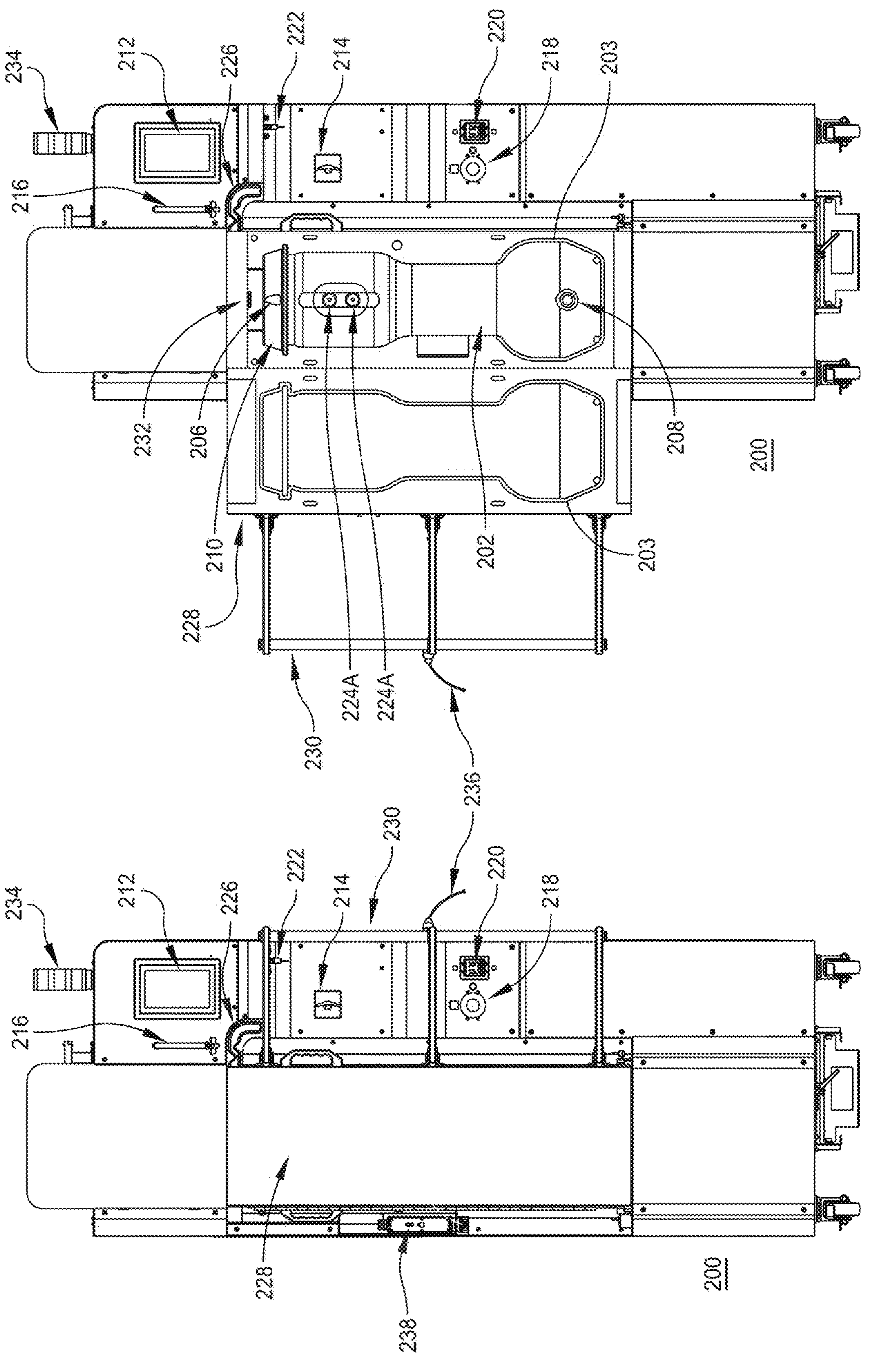
FIG. 45C is a schematic showing a front view of the spray drying apparatus with handle of the door being engaged and the door being opened.

Briefly, guide 4 fits into receiver 204 of spray drying apparatus 200 which also properly aligns disposable 100 with drying apparatus 200 (FIGS. 45B and 45C). Guide 4 also aligns spray drying head 2 with respect to spray dryer 200 in a specific orientation such that drying gas inlet 22 receives the drying gas source (not shown). Ridge 9 fits into ridge receiver 207 of spray dryer 200 and provides support. Guide 4 along with ridge 9 allows alignment of disposable 100 with spray dryer 200 in a latitudinal orientation (e.g., in a plane defined by the top surface and bottom surface of the spray drying apparatus) which keeps the disposable secured so it does not move up and down within the spray drying chamber housing of the dryer. Additionally, ridge 9 of disposable 100 fits into receiver 404 of finisher 400 to secure disposable 100 to finisher 400 while finisher 400 is moving the plasma and sealing and separating the disposable to turn it into dried plasma unit 60. See FIGS. 46A-C. This alignment arrangement also provides for easy, universal attachment of the disposable to both the dryer and the finisher.

First locator, locator 206 (FIGS. 45B, 45C and 46A), is positioned on spray drying apparatus 200 and the second locator, locator 26 (FIGS. 42A and 43A) is positioned on spray drying disposable 100 such that the first and second locator engage during installation of disposable 100 into spray drying apparatus 200 to allow for alignment of the disposable with the spray drying apparatus. The same locator, locator 26 (the second locator), on the disposable also is used to align the disposable with a third locator, locator 452 (see FIGS. 47A-C), on spray drying finishing apparatus 400, the apparatus that directs the dried plasma into specific compartments of the disposable, seals and separates the dried plasma into a plasma unit having the dried plasma. This locating arrangement aligns the disposable to the spray drying apparatus axially, e.g., about an axis defined by the center of a receiver of guide 4 (see Axis A of FIG. 43A). This locating arrangement allows for easy universal attachment of the disposable to both the drying apparatus and the finishing apparatus.

As part of the disposable, spray drying head 2 includes nozzle assembly 20. This nozzle assembly allows the spray drying of the plasma to occur within the disposable. Overall, the design of the system has a spray dryer and disposable modified to have a nozzle as part of the disposable instead of the spray dryer so that spray drying occurs entirely within the disposable. This design helps keep the plasma in the disposable throughout the drying and finishing process, and out of the parts of the dryer or finisher which would require decontamination between each use. The design also minimizes external pathogen contamination by keeping the plasma within the disposable during the entire process. The nozzle assembly coordinates the plasma flow and the pressurized/aerosolized gas flow such that both are emitted at the proper rates and air flow to atomize the liquid plasma at tip of the nozzle where it is ready for rapid mixing with the drying gas. Spray drying head 2 of disposable 100 further includes plenum 6 and baffle plate 8 that guides the drying air for rapid mixing with aerosolized plasma and creates an air curtain to minimize buildup of dried plasma on the drying chamber wall.

Plasma Drying Chamber Overview

Drying chamber 28 is the area of the disposable where the plasma dries. The drying chamber is designed to capture the dried plasma while allowing the humid air to exit. The design of the drying chamber also allows the drying chamber to be sealed and separated in such a way as to form the commercial dried plasma unit.

Drying chamber 28 has three general areas, the upper portion defined by Dimension X (See FIGS. 44 and 46A), the mid-section defined by Dimension U, the area between locations 44A and 44B, and the bottom portion defined by Dimension V, the portion below location 44B, that includes filter 36 and a separator 38. The upper portion is a space in which the atomized liquid plasma hits the drying gas and evaporates the liquid within the droplet and dries. In particular, the atomized plasma rapidly mixes with the drying gas and dries, as further described herein. As the plasma rapidly mixes and dries, it circulates and moves in a downward direction toward the filter. Most of the evaporation occurs in the upper portion of drying chamber 28 (Dimension X) but it does continue to dry as the plasma falls into the midsection portion (Dimension U) and the lower portion (Dimensions V) of drying chamber 28.

Drying chamber 28 also includes midsection 46, defined by Dimension U, that has "seal and separate" locations 44A and 44B, label 40, spike ports 42A and 42B and hanging slot 34. Midsection 46 also includes locator pin openings 32C. The mid-section is later processed by the spray drying finishing apparatus which involves moving dried plasma into certain locations of the plasma drying chamber and sealing and separating at or near cut locations 44A and 44B. The section between locations 44A and 44B becomes dried plasma unit 60 that will eventually be rehydrated and transfused into patients.

Figure 47C:
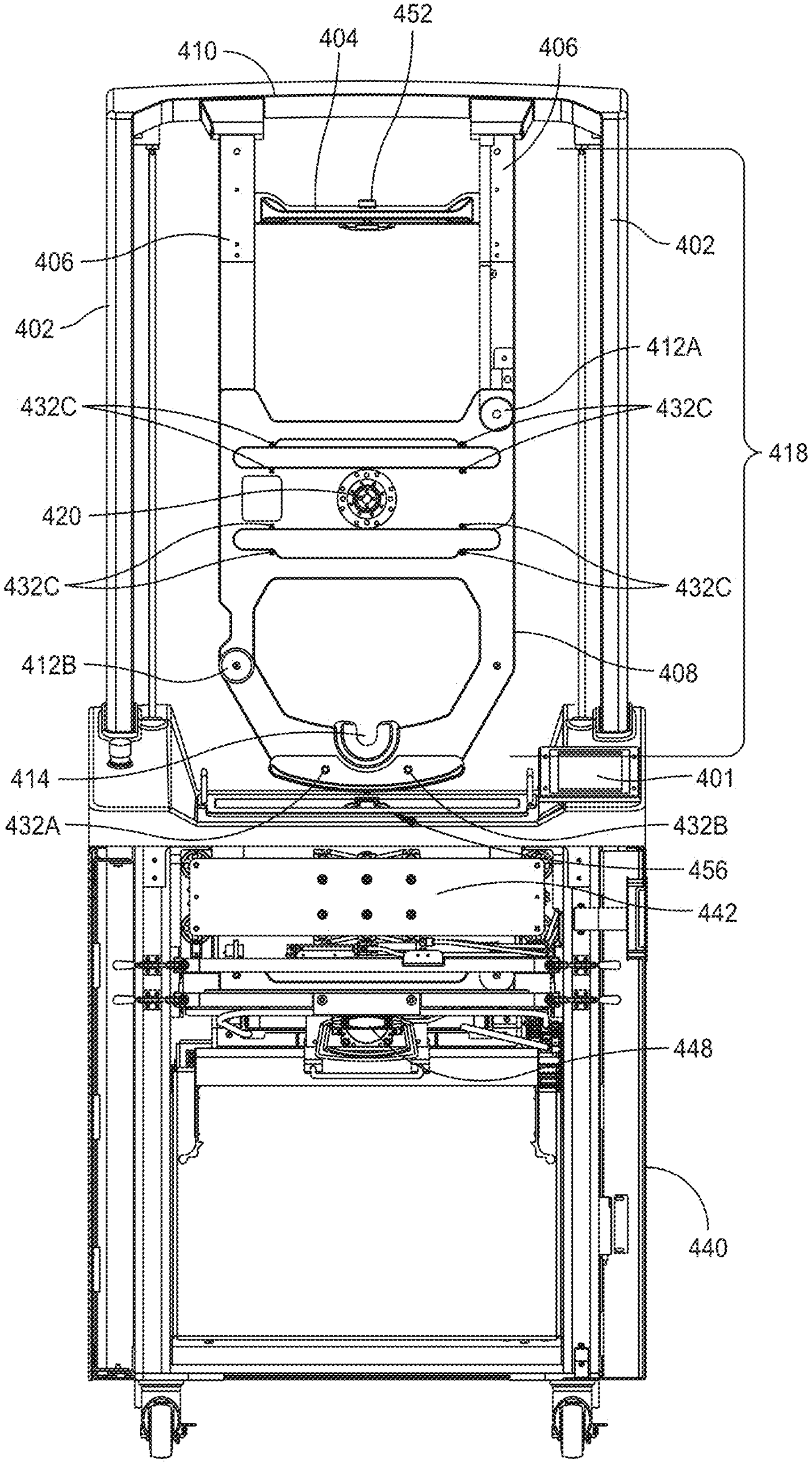
FIG. 47C is a schematic showing a front view of the finishing apparatus of FIG. 47B with the shuttle in the raised position and without the disposable attached.
Figure 48A:
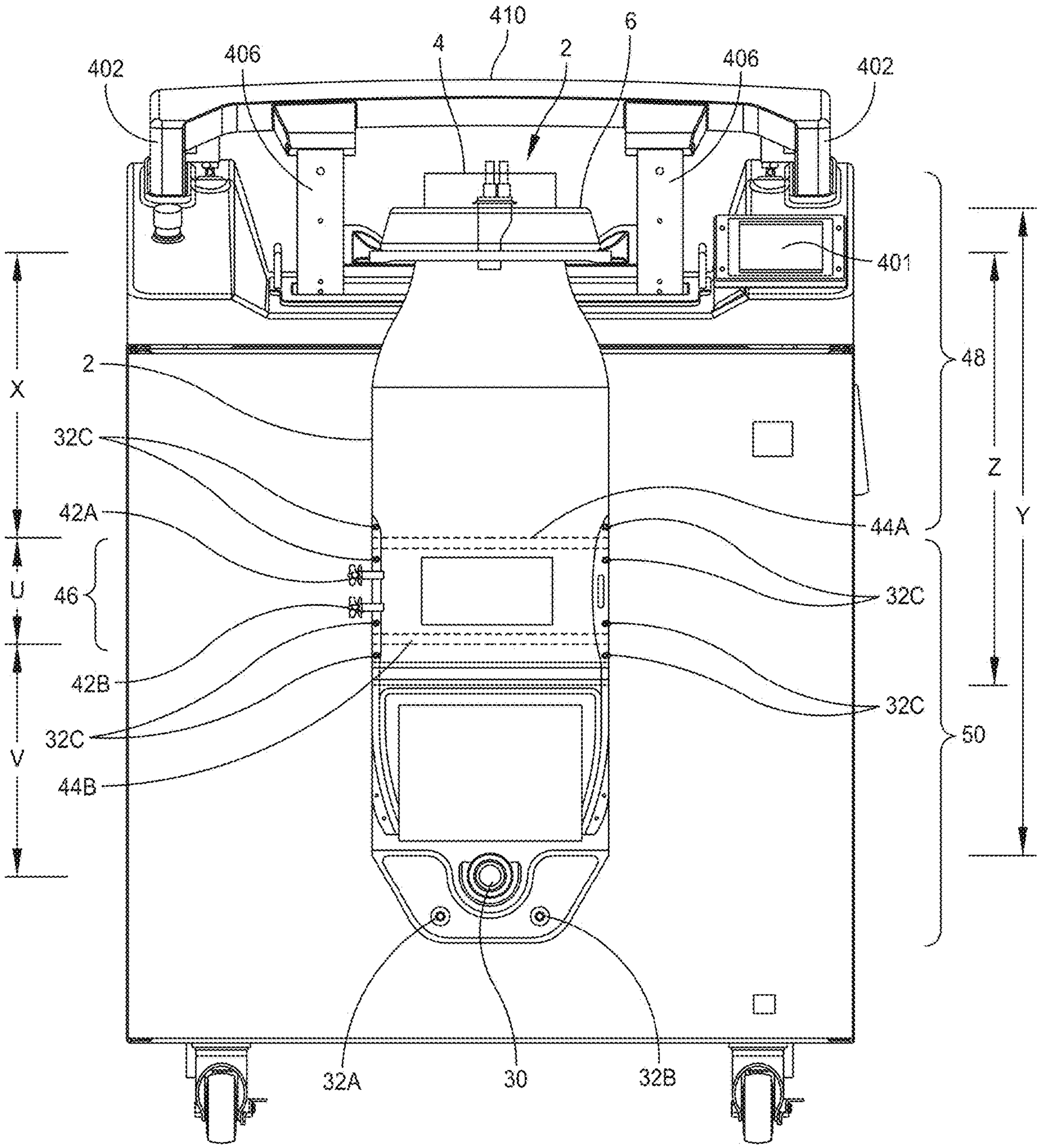
FIG. 48A is a schematic showing a front view of the finishing apparatus in the loading position with the spray drying head of the disposable aligned thereto.

Disposable 100 further includes a positioning arrangement to reversibly attach the outer wall of disposable 100 to finishing apparatus 400. Positioning openings 32A, 32B, and 32C are present on the outer edge of the wall of spray drying disposable device 100. (FIGS. 42A, 48A). Positioning pins 432A, 432B and 432C are located on finishing apparatus 400 such that when positioning openings 32A, 32B, and 32C are placed around positioning pins 432A, 432B and 432C of finishing apparatus 400, drying chamber 28 of disposable 100 is aligned with on the finisher apparatus. See FIGS. 47C, 48B, 48C.

The lower section of drying chamber 28 includes lower filter 36 (also referred to herein as a "capture filter"), lower filter separator 38, drying gas outlet port 30, and locator pin openings 32A and 32B. Optionally, gas outlet 30 may be covered by a removable cover such as a self-adhesive paper label or similar. In an embodiment, this cover should be removed just prior to installation of the drying chamber into the spray dryer 200. Briefly, the lower filter allows for separation of the dried plasma from the humid air and the separator acts as a spacer between the drying chamber wall and the filter to allow air to more easily pass and prevent pressure buildup. Humid air refers to the air traveling through the drying chamber and includes the combination of the drying gas, the aerosolized gas and the moisture that has been removed from the plasma droplets. During the drying of the plasma, the humid air passes through lower filter 36 and lower filter separator 38, through air flow channels, and out of gas outlet 30 leaving dried plasma in lower filter 36.

Figure 46A:
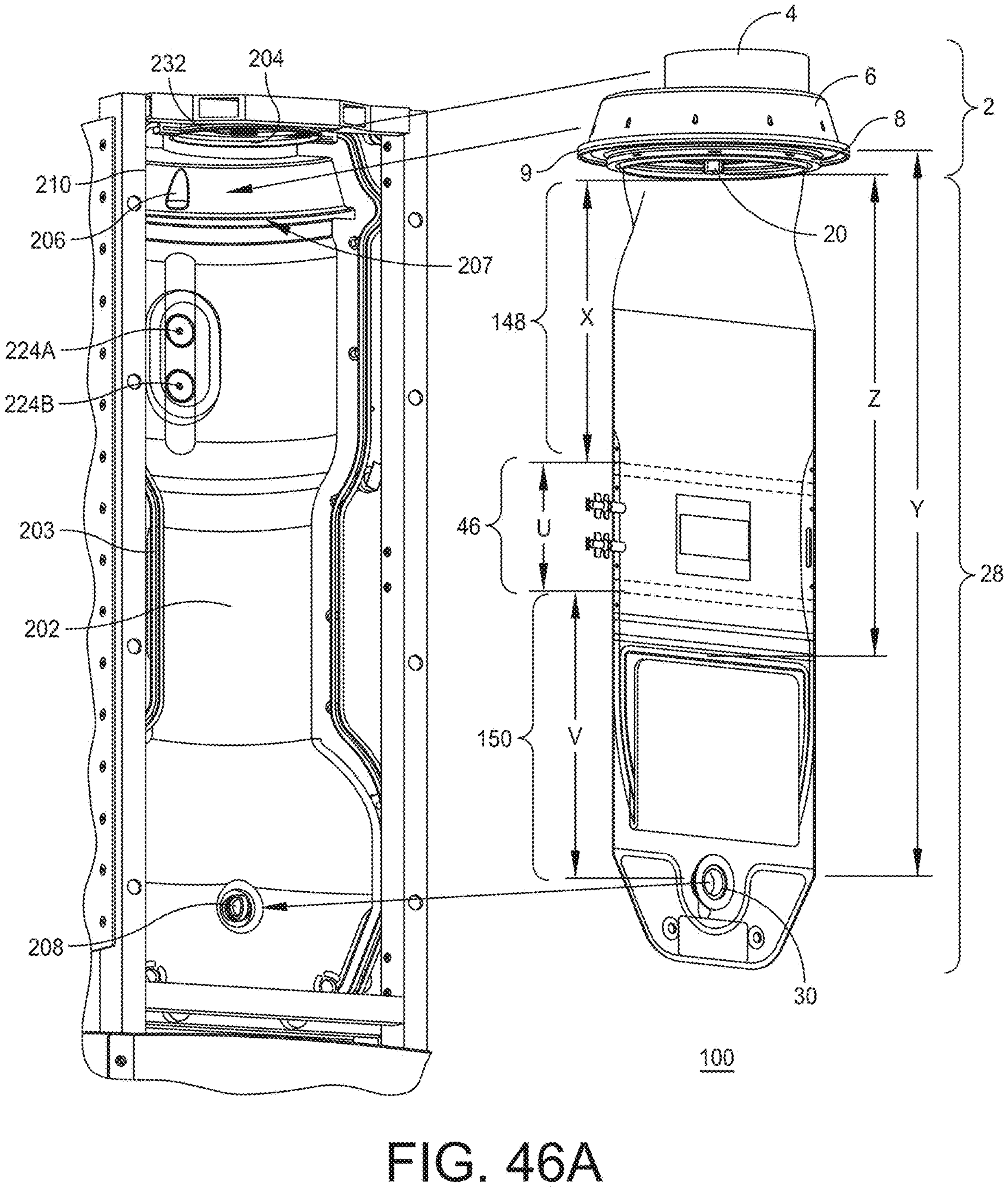
FIG. 46A shows the alignment elements aligning the spray drying disposable device and the spray drying apparatus.
Figure 48B:
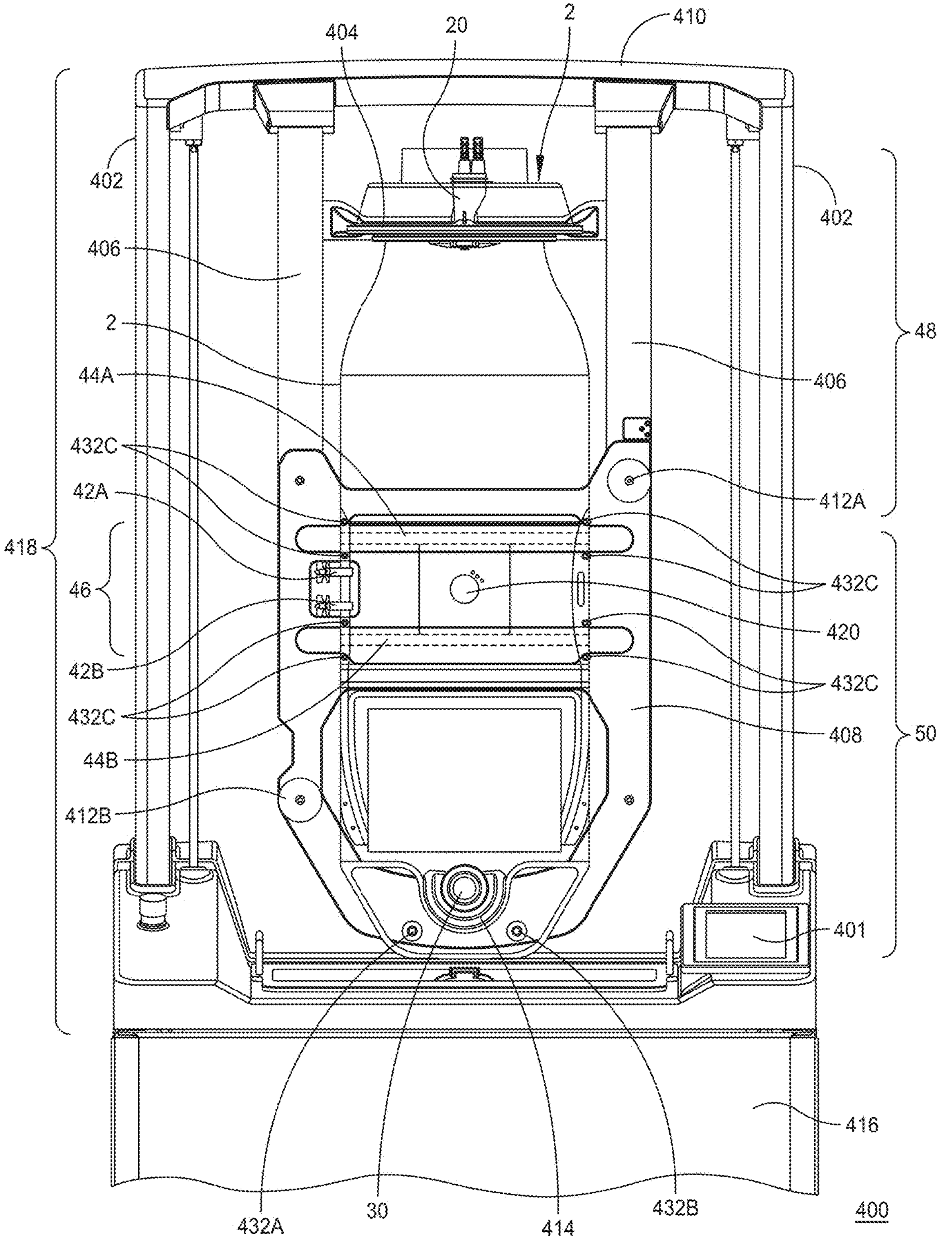
FIG. 48B is a schematic showing a front view of the finishing apparatus in the raised position with the disposable aligned thereto.
Figure 48C:
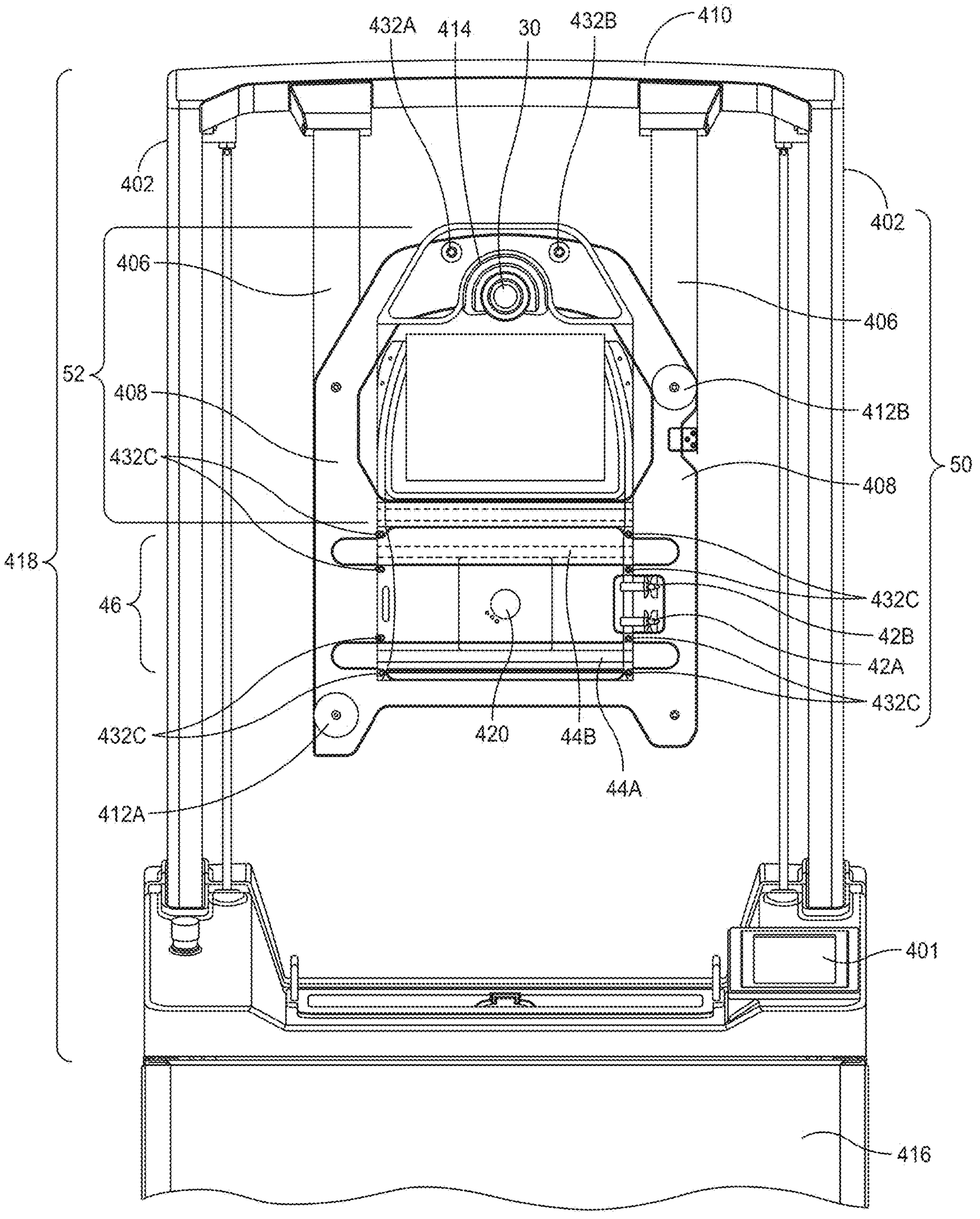
FIG. 48C is a schematic showing a front view of the finishing apparatus in the raised position with a portion of the disposable attached thereto, after the first seal and separate step is completed and the frame is rotated into position.

Disposable 100 further includes another alignment arrangement that relates to gas outlet 30 of disposable 100 and gas exhaust port 208 of dryer 200. The spray drying apparatus has gas exhaust port 208 to allow the drying gas to exit and the bottom portion of disposable 100 has gas outlet 30 that fits into the exhaust port 208 of dryer 200. (FIGS. 45B, and 46A). Additionally, spray drying finishing apparatus 400 has receiver 414 for the drying gas outlet 30 to secure the bottom of disposable 100 to finishing apparatus 400. (FIG. 48B, 48C). Again, this drying gas arrangement allows for universal attachment of the disposable to both the drying apparatus and the finishing apparatus.

Additionally, the entire length of the disposable (as measured from the top of the spray drying head to the very bottom of the drying chamber) is limited to about 40 inches or less (e.g., about 40, 39, 38, 37, 36, 35, 34, 33, 32, 31, 30, 29, 28, 27, 26, 25, or 24 inches or less) and preferably about 34.8 inches. A disposable having a length of about 40 inches or less was difficult to achieve because the drying of the plasma occurs in a smaller space and smaller volume but does so gently without degrading plasma proteins. The disposable length, as measured from the bottom of spray drying head 2 or bottom of baffle plate 8 to bottom of filter 36, shown as dimension Y in FIG. 46A, is about 31 inches or less (e.g., about 31, 30, 29, 28, 27, 26, 25, 24, 23, 22, 21, 20, 19 inches or less) and in an embodiment preferably about 25.9 inches. In another aspect, the area of disposable 100 encompassed by Dimension Z, the length from the bottom of spray drying head 2 and the top of filter 36, is about 22 inches or less (e.g., about 22, 21, 20, 19, 18, 17, 16, 15, 14 inches) and preferably about 19.11 inches. In yet another, the length of Dimension X, the length between the bottom of spray drying head 2 and the top section 46, is less than about 16 inches (e.g., about 16, 15, 14, 13, 12, 11, 10, 9, 8 inches) and preferably about 12.14 inches. In an embodiment, the length of disposable can be modified or shortened. For example, the length of the disposable of the present invention can be further shortened along dimension X by about 1 inch to about 8 inches (e.g., by 1, 2, 3, 4, 5, 6, 7, or 8 inches) thereby reducing the overall length by the same amount. In other embodiments, the disposable can also be shortened anywhere along Dimension Y and Z by the same amount.

Computational Model

Figure 42B:
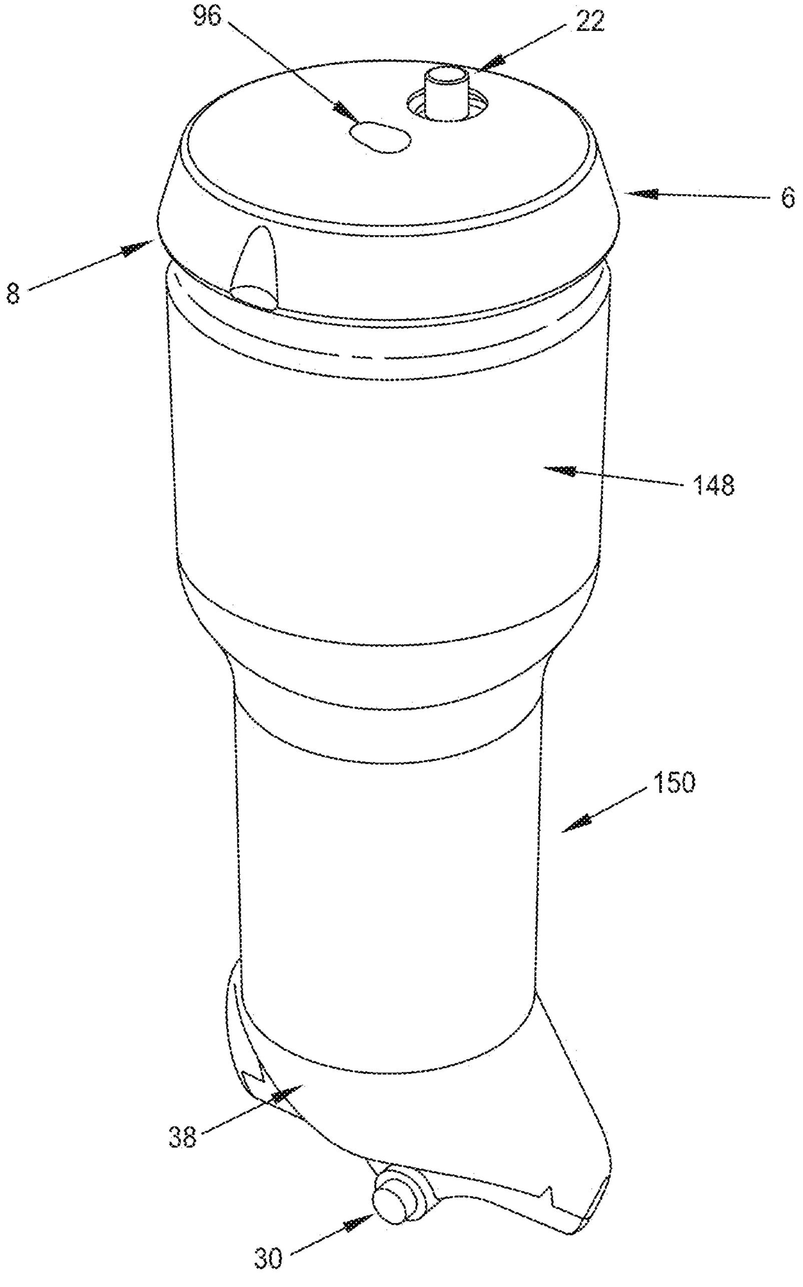
FIG. 42B is a model representation of the three-dimensional flow geometry of the flow model of the disposable during operation. This model is used to create the computer flow models described herein.

For some of the figures, a computational model was used to show flow paths, particle evaporation and the like. FIG. 42B shows the three-dimensional flow geometry of the disposable during operation that was used for the model.

The three-dimensional model showing in FIG. 42B was based on the disposable shown in FIG. 42A and the dryer shown in FIGS. 45A-C. These computer simulations show flows and mixing processes were created by first building the three-dimensional flow domain geometry. See FIG. 42B. This geometry was extracted from a computer aid design (CAD) model of the system hardware to create a high-fidelity representation of the flow region inside the ODP system. The flow domain of 0.0195 $m^3$ volume was discretized into 3.3M spatial cells to generate a computational mesh using the commercially available Ansys-Gambit mesh meshing software. The flow model was calculated using a commercially available computer code; Ansys-Fluent version 2019-R1 running on an HPZ840 multi-processor workstation.

The simulation utilized a steady-state segregated solver assuming ideal gas properties, K-E turbulence model and the following:

- Drying gas inlet temperature=114C
- Drying chamber exhaust temperature=65C
- System heat loss=0.18 kW
- Drying gas flow=750 slpm
- Atomizer aerosol gas flow=40 slpm
- Feed rate=13.5 mL/min, and varies with exhaust gas temperature
- Liquid water droplets with 8.5% non-volatile mass, 5 micron diameter (monodispersed size)
- Exhaust port pressure=2.76 kPa (0.4 psig)

The inlet and product capture filters are modeled using a 'porous zone' function with flow resistance values set to match the measured pressure during operation in the drying gas manifold of 71.7 kPa (10.4 psig) and 27.6 kPa (4 psig) in the drying chamber at the start of a batch.

To calculate the average droplet diameter and temperature during the constant-rate evaporation period for a given set of process conditions, two customized c programs, "prsc_udf_multi_2017.c" and "processdata_multi_2017.c", are developed at PARSEC to obtain an averaged droplet drying pathway from a converged Fluent coupled dpm solution. The program "prsc_udf_multi_2017.c" is used to export droplet tracking data step by step for information interested. The program "prsc_udf_multi_2017.c" reads exported data file generated from the first program, and then get averaged pathway from all tracked particles. Its output file can be read into Excel file.

Figure 43B:
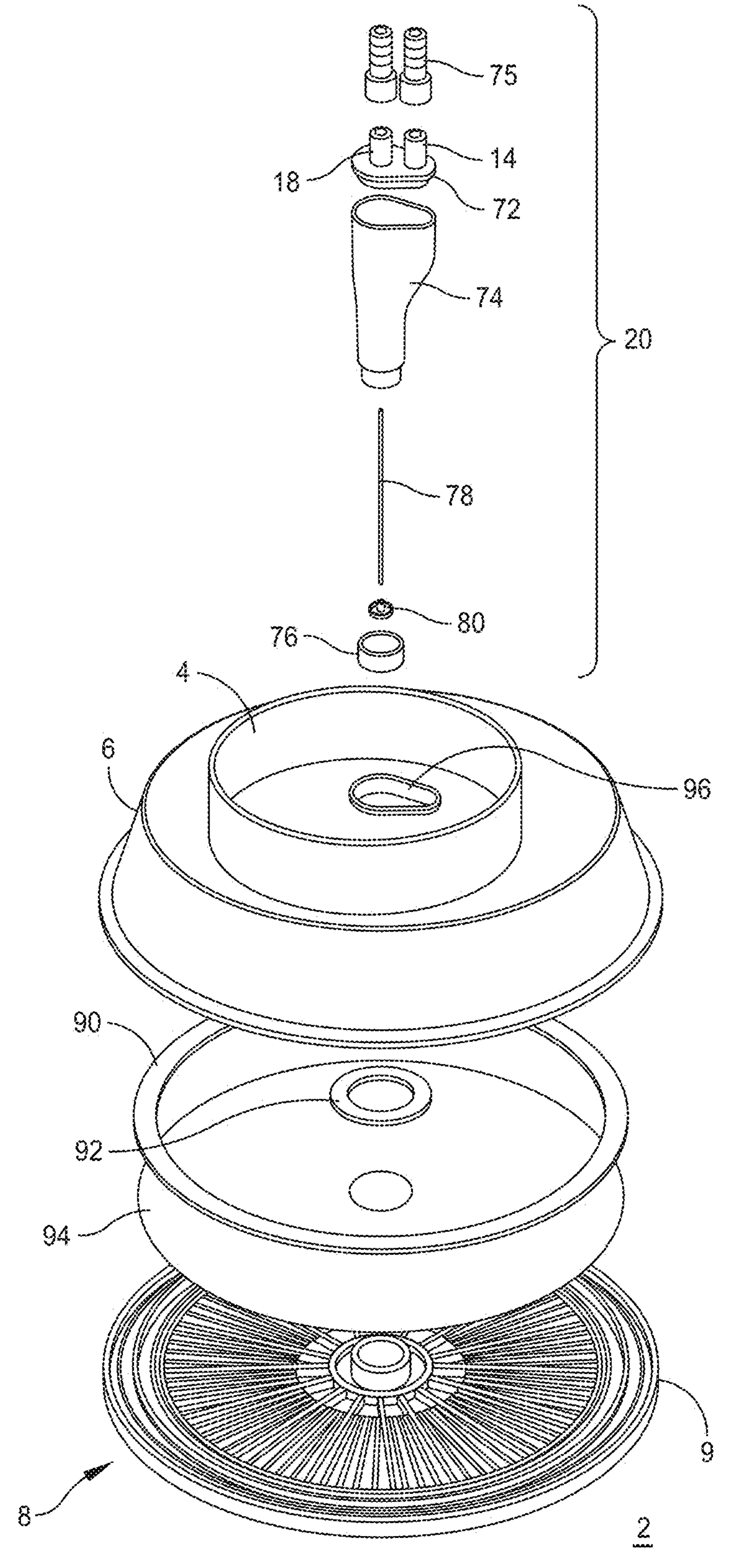
FIG. 43B is a schematic showing an exploding view of the spray dry nozzle assembly and the spray drying head of spray drying disposable device shown in FIG. 42A.
Figure 43C:
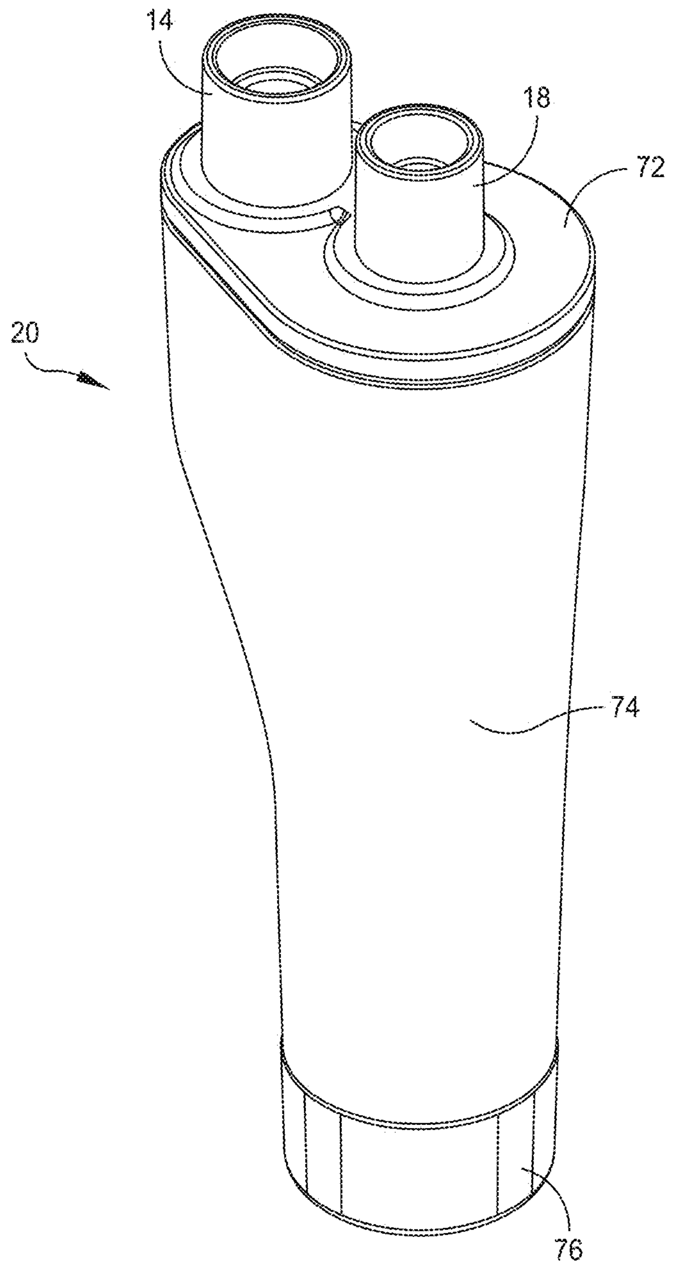
FIG. 43C is a schematic showing a perspective view of the spray dry nozzle assembly from the spray drying head of spray drying disposable device.
Figure 43D:
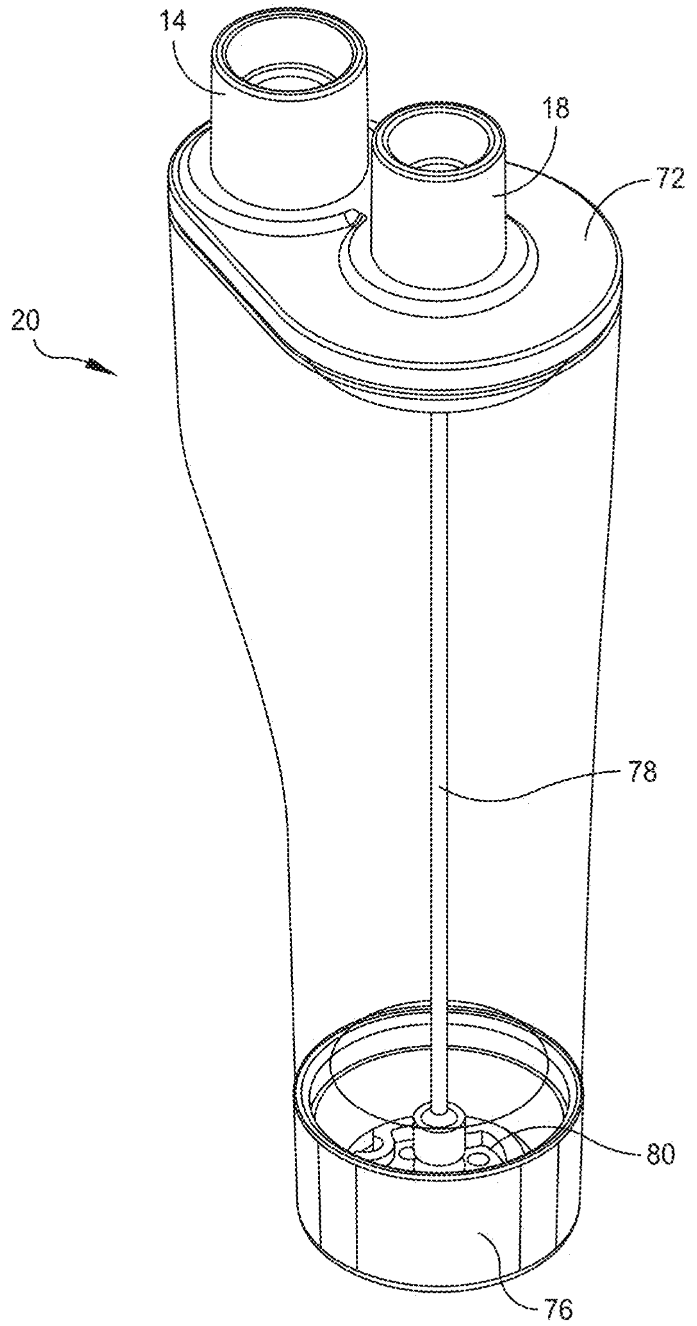
FIG. 43D is a schematic showing a perspective view of the spray dry nozzle assembly of FIG. 43C but with the aerosol reservoir housing being transparent to show the inner structures of the assembly.
Figure 43E:
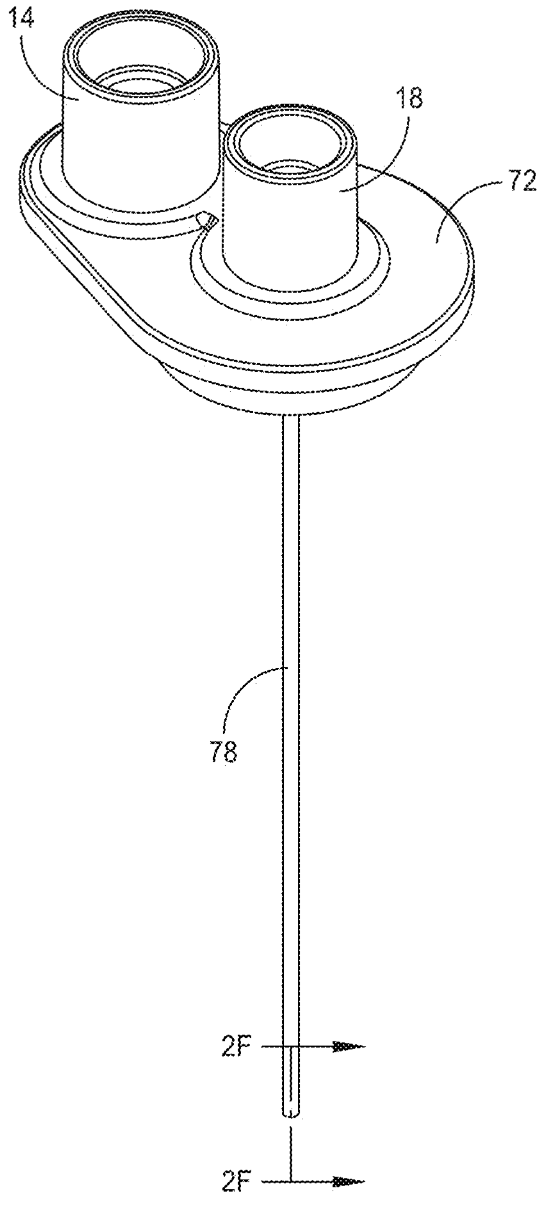
FIG. 43E is a schematic showing a perspective view of the spray dry nozzle assembly of FIG. 43C but with the aerosol reservoir housing, the nozzle cap and nozzle cap insert being removed and showing the manifold and the cannula.
Figure 43F:
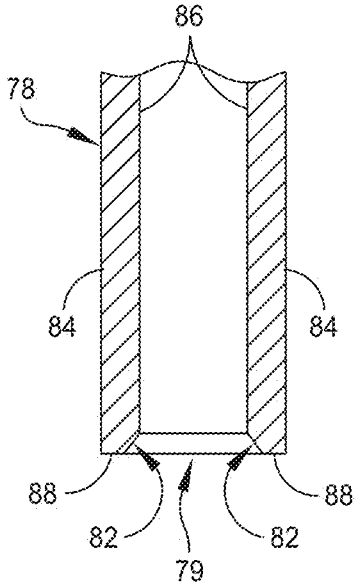
FIG. 43F is a schematic showing a front view of an embodiment of the angled edge cannula that is part of the spray dry nozzle assembly.
Figure 43G:
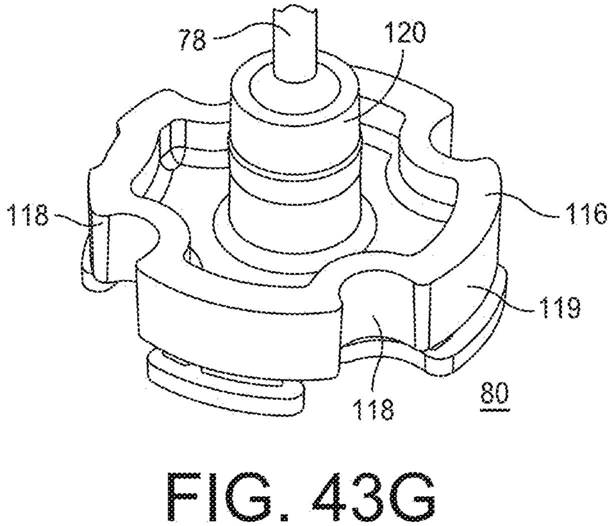
FIG. 43G is a schematic showing a perspective, top view of nozzle cap insert that guides the cannula and aerosolized air.
Figure 43H:
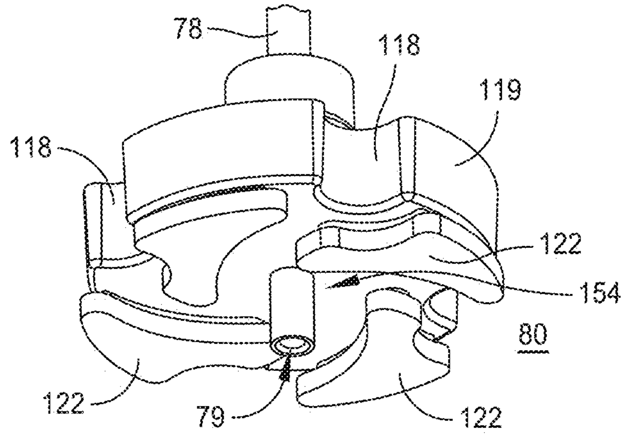
FIG. 43H is a schematic showing a perspective, bottom view of nozzle cap insert having the cannula inserted therein.
Figure 43I:
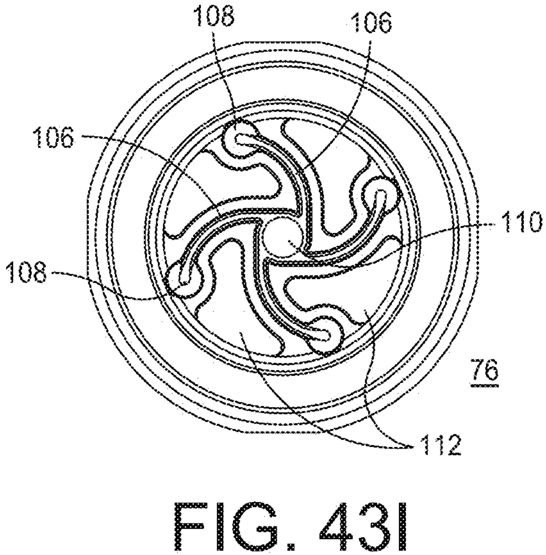
FIG. 43I is a schematic showing a top view of the nozzle cap.
Figure 43I:
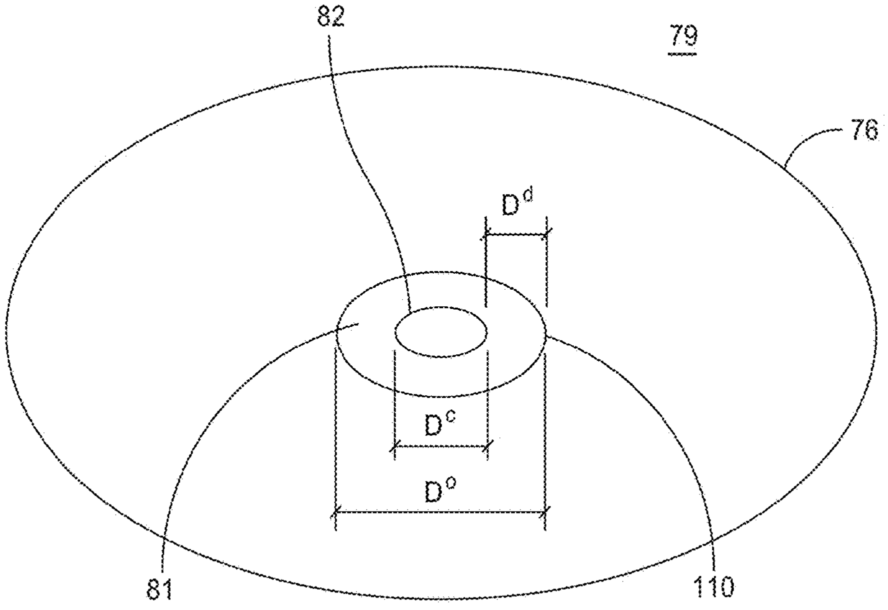
Figure 43I:
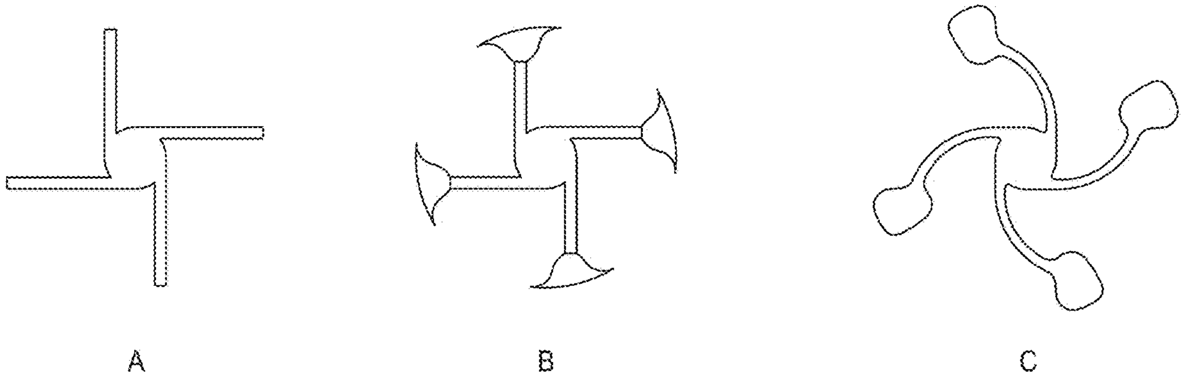
Figure 43I:
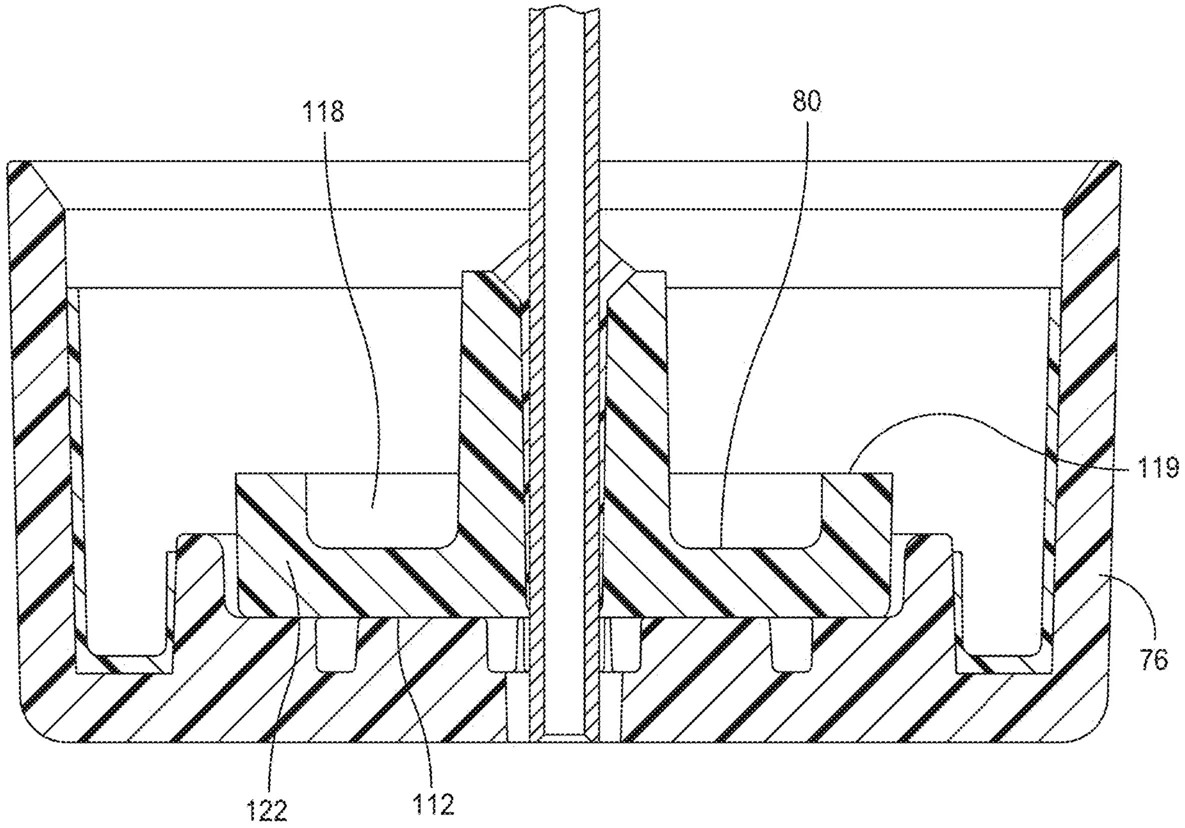
Figure 43J:
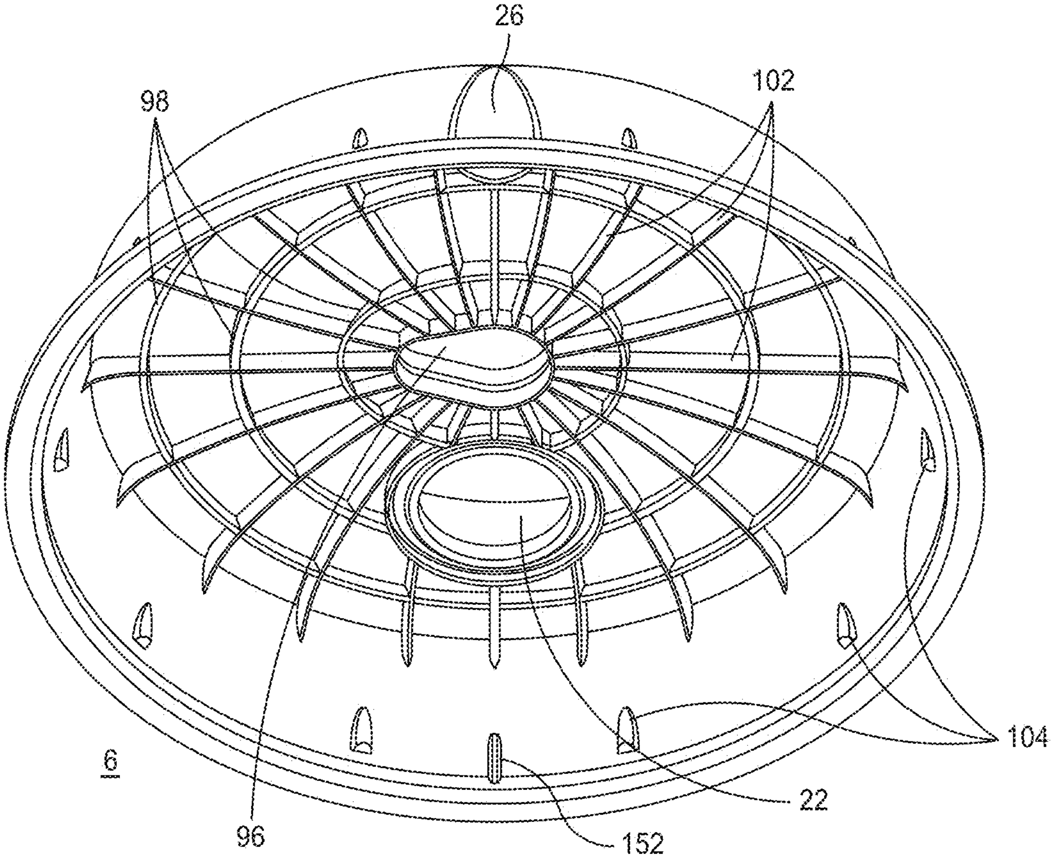
FIG. 43J is a schematic showing a perspective, bottom view of the plenum of the spray drying head.
Figure 43K:
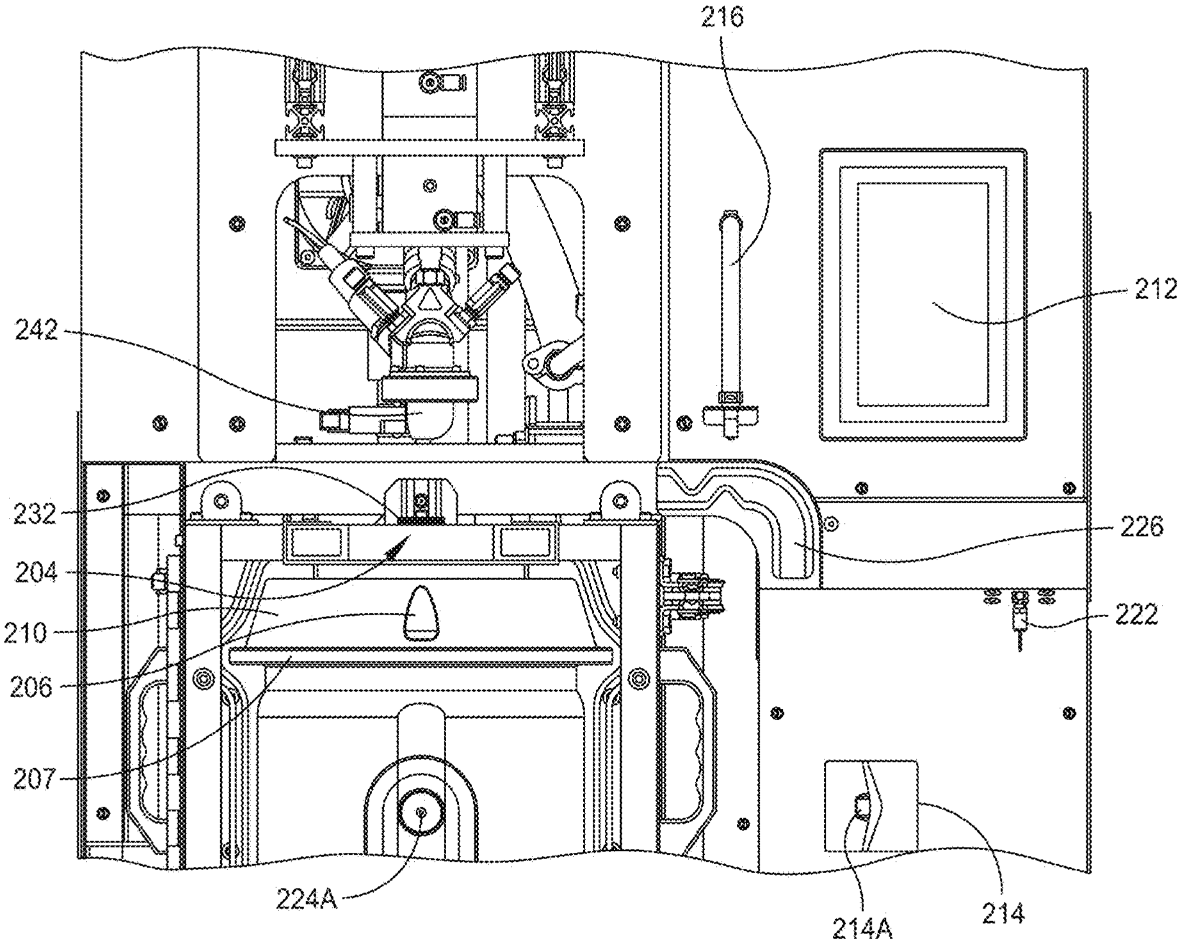
FIG. 43K is a schematic showing a partial front view of the spray dryer showing, in part, the drying gas deflector.
Figure 43K:
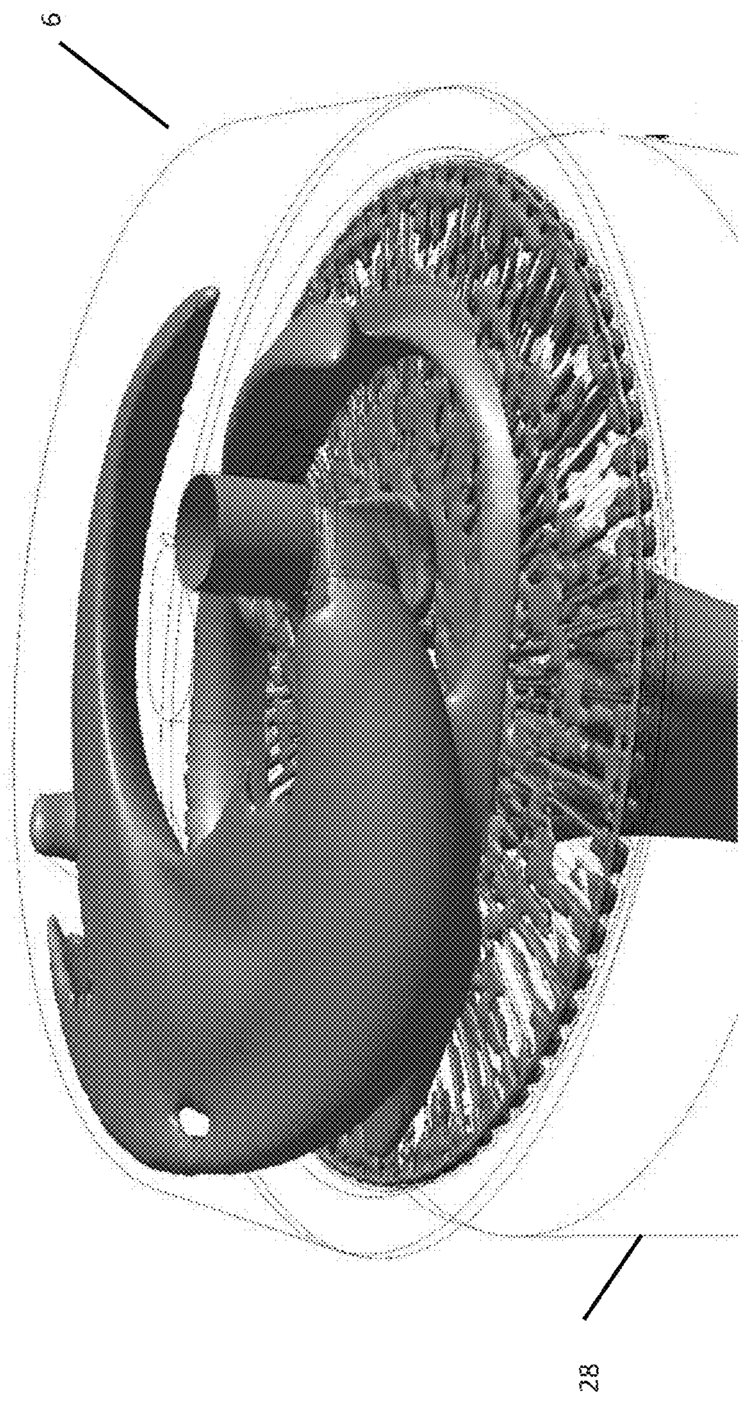

The data shown in FIGS. 42B, 43Ka, 43Ma, 43Na, 43O, 43P, 43S, 43Sa, and 43T were generated using this model.

Overview of the Spray Dryer

Spray dryer 200 of the present invention provides a donor plasma liquid flow (e.g., pretreated), a drying air flow, a pressurized aerosol gas flow, disposable deflation air line, a disposable exhaust line, a housing exhaust line, and a leak detection line.

Along with these flow lines, spray dryer 200 of the present invention further includes a leak detection methodology 1000 that utilizes a series of pressure transducers, flow sensors and valves to assess if disposable 100 has a leak during spray drying.

Spray dryer 200 further includes a pressure detection methodology 1200 that allows pressure transducers residing outside the wall of disposable 100 to measure pressure inside of disposable 100. This process involves allowing the disposable to heat up which allows the disposable wall to soften. During use, the disposable wall exerts force against force sensors PT08 224A and PT09 224B which measures such force. The amount of force is used to calculate the amount of pressure within the disposable. If the pressure within disposable 100 is above a set amount (e.g., greater than 7.02 psi), then the computer system causes dryer 200 to enter fail safe mode. If the pressure is within a set acceptable amount (e.g., between about 6.7 and about less than 7.02 psi), then the computer system determines if enough plasma has been dried, by determining the amount of donor plasma left in the donor plasma bag. If a sufficient amount of plasma has been dried, then the computer system communicates that the drying run is a success and the finishing process can begin. If an insufficient amount has been dried, then the drying run fails and disposable 100 is discarded.

Additionally, dryer 200 includes methodology 1400 that determines the integrity of lower filter 36, baffle filter 94 and/or the plenum interface. This methodology utilizes pressure transducers at the inlet and in the housing, and determines the slope of the pressures during spray drying. The slope is compared against a model and when the slope deviates from the model, then the computer system determines that disposable 100 fails.

Overview of Finisher

Once spray drying is completed on dryer 200, finisher 400 or 400' of the present invention moves the plasma to the desired compartment, and then seals the walls of the disposable and cuts the walls of the disposable to form a dried plasma unit. Finisher 400 or 400' provides an impactor, a sealer, a separator, and air extraction.

Overview of Workflow

An overview of the process to use the disposable, spray dryer and finisher described herein, is as follows. The spray drying plasma methodology of the present invention includes pretreating a donated liquid plasma unit or defrosted previously frozen liquid plasma unit, drying the liquid plasma using a spray drying apparatus with the spray drying disposable device that results in a disposable having the dried plasma, finishing the disposable using the finishing apparatus that is designed to seal and separate the disposable, and transform the disposable into a dried plasma unit. The unit can be used or stored. When ready for use, the plasma unit is rehydrated and ready for transfusion into a recipient.

With respect to pretreatment, the pretreatment process involves adding biocompatible components (e.g., a spray dry stable acidic substance) to the liquid plasma (or defrosted fresh frozen plasma) that protect the plasma proteins during the spray drying process which involves high temperatures and pressures.

In an embodiment, making the pretreatment solution includes adding the following to a solvent, such as SWFI: between about 3.0 to about 7.0 (e.g., 3.0, 4.0, 4.5, 5.0, 5.5, 6.0, 6.5, and 7.0) mmol HCl and about 15 mmol and about 30 mmol glycine (e.g., about 15, 17, 20, 22, 25, 27, 30 mmol glycine) in 50 mL of solvent to obtain 260 mL of formulated plasma. In yet other words, glycine in an amount of about 440 mM, and HCl in an amount of about 106 mM is present in the pretreatment solution. In an embodiment between about 290 mM to about 570 mM (e.g., about 290, 300, 350, 400, 450, 500, 550, and 570) glycine and about 70 mM to about 140 mM (e.g., 70, 80, 90, 100, 110, 120, 130, 140 mM) HCl is present in the pretreatment solution. The pretreatment container is commercially available and can be formulated, filled and finished by e.g., Berkshire Sterile Manufacturing (Lee Massachusetts USA). In an embodiment the pretreatment solution has about 440 mM/50 ml of glycine and 106 mM/50 ml of hydrochloric acid. (The United States Pharmacopeial Convention ("USP") monograph (12601 Twinbrook Parkway Rockville, MD 20852-1790, USA)). The pretreatment solution, when combined with liquid plasma to form a formulated plasma, protects the plasma proteins during the drying process. The formulated plasma has a pH in a range between about 5.5 and about 7.2 which offsets spray drying impacts on pH to yield a final rehydrated product that is at normal physiologic pH, a pH range between about 6.5 and 7.8 (e.g., about 6.5, 6.6 6.7, 6.8, 6.9, 7.0, 7.1, 7.2, 7.3, 7.4, 7.5, 7.6, 7.7, 7.8). pH lower than 6.5 or higher than 7.8, in certain instances, can be detrimental to the recipient. The resulting dried plasma product from the present invention is a plasma that retains its von Willebrand Factor and other blood proteins, and has fewer cholesterol crystals, less particles, less pathogens and a well-controlled pH with the aforementioned pretreatment step. Moreover, the resulting dried plasma has certain properties which are different from and superior to that of freeze-dried plasma.

A sterile connecting device (SCD), as is known in the art, is used to connect the plasma unit to the pretreatment container and the liquid plasma and in an embodiment, a fixed volume of plasma is transferred utilizing, for example, a blood collection monitor/mixer. After the liquid plasma is transferred to the pretreatment container, in an embodiment, it is gently mixed in the pretreatment container by inversion. Other mixing methods such as rocking, shaking and agitating, can be used. Additionally, the mixing can be done by the operator or a device known in the art. The bag that contained the liquid plasma is tube sealed, separated, and discarded. Pretreatment container 64 having the pretreatment solution and the liquid plasma (i.e., formulated plasma 66) is then connected to the disposable device at plasma tube 16 utilizing an SCD, resulting in a modified spray drying disposable device, shown in FIG. 42A.

Spray drying disposable device 100 is a sterile, non-pyrogenic, single user container (e.g., about 35 inches long) which utilizes a pathogen retentive filter to filter air before it enters the drying chamber and as air exits the drying chamber. See FIG. 42A. The spray drying disposable is aseptically connected to the liquid plasma at the plasma tube, tube 16.

Briefly, the drying process is as follows. See FIGS. 45A-4C, 46A-5B. In an embodiment, pretreated plasma is aseptically spray dried in spray drying disposable device 100. See FIG. 45A-4C. During the process, in an embodiment, a positive airflow is maintained. Pretreated plasma is atomized using a nozzle contained within the single use spray drying disposable device creating fine plasma droplets. These droplets are then exposed to heated air. The resulting dried plasma particles are captured in filter 36 of drying chamber 28. The spray drying disposable device is then undocked from the spray drying apparatus and taken to the finishing apparatus.

An overview of the finishing process is as follows. See FIGS. 47A-47C, 48A-C, 34. Once undocked from spray drying apparatus 200, disposable device 100 having dried plasma is transferred to finishing apparatus 400. Finishing apparatus 400 mechanically, acoustically or otherwise impacts or agitates the spray drying disposable device containing dried plasma to eventually consolidate dried plasma powder in the portion of the spray drying disposable device that becomes the spray dry plasma unit. The finishing apparatus utilizes an impactor to first assist the dried plasma in moving to the bottom of the disposable, and then in a second instance to the compartment that becomes spray dried plasma unit 60. Spray dry plasma unit 60 is sealed and separated from the rest of the disposable device utilizing impulse sealing. This step is the final closure step to create plasma unit 60. In an embodiment, the seals are visually inspected and excess portions of the disposable device are discarded and dried plasma unit 60 is produced (see FIG. 49).

With respect to an overview of the dried plasma storage process, dried plasma unit 60 is removed from the finishing apparatus and stored in a re-sealable moisture barrier foil pouch containing a desiccant. See U.S. Pat. No. 9,561,184. In an embodiment, the dried plasma unit is quarantined until completion of all required blood screening tests and stored at refrigeration. Upon meeting final release criteria, the pouch is opened and the dried plasma unit is relabeled for release. The dried plasma unit then placed in a resealable or other pouch, sealed, and stored following storage protocols.

In an embodiment, the dried plasma unit is compatible with commercially available fluid or other transfer sets for rehydration with sterile water for injection (SWFI). Dried plasma unit 60, once rehydrated, is also compatible with blood administration sets for transfusion. In a particular embodiment, spray dried plasma unit 60 is rehydrated within its existing container using an appropriate amount of sterile water (e.g., 200 mL, 208 mL) for injection prior to transfusion.

Detailed Description of Spray Dry Disposable

Detailed Description of the Spray Drying Head

Referring to FIG. 42A, a perspective view of spray drying disposable device 100 is shown. As described above, the disposable has generally two portions, spray drying head 2 and drying chamber 28. The spray drying head includes plenum 6, guide 4, baffle plate 8, baffle filter 94, nozzle 20, and locator notch 26 (also referred to as a "second locator" herein).

In an aspect, the purpose of spray drying head 2 is, in part, to A) assist in securing disposable 100 to dryer 200, B) coordinate the flow of the drying air, the aerosolized pressurized gas and the plasma flow, C) house the nozzle assembly, and D) house the baffle filter.

With respect to securing disposable 100 to dryer 200, the system of the present invention includes an integrated and universal alignment system. In an embodiment, locator notch 26 on plenum 6 is shown in FIG. 43A. FIG. 43A also better shows plenum 6, guide 4, baffle plate 8 and ridge 9. Locator notch 26, also referred to as a second locator, aligns with locator projection 206 (shown in FIGS. 43K, 45B, 45C, and 46A), also referred to as a first locator, on spray drying apparatus 200. This locating arrangement allows for spray drying head 2 of disposable 100 to be aligned axially with spray drying apparatus 200. The locating arrangement can include any arrangement that attaches, fits, complements or otherwise communicates the locator on the disposable with the locator on the drying apparatus. Examples of locating arrangements can include a recess/projection arrangement, complementing shape arrangement, hook/receiver arrangement, channel and groove arrangement, a latch and catch arrangement, a magnetic arrangement, and the like. In FIG. 46A, the male locator is on the spray drying apparatus and a complementing female locator is on the disposable, but the arrangement can be reversed. The complementing nature of the arrangement allows for easy matchup and alignment by the operator and can prevent the door from closing unless the disposable is aligned in the spray drying apparatus. In an embodiment, the locating arrangement can include any arrangement that allows for alignment between the locator on the disposable and the locator on the drying apparatus and also allows for alignment between the disposable and the finishing apparatus. In another embodiment, the drying apparatus and the finishing apparatus have the same locator that fits the locator on the disposable to create a universal alignment. Having a universal arrangement reduces the training needed and increases muscle memory because the operator inserts the disposable into the spray dryer and the finisher in a similar way.

When the first locator of the spray drying apparatus and the second locator of the disposable are aligned, in an embodiment, the system of the present invention provides positive feedback to the operator. In an embodiment, spray drying apparatus 200 has spring clip 232 mounted to the top of the drying chamber housing and engages guide 4 when the disposable is aligned and secured in the spray drying apparatus. See FIG. 46A. Spring clip 232 is optional. In this case, the positive feedback to the operator is an audible "click". Such feedback can include an audible indicator (e.g., an audible click) or a visual indicator (e.g., a sensor providing a communication to the display indicating alignment). Retention clip 232 is an alignment element as well since it aligns with ridge 9, further described below.

FIG. 43A also shows guide 4 which is off set from the center of baffle plate 8. The off-set design of the guide on plenum 6 allows disposable 100 to be attached to the receiver 204 (shown in FIGS. 45B and 46A) of spray drying machine 200 in a specific orientation. Prior to inserting the disposable device into the dryer, the operator removes and discards the adhesive covers, if present, from the top, exposing drying gas inlet port 22, and the bottom, exposing gas outlet 30. Use of such covers is optional. In a preferred embodiment, the operator removes and discards the adhesive cover from drying gas inlet port 22 only and inserts spray drying head 2 into spray drying head receiver 404. The cover the drying gas outlet 30 at the bottom of the disposable can be removed later, just before it is ready to be attached to the gas exhaust port 208. The operator generally aligns and inserts ridge 9 formed by baffle plate 8 on spray drying head 2 of disposable 100 into groove 207 of spray dryer 200. See FIG. 46A. Once engaged, the operator can use his/her hands to further push spray drying head 2 inward and it will self-align with groove receiver 207 so long as notch locator 26 on spray drying head 2 is within about 30 degrees (e.g., within about 30, 25, 20, 15, 10, 5 degrees) with respect to alignment with projection locator 206 on dryer 200. The insertion and alignment of the spray drying head can be done rapidly e.g., within 10 seconds (2-5 seconds). Receiver 204 of guide 4 also serves as drying gas inlet on the spray dryer and provides the drying gas source (not shown). Ridge 9 of spray drying head 2 also provides support and fits complementarily into groove 207 of receiver 210. It also allows spray drying head 2 of the disposable 100 to be aligned latitudinally with respect to dryer 200.

In an embodiment, receiver 210 has groove 207, as shown in FIG. 45B. The ridge and groove arrangement between the spray drying head and the dryer can be any arrangement that allows the spray drying head to fit within the drying chamber housing 202 such that the arrangement provides support and latitudinal alignment. In addition to groove 207, the receiver can be a shelf, ledge, arm, stopper, base or other structure that engages the baffle plate and allows the spray drying head to remain stable throughout the spray drying process.

The operator then inserts the disposable device by placing guide 4 into receiver 204 of the spray drying apparatus 200. Once inserted and aligned, the spray drying disposable can no longer move up and down. When using this guide and the locating arrangement, described above, they align the disposable so that it cannot move up and down and cannot move axially about the axis defined by the center of guide 4. As shown in FIGS. 45B and 46A, the guide fits into receiver 204 and does so such that the fit is snug or tight. In this embodiment, once the spray drying end is aligned and in an engaged position, then the operator can remove the bottom adhesive cover at drying chamber gas outlet 30 and attach it to the gas exhaust port 208, as further described herein.

When the locating arrangement (locators 26 and 206) is aligned, guide 4 is inserted into receiver 204, ridge 9 is inserted into groove receiver 207, and retention clip 232 is engaged, in an embodiment, spray drying head is inserted, secured and aligned. Specifically, in an embodiment, retention clip 232 engages ridge 9 to hold the spray drying head 2 in place. Retention clip 232 provides an audible indicator that the spray drying head is properly aligned and inserted. In the embodiment shown in FIGS. 45B, 45C and 31A, the retention clip is a spring clip. The retention clip can be any type of retainer that engages ridge 9 and include, for example, a fastener, pin, clasp, slide and the like. The retainer can be made from metal, plastic, rubber and the like. The retainer that engages the spray drying head is optional.

Although in the embodiment shown in FIGS. 45B, 45C, and 46A, a spring clip is used as an audible indicator to allow the operator to know that spray drying head 2 of disposable 100 is properly inserted and aligned with dryer 200, any type of indicator can be provided. The indicator can be audible, vision or tactile. In an embodiment, a sound indicator provides audible feedback mechanically or otherwise of correctly completed loading of spray drying head 2 of disposable 100. An audible indicator can be mechanical, like the sound of a spring clip locking into place, or can be generated by sensor (mechanical or pressure/contact sensor) that receives a signal of correct positioning of spray dry head 2 in dryer 200 and communicates with an actuator or processor that provides a visual indicator to the operator, for example, on display 212 or on indicator light 234. In an alternative embodiment, the sensor can send feedback to a processor that causes a sound indicator to a speaker to inform the operator of proper placement. In yet another embodiment, the feedback can be in the form of a tactile response, e.g., a vibration to inform the operator of incorrect or correct placement. Feedback can include an audible indicator (e.g., an audible click) or a visual indicator (e.g., a sensor can provide a communication to the display indicating alignment).

FIG. 43B is an exploding view of spray drying head 2 and shows the parts of spray dry nozzle assembly 20 along with plenum 6, outer filter sealing ring 90, inner filter sealing ring 92, plenum filter 94 and baffle plate 8 having ridge 9. Nozzle assembly 20 includes, going from top to bottom in FIG. 43B, strain relief valve 75, plasma and pressurized aerosol gas manifold 72, aerosol reservoir 74, cannula 78 having opening 79, liquid nozzle cap insert 80, and nozzle cap 76. The nozzle cap 76 has opening 110 whose inner wall has a diameter, defined by Diameter $D^o$ (See FIG. 43Ia). FIG. 43Ia also shows cannula 78 that has an outer wall (outer diameter) defined by Diameter $D^c$. Diameter $D^o$ is slightly larger than Diameter $D^c$ and the difference is defined by Distance $D^d$. The resultant difference in diameter, Distance $D^d$, creates annulus 81 through which pressurized air received from aerosol reservoir housing 74 forms a vortex and flows to the drying chamber 28 to facilitate the formation of small droplets of fluid to be dried. See Example 27.

Accordingly, the length of the cannula ranges between about 2 and about 5 inches, and in an embodiment, is 3.500 inches+/−. 005 inches.

More specifically, referring to FIG. 43A and FIG. 43B, spray dry nozzle assembly 20 has plasma flow inlet 18 connected to pretreated liquid plasma 66 (shown in FIG. 42A) via plasma tube 16 and pressurized aerosol gas inlet 14 connect to the pressurized gas source (not shown) via aerosol tube 10 and aerosol filter 12. Additionally, drying gas inlet port 22 is shown in FIGS. 42A and 43A and communicates with the drying gas source (not shown). When the plasma source, pressurized gas source, and drying gas source combine, the liquid plasma particles are formed under pressurized (aerosolized) gas and dried into a fine dried plasma (e.g., a plasma powder).

FIGS. 43C and 43D show a detailed perspective view of spray dry nozzle assembly 20. In particular, FIGS. 43B and 43J show where and how the spray dry nozzle assembly fits within assembly opening 96 of plenum 6 of spray dry head 2. Plasma and pressurized aerosol gas manifold 72 coordinates and directs the plasma source via inlet 18 and the pressurized aerosol gas source via inlet 14. Strain relief 75 fits and communicates with manifold 72 to provide support to tubes 10 and 16 and prevent them from collapsing under pressuring during packaging, transport and spray drying. Strain relief 75 also prevents the tubes from collapsing in the packaging and in transit. Spray dry nozzle assembly 20 includes aerosol gas reservoir housing 74 through which the pressurized aerosol gas is held and builds before being released through liquid nozzle cap insert 80 and nozzle cap opening 110 (shown in FIGS. 43G, 43H, 43I, 43Ia, and 43Ic). Nozzle assembly 20 is housed by aerosol gas reservoir housing 74 and secured by nozzle cap 76. Liquid nozzle cap insert 80 guides cannula 78 and holds the cannula in place during use. Annulus 81 is disposed between the outer surface of cannula 78 and inner surface of opening 110. The design of liquid nozzle cap insert 80 and nozzle cap 76 allow the pressurized aerosol gas to flow though annulus 81 in a vortex pattern to maximize aerosolization and promote rapid mixing of the aerosolized plasma droplets with the drying gas, as further described herein. The entire nozzle assembly 20 is secured to opening 96 of plenum 6 which includes baffle plate 8 having ridge 9, with filter 94 therebetween and sealed by inner filter sealing ring 92 and outer filter sealing ring 90. See FIG. 43B.

FIG. 43D shows the aerosol gas reservoir housing 74 as transparent so that cannula 78 and attachment to liquid nozzle cap insert 80 and nozzle cap 76 can be seen and FIG. 43E shows manifold 72 and cannula 78 with the aerosol gas reservoir housing 74, liquid nozzle cap insert 80 and nozzle cap 76 removed. FIG. 43F shows the bottom tip, the end opposite the manifold, of cannula 78 having outer wall surface 84, inner wall surface 86, flat edge 88, and beveled or angled edge 82 (e.g., a chamfer) at the bottom surface of the cannula.

It has been discovered that a cannula with an angled edge (e.g., chamfer) on the inside diameter, when used in spray drying to create the atomized plasma particles, assists or allows many of the proteins in the plasma to remain intact, functional, or both. Hence, the angled edge cannula of the present invention reduces the amount a protein degrades during spray drying because the angled edge cannula reduces shear on the passing liquid plasma film.

In a particular embodiment, a blood protein, vWF, was measured. vWF is considered a more fragile, easily degradable protein, as further described herein. In an embodiment, using spray dry nozzle with the angled cannula of the present invention, vFW recovery is maintained, as compared to a nozzle with a non-angled cannula. In fact, based on the data described in Example 28, using a composite nozzle with a chamfered cannula resulted in an increase in vFW recovery, as compared to both a composite nozzle having non-angled cannula and to a benchmark stainless steel nozzle (as Buchi Model no. 4244 Buchi Corporation of New Castle, Delaware United States). In an embodiment, using a nozzle with an angled cannula resulted in an increase in an amount at least ranging between about 1% and 25% (e.g., 1, 2, 3, 4, 5, 6, 7, 8, 9, 10, 11, 12, 13, 14, 15, 16, 17, 18, 19, 20, 21, 22, 23, 24, and 25%) in functional vFW recovery, as compared to a nozzle having non-angled cannula. In particular, as described in Example 28, the data show that spray drying with a chamfered cannula having an angle of 45 degrees and length of 0.005" increased the vWF RCO assay result by about 9%-22%, as compared to the same system operated with a composite nozzle having a cannula without the angled edge and, surprisingly, 3.7% better as compared to the benchmark control Buchi nozzle.

Among the plasma proteins maintained throughout the spray drying process using an angled-edge cannula, includes von Willebrand Factor (vWF). vWF is involved in clotting, repairing vascular injury and platelet adhesion. In particular, vWF is a large adhesive glycoprotein with established functions in hemostasis. It serves as a carrier for factor VIII and acts as a vascular damage sensor by attracting platelets to sites of vessel injury. The regulation of vWF multimeric size and platelet-tethering function is carried out by ADAMTS13, a plasma metalloprotease that is constitutively active. It is secreted into blood and degrades large vWF multimers, decreasing their activity. Unusually, protease activity of ADAMTS13 is controlled not by natural inhibitors but by conformational changes in its substrate, which are induced when vWF is subject to elevated rheological shear forces. This transforms vWF from a globular to an elongated protein. This conformational transformation unfolds the vWF A2 domain and reveals cryptic exosites as well as the scissile bond. To enable vWF proteolysis, ADAMTS13 makes multiple interactions that bring the protease to the substrate and position it to engage with the cleavage site as this becomes exposed by shear forces. ADAMTS 13 (a disintegrin and metalloproteinase with a thrombospondin type 1 motif, member 13), also known as von Willebrand factor-cleaving protease (vWFCP), is a zinc-containing metalloprotease enzyme.

Without being restricted to a theory of operation, it is believed that during spray drying, the plasma proteins are subject to considerable shear forces due to the spraying mechanism as the solutions are fluidized out of the end of a fine nozzle to form the droplets in contact with drying air. The process of unfurling multimeric vWF is expected to be triggered by the hydrodynamic forces of elevated shear stress during spray drying in combination with air-liquid interface stress. The shear-induced structural change of vWF, when combined with other physical factors associated with spray drying, such as high temperature and/or unfavorable pH as well as the air-liquid interface stress, may lead to protein denaturation (if unfolded vWF fails to refold properly post-spray drying) and proteolytic degradation (unfolded vWF exposes proteolytic sites for ADMATS13), impairing the vWF activity in the spray dried plasma, as well as other proteins.

Spray drying system of the present invention can be optimized to reduce the protein damage caused by shear force and temperature and the specially designed cannula of the present invention helps to minimize shear and damage to the proteins include vWF.

The cannula of present invention, in an embodiment, has a bottom edge wherein at least a portion of the bottom edge is angled, referred to herein as an angled edge cannula. In an instance, the entire bottom edge can be angled or a portion of the bottom edge can be a flat edge (e.g., about a 90° angle from the outer wall surface or the inner wall surface). In another embodiment, a portion of the bottom edge of the cannula is a flat edge, like flat edge 88, (e.g., about 90° from the outer wall surface or inner wall surface) and a portion of the bottom edge of the cannula is angled, like angled edge 82, (e.g., 45° angle from the outer wall surface, or 135° angle from the inner side wall surface), as shown in FIG. 43F. This embodiment shown in FIG. 43F can edge having a flat edge (90° from the outer wall) from which a 45° angle is formed is referred to as a "chamfer" or as having a "chamfered edge."

In the case in which the cannula has a bottom edge and the entire bottom edge is angled from the outer wall to the inner wall, the angle as measured from the outer wall surface ranges from about a 30° angle to about a 60° angle (e.g., about a 30°, 35°, 40°, 45°, 50°, 55°, 60° angle) and as measured from the inner wall surface ranges from about a 120° angle to about a 150° angle (e.g., about 120°, 125°, 130°, 135°, 140°, 145°, 150° angle). The length of the angled bottom edge ranges between 0.001 inches and about 0.010 inches (e.g., about 0.001, 0.002, 0.003, 0.004, 0.005, 0.006, 0.007, 0.007, 0.008, 0.009, 0.010 inches).

In the case in which the cannula has a bottom edge having a portion that is a flat edge and a portion that is angled, the flat edge is about 90° angle (e.g., between about 85% to about 95%) from the outer wall surface. The angled edge has an angle, as measured from the outer wall surface (imagining that the angled edge intersects the outer wall surface) ranges from about a 30° angle to about a 60° angle (e.g., about a 30°, 35°, 40°, 45°, 50°, 55°, 60° angle), and in an embodiment, is 45°+/−5° and as measured from the inner wall surface ranges from about a 120° angle to about a 150° angle (e.g., about 120°, 125°, 130°, 135°, 140°, 145°, 150° angle), and in an embodiment, is 135°+/−5°. See FIG. 52 for an example of a 45° and a 30° angled edge. The length of the flat edge portion ranges between 0.001 inches and about 0.009 inches (e.g., about 0.001, 0.002, 0.003, 0.004, 0.005, 0.006, 0.007, 0.007, 0.008, 0.009 inches) and the length of the angled edge portion ranges between about 0.001 inches and about. 009 inches (e.g., about 0.001, 0.002, 0.003, 0.004, 0.005, 0.006, 0.007, 0.007, 0.008, 0.009 inches), and in an embodiment, is 0.005+/−0.003. The ratio between the length of the flat edge and the length of the angle edge has a range between about 5 and about 500 percent. In an embodiment, the flat edge adjoins the outer wall surface and the angled edge adjoins the inner wall surface.

The angled edge cannula, accompanied with or without a flat edge, results in less stress/shear on the plasma droplet exiting the cannula, as compared to a non-angled cannula, having a 90° angle. While not being bound to any particular theory, it is believed that when a plasma droplet exits a 90° non-angled cannula edge, a portion of the plasma droplet or plasma film undergoes a shearing effect and, in the process, degrades a high percentage of the plasma proteins therein. In this case, the 90° non-angled cannula exerts a shearing force on the droplet, thereby degrading the proteins in the plasma. As the plasma droplet exits cannula having an angled edge, as in the present invention, less sheer on the plasma droplet is exerted. As the plasma is drawn out by the air flow of an angled edge cannula, it accelerates based upon the plasma feed rate and the plasma gets pulled around the cannula edge. Unlike a cannula having a 90° non-angled edge, the plasma is not forced to make a 90 degree turn. By softening the turn that the plasma makes as it exits the cannula by angling the edge of the cannula, less shear is exerted upon the liquid film as it is drawn out. The liquid plasma film that exits out of an angled cannula is thicker and accelerates more slowly thereby reducing shear exerted on the liquid.

The inner diameter of the cannula ranges between about 0.010 inches and about 0.040 inches, and in an embodiment, is 0.030 inches+/−0.002 inches and the outer diameter ranges between about 0.030 inches and about 0.060 inches, and in an embodiment, is 0.050 inches+/−. 0005 inches. The angled edge of the cannula impacts the size of the atomized droplet. When exiting an angled cannula, the droplet sizes in this range is between about 5 microns and about 35 microns and in an embodiment the droplet size is about 10 microns. Small droplet size which is defined in part by the angled edge of the cannula, promotes rapid mixing, faster evaporation and reduced drying time. See FIG. 43T which shows that the larger the droplet size the longer it takes for the droplet to evaporate with higher drying gas temperatures. The shape of the droplet is created by its surface tension dominates and creates a sphere after exiting the cannula. Droplet size is also primarily impacted by the pressurized gas rate ratioed to the liquid feed rate (ALR) and nozzle design.

The cannula of the present invention can be made from a stainless-steel material suitable for medical devices. Examples of the grade of stainless steel that can be used is grade 304 and 316 stainless steels. The stainless steel used for the cannula of the present invention is commercially available e.g., from Bergsen Metals (Santa Fe Springs, California, USA) or Fort Wayne Metals (Fort Wayne, Indiana, USA). The nozzle assembly (except for the cannula), nozzle insert, nozzle cap, plenum and baffle plate, outer filter ring, inner filter ring and the like can be made from plastic used in medical devices, such as a polycarbonate, polypropylene, polysulfone or combination thereof. Each aforementioned part can be made from the same material, from different materials or a combination thereof. Such plastic is commercially available and can be purchased from e.g., Covestro AG (Kaiser-Wilhelm-Allee 6051373 Leverkusen, Germany), Teknor Apex (Pawtucket, Rhode Island USA), Colorite Plastics of NJ Inc (101 Railroad Ave, Ridgefield, New Jersey USA), American RENOLIT Corporation (301 Berkeley Drive, Suite B, Swedesboro, New Jersey USA), and Exxon Mobile (Technology Centers, Baytown, TX USA 77520, United States),), or molded from e.g., Egli Machine (Sidney, NY USA) Co, and Southwest Mold, Inc. (Tempe, AZ USA). Other materials now know or later developed can be used for the cannula and/or nozzle so long as when combined result in a maintenance or increase in vWF recovery in plasma after spray drying.

A stainless-steel nozzle, such as Buchi Model no. 4244 (Buchi Corporation of New Castle, Delaware United States), is often used in spray drying but it is expensive to manufacture or buy, especially for a disposable device that is discarded after each spray drying run. For example, a common Buchi stainless steel nozzle body, part No. 4244, costs between $1000 and $2000. The nozzle assembly of the present invention is a composite nozzle for use in spray drying and especially spray drying of delicate materials such as human blood plasma at a cost of less than $30.00, orders of magnitude less than stainless steel nozzles, such as the Buchi Model no. 4244. The described Buchi nozzle serves as a useful benchmark for a composite nozzle as it had been used by the applicant to make dried human blood plasma that preserved the proteins in blood plasma to a regulatorily acceptable level.

As indicated, most of the nozzle assembly, except for the cannula which is made from a stainless-steel material, is made from a less expensive plastic material, as described above. As such, the nozzle assembly is also referred to as a "composite nozzle" or "composite nozzle assembly" to refer to the two or more different types of materials used to make the nozzle assembly (e.g., a stainless-steel cannula and a polycarbonate nozzle insert and nozzle cap). Example 28 shows that a chamfered cannula of a composite nozzle assembly provides for improved vWF recovery as compared to one that has a unchamfered cannula, and vWF recovery about as good as an expensive stainless-steel nozzle.

When the plasma exits the tip of the cannula, it is exposed to the pressurized aerosol gas at nozzle cap 76. More particularly, the pressurized aerosol gas exits in a vortex pattern through the annulus 81 and hits the liquid plasma droplets flowing from the chamfer edge/angled edge 82 of cannula 78 and the plasma atomizes to form a plume. When the atomized plasma exits the spray dry nozzle assembly, it is exposed to the drying gas and dries into plasma powder in the drying chamber. In an embodiment, the tip of cannula 78 is flush with the distal end of opening 110.

Liquid nozzle cap insert 80 secures the bottom portion of cannula 78 and guides the pressurized aerosolized gas flow. FIG. 43G shows a perspective top view liquid nozzle cap insert 80. As can be seen, cap insert 80 has insert wall 116 and cannula anchor 120 which has an opening (not shown) through which cannula 78 extends. The top of insert wall 116 forms a ridge and the side of insert wall 116 defines a series of recesses 118 and projections 119. Cannula anchor 120 supports the tip of cannula 78 during plasma flow. Angled edge 82 of cannula 78 through which the plasma exits and annulus 81 through which the pressurized aerosol gas is emitted create the actual nozzle. Cannula anchor 120 is a hollow, cylindrical base but can be of any shape so long as the cannula is supported, and its position maintained during spray drying. The recesses of the wall, recesses 118, allow for the pressurized air to pass from the reservoir (defined by reservoir housing 74) to the area between nozzle cap insert 80 and nozzle cap 76 before exiting the center opening 110 of nozzle cap 76. When the pressurized air exits center cap opening 110, the air exists through annulus 81 defined by the outer wall of cannula 78 and inner wall of opening 110. More specifically, when the cap insert 80 is secured to cap 76 and cannula 78 resides within opening 110, the pressurized air exits through annulus 81. See FIG. 43Ia. As such, the diameter of opening 110 is greater than the outer diameter of cannula 78. In particular, opening 110 of nozzle cap 76 has an inner wall with a diameter, defined by Diameter $D^o$ (See FIG. 43Ia). FIG. 43Ia also shows cannula 78 that has an outer wall defined by Diameter $D^c$. Diameter $D^o$ is slightly larger than Diameter $D^c$ and the difference is defined by Distance $D^d$. The resultant difference in diameter, Distance $D^d$, creates annulus 81 through which pressurized air received from aerosol reservoir housing 74 forms a vortex and flows to the drying chamber 28 to facilitate the formation of small droplets of fluid to be dried. In an embodiment, the outer diameter of cannula 78, Diameter $D^c$, is between about 0.030 and about 0.070 inches (e.g., 0.030, 0.040, 0.050, 0.060, 0.070) and the diameter of opening 110 is between 0.075 and 0.100. For ease of use, "Distance $D^d$" is also referred to as the "radial distance of annulus 81." In an embodiment, the Diameter $D^c$ is 0.050+/−0.0005 inches and the Diameter $D^o$ is 0.082+/−0.001 inches. The radial distance between the outside surface of cannula 78 and the inner surface of opening 110, Distance $D^d$, is the space through which the rotating vortex of pressurized aerosol gas flows and assists in creation of small droplets of plasma to mix with the hot drying gas during spray drying. In an embodiment, $D^d$ has a range between 0.005 and 0.030 inches (e.g., 0.015 and 0.021 inches).

Along these lines, the data from Example 27 show that that the radial distance of annulus 81, $D^d$, has an impact on both the yield for dried product from the drying process and on the preservation of vWF. Yield is the ratio of starting solids in the to-be-dried liquid material by weight to dried material recovered by the drying process by weight.

Before the present invention, one source of loss of yield occurred when dried sprayed material that was not fully dried and retaining residual moisture above about 2.5% contacted and stuck to the interior structures of the drying disposable during drying without being recoverable.

Example 27 describes the reduction in the amount of material visibly stuck to the underside of baffle plate 8 after completion of the drying cycle. The data described in Example 27 show that overall yield by weight was increased by changing the radial distance of annulus 81 $D^d$ from 0.021" to 0.015". The yield was acceptable with the annulus dimension at 0.021". However, the yield percentage was improved by more than 2.2% by reducing the annulus width/diameter to 0.015". Other features of disposable 100 increase yield and include, in part, drying jets 142 that form an air wall within plasma drying chamber 28, as further described herein.

Example 27 also described in increase in the recovery of vWF as measured by Ristocetan (RCO) assay by changing the radial distance of annual 81 from 0.021" to 0.015." The vWF recovery was acceptable with the annulus dimension at 0.091". However, vWF recovery was increased by more than 2.0% by reducing the annulus width to 0.082". Other features of disposable 100 also increase vWF recovery and include, in part, the angled edge cannula 78, as described herein.

The space between nozzle cap insert 80 and nozzle cap 76 before exiting the center opening 110 of nozzle cap 76 is generally referred to herein as the "vortex generator" which includes a series of channels and curved pads, as further described below. Pressurized air passes through recesses 118 that act as openings in nozzle assembly 20 to allow air to enter and travel down the channels and between the curved pads. See FIGS. 43G, 43H, 43I and 43Ic.

Referring to FIG. 43H, the bottom of surface of cap insert 80 not occupied by pads 122 on the underside of projections 119/recesses 118 and will act as walls for the channels in the vortex generator. Pads 122 form a kidney-like shape that assists in locating recesses 118 for the vortex air flow pattern. The nozzle cap, cap 76, shown in FIG. 43I, has complementary receivers 112 to receive the pads from the cap insert 80. The complementary fit between nozzle insert 80 and nozzle cap 76 is shown in FIG. 43Ic (as a cross-section). Nozzle cap 76 also has nozzle cap channels 106 extending from bulbous head 108 and ending at opening 110. The surface of the bottom of cap insert 80 that is not occupied by pads 122 and further complemented by channels 106 of cap 76, is the space through which the pressurized air flows. The vortex generator includes the recesses 118 and the surface of the bottom of cap insert 80 that is not occupied by pads 122, bulbous heads 108 and channels 106 of cap 76, the shape and position of each cause the pressurized air to form a vortex air flow pattern. Bulbous head 108 receives the pressurized air flow through recess 118 and the curved ramp like surface of channel 106 provides a curved boundary for the air to flow. In other words, recesses 118 is an entrance port and feeds the air flow and channels 106 feeds the vortex. Channels 106 are arched and further accentuates the curved air flow and directs the tangential air flow toward opening 110 in which cannula 78 resides. These channels, channels 106, guide the air in a circular fashion from bulbous head 108 to nozzle cap opening 110, all working in concert to expel pressurized air as a vortex through opening 110. The design provides tangential momentum to provide an efficient generation of a vortex. Channels 106 are in the form of an arc or curve, and the radius of the curvature ranges from about 0.10 inches to about 0.25 inches, and in an embodiment about 0.140+/−0.010 inches radius. The vortex generated includes 4 channels but can have between about 2 and 12 channels (e.g., 2, 3, 4, 5, 6, 7, 8, 9, 10, 11 or 12 channels). Other types of shaped channels can be used. FIG. 43I shows the design molded into nozzle cap 76. Designs A and B both show more linear channels but Design A have no equivalent of a bulbous head and Design B shows a bell-shaped head. Design C is similar to the design shown in FIG. 43I but with a lobe instead of a bulbous shape at the end. The present invention includes nozzle caps having Designs A and B but found the Design C appears to be a more efficient vortex generator. The various designs demonstrate that any combination of channels, heads and shapes can be used to generate a vortex in the annulus. Other types of channels include conical shaped channels including convert or divergent cone shapes and the like.

Figure 43L:
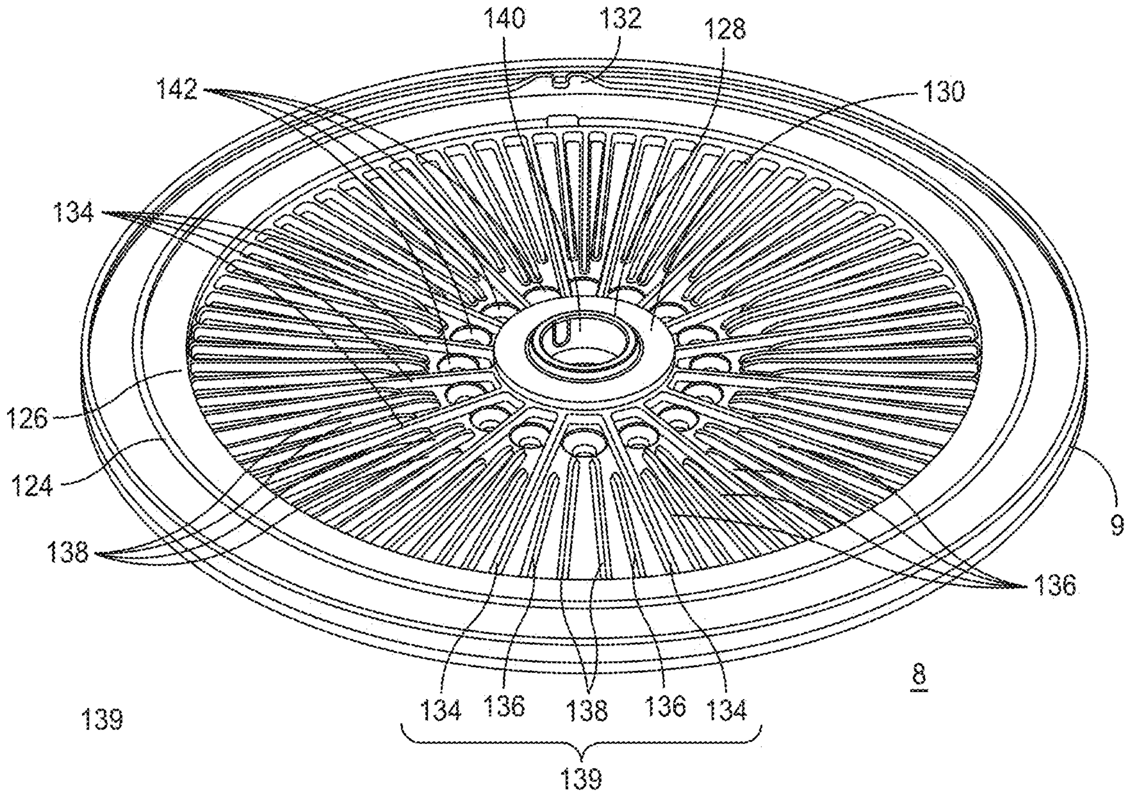
FIG. 43L is a schematic showing a perspective, top view of the baffle plate of the spray drying head.
Figure 43L:
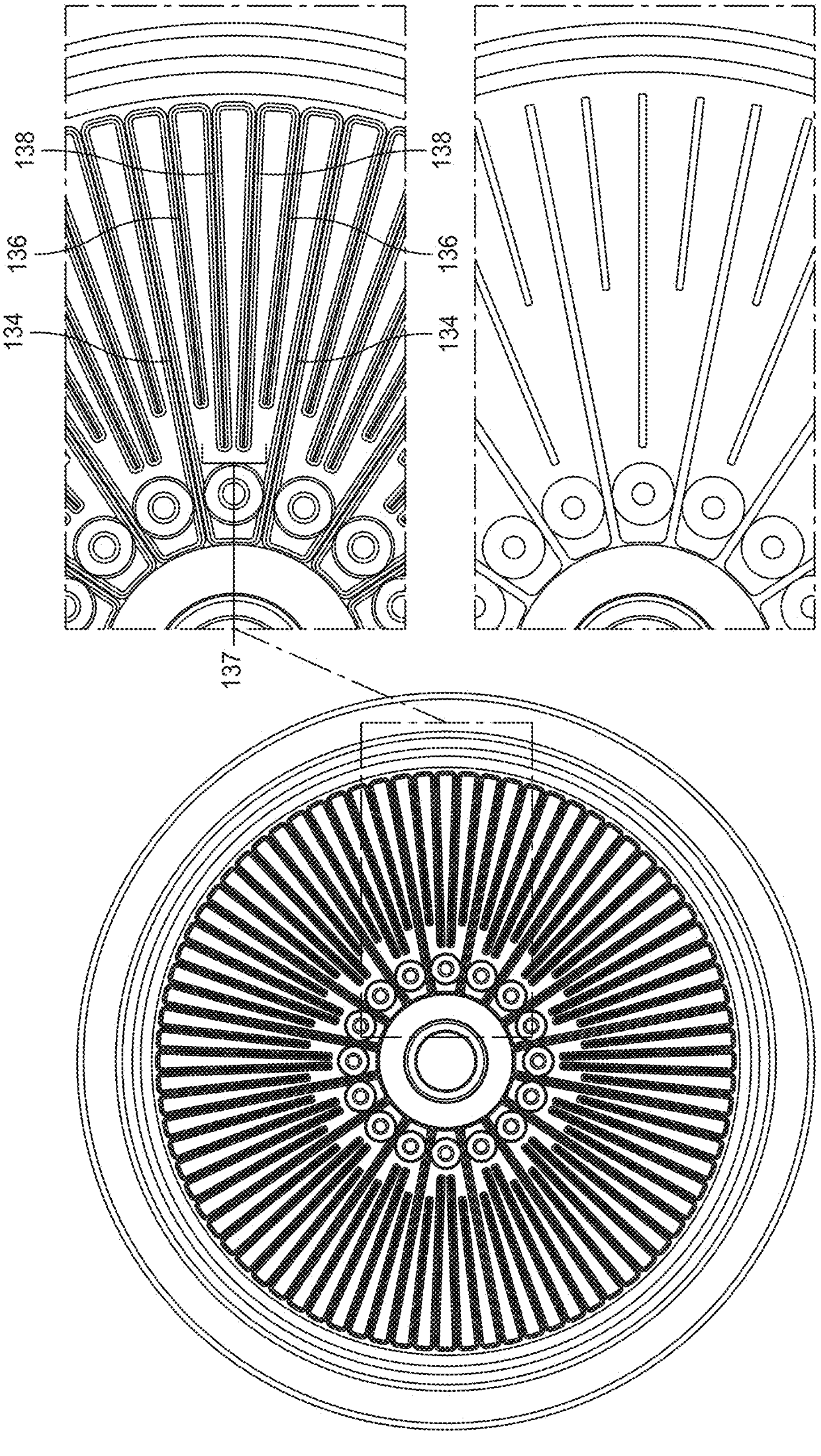
Figure 43M:
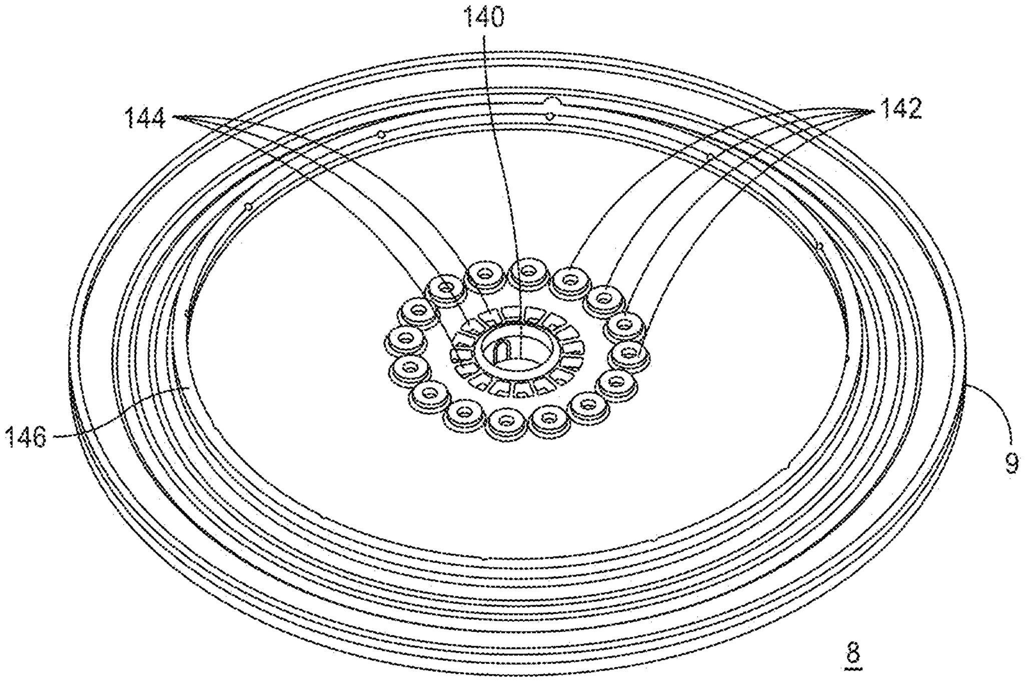
FIG. 43M is a schematic showing a perspective, bottom view of the baffle plate of the spray drying head.
Figure 43M:
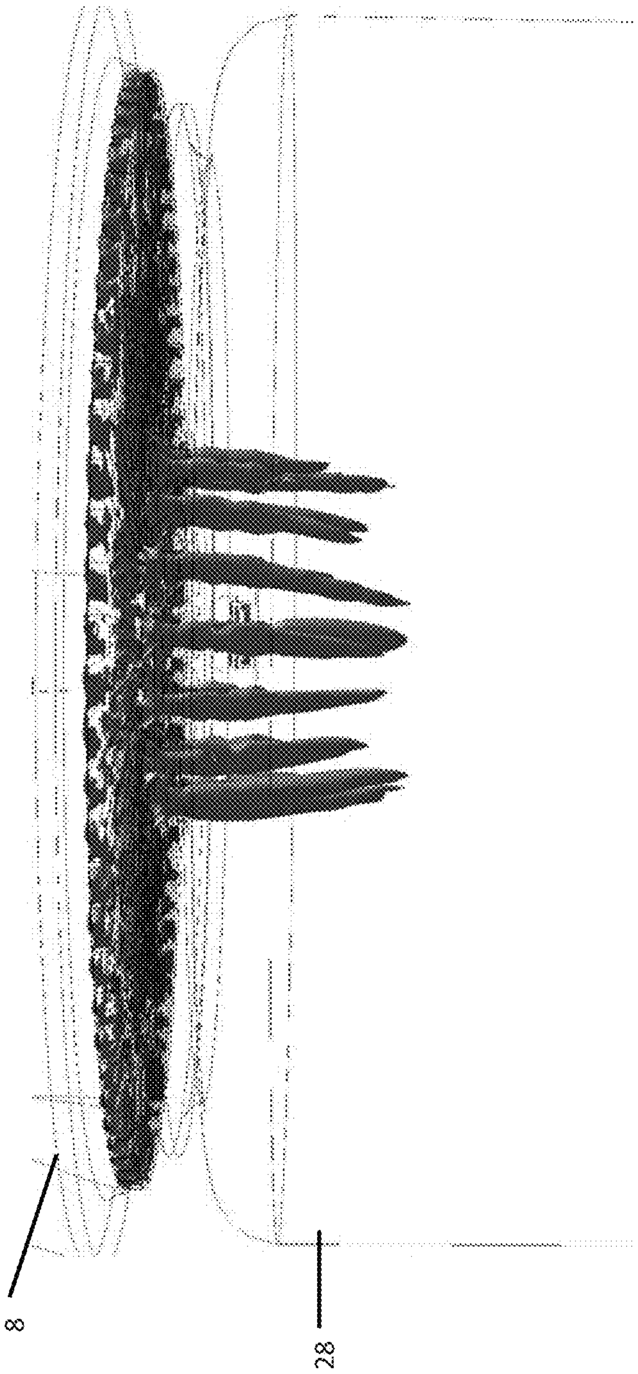
Figure 43N:
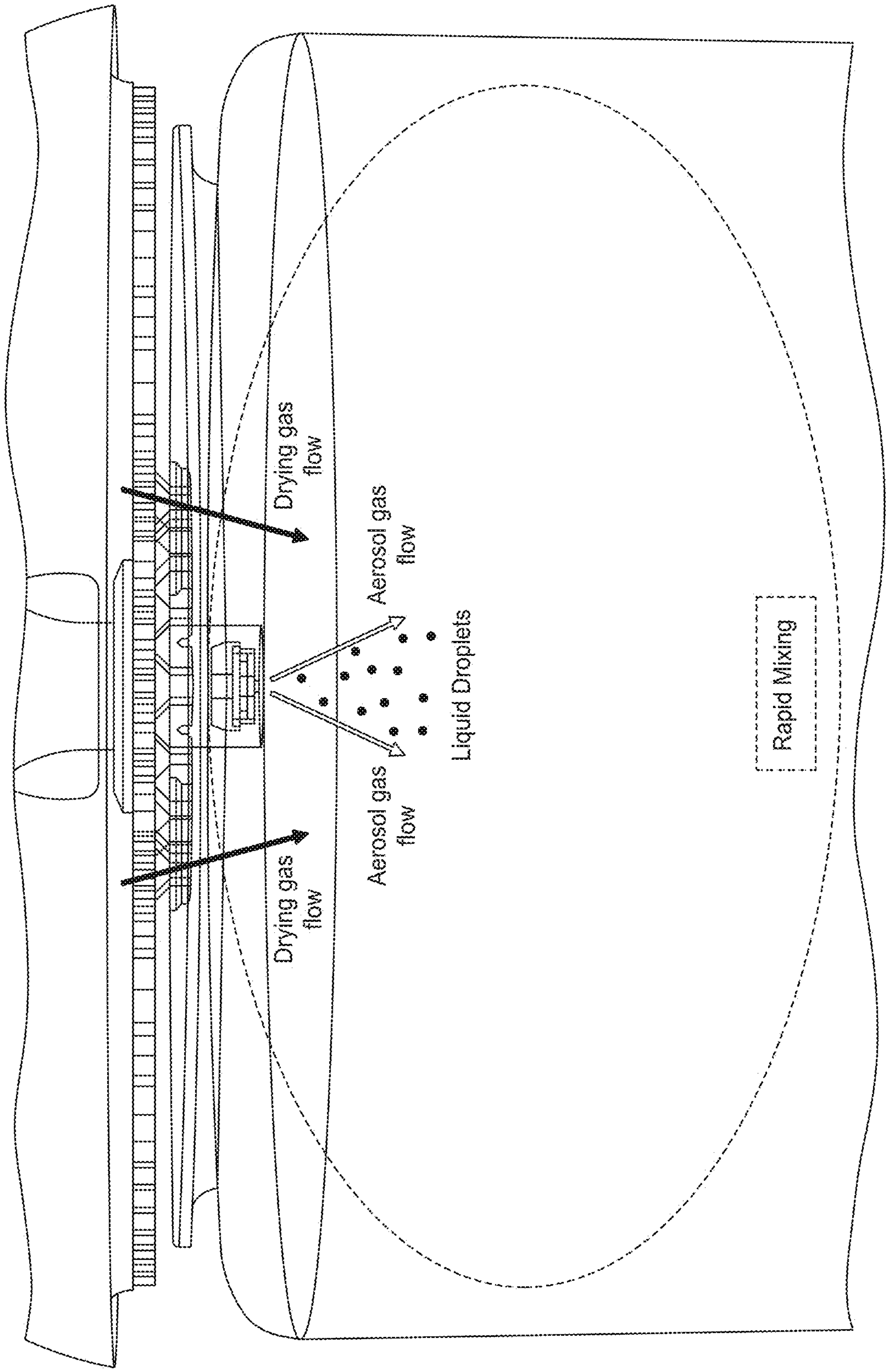
FIG. 43N is a schematic showing a schematic showing the droplet plume formation, aerosol gas flow and drying gas flow that promotes rapid mixing in the disposable of the present invention.
Figure 43N:
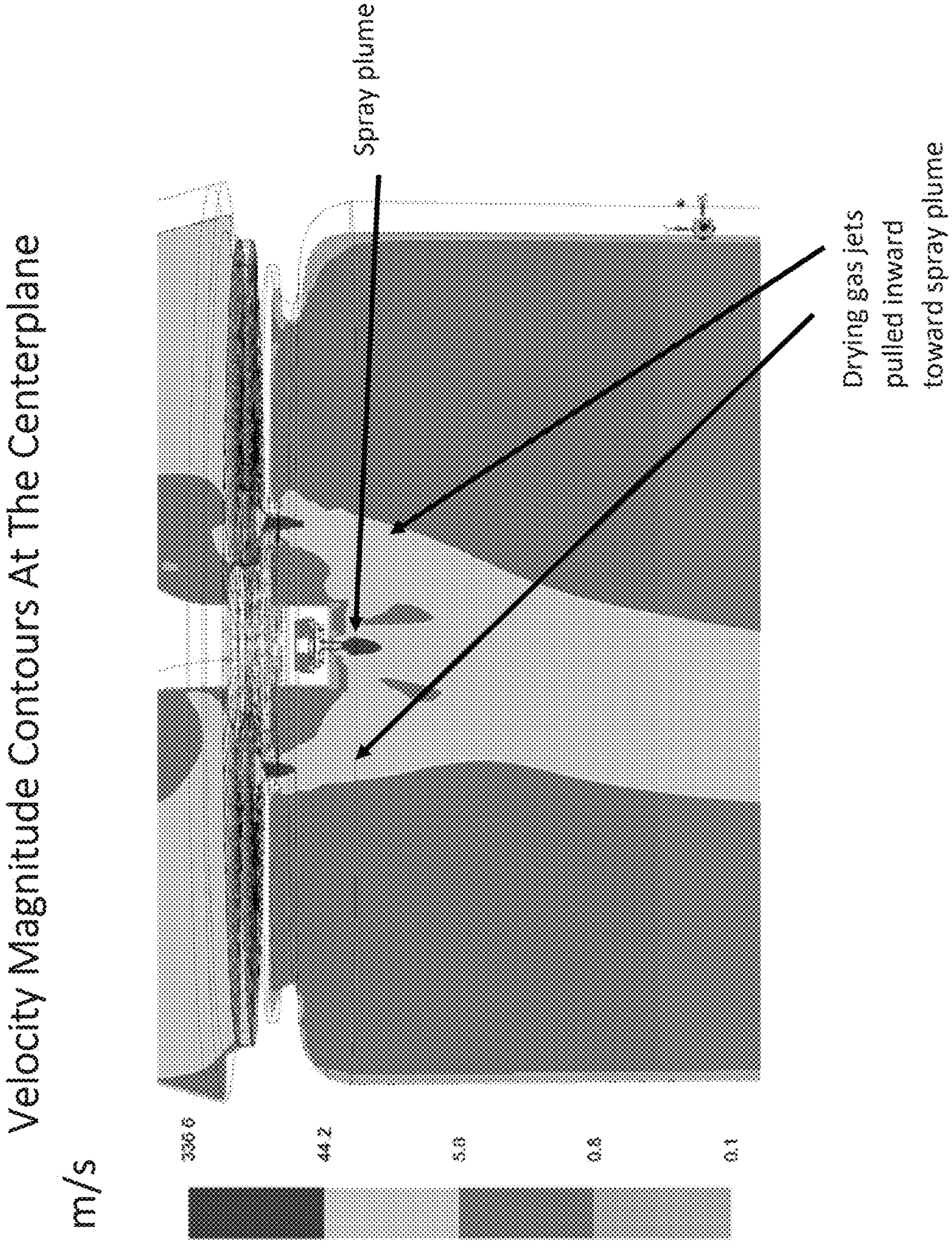
Figure 43P:
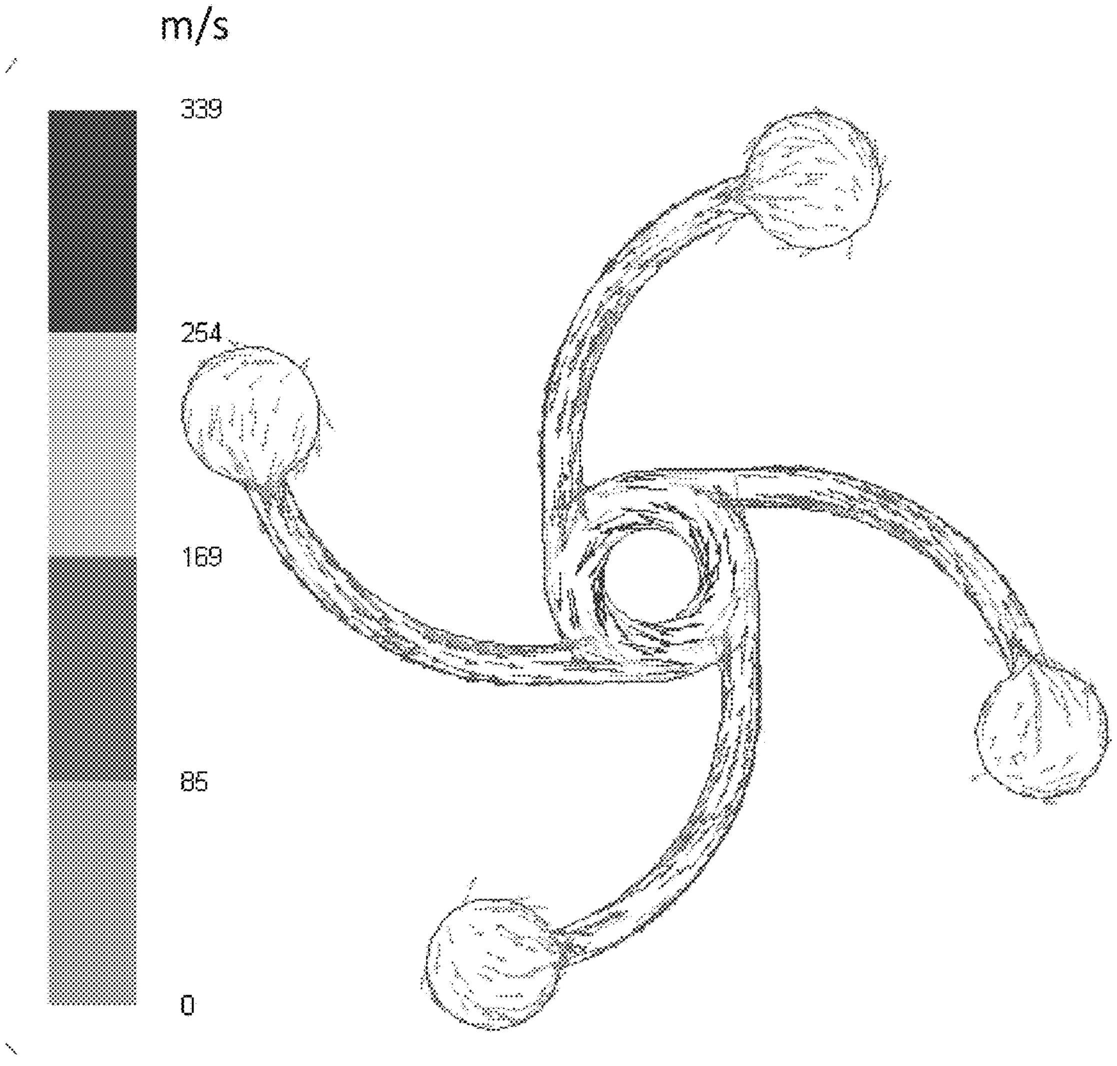
FIG. 43P is a model representation showing gas velocity magnitude flow (m/s) in parts of the vortex generator.

As the vortex is generated, pressure and velocity flow patterns are shown in FIGS. 43O and 43P. FIG. 43O shows the static gas pressure in psig at the top and tangential velocity contours in the pressurized aerosol gas flow in m/s at the bottom. As can be seen, there is an inverse relationship between pressure and velocity. In areas where the pressure is increased, the velocity is decreased and vice versa. In particular, at bulbous head 108 where the pressurized gas enters the vortex generator, there is higher relative static gas pressures (e.g., about $2.54\times10^1$ psig) and relatively low velocity flow rates (e.g., about $2.00\times10^1$ m/s). Conversely, at annulus 81, relatively low or negative gas pressures (e.g., about −2.24 psig) and higher velocity (e.g., between about $-1.58\times10^2$ to about $-3.75\times10^2$ m/s). As the pressurized aerosol gas travels along the curved nozzle cap channel 106, the pressure and velocity are at rates in between. As such, the vortex generator of the present invention has gas pressure of between about $2.54\times10^1$ psig to about −2.24 psig and velocity at a rate between about $2.00\times10^1$ m/s and about $-3.75\times10^2$ m/s. In an embodiment, any vortex generator can be used with the present invention so long as gas pressure and velocity are produced in these ranges. Similarly, FIG. 43P shows a more detailed velocity pattern that occurs in annulus 81. The pressurized gas moves between exits of channels 106 as it integrates into the vortex. The pressurized gas accelerates when it enters annulus 81 and becomes a vortex.

The vortex generator in this embodiment includes a curved pad/ramp, a bulbous head to receive the pressurized air flow and curved channels extending to the exit opening. The present invention can include other vortex generator elements such as wings, edges, wedges, vanes and the like. Other shaped channels can also be employed to create a vortex generator. One of skill in the art can utilize other vortex generators of residing within the insert and the cap of the nozzle assembly of the present invention so long as the pressurized air exits between the inner surface of opening 110 and the outer surface of the cannula 78 in a vortex.

The pressurized air circulates between the outer surface of cannula 78 and the inner surface of opening 110. Specifically, the pressurized gas exits through annulus 81. The plasma is pumped through cannula 78 by peristaltic pump 214 at approximately room temperature. The plasma travels down the inside of stainless-steel cannula 78 and is drawn out of cannula 78 by the pressurized aerosol air flow exiting annulus 81. The high-speed aerosolization air flow atomizes the liquid droplets. In an embodiment, the steady-state plasma feed rate is between about 6 and about 23 mL/min (e.g., 6, 7, 8, 9, 10, 11, 12, 13, 14, 15, 16, 17, 18, 19, 20, 21, 22, or 23). In a preferred embodiment, 13.5 mL/min is the steady-state feed rate after system is warmed-up, in thermal equilibrium.

In an embodiment, the plasma feed rate is related to or dependent on the outlet temperature. This is done in a closed loop. As the outlet temperature lowers, the system adjusts to lower the plasma feed rate. Conversely, as the outlet temperature increases, the system increases the plasma feed rate. The outlet temperature may be lower when the spray dryer is warming up or when time passes between spray drying runs, for example. In particular, in an embodiment, the plasma feed rate can be modulated as follows:

TABLE 7

| Dryer Inlet Temperature C. | System heat loss kW | Dryer Outlet Temperature C. | Dryer Outlet Relative Humidity % | Plasma feed rate mL/min | Reduction in feed rate % change |
|---|---|---|---|---|---|
| 114 | 0.18 | 65 | 11.7 | 13.5 | |
| 100 | 0.18 | 59.3 | 11.8 | 10.5 | 22.2% |
| 80 | 0.18 | 50 | 11.8 | 6.6 | 51.1% |

Chart values calculated based upon thermodynamic principles, assuming constant system heat loss, full droplet evaporation, and a dryer outlet relative humidity of <11.8%.

As such, when the outlet temperature is lower, the plasma feed rate lowers to maintain the target drying chamber outlet temperature needed to dry the plasma to a residual moisture of less than 2%. When the outlet temperature is higher within the range, the plasma feed rate can also be increased, and still maintain a residual moisture content of plasma of less than 2% only if the total gas flow can be increased and/or the drying chamber outlet temperature is allowed to increase to maintain target system relative humidity.

In an embodiment, the closed loop includes exhaust temperature ranging between about 62° C. and about 68° C. and plasma feed rates ranging between about 6 and about 23 mL/min.

Just below the cannula there is negative pressure, while pressurized gas flow is at a high velocity. Generally, the velocity increases along a pathway of decreasing static pressure. The pressurized aerosol gas travels through the series of channels 106 and creates a vortex flow which both atomizes the plasma droplets and directs the initial droplet trajectory. Aerosol flow rate is between about 20 splm and about 60 slpm (e.g., about 20, 25, 30, 35, 40, 45, 50, 55, 60 slpm) and in an embodiment is about 40 slpm. This occurs with a pressure of between about 180 kPa to about 260 kPa (e.g., about 180, 190, 200, 210, 220, 230, 240, 250, 260 kPa) and in an embodiment about 227.5 kPa (33 psig). The aerosol flow acts to draw the liquid feed out of the cannula where it forms a film across the end. The expansion of the aerosol gas as it exits the opening locally cools the near nozzle gas field, which also acts to delay evaporation slightly by cooling the liquid droplets. Also, in an embodiment, the pressure just below the end of cannula is less than that inside the cannula and pressurized gas velocity is accelerating when traveling along the outside surface of the cannula. Upon exit, the spherical plasma droplets hit the pressurized gas to aerosolize and form a spray plume which is surrounded by a ring of drying gas jets, which are further described below. See FIG. 43N. The mixing of aerosol and drying gas sets the initial conditions for the evaporation process.

Figure 43Q:
FIG. 43Q is a schematic showing the transformation of a liquid droplet to a dried particle using the disposable of the present invention.

FIG. 43Q is a schematic that shows the liquid plasma droplet undergoing the drying process. The plasma droplet is atomized at the nozzle assembly cannula exit into the drying chamber and is generally spherical. The dried plasma particle is formed with heat and mass transfer. Drying takes place in two stages. These are: evaporative drying stage (constant rate) drying which occurs in the initial drying (e.g., in, less than 1 second) and falling rate drying (diffusion limited) which occurs after the evaporative drying stage and continues so long as the dried particle is subject to ambient relative humidity lower than its internal relative humidity.

Figure 43R:
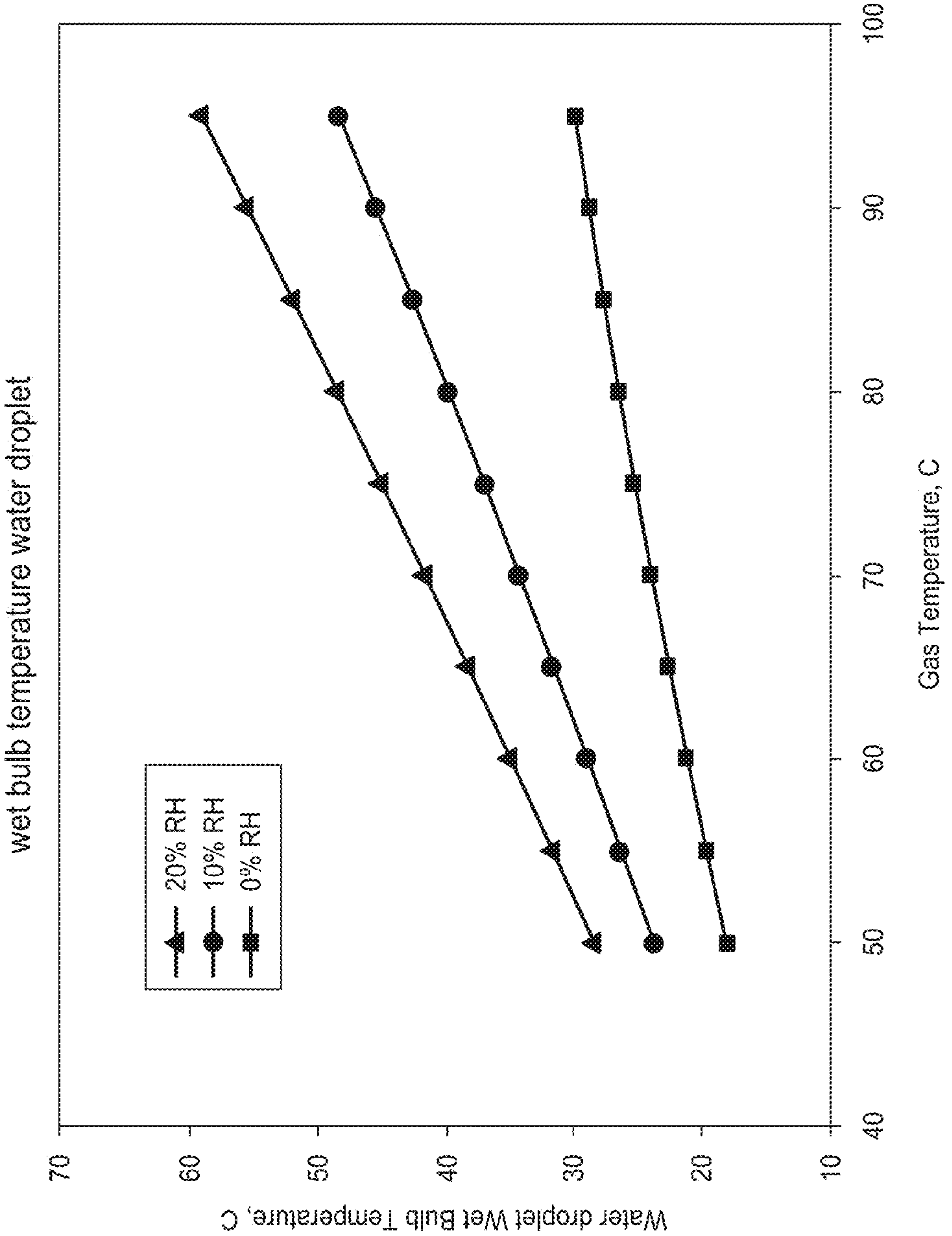
FIG. 43R is a line graph showing the droplet wet bulb temperature in ° C. and drying gas temperature in ° C. of water droplets dried to particles having 0% Relative Humidity (RH), 10% RH and 20% RH. This particular graph illustrates the concept but is not specific to plasma.
Figure 43S:
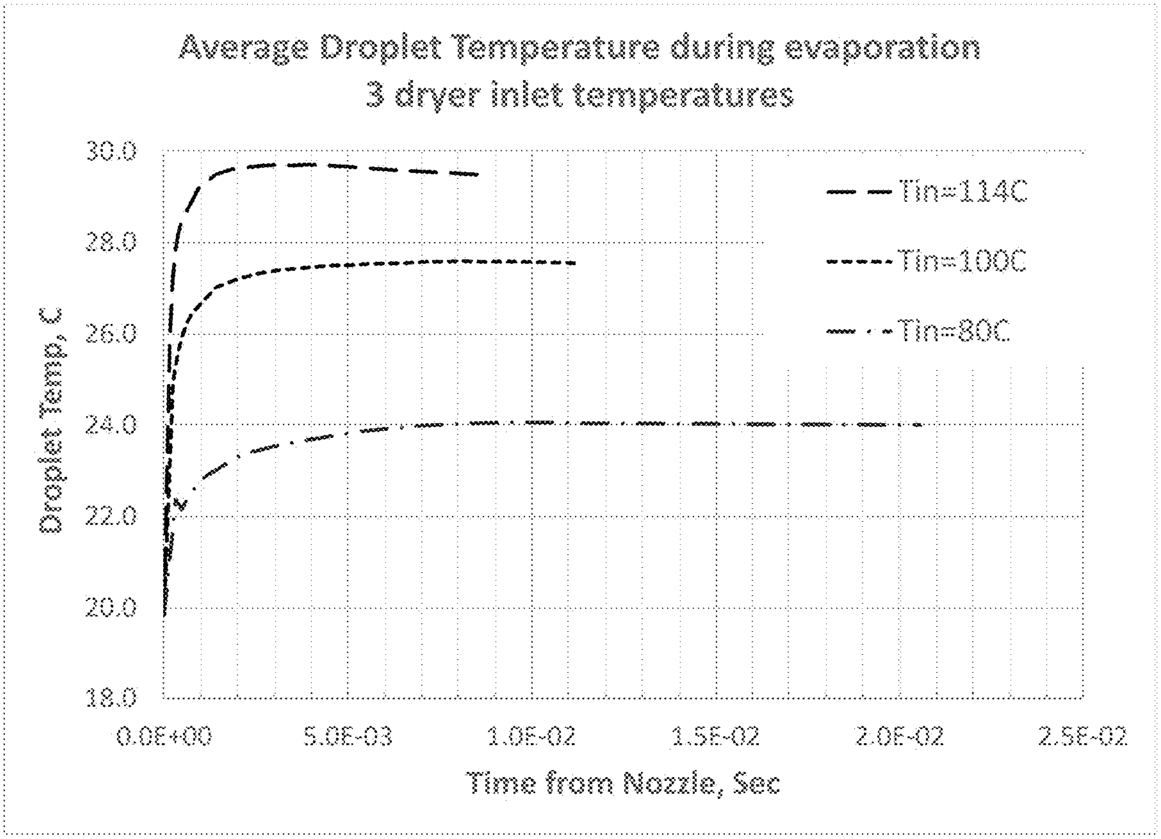
FIG. 43S is a line graph showing the evaporation mass transfer of droplet temperatures over time for all the averaged droplet trajectories average with three simulated drying gas inlet temperatures of 80° C., 100° C., and 114° C. in the model. Note the evaporation process cools the droplet to keep the delicate liquid protein below 30° C.
Figure 43S:
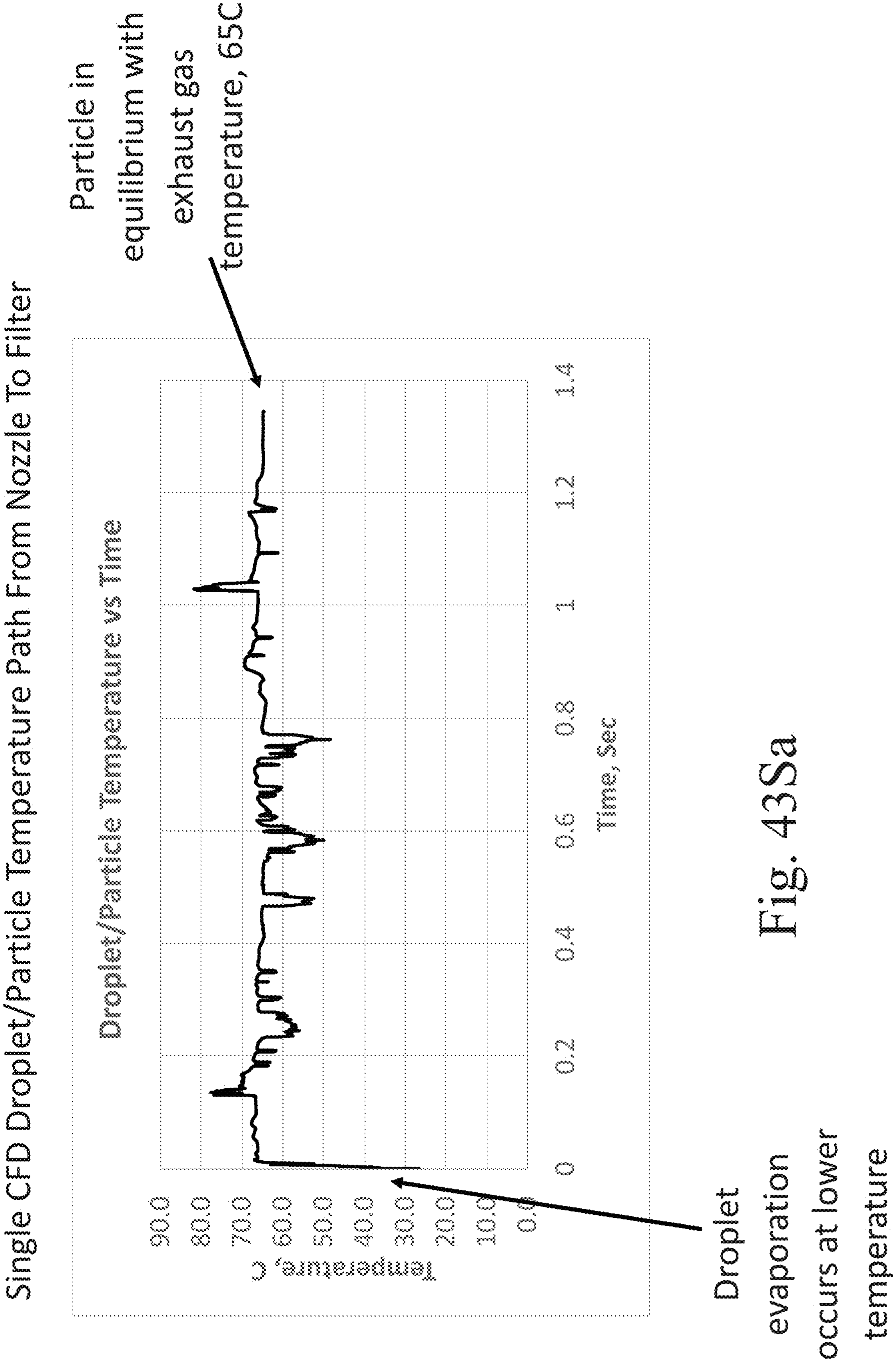

The factors involved in the evaporative drying stage of the plasma droplet include the temperature of the plasma and the drying gas, the surface area of the droplet, the humidity in the drying gas and the air circulation within the plasma drying chamber. When initially exiting the nozzle assembly, the temperature of the drying gas is between about 90° C. to about 130° C. (e.g., between about 100° C. to about 114° C.) and the temperature of the plasma droplet is between about 20° C. and about 65° C. in the plume as shown in FIG. 43Sa. The heat flows from a point of higher temperature to that of a lower temperature, and in this case the drying gas heat flows to the plasma droplet. With respect to the surface area, the droplet is spherical thereby maximizing its surface area and the droplet size is very small so the mass and heat transfer can happen quickly. The relative humidity in the drying gas is very dry (e.g., about 0.1% RH) and therefore the low humidity of the surrounding drying gas promotes evaporation of the plasma particle. Finally, as described in more detail below, the drying gas is emitted using several drying gas jets in an angled and downward direction into the plasma drying chamber and into the plume of atomized droplets to initiate rapid mixing of the drying air and the atomized droplets, which increases the rate of evaporation of the liquid droplets. The drying rate is constant and as the liquid particle evaporates and loses moisture, the moisture transfers from the liquid plasma droplet to the drying gas, and the heat from the drying gas transfers to the plasma droplet making it into a dried particle. The plasma droplet enters the drying chamber essentially at room temperature and the temperature stays constant the majority of the evaporation period. See FIG. 43S. Once most all of the moisture leaves the particle, the temperature of the particle increases to equilibrate with the dryer chamber exit temperature of 65° C. During evaporation, the droplet is maintained at a lower temperature thereby protecting heat sensitive proteins such as vWF. See FIG. 43S. During the evaporation process, the temperature of the liquid droplet and the proteins therein experience a lower temperature, the thermodynamic wet bulb temperature, compared to the inlet drying gas temperature, thereby protecting the proteins. See FIG. 43R. Evaporation reduces protein temperature to near the thermodynamic wet bulb value and when the evaporation slows the particle temperature rises. See FIG. 43Sa.

The starting liquid droplet size produced by the nozzle assembly impacts the residence time in the drying chamber needed to complete evaporation. The larger the liquid droplet, the smaller the ratio of evaporation surface area to droplet mass and the slower the mass transfer rate from the droplet. This slower rate requires a greater distance between nozzle assembly 20 and the lower filter 36 to avoid overly wet particles depositing on the filter membrane of lower filter 36. An overly wet particle causes "plugging or blinding" of the porous filter membrane and the inability to complete the process as the chamber pressure would elevate excessively, preventing production of powder. See FIG. 43T.

Figure 43T:
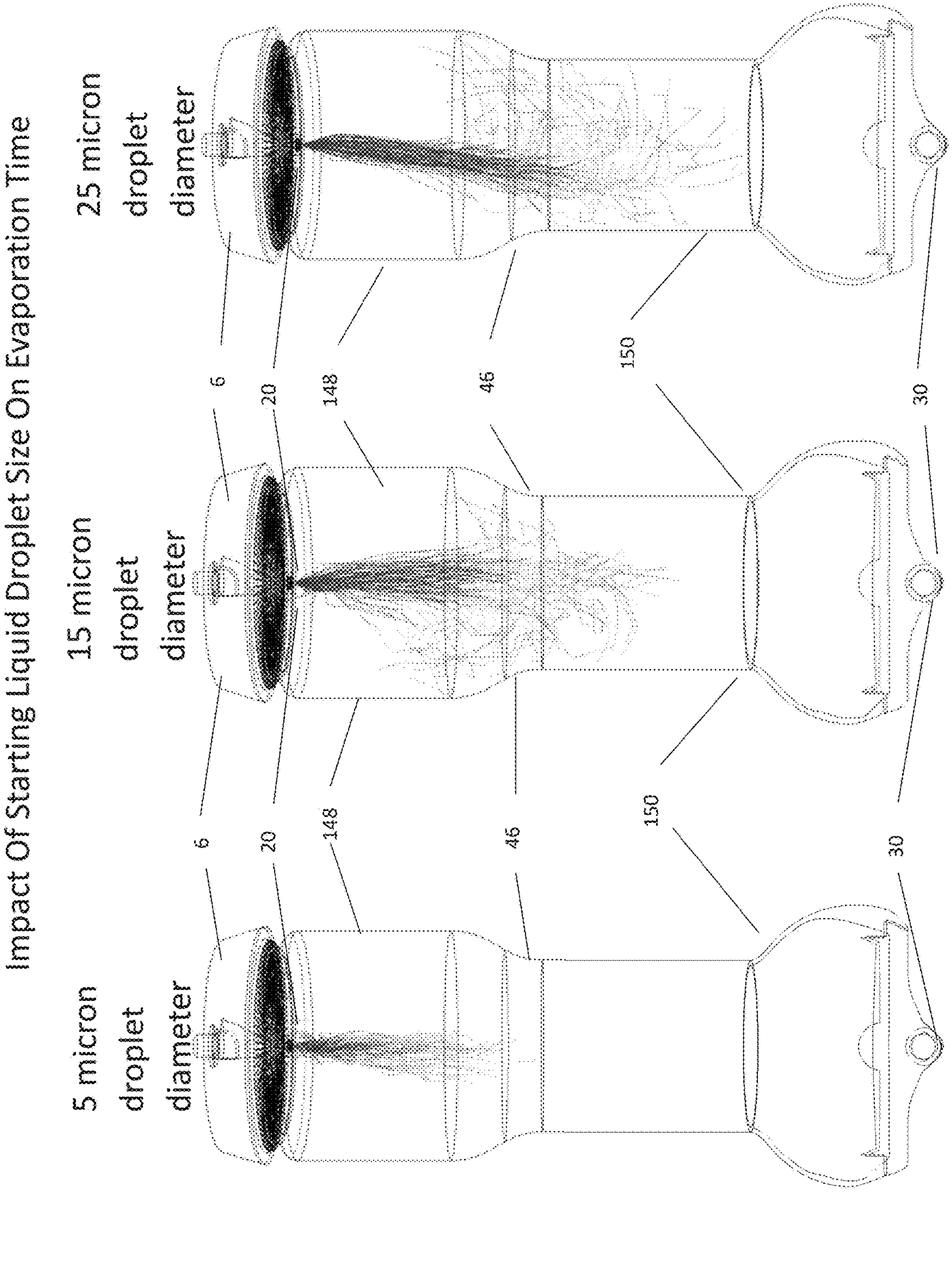
FIG. 43T is a model representation showing the path of droplets having a size of 5 microns, 15 microns and 25 microns, during evaporation, and the figure shows that smaller droplet size allows for more rapid evaporation mass transfer in a shorter path, enabling a physically smaller drying chamber.

Additionally, FIG. 43T shows that in all cases, the majority of the evaporation occurs in the upper portion of disposable 148. This is particularly seen when using a small droplet size, e.g., under 15 microns. As seen from FIG. 43T, the drying chamber can be shortened to that where the majority of the evaporation occurs while still allowing a dried particle to achieve less than 2.5% residual moisture before being deposited on lower filter 36. In other words, in an embodiment, drying chamber 28 can be shortened by an amount between about 8 inches and 1 inch when the droplet size is below about 15 microns and achieves a residual moisture of below about 2.5%.

Turning to the plenum, the functions of the plenum include 1) allowing for the introduction and flow of the drying gas to the disposable, 2) housing the nozzle assembly, and 3) provide support for the drying chamber during the spray drying process. The underside of plenum 6 is shown in FIG. 43J. Plenum 6 has two openings, opening 96 to receive nozzle assembly 20 and drying gas inlet port 22 to receive the drying gas.

Nozzle assembly receiver opening 96 is complementary in shape to the top of nozzle reservoir housing 74 and manifold 72. The top of nozzle assembly 20 is secured in opening 96. The length of nozzle assembly coincides with the height of plenum 6 such that the bottom of nozzle assembly 20 extends past baffle plate 8. See FIGS. 46A and 46B. In certain embodiments, the cannula is flush with the nozzle assembly and the baffle plate. Nozzle assembly 20 can be secured with adhesive, fasteners, or with an interlocking assembly (e.g., a spring latch, screw fit and the like).

The other opening of plenum 6 is drying gas inlet port 22 which receives the drying gas. The drying gas source (not shown) flows into the plenum through drying gas inlet deflector 242, which is shown in FIG. 43K. Once the disposable is secured and aligned, and the door to the spray dryer is closed and spray drying begins. Drying gas inlet deflector 242 lowers through drying gas inlet port 22 to provide the drying gas to plenum 6. Drying gas inlet deflector 242 has the shape of an elbow so that the drying gas flows toward the far inside side wall of the plenum creating a tangential mixture, as shown in FIG. 43Ka. The right angle of deflector 242 distributes the drying gas throughout plenum 6, creating a low velocity, highly uniform pressure reservoir. Uniformity is desired to create low velocity, uniform pressure of the drying gas as it exists each of drying jets 142. When the drying gas is not deflected off the side of plenum 6 but instead in a downward direction, the air pressure can be asymmetrical with drying jet closer to the drying gas inlet experiencing high pressures as compared to those farther away from the inlet. Accordingly, the present invention includes a drying gas inlet that is deflected to the side of plenum e.g., with a 90-degree elbow as is the case with deflector 242. Other geometries of deflector 242 can be employed to create a uniform air pressure in plenum 6. For example, the deflector can be angled at degree less than a 90-degree angle, as measured from the top surface of the plenum. For example, the deflector can have angle ranging between about 60 and about 110 degrees relative to the top surface of plenum 6 so that the drying gas pressure across the width of plenum 6 is substantially uniform. Alternatively, more than one drying gas inlet from opposing sides can be used to create a substantially uniform drying gas pressure across the width of plenum 6.

As shown in FIG. 43J, plenum 6 has concentric ribs 98 and radiating ribs 102. These ridges provide support for the structure of plenum 6. The additional support provided by the concentric and radiating ribs allow the plenum to withstand the pressure and heat of the spray drying process. Since the drying gas is a low velocity, uniform pressure air container, concentric ribs 98 and radiating ribs 102 do not contribute to or affect the drying gas air flow. Similarly, the projections on the inside side wall of the plenum, projections 104, are used in the injection molding process when making the plenum and are not involved in the drying gas flow.

Referring to FIGS. 43L, 43La, and 43M, the baffle plate has several functions as follows: A) serves as a support in securing disposable 100 when the disposable is aligned and inserted into spray dryer 200, B), creates drying gas air flow channels and releases the drying air into plasma drying chamber 28 of disposable 100, and C) supports baffle filter 94.

FIG. 43L shows the top, inside view of baffle plate 8. The inner surface of baffle plate 8 has baffle plate nozzle opening 140 through which a portion of nozzle assembly 20 resides. Baffle plate 8 also includes raised outer ring 124 with its base 126 and raised inner ring 128 with its base 130. Outer sealing ring 90 is placed around outer ring 124 and inner sealing ring 92 is placed round inner ring 128. The sealing rings prevent drying gas from flow out the edges of filter 94 and instead the drying gas flows through it. The inner side of baffle plate 8 further includes locator 132 for insertion of locator notch 26 of plenum 6. The plenum and baffle plate have locators to align one another. Baffle plate 8 has baffle locator 132 that receives plenum locator 152 on plenum 6.

Baffle plate ribs, 134, 136 and 138 provide support to baffle plate filter 94 (shown in FIG. 43L) while keeping most of the surface of filter 94 lifted off the baffle plate during use. The baffle plate ribs also act as a guide for the drying gas flow. It has been determined that if the baffle plate filter 94 lies flat on the inner side of baffle plate 8 without ribs, the drying gas flow slows and does not freely flow through the plurality of drying jets 142. To obviate that phenomenon, in particular, baffle plate 8 has radiating ribs 134 which connects inner ring base 130 with outer ring base 126. Each radiating rib 134 has a consistent profile throughout its length and allows the filter to sit in a raised position, as compared to resting directly on inner surface of the baffle plate. Radiating ribs 134 also form pie-shaped air channel 139 leading to drying jet 142. Radiating ribs 134 are the side walls of pie-shaped air channel 139. Baffle plate 8 has two types of ribs that extend from outer ring base 126 but do not connect with or reach inner ring base 130. Of these types of ribs, there is shorter radiating rib 136 and intermediate radiating rib 138. Both shorter radiating ribs 136 and intermediate radiating ribs 138 have a consistent profile in height as it proceeds from outer ring base 126 inward and then quickly tapers at tapered end 137. The tapered end 137 aids in supporting the filter without creating a corner on which the filter could be pierced. In particular, baffle filter 94 rests atop ribs 134, 136 and 138 and is pressed against the ribs during spray dryer operation by air pressure e.g., of about 11.5 psig. The tapered ends on ribs 136 and 138 reduce the stress placed on the baffle filter, prevents damage to the filter and reduces loss of filtration efficiency. See FIG. 43La. The ribs keep baffle filter 94 from adhering to the inner baffle plate surface. Connecting ribs and non-connecting ribs are interspersed on the baffle plate inner surface and in the embodiment shown in FIG. 43L form a pattern within pie-shaped air channel 139 (e.g., connecting rib, shorter non-connecting rib, two intermediate non-connecting ribs, shorter non-connecting rib, connecting rib, etc.). Each pie-shaped air flow channel 139 defined by two connecting ribs on either side. The connecting and non-connecting ribs can be any pattern so long as they provide support for baffle filter 94 while also allowing drying gas to flow through filter 94 and beneath filter 94 and through the air channels 139 to drying jets 142. For example, FIG. 43La shows another arrangement of ribs 136 and 138.

In an embodiment, the pressure drops when the drying gas passes baffle filter 94. The input drying air pressure in plenum 6 before traveling through the filter into the pie-shaped air flow channel 139, during operation, is between about 8 and about 15 psig, and in an embodiment is approximately 10.4 psig, When the drying gas passes baffle filter 94, the pressure drops by about 40-60% or in an embodiment by approximately 6 psig, The pressure decrease across baffle filter 94 is utilized to aid the uniform distribution of drying gas being injected into the drying chamber as shown in FIG. 43Ma. This feature helps to minimize asymmetric drying within the chamber to enable the overall shorter length. The resultant pressure in the drying chamber 28 in area defined by Dimension Z ranges between about 4 psig and about 7 psig and in an embodiment is approximately 5.5 psig. Although further described later herein, lower filter 36 of disposable 100 causes a pressure drop by about 40-80% or in an embodiment by approximately 3.0-5.5 psig that increases as dried plasma accumulates on the filter resulting in exiting air pressure of approximately 1-2.5 psig. In an embodiment, the gas exhaust port 208 of spray dyer 200 is slightly constricted so that the exhaust gas leading to the outside is about 1.5 to about 3 psig. If there are valves, sensors or tubing length past the exhaust exit those will add a small pressure increase.

In an embodiment, the flow of drying gas passing through and over the baffle plate 8 is not restricted. In an aspect, the height and placement of the ribs 134, 136, 138 of baffle plate 8 are such that the baffle plate filter 96 does distort somewhat under the pressure of the drying air but has no material effect on the pressure drop. Note that baffle plate filter 96 does create a pressure drop as the drying gas passes through it, as described above, but not so with baffle plate 8 itself. The cross-sectional area of pie shape channels 139 is equal to or greater to the cross-sectional area of the opening of the drying gas inlet deflector 242. Or alternatively, the cross-sectional area of pie shape channels 139 are equal or greater to the sum of the cross-sectional area of sum of all of the openings of the drying gas jets 142.

The data shown in Example 8 show that that air flow channels 139 of baffle plate 8 shown in FIG. 43L does not impede the bacterial filtration efficiency (BFE) of baffle filter 94 permitting a greater than log 6 reduction of pathogens when challenged by *S. aureus* in BFE under American Society for Testing and Materials (ASTM) F2101-14 and does not damage the baffle filter 94 during operation of the spray dryer 200. See Examples 8 and 9.

In an embodiment, baffle filter 94 is a 0.2 micron filter (e.g., 0.22 micron filter) that prevents pathogens that may be introduced into the drying gas from entering the drying chamber. The filter can be at least a 0.2 micron filter, e.g., a 0.1 micron filter or less so long as drying gas can flow through as described herein. The filter is strong enough to withstand heat and pressure of the spray drying process but flexible enough to not tear when pressed against the ribs as air flows through it. The baffle filter is such a filter and can be a 0.4-micron depth or membrane filter. The filter is commercially manufactured by Gore (231 East Oak Street Bozeman, Montana USA) Lydal (Rochester New Hampshire USA), Teijin (Chiyoda City, Tokyo, Japan), or Sabeu (Northeim, Germany). Any type of commercially available filter can be used so long as can prevent pathogens from being introduced into the drying chamber, but porous enough to allow drying gas to pass through it at the flow rates specified. The baffle filter and lower filter can be made from e.g., a polyethylene filter matrix. In an embodiment, baffle filter 94 is commercially available from Sabeu of Northeim Germany as Art. No. 063090.

Referring to FIG. 43M, the underside of the baffle plate can be seen. After the drying gas passes through baffle filter 94 it exits through a plurality of drying gas jets 142. In an embodiment, drying gas jets 142 have centerlines along their length that are parallel to one another and perpendicular to the baffle plate 8. Despite the mechanical structure described of jets 142 the drying gas air exiting from them does so in an inwardly angled manner toward the center line of drying chamber 28. FIG. 43N and FIG. 43Na shows the flow pattern of drying gas jets 142.

Drying gas jets 142 effectively create an "drying gas air wall," as shown in FIG. 43Ma, within plasma drying chamber 28 while promoting rapid mixing with the atomized plasma particles. The drying jet air flow are directed, in part, to the plume of atomized liquid plasma droplet for rapid mixing. The drying gas air wall minimizes build-up of dried plasma on the inner wall of plasma drying chamber 28.

A plurality of indentations 144 exists inside the plurality of drying gas jets 142. Indentations 144 are used to provide additional support to the structure so that plenum 6 and baffle plate 8 do not buckle during spray drying and are not involved in the air flow. Drying gas jets 142 are concentrically positioned in relation to indentations 144. In the embodiment shown in FIG. 43M, there are 16 drying jets 142. The present invention can have more or less drying jets, ranging from 2-32 jets.

Additionally, drying gas jets 142 are not flush with the baffle plate but extend past the plane of baffle plate, similar to the nozzle assembly. Extending nozzle assembly 20 and drying gas jets 142 past the plane of the baffle plate allows for drying of the plasma to occur away from the baffle plate surface so that the dried plasma build up is reduced on the baffle plate's outer surface and/or to the bottom surface of the nozzle assembly during the drying process.

In light of the structures above, the heated drying gas dries the atomized plasma droplet as follows. Heated drying gas is fed to the top of the plenum through deflector 242 at flow between about 500 slpm to about 1000 slpm (e.g., about 500, 550, 600, 650 700, 750 800, 850, 900, 950, 1000 slpm) and in an embodiment at about 750 slpm. Heated drying gas enters the plenum at a temperature between about 100° C. to about 130° C. (e.g., about 100, 105, 110, 115, 120, 125, 130° C.) and in an embodiment at about 114° C. Deflector 242 diverts gas 90 degrees to aid uniformity of the air flow within the plenum. Drying gas is forced through baffle filter 94 (e.g., a 0.2 micron, sterilizing rated filter) which sits on the top side of the baffle plate. As described above, baffle plate 8 is designed with channels to create pie shaped air channel 139 with the filter providing the top surface of the channels. Pie shaped ducts 139 direct the drying gas to the 16 individual drying gas jets 142. This flow structure creates jets which are directed inward, toward the atomizer to aid on the plume containment. The mixing of the heated drying gas, aerosol gas, liquid droplets and water vapor drive the evaporation to convert the plasma into dried powder. That process will largely be completed in less than one second at the present invention's spray drying process conditions, with individual particles formed in the upper portion, defined by Dimension X of drying chamber 28.

Inner concentric ridge 146 of on outer side of baffle plate 8 is the base for attachment of the wall of plasma drying chamber 28. Plasma drying chamber 28 can be attached to baffle plate 8 with a collar or ring, an adhesive, a fastener and the like. Plasma drying chamber 28 can also be attached to baffle plate 8 at ridge 146 by heating welding the chamber to baffle plate 8. A point of attachment can also be molded as part of the baffle plate. The drying chamber can be attached to the baffle plate in any number of ways that are commercially available.

Detailed Description of the Drying Chamber

As mentioned herein, the purpose of drying chamber 28 is: A) to allow for the drying of sprayed plasma while preserving proteins and their function, B) to capture the dried plasma while allowing the gas to exit, and C) to later transform into the commercial dried plasma unit without a filter. The drying chamber in an embodiment is a sterile, non-pyrogenic, single use dual purpose chamber, where the plasma is dried, collected and stored in a portion of the chamber for use.

Exploding FIG. 44 and FIG. 46A show drying chamber 28 which includes an upper section defined by length X, a midsection defined by length U and a lower section defined by length V.

Upper portion 148 is attached to baffle plate 8 via baffle plate ring 156 at outer concentric ring 146. Through baffle plate 8 protrudes nozzle assembly 20. As mentioned above, nozzle assembly 20 and dry gas jets 142 extend past the plane defined by baffle plate 8. As such the convergence of the atomized plasma occurs in upper portion 148 of plasma drying chamber 28. Most of the drying of the atomized plasma particle occurs in upper portion 148 although the plasma does continue to dry as it travels along the length of drying chamber 28. When the pressurized air is in the nozzle assembly, it is a vortex configuration. As the plasma film exits the cannula and the pressurized air exits the annulus as a vortex, the droplets aerosolize or atomize, and form a plume, and the vortex configuration weakens and widens as it travels downward, as shown in FIG. 43N. Meanwhile, drying gas jets 142 direct gas so that the flow is angled inwardly toward the plume to contain the plume and rapidly mix with the aerosolized plasma droplets. The combination of the weakened vortex and the flow from the angled drying gas flow dilute the spray plume of plasma droplets to get more drying gas around the plasma droplet to promote rapid mixing of the drying gas and the droplets. This action promotes efficient evaporation of the plasma droplet, which occurs nearly entirely in the upper portion of the drying chamber. When rapid mixing occurs, as it does with the present invention, the droplet evaporates and does so relatively quickly and at a lower temperature than the drying gas, which preserves the plasma proteins. See FIG. 43S. In contrast to freeze dried plasma, the rapid drying of the plasma of the present invention largely obviates the formation of crystals, especially undesirable cholesterol crystals in the dried plasma.

The gas flow from drying air jets 142 form an air curtain to impede the dried plasma particles from depositing on the inner side wall of the drying chamber. Additionally, the angled air wall formed from drying jets 142 also serve to direct the dried plasma particles in a downward direction toward lower filter 36.

Although most of the plasma undergoes evaporation and dries in upper section 148, drying of plasma continues in midsection 46, defined by Dimension U. Midsection 46 that has "seal and separate" locations 44A and 44B, label 40, spike ports 42A and 42B and hanging slot 34. "Seal and separate" locations 44A and 44B are the locations at which drying chamber 28 is cut to create dried plasma unit 60 (shown in FIG. 49). As described herein, a finishing apparatus, apparatus 400, moves the plasma within the disposable and seals and separates at locations 44A and 44B to isolate midsection 46 and remove upper portion 148 and lower portion 150 of the disposable to create the dried plasma unit. Spike ports 42A and 42B are for use with the dried plasma units. The spike ports can be used to reconstitute the dried plasma with a reconstitution solution or sterile water for injection (SWFI). Spike ports are plugging and/or connecting devices, and can be in the form of a "twist off" to expose the connecting port used for an aseptic environment. Other commercially available connectors and adaptors for spike ports can be used so long as it is appropriate for an aseptic environment. Hanging slot 34 is an opening that is used to attached plasma bag 64 to an IV (intravenous) pole. Spike ports 42A and 42B, and hanging slot 34, are made and used in the same way as those on IV medical bags. Midsection 46 also includes locator pin openings 32C. Locator pin openings 32C are used to secure disposable 100 to finishing apparatus 400 so that disposable 100 stays in place during sealing and separating, as further described herein.

Although most of the plasma undergoes evaporation and dries in upper section 148, the drying does continue in lower section 150, defined by Dimension V. Referring to exploding view of the disposable in FIG. 44, the lower section of drying chamber 28 includes lower filter 36, lower filter separator 38, drying gas outlet port 30, and locator pin openings 32A and 32B. The humid air (e.g., the drying gas, the aerosolized gas and removed moisture from the plasma aerosolized droplets) passes to the lower section 150 through lower filter 36, lower filter separator 38 and out gas outlet 30, which is secured to gas exhaust port 208. The humid air travels through the channel or space between filter 36 and the outer wall of drying chamber 28 and then out through gas exhaust port 208 and is filtered and emitted to outside air.

When air is exhausted to the outside air, a filter is used to prevent contamination of plasma in the spray dryer in case of a breach. Such a filter can be a HEPA filter, a UPLA filter, and the like. A HEPA filter for filtering the exhausted air can be purchased commercially.

Lower/capture filter 36 separates the dried plasma from the humid air. In particular, lower filter 36 traps the dried plasma particles/powder while allowing the humid air to pass. The dried plasma builds up on the filter throughout the drying process. The goal of the drying process is to complete most of the evaporation (i.e., complete the mass transfer process) of the plasma droplet before the dried particle hits the filter surface. Effective evaporation occurs when rapid mixing of the drying air with an atomized plasma droplet size distribution having a size between about 1 microns and about 35 microns. Rapid mixing, as described herein, is enhanced by the vortex flow of pressurized air, the droplet size of the atomized plasma droplet and the drying gas flow. The length of the drying chamber is dependent on the atomized plasma droplet size. A shorter drying chamber provides less time for the droplet to complete the evaporation/mass transfer, and for a longer drying chamber, a larger the droplet can be used. The completion of the evaporation process of a particular droplet size depends, in part, on the drying chamber length. As the initial plasma particles gathers on the filter; subsequent dried plasma particles create a depth of powder that the air flow permeates across and pressure in the system does build but still allows humid air to effectively pass. When the dried plasma particle has a residual moisture of less than 2%, the humid air can pass through the dried plasma on the lower filter 36, through lower filter 36, and out gas outlet 30/gas exhaust port 208.

The dried plasma produced of the present invention is a fine, highly amorphous and quite dry (e.g., less than 2% residual moisture) powder so that little or no clogging of lower filter 36 occurs.

The initial powder when entering the lower filter is exposed to chamber outlet temperature for the duration of the batch, while subsequent powder has less residence time in the filter. The percent residual moisture in the plasma dried with the disposable and dryer of present invention is very low, e.g., below about 2.5%, 2%, 1%, preferably about 1.46% residual moisture, as measured by Karl Fischer moisture sensor, Model No. C30S Compact KF Coulometer (Mettler Toledo Billerica Massachusetts USA). This is a very low moisture level which is due to effective and efficient evaporation of the plasma droplet occurring in the upper portions of drying chamber 28 and the process conditions. In this aspect, powder moisture level is in equilibrium with chamber outlet air stream relative humidity. Plasma particles with higher moisture levels would build up on lower filter 36 and cause the humid air to pass through the filter at a slower rate thereby building up pressure within the chamber. Essentially, plasma particles with too much moisture and inefficient evaporation would clog the filter and prevent or severely reduce flow of the humid air. The present invention, however, has efficient evaporation thereby allowing humid air to pass through the captured dried plasma particles. Dried plasma with low moisture improves protein stability during storage.

In an embodiment, lower filter 36 is a 0.2 micron filter such that the pore size is small enough to prevent the plasma particle from passing through while allowing the humid air to pass with minimal pressure build-up. The filter can be at least a 0.2 micron filter, e.g., a 0.1 micron filter or less so long as humid air can flow through as described herein. Lower filter 36 is commercially available from Lydall Inc. of Rochester New Hampshire USA as model no. 70L02A.

Lower filter 36 is supported by a filter frame built in or attached to filter 36 and that can also be attached to the inner wall of plasma drying chamber 28. Filter 36 is attached to the entire circumference of the inner wall. In other words, the filter frame or the filter itself is attached all the way around the inner wall of drying chamber 28 such that there is no opening between the inner wall and the point of attachment of filter 36. The attachment of the filter to the inner wall in this fashion forms a barrier to the dried plasma particles and humid air which forces the plasma and humid air to move downward toward gas outlet 30 with filter 36 trapping the dried plasma while allowing the humid air to pass. Filter frame 37 is attached to inner surface of drying chamber 28 by heat welding. In other embodiments, the filter frame can be attached to the inner surface of drying chamber 28 by combined adhesive (e.g., UV adhesive) and RF welding e.g., by Dielectrics unit of UFP, Inc. of Chicopee Massachusetts USA.

Figure 44A:
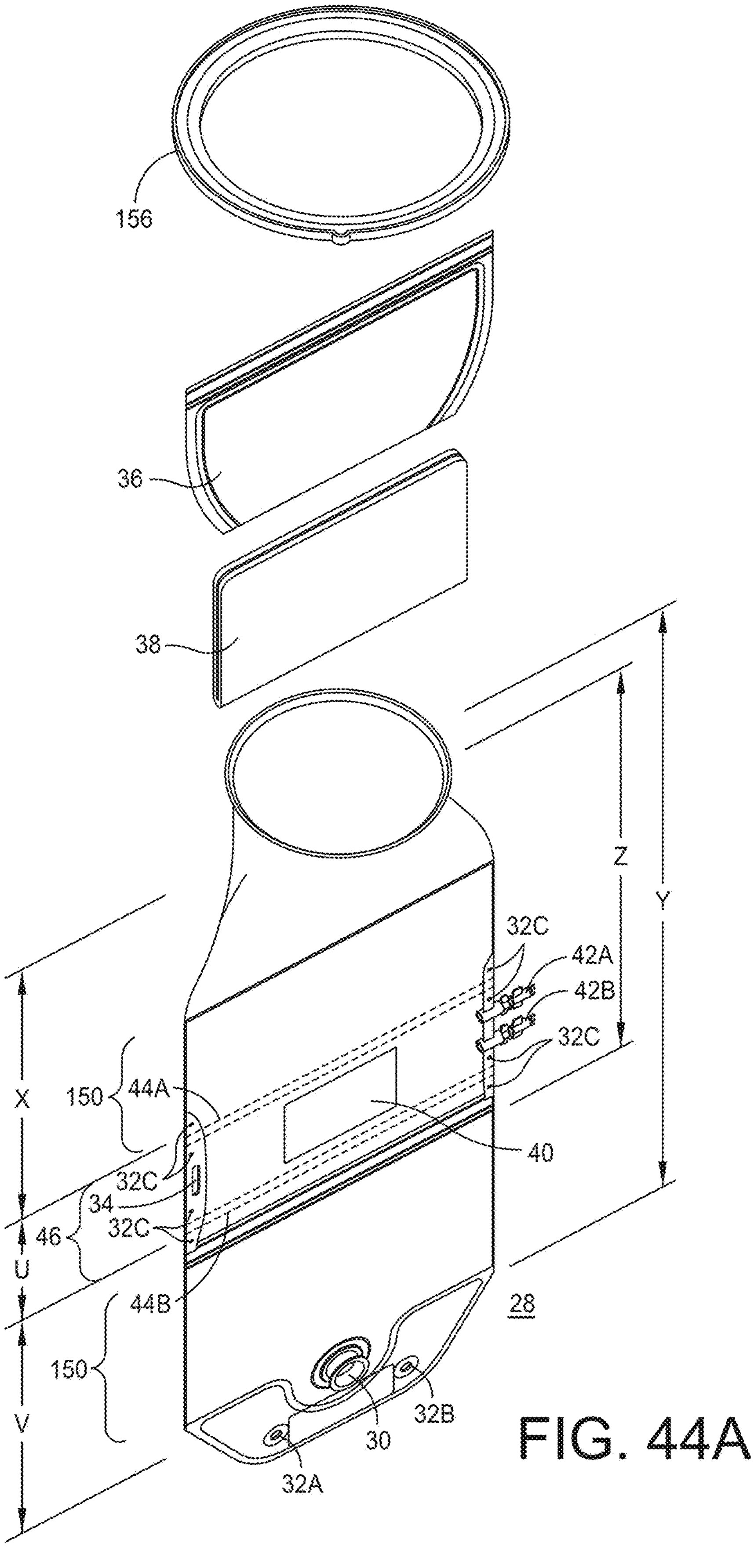
FIG. 44A is a schematic showing an exploding view of the drying chamber of the spray drying disposable shown in FIG. 42A.
Figure 44B:
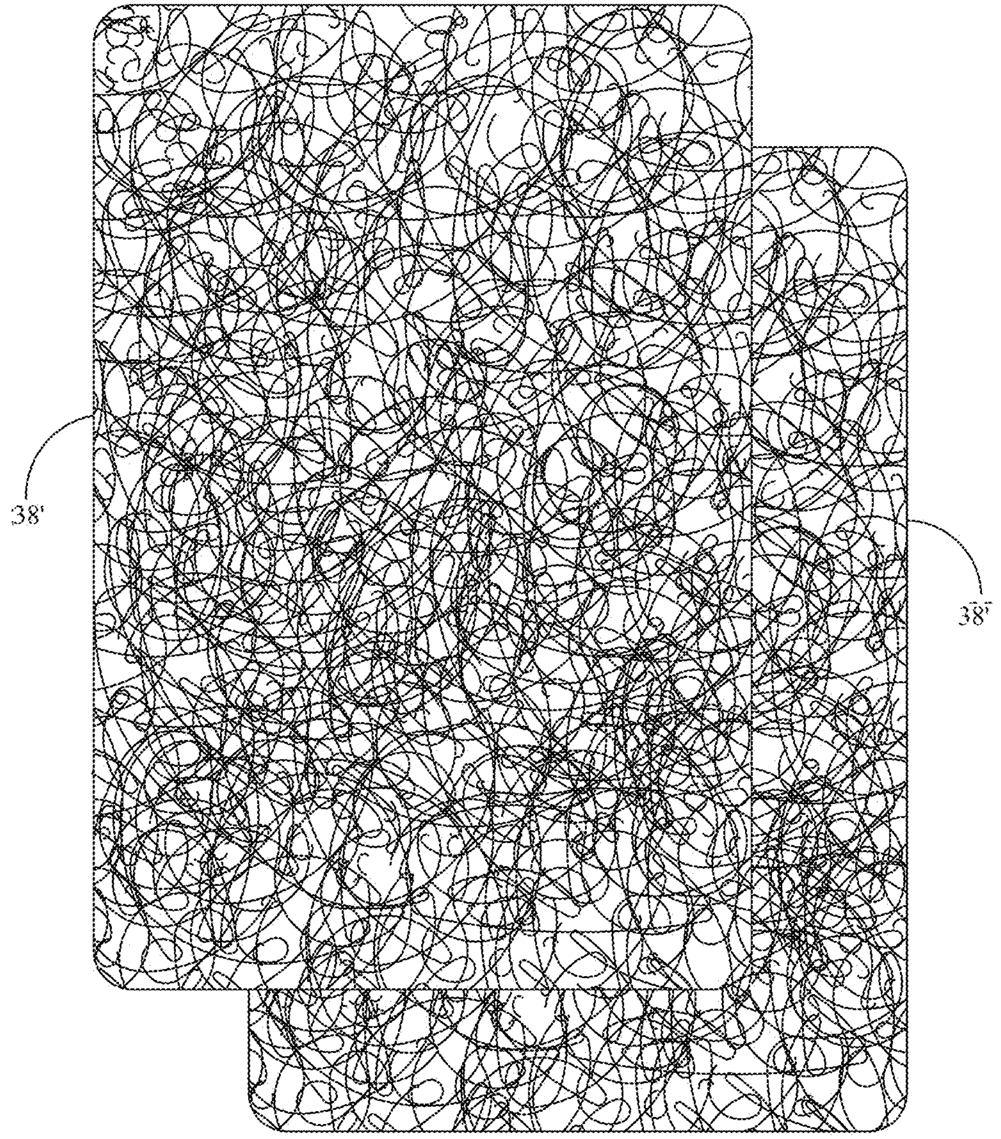
FIG. 44B is a schematic showing a front view of a separator or spacer that can be used in the drying chamber of the spray drying disposable.

Lower filter separator 38, as shown in FIGS. 44A and 44B, is positioned between filter 36 and the inner wall of drying chamber 28. Separator 38 acts in a similar way as the ribs of the baffle plate and lifts the filter away from the inner wall of drying chamber 28. The separating/lifting action prevents the filter from adhering to the inner wall of drying chamber 28 to allow the humid air to pass more easily and prevent pressure build-up. Lower filter separator 38 can be textured or ribbed to maintain space between filter 36 and the inner wall of drying chamber 28. In an embodiment, filter separator 38 is ribbed with a plurality of spacers. See FIGS. 42A and 44A. In another embodiment, filter separator 38' has a porous and coarse circular weave of filaments. See FIG. 44B. In the embodiment shown in FIG. 44B, the separator is two pieces. The separator can be made from a single piece or multiple pieces (e.g., 1, 2, 3, 4, 5, 6 pieces). Any type of spacer or standoff can be used to maintain separation between filter 36 and the inner wall of drying chamber 28. Another example of a separator includes a flexible three-dimensional matrix of polymeric filaments. In the embodiment showing in FIG. 44, separator 38 surrounds most of filter 36. In other embodiments, separator 38 only need to surround enough of filter 36 to maintain a space between filter 36 and inner wall of drying chamber 28. Spacer/separator 38 is made from a material that can withstand the heat and pressure of the spray drying process and does not affect the plasma. In an embodiment, the separator is injection molded and can be made from olefins or thermoplastic elastomers such as polyester or polypropylene. In another embodiment, the separator can be made from nylon with a thermoplastic polyurethane frame. In the embodiment shown in FIGS. 42A and 44A, separator 38 is Baltex NPD 88 grade with a width is 8.750 in +/−0.65, height is 13.000 in +/−0.65, thickness is about 0.197 inches. The material used for this embodiment is 100% Polyester Spacer Mesh Fabric. In the embodiment shown in FIG. 44B, separator 38' is two pieces and is from Model 02257 (Freudenberg Filtration Technologies Weinheim, Baden-Wuerttemberg, Germany) with a width of about 8.80 in +/−0.06, height of about 6.40 in +/−0.06 and thickness of about 0.197 in +0.030/−0.010. During the drying of the plasma, the humid air passes through lower filter 36 and lower filter separator 38 or 38' and out of gas outlet 30 leaving dried plasma in lower filter 36.

Another important aspect relates to the length of disposable 100. In earlier versions, the disposable was about 66 inches long. The longer disposable allows for more time, space and heat to dry the plasma particle. However, the longer disposable was difficult for an operator to install and use, cumbersome and difficult to handle. See Example 30 and 31. In fact, a 66-inch-long disposable is longer than the height of many operators such as a US female of 5'6" height who is in the 79$^{th}$ percentile, according to CDC MHANES 2015-2016 data. Males of 5'6" and shorter comprise the 14$^{th}$ percentile for the US according to the same data which is still sizable number of potential operators of the present invention.

Shortening the disposable to that shown in FIG. 42A posed several challenges. A shorter disposable means that there is a shorter drying chamber. A shorter drying chamber means that the plasma particle had to be evaporated and dried in less distance, in a smaller volume, and in less time and all without damaging the proteins in the plasma. In other words, the plasma had to dried gently but faster and in less space.

Despite these obstacles, the present invention includes disposable 100 having a length of about 40 inches or less (e.g., about 40, 39, 38, 37, 36, 35, 34, 33, 32, 31, 30, 29, 28, 27, 26, 25, or 24 inches or less) and preferably about 34.8 inches. At 34.8" in length the disposable 100 is readily handled, installed in and removed from the dryer and other portions of the processing equipment by minimally trained personnel in the range of heights from the 5$^{th}$ (4'11") to the 99$^{th}$ (6'6") percentile of men and women according to data for the United States. See Examples 30-33.

The disposable length, as measured from the bottom of spray drying head 2 or bottom of baffle plate 8 to top of the bottom filter 36, shown as dimension Y in FIG. 44, is about 31 inches or less (e.g., about 31, 30, 29, 28, 27, 26, 25, 24, 23, 22, 21, 20, 19 inches or less) and in an embodiment preferably about 25.90 inches. In another aspect, the area of disposable 100 encompassed by Dimension Z, the length from the bottom of spray drying head 2 and the top of filter 36, is about 22 inches or less (e.g., about 22, 21, 20, 19, 18, 17, 16, 15, 14 inches) and preferably about 19.11 inches. In yet another, the length of Dimension X, the length between the bottom of spray drying head 2 and the top section 46, is less than about 16 inches (e.g., about 16, 15, 14, 13, 12, 11, 10, 9, 8 inches) and preferably about 12.14 inches.

In fact, when comparing the earlier developmental version of the disposable, having the length of the disposable was about 66 inches and Dimension Z was about 48 inches, to the disposable of the present invention, the difference in the overall length is about 30 inches or a 46% reduction and the difference in Dimension Z is about 29 inches or a 60% reduction. The significant difference can be accomplished by shortening the entire length of disposable or along Dimensions X, Y, and/or Z. In another embodiment, the length of the present invention can be further shortened along dimension X by about 1 inch to about 8 inches (e.g., by 1, 2, 3, 4, 5, 6, 7, or 8 inches) thereby reducing the overall length by the same amount. In an embodiment, length X ranges between about 30 and about 37 inches. In other embodiments, the disposable can also be shortened anywhere along Dimension Y and Z by the same amount.

This shorter disposable, disposable 100, dries liquid plasma that retains protein function of even the most fragile proteins such as von Willebrand's factor and other proteins. The spray drying system of the present invention and that shown in the figures meets FDA vWF requirements.

Shortening the length of the disposable 100, which includes spray dry head 2 and plasma drying chamber 28, of the present invention results in a system that is significantly more usable by operators of a variety of statures than that of the prior art. For example, the height of the upper loading slot for the prior art dryer using the described 66" inch disposable was 72.5 inches (over 6') as compared to only 54" for dryer 200 shown in FIGS. 45 and 46. The lower (exhaust), bending or stooping, loading height of the prior art dryer using the 66" disposable described here was a mere 16" above the floor while that of disposable 100 in dryer 200 described here is a much more comfortable 27.5". Multiple episodes of human factors testing (see Examples 30-33) demonstrated that the shorter disposable permits unencumbered installation of disposable 100 into the spray dryer 200 by an operator in the 5$^{th}$ percentile (4'11") to 95$^{th}$ (6'6") percentile of height in the US. The shorter disposable allows for easier reaching and stooping or bending actions required by the operator to install the disposable in the spray dryer to and to safely and effectively mount and dismount the disposable before and after spray dryer operation.

The plasma drying chamber tubing, baffle plate ring 156, exhaust port, and the like are made from blown or flat polyvinyl chloride (PVC) and are heat welded to form the drying chamber. The baffle plate ring 156 which is heat welded to disposable and once heat welded, the disposable can be attached to the baffle plate with an adhesive, for example. The drying chamber, in an embodiment, when in use, expands to take on the shape of the enclosure, the spray drying chamber housing of the dryer. Other commercially available materials and other vinyl materials can be used to make the plasma drying chamber of the present invention. Sheets of PVC material are molded by injection molding and/or heat welded to form the spray drying chamber and then sterilized.

The plasma drying chamber of the present invention, in an embodiment, functions as a single use chamber where spray drying occurs. Sterilization by gamma or X-ray irradiation provides Plasma Drying Chamber's sterility. The drying chamber development and manufacturing occurs under ISO 13485 design controls. Certification of the materials contacting the drying air or donor plasma within the drying chamber assembly provides lot traceability. Certification provides the toxicity testing and certification for human use.

The overall size of the spray dryer is generally much smaller than other manufacturing-type spray dryers which are often quite large and inappropriate for use in a blood center, military field medical unit or similar location. The spray drying system of the present invention is designed to fit and be used in a blood component lab, whereas other manufacturing spray dryers are used generally in a large industrial scale facility.

As discussed above and in co-pending application Ser. No. 17/945,129, entitled "Usability Of A Disposable For A Spray Drying Plasma System", filed on even date herewith, the entire teachings are incorporated herein by reference), the spray dryer of the present invention is largely automated and usable by persons with limited training. This in contrast to high training and skill demands associated with industrial spray drying or laboratory spray drying as, for instance, by the spray dryers sold by Buchi Corporation (19 Lukens Drive, Suite 400 New Castle, DE 19720 United States, Model No. 4244).

As further described in a co-pending related patent application (Application No. 17945126), the liquid plasma pretreated before undergoing the spray drying process. The pretreatment solution protects plasma clotting factors during the spray drying process. A fixed volume of never frozen or frozen plasma (e.g., about 260 ml) is transferred to a plasma pretreatment container, which contains a spray dry stable acidic substance (SDSAS) e.g., 50 mL of glycine and hydrochloric acid solution. In an embodiment, single donor plasma expressed from collected whole blood or by apheresis which has never been frozen and is less than 24 hours old from collection is desirably utilized for this process. The plasma is collected from blood by standard techniques known to those of ordinary skill in the art, as described herein. Plasma is collected through a process call plasmapheresis. Plasmapheresis refers to a procedure in which the plasma is separated from the blood either by centrifugation or membrane filtration. The system process is also usable with pooled plasma if such is desired and with starting blood plasma material made with any currently available anti-coagulation system such as those known as CPD, CP2D, ACD-A and ACD-B. A sterile, non-pyrogenic, single-use container with SDSAS e.g., a 50 ml solution glycine and hydrochloric acid packaged in a 500 ml container within an overwrap pouch. In an embodiment, the process of the present invention includes converting a single donor unit of plasma which is collected by standard procedures into a single unit of spray dried plasma.

The in vitro characterization data demonstrate that the spray drying process effects of the system are comparable between units spray dried with different starting materials. Units manufactured from apheresed plasma (ACD-A anti-coagulation treatment) showed similar percent change due to manufacturing effects on the starting material as compared to units spray dried from whole blood derived plasma (CPD anti-coagulation treatment). A statistical analysis (ANOVA) was performed on the percent change pre and post manufacturing between the two starting materials across 20 assays including clotting times, coagulation function, and activation markers. Of the 20 assays, total protein concentration, PT, TT, and Factor VIII and XIII activities were determined to be statistically significantly different, however, the mean percent change is similar, and the mean values are all within the clinical reference range. In summary, the in vitro test results support the conclusion that the manufacturing impact on both apheresed and whole blood plasma is comparable, and the coagulation profile is within ±20% of their paired control or within the normal reference range.

Detailed Description of Spray Dryer

Spray dryer 200 provides pressurized aerosol gas, the plasma, and drying gas to disposable 100 and an exhaust for humid air. Disposable 100 is placed within the dryer and the dryer feeds the pressurized gas, plasma and drying gas such that the drying can occur within the disposable.

FIG. 45A is a front view of spray drying apparatus 200 with the door closed and FIG. 45B shows the spray drying apparatus 200 without the door so that the inner portions of the dryer can be seen. The disposable is placed in the dryer for spray drying. FIG. 45B shows first locator, projection locator 206, which receives notch locator 26 of disposable device 100. Additionally, receiver 204 (see FIGS. 45B and 46A), above projection locator 206, allows the disposable to be easily received such that it is aligned. FIGS. 45B and 45C also show spray drying head receiver 210 to receive the spray drying head 2 including the baffle 6.

At the top, spray drying apparatus 200 includes aerosol line 216 that provides a pressurized spray gas source (not shown). The gas source provides clean dry air with a dew point of minus 40° C. such as the Atlas-Copco SF 22 oil free scroll compressor combined with an Atlas-Copco CD45 desiccant dryer (Atlas Copco Manufacturing company, Nacka Municipality, Sweden). The pressurized gas source need not be located nearby the spray dryer 200 but can optionally be located at a distance and in a different space. Such devices are intended to be and are readily connected to or in communication with the device receiving the pressurized air. Spray drying apparatus 200 heats air from the source to the appropriate temperature (e.g., in a range between about 100° C. to about 120° C. (e.g., about 100, 105, 110, 115, 120° C.) and in an embodiment at about 114° C. See FIG. 45A-45C. In an embodiment, there are redundant in-line filters (e.g., 0.2 μm or smaller commercially available filters), as further described herein, in the drying gas line and aerosolizing gas line, in addition to the filter in the spray drying disposable device.

Display 212 provides instructions and information to the operator. The aerosol line 216 is in close proximity to installed spray drying head 2 in dryer 200. Aerosol line 216 has a Luer lock that attaches to aerosol filter 12 (which can also be a Luer lock). In an embodiment, they screw together. Aerosol line 216 is in close proximity to aerosol filter 12 and aerosol tube 10 when spray drying head 100 is installed into dryer 200. In an embodiment, the aerosol line 216 exits the drying head 2 between about 4 and 10 inches with about 6 inches being a desirable distance, as measured from the top of spray drying head 2 to the point of attachment at aerosol filter 12. Additionally, aerosol line 216 is oriented downward with Luer lock filter at the bottom such that it is within easy reach for an operator to attach aerosol filter 12 to aerosol line 216 at about 4'6" and 5'6" above the floor with about 5' being a desirable distance.

Indicator light 234 (See FIG. 45A) is located above display 212 to provide color/visual information (e.g., green=go, red=problem, yellow=assistance needed) to the operator. Below display 212, is a peristaltic pump 214 that pumps the liquid plasma through guide 226 into the nozzle of spray drying head 2. The peristaltic pump 214 has a plump latch 214A used to secure plasma tube 16. Peristaltic pump 214 provides the plasma to the disposable at the rate described herein. Dryer 200 also includes hook 222 that hangs the plasma bag, and emergency off switch 218 and circuit breaker 220. See FIGS. 45A, 45B, 45C. Tubing guide 226 allows the user to easily place and align plasma tube 16 that leads to the pretreated liquid plasma bag 64 and the aerosol tube 10 that attaches to aerosol line 216. Aerosol tube 10 attaches to aerosol line 216, providing pressurized gas source (not shown). via aerosol filter 12 which has a screw lock (e.g., Luer lock or Luer taper).

Figure 46B:
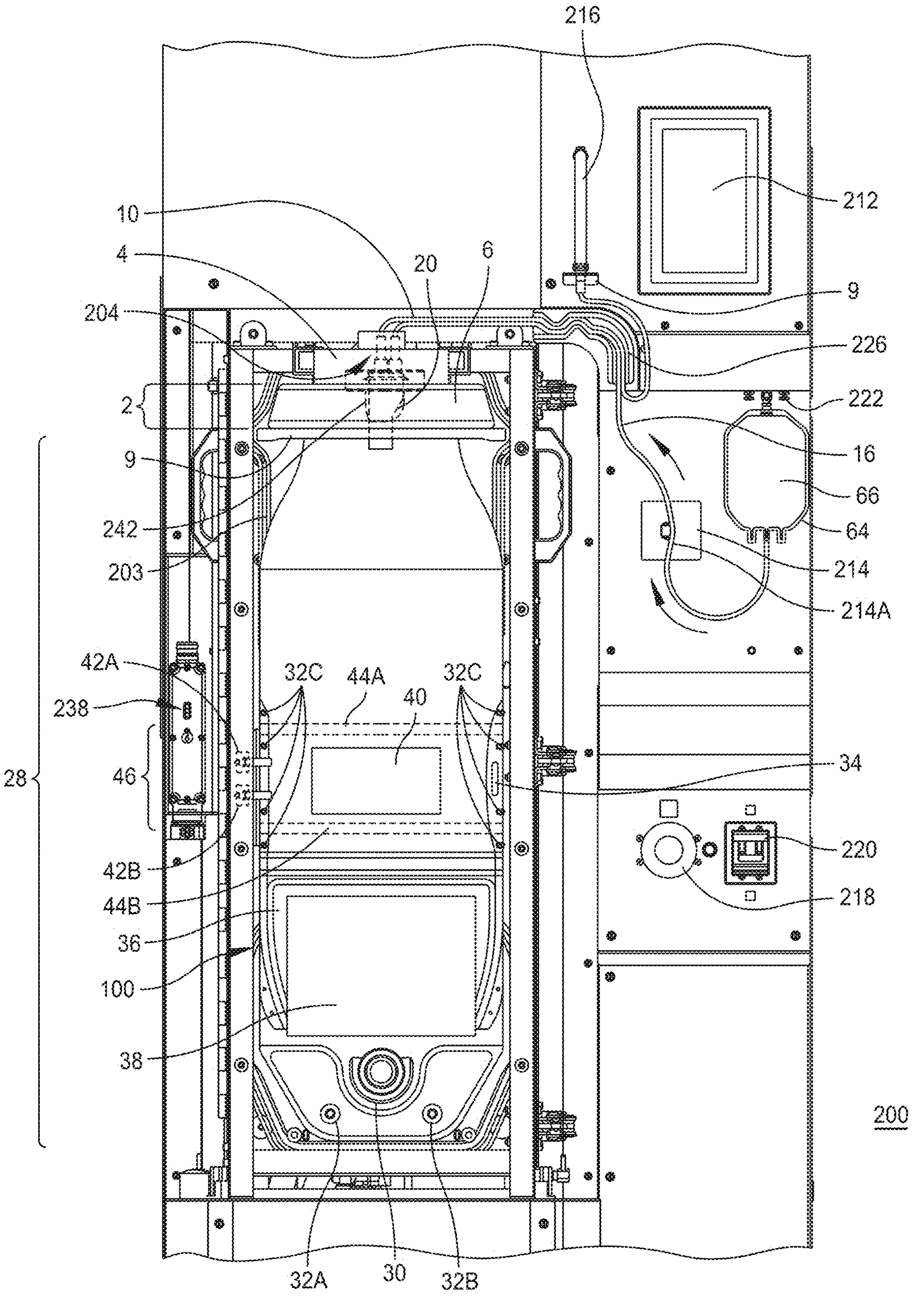
FIG. 46B is a schematic showing a partial front view of the spray drying apparatus without the door and with the spray drying disposable device installed and deflector engaged.

FIG. 46B shows spray dry disposable 100 installed in dryer 200. In this figure, the positional relationship between aerosol filter 12 of disposable 100 aerosol line 216 is shown. The plasma/aerosol guide, guide 226, is provided to protect the path of the plasma tubing 16 and aerosol tubing 10. The plasma tubing provides a flow of liquid (to-be-dried) plasma 66 that travels from liquid plasma bag 64 through pump 214 and to disposable 100 during spray drying. The aerosol tubing 10 provides a continuous flow of pressurized air flow from aerosol line 216 to disposable 100. Continuous flow of the plasma and pressurized air is necessary to ensure continuous spray drying, thereby making this guide an important aspect of the present invention. Plasma/aerosol guide 226 allows for the tubes to be properly placed to ensure that the tubing does not kink or buckle during operation. Plasma/aerosol guide 226 is well placed between plasma bag hook 222 and plasma flow inlet 18 on the installed disposable and between aerosol tubing 10 and aerosol line 216 and aerosol inlet 14 on the installed disposable. The placement of plasma/aerosol guide 226 allows for easy threading of both plasma tubing 16 and aerosol tubing 10. Once disposable 100 is aligned, the operator threads tubing 10 and 16 through plasma/aerosol guide 226. In an embodiment, plasma/aerosol guide 266 has a retention notch to retain the plasma tubing and/or aerosol tubing within the plasma/aerosol guide during operation of the spray dryer. In an embodiment, plasma/aerosol guide 226 is immediately visible to an operator having a height between the $5^{th}$ and $95^{th}$ percentile when loading when standing in front of the dryer (e.g., about 2 feet from the dryer).

FIG. 46B also shows placement of aerosol line 216, which provides the pressurized gas source. Once the operator threads aerosol tube 10 through plasma/aerosol guide 266, the operator attaches aerosol filter 12 to aerosol line 216 by connecting the Luer lock or screw lock. In this embodiment, the connection is an easy connection to make and only involves the alignment and turning of the Luer lock/screw lock. The proximity of spray drying head 2, plasma/aerosol guide 226 and aerosol line 216 allows the operator to thread and attach the aerosol line quickly and easily.

Similarly, plasma tubing 16, once threaded through plasma/aerosol guide 226, is threaded through peristaltic pump 214 and latch 214A is closed over plasma tubing 16 to keep it in place during spray drying. Again, the proximity of the proximity of spray drying head 2, plasma/aerosol guide 226 and peristaltic pump 214 allows for quick and easy threading and securing.

The operator controls (e.g., display 212, pump latch 214A, tubing guide 226 aerosol line 216, door handle 230) are positioned to be readily viewable and operable by an operator of a wide range of statures. Operators of a shorter stature could not readily see display 212 in an earlier version. The problem was addressed with the present invention and now 99% of all persons of varying statures can easily see and access display 212. These controls are within about 12, 13, 14, 15, 16, 17, 18, 19, 20 inches of one another, and in an embodiment they are about 15 inches from one another. In an embodiment, the controls are immediately visible to an operator having a height between the $5^{th}$ and $99^{th}$ percentile when loading when standing in front of the dryer (e.g., about 2 feet from the dryer). Not only are the controls in close proximity to one another but are positioned to be in close proximity to the part to which they attached or are used. Additionally, the controls are oriented toward the direction of attachment of the respective part. Furthermore, the layout of the plasma/aerosol guide 226, pump latch 214A, and aerosol line 216 are logically placed in accordance with flow of air/plasma.

Dryer 200 includes gasket 203. Gasket 203 resides along the perimeter of housing 202 and or the inside of door 228. Gasket 203 has a partial hourglass shape when viewing dryer 200 from the front. Gasket 203 helps to create a seal between door 228 and housing 202 to assist in keeping gas between housing 202 and disposable 100 during spray drying operation. Gasket 203 acts as an insulator to keep gas from escaping from dryer 200. Gasket 203 can be made from rubber or similar material that can be molded into the slot or recess in which it resides.

Similarly, emergency shut off 218 is positioned to be easily locatable by the operator but specifically positioned to be lower and away from the operator controls described above. The idea is to encourage the operator to make a deliberate decision to use it by placing emergency shut off 218 away from the main controls. Next to emergency shut off 218 is circuit braker 220. Emergency shut off 218 and circuit braker 220 provide two ways to turn off dryer 200 in case of emergency.

FIGS. 45A-4C also show spray drying apparatus 200 that includes exhaust port 208 that receives gas outlet port 30 of disposable device 100. The alignment arrangement of the present invention, in an embodiment, includes the attachment of gas outlet 30 of disposable 100 to the gas exhaust port 208 of spray dryer 200 or the gas outlet receiver 414 of finishing apparatus 400. (See FIGS. 46A-C and FIGS. 47A-C). During spray drying, the attachment of the gas outlet 30 of disposable 100 to gas exhaust port 208 of spray dryer 200 allows disposable 2 to stay in place during plasma drying process by anchoring the bottom portion of the disposable to the dryer. Similarly, finisher 400 is designed to receive gas outlet 30 of disposable 100 via gas outlet receiver 414 to keep the disposable in place during the process of shaking/impacting the plasma into place, removal of air, sealing and separating. Gas outlet 30 of the disposable device 100 is made from a strong, rigid plastic material and is a cylindrical outlet with a lip. Exhaust port 208 of spray dryer 200 has an O-ring and a gasket that allows the lipped cylindrical gas outlet 30 to be secured to create a firm attachment. Gas outlet receiver 414 of finishing apparatus 400 has a receiver that has a "U" shaped slot so that the gas outlet can be firmly attached to the finishing apparatus and remain attached during the finishing process. The gas outlet of the disposable, the gas exhaust port on the spray dryer and/or the gas outlet receiver can include any arrangement to attach the gas outlet of the disposable to stay intact during use of the apparatus or finisher to which it is attached. The gas exhaust port or gas outlet receiver can be made from stainless steel, plastic, rubber and the like.

Put another way, in an embodiment as shown in FIG. 46A, to align the spray dry disposable device 100 in spray drying apparatus 200, the operator should insert the off-set guide 4 of the disposable 100 into receiver 204 of the dryer 200, align the locating arrangement on the disposable and the dryer, thereby engaging the retention clip, and insert the gas outlet of the disposable into the exhaust gas port of the dryer. Once these alignment elements are engaged, the disposable is aligned into place and ready to be locked. After attaching the plasma source and the pressurized gas source, the operator can lock the door of the spray drying chamber housing and the spray drying process can begin. The operator locks door 228 by engaging handle 230 by swinging the handle right and then left, and locking it into place. See FIG. 45C. The operator can lock the door by inserting key 236 into keyhole 238. In another embodiment, one or any combination of these alignment arrangements can be engaged so that the disposable is aligned with the spray drying apparatus.

If the operator improperly aligns disposable 100 with the dryer 200 (e.g., inserts spray drying head 2 with locator notch 26 facing outward), then ridge 9 will not completely sit in groove 207 and spring clip 232 does not engage with spray drying head 2. In this case, when the operator attempts to close door 228, door 228 will not close. If door 228 is not fully closed and handle 230 cannot lock into place, then the dryer cannot proceed with drying. Preventing the drying when disposable 100 is not properly aligned and installed ensures safety of operation.

In another embodiment, the operator inserts disposable 100 with locator notch 26 within 30 degrees (e.g., within 30, 25, 20, 15, 10, 5 degrees) of locator projection 206. In other words, the operator may come close but does not perfectly align the locator notch arrangement. In this case, when the operator closes door 228, spray dry head 2 self-aligns so that locator projection 206 inserts into locator notch 26. As door 228 closes, it applies force to spray drying head 2 and spray drying head 2 slides along receiver 210 in a circular fashion until locators 26 and 206 align, ridge 9 fully sits within groove 207 and spring clip 232 is engaged. Although aligning the spray drying head is an easy task that does not require much force and/or training, if operator incorrectly inserts spray drying head 2 where it is within about 30 degrees of properly locator notch alignment, the system will self-correct the spray drying head installation.

In an embodiment, dryer 200 automatically monitors and controls at least four processes (e.g., pretreated plasma flow, aerosol air flow, drying air flow, and exhaust air flow) as well as ensuring the drying process is completed within operating ranges. In an embodiment, dryer 200 contains an array of sensors and actuators that allow for the automated control of the spray drying process.

In an embodiment, the dryer can be run according to these parameters:

TABLE 8

| Process Parameters | | | | |
|---|---|---|---|---|
| Process Parameter | Permissible Range | Tolerance | Measurement Units | Description |
| Drying air flow rate | 750 slpm | +10 slpm | Standard Liters per minute | Drying air flow rate into the spray drying chamber (independent parameter) |
| Drying air inlet temperature | 110-120 | ±1° C. | Degrees Centigrade | Drying air temperature into the spray drying chamber (independent parameter) |
| Plasma feed rate | 5-20 mL/min | N/A controlled by exhaust temperature | Grams per minute | Plasma flow rate to the two-fluid nozzle (independent parameter) |
| Aerosol air rate | 30-50 slpm | ±1 slpm | Standard Liters per minute | Aerosol air flow rate to the two-fluid nozzle (independent parameter) |
| Exhaust air outlet temperature | 60-70° C. | ±1° C. | Degrees Centigrade | Air temperature leaving the Plasma Drying Chamber (dependent parameter) |

plasma bag 66. Before after and during the spray drying process, the weight of plasma bag 66 and any amount of donor plasma is weighed and the weight is communicated to the computer system, having among other items, memory, storage, and a processor. With the weight of the plasma bag having pretreated plasma, one can determine the amount of pretreated donor plasma being dried. In an embodiment, the pretreated plasma has weight of between 330 and about 385 g, which means the volume of the pretreated plasma is between about 335 ml and about 395 ml. This is determined using a calculation of the density of pretreated plasma which is between about 1.02 and 1.025 g/mL. Plasma tube 16 is ⅛ inch and in an embodiment, the flow rate is set at 13 g/min.

Dryer Architecture

Figure 46C:
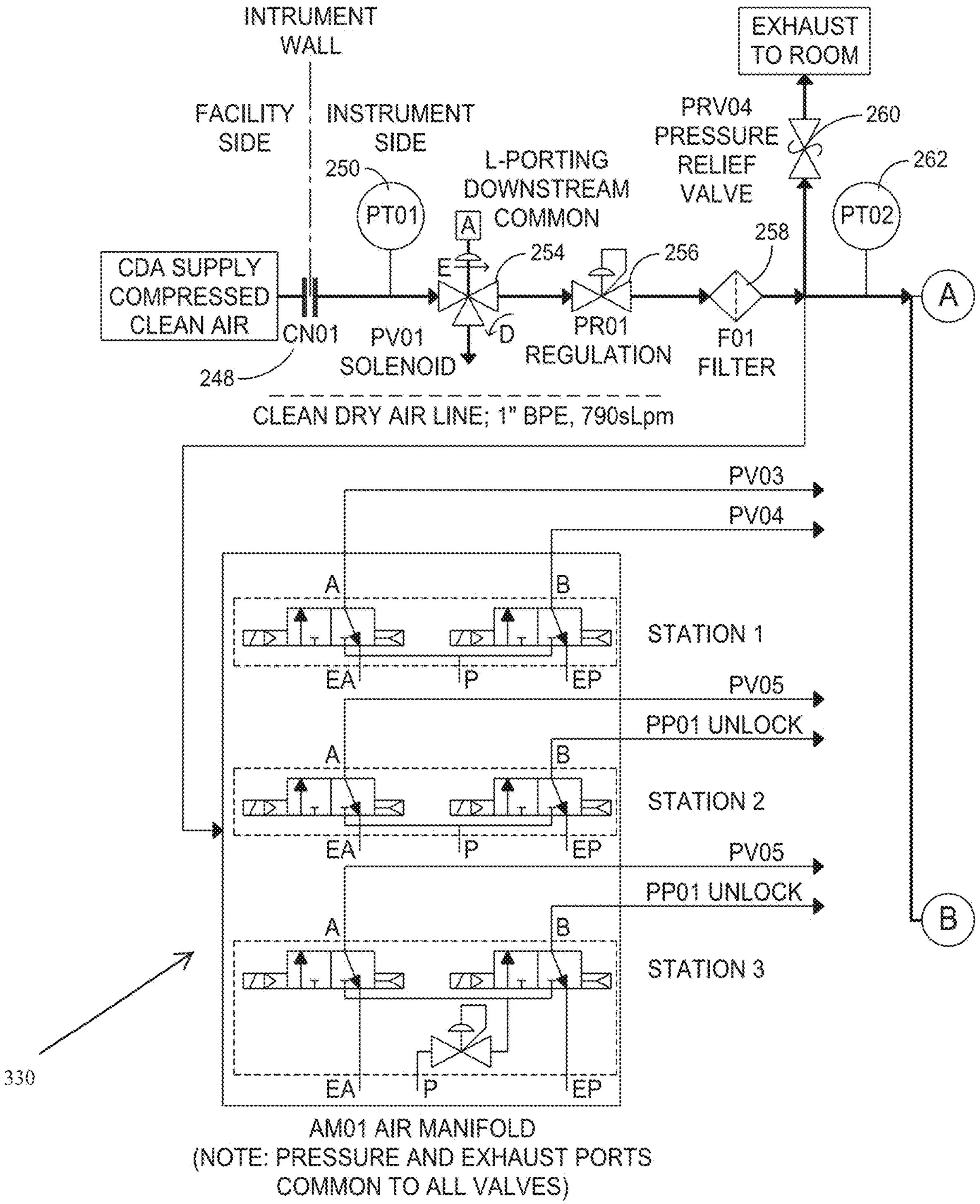
FIG. 46C is a schematic showing the architecture of dryer 200. Abbreviations included are: AM—Air Manifold, B—Transfer Bag, CN—Connector, DPT—Differential Pressure Transducer, F—Filter, FS—Flow Sensor, H—Heater, MFC—Mass Flow Controller, OS—Sensor, P—Peristaltic Pump, PP—Pneumatic Piston, PR—Pressure Regulator, PRV—Pressure Relief Valve/Rupture Disk, PT—Pressure Transducer, PV—Valve (Arrow Down Is Fail Closed, Arrow Up Is, Fail Open), S—Scale, SS—Solenoid, TC—Thermocouple, TS—Thermocouple Sensor, and TT—Temperature Transducer.
Figure 46C:
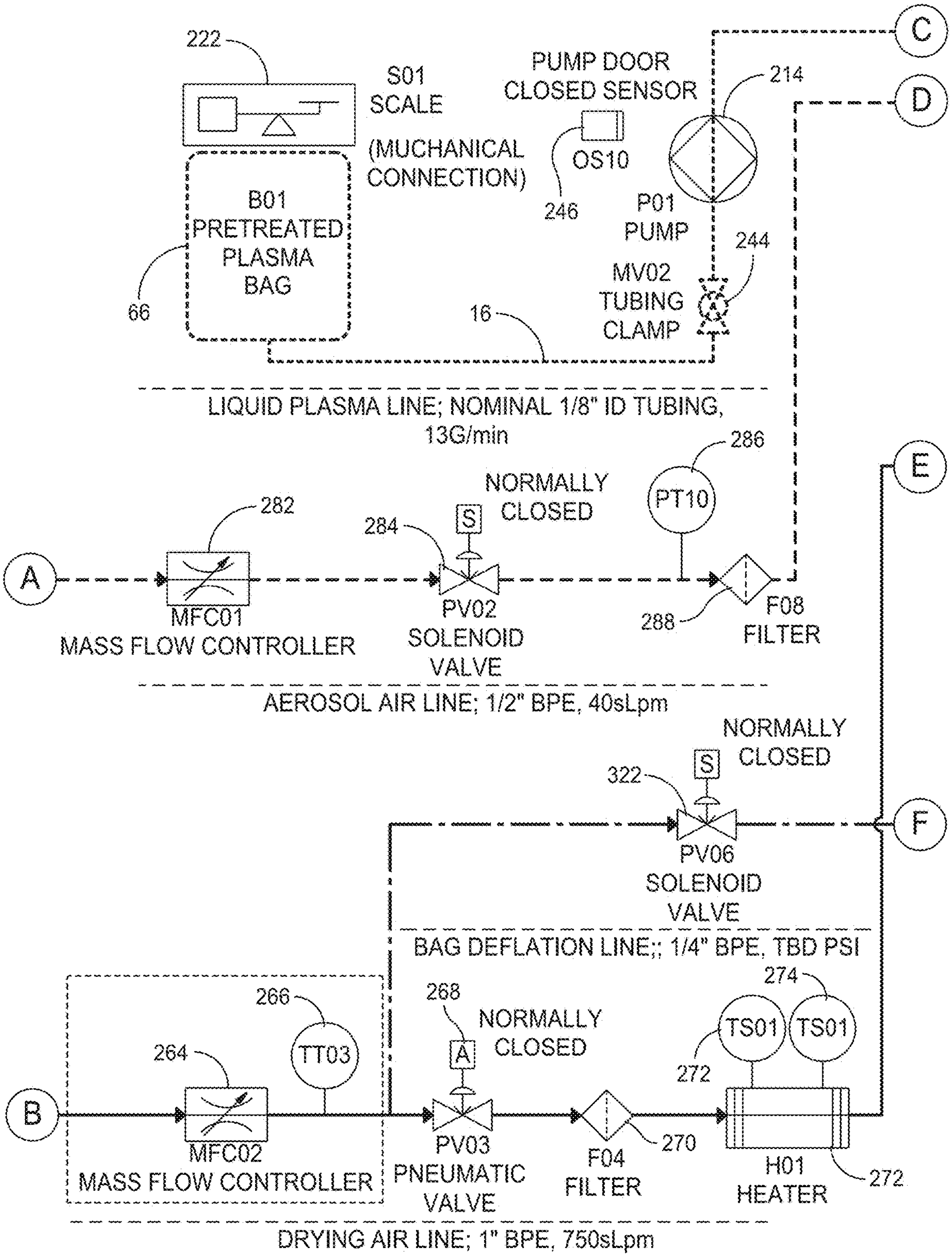
Figure 46C:
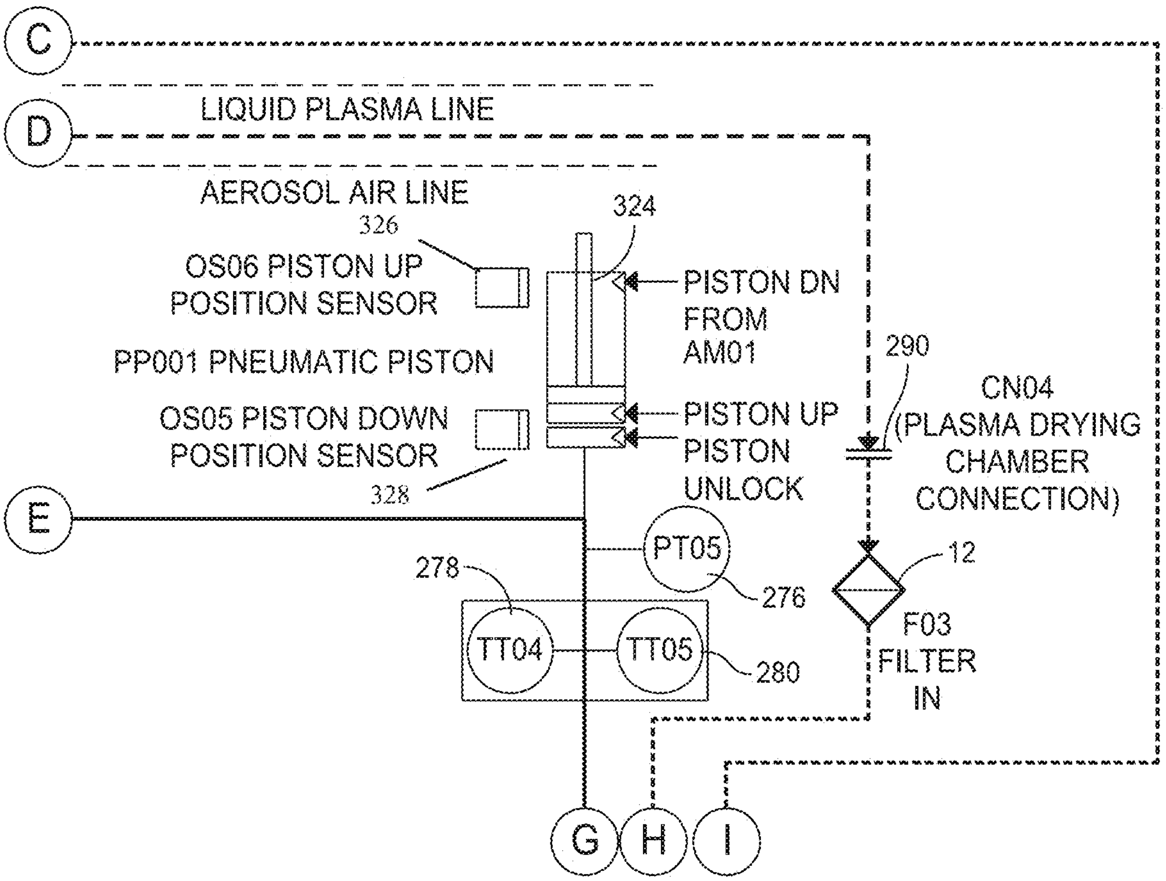
Figure 46C:
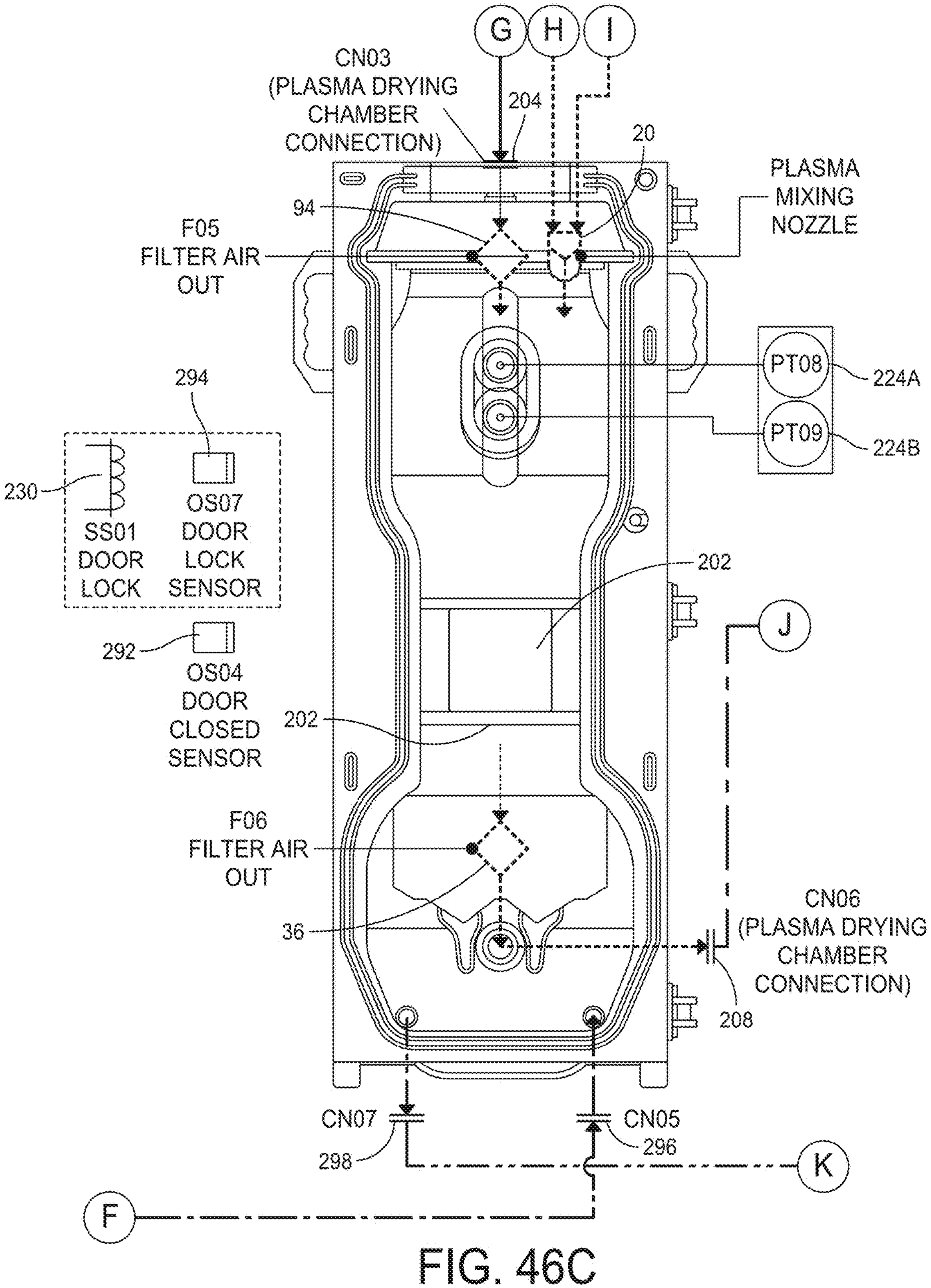
Figure 46C:
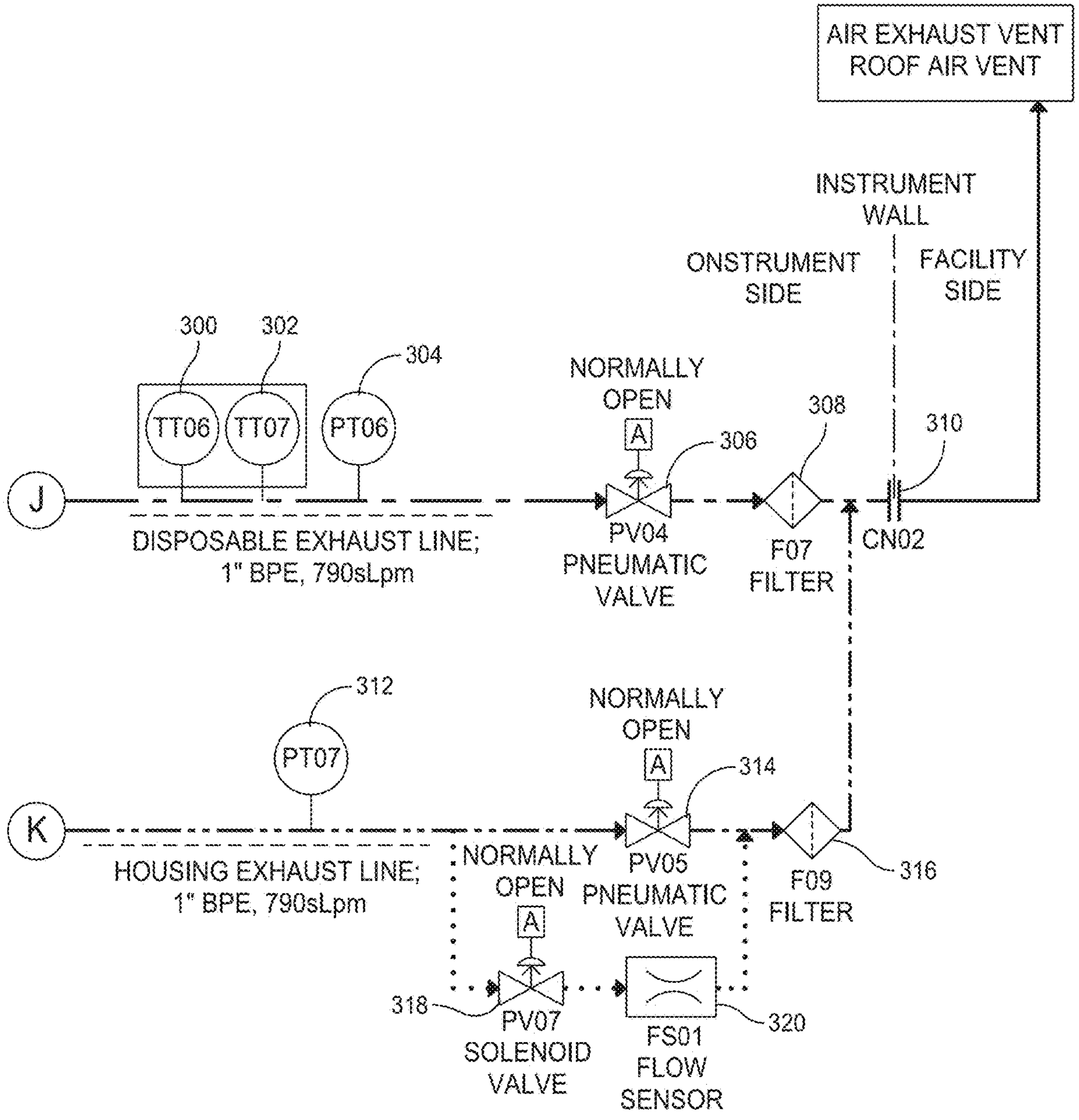
Figure 46E:
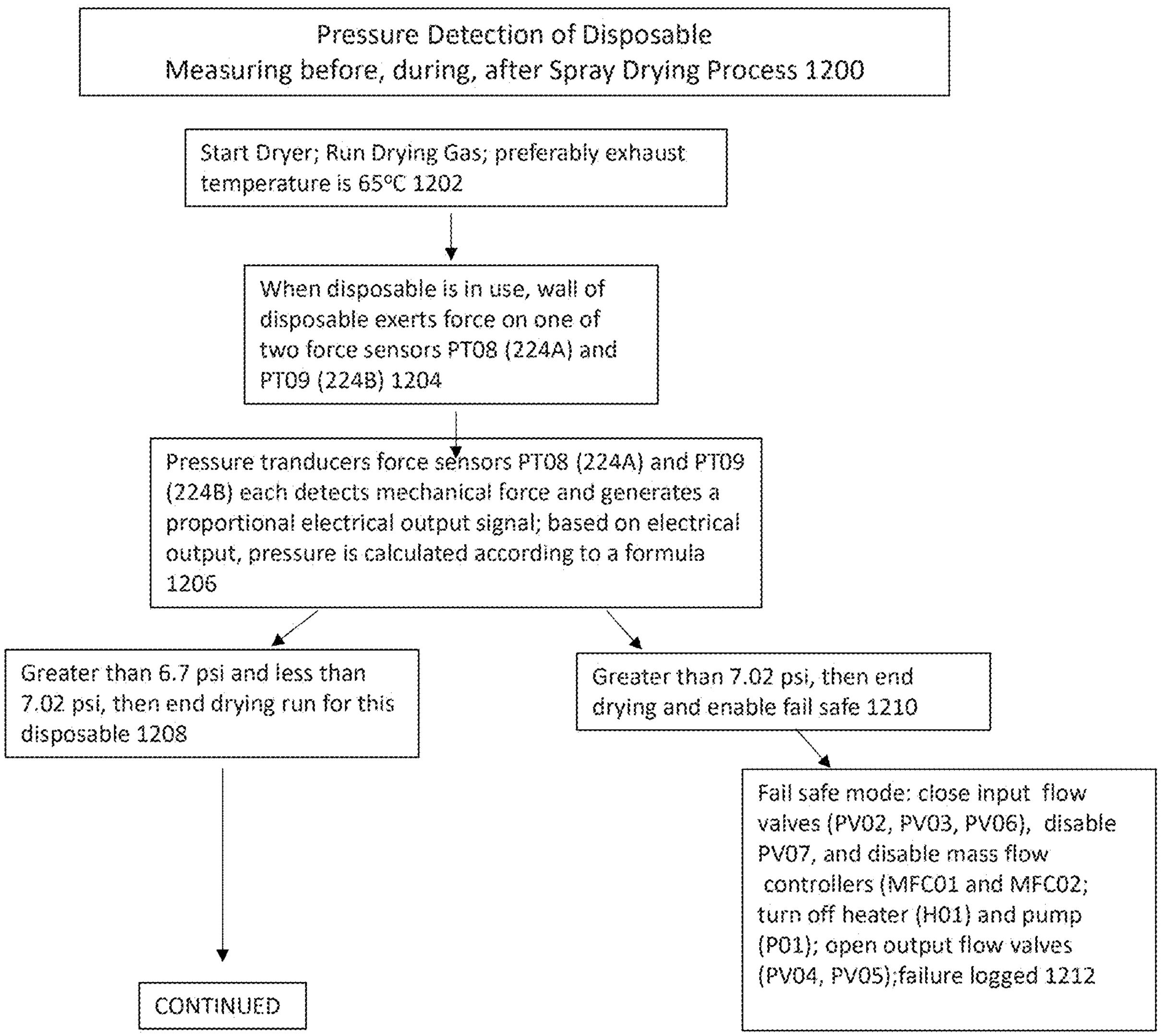
FIG. 46E is a flow chart showing the steps of the pressure detection method employing the spray dryer and spray drying disposable.
Figure 46E:
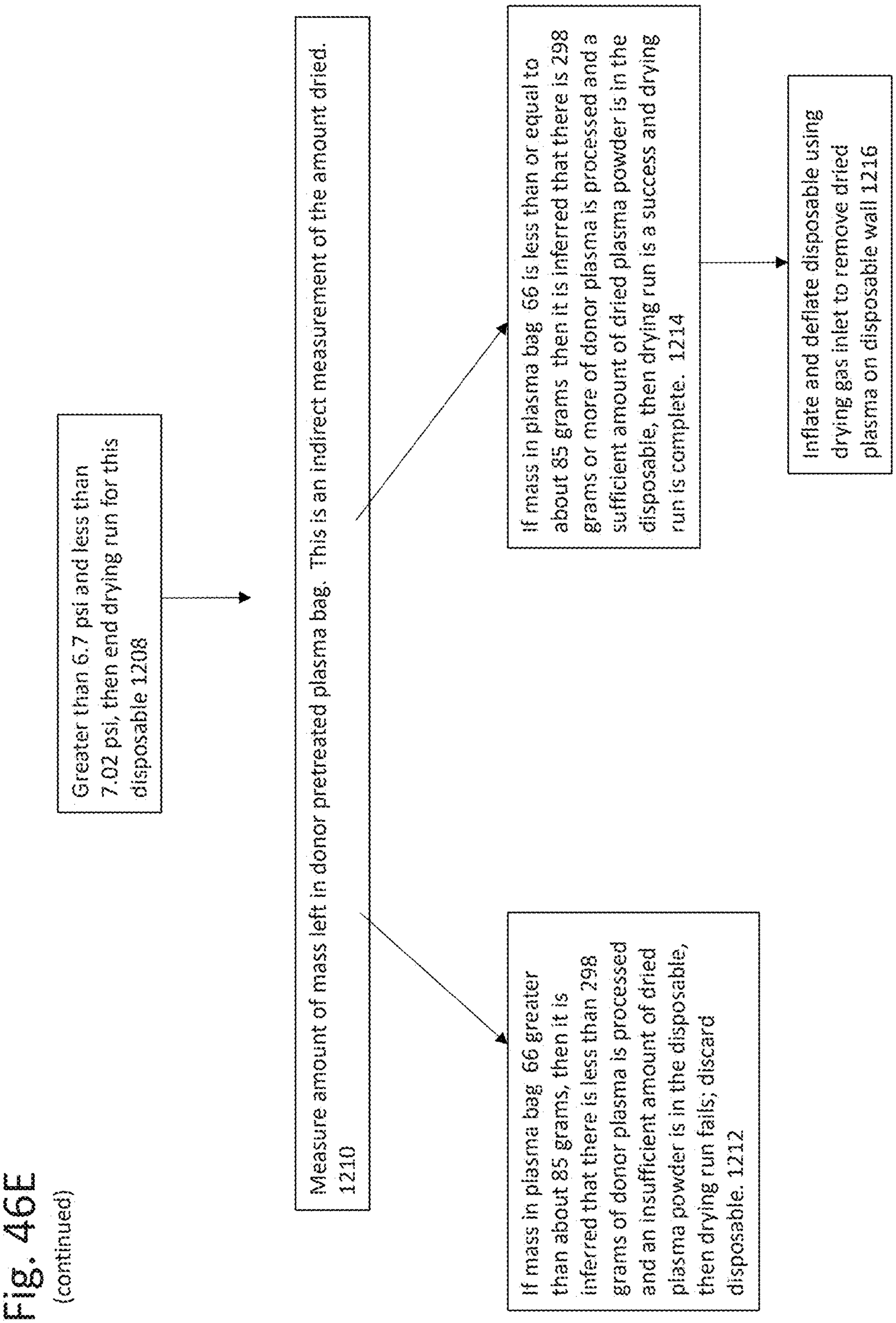

The architecture of dryer 200 is shown in FIG. 46C. Dryer 200 coordinates and/or drives at least the following flow paths: pretreated or donor plasma flow line (Lines C, I), the drying air line (Lines B, E, G), the pressurized aerosol gas air line (Lines A, D, H), disposable deflation line (Line F), disposable exhaust line (Line J), enclosure/housing exhaust line (Line K) and leak detection line (Line L). Such flow lines are examples of providing flow of plasma, drying gas, pressurized aerosol gas and/or the exhaust. Any number of flow configurations can be arranged so long as the dryer provides donor plasma, drying gas and pressurized aerosol gas to the disposable and an exhaust line for humid air. Additional lines or fewer flow lines than shown in the figures can provide these flow lines. For example, in an embodiment the clean dry air is the source of both the drying gas and the pressurized aerosol gas. In this embodiment, the line is shared until the pressurized aerosol line branches off into a separate line. Similarly, the disposable exhaust line and the housing exhaust line can be combined into a single line before passing through a filter and mixing with outside air.

The Plasma Flow Line

The plasma flow line provides the donor plasma that is in liquid form to nozzle 20 of disposable 100 at a rate ranging between about 5 and about 20 mL/min for atomization and drying. In an embodiment, the donor plasma is pretreated, as described herein.

The plasma flow line is labeled as Line C in FIG. 46C. The plasma flow begins with the plasma bag B01, also referred to herein as plasma bag 66. As described above, plasma bag 66 is attached to hook 222. Hook 222 in this embodiment is a hook scale S01 that provides the weight of The pretreated plasma travels through plasma tube 16 and through peristaltic pump 214, P01, which regulates the plasma flow rate. Tubing clamp 244 resides between plasma bag 66 and peristaltic pump 214 and can be used to manually open or close plasma tube 16. Peristaltic pump 214 has a door or latch 214A. Sensor 246, designated as sensor OS10 in FIG. 46C, resides at peristaltic pump latch 214A to assess the latch status of open or closed. When the sensor detects a closed latch 214A the signal is communicated to the computer system which communicates to peristaltic pump 214 to proceed with pumping the pretreated plasma. In the event that peristaltic pump latch 214A is not closed, the computer system will display a communication to the user to close the latch 214A. Sensors, in general, are devices that provide input data to the system and the system converts analog data from the sensor (e.g., if the latch is closed) to digital data. The plasma flows past peristaltic pump 214 at a rate designated by pump 214 to nozzle assembly 20, shown as position I in FIG. 46C. Pump 214 is directed by the computer system as to the rate, and as to proceed or to stop, once the drying is complete or the desired weight of the pretreatment plasma bag is achieved (e.g., between about 66 grams and about 85 grams). At the nozzle assembly, the plasma comes into contact with pressurized aerosol gas and atomizes, as described herein. Note that FIG. 46C shows where nozzle assembly 20 would be if disposable 100 was inserted into dryer 200. The plasma flow rate when it enters the nozzle is between about 5 and about 20 mL/min.

The Drying Gas Flow Line

The drying gas flow line provides clean, heated dry air to atomized liquid plasma droplets to dry them during rapid mixing in disposable 100, as further described herein.

In the embodiment shown in FIG. 46C, the drying air line is the source for the drying gas and the pressurized aerosol gas. In other embodiments, they can be separate systems.

The drying air line begins at the Compressed Dry Air (CDA) supply and follows Lines B, E and ends at G, as shown in FIG. 46C when the dryer is running. As described above, the CDA is commercially available. The CDA system is connected to dryer 200 via connector 248, designated CN01 in FIG. 46C. Once entering dryer 200, the clean air travels through a pressure transducer PT01 250, ball valve PV01 254 and pressure regulator PR01 256. A pressure transducer is an electromechanical device designed to measure pressure. Pressure transducers sense applied pressure and provide an output consisting of an electrical signal that indicates the amount of pressure. In an embodiment, pressure transducers have an electrical output that is directly proportional to the applied pneumatic pressure. Pressure transducer PT01 250 measures the pressure of the drying gas in the line and communicates the pressure via a digital signal to the computer system. The pressure of the clean air at pressure transducer PT01 250 ranges between about 80 psig and about 120 psig. The line is a 1 inch line traveling, in an embodiment, at a rate of 790 sLpm. The range of the rate of the drying gas is between about 10 to about 1000 slpm. A solenoid valve is an electrically controlled valve. Solenoid valves in dryer 200 have an electric coil with a movable ferromagnetic core and plunger in its center. The solenoid valve drives valve PV01 254. Valve PV01 254 is a pneumatically actuated three-way ball valve where the actuation air pressure is controlled by a solenoid valve. When commanded to open, the solenoid valve is energized whereby allowing actuation air to flow to the pneumatic actuator. This air pressure then rotates the ball valve 90°, allowing drying gas to flow. In particular, this valve uses air pressure to rotate the ball 90° to allow the downstream line to be connected to either ambient air (when 'closed' or 'off') or to the pressurized CDA air (when 'open' or 'on'). The controlling air pressure is itself enabled/disabled via the solenoid valve. This solenoid valve only controls the air that in turn actuates the valve PV01 254. Downstream of the pneumatically actuated ball valve PV01 254 is a tee-port which allows for inline supply of drying gas but also allows a small amount to be diverted to the air manifold, which is further discussed herein. Similarly, a pressure regulator, such as PR01 256, regulates system flow pressure in response to upstream or downstream pressure changes. When the drying gas leaves pressure regulator PR01 256, pressure of the clean air is between about 70 and about 80 psig and flows at a rate between about 10 and about 790 slpm. The clean air travels through filter F01 258, which is a 0.2 micron hydrophobic polytetrafluoroethylene filter, suitable for filtering out pathogens. This filter ensures that pathogens from the CDA supply do not contaminate the drying process. After passing through filter F01 258, excess pressure, if any, is relieved through pressure relief valve PRV04 260 by allowing the pressurized air to flow from an auxiliary passage out of the system and exhaust to the room. Pressure transducer PT02 262 measures the pressure clean air in the line to ensure that the pressure is in the desired range before heating. The pressure of the clean air at pressure transducer PT02 262 ranges between about 70 psig and about 80 psig.

Following Line B designated in FIG. 46C the clean dry air flows through mass flow controller MFC02 264. A mass flow controller is a device used to measure and control the flow of the clean dry air. Mass flow controllers used with the dryer of the present invention have an inlet port, an outlet port, a mass flow sensor and a proportional control valve. Mass flow controller MFC02 264 regulates the flow of the clean dry air in a range between about 0 and about 1,000 slpm. The clean dry air flows through temperature transducer TT03 266 and measures the temperature of the air and converts the temperature to a digital signal which is sent to the computer system. During use, the temperature at temperature transducer TT03 266 measures in a range between about 10° C. and 35° C. Based on the temperature of the clean dry air at temperature transducer TT03 266, the computer system calculates the amount of heat needed to bring the temperature of the clean dry air to a range between about 110° C. and about 120° C. This amount needed to heat the clean air is communicated by the computer system to heater H01 275 which applies the calculated amount of heat to the clean dry air to thereby obtain heated drying gas used to dry the atomized liquid plasma. Thermocouple sensors TT04 278 and TT05 280 measure temperatures to ensure that the proper temperature range has been achieved.

After passing through mass flow controller MVC02 264 and temperature transducer TT03 266, the heated dry air flows through the pneumatically controlled ball valve PV03 268 and filter F04 270. The pneumatically controlled ball valve uses air pressure to open or close a valve. Station 1A of air manifold AM01 330 is used to control valve PV03 268. Pneumatically controlled ball value PV03 268 is activated when MFC02 is commanded to start flowing. This acts as a safety control in the event MFC02 fails to control the flow of air, the valve closes. During the spray drying processes, to direct air to Line B, pneumatic valve PV03 is opened and solenoid valve PV06 322 is closed. When the disposable deflation line is used after spray drying is completed, pneumatic value PV03 268 is closed and solenoid valve PV06 322 to divert air flow from the clean dry air from Line B to Line F. Filter F04 270 is a redundant filter to ensure that pathogens are not introduced to the plasma during drying. Filter F04 270 is a 0.2 micron hydrophobic polytetrafluoroethylene filter.

Continuing with the heated dry gas, following Line E, when disposable 2 is installed, the drying gas passes by pressure transducer PT05 276 which measures the pressure of the heated drying gas just before entering disposable 2. The pressure of the clean air at pressure transducer PT05 276 ranges between about 10 and about 20 psig. In addition to measuring the pressure, temperature transducer TT04 278 and temperature transducer TT05 280 redundantly measure the temperature of the heated drying gas, which ranges between about 110° C. and about 120° C. At position G of FIG. 46C, the heated drying gas enters inlet deflector 242 (the elbow) and into plenum 6 of spray dry head 2 to provide the uniform air pressure, as described herein. The heated drying gas flow rate when it enters the nozzle is between about 720 and about 780 slpm and a temperature between about 110° C. and about 120° C.

Pneumatic piston PP01 324 lowers deflector 242 into spray dry head 2 during spray drying, and lifts deflector 242 when spray drying is completed. Piston PP01 has can be locked or unlocked, and in an up position (when not in use) and in a down position (during spray drying). Piston PP01 324 has sensor OS06 326 to detect that the piston PP01 324 is in the up position, and sensor OS05 328 to detect that piston PP01 324 is in the down position. When not in motion, the piston is locked to prevent unwanted motion. Prior to the start of spray drying, the computer system sends a signal to piston PP01 324 to lower into plenum 6 of spray dry head 2 to provide the uniform air pressure for spray drying. The deflector 242 includes a ball-in-socket style gimble. During manufacturing, the gimble allows the deflector 242 to be aligned with disposable 2 to form a leak-free seal when in use.

The drying gas line has an internal pathway used for the disposable deflation line. When the spray drying is completed, the removal of the humid air is assisted with the bag deflation line, Line F. The bag deflation line actually injects air between the outer wall of disposable 100 and inner wall of plasma drying chamber housing 202 effectively squeezing the air within disposable 100 through exhaust 208 via Line J.

The air used for the disposable deflation line branches from the clean air drying gas line, Line B, after flowing past mass flow controller MFC02 264, and travels through solenoid valve PV06 322 using Line F. To divert air to Line F, pneumatic valve PV03 is closed and solenoid valve PV06 322 is opened. On the other hand, during the spray drying processes, to direct air to Line B, pneumatic valve PV03 is opened and solenoid valve PV06 322 is closed. When traveling through Line F, the disposable deflation line, the flow enters housing 202 through connector CN05 296. The disposable deflation line is used after drying is complete, and pneumatic valve PV03 268 is closed and solenoid valve PV06 322 is opened to allow air to travel to housing 202 to assist in pushing the humid air out of disposable 100.

The Pressurized Aerosol Gas Flow Line

The pressurized aerosol gas flow line provides a pressurized gas flow at flow rates sufficient to atomized the donor plasma droplets at nozzle 20 of the disposable 100. The pressurized aerosol gas flow rate when it enters the nozzle is between about 30 and about 50 slpm.

The aerosol pressurized line also stems from the compressed clean air source. after passing filter F01 258, the clean air line supply branches into Line A in FIG. 46C. A portion of the clean dry air branches off and flows through mass flow controller MFC01 282, following Line D. Since the mass flow controller is a device used to measure and control the flow of the clean dry air, in this case, the mass flow controller increases the flow of the clean dry air sufficient such that when it reaches nozzle 20 in drying chamber 28 of disposable 2, the donor plasma atomizes. Mass flow controller MFC01 282 causes the flow of the clean dry air to become pressurized and flow in a range between about 30 and about 50 slpm. This results in the aerosol pressurized air that atomizes the liquid plasma droplets. The aerosol pressurized air passes through solenoid valve PV02 284 and pressure transducer PT10 286. Solenoid valve PV02 284, in its resting position, has a plunger that closes off the opening in the line. When an electric current is applied, the coil creates a magnetic field which exerts a force on the plunger to open the line. Pressure transducer PT10 286 measures pressure and provides an output consisting of an electrical signal that indicates the amount of pressure. In an embodiment, pressure transducer PT10 288 measures the pressure of the pressurized aerosol gas in the line and communicates the pressure via an electrical signal to the computer system. The pressure of the clean air measured by pressure transducer PT10 286 ranges between about 20 and about 40 psig. The pressurized aerosol gas passes through filter F08, a 0.2 micron hydrophobic polytetrafluoroethylene filter, to filter out pathogens and proceeds to Line D. Filter F08 is another redundant filter to ensure that any pathogens in the clean dry air does not enter the drying chamber.

The aerosol pressurized air passes through aerosol line 216 of dryer 200 and through aerosol filter 12 of disposable 2, as described further herein, to end at position H which is at nozzle 20, as shown in FIG. 46C.

Plasma Drying Chamber Housing 202 of Dryer 200

The drying chamber housing 202 of dryer 200 houses disposable 100 during use and is described herein in detail.

With respect to FIG. 46C, baffle filter 94 is designated as filter F05 and lower/capture filter 36 is designated as filter F06, which are both described herein in detail. The disposable is attached at receiver and drying gas inlet 204, designated as connector CN03, which is also described herein. Dryer 200 includes pressure transducer PT08 224A and pressure transducer PT09 224B, which are further described herein. Dryer 200 further includes sensor OS04 292 to determine if door 228 is closed and a sensor OS07 294 to ensure that door 228 is locked with door handle 230 (SS01). Gas exhaust port 208 is designated as connector CN06 and leads to Line J for the disposable exhaust line for the exit of humid air. connector CN05 296 is the connector to the disposable deflation line, designated as Line F, as further described herein, and connector CN07 298 is the connector to the enclosure exhaust line, designated as Line K, as further described herein.

Disposable Exhaust Line

The disposable exhaust line, designated as Line J, exhausts the humid air during the spray drying. As described herein, the humid air is a mixture of the drying gas, the pressurized aerosol gas and the evaporated moisture from the plasma droplets. The humid air that is in disposable 100 during spray drying exits through this disposable exhaust line, Line J.

Referring to FIG. 46C, the disposable exhaust line in an embodiment is 1" inner diameter flowing at 790 sLpm. The humid air initially exits from gas exhaust port 208 and passes by temperature transducer TT06 300 and temperature transducer TT07 302 which measures the temperature of the humid air upon exit of disposable 100, followed by pressure transducer PT06 304 that measure the pressure and flow. During spray drying, the temperature range of temperature transducer TT06 300 and temperature transducer TT07 302 ranges between about 15° C. and about 75° C. During spray drying, pressure transducer PT06 304 measures the pressure that ranges between about 0 and about 5 psig and flow that ranges between about 10 and about 790 slpm. The exhaust air passes through normally open pneumatic valve PV04 306. The pneumatic valve uses air pressure to open or close a valve. Station 1B of air manifold AM01 330 is used to control valve PV04 306. Pneumatic value PV04 306 is normally open and remains open in the event of a system shut down or over pressurization. This acts as a safety control because air flow is allowed to exit the system. Before exiting through connector CN02 310, the humid air passes through filter F07 308 to mix with the outside air. Filter F07 308 is a 0.1 micron hydrophobic polytetrafluoroethylene filter.

Housing/Enclosure Exhaust Line

The enclosure exhaust line is to remove air that is in the plasma drying chamber housing but outside of disposable 100. Humid air in disposable 100 exhausts through Line J but any residual air in the housing between the outer wall of disposable 100 and inner wall of housing 202 after drying is completed or if there is a failure, is removed through this path, Line K.

Residual air from housing 202 exits via connector CN07 298 and flows past pressure transducer PT07 312 measures the pressure and flow. The residual air passes through normally open pneumatic valve PV05 314. The pneumatic valve uses air pressure to open or close a valve. Station 2A of air manifold AM01 330 is used to control valve PV05 314. This valve remains open in the event of a system shut down or over pressurization. This acts as a safety control because air is allowed to freely flow out from the system, even when powered off. Before exiting through connector CN02 310, the residual air passes through filter F09 316 before the humid air exits to the outside. Filter F09 316 is a 0.1 micron hydrophobic polytetrafluoroethylene filter.

Line K further includes an internal pathway for leak detection, such method is further described herein. This line measures the flow of residual air between the disposable and the housing. The internal loop includes solenoid valve PV07 318 and flow sensor FS01 320. The solenoid valve has an electric coil with a movable ferromagnetic core and plunger in its center. During spray drying, solenoid valve PV07 318 remains closed. In the rest position, the plunger stays closed. When an electric current is applied, the coil creates a magnetic field which exerts a force on the plunger to open the line. The FS01 320 flow sensor measures air flow. The flow sensor FS01 320 includes pressure transducers that measure pressure across an internal flow restriction, from which flow can be calculated. In this case, the flow sensor measures the actual mass flow rate of the residual air. This internal loop is used for leak detection, as further described herein.

Dryer Air Manifold

The air manifold AM01 330 a branching chamber, extracts a small amount of clean dry air to create mechanical motion. The extracted air is used to actuate the pneumatic valves (PV) and pneumatic pistons (PP) in spray dryer 200. The manifold shows three stations, station 1, station 2 and station 3. Multiple actuators are part of each station. Station 1 actuates pneumatic valves PV03 268 and PV04 306, station 2 actuates pneumatic valve PV05 314, and piston PP01 324 (unlock), and station 3 actuates piston PP01 324 (down) and piston PP01 324 (up). The air manifold is commercially available, such as a multiport solenoid valve such as the SMC SY3000 (airline hydraulics, North Kingstown, RI). In the unpowered state, pneumatic valve PV03 268 is normally closed and pneumatic valve PV04 306 and pneumatic valve PV05 are normally opened. In the unpowered state, pneumatic piston PP01 is locked and during drying pneumatic piston PP01 324 is in the down position. The arrangement of stations and actuators can vary as desired. Although an air manifold is used to actuate the valves and pistons of the spray dryer, any commercial device can be used, such as a motor.

Leak Detection Method and System 1000

The present invention includes leak detection methodology 1000 which Dryer 200 undergoes, in an embodiment. FIG. 46D. Dryer 200 has been designed to determine if a leak exists in disposable 100, or put another way, to determine the integrity of disposable 100. In an aspect, the leak detection function of dryer 200 is performed after installation of disposable 100, and after spray drying. This test helps to determine if disposable 100 can withstand or has withstood the pressure and flow of the dryer 200. Dryer 200 and methodology 1000 utilizes two methods to determine if a leak in the disposable exists. The first is the pressure decay method, methodology 1030, and the second is the flow sensor method, methodology 1032. The two leak detection methods can be used individually or together.

Both methods include the steps of starting dryer 200 and loading disposable 100, as described herein. Dryer 200 warms up until the exhaust temperature, as measured at temperature transducer TT06 300 and temperature transducer TT07 302, measures to a set temperature, e.g., 65° C. The temperature transducers send a signal that the set temperature is met, and the computer system commands mass flow controller MFC02 to stop. In this step 1002, the drying gas is stopped by commanding mass flow controller MFC02 to stop flow and closes pneumatic valve PV03.

In addition to stopping the flow of the drying gas, the exhaust line is also closed in step 1004. In Step 1004, the computer system communicates with pneumatic valve PV04 306 and causes it to temporarily close during the leak detection test.

In the pressure decay method, methodology 1030, the drying gas slowly pressurizes the disposable at a flow rate of about 50 SLPM, in step 1006, until the pressure of about 2 psig, as measured by pressure transducer PT06 304 at drying gas outlet 208. The disposable, in this step, can be pressurized to a range between about 1.5 psig and about 4 psig, and the flow rate can range between about 1 SLPM and about 50 SLPM. This pressurization is done with mass flow controller MFC02 264.

The pressure decay method then includes step 1008 which is to wait for a period of time (e.g., about 30 seconds, 1 minute, 1.5 minutes, 2 minutes, 2.5 minutes, 3 minutes, 3.5 minutes, 4 minutes, 4.5 minutes, 5 minutes). In an embodiment, the method includes a wait of a about 1 minute.

After the period of time passes, pressure transducer PT06 304, in step 1010, measures the pressure and sends a digital signal representing the value to the memory of the computer system. If the value of the pressure is such that there is a decrease below a set amount (e.g., threshold amount), then the disposable is discarded, in step 1012. If the value of the pressure in step 1014 is above the acceptable set amount, then the disposable is determined to be acceptable for spray drying by this test. The threshold amount of pressure ranges between about 1 psig and about 3.5 psig, and in an embodiment is about 1.3 psig. In other embodiments, instead of using a set amount, the computer system, using a processor, can calculate the percentage of change in the pressure decrease or can calculate the pressure decay by determining the change in volume instead of pressure.

In the second leak detection method, methodology 1032, the flow sensor method involves closing pneumatic valve PV05 314 in enclosure relief line, line K in FIG. 46C, in step 1016. By closing pneumatic valve PV05 314, this allows drying gas to flow through leak detection line, Line L. The computer system sends pneumatic valve PV05 314 a signal to close in step 1016 and then sends a signal to open solenoid valve PV07 318 in step 1018. Steps 1016 and 1018 can occur simultaneously or sequentially. Once both steps are completed, the air flow is measured using sensor FS01 320 in step 1020. Instead of measuring pressure, and inferring air flow, in this step the air flow is directly measured. The computer system compares the measured air flow amount to a set air flow amount using a processor. If the average air flow is less than a set amount, in step 1022, then the software determines that disposable 100 is good for use in the spray drying process. However, in step 1024, if the air flow is above the set amount, then the computer system determines that disposable 100 should be discarded. The set air flow amount (e.g., threshold flow amount) to which to compare the measured air flow amount ranges in an amount between 10 $cm^2$/min and 30 $cm^2$/min (e.g., 10, 12, 14, 16, 18, 20, 22, 24, 26, 28 and 30 $cm^2$/min). In an embodiment, the set air flow amount is 20 $cm^2$/min.

Once one or both tests are completed, then step 1026, the computer system communicates that the test is complete and actuates valves as follows. Pneumatic valve PV04 306 is opened in the exhaust line, Line J, pneumatic valve PV05

314 is opened in enclosure/housing exhaust line, Line K, and solenoid valve PV07 318 in leak detection line, Line L, is closed.

In an embodiment, pressure decay method 1030 or flow sensor method 1032 can be used independently or together. When one of the methods is employed in the spray drying system, then the result of that test determines if disposable 100 is suitable for use in the spray drying process. In the instance that both methodologies are employed, as in step 1028, both test results (e.g., the leak detection pressure value or the leak detection flow value) are compared and if both results indicate that disposable 100 is suitable for use, then the computer system communicates that the spray drying for disposable 100 can be used or the spray drying can proceed. In the instance in which both methodologies are employed and one test indicates that spray dry disposable 100 should be used and the other indicates that it should not, then disposable 100 should be discarded and not used in the spray drying process. This comparison is embodied in step 1028 and is performed by a processor in the computer system according to a programed routine. The results of the determination are communicated to the user. The results, in an embodiment, are communicated that disposable 200 is suitable or not suitable to an output device such as display 212 on dryer 200. In other embodiments, the communication can be printed, provided by sound (e.g., by a digital voice indicating to remove disposable 200) or visually by indicator light 224 (e.g., red to stop and remove disposable 100 or green to go).

Disposable Pressure Detection Method and System 1200

The present invention further includes disposable pressure detection method and system 1200. See FIG. 46E. This methodology allows dryer 200 to measure pressure inside disposable 100 using pressure sensors residing outside disposable 100. Although the sensors reside in housing 202, especially once the heated drying gas floods disposable 100, the material of wall of disposable 100 conforms, in part, to the shape of the inner wall of housing 202. This is due to the flexibility of the disposable wall. When doing so, pressure sensors mounted to the inner wall of housing 202 measures pressure exerted by the outer wall of disposable 100, which represents the air pressure inside disposable 100. This test can be performed before, during, after spray drying process.

Disposable pressure detection methodology 1200 begins with step 1202 in which dryer 200 is started, and drying gas is running and heated to an inlet temperature of at least about 65° C. or greater (e.g., to about 130° C.), as measured by either temperature transducer TT04 278 or temperature transducer TT05 280 or both. In an embodiment, this method can be performed with and without a heated disposable. In another embodiment, the spray drying apparatus is heated such that the exhaust temperature ranges between about 55° C. and about 75° C. or the inlet temperature between about 110° C. and about 120° C. In an embodiment, one, two or three temperature sensors or transducers can be used.

Once the heated drying air from line E enters drying gas inlet 204, the heated air causes disposable outer wall to exert force on one or both of pressure transducer PT008 224A or pressure transducer PT009 224B. The pressure transducers detect the pressure and generate an electrical signal proportional to the detected pressure. The pressure detected is proportional to the amount of mechanical force exerted on the pressure transducer. The proportional digital signal value is generated and communicated to the memory of the computer system. The processor of computer system calculates the amount of pressure in disposable 100, according to the following formula in step 1206:

$$\text{Drying chamber pressure } (PT08/PT09) = (\text{Digital Signal } mV)\times(\text{Gain})-\text{Offset}$$

wherein Gain ~2, Offset ~−0.1

During manufacturing the gain and offset of PT008 224A and PT009 224B are determined by referencing the digital signals to a known, calibrated pressure gauge. The disposable 2 is pressurized, as described herein, to various pressure (e.g., 1.0, 3.0, 5.0, about 6.0 psig). The output digital signals are then plotted on a chart against the calibrated gauge pressure. A line in the form of y=(m)×(x)+b can then be drawn, where (m) is the gain and b is the offset. This is repeated for both PT008 224A and PT009 224B.

If the pressure gets too high, then the dryer enters its fail-safe mode in step 1210. In particular, if the set fail-safe pressure (e.g., a second threshold pressure amount) is greater than between 7.1 psi and about 8 psi (e.g., about 7.1, 7.2, 7.3, 7.4, 7.5, 7.6, 7.7, 7.8, 7.9, about 8.0 psi) or greater, then the dryer enters fail-safe mode. In this case, the computer system communicates that the pressure in this range and enters failed safe mode. This is communicated to the operator via an output device (e.g., display 212), as described herein. In other embodiments, the communication can be printed, provided by sound, or visually by indicator light 224. Fail-safe mode in general means, in an embodiment, shutting dryer 200 down and stopping the drying gas and plasma from flowing in and allowing any humid air to flow out. Step 1212. As such, the computer system communicates and actuates the following valves in the inflow side by closing valves pneumatic valve PV02 284, pneumatic valve PV03 268, solenoid valve PV06 322, mass flow controller MFC01 264 and mass flow controller MFC02 282, and stopping heater H01 275 and peristaltic pump PO1 214. On the outflow side, the computer system communicates and actuates by opening output valves (PV04, PV05), disabling PV07, to allow the humid air to be filtered and exit/mix with the outside air. Fail-safe mode may also be entered if the system detects excessive heater temperature at TS01 272 or TS02 274, excessive aerosol pressure at PT10 286, or excessive drying air pressure at PT05 276.

If the pressure measures within a set pressure amount (e.g., a first threshold pressure amount), then the drying run ends. In an embodiment when the drying run ends, the set pressure amount ranges between about 5.0 and about 7.0 psi (e.g., about 5.0, 5.5, 6.0, 6.5, and 7.0 psi). In an embodiment, the set pressure amount is between about 6.7 psi and about 7.02 psi. Step 1208. In this case, the computer system communicates that the drying run for disposable 100 has ended to the operator via an output device (e.g., display 212), as described herein.

When the pressure reaches the set pressure amount in step 1208, the computer system then determines if enough pretreated plasma has been processed for a finished dried plasma unit (e.g., a plasma unit with a sufficient amount of plasma that can be used for transfusion after reconstitution). During a drying operation, the pressure with the disposable 100 gradually increases by about 2 psi. The end of the drying operation can be determined by the pressure exceeding the limit described in step 1208, or by the detection of a sudden rise in the exhaust temperature as measured by TT06 300 or TT07 302. When the exhaust temperature has risen ~1.5° C. above the setpoint (e.g., 66.5° C.) the computer system communicates that the drying run for disposable 100 has ended to the operator via an output device (e.g., display 212), as described herein.

The amount of plasma dried or processed can be measured directly or indirectly. In an embodiment, the amount of dried plasma is measured indirectly by determining the amount of donor plasma is left in formulated pretreated plasma bag 66. The less that is left in plasma bag 66, the more that is dried, and vice versa. There is a minimal amount of plasma left in the tubing. Accordingly, in an embodiment, to obtain a processed amount of dried plasma of between about 15 grams and about 20 grams (e.g., 15, 16, 17, 18, 19, or 20 grams) without the weight of the bag, the total amount of pretreated donor plasma that is processed (e.g., the threshold processed plasma mass) ranges between about 280 grams to about 390 grams (e.g., about 280, 290, 300, 310, 320, 330, 340, 350, 360, 370, 380, or 390 grams). In an aspect, the amount of starting pretreated donor plasma is between about 320 grams and about 390 grams (e.g., 320, 330, 340, 350, 360, 370, 380, or 390 grams). Note that the pretreated donor plasma has between about 50 and about 60 grams of pretreatment solution and about 220 and about 340 grams of donor plasma.

In other embodiments, other indirect measurements can determine the amount of plasma processed and they include determining the volume traveling through plasma tubing 16 or pump 216. Since the density of the pretreated donor plasma is between 1.02 and 1.03 grams per milliliter the mass of processed plasma can be determined if the volume is known.

Other embodiments include direct measurement of processed dried plasma. In such an embodiment, weight of disposable before and after spray drying can be obtained, the difference being the weight of the spray dried plasma.

The indirect mass measurement of the donor pretreated plasma bag or the direct measurement of the dried plasma in disposable 100 is communicated to the computer system whose processor determines if a sufficient amount of pretreated plasma has been processed. If a sufficient amount of pretreated plasma has been processed, as described herein, then the drying run is considered complete and the drying run is a success. Step 1214. This result is communicated to the operator, as described herein, and optionally, disposable 100 is inflated and deflated, in step 1216, to assist in removing the dried plasma from the inner wall of disposable 100. Inflation of disposable 100 occurs by allowing the drying gas to run, and deflation of disposable 100 occurs through line F, as described herein.

In the event that an insufficient amount of dried plasma powder has been processed, in step 1212, then the drying run fails and disposable 100 having a partial amount of dried plasma is discarded. This result is communicated to the operator, as described herein.

Detection of Spray Drying Head Interface Integrity Method and System 1400

The present invention includes methods for detecting the integrity of spray dry disposable 100 including its filters and its interface with dryer 200. In particular, the present invention includes method 1400 that determines if the lower filter/capture filter 36, baffle filter 94, or the interface of deflector 242 with plenum 6 are compromised. Additionally, methodology 1400 would also detect a defect in seals or integrity of disposable 100.

This methodology allows for direct detection of spray drying disposable failure, and allows to maintain isolation of the plasma to protect the operator.

Methodology 1400 begins with monitoring pressure above spray drying head 2 of disposable 100 and pressure within housing 202 of dryer 200. Generally, monitoring these pressures and comparing their values at various time-points allows for a determination of the integrity of disposable 100 or the integrity of the interface of disposable 100 and dryer 200. Pressure generally rises over the time during a spray run in a controlled fashion at a slope. Simply put, when the pressure measurements deviate from this slope, then such deviation indicates failure of disposable 100 or its interface with dryer 200.

Figure 46F:
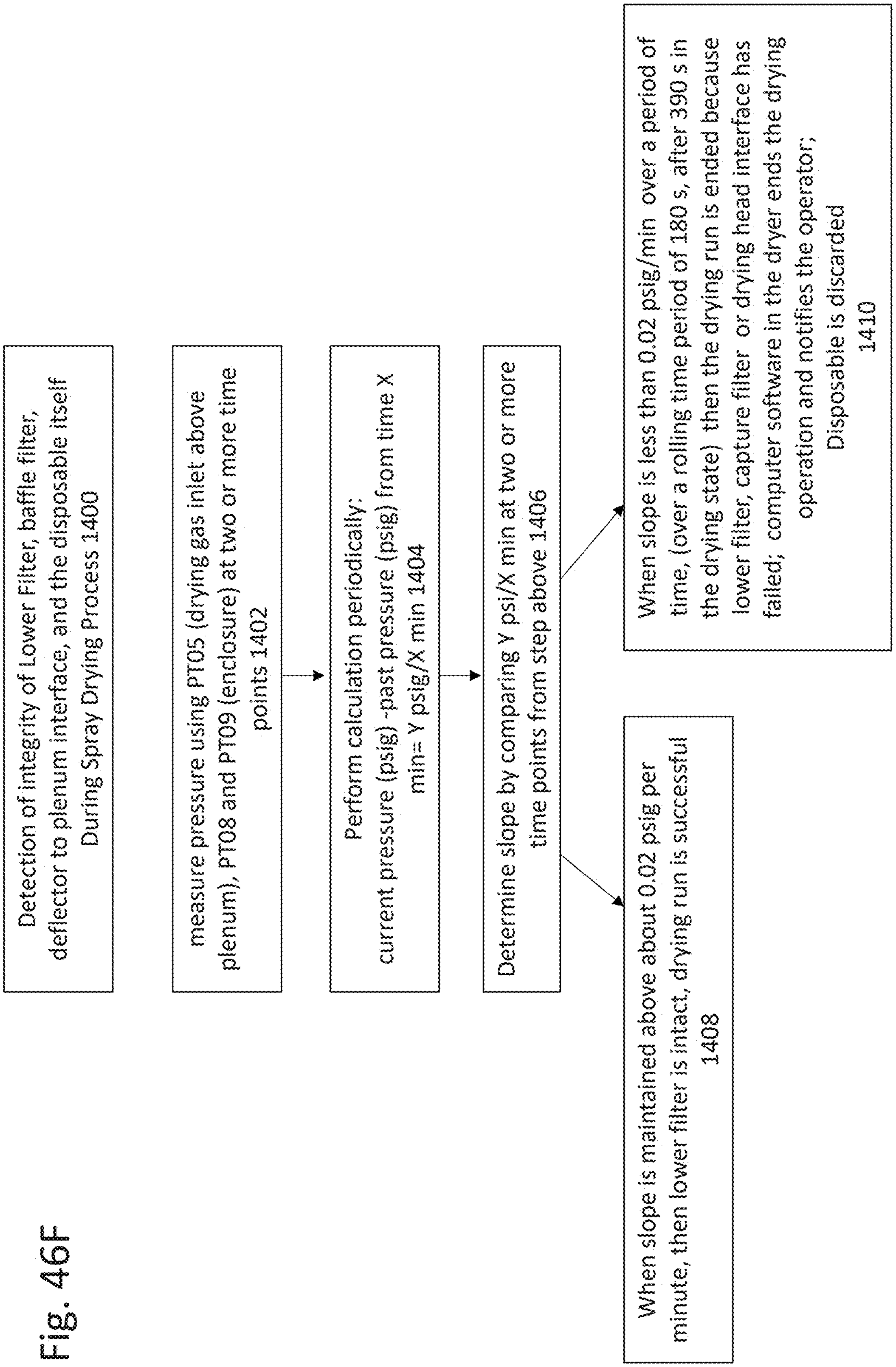
FIG. 46F is a flow chart showing the steps of the method for detecting integrity of filters and disposable interface employing the spray dryer and spray drying disposable.

Referring to FIG. 46F, step 1402 starts methodology 1400 with monitoring pressure at pressure transducer PT05 276, residing in the drying gas line, line E, just before or as the drying gas enters disposable 100 at the drying gas inlet 242. The method also includes monitoring pressure transducer PT08 224A and pressure transducer PT09 224B which are located in housing 202 and are used to measure pressure inside disposable 100. Monitoring these pressures refers to measuring pressure at two or more time points, step 1402, and comparing them to determine a slope step 1404. As described herein, the pressure measurement is translated to a digital value that is proportional to the amount of pressure sensed. The digital value of the pressure from any one of these transducers is communicated to the computer system that performs the comparison of these pressure values and determines a slope using its processor.

In an embodiment, since there are two pressure transducers in housing 202, the average of the two sensors are used in the calculations below.

In particular, the formula used to compare the pressure values is performed periodically and is as follows:

$$\text{current pressure } (psig) - \text{past pressure } (psig) \text{ from time } X \text{ min} = Ypsig/X \text{ min}$$

The slope, in step 1406, is determined by comparing Y psi/X min at two or more time points from step 1404.

Put another way, the formula to determine slope is as follows:

$$\text{Slope} = \frac{\Delta y}{\Delta x} = \frac{Y2 - Y1}{X2 - X1} = \frac{\text{rise}}{\text{run}}$$

Using the slope formula above, the slope is equal to the change in psi over the change in time. The slope for the drying run can be determined, in an embodiment, by performing drying runs and measuring the pressure and determining the slope, as described herein. The disposable and dryer can be visually inspected after each drying run to determine if the filters and/or interface integrity were compromised. For the inventive spraying drying system described herein, when a slope is above about 0.02 psig/minute or in a range between about 0.02 psi/minute to about 0.2 psig per minute (e.g., slope threshold), then capture/lower filter 36, baffle filter 94 and interface of deflector 242 and plenum 6 are considered to be intact, and the drying run is determined to be successful. See Step 1408. In case of a defect in baffle filter 94 and/or lower filter 36, the slope is outside of this range. See Step 1410. In practice for certain cases, a defect can be reflected when there is an instantaneous drop in pressure (e.g., the slope is still less than 0.02 psig/minute).

The slope calculation is determined, in an aspect, after at least about 4 minutes pass and measured periodically for about 35 minutes, the typical time of the duration of the spray dry run. In an embodiment, the slope is calculated periodically at a time point ranging from every 1 minute to every 10 minutes (e.g., about 1, 2, 3, 4, 5, 6, 7, 8, 9, 10 minutes). In the embodiment shown in FIG. 46F, the slope is calculated every 3 minutes (180 seconds).

Figure 46G:
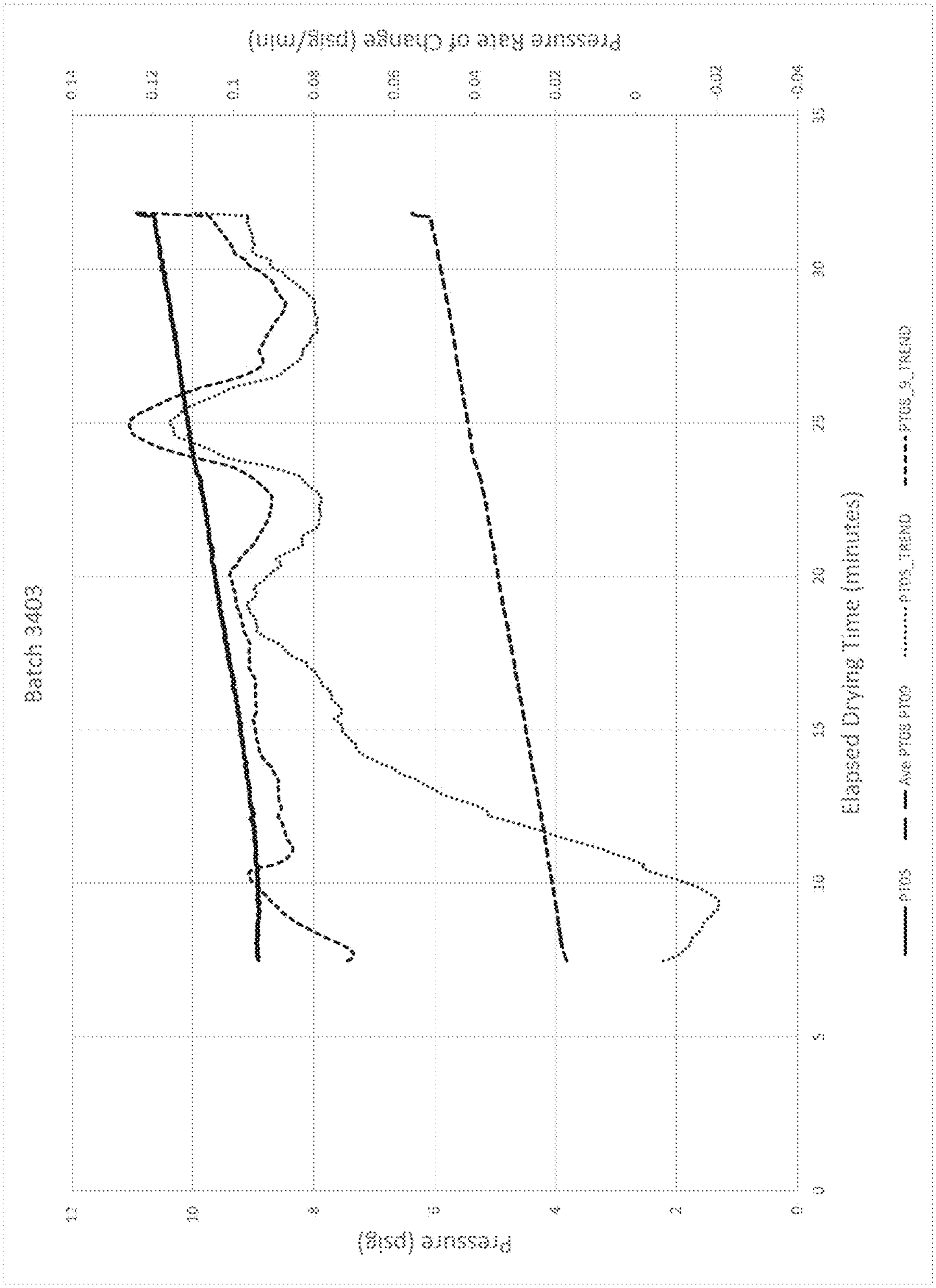
FIG. 46G is a line graph showing the slope employing the method for detecting integrity of filters and showing that the filters are intact by measuring Pressure (psig), elapsed time (min) and pressure rate of change (psi/min).
Figure 46H:
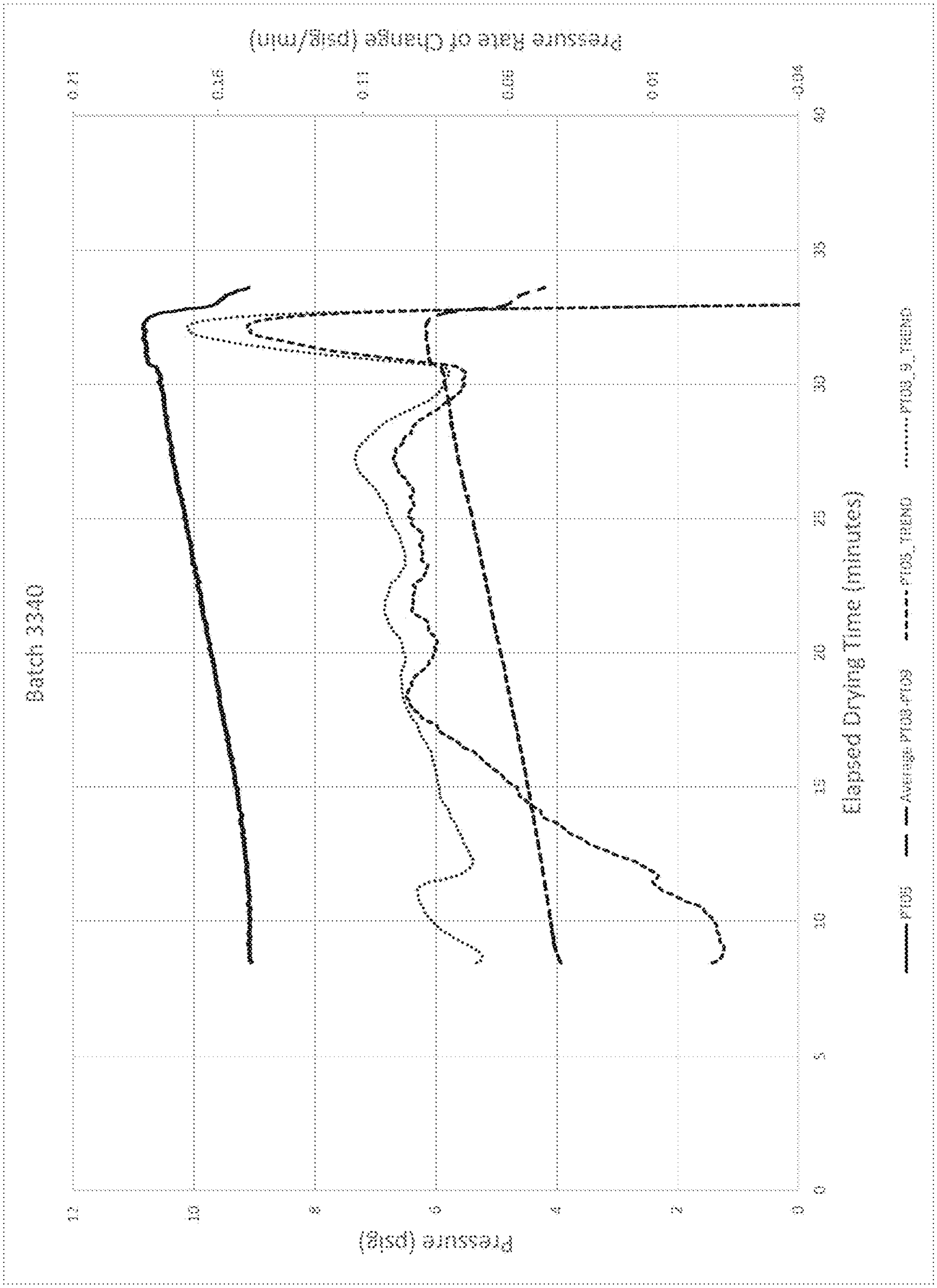
FIG. 46H is a line graph showing the slope employing the method for detecting integrity of filters and showing that the capture filter has failed intact by measuring Pressure (psig), elapsed time (min) and pressure rate of change (psi/min).
Figure 461:
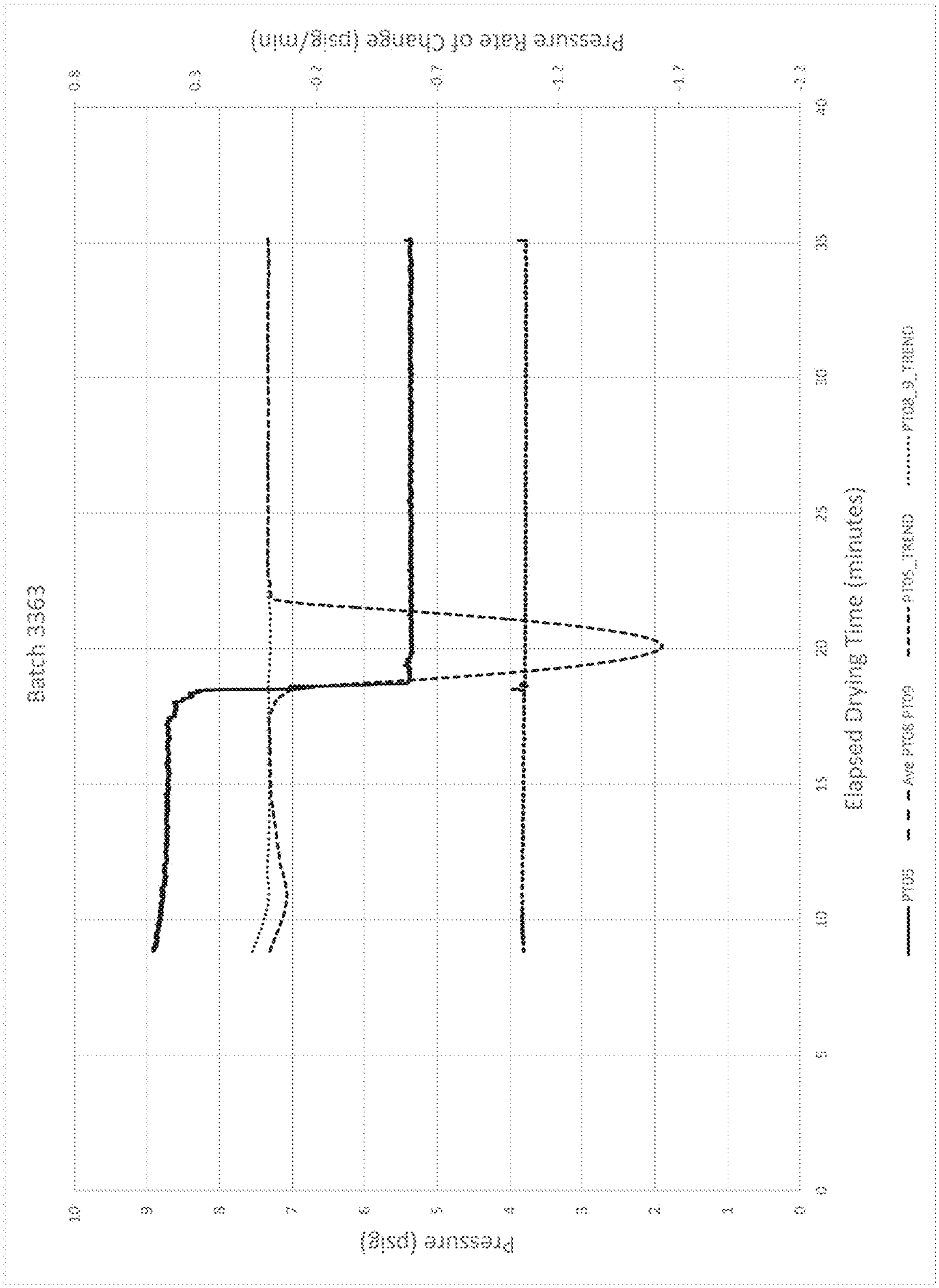

An example of calculated slopes of a spray drying run can be seen in FIG. 46G. FIG. 46G shows the pressure values (on left Y axis) of pressure transducer PT05 176 at the drying gas inlet, and pressure transducer PT08 224A and pressure transducer PT09 224B, located in housing 202, over time (on X axis), starting at about the 6 minute mark until about the 32 minute mark. On the right Y axis, the slope or pressure rate of change in psi/min is shown. As can be seen, the slope (e.g., pressure rate of change) is about 0.02 psi/min. FIG. 46H shows a failure of lower/capture filter 36 and FIG. 46I shows a failure of baffle filter 94. In both cases, there is a rapid drop below a slope of 0.02 psi/min.

In the event that the slope is determined to go below the set amount (e.g., 0.02 psi/min), then computer software sends instructions to end the drying run and notify the operator via an output device, as described herein. The disposable is discarded.

Computer System

In addition to the sensors and actuators described herein (e.g., connectors, differential pressure transducer, flow sensors, heaters, mass flow controllers, sensors, pumps, pneumatic piston, pressure regulators, pressure relief valve, pressure transducers, valves, scale, solenoids, thermocouple, thermocouple sensors, temperatures transducers, and the like), the spray dryer 200 shown in FIGS. 45A-C and 46A-B and finisher 400 or 400' shown in FIGS. 47-48 further includes a computer system. The computer system includes, among other devices, a controller including one or more processors, a bus or other communication mechanism coupled to the one or more processors for communicating information, and a main memory (e.g., RAM) and/or other dynamic storage device, coupled to the bus for storing information and instructions that are executed by processor. This computer system is integrated together with the sensors/actuators and control systems to enable computer control of the sensors/actuators operation and data collection and communication. The main memory also can be used for storing temporary variables (e.g., pressure, flow rate, time, etc.) or other intermediate information during execution of instructions to be executed by the controller. Such computer system also includes ROM or other static storage device coupled to the bus for storing static information and instructions for processor. A physical computer-readable storage device, such as a solid-state memory device, is provided and coupled to the bus for storing information. Output devices of the computer system can be provided, for example, to allow various information to be viewed or otherwise perceived in connection with execution of the instructions. The input devices can be provided, for example, to allow a user to make selections, enter data or various other information, or interact in any of a variety of manners with the processor during execution of the instructions. The computer system is also coupled via the bus to one or more display or output devices (e.g., screen display, touch screen, light beacon, sound indicators, etc.), one or more input devices (touch screen, etc.).

In accordance with the disclosed methods, in at least some aspects, the methods are implemented utilizing the computer system in response to controller executing one or more sequences of one or more instructions contained in a physical memory device attached to the bus, such as the main memory. Execution of the sequences of instructions causes the controller to perform at least some of the process steps described herein.

The memory device(s) bear instructions configured to cause the controller to determine, in combination with inputs from the sensors/actuators to carry out the steps of dryer 200 or finisher 400 or 400' described herein.

The term "computer-readable medium" as used herein refers to any physical medium that participates in providing instructions to processor(s) for execution (e.g., non-volatile media, volatile media, magnetic media, optical media, solid state media, etc.). The computer system utilized in combination with dryer 200 or finisher 400 or 400' also advantageously, but optionally, includes a communication module coupled to the bus, such communication interface providing a two-way data communication coupling to a network link (e.g., an integrated services digital network (ISDN) card, modem, local area network (LAN) card, wireless link, etc.). The network link provides data communication through one or more networks to other data devices (e.g., the network link may provide a connection through local network to a host computer or to data equipment operated by an Internet Service Provider (ISP)) and the computer system is configured to send and receive data through the network(s), network link(s), and communication interface(s). A communication module can be configured to implement a communication protocol based on Bluetooth® technology, Wi-Fi, Wi-Max, IEEE 802.11 technology, a radio frequency (RF) communication, an infrared data association (IrDA) compatible protocol, or a shared wireless access protocol (SWAP).

Detailed Description of the Finisher

Once the spray drying is complete, the disposable having the spray dried plasma is transferred to the finishing apparatus.

Referring to FIG. 47A-F, finishing apparatus 400 and 400' is shown. In particular, the function of the finishing apparatus is to move the plasma in the designated portion of the disposable, remove any excess air in the disposable, if any, and seal and separate to result in a plasma unit having dried plasma (dried plasma unit 60). Plasma unit 60 can later be rehydrated e.g., within 5 minutes or less and transfused into a patient.

In particular, finishing apparatus 400 or 400' has base 440 or 440' and shuttle 418 or 418'. Base 440 or 440' includes an electrical source, an impactor 442 or 442', heat sealer and separator 448 (heat sealer 448' and separator 450'), and an air extractor 456 or 456'. The impactor 442, in the embodiment shown in FIGS. 47B and 47C, includes magnets and springs and impactor 442', shown in FIGS. 47E-H, 48D-F, uses a pneumatic cylinder. In an embodiment, impactor 442 or 442' can include any combination of elements that allow an impacting force to be applied to the disposable sufficient to move the dried plasma to the desired compartment, as further described herein. Sealer 448 or 448' can be an impulse sealer, a heat sealer, electric heater, radio frequency sealer, and the like. Separator 448 or 450', in an aspect, is a cut wire or heat cutter but can be any device that can separate and cut the disposable once it is sealed. The sealer and separator can be the same device, as shown as sealer/separator 448 in FIGS. 47B-C, or two separate devices, as shown as sealer 448' and separator 450' in FIGS. 47E, 47F, 48E and 48F.

Figure 47A:
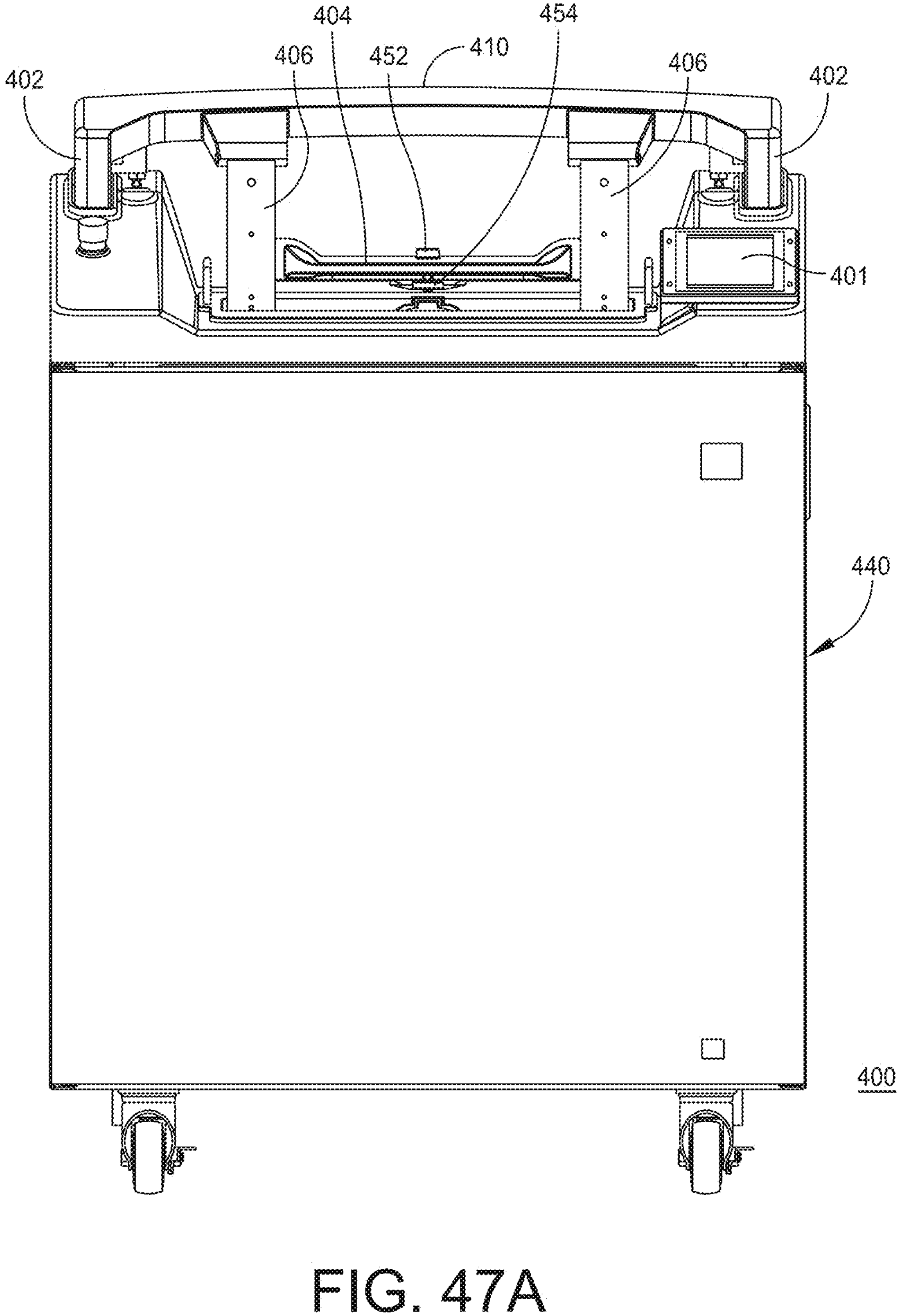
FIG. 47A is a schematic showing a front view of the finishing apparatus in the loading position and without the spray drying disposable attached.
Figure 47B:
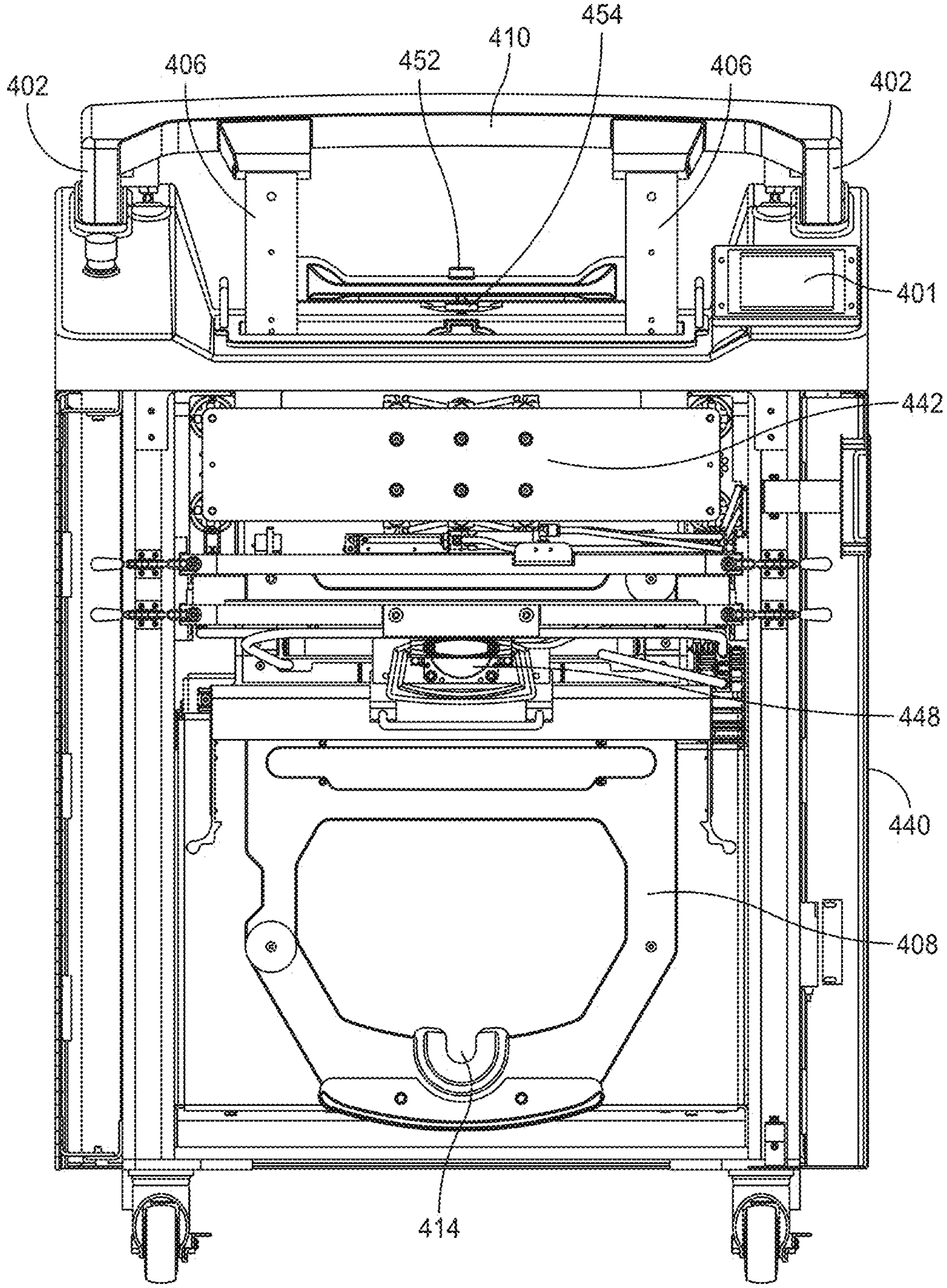
FIG. 47B is a schematic showing a front view of the finishing apparatus of FIG. 47A but without the front cover with the shuttle in the lowered position.
Figure 47D:
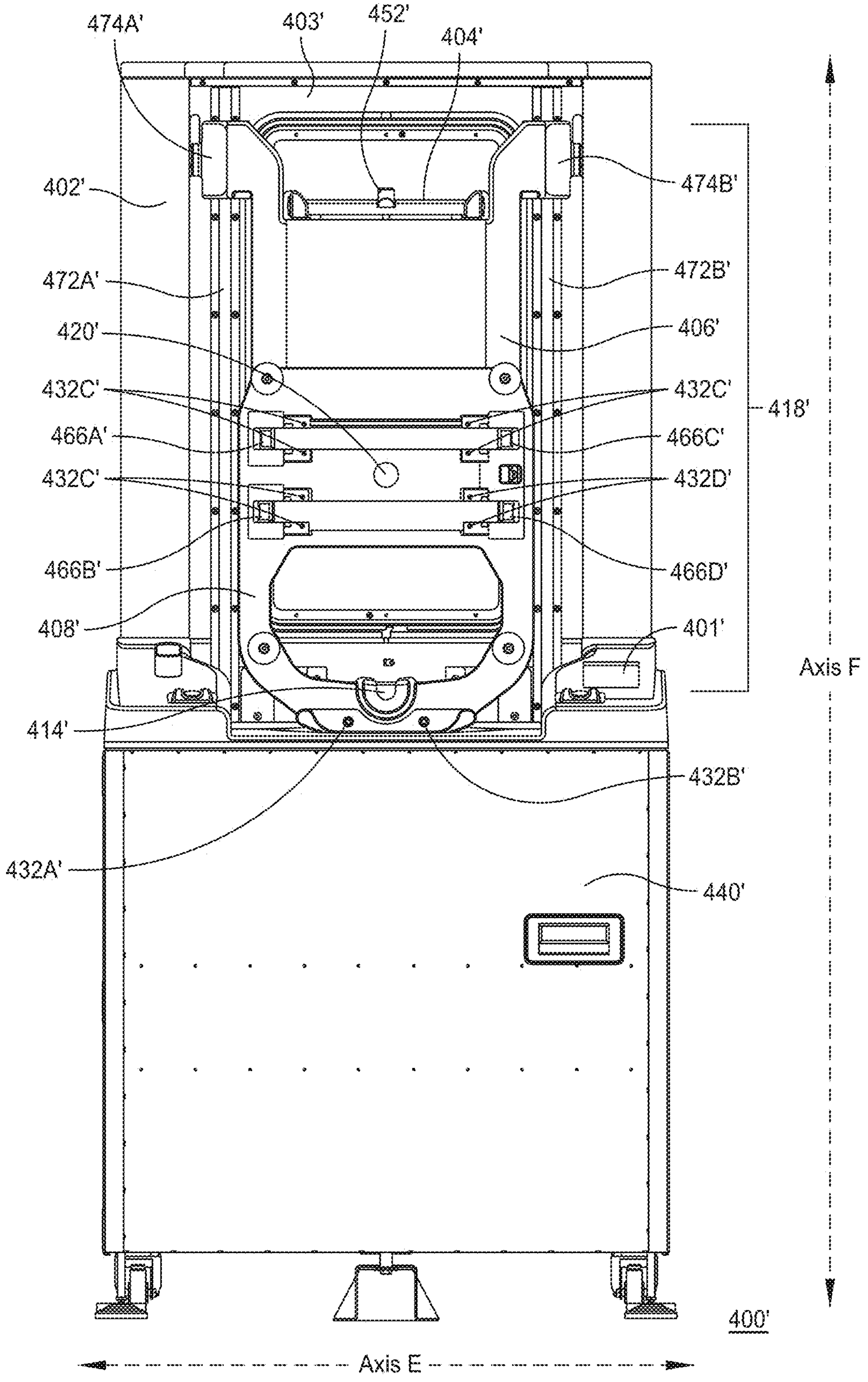
FIG. 47D is a schematic showing a front view of another embodiment of the finishing apparatus in the raised position and without the spray drying disposable attached.
Figure 47E:
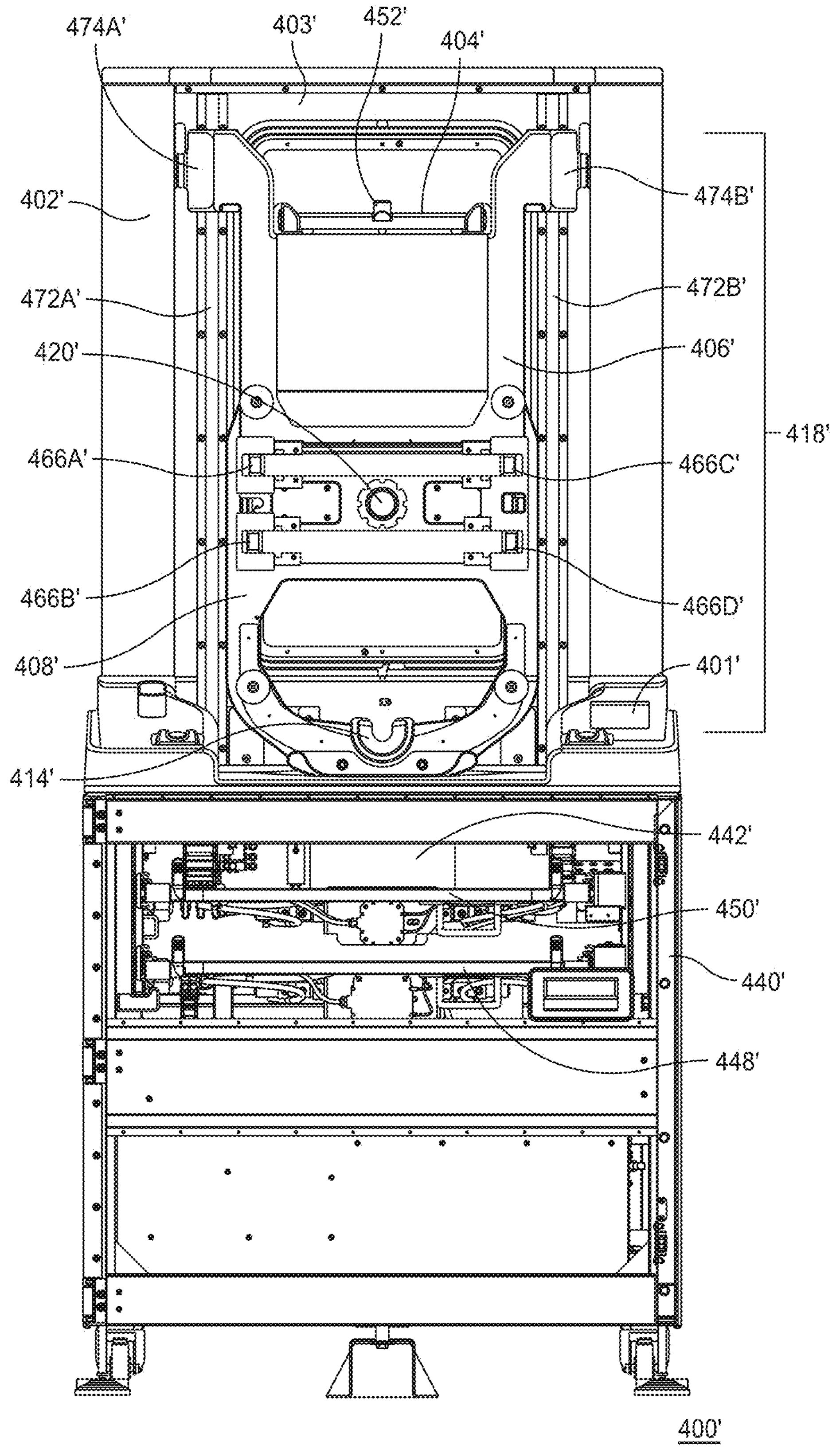
FIG. 47E is a schematic showing a front view of the finishing apparatus of FIG. 47D but without the front cover with the shuttle in the raised position.
Figure 47F:
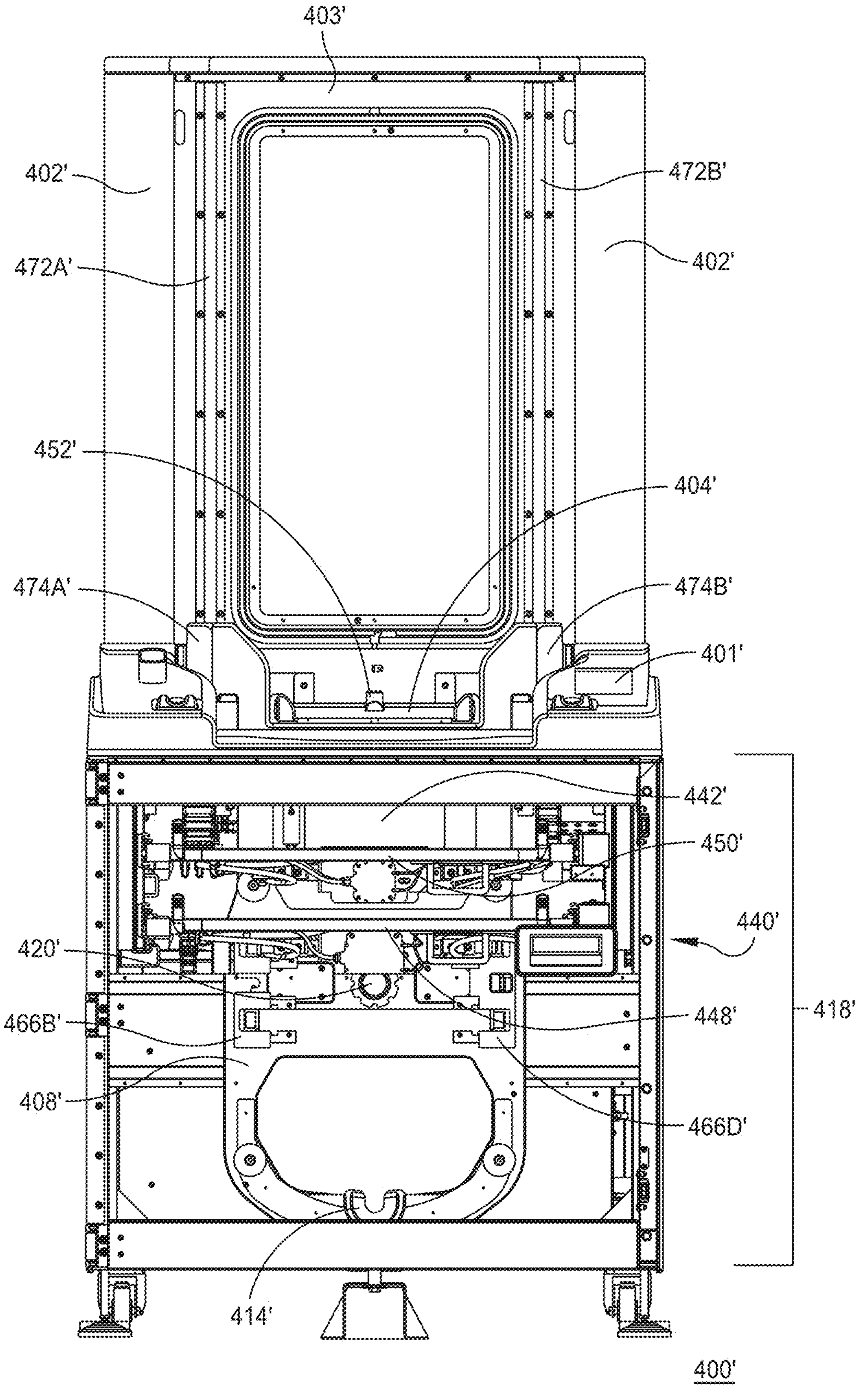
FIG. 47F is a schematic showing a front view of the finishing apparatus of FIG. 47D but without the front cover with the shuttle in the lowered position.
Figure 47G:
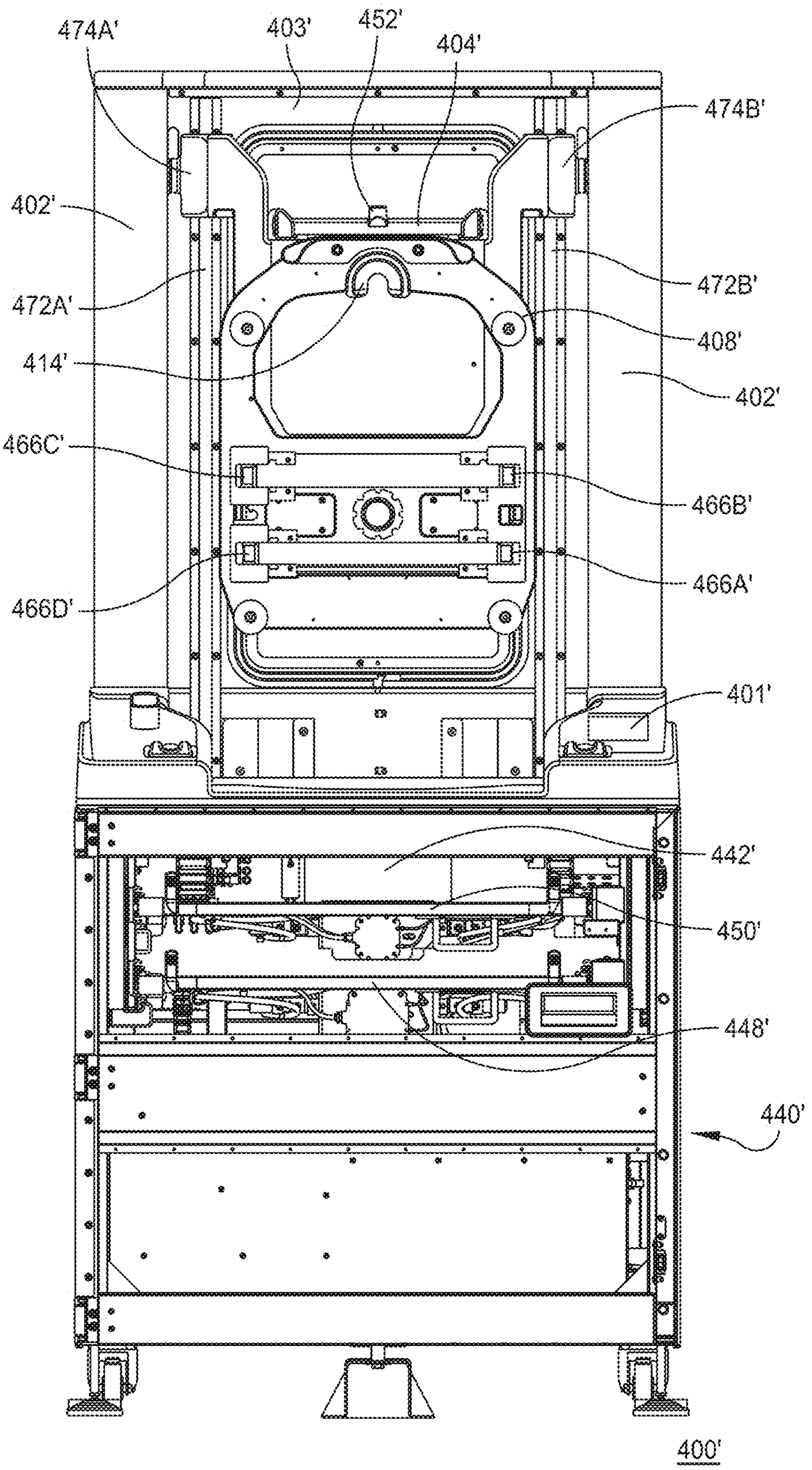
FIG. 47G is a schematic showing a front view of the finishing apparatus of FIG. 47D but without the front cover with the shuttle in the raised and inverted position.
Figure 47H:
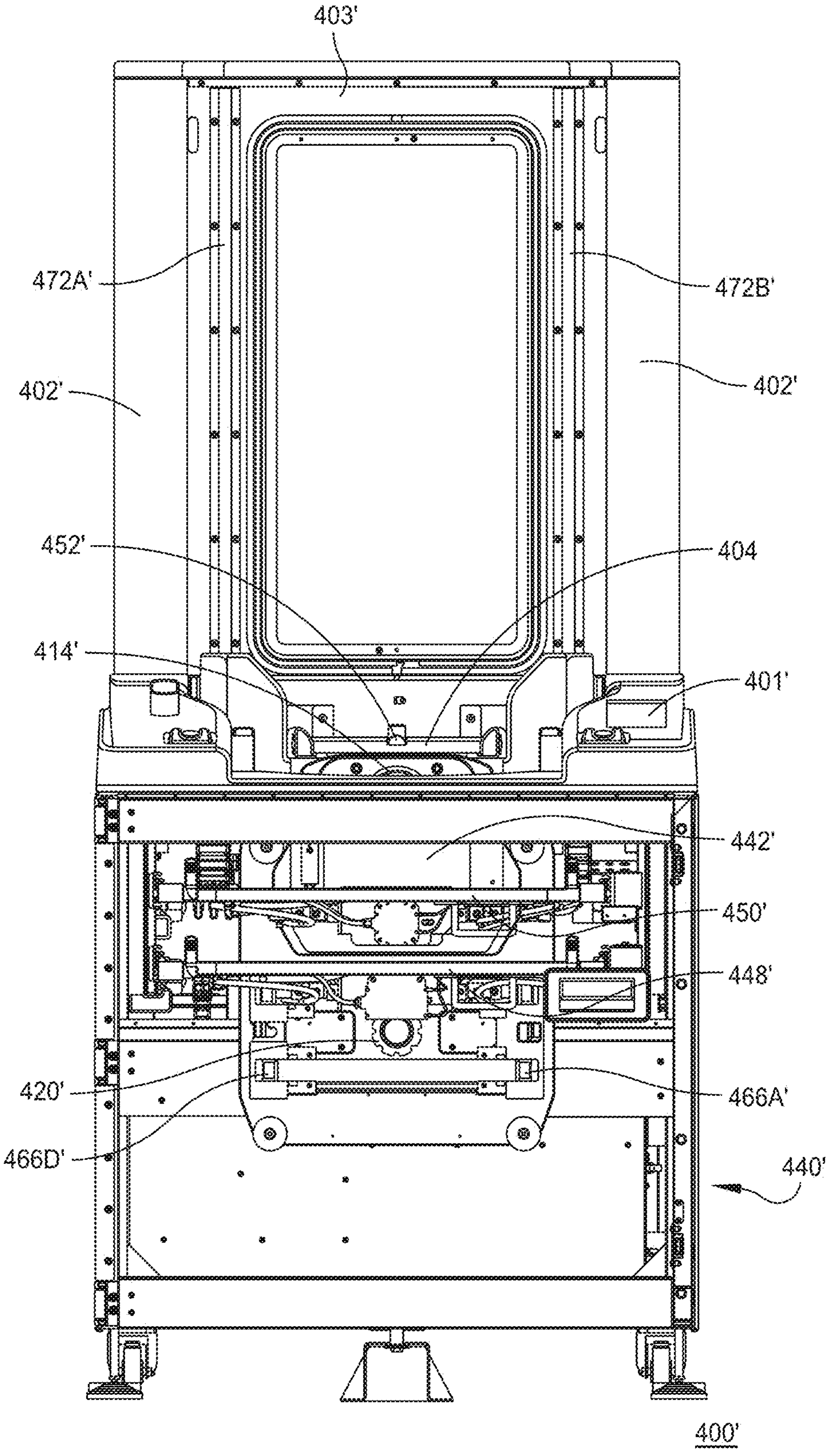
FIG. 47H is a schematic showing a front view of the finishing apparatus of FIG. 47D but without the front cover with the shuttle in the lowered and inverted position.
Figure 47I:
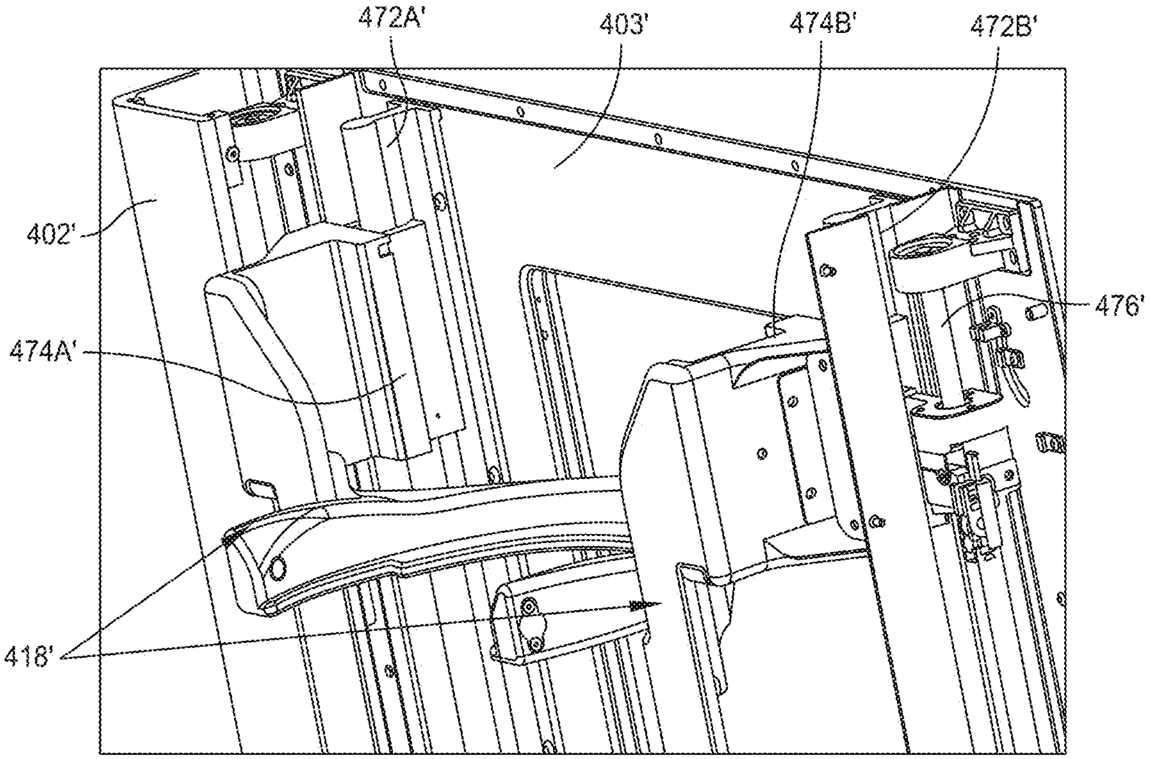
FIG. 47I is a schematic showing a close-up perspective view of a portion of the rail system of the finishing apparatus of FIG. 47D

Finishing apparatus 400 has sliding frame 402 and shuttle 418 that move together and finishing apparatus 400' has stationary frame 402' that guides movable shuttle 418'. FIGS. 47A, 47B, 48A show finishing apparatus 400 with the shuttle and frame in a lowered position while FIGS. 47C, 48B, 48C show the shuttle and frame in certain upper positions. FIGS. 47F, and 48E show finishing apparatus 400' with the shuttle in a lower position and FIGS. 47D, 47E, 48D, 48F show the shuttle in certain upper positions. FIG. 47G show the shuttle in the inverted, upper position and FIG. 47H show the shuttle in the inverted, lowered position. Stationary frame 402' of finisher 400' has a rail system that allows for shuttle 418' to move up and down. In particular, rails 472A' and 472B' are mounted to back plate 403' and utilizes guide 474A' and 474B'. See FIG. 47I. Guides 474A' and 474B' and rails 472A' and 472B' shown in FIG. 47I is a tongue and groove fit. Rails 472A' and 472B' are fixed and guides 474A' and 474B' move up and down the rails, which in turn, moves shuttle 418'. The mechanism that drives shuttle 418', shown in FIG. 47I, is lead screw 476'. A lead screw is fixed at its ends with the nut rotating while moving back and forth along the length of the screw shaft. The rotation of the nut is powered by a motor. In addition to using a lead screw, the finisher can use any method for moving the shuttle including a chain, strap, and any other mechanism that allows the shuttle to move up and down the rails. In the embodiment of using a rail system and lead screw, the lead screw moves up and down with precision.

More specifically, the spray drying disposable device 100 is aligned in finishing apparatus 400 or 400' as follows. In an aspect, this is accomplished by inserting plenum 6 of spray drying head 2 (by aligning locator notch 26 and the ridge 9) into the spray drying head receiver 404 or 404', attaching gas outlet 30 of the disposable into gas outlet receiver 414 or 414', and securing positioning pin openings 32A-C around positioning pins 432A-C or 432A'-C'. See FIGS. 48A-48D. In an embodiment, when all three alignment elements are engaged, namely, the locator arrangement, the gas port arrangement and the positioning arrangement for the outer wall of the disposable, the disposable device is aligned in and secured to the finishing apparatus. In other embodiments, any combination of these alignment elements can be utilized so long as the disposable is aligned and secured to the finishing apparatus.

In a further embodiment, gas outlet receiver is positioned to accommodate any changes in the length of the disposable or the configuration of the disposable gas outlet 30 caused by the heat and pressure stresses of the spray drying process accomplished by the spray dryer apparatus. Similarly, the location of the positioning pins 432A-C or 432A'-C' are positioned to accommodate and any changes in the length of the disposable or the configuration of the positioning pin openings 32A-C caused by the heat and pressure stresses of the spray drying process accomplished by the spray dryer apparatus.

As described above, the second locator, locator 26, on disposable 100 is aligned with third locator 452 or 452' in spray dry head receiver 404 or 404' during the finishing process. In an embodiment, the spray drying head 2 is inserted into spray dry head receiver 404 with the locators aligned when finisher 400 is in the loading position, as shown in FIGS. 47A, 47B and 48A (shown in loading position with spray dry head attached). In finisher 400', spray drying head 2 is dropped into spray dry head receiver 404' with locators aligned, when finisher 400' is in the loading position. In the embodiments shown in FIGS. 47E and 46D, the loading position is approximately two thirds the way up the rails. In an aspect, the third locator of the finisher and the first locator of the spray dryer are the same shape and size and align with the locator on the spray drying disposable. As with the locating arrangement for the spray drying head, this locating arrangement axially aligns in the spray drying disposable with the finisher. The locating arrangement can include any arrangement that attaches, fits, complements or otherwise communicates with the locator on the disposable and the locator on the finishing apparatus. Examples of locating arrangements can include a recess/projection arrangement, complementing shape arrangement, hook/receiver arrangement, channel and groove arrangement, a latch and catch arrangement, a magnet arrangement, and the like. In the embodiment in FIG. 48A, the male locator is on the spray drying finishing apparatus and a complementing female locator is on the disposable, but the arrangement can be reversed.

Spray drying head receiver 404 or 404' also aligns spray drying head 2 latitudinally. Receiver 404 of the spray drying head allows spray drying head 2 of disposable 100 to be aligned latitudinally with respect to finisher 400 or 400'. In an embodiment, spray dryer head retention clip 454 secures the spray dryer head 2 during the finishing process. See FIG. 47A. Retention clip 454 is optional. Baffle plate ridge 9 of spray drying head 2 also provides additional support when inserted into receiver 404 or 404'. Once inserted and aligned, spray drying disposable 100 can no longer move up and down. When using the receiver and the locating arrangement, they align the disposable so that it cannot move up and down and cannot move axially as defined by an axis through the center of the spray drying head once inserted into the finisher. As shown in FIG. 48A, the spray drying head fits into receiver 404 and does so such that the fit is snug or tight.

In an embodiment, receiver 404' can be further configured to facilitate insertion, alignment and retention of spray dry head 2. Finisher 400' has receiver 404' shown as a top view in FIG. 48G and shown as a perspective view in FIG. 48H. Baffle plate ridge 9 of spray dry head 2 slides into receiver 404 or 404'. In the case of receiver 404', the upper and front surfaces that have a partial tapered edge, ramps 458A and 548B, to allow the operator with room to slide the spray dry head 2 into receiver 404' from the top, in a tilted, downward motion, generally along Axis C. The partial tapered surface tapers from the upper surface to the inside surface along the front surface forming a ramp. FIG. 48H. The ramps, in an embodiment, partially taper leaving a portion of the front surface and inner surface such that the non-tapered front inside surface creates a lip, lip 462A' or lip 462B'. Lips 462A' and 462B' form part of bumpers 460A' and 460B'. Bumpers 460A' and 460B' prevent the spray drying head from being removed along Axis D, e.g., after baffle plate 8 of spray drying head 2 is fully inserted and lying flat.

Bumpers 460A' and 460B' are curved and configured to receive baffle plate ridge 9. The bumpers are formed as the receiver continues along circular perimeter for greater than 180 degrees. The receiver has a circular parameter ranging between about 210 and about 260 degrees including bumpers 460A' and 460B' which each form between about 15 and about 40 degrees (e.g., about 15, 20, 25, 30, 35, or 40 degrees) of the perimeter. Receiver 404' also includes a spring-operated ball detents 464A' and 464B' instead of a retain clip. These detents act as a catch to secure baffle plate ridge 9 in receiver 404'. The detents are optional and other types of catches (e.g., can be used to further secure baffle plate ridge 9 in receiver 404'. In an embodiment, detents 464A' and 464B' make an audible "click" to signal to the operator that the baffle plate ridge is properly secured.

The positioning arrangement (e.g., the pins and openings arrangement 32A-C and 432A-C or 432A-C') is located preferably at each corner of the outer wall of the plasma unit-to-be and above and below seal and separation locations 44A and 44B. The positioning arrangement shown is a pin and opening arrangement but can be any arrangement that allows the side walls of the disposable to be secured properly to the finisher while the finisher is in use. Compare FIGS. 47C and 48B. In addition to a pin and opening arrangement, other examples of other positioning arrangements include a hook/receiver arrangement, channel and groove arrangement, a latch and catch arrangement and the like. In the embodiment, the pins are positioned on the finisher and the openings are positioned on the disposable, but these can be reversed.

Finisher 400 or 400' can include a tensioning system that stretches the wall of disposable 100 during sealing and/or separating. In an aspect, stretching the disposable wall assists in ensuring a better, more complete seal and reduces wrinkles in the seal. In certain embodiments, if the disposable wall does not have enough tension in it, wrinkles can be embedded in the seal and the seal can fail. By increasing the tension in the disposable wall, a decrease in wrinkles and/or failed seals occurs, as compared to a non-tensioned disposable wall. Finisher 400' has two positioning pins 432C' attached to each tensioner 466A', 466B', 466C' and 466D'. See FIG. 47D. Any arrangement of positioners and tensioners can be used so long as disposable 100 remains secured to the shuttle frame and the disposable wall has tension during sealing and/or separating. During sealing and/or separating, the tensioners move apart from one another along Axis E to create tension on the disposable wall.

Figure 48D:
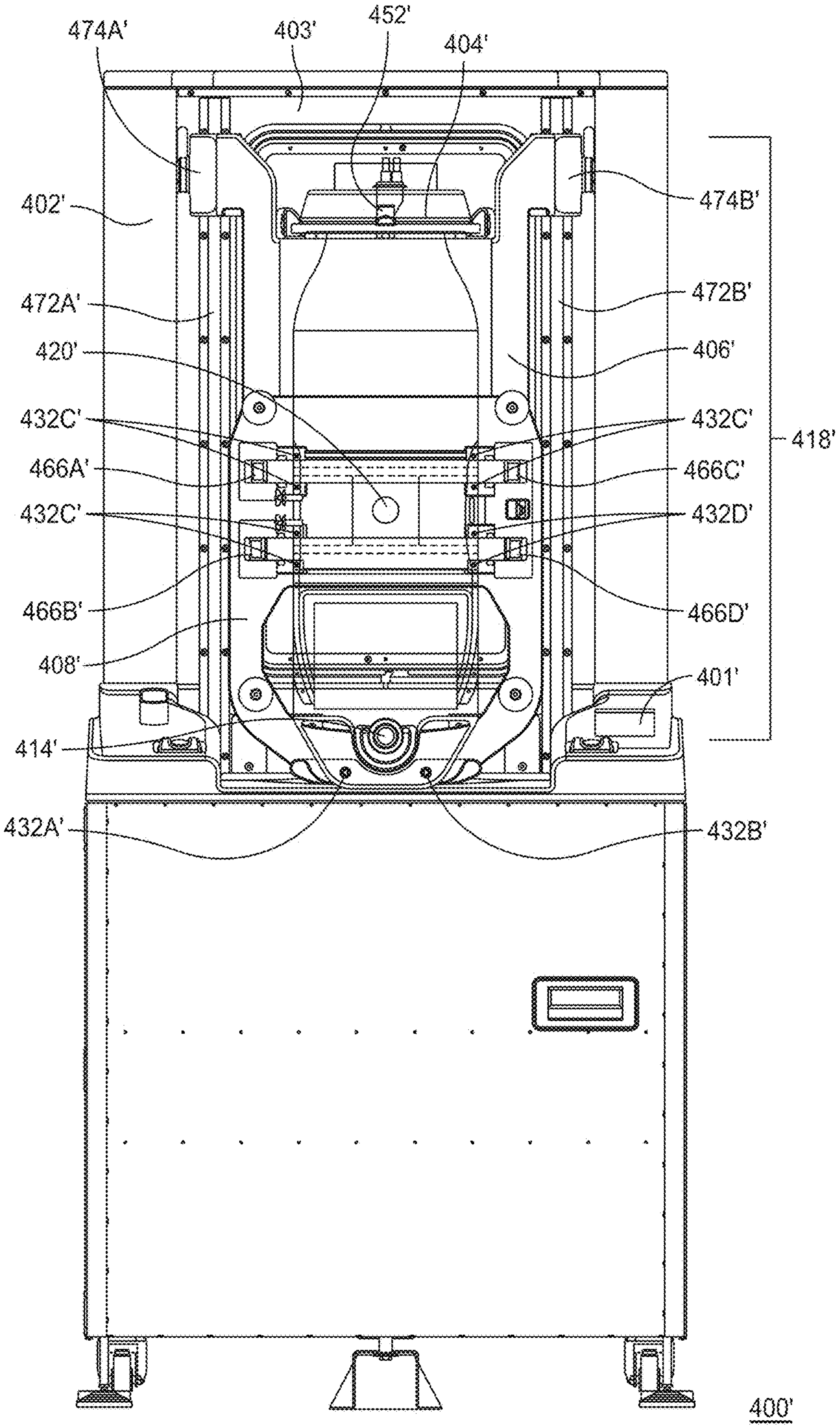
FIG. 48D is a schematic showing a front view of another embodiment of the finishing apparatus in the raised position and with the spray drying disposable attached.
Figure 48E:
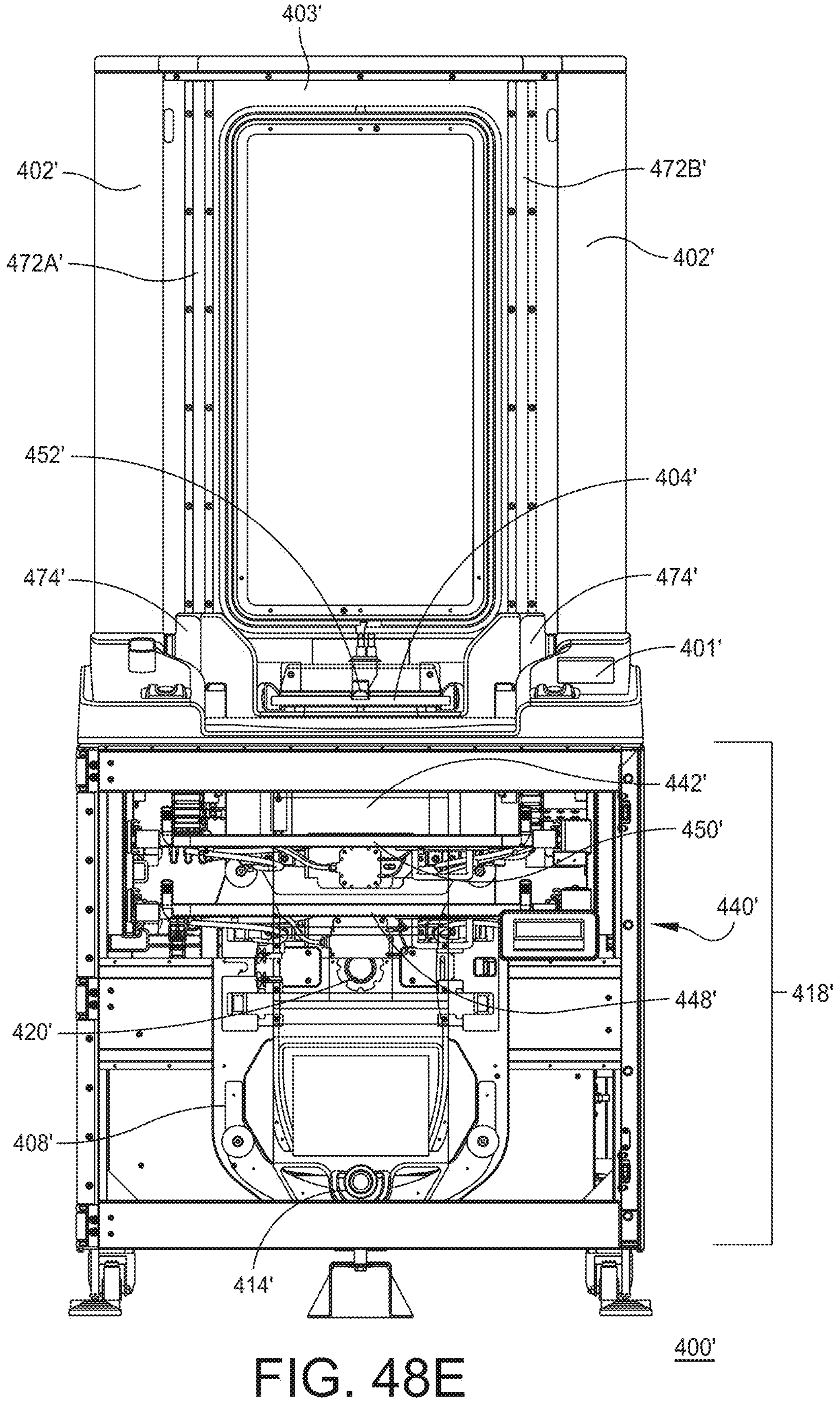
FIG. 48E is a schematic showing a front view of the finishing apparatus shown in FIG. 48D in the lowered position and with the spray drying disposable attached.
Figure 48F:
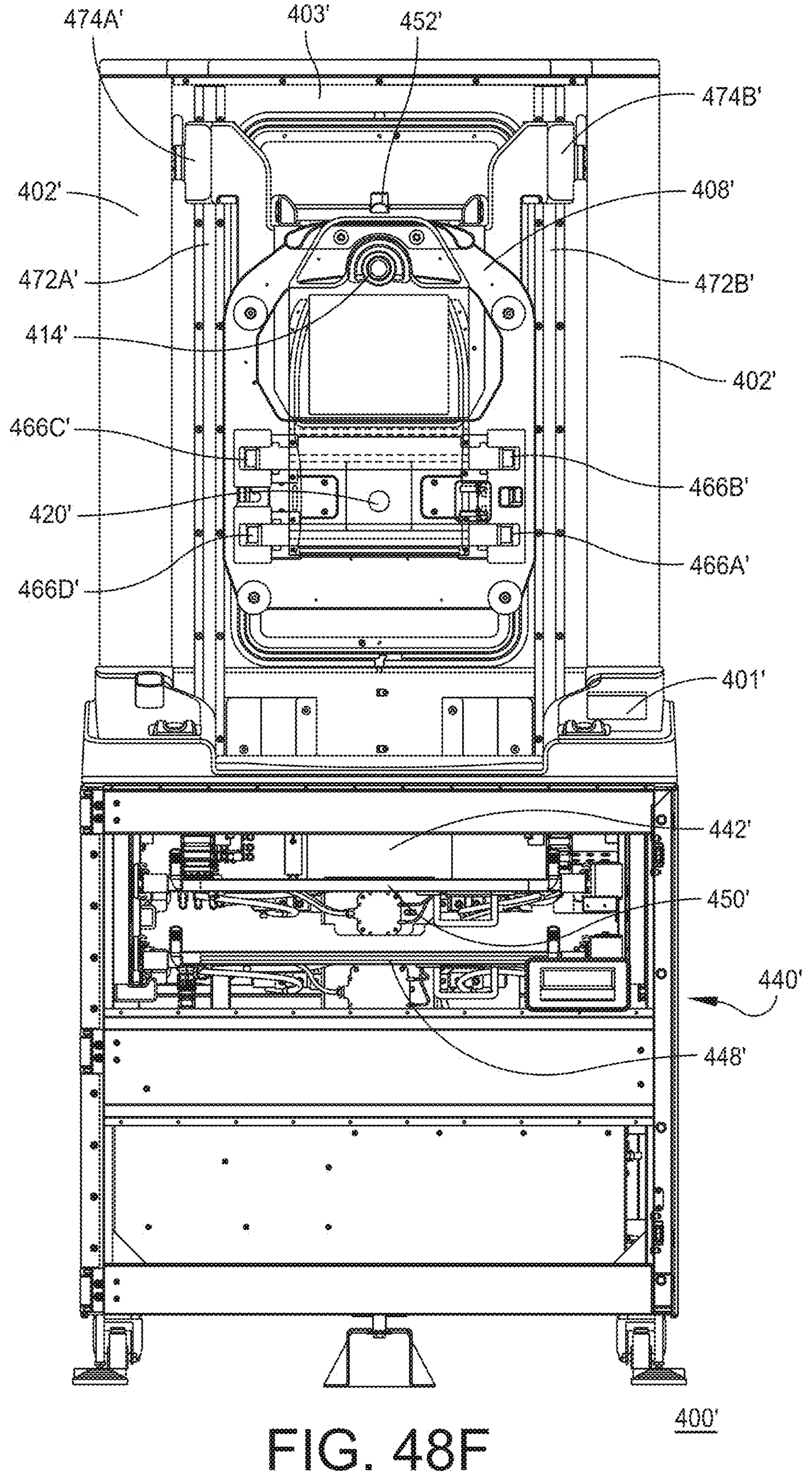
FIG. 48F is a schematic showing a front view of the finishing apparatus shown in FIG. 48D in the raised and inverted position and with the spray drying disposable attached.
Figure 48G:
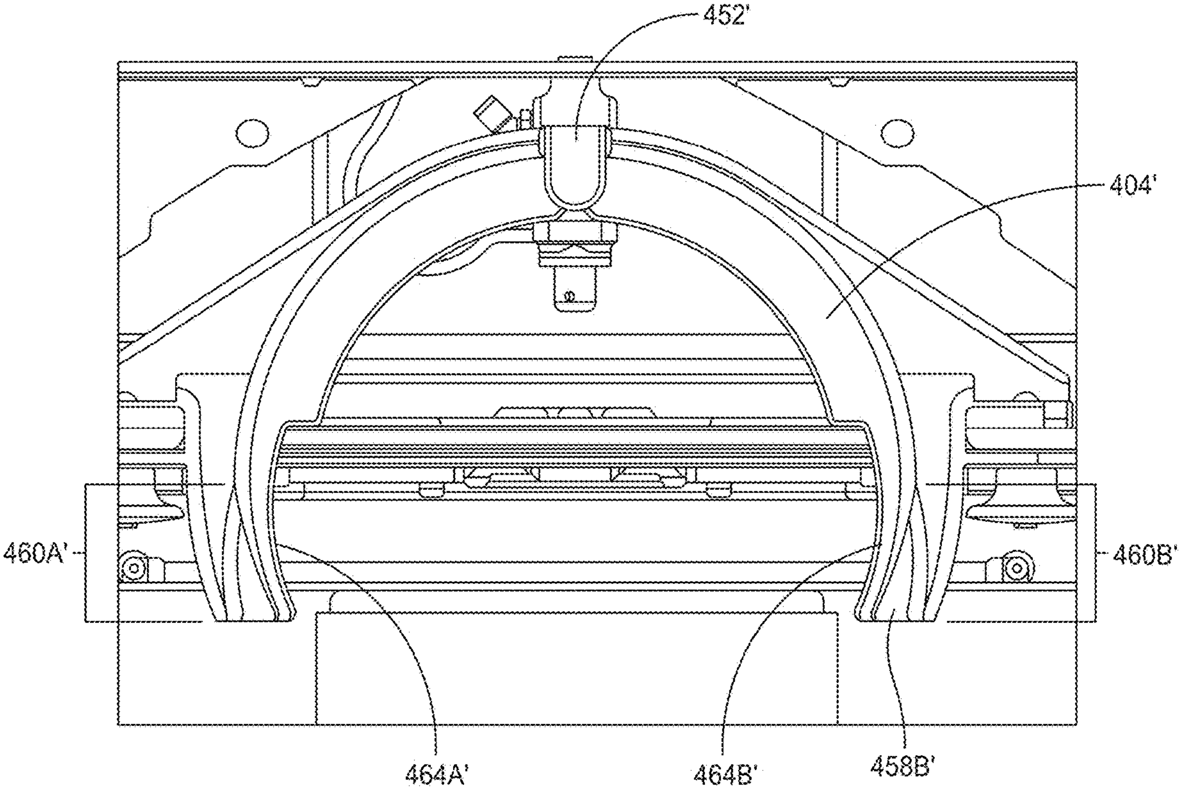
FIG. 48G is a schematic showing a close up, top view of the receiver of the finishing apparatus shown in FIG. 48D.
Figure 48H:
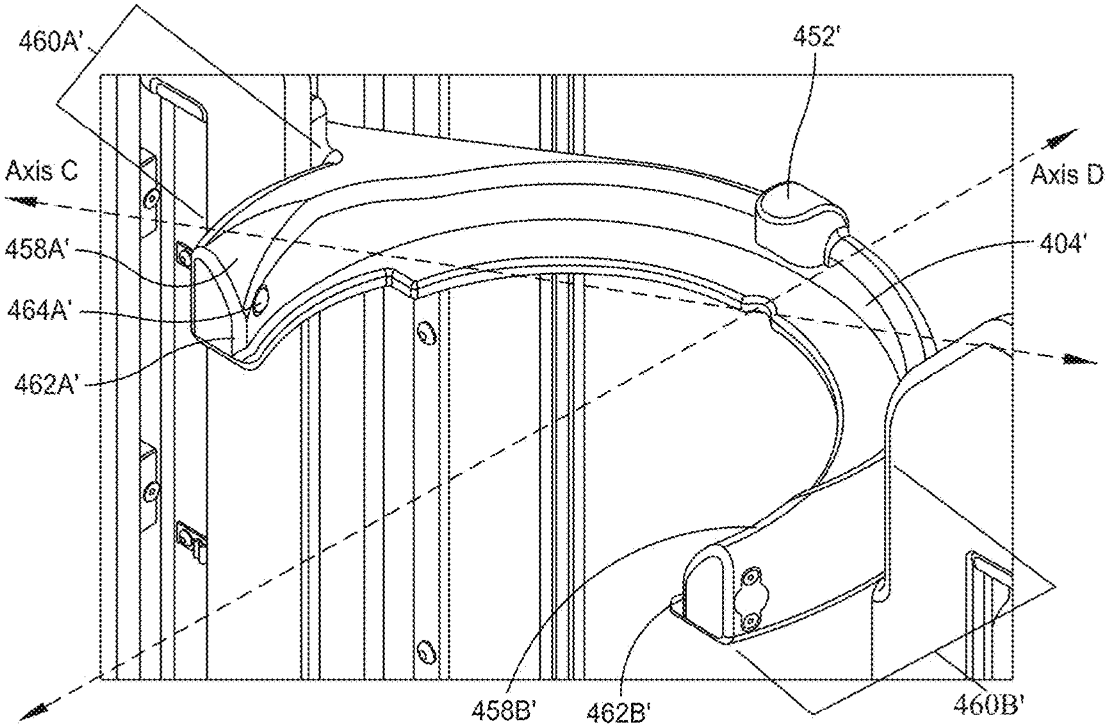
FIG. 48H is a schematic showing a close up, perspective view of the receiver of the finishing apparatus shown in FIG. 48D.
Figure 48I:
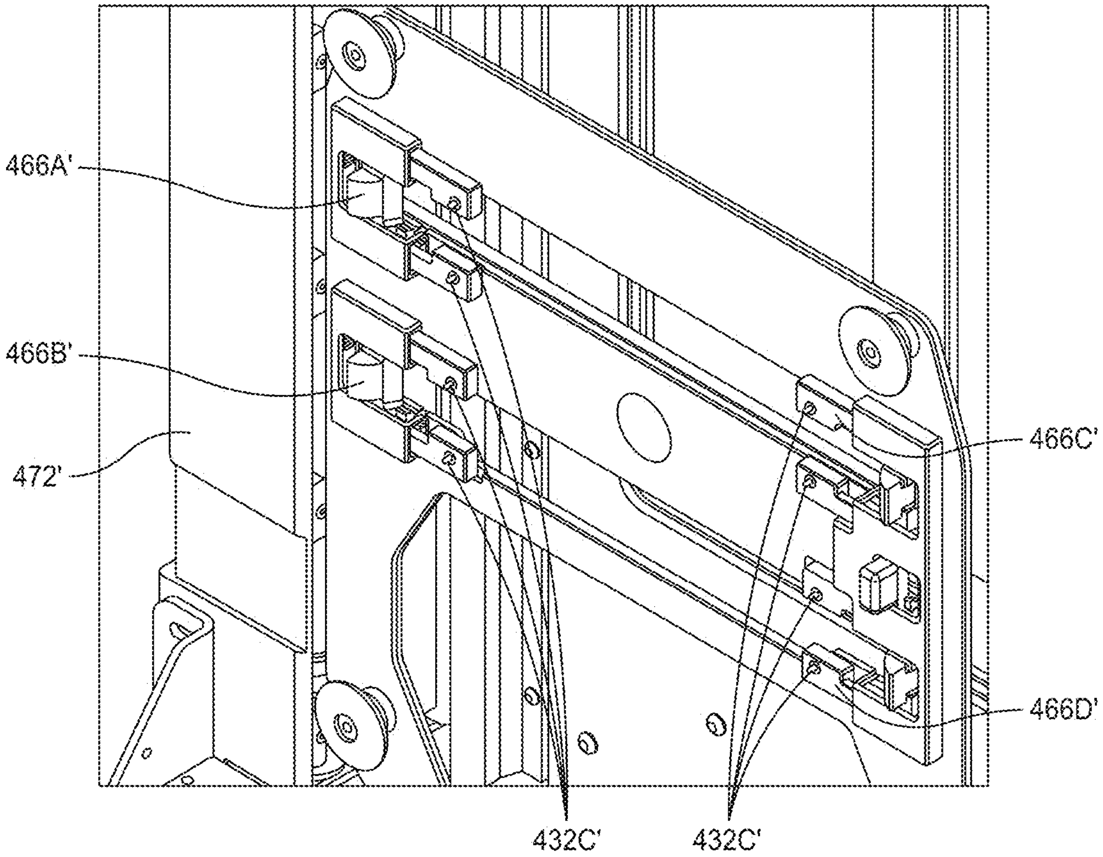
FIG. 48I is a schematic showing a close up, perspective view of the tensioner of the finishing apparatus shown in FIG. 48D.
Figure 48J:
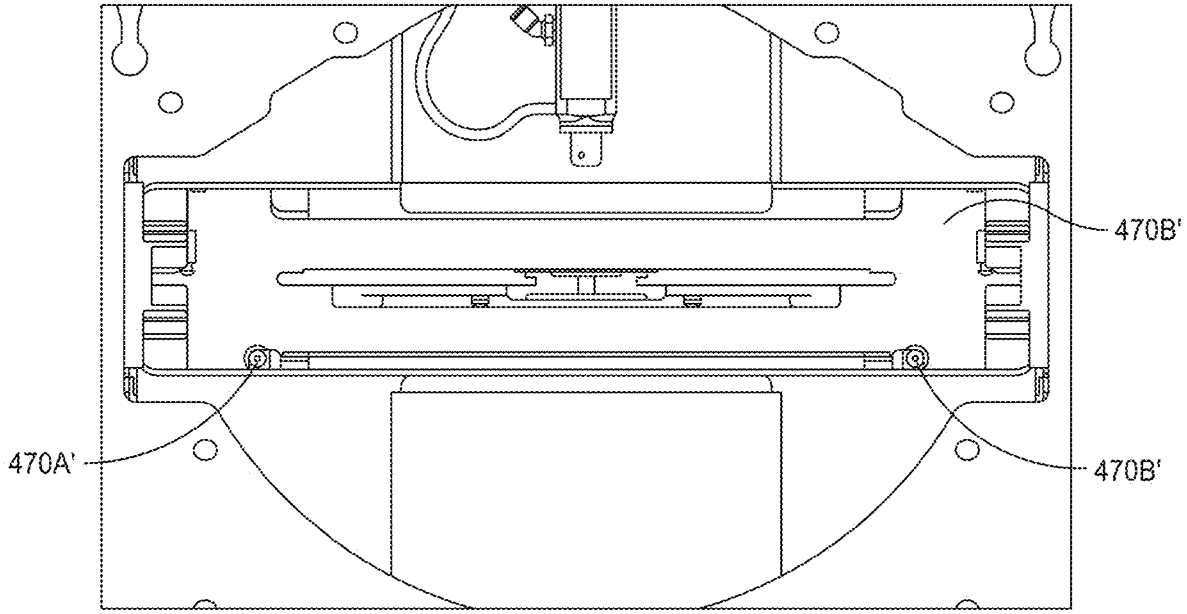
FIG. 48J is a schematic showing a close up, perspective view of the separator having a roller that engages the tensioner of the finishing apparatus shown in FIG. 48D.

In the embodiment in FIG. 48I, the structure of tensioners 466A', 466B', 466C' and 466C' has a sideways "U" shape each with the two positioning pins 432C'. The structure of tensioner 446C' includes a ramp that engages with roller 470A' or roller 470B' in the sealer and/or separator such that when they engage, the tensioners move apart from one another along Axis E. FIGS. 47D, 48J. This movement creates tension in the disposable wall such that during sealing by heat sealer 448' or separator 450', wrinkles in the seal are reduced and/or failed seals are reduced. In an embodiment, tension is measured to be about 2 and about 3 lbf.

Tension can also be created vertically, along Axis F. Tensioning can be done by repositioning the pins so that they are farther away from one another to stretch the disposable in any direction. Finisher 400' also includes pins 432A and 432B are positioned a bit farther away from 42C and this will create tension along Axis F. In an embodiment, tension is measured to be about 1 and about 2 lbf.

The tensioning system can be accomplished in other ways so long as the disposable wall is held taught during sealing and/or separating. In some embodiments, after sealing the disposable with a heat sealer, the process can cause the disposable to stretch some during the heating process and so applying tension during the separation step assists in cleaner separation. Such tension can be provided with springs, reversable locks, slides, belts, and the like. Any type of tensioner can be used with this system so long as the disposable wall is under tension during sealing, separating or both.

Once the disposable device is aligned and secured to the finishing apparatus, as shown in FIGS. 48B and 48D, shuttle 418 or 418' lowers into the finishing apparatus where impactor 442 or 442' apply repeated impacts to the side wall of disposable 100. This "impact" action, or alternatively a shaking action, applied to disposable 100 allows dried plasma that may have adhered to the inner wall of disposable 100 or may be embedded in the filter to release and move into the lower portion of disposable 100. In an embodiment, the impact action can be achieved in a number of ways so long as the dried plasma moves to the desired portion of disposable 100. In the embodiment shown in FIG. 48B, finisher 400 utilizes spring magnets attached to plates as the impactor. In the embodiment shown in FIG. 48D, impactor 442' of finisher 400' is a pneumatic cylinder attached to plates or paddles. In addition to a magnet system or pneumatic system, several other types or combinations of systems can be used for impacting. For example, a combination of compressed air and plates can be used to create the impacting action against the disposable wall. In this embodiment, the compressed air can be obtained from the drying gas source and any suitable in line regulator or controller. In yet another embodiment, a shaking action can be applied using a vibration source (e.g., magnetic coil, or piezo crystal or the like) or source of sound waves that translate into mechanical movement (e.g., the shaking or impacting action). The impacting action can be achieved by other ways including, a traditional shaking action, vacuum action and the like.

Figure 48K:
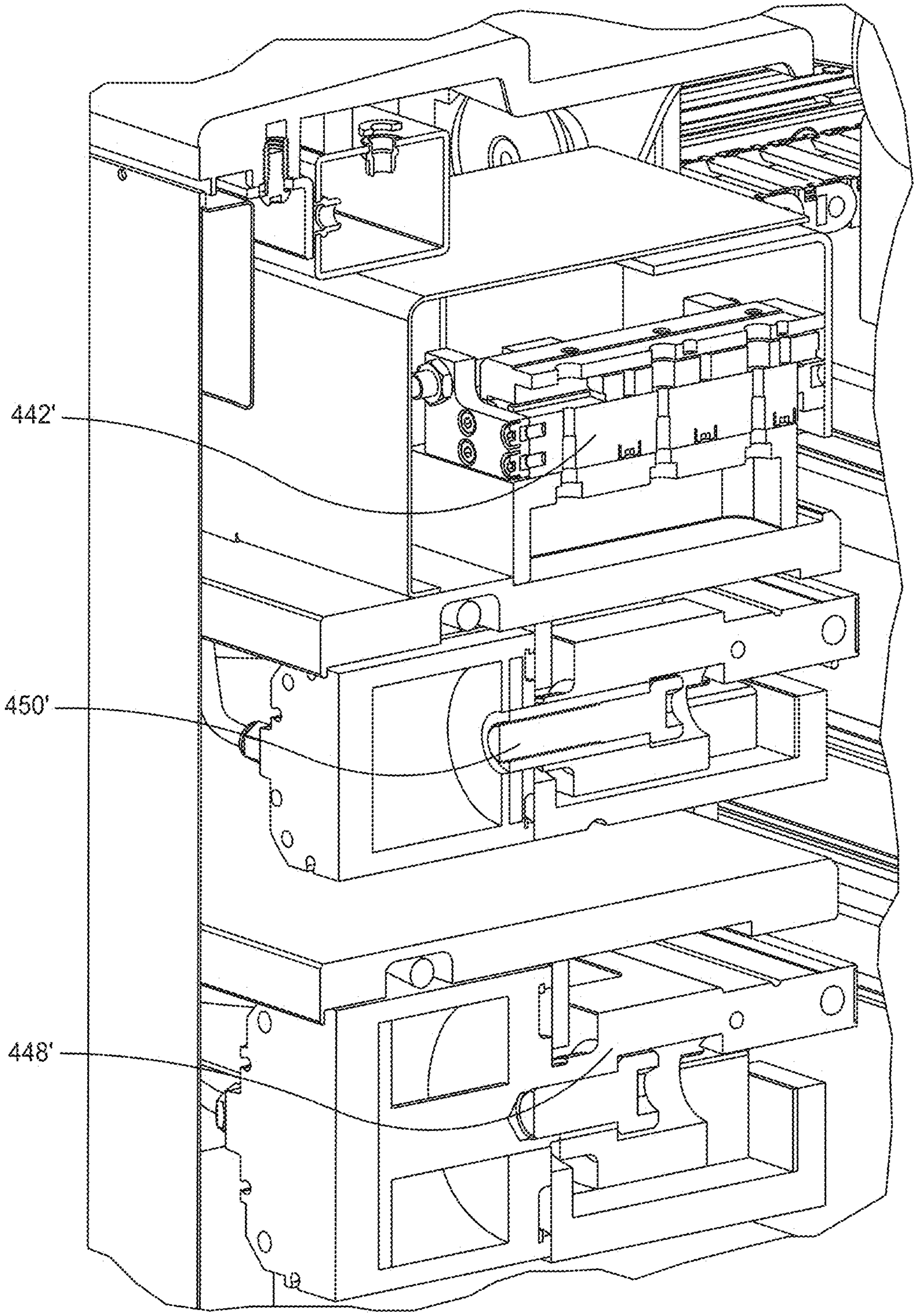
FIG. 48K is a schematic showing a close up, perspective view of the impactor, separator and sealer of the finishing apparatus shown in FIG. 48D.
Figure 48L:
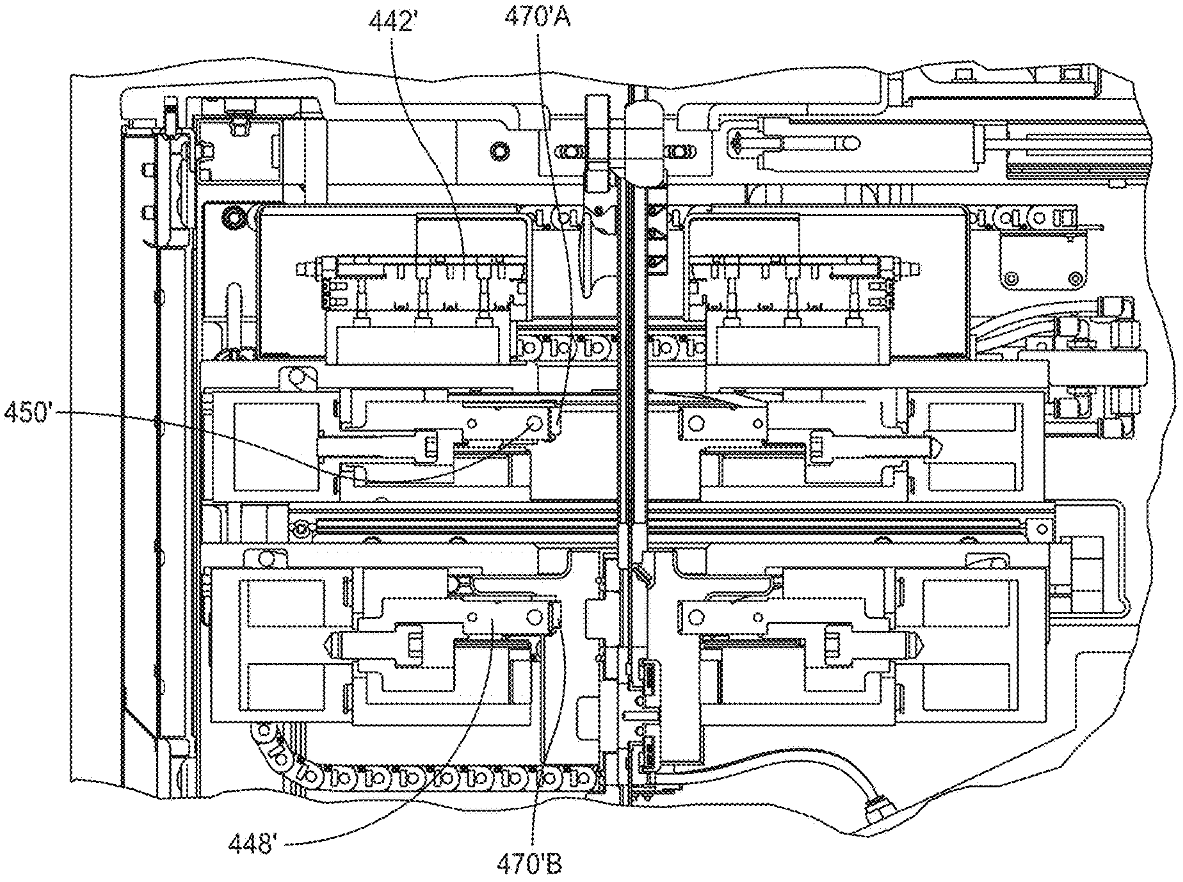

FIGS. 48K and L show impactor 442', separator 450' and sealer 448'. Separator 450' and sealer 448' are mounted to jaws. In this embodiment, separator 450' is a cut wire and sealer 448' is a flat heat-sealing band. Tensioning rollers 470A' and 470B' that engage with tensioner ramps are more easily seen in FIG. 48L, and they are attached to the jaws of separator 450' and sealer 448'

After impacting and the dried plasma moves into to the bottom compartment e.g., defined by Dimension V, the finishing apparatus applies tension to disposable 100 and heat seals (e.g., using impulse sealer 448 or 448') and separates top portion of the bag at location 44A, i.e., disposable top portion 48. See FIGS. 44,48A, 48D and 48E. This first seal and separation action effectively forms one of the side walls of the dried plasma unit 60. The remaining portion of the disposable device, bottom disposable portion 50 (i.e., defined by the combined Dimensions U and V), includes the bottom portion up to location 44A at which point the bag is cut and sealed. This disposable device with a single cut can also be referred to as the as a modified spray drying disposable device. Shuttle 418 or 418' will automatically or manually raise upwards once the first seal and separate is complete. The operator then inspects the seal checking for unsealed portions, voids, or wrinkles that extended throughout the entire width of the seal. Top disposable portion 48, the portion of the disposable from locator line 44A to spray drying head 2 can now be discarded.

As shown in FIGS. 48C and 48F, the operator will then rotate or invert lower shuttle disposable shuttle frame 408 or 408' using knobs 412A and 412B or knobs 412A' and 412B' about pivot point 420 and secure it lower disposable shuttle frame 408 so that it overlaps upper disposable shuttle frame 406. In an embodiment, the operator grasps the knobs 412A and 412B or knobs 412A' and 412B' and rotates the shuttle clockwise 180° until it is in place. This could also be done automatically or mechanically with the engagement of a switch or computer display. A lock can be used to keep the lower disposable shuttle frame 408 in place, before rotation or after rotation. FIG. 48D shows lock 478' which is a spring user actuated lock to keep the lower shuttle frame in place. The lock can latch to the frame during use. Since bottom disposable portion 50 is still attached to the lower frame of the finishing apparatus by the positioning arrangement and by the gas outlet arrangement, the bottom disposable portion (e.g., the portion from location 44A to gas outlet 30) also rotates and when locked into position. FIGS. 48C and 48F. In an embodiment, sensors can be used to ensure that the frame is in the locked position. As shown in FIGS. 48C and 48F, the disposable is now upside down with gas outlet 30 and gas outlet receiver 414 or 414' upward.

Once the operator indicates to the finishing apparatus that the bottom frame has been locked and superimposed over upper frame, the finishing apparatus repeats the impacting process to further shake or loosen the dried plasma that may be in the filter or surrounding area so that it falls into the section of the disposable that will become the dried plasma unit 60, i.e., plasma unit portion 46. The air extractor will engage with the disposable 100 and remove any remaining air through gas outlet 30 and the exhaust (not shown) of the finishing apparatus. In an embodiment, some air is left in the dried plasma unit 60 (e.g., less than about 15 mL in a plasma unit). In an embodiment, the finisher measures the vacuum level from about −4 psi to about −0.5 psi. The vacuum level is an indicator of the amount of air left in the plasma unit. In one aspect, when the vacuum level at −3 psi, less than about 15 mL of air left in plasma unit 60. The alignment elements of the present invention including the gas outlet/gas outlet receiver and the positioning arrangement allows the modified spray drying disposable device to remain aligned, even after its top portion having the spray drying head has been separated away. The finishing apparatus then performs a second seal and separate to the disposable at line location 44B, above port 42A. See FIG. 48C and Step 820, FIG. 51C. Once completed, the finishing apparatus raises shuttle 418 or 418' and the operator can discard disposable device filter portion 52, the portion having the gas outlet, lower filter and filter separator. Once completed, the finishing apparatus manually or automatically raises shuttle 418 or 418' and the operator will inspect the seal. The second seal and separate action effectively seal the entire disposable from the open air and forms the plasma unit 60. As shown in FIG. 49A, portion 46 of the disposable, now that both sides have been sealed and separated, results in dried plasma unit 60 having dried plasma 62.

Sensors can be used to ensure that shuttle 418 or 418' is in the proper position for impacting, sealing and/or separating. Sensors can be positioned in the base of finisher 400 or 400' and in an embodiment, reflectors can be mounted to the shuttle. When the sensor signal or laser is reflected back to the sensor as the shuttle mounted reflector passes by, the computer system of the finisher can determine where the shuttle is in relation to the impactor, sealer and/or separator. In an embodiment, the computer system stops the shuttle at approximately 1 inch after the reflector passes.

The finishing processes described here as performed by finisher 400 or 400' is a preferred embodiment but the process (moving the plasma to the desired compartment, and sealing the plasma drying chamber to create the dried plasma unit) can be done manually using readily available tools such as scissors and a heat sealer of the appropriate size and able to make the two described seals.

The sealing and separation of the unit of the preferred embodiment of the present invention described here is a multi-step, semi-automated process that takes place within finisher 400 or 400'. Finisher 400 or 400' is responsible for monitoring and controlling at least five processes to create the unit: the consolidation of the dried plasma powder on the outlet filter, the sealing and removal of the upper portion of disposable 100, the inversion and consolidation of the dried plasma powder, removal of excess air, and the sealing and separation of the lower portion of disposable 100. Finisher 400 or 400' ensures the sealing processes are completed within certain operating ranges. Finisher 400 or 400' contains an array of sensors and actuators that allow for the automated control of the sealing process and provides for back-lit Operator visual inspection of each heat seal of the film.

Finisher Architecture

Finisher 400 or 400' architecture is shown in FIG. 49B. Finisher 400 or 400' coordinates and/or drives at least the following flow paths: air line (Line A), an extraction vacuum line (Line B), an extraction piston line (Lines C, D), a impactor line (Lines E, F, G, H, N, O, T, U), a cutting line (Lines I, J, P, Q, V, W) and a sealing line (Lines K, L, M, R, S, X, Y). Any number of flow configurations can be arranged so long as the finisher provides impaction, sealing and separating to the disposable having dried plasma. Additional lines or fewer flow lines than shown in the figures can provide these flow lines.

Finisher—Air Line

The air line begins with a Compressed Dry Air (CDA) supply, as described herein, and follows Line A. The air line does not need to be clean dry air but can be any source of air. In an embodiment, the same CDA source for dryer 200 can be used for finisher 400' or separate one can be used. The CDA system is connected to finisher 400' via connector CN101 502 in FIG. 49B. Once entering finisher 400', the compressed air travels through solenoid valve PV101 504. As described herein, a solenoid valve is an electrically controlled valve. Solenoid valves in finisher 400 or 400' has an electric coil with a movable ferromagnetic core and plunger in its center. In the rest position of solenoid valve PV101 504, the plunger closes off the opening in the line. When an electric current is applied, the coil creates a magnetic field which exerts a force on the plunger to open the line. Solenoid valve PV101 504 is an L-port which allows for inline supply of compressed air but also allows a small amount to be diverted to the air manifold, which is further discussed herein. The compressed air travels through PR101 506. A pressure regulator, such as PR101 506, regulates system flow pressure in response to upstream or downstream pressure changes. When the drying gas leaves pressure regulator PR101 506, pressure of the compressed air is between about 70 psi and about 80 psi. Generally, the finishing involves a static pressure system. The compressed air travels through pressure transducer PT101 508. Pressure transducer PT101 508 measures the pressure of the drying gas in the line and communicates the pressure via a digital signal to the computer system. The pressure of the compressed air at pressure transducer PT101 508 ranges between about 70 psi and about 80 psi After passing through pressure transducer PT101 508, excess pressure, if any, is relieved through pressure relief valve PRV101 510 by allowing the pressurized air to flow from an auxiliary passage out of the system and exhaust to the room.

The compressed dry air line feeds flow to an air manifold ARM101 572 to pneumatically actuate pistons used in impacting, sealing, air extraction, and separating.

Finisher—Extraction Vacuum Line

The extraction vacuum line exits air manifold ARM101 572 and travels to vacuum generator VG101 512 and follows Lines B. The vacuum generated is used to remove excess air from the disposable to facilitate long term storage. The excess air from disposable 100 is removed by created a vacuum and sucking the air through filter F101 514. Filter F101 514 is a 0.1 micron filter, suitable for filtering out pathogens before the air exits to the atmosphere. This filter ensures that pathogens from the finishing process do not contaminate the outside air. After passing through filter F101 514, the excess air passes through pressure transducer PT102 516. The pressure of the excess air at pressure transducer PT101 516 ranges between about −2 psi and about −13 psi. The air then passes through check valve CV101, which is a one-way valve that prevents backward flow of air. The air then passes through speed controller SC101 518 which is used to slow down the rate of air extraction so that the system can react at the ideal moment that corresponds to the ideal amount of air remaining in the disposable. The excess air travels out vacuum generator VG101 512 via a muffler and out to join the outside air. The muffler is intended to reduce the sound level of the air exiting the vacuum generator and into the ambient air.

Finisher—Air Extraction Piston Line

The air extraction piston line is used to engage and disengage the air extraction nozzle that removes the excess air from the disposable, as described herein and follows Lines C and D. The air passes through speed controller SC102 520 which is used to slow down the air extraction slide piston to reduce wear. The air travels to air extraction slide PP101 522. Air extraction slide PP101 522 is a pneumatic piston that actuates the air extraction slide to remove residual air from disposable 100 having dried plasma. Air extraction home sensor SR101 524 is used to determine when the air extraction piston is in its home position.

Finisher—Impactor Line

The impactor line is used to move dried plasma particles into the desired compartment of the disposable, as described herein and follows Lines E, F, G, H, N, O, T, and U. This line has two lines, one going to the front impactor plate and the other going to the rear impactor plate. The line comes from the air manifold and travels through speed controller SC104 526 to power pneumatic piston PP102 plasma release slide front 528 and through speed controller SC106 530 to power pneumatic piston PP103 plasma release slide front 532. This pneumatic piston actuates the plates or paddles of the impactor. Home sensors front SR106 534 and plasma release extended sensor front SR116 536, and plasma release home sensor SR107 538 and plasma release extended sensor rear SR117 540 are used to confirm the piston location during the impacting process to ensure operator safety. These sensors use a laser and a reflector mounted on the shuttle such that when the shuttle mounted reflector reflects the laser, the sensor determines receives a signal indicative of the piston location the shuttle within the base. The signal is sent to the computer system of the finisher to determine the location of the piston and, when in the proper determined location, provides instructions to the impactor to proceed with impacting.

Finisher—Separator Line

The separator line is used to cut one part of disposable 100 away from another part of disposable 100 to form a dried plasma unit, as described herein, and follows Lines I, J, P, Q, V and W. This line has two lines, one going to the front cutting slide and the other going to the rear cutting slide. The line comes from the air manifold and travels through speed controller SC109 542 to power pneumatic piston PP104 cutting slide front 544 and through speed controller SC113 546 to power pneumatic piston PP105 cutting slide rear 548. This pneumatic piston actuates the wire cutter, the separator. Home sensor front SR108 550 and cutting system extended sensor front SR118 552, and cutting system home sensor SR109 554 and cutting system extended sensor rear SR119 556 are used to confirm the pistons' locations to ensure functionality and operator safety. These sensors, such as SR121 557, use a laser and a reflector mounted on the shuttle such that when the shuttle mounted reflector reflects the laser, the sensor determines receives a signal indictive of the location the shuttle within the base to find the separating position. The signal is sent to the computer system of the finisher to determine the location of the shuttle and, when in the proper determined location, provides instructions to the separator to proceed with cutting the heat seal.

Finisher—Sealing Line

The sealing line is used to seal the disposable wall to itself to form a dried plasma unit, as described herein and follows Lines K, L, M, R, S, X, Y. This line has two sets of two lines. The first set is a low pressure line coming from station 6 of the manifold which connects to the extend side of both the front and rear sealing pistons PP106 568 PP105 569. The pressure is regulated between 10 and 20 psi using a manifold mounted regulator SY30M-N6-A1. A speed controller SC112 566 is located on the rear piston extend line. This speed controller slows down the movement of the rear piston slide so that the front piston slide will engage with the tensioners and provide appropriate tension to the disposable before sealing starts. Pressure transducer PT103 560 measures the pressure of the air in the line and communicates the pressure via a digital signal to the computer system. The pressure of the clean air at pressure transducer PT103 560 ranges between about 10 and about 20 psi when low pressure is applied. The second set of lines is at a high pressure between 70 psi and 80 psi. The high pressure and low pressure lines are connected via shuttle check valve CV102 558, which is a three-way shuttle valve that prevents backward flow of air. The check valve CV102 558 allows the sealing pistons to be engaged initially with low pressure air from station 6 then with high pressure air supplied via station 7 of the manifold. When high pressure is engaged, pressure transducer PT103 560 will read between 70 and 80 psi. Home sensors, SR110 562, SR111 563, SR112 567, and SR113 564 determine the position of both the front and rear sealing pistons to ensure correct functionality and safety.

These sensors use a laser and a reflector mounted on the shuttle such that when the shuttle mounted reflector reflects the laser, the sensor SR120 565 determines receives a signal indictive of the location the shuttle within the base to align with the sealing jaws. The signal is sent to the computer system of the finisher to determine the location of the shuttle and, when in the proper determined location, provides instructions to the sealer to proceed with heat sealing at the set location on the disposable, as described herein.

Finisher Air Manifold

The air manifold AMC101 572, a branching chamber, extracts a small amount of clean dry air to create mechanical motion. The extracted air is used to actuate the pneumatic valves (PV) and pneumatic pistons (PP) in finisher 400'. The manifold shows seven stations and multiple actuators are part of each station. Station 1 actuates the extraction line, station 2, actuates extraction piston line, stations 3 and 4 actuate the impactor line, station 5 actuates separator line, station 6 actuates the low pressure sealing line, and station 7 actuates the high pressure sealing line.

The arrangement of stations and actuators can vary as desired. Although an air manifold is used to actuate the valves and pistons of the spray dryer, any commercial device can be used.

Detailed Description of Workflow

Before spray drying liquid plasma, the operator should prepare the spray drying apparatus (FIGS. 45A-4C) and finishing apparatus (FIGS. 47A-C and 48A-C). The operator ensures that spray drying apparatus 200 and finishing apparatus 400 are on and ready. The operator should also, in one aspect, tap "WAKE" on display 212, and open the door to the spray dryer (e.g., pull large, hinged handle 230 out and to the right to unlatch door 228 and then pull handle 230 to the left). See FIG. 45C. Optionally, paper labels or other demountable closure may be attached over the inlet port 22 and the gas outlet port 30. In another embodiment, the operator can attach the appropriate part of the disposable to the dryer in an alternating fashion. For example, the operator can and attach guide 4 of spray dry head 2 to drying receiver 204 of the spray dryer 200, and then the operator can attach gas outlet 30 to gas exhaust port 208.

To pretreat the liquid plasma, referring to FIG. 51A, the operator follows the steps of pretreatment methodology 600. The operator starts with Step 602 and prepares the equipment (e.g., Sterile connection Device (SCD), collection monitor/scale, tube sealer and barcode scanner) and collects the supplies (e.g., Unit of Plasma, Pretreatment bag, Spray Drying Disposable, Site-specific supplies (labels, tracking documentation)) of Step 604. The operator then makes a sterile connection (Step 606) between the liquid plasma bag tubing and the pretreatment container tubing. See FIGS. 42A and 51A. Now the liquid plasma bag and the pretreatment container have a sterile connection. When doing so, in an embodiment, it is preferable that the total tubing length after the sterile connection is approximately between about 15 and 20 inches long to enable hanging of the plasma unit for transfer into the pretreatment container without tension so that the blood collection monitor can accurately control the transfer of the plasma to the pretreatment bag. The pretreatment container having the pre-treatment solution is properly labeled. In particular, the pretreatment solution is a glycine and hydrochloric acid solution having between about 15 mmol and about 30 mmol (e.g., about 15, 20, 25, and 30 mmol) of glycine and a range between 3 mmol and about 7 mmol (e.g., about 3, 4, 5, 6, and 7 mmol) of hydrochloric acid. The formulated plasma has a pH in a range between about 5.5 and about 7.2 which offsets spray drying impacts on pH to yield a final rehydrated product that is at normal physiologic pH, a pH range between about 6.8 and 7.6. In another embodiment, pretreatment of the plasma is optional.

In an embodiment, mixing the liquid plasma with the pretreatment solution is done by transferring the plasma to the pretreatment container. This can be accomplished by first hanging the liquid plasma bag from the upper bag hook of the collection monitor/scale and by hanging the pretreatment container on the lower hook. See Step 608 of FIG. 51A. The tubing is guided through the mechanical tube clamp (Step 610) on the collection monitor/scale and secured in place. The weld on the tubing is pinched and the Hemostat/manual clamp is released to ensure plasma flow. See Step 612.

The mixing of liquid plasma and the pretreatment container having the pretreatment solution (e.g., 50 mL) can be done manually or can be automated via a commercially available collection monitor, a tray shaped scale, or other similar device. In an embodiment, the process is automated, and the transfer volume is set to 260 mL (e.g., between 240 and 280 mL). Once the START button is pressed, the plasma is transferred. Step 614. When 260 mL of plasma has been transferred, in an embodiment, the mechanical clamp on the collection monitor will automatically close, stopping the flow of plasma. The tubing is removed from the collection monitor and the pretreated liquid plasma can be manually agitated, shook, rocked, or otherwise mixed as described in Step 616. This process can also be automated using a commercially available laboratory rocker, agitator or the like.

Using a tube sealer, the pretreatment container having the pretreated liquid plasma is separated from the rest of the tubing and original liquid plasma bag. In an embodiment, the operator, in Step 618, using a tube sealer, triple heat seals the tubing above the manual clamp; separates the tubing at the middle seal.

In another embodiment, the pretreatment solution can be added to the liquid plasma bag or the two can be mixed into a third bag.

In an embodiment, once the plasma has been transferred, it is be placed into the dryer for drying in 4 hours or less (e.g., about 4 hours, 3 hours, 2 hours, 1 hours, 30 minutes, 15 minutes, 10 minutes, 5 minutes or less).

The plasma pretreatment bag having the pretreated plasma is also referred to herein as a "plasma bag," "liquid plasma bag," or "pretreated plasma bag." The pretreated plasma bag is connected to the spray drying disposable device at the plasma inlet tube, tube 16, as described in Step 620 to thereby obtain the modified disposable. The tubing from the pretreated plasma bag is connected to the plasma inlet tube via a SCD connection. In an embodiment, the operator should make the connection long enough to fit the modified spray drying disposable in the dryer. In an aspect, the operator can make the SCD union about 1 to about 2 inches (e.g., about 2.54 cm to about 5.08 cm) from the distal end of the spray drying disposable device tubing to ensure the total tubing length, after the sterile connection, is approximately 43 inches (e.g. about 101.6 cm) long. This will facilitate installation in the spray dryer. After the connection is made, the operator can label the disposable to apply, for example, a matching blood center number or other identifier. The operator can then hang the modified disposable on the drying apparatus bag hook 222 and pinch the tubing to ensure the SCD weld is opened.

The spray drying apparatus is prepared. FIG. 51B shows a flow chart describing methodology 700, detailing the steps the operator takes to dry the plasma using the spray dryer. To prepare the spray drying apparatus, the operator, as shown in Step 702, will ensure that the spray drying apparatus 200 displays the READY screen by pressing WAKE if necessary. The screen will then prompt the user to load drying chamber 202. As described in Step 704 (FIG. 51B), the operator opens door 228 of spray drying apparatus 200 as shown in FIG. 45C. The operator pulls large, hinged handle 230 out and to the right to unlatch the door and then pulls the handle to the left to allow the entire door panel to open. See FIG. 45C. The operator hangs the pretreated plasma bag from plasma bag hook 222 and disposable device 100 is aligned and inserted into the spray drying machine 200, as described herein. See Step 706 of FIG. 51B and FIG. 46A.

Once guide 4 is attached to receiver 204 and the operator tucks the disposable device edges and ports into the spray drying apparatus. The ports are tucked into for the port receiver (not shown). The operator ensures that the drying chamber is fully installed and all edges are tucked into the drying chamber cavity. In accordance with the alignment shown in FIG. 46A, the operator connects gas outlet 30 at the bottom of disposable device 100 into exhaust gas port 208 of dryer 200. The operator removes aerosol filter cap, if present, from the aerosol filter and attaches the aerosol tube 10 to aerosol filter 12. This step connects aerosol tube 10 to aerosol line that leads to pressurized gas source 216 via filter 12.

Once the disposable device is aligned and connected to the drying gas source, the pressurized gas source, the plasma source and the exhaust port 208, the operator prepares peristaltic pump 214, which pumps the liquid plasma into the disposable device. This is done by opening the peristaltic pump latch 214A and routing the pretreated plasma bag tube 16 through peristaltic pump 214 and plasma/aerosol guide 226 in the direction of the flow (i.e., plasma will flow from the pretreated plasma bag to disposable device). Step 708, FIG. 51B. Once routed through the pump in the plasma flow direction, the operator closes the pump latch.

The operator closes the door and inserts the key 236 into the manual safety lock 238. Step 710, FIG. 51B. In an embodiment, key 236 is attached to handle 230 of the door and keyhole 238 is on the left of spray drying apparatus 200. This is a safety feature and the spray drying device will not allow the operator to progress to the next step until this step is performed. This is indicated on display 212. Once closed and locked, the screen prompts the user to unclamp the plasma line. The operator releases the plasma by unclamping any Hemostat or manual clamp. At this point, with the covers removed and the door closes, the disposable is no longer exposed to open air/environment. In this case, the time from when the operator removes the first adhesive cover to close the door ranges between about 30 to 90 seconds.

Once the door is closed and the key is inserted, the operator confirms that this step is completed by utilizing the interactive display and pressing "CONFIRM", the spray drying apparatus will automatically run integrity checks. See Steps 710-712, FIG. 51B.

If there are no issues, the drying apparatus will automatically begin the drying process; the screen displays the estimated time remaining until completion. In an embodiment, the drying beacon, an indicator on the machine, remains a solid green as the normal operation of the instrument continues. The rapid drying process time is approximately 35 minutes but can range from about 20 minutes to 60 minutes (e.g., about 20, 25, 30, 25, 40, 45, 50, 55, 60 minutes).

Put another way, in an embodiment as shown in FIGS. 45A-C and 46A, to align the spray dry disposable device 2 in spray drying apparatus 200, the operator should insert the off-set guide 4 of the disposable 100 into the receiver 204 of dryer 200, align the locating arrangement on the disposable and the dryer, insert the gas outlet of the disposable into the exhaust gas port of the dryer. Once these three alignment elements are engaged, the disposable is aligned into place and ready to be locked. After attaching the plasma source and the pressurized gas source, the operator can lock the door of the spray drying chamber housing and the spray drying process can begin. In another embodiment, any combination of these alignment arrangements can be engaged so that the disposable is aligned with the spray drying apparatus.

The parameters for drying are described herein.

Once drying completes, the screen prompts the operator to clamp and remove the plasma pretreatment container, which should be hanging from hook 222 outside of the closed door. Indicator light 234 indicates that the drying process is complete by changing the flashing color or pattern, and in an embodiment the indicator light will flash green. Step 712, FIG. 51B.

To remove the disposable device, the operator re-engages the clamp on the plasma tube and seals and separates the plasma tubing after or up flow from the pump. Step 712, FIG. 51B. This step prevents any residual liquid plasma in the pretreatment plasma bag to enter the disposable device. Once the plasma tubing 16 is sealed and cut then the operator can open the door to spray drying apparatus 200. The operator opens latch 214A on peristaltic pump 214 and removes the plasma tubing from peristaltic pump 214 and can then discard the tubing and pretreatment plasma bag 64 which had formulated plasma 66.

Once the operator communicates with the spray drying apparatus that this step is completed by e.g., pressing CONFIRM on the interactive display, the operator can then remove the disposable device. Removing the disposable device involves unlatching the manual safety lock using the key and engaging the door handle to unlock and open the door.

Once the door of the spray drying is opened, the operator disconnects gas outlet 30 of the disposable device from gas exhaust port 208 of the spray drying apparatus. Step 714, FIG. 51B The operator then disconnects the aerosol line 10 from the pressurized gas source 216. The disposable device having the dried plasma can be removed from the spray drying apparatus. In an embodiment, the operator closes the door of the spray drying apparatus to keep the machine warm and ready for the next drying run. Step 716, FIG. 51B. The operator is now ready to move the spray drying disposable with the dried plasma to the finishing apparatus. Step 718, FIG. 51B.

The next part of the process, the finishing process, involves sealing and separating portions of the disposable device having the dried plasma to turn it into a spray dried plasma unit. Finishing methodology 800 of FIG. 51C refers to the steps needed to convert the spray drying disposable 100 having the spray dried plasma into spray dried plasma unit 60.

Also, referring to FIG. 47 and FIG. 48, finishing apparatus 400 or 400' is shown. As described herein, FIGS. 47A-H show finishing apparatus 400 or 400' without disposable device 100 attached and FIGS. 48A-FIG. 48F show finishing apparatus 400 or 400' with disposable device 100 attached. Specifically, FIG. 47A shows finishing apparatus 400 in the lowered position ready to be loaded and FIG. 47D shows finishing apparatus 400' in the upper position ready to be loaded. FIG. 47B shows the inside of base 440 when apparatus 400 is in the lowered position and FIG. 47F shows the inside of base 440' when apparatus 400' is in the lowered position. FIG. 47C shows finishing apparatus 400 in the raised position without disposable 100 attached and FIG. 47E shows finishing apparatus 400' in the raised position without disposable 100 attached.

The screen 401 or 401' of finishing apparatus 400 or 400' will display the phrase "STANDING BY." When the operator communicates to the finishing apparatus e.g., by tapping "WAKE," the screen 401 or 401' will prompt the operator to load the plenum 6 of the disposable device 100 onto the spray dry head receiver 404 in the lower position of finisher 400 or in into spray dry head receiver 404' in the load position of finisher 400'. See Step 802, FIG. 51C. The finisher can have additional positions for loading, rotating the frame, inspecting seals and/or for removing the finished product. In an embodiment, the finisher can have two or three additional positions. In the embodiment when there are two positions, the lower position is the loading and processing position and the upper position is for inspection, rotating the frame and removal of the dried plasma unit. In the embodiment when there are three positions, then one position is an intermediate position for loading, one position is down for processing the disposable and the upper position is for inspection, frame rotation and removal of the dried plasma unit. In yet another embodiment, the following positions exist: Start—load spray drying head of disposable, Home—raised position load pins of disposable, Seal—bottom position—sealing position, End—end of travel for plasma release operation, Cut—separate location, and Inspection—location for inspection.

The operator loads the disposable device having dried plasma onto shuttle 418 or 418', as shown in FIG. 48A or 48D by inserting plenum 6 of the disposable device into the spray dry head receiver 404, at the top of the shuttle. See Step 804 of FIG. 51C. The operator can coil the remaining tubing and insert it into guide 4 of the spray drying head 2.

As described herein, the second locator, locator 26, on the disposable is aligned with third locator 452 or 452' in spray dry head receiver 404 or 404' during the finishing process.

Once the spray drying head of the disposable is attached to the finisher as shown in FIG. 48A or 48D, the operator communicates this to the finishing apparatus e.g., by pressing CONFIRM. See Step 806 of FIG. 51C. When the shuttle is in the raised position, as shown in FIGS. 48B and 48D the operator secures the rest of the disposable device having dried plasma. See Step 806 of FIG. 51C. This is the raised position (FIGS. 48B and 48D). When in the raised position, the gas outlet 30 is attached to the bottom of the shuttle by inserting the exhaust outlet downward into ‘U’ shaped exhaust outlet receiver 414 or 414'.

In particular, the finisher is designed to receive gas outlet 30 of the disposable to keep the disposable in place during the process of moving the plasma into place, removal of air, sealing and separating. Gas outlet receiver 414 or 414' of the finishing apparatus has a receiver that has a “U” shaped slot so that the gas outlet can be solidly attached to the finishing apparatus and remain attached during the finishing process.

The operator then attaches the disposable device having dried plasma using the positioning arrangement. The positioning arrangement (e.g., the pin and opening arrangement, or pin and grommet arrangement) is located preferably at each corner of the outer wall of the plasma unit-to-be (see positioning openings 32C) and above and below location lines for seal and separation 44A and 44B. Positioning openings 32A and B are located on either side of the outlet port and attached to positioning pins 432A and 432B or pins 432A' or 432B'. The positioning arrangement shown is a pin and opening arrangement but can be any arrangement that allows the side walls of the disposable to be secured to the finisher while the finisher is in use. In addition to a pin and opening arrangement, other examples of other positioning arrangements include a hook/receiver arrangement, channel and groove arrangement, a latch and catch arrangement and the like. In the embodiment, the pins are positioned on the finisher and the openings are positioned on the disposable but these can be reversed.

When the disposable device is aligned and securely loaded, the operator communicates this to the finishing apparatus e.g., by press CONFIRM. The operator then instructs the finishing apparatus to proceed with the finishing process e.g., by pressing RUN. See Step 808, FIG. 51C. Shuttle 418 having the disposable aligned and secured thereto will automatically begin to lower. In the embodiment shown in FIGS. 47A-C and FIGS. 48A-C, finishing device 400 has shuttle 418 and sliding frame 402, upper disposable shuttle frame 406, and lower disposable shuttle frame 408 raise and lower into position, as described herein. In another embodiment, frame 402' is stationary and upper disposable shuttle frame 406, and lower disposable shuttle frame 408 move along rails. In the embodiment shown in FIGS. 47D-I and FIGS. 48D-L, finishing device 400' has shuttle 418' that moves along stationary frame 402' using a rail system, as described herein.

Finishing apparatus 400 or 400' automatically initiates plasma consolidation and executes the first sealing and separating process. Step 810 of FIG. 51C. In an embodiment, the screen displays the estimated remaining time until completion. Shuttle 418 or 418' lowers into finisher 400 the dried plasma powder is moved e.g., by the impacting action, as described herein. The first seal and separate action seals top disposable portion 48 (see FIG. 48A).

Once the shuttle has risen to the top and stopped moving, the screen will prompt the user to Inspect Seal #1 and an inspection light will illuminate. Step 812 of FIG. 51C. The operator inspects the seal to ensure that the seal is fully formed and uniform. The operator, optionally, can tilt the shuttle outward by hinge (not shown) as needed obtain a better view of the seal for inspection purposes. Upon inspection, the seal, in an aspect, should not contain a channel (gap or unsealed area) that runs through the full width of a weld or seal. Ideally, a plasma unit that contains a wrinkle on the interior of the unit bag but is flat welded at the seal with no channel is acceptable. Discoloration and small gaps or wrinkles that do not run the entire width of the weld are acceptable.

If the seal is acceptable, the operator can indicate this to the finisher e.g., by pressing “ACCEPT” and continue with the process. If the seal is not acceptable, then the operator can also indicate this e.g., by pressing REJECT, discard the entire Plasma Drying Chamber, and press CONFIRM.

Once the operator deems the seal to have been properly made by the finisher, the operator can discard the disposable top portion 48, from location 44A to the spray drying head 2. See FIG. 48 and Step 814, FIG. 51C. This first seal and separation action effectively forms one of the side walls of the dried plasma unit and the seal is located above port 42A. The top disposable portion 48, the portion of the disposable from location 44A to spray drying head 2 can now be discarded.

As shown in FIG. 48C, the operator will then rotate or invert lower shuttle disposable shuttle frame 408/408' using knobs 412A/412A' and 421B/412B' about pivot point 420/420' and secure lower disposable shuttle frame 408/408' so that it overlaps upper disposable shuttle frame 406/406'. See Step 816, FIG. 51C.

Once the operator indicates that the bottom frame has been locked and superimposed over upper frame, e.g., by pressing “CONFIRM” and then “RUN”, the finishing apparatus lowers. See Step 818, FIG. 51C. In an aspect, the screen will flash a warning notification and the shuttle will automatically begin to lower. As further described herein, finishing apparatus 400 or 400' automatically initiates the impactor to allow for plasma consolidation, air evacuation, and executes the second seal at location 44B above port 42B (in the inverted position show in FIG. 48C). In an embodiment, the screen displays the estimated time remaining until completion.

Once the shuttle has risen to the top and stopped moving, the screen, in an embodiment, will prompt the operator to inspect the second seal and an inspection light will illuminate. See Step 822, FIG. 51C. Again, the operator can optionally tilt the shuttle outwards as may be necessary to properly inspect the second seal. The seal is located above the rehydration ports. If the seal is acceptable, the operator can inform the finishing apparatus e.g., by pressing “ACCEPT” to continue with the process. Again, if the seal is not acceptable, the operator can inform the finishing apparatus by e.g., pressing “REJECT”, discard the entire Plasma Drying Chamber.

Once the seal is accepted, in an embodiment, the screen will display “RUN COMPLETE” or similar indicator on the finishing apparatus’ screen. The operator can discard disposable device filter portion 52, the portion having the gas outlet, lower filter and filter separator. See Step 824, FIG. 51C. As shown in FIG. 49A, the remaining portion, portion 46 of the disposable, now that both sides have been sealed and separated, results in dried plasma unit 60 having dried plasma 62. See Step 824, FIG. 51C. In an embodiment the operator, will rotate the shuttle 418 or 418' back to the home position, or original position as shown in FIGS. 47C, and 48B. See Step 824, FIG. 51C.

Dried plasma unit 60 is then stored. In an embodiment, storage includes two stages, storage methodology 900 of FIG. 51D. The first stage is storage until testing of the plasma is competed and cleared for use (e.g., referred to as "quarantine storage") and the second stage involves storage of the unit after clearance but prior to transfusion into a recipient.

For the first stage storage or quarantine storage, the operator places dried plasma unit 60 in a storage pouch so that the label on the plasma unit is visible through the clear side. Step 902, FIG. 51D. The storage pouch in an embodiment has a clear side and a foil side. A desiccant is placed in the storage pouch, between the plasma unit and the foil side of the pouch. Step 904, FIG. 51D. The operator then makes an initial seal at the top of the pouch. Step 906, FIG. 51D. A commercially available pouch sealer can be used to make a more permanent seal sufficient for longer term storage. An example of a commercially available pouch sealer is the Midwest Pacific Impulse Heater Sealer model No. MP-12 from PackCo Inc. of Lake Ozark Missouri USA. The operator ensures the storage pouch sealer is turned on and places the pouch across the welding plane. The operator closes the welding arm and holds the arm in place for a period of time sufficient to make the weld e.g., between about 1 and 60 seconds and in an embodiment less than 10 seconds. An acceptable weld is one, for example, that contains no channel (gap or unsealed area running through the full width of a weld) and has no discoloration. A weld that contains a wrinkle on the interior of the storage bag but is flat welded at the seal with no channel is also acceptable. However, a weld is unacceptable if the weld contains a channel (gap or unsealed area running thru the full width of a weld), has discoloration, or contains a wrinkle on the interior of the storage pouch that continues through the full width of the welded area creating a channel.

Once an acceptable weld is achieved, the operator then places the sealed dried plasma unit in quarantine. Step 908, FIG. 51D. In an embodiment the sealed dried plasma unit stored in quarantine during the first stage at a temperature in a refrigerated range between about 1° C. and about 6° C. In another aspect the dried plasma unit can be stored at room temperature (e.g., between about 18 to 25° C.).

After release testing is complete and the product is determined safe for use, then the dried plasma unit can be stored until it is ready to be used for transfusion. This is the second storage stage.

The operator opens the sealed outside pouch e.g., using a scissors and the point of cutting away the seal can be marked with a notch. Step 910, FIG. 51D.

The operator can then apply final product labeling on the dried plasma unit and place the unit with the final label into the same storage pouch. Step 912 & 914, FIG. 51D. The storage pouch sealer is again used to make a final seal on the on the pouch containing the dried plasma unit that has been approved for use. Step 916, FIG. 51D. The criteria for an acceptable seal are described above. The process described for the initial seal is repeated and the seal is completed. The dried plasma unit is ready for use or placed in inventory. Step 918, FIG. 51D.

The spray dried plasma unit that has been tested, approved and sealed in a pouch is then stored for a period of time ranging from about 1 minute to about 30 months at a temperature ranging between about 1° C. and about 45° C. In an embodiment, spray dried plasma of the present invention can be stored at room temperature for about 1 hour to about 12 months. In an embodiment, spray dried plasma of the present invention can be stored at refrigerated temperature for about 1 hour to about 24 months. In an aspect, refrigerated temperatures are between about 1° C. and about 6° C. and room temperatures are between about 20 and about 25° C.

In an embodiment, plasma unit 60 is packaged in a pouch, a high moisture barrier bag consisting of an opaque Polyethylene Terephthalate (PET) aluminum foil laminate on one side and a transparent PET double layer laminate on the other. In this embodiment, a 10-gram molecular sieve desiccant packet is placed in the pouch before sealing. Plasma unit 60 can be packaged in the overwrap pouch with a desiccant such that the label is visible through the transparent laminate. Such pouches are commercially available from e.g., Technipaq Inc. (Crystal Lake, IL USA).

The methods of the present invention further include reconstituting the dried plasma using a reconstitution solution. The reconstitution solution can be mixed with the dried plasma using one of spike ports 42A or 42B of the dried plasma unit 60. In a preferred embodiment, sterile water for injection is used for the reconstitution solution. In other embodiments, the reconstitution solution includes distilled water, or in the case where pre-treatment step is not performed, the reconstitution solution could be, for example, an amino acid (e.g., glycine), and/or a buffered solution (e.g., an acid such as hydrochloric acid or citric acid). The amount of reconstitution solution used to rehydrate the dried plasma is in a range between about 218 ml and about 200 ml. Additionally, once the reconstitution solution is added, a step of the method includes shaking the reconstitution plasma unit to ensure the mixing and uniformity of the reconstitution solution and dried plasma. The reconstituted plasma is ready for transfusion into a recipient. A recipient can be human, primate, animal and the like.

The methods further include transfusing a recipient in need thereof. The reconstituted plasma unit is administered the same as any plasma. In an embodiment, the method includes transfusing the recipient intravenously with the reconstituted plasma Detailed Description of Methods and Parameters Overall, in an embodiment as shown in FIGS. 47A-C and 48A-C, to align the spray dry disposable device 2 to finishing apparatus 400, the operator should employ the apparatus described to align the locating arrangement and ridge on the disposable with the finisher, insert the gas outlet of the disposable into the gas port receiver of the finisher and position the openings of the bag over the positioning pins on the finisher. Once these alignment elements are engaged, the disposable is aligned into place and ready to be processed. In another embodiment, one or any combination of these alignment or positioning arrangements can be engaged so that the disposable is aligned with the finisher.

The alignment and positioning arrangements described herein can be used independently or in any combination with one another.

In addition to securing, aligning and/or positioning the spray drying disposable device within the spray drying apparatus using one of more of the alignment elements described herein, the methods of spray drying plasma further include providing plasma to a spray drying apparatus; engaging the spray drying apparatus to spray dry the plasma to form dried plasma powder; and engaging the finisher to create a dried plasma unit. The methods further include storing the dried plasma unit until ready for rehydration and transfusion.

In addition to aligning/securing the spray drying disposable device within the spray drying finisher using one of more of the alignment elements described herein, the methods of finishing the process (e.g., transforming the disposable having dried plasma into a plasma unit having dried plasma) further include engaging the finisher to lower the shuttle so that the finisher impacts and seals and separates the spray dry disposable at a first point. Once the shuttle raises, the operator discards the upper portion of the disposable, as described herein, and rotates the lower frame such that the lower frame is superimposed over the upper frame. The shuttle having the superimposed frame lowers and the finisher impacts and seals and separates the modified disposable at a second point to thereby create the plasma unit having dried plasma. The methods further include storing the dried plasma unit until ready for rehydration and transfusion.

In some embodiments, spray drying the plasma includes: directing plasma to a spray nozzle at a plasma flow rate; directing a heated drying gas to a drying chamber at an inlet temperature and a drying gas flow rate; directing a spray gas to the nozzle at a pressurized aerosol gas flow rate; combining the plasma and pressurized aerosol gas at the nozzle to atomize the plasma and dry the plasma; and combining the atomized plasma and drying gas to dry the atomized plasma.

Some embodiments include, during the spray drying, maintaining the plasma at a temperature between about 55° C. and about 85° C. The average temperature to which the plasma particle is exposed is about 65° C.

In some embodiments, the inlet temperature of the spray dryer is in the range of 100-130° C. (e.g., 114° C.). In an embodiment, the exhaust temperature of the spray dryer is between 55° C. and 85° C. (e.g. about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85° C.) In an embodiment, the exhaust temperature is about 65° C.

In some embodiments, the plasma flow rate is in the range of about 2 mL/min to about 50 mL/min (e.g., in an embodiment in a range from about 6 and about 23 mL/min) at a temperature of 15° C. and 35° C. (e.g., at ambient temperature). In some embodiments, the drying gas flow rate is in the range of about 500 L/min and about 1000 L/min at a temperature of between about 100° C. and 130° C. (heated). In some embodiments, the pressurized aerosol gas flow rate is in the range of about 25 L/min and about 65 L/min (e.g., 40 L/min).

In an embodiment, the exhaust rate of the air in the disposable during the finishing process is about 790 slpm. In an embodiment, the exhaust temperature of the air in the disposable during the finishing process is between about 63.5° C. and about 66.5° C.

Certain embodiments, the reconstitution solution includes at least one selected from the list consisting of distilled water, and saline solution. In some embodiments, especially when pretreatment is not performed, the reconstitution fluid is a buffered solution, has an amino acid (e.g., glycine) or both. In a preferred embodiment, Sterile Water For Infusion (SWFI) is used as a reconstitution solution.

Methods of spray drying plasma can be found in U.S. Pat. Nos. 8,533,971, 8,595,950, 8,434,242, 8,601,712, 8,533,972, and 10843100, the entire teachings of which are incorporated herein by reference.

Kits and Systems

The present invention further includes a kit or system having the components described herein. In an embodiment, the kit of the present invention includes the spray drying disposable device, and/or parts thereof, as described herein including those having the alignment elements described herein. In an embodiment, a kit of the present invention includes the disposable device, rehydration solution (e.g., SWFI), clamps, tubing and the like. In a preferred embodiment the SWFI is provided in a pre-measured container supplied as part of a kit with the other components of the system. However, if needed, SWFI from any source can be substituted for the pre-packed SWFI of the kit so long as the amount of SWFI used in the rehydration is the same as that specified. In an embodiment, the single use container is 200 mL of sterile water for injection (SWFI) is packaged in a 250 mL bag within an overwrap pouch. The kit can further include a rehydration Tubing Set e.g., a commercially approved standard sterile fluid transfer set (e.g. Fenwal Plasma Transfer Sets with Two Spikes 4C2243 or equivalent) to transfer the SWFI into the unit. Additionally, a Transfusion Tubing Set can also be included to transfuse rehydrated plasma into a patient. An example is a commercially approved standard sterile transfusion set/administration set (e.g. Fenwal Blood Component Recipient Set with Standard Blood Filter and Luer Adapter 4C2160 or equivalent). The system of the present invention includes the spray drying disposable device, the spray drying apparatus and the spray drying finishing device, and/or parts thereof, each with one or more of alignment elements described herein.

Clean Dry Air System Used with the Spray Dryer

In an embodiment, the drying gas source is an Atlas-Copco SF 22+ compressor (Atlas Copco Nacka Municipality, Sweden) in conjunction with an Atlas-Copco CD45 desiccant drying system supplying clean dry air (CDA) to the spray dryer and heats air to the appropriate temperature for spray drying. The CDA supply is used, in an embodiment, for the supply for the drying gas and for the pressurized gas. In certain embodiments spray drying nozzle assembly 20 includes a "manifold" that coordinates the plasma and aerosol lines. In an embodiment, there are redundant in-line 0.2 μm commercially available sterilizing grade hydrophobic filters in the drying gas line and pressurized aerosol gas line. A unidirectional positive airflow is maintained at the dryer aerosol gas and drying gas outlet ports during the spray drying process.

Numerous filters exist to filter air going in and out of the system. For example, the drying gas supply or source is filter with a 0.2 micron filter (e.g., Millipore Series 3000 0.2 micron filter CTGB71TP3 from Millipore Sigma of Danvers MA USA). Similarly, the pressurized/aerosol gas source also has a 0.2 micron filter (e.g., Millipore Series 3000 0.2 micron filter CTGB71TP3 from Millipore Sigma of Danvers MA USA). Both the consumable exhaust line and enclosure exhaust line to the outside air are filtered in an embodiment by a 0.1 micron filter (e.g., consumable exhaust line to outside air—Saint Gobain 1000 SLPM 0.1 micron filter LI2F010NTCTC from Saint Gobain Performance Plastics of Worcester MA USA; and enclosure exhaust line to outside air—Saint Gobain 50 SLPM 0.1 micron filter LI2F010NCTC from Saint Gobain Performance Plastics of Worcester MA USA).

The spray dryer of the present invention utilizes, in an embodiment, a source of clean, oil-free, dry air to provide a minimum of 790 standard liters per minute (SLM) of Clean Dry Air (CDA) to the Frontline Dryer including the Plasma Drying Chamber. The air is dried to −40° F. dew point. An acceptable CDA is available e.g., from Atlas-Copco although blood centers or other users may source alternative systems which meet the same or similar specifications.

The Atlas-Copco 30 HP Model SF22 System has three primary elements:

a. Oil Free Air Compressor—Atlas Copco 30 HP Model SF22+ Oil Free, multicore, rotary scroll air compressor package. The SF22+ contains four (4) 7.5 HP scroll compressors controlled by a microprocessor that will rotate their operation and even the wear hours over time. The package produces 100% oil free air and is extremely quiet (65 dB (A)). The full load capacity of the SF22+ package is 86.4 CFM@100 PSIG.
b. Heatless Desiccant Air Dryer—The Atlas Copco CD50+ desiccant air dryer is rated to dry the full capacity of the SF22+ package to the −40° F. pressure dewpoint continuously. The dryer is provided with optional demand dew point purge control which will conserve compressed air and increase efficiency by constantly monitoring the net delivered dew point and delaying the switch/purge cycle until needed based on the load. A coalescing pre-filter 0.1 μm/0.01 ppm and dust removal after filter (1 μm) for desiccant dust are included.
c. 240 Gallon Air Receiver Tank-A vertical 240-gallon air receiver is provided to serve as a reserve buffer of clean dry air for the spray drying application. A pressure gauge kit and safety relief valve are included.

This CDA can drive up to two dryers of the system of this preferred embodiment of the present invention.

This CDA system air purity has received ISO 8573-1 Class 2.2.1 certification, Edition 3 2010. The tubing segments connecting all elements are stainless steel with mechanical (not welded) connections. The pressure and mass flow controlled CDA output, flow through a 0.2 μm filter, before entering the dryer.

Sterile Water for Injection (SWFI)

The SWFI supplied with the system kit is nominally 200 mL of sterile water for injection packaged in a 250 mL polyolefin bag, in an overwrap pouch and terminally sterilized by steam. Optionally, the pre-measured SWFI can be a different size (e.g., 208 mL) to account for example for evaporative loss of SWFI during storage. In normal circumstances the clinician/end user rehydrates a unit with a unit of the supplied system SWFI. The plasma unit receives the SWFI transfer via spike ports using off the shelf tubing sets (e.g. Fenwal Inc (Deerfield, IL USA) Plasma Transfer Sets with Two Spikes 4C2243 or equivalent). The amount of SWFI provided may be adjusted as needed to account for water that does not transfer to dried plasma in practical application.

In exigent circumstances 200 ml of SWFI supplied by the user may be substituted for the pre-measured, supplied system SWFI.

In an embodiment, all materials used in the assembly that directly contact the drying air or the donor plasma meet the ISO 10993 biocompatibility guidelines for an external communicating device, blood path indirect, limited contact duration.

The present invention may be utilized in a wide variety of fields including but not limited to veterinary, drug processing, preservation of microbes, animal feed manufacture, ceramics and any other in which spray drying is applicable.

The present invention can be utilized in a wide variety of environments including blood center component processing laboratories as may be found in the United States and Canada, blood component laboratories in other countries, and adverse environments such as battlefields or areas of unrest and regions of natural disaster or extreme weather conditions.

Additionally, the present invention can be utilized by personnel with very limited training or supervision.

The invention described and claimed herein may be utilized in a wide variety of fields including but not limited to veterinary, drug processing, preservation of microbes, animal feed manufacture, ceramics and any other in which spray drying is applicable. Additionally, the invention described and claimed herein may be utilized in a wide variety of environments including blood center component processing laboratories as may be found in the United States and Canada, blood component laboratories in other countries, and adverse environments such as battlefields or areas of unrest and regions of natural disaster or extreme weather conditions.

The invention described and claimed herein may be utilized by personnel with very limited training or supervision.

Plasma Product

The present invention relates to spray dried plasma. Spray dried plasma is obtained using the spray drying devices and disposables, as further described herein. The spray dried plasma of the present invention has one or more or any combination of the following characteristics:

1) is largely amorphous, as defined as lacking definite form, e.g., with small particles (<20 microns) of proteins and lipids with high specific surface area and small diffusion length, the largely amorphous dried particles differ from lyophilized plasma which typically forms a consolidated, porous “cake”;
2) when reconstituted has very few or no crystals (e.g., cholesterol) made by the drying process;
3) when reconstituted, because the system of the present invention does not create particulates, the number of larger particulates is reduced, and in particular, mean size of particulates is reduced when measuring with a Coulter Multisizer 4 by the electrical sensing zone method for particulates having a size between about 2 μm and 60 μm, as compared to particulates in the donor plasma;
4) has low residual moisture;
5) reconstitutes rapidly in under four minutes, as measured from first touch by a user to completed reconstitution with no visible clumps;
6) is stable when stored under refrigeration, at room temperature, at elevated temperatures or a combination of those and allows for storage for longer periods of time, as compared to liquid plasma;
7) is stable for 4 hours or greater (e.g., up to 26 hours) after reconstitution and product stays aseptic;
8) when reconstituted, exhibits protein functionality of the most plasma proteins including fragile proteins, such as von Willebrand’s factor, and other active proteins in the donor plasma;
9) when reconstituted with Sterile Water for Injection (SWFI), reconstituted plasma is at a near normal plasma pH (not abnormally high (alkalotic)) which is preferable for use in transfusion, and is ready for transfusion without treatment with or storage in $CO_2$ or other post-drying pH adjustment; and 10) when reconstituted, does not activate complements (C5a, C3a) as compared to apheresed plasma (Complement activation is involved in inflammation).

The spray drying plasma of the present invention is for use in transfusion medicine and otherwise, and is an alternative to liquid plasma, frozen plasma or freeze-dried plasma. In an embodiment, the dried plasma product of the present invention is a standardized dose of dried plasma, referred to herein as a "plasma unit," "dried plasma unit," "plasma product," or "unit", intended for rapid rehydration at the point of care. The dried plasma of the present invention allows regional blood centers and others to prepare a single donor unit of plasma or pooled plasma in a dried form that can be stored, shipped, and transfused more easily than frozen plasma.

The dried plasma unit of the present invention is, in part, a source of plasma proteins for patients who are deficient or have defective plasma proteins for which there are no specific replacement factors available. The dried plasma unit of the present invention can also be used for those who are in need of blood volume and/or coagulation factor treatment such as external or internal bleeding or disease state. The dried plasma unit of the present invention provides a plasma product where conventional plasma (such as fresh frozen plasma (FFP) or plasma frozen within 24 hours (PF24)) is unavailable or impractical for use such as pre-hospital transfusions, rural/austere hospitals and military applications.

Additional indications for use of the dried plasma unit of the present invention include the management of preoperative or bleeding patients who require replacement of multiple coagulation factors (e.g., liver disease, Disseminated Intravascular Coagulation (DIC)) as well as patients undergoing transfusion who have clinically significant coagulation deficiencies. The plasma of the present invention, when reconstituted, allows for clot formation.

The dried plasma unit of the present invention is suitable for use for massive transfusion as it can induce clot formation and does not expose the recipient to risks of high pH, cholesterol or other crystals, particulates, or complement activation, as compared to other blood products now available or expected to be available for transfusion.

To better understand the characteristics of the plasma, a description of the spray drying system, disposable and methods are described herein.

Plasma Characteristics:

Dried Plasma is Amorphous and has Few or No Crystals

The present invention relates to a reconstituted previously spray dried plasma which is made by a process which creates very few or no crystals (e.g., cholesterol crystals). "Reconstituted plasma" as used herein refers to reconstituted plasma that was spray dried using the methods, disposable and spray drying system described herein. In a particular embodiment, the reconstituted plasma, in an embodiment, has no or few crystals visible with a phase contrast microscope set at 100×, 400× or both. Cholesterol crystals are cholesterols that form a type of lattice structure, often an elongated rod-like crystal morphology or thin quadrilateral plate morphology. In another embodiment, the reconstituted plasma has less crystals (e.g., cholesterol crystals), as compared to reconstituted plasma that has previously been lyophilized. Crystals in reconstituted lyophilized plasma have been observed in a range between about 1 and about 3 μm. The formation of dried plasma with little or no crystals is the result, in part, of the spray drying process, the design of the nozzle of the disposable, the rapid mixture of the liquid plasma droplet and the drying gas during spray drying, the droplet size, and the parameters at which the plasma is dried. These aspects are further described herein.

While not adhering to any particular theory, it is believed that the spray drying plasma using disposable 100 and dryer 200, as described herein, allows for rapid mass transfer (e.g. less than 1 second) to convert the liquid plasma to an amorphous dried material. As a result, crystalline solid production for many molecules including cholesterol is suppressed as the minimum required time and mobility needed for the molecules to orient themselves in a low energy crystalline state is not present during the manufacture of the spray dried plasma of the present invention. In contrast, lyophilization has a long-time window (e.g., hours or days) allowing time for crystal formation including cholesterol crystals, to form and stabilize. See Examples 1 and 2.

Examples 1 and 2 describe the observance of no crystal formation in the rehydrated spray dried plasma of the present invention but present in lyophilized plasma. Crystals can be identified with microscopic examination, and namely through compound microscopy, phase contrast microscopy, or electron microscopy at various magnifications (e.g. 40×, 80×, 100×, 200×, 400×, 800×, 1000×, and 2000×). In an embodiment and in the Examples, crystals are seen in all of the lyophilized plasma samples at 100× and 400×.

In an aspect, cholesterol crystals are undesirable in blood plasma. The process of freeze drying/lyophilization creates such crystals in the rehydrated freeze-dried plasma product. Lyophilized human blood plasma has crystal formation when reconstituted and so the recipient receives cholesterol crystals when transfused with reconstituted plasma that was previously freeze-dried. Cholesterol crystals are undesirable in the human body because they induce inflammation in atherosclerosis which could lead to heart attacks and strokes. Furthermore, cholesterol cannot be easily degraded by mammalian cells and so they have a lasting effect. In particular, cholesterol crystals are known to have the following undesirable characteristics:

1) Excess cholesterol is excreted in the bile and transported in specialized transporter molecules (HDL, LDL) and modified by cells, but not degraded. In certain instances, cholesterol crystals are formed in the bile and are involved in the formation of stones;
2) Cholesterol crystals are formed during the formation of the atherosclerotic plaque. Excessive crystal growth is implicated in plaque rupture and severity of symptoms is related to cholesterol crystal content;
3) Cholesterol crystals are spread through the body as a result of plaque rupture. Cholesterol crystals released from the atherosclerotic plaque can spread to almost any organ. Effects can vary between relatively benign skin manifestations to multi organ failure and such symptoms are exhibited within a few hours to 5 months after exposure;
4) Cholesterol crystals derived from human atheroma, a degeneration of the walls of the arteries caused by accumulated fatty deposits and scar tissue, can still be found well after vessel repair. Furthermore, it has been shown that large crystals damage the endothelial cells, whereas small crystals seem to have fewer damaging effects; and
5) Cholesterol crystals activate the immune system and induce inflammation processes.

The effects of cholesterol crystals can be immediate or late, and can vary from patient to patient. If cholesterol crystal related effects (mild or serious) are seen in the patient they could be interpreted as part of the patient's disease or due to dietary behavior, and not as caused by the treatment with reconstituted lyophilized plasma.

Figure 7:
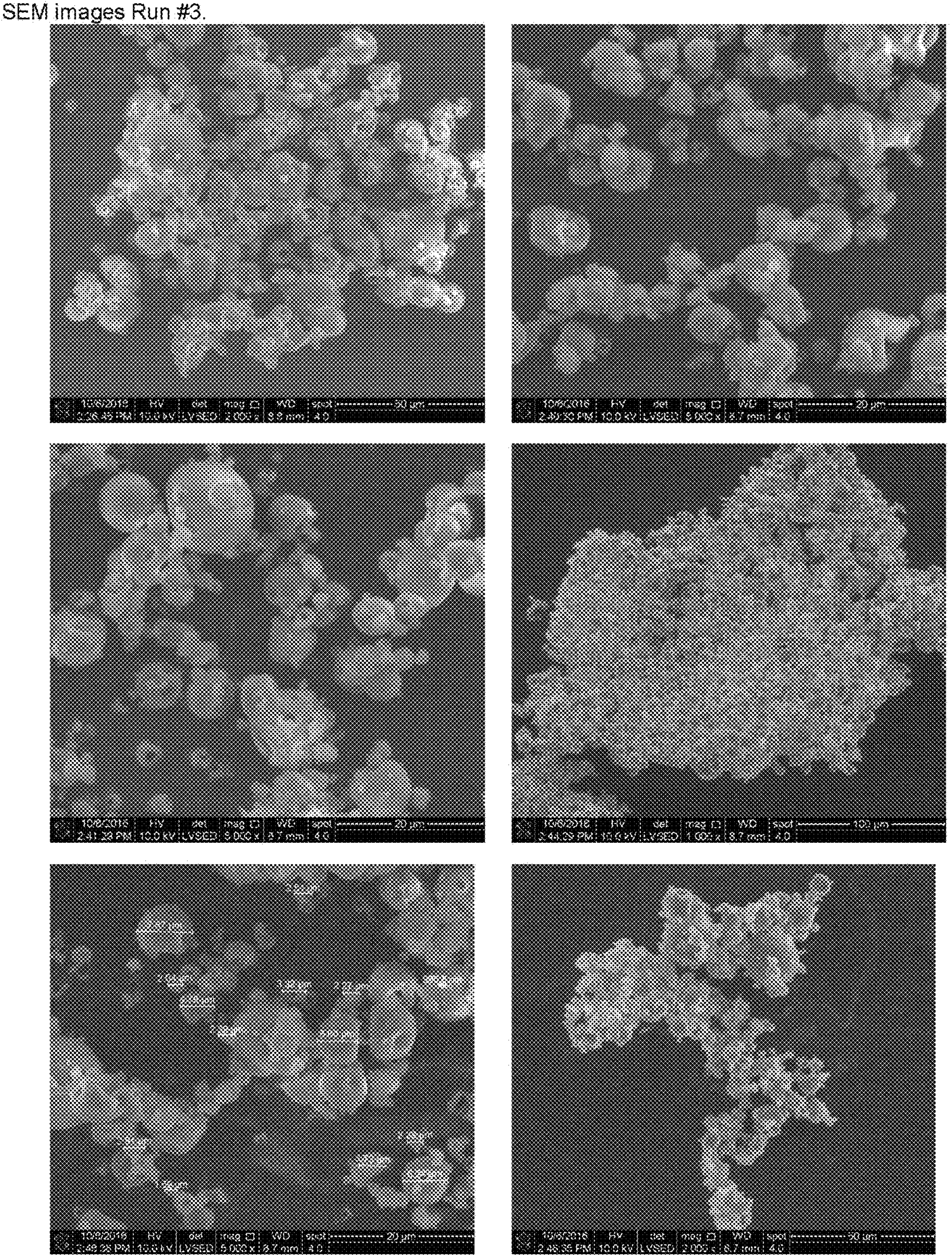
FIG. 7 is a panel of black and white photos of Scanning Electron Microscopy (SEM) of spray dried plasma particles of Run #3, upper left panel at 2000×, upper right panel at 5000×, middle left panel at 5000×, middle right panel at 1000×, lower left panel at 5000× with measurements overlaid thereon showing sizes between 0.99 μm and 7.87 μm and lower right panel at 2000×. These photos illustrate the small size and amorphous character of the present invention.

Based on the undesirable effects of cholesterol crystals, the dried plasma of the present invention is preferable for transfusion, as compared to lyophilized plasma. Reconstituted plasma of the present invention does not contain crystals (e.g., cholesterol crystals) visible at 100× and 400× and is largely amorphous. "Amorphous" refers to a non-crystalline solid in which the atoms and molecules are not organized in a lattice pattern and lacking long-range order. While freeze drying promotes cholesterol crystal formation by super cooling, the spray drying process of the present invention minimizes or avoids crystal formation by promoting rapid mixing and rapid mass transfer in which a plasma droplet is dried into an amorphous plasma particle in less than a second. Note that crystals originating from a donor may be present in the finished product. The spray drying process does not create additional crystals in the plasma. If certain crystals are present in the donor plasma, then they may also be present in the reconstituted previously spray dried plasma. For example, it is possible that uric acid crystals or calcium phosphate crystals present in the donor plasma may also be found in the reconstituted plasma unit. As such, the reconstituted previously spray dried plasma of the present invention is largely amorphous or substantially amorphous (e.g., at least about 99%, 98%, 97%, 96%, 95%, 94%, 93%, 92%, 91%, 90% amorphous). As a result, crystalline solid production for many molecules including cholesterol is suppressed as the conditions needed for crystalline formation is not present during the spray drying of the present invention. In contrast lyophilization process promotes crystal formation including cholesterol crystal formation by providing time and conditions for crystalline formation. See FIGS. 1-4. FIG. 7 provides photos that illustrate the small size and amorphous character of the present invention.

As a consequence, the dried plasma of the present invention is largely, substantially, or wholly amorphous in structure with few or no crystals (e.g., cholesterol crystals). Since the spray drying process described herein does not produce crystals, the reconstituted plasma of the present invention has few or no crystals, except for those crystals present in the corresponding donor plasma.

The Mean Size of Particulates in Reconstituted Plasma of the Present Invention is Reduced Particulates of various kinds such as protein aggregates, platelets and microparticles naturally occur in blood plasma including that of humans. When plasma containing excessive or large particulates is transfused to a recipient, these protein aggregates or particulates may react with the recipient's body to cause inflammation or other immunological reactions, even though those particulates may have been benign to the donor.

As described herein, the term "particulates" differs from the term "particles." "Particulates" refer to protein aggregates, platelets and microparticles in reconstituted plasma. "Particles" refer to the individual discreet components that make up the dried plasma.

Particulate studies have been done for the dried plasma of the present invention and it has been determined that there is no increase in particulate size or distribution in the rehydrated units of the dried plasma of the present invention compared to its paired control. The particulate size analysis data supports that the rehydrated plasma of the present invention does not exhibit protein aggregates or other particulates after storage and rehydration.

In other words, when reconstituted, the rehydrated plasma exhibits a reduced mean size of particulates when measuring with a Coulter Multisizer 4 by the electrical sensing zone method for particulates having a size between about 2 μm and 60 μm, as compared to particulates in the donor plasma. Unlike the spray dried plasma of the present invention, lyophilized plasma has not been reported to reduce particulate size or quantity in the resulting, reconstituted plasma for transfusion.

The reconstituted plasma of the present invention has a reduced mean size of particulates, as compared to that found in the originating donor plasma. Without being committed to a particular theory, it is believed that the spray drying process of the present invention reduces the larger particulates in donor plasma into smaller sizes but the proteins, even delicate proteins, remain functional and integral. See Example 3.

A particulate analysis characterization study was conducted to evaluate spray drying manufacturing effects, in-use stability and product shelf-life effects on protein aggregation and other particulates. See Example 3. The particulate size analysis data supports that rehydrated dried plasma units of the present invention do not exhibit protein aggregates or other particulates due to manufacture and storage up to 7.5 months at room temperature, up to 24 months refrigeration or after a combined storage temperature of 1 year refrigerated+6 months room temperature when compared to (1) its paired control and (2) after t=4 hours post rehydration.

Particulates, as measured by the electrical sensing zone method in the range of 2 to 60 microns, are not increased in mean size when compared to a paired control that has not been spray dried. As measured, particulates in reconstituted plasma ranged in size between about 2 μm and about 3.5 μm, as compared to donor plasma which range in size between about 2 μm and about 7 μm. See FIG. 5 (7.5 months room temp) and FIG. 6 (12 months refrigeration). In an embodiment, the largest particulate size of reconstituted previously spray dried plasma is about 50%, 45%, 40%, 35%, 30%, 25%, 20%, 15%, 10% 5%, 4%, 3%, 2%, 1%, as compared to largest particulate size found in donor plasma. See Tables 11 and 12 of Example 3. As described further herein, plasma proteins participate in and allow for clot formation including fragile proteins such as von Willebrand factor (vWF). In all instances, the mean size of particles in the 2 μm to 60 μm range was reduced in the reconstituted spray dried plasma of the present invention as compared to the paired, not sprayed dried plasma control. Additionally, the mean size of particulates is reduced, as compared to donor plasma when measured in the range of in the about 2 μm to about 60 μm range. The percentage of particulates having a mean size ranging between about 2 μm to about 60 μm range in reconstituted plasma of the present invention is reduced as compared to donor plasma. In an embodiment, the particulates having a mean size ranging about 2 μm to about 60 μm range found in reconstituted previously spray dried plasma is about 60%, 50%, 40%, 30%, 25%, 20%, 15%, 10% 5%, 4%, 3%, 2%, 1% less as compared to the number found donor plasma.

Particulate analysis for determining particulate size, particulate quantity and distribution can be obtained using a Beckman Coulter Multisizer 4 (electrical sensing zone method) e.g., performed in the range of 2 to 60 μm.

The Spray Dried Plasma of the Present Invention has Low Residual Moisture, e.g., Less than 2.5% Residual Moisture As described herein, the spray drying system of the present invention is designed to produce a low residual moisture dried plasma powder. The low residual moisture 1) reduces any potential clogging of the lower filter, 2) facilitates faster reconstitution to create a plasma unit suitable for transfusion, and 3) contributes to stability during storage, including storage time, storage temperature and for storage in different environments.

The low residual moisture plasma unit is obtained by using the disposable described herein and dried with the parameters described herein. In particular, the low residual moisture of the dried plasma is attributable to a number of aspects of the spray drying system that promote rapid mixing of the drying gas and the plasma droplets during spray drying. Rapid mixing allows for rapid mass transfer/evaporation which results in a low residual moisture plasma product and contributes to the very compact dimensions of the spray drying disposable of the present invention, especially the plasma drying chamber.

For example, as described herein, the design of liquid nozzle cap insert 80 and nozzle cap 76 allow the pressurized aerosol gas to flow though annulus 81 in a vortex pattern to maximize aerosolization and promote rapid mixing of the aerosolized plasma droplets with the drying gas, as further described herein.

Also as described herein, small droplet size which is enhanced by the angled edge of the cannula, promotes rapid mixing, faster evaporation, reduced drying time and, in part, provides a low residual moisture plasma product. See FIG. 43T which shows that the larger the droplet size the longer it takes for the droplet to evaporate with higher drying gas temperatures. Droplet size is also impacted by the ratio of the pressurized gas flow rate to the liquid feed rate and nozzle design.

Additional factors involved in the rapid mass transfer and evaporative drying stage of the plasma droplet also include the temperature of the plasma and the drying gas, the surface area of the droplet, the humidity in the drying gas and the air circulation within the plasma drying chamber. As described herein, when initially exiting the nozzle assembly, the temperature of the drying gas is between about 90° C. to about 130° C. (e.g., between about 100° C. to about 114° C.) and the temperature of the plasma droplet is between about 20° C. and about 65° C. in the plume as shown in FIGS. 43S and 43Sa. The simulated droplet temperatures in FIG. 43S were obtained by averaging over all droplet trajectories during the period of constant rate evaporation and indicate that over the range of drying gas inlet temperatures during the early near nozzle evaporation the proteins do not experience those high drying gas inlet temps. In fact, plasma proteins are protected by the energy loss due to evaporation when the proteins are most vulnerable, which is in the liquid state. FIG. 43Sa focusses on a single droplet to aerosol particle pathway. FIG. 43Sa shows a longer time-line and indicates the highest temperature the protein will experience is in the solid state, after evaporation and while in the capture filter. The heat flows from a point of higher temperature to that of a lower temperature, and in this case the drying gas heat flows to the plasma droplet. With respect to the surface area, the droplet is spherical thereby maximizing its surface area and the droplet size is very small so the mass and heat transfer can happen quickly. The relative humidity in the drying gas is very low and therefore the low humidity of the surrounding drying gas promotes evaporation of the plasma particle. Finally, as described in more detail herein, the drying gas is emitted using several drying gas jets in an angled and downward direction into the plasma drying chamber and into the plume of atomized droplets to initiate rapid mixing of the drying air and the atomized droplets, which increases the rate of evaporation of the liquid droplets.

Yet another factor, as described herein, that contributes to a low residual moisture product is the starting liquid droplet size produced by the nozzle assembly. This impacts the residence time in the drying chamber needed to complete evaporation and a small droplet size allows evaporation to happen more quickly. The smaller the liquid droplet, the larger the ratio of evaporation surface area to droplet mass and the faster the mass transfer rate from the droplet. As seen from FIG. 43T, the drying chamber can be shortened to that where the majority of the evaporation occurs while still allowing a dried particle to achieve less than 2.5% residual moisture before being deposited on lower filter 36.

The percent residual moisture in the plasma dried with the disposable and dryer of present invention is very low, e.g., below about 2.5%, 2%, 1%, preferably about 1.46% residual moisture, as measured by Karl Fischer moisture sensor, Model No. C30S Compact KF Coulometer (Mettler Toledo Billerica Massachusetts USA). This is a very low moisture level which is due to effective and efficient evaporation of the plasma droplet occurring in the upper portions of drying chamber 28 and the process conditions. In this aspect, powder moisture level is in equilibrium with chamber outlet air stream relative humidity.

Dried plasma with low moisture improves reconstitution time and protein stability during storage.

The Dried Plasma of the Present Invention Reconstitutes Rapidly e.g., Under Four Minutes The principal reason human plasma is not available as widely as needed is that, before the present invention, blood plasma, in general, could only be stored frozen for long periods or as a liquid for very short periods. Accordingly, if a large amount of plasma is needed (e.g., such as in a mass casualty event), it may not be available in such quantities, or if plasma is needed in an emergency, it may not be available in time since it has to be thawed which can take 30-45 minutes or more.

The spray dried plasma of the present invention can be stored for longer periods of time, as described herein, and can be rapidly reconstituted in under four minutes from first contact by the user to completed reconstitution. The phrase "reconstituted" or "rehydrated" are used interchangeably herein and refers to mixing the dried plasma of the present invention with a reconstitution solution (e.g., Sterile Water for Injection (SWFI)) to obtain a liquid plasma suitable for transfusion.

Rapid reconstitution is attributable, in part, to the amorphous nature, low residual moisture, small particle size, increased surface area of the particles of the dried plasma and the amount of air present in the plasma unit bag (e.g., between about 3 and about 15 mL volume of air). Low residual moisture levels of about 2.5% or less of the dried plasma assist in faster reconstitution because the low residual moisture does not contribute to clumping of the plasma particles into larger agglomerates with less surface area. In the case of a dried plasma (e.g., solute), the interactions between the dried plasma particles and the solvent (e.g., SWFI) are strong such that the individual solute particles separate from each other and, surrounded by solvent molecules, enter the solution to form liquid plasma. The drier the particles, the faster they will enter the solution. Similarly, the smaller the dried plasma particle and more exposed surface area of the particles exist, the easier it is for the solution (e.g., SWFI) to surround the particle and for the particle to enter into solution. In an embodiment, particle size of the dried plasma is between about 1 and about 7 microns. Particle analysis for determining particle size of the dried plasma, particle quantity and distribution can be obtained using a Scanning Electron Microscopy (SEM). See Example 7.

The methods of the present invention further include reconstituting the dried plasma using a physiologically compatible reconstitution solution. The reconstitution solution can be mixed with the dried plasma using one of spike ports 42A or 42B of the dried plasma unit 60. The reconstitution solution is connected to the dried plasma bag with one of the spike ports and the water is manually pushed into the dried plasma bag and mixed. Further, the spray dried formulated plasma of the present invention may be reconstituted with sterile water (e.g., sterile water for injection (SWFI) or similar) or clean, non-sterile water and, if desired, filtered after reconstitution. In normal circumstances the clinician/healthcare provider/end user rehydrates a unit with a unit of the supplied system SWFI. In a preferred embodiment, sterile water for injection is used for the reconstitution solution. In the case in which SWFI is not available, in an aspect, distilled water may be used. In other embodiments, for example when a pretreatment step is not performed, the reconstitution solution further includes amino acid (e.g., glycine), or a buffered solution (e.g., acid such as hydrochloric acid or citric acid). The plasma unit having the dried plasma and the bag weighs between about 45 grams and about 55 grams (e.g., about 50 grams). The dried plasma weighs between about 15 grams and about 25 grams (e.g., about 17 grams). The plasma unit bag weighs about 28 grams to about 38 grams (e.g., 33 grams). The amount of reconstitution solution used to rehydrate the dried plasma is in a range between about 175 mL and about 230 mL (e.g., 200 mL and about 225 mL). When the dried plasma is rehydrated with the reconstitution solution to thereby create a plasma unit ready for transfusion, the rehydrated plasma unit has a final volume of between about 180 mL and about 236 mL (e.g., about 205 mL and about 231 mL) or about 197 grams and about 247 (e.g., about 217 grams and about 242 grams). In a further embodiment the reconstitution solution is pre-measured to 208 mL or other volume to allow for potential evaporative loss in storage.

It is contemplated that the reconstituted spray dried formulated plasma of the present invention has a pH of about 6.5 to about 7.8, or about 6.9 to about 7.5 (e.g., 6.5, 6.6, 6.7, 6.8. 6.9. 7.0. 7.1. 7.2. 7.3. 7.4. 7.5, 7.6, 7.8). The amounts of the pretreatment components, further described herein, can be adjusted to achieve the designed pH of the reconstituted spray dried formulated plasma.

Additionally, once the reconstitution solution is added, a step of the method includes shaking, rocking and/or agitating the reconstitution plasma unit to ensure the mixing and uniformity of the reconstitution solution and dried plasma. The reconstituted plasma is ready for transfusion into a recipient. Examples of recipients include human, primate, mammal, animal and the like. In an embodiment, this method of reconstituting a dried plasma unit can be done in under 7 minutes (e.g., 7, 6, 5, 4, 3, and 2 minutes) and preferably under about 3.5 minutes, measured at the initial timepoint, time 0, (the time of the first contact of the reconstitution solution with the dried plasma unit) until the final time point which is the time that the plasma is reconstituted with the reconstitution solution having no visible clumps that can be seen with the naked eye (total reconstitution time).

This method was carried out by various individuals, some trained as a medic and others untrained and timed. Rehydration was achieved on average in less than about 4 minutes.

In a preferred embodiment the SWFI is provided in a pre-measured container supplied as part of a kit with the other components of the system. However, if needed, SWFI from any source can be substituted for the pre-packed SWFI of the kit so long as the amount of SWFI used in the rehydration is the same as that specified. In an embodiment, the single use container is 200 mL of sterile water for injection (SWFI) is packaged in a 250 mL bag within an overwrap pouch. The kit can further include a rehydration Tubing Set e.g., a commercially approved standard sterile fluid transfer set (e.g. FENWAL™ Plasma Transfer Sets with Two Spikes 4C2243 or equivalent) to transfer the SWFI into the unit. Additionally, a transfusion tubing set can also be included to transfuse rehydrated plasma into a patient. An example of a commercially approved standard sterile transfusion set/administration set is FENWAL™ Blood Component Recipient Set with Standard Blood Filter and Luer Adapter 4C2160 or equivalent.

The Spray Dried Plasma of the Present Invention is Stable when Stored Under Refrigeration, at Room Temperature or at Elevated Temperatures and Allows for Storage for Longer Periods of Time The spray dried plasma stability is achieved in part by its low residual moisture. The low residual moisture in the spray dried plasma enables for storage at various temperatures and for longer periods of time.

"Stability" or "Shelf-life Stability" or "Unit Stability" refers to stored spray dried plasma, when reconstituted, behaves comparably to plasma that has been dried but not stored. Stability includes comparing amounts of various plasma proteins and their function (e.g., vWF, Factor V, Factor VIII, etc.) and/or plasma characteristics (e.g., pH, particle size, etc.) present in reconstituted spray dried plasma before (time=0 seconds) and after storage (e.g., up to 48 months at refrigeration, up to 12 months at room temperature). Stability involves comparing the respective value of one or more of these proteins/characteristics before and after storage to determine similarity to one another or to determine if the value is within the clinical range. In an embodiment, the values a plasma protein/characteristic after storage are within about 25% or less (25%, 20%, 15%, 10%, 9%, 8%, 7%, 6%, 5%, 4%, 3%, 2%, and 1%), as compared that before storage. In an embodiment, the values of plasma proteins/plasma characteristics after storage are within the clinical range for that plasma protein. Such plasma characteristics include pH, Osmolality (mOsm/kg), particulate size, particulate quantity and particulate distribution. Plasma proteins and their function include e.g., Total Protein (mg/ml), Activated Partial Thromboplastin Time (aPTT)(s), Prothrombin Time(s), International Normalized Ratio (INR(s)), Thrombin Time(s), Factor V (%), Factor VII (%), Factor VIII (%), Factor IX (%), Factor X (%), Factor XI (%), Factor XIII Activity (%), Factor XIII Antigen (%), Protein C Activity (%), Protein S Activity (%), Fibrinogen (mg/dL), Plasminogen (%), Plasmin InhibitorPI (%), Antithrombin III (%), von Willebrand Factor Antigen (% or IU/dL), von Willebrand Factor Ristocetin Cofactor (% or IU/dL), C5a (ng/ml), Prothrombin Fragment F 1+2 (pmol/L), Thrombin-Antithrombin Complex (TAT) (μg/L), Protein (mg/mL) and the like. Measuring such plasma characteristics and plasma proteins are known in the art. In another embodiment, the acceptable or clinical range for von Willebrand Factor Ristocetin Cofactor (VWF:RCo) is between about 50 and about 200 IU/dL, or about 50 and about 200 IU/dL, and von Willebrand Factor Antigen (VWF:Ag) value is between about 50 and 200 IU/dL.

In an embodiment, the clinical reference range for determining shelf life or unit stability is as follows:

TABLE 2

| Plasma protein/Plasma Characteristic | Clinical Reference range |
|---|---|
| Activated Partial Thromboplastin Time aPTT (s) | (22-35) |
| Prothrombin time PT (s) | (10-14) |
| International Normalized Ratio INR | (0.9-1.1) |
| Thrombin Time TT (s) | (14.5-20.5) |
| Fibrinogen Fib (mg/dL) | (150-400) |
| Factor V Activity FV Act (%) | (50-200) |
| Factor VII Activity FVII Act (%) | (50-200) |
| Factor VIII Activity FVIII Act (%) | (50-200) |
| Factor IX Activity FIX Act (%) | (50-200) |
| Factor X Activity FX Act (%) | (50-200) |
| Factor XI Activity FXI Act (%) | (50-200) |
| Factor XIII Activity FXIII Act (%) | (57-192) |
| Factor XIII Antigen FXIII Ant (%) | (75.2-154.8) |
| Protein C Activity PC Act (%) | (75-150) |
| Protein S PS Act (%) | (60-150) |
| Antithrombin III Activity AT III Act (%) | (80-120) |
| Plasminogen PLG (%) | (70-150) |
| Plasmin Inhibitor PI (%) | (85-156) |
| von Willebrand factor ristocetin cofactor assay VWF:RCo (% or IU/dL) | (50-200) |
| von Willebrand factor antigen VWF Ant (% or IU/dL) | (50-200) |
| Thrombin-Antithrombin TAT (μg/L) | (0-4) |
| Prothrombin Fragment 1 + 2 PF1+2 (pmol/L) | (91-137) |
| Complement component 5a C5a (ng/ml) | (4.7-74)* |
| pH | (7.35-7.45) |
| Protein (mg/mL) | (6-8.3) |
| Osmolality (mOsm/kg) | (>240) |

*clinical reference ranged for apheresed plasma

The data shows that the dried plasma is stable after being stored as a dried plasma for a time period up to about 24 months at refrigerated temperatures (2-8° C.), 6 months at a Room Temperature (20-25° C.) and 3 months elevated Room Temperature (30° C.). Example 5 describes experiments performed that verified that the spray dried plasma unit remained stable during storage.

The spray dried plasma of the present invention, after release testing is complete and the product is determined safe for use, as described herein, can be stored at elevated temperatures, room temperature, refrigerated temperatures, freezing temperatures or a combination thereof. In certain aspects, spray dried plasma is refrigerated to enable storage for longer periods of time.

The dried plasma of the present invention can be stored between a temperature of −80° C. and 45° C. Room temperature is considered between about 20° C. and 30° C. In an aspect, refrigerated temperatures are between about 1° C. and about 6° C. The terms "cooling," "cold temperature," "temperature below room temperature," and "temperature below ambient temperature," interchangeably refer to any temperature between 1° C. and 20° C. In any of the embodiments of the invention described herein, the temperature is selected from the group of temperatures consisting of 45° C., 44° C., 43° C., 42° C., 41° C., 40° C., 39° C., 38° C., 37° C., 36° C., 35° C., 34° C., 33° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., 0° C., −1° C., −5° C., −10° C., −20° C., −30° C., −40° C., −50° C., −60° C., −70° C., and −80° C. In some embodiments, the spray dried plasma of the present invention is stored at a temperature of less than about 15° C., preferably less than 10° C., and more preferably less than 5° C. In some other embodiments, the spray dried plasma of the present invention is stored at room temperature. In other embodiments, the spray dried plasma of the present invention is stored at warm temperatures, e.g., above 23° C. In further embodiments, the spray dried plasma of the present invention can be stored in freezing temperatures (e.g., 0° C. to −80° C.). It is noted that although the dried plasma product can be stored in freezing temperatures, it does not need to be maintained in freezing temperatures to be stable for transfusion. On one hand, storage conditions can be carefully monitored, and on the other, storage conditions can be an array of temperatures depending on circumstances on the ground. In yet another embodiment, the dried plasma can be stored at a combination of temperatures.

As used in all of the aspects and embodiments of the invention herein, the term "period of time" or "time period" refers to a duration of time during which spray dried plasma of the present invention is stored at any given temperature. The term "period of time" can range from seconds to minutes to hours to days to weeks to months to years. In preferred embodiments, the term "period of time" refers a number of hours including about 3 to about 120 hours, e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120 hours. In certain embodiments the period of time for which spray dried plasma of the present invention can be stored include about 1 and about 30 days (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30). In certain embodiments the period of time for which spray dried plasma of the present invention can be stored include about 1 and about 48 months (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months).

In an embodiment, spray dried plasma of the present invention can be stored at room temperature for at least about 1 hour to about 7.5 months. In an embodiment, spray dried plasma of the present invention can be stored at refrigerated temperature for about 1 hour to about 48 months. In an aspect, the spray dried plasma of the present invention can be refrigerated on any day or days during storage.

In various other embodiments, the spray dried plasma of the present invention is stable and preserves the functionality of plasma proteins and/or plasma characteristics during the time period, when compared to corresponding clinical reference ranges or that prior to storage, or compared to thawed previously frozen plasma over the same period of time following spray drying. In an embodiment, spray dried plasma samples stored between a temperature of −80° C. and 45° C. are suitable for transfusion after extended periods of storage time, in an embodiment, for at least about 2 days, at least about 7 days, at least about 2 weeks, at least about 3 weeks, at least about 1 month, at least about 2 months, at least about 3 months, at least about 6 months, at least about 9 months, at least about 1 year, or at least about 1½ years, about 2 years, about 3 years, about 4 years, or longer.

The invention, in certain aspects, provides a novel method of storing a spray dried plasma in which the steps include obtaining plasma from a donor and drying the plasma using the methods and systems described herein, and storing the plasma for a period of time without a substantial loss or subclinical loss of one or more plasma protein amounts and/or plasma characteristics.

The Spray Dried Plasma of the Present Invention is Stable after Reconstitution for Up to 26 Hours Prior to Use The spray dried plasma stability also refers to the characteristics of spray dried plasma that has been reconstituted for a period of time and which is suitable for transfusion. The reconstituted previously dried plasma of the present invention remains stable and ready for transfusion for up to 26 hours, when reconstituted plasma is stored at room temperature, at refrigerated temperature, or at elevated temperature.

"Stability" or "In Use Stability" also refers to previously spray dried plasma that has been reconstituted for a period of time (e.g., at 2 hours, 4, hours, 6 hours, 8 hours, 10 hours, 12 hours, 14 hours, 16 hours, 18, hours, 20, hours, 22 hours, 24, hours or 26 hours) and behaves comparably to spray dried plasma immediately or contemporaneously after reconstitution (e.g., from 0-5 hours, 1-15 minutes). Stability includes comparing amounts of various plasma proteins, their function (e.g., vWF, Factor V, Factor VIII, etc.) and/or plasma characteristics (e.g., pH, particle size, etc.) present in reconstituted previously spray dried plasma before (time=0 seconds) and after storage (e.g., time=26 hours) of reconstituted plasma. In another embodiment, stability includes determining the amounts of various plasma proteins, their function (e.g., vWF, Factor V, Factor VIII, etc.) and/or plasma characteristics (e.g., pH, particle size, etc.) present reconstituted previously spray dried plasma after storage to determine that one or more fall within the corresponding clinical reference range. Stability involves comparing the respective value of one or more of these proteins/characteristics before and after reconstituted storage to determine similarity to one another, or the respective value to its clinical reference range. In an embodiment, the values of a plasma protein/characteristic after reconstituted storage is within about 25% or less (25%, 20%, 15%, 10%, 9%, 8%, 7%, 6%, 5%, 4%, 3%, 2%, and 1%), as compared that before reconstituted storage. When one or more values of plasma proteins after storage are within 25% of that prior to storage or within the clinical reference range, the reconstituted previously dried plasma is suitable for transfusion. Such plasma characteristics include pH, Osmolality (mOsm/kg), particulate size, particulate quantity and particulate distribution. Plasma proteins and their function include e.g., Total Protein (mg/ml), Activated Partial Thromboplastin Time (aPTT(s)), Prothrombin Time(s), International Normalized Ratio (INR(s)), Thrombin Time(s), Factor V (%), Factor VII (%), Factor VIII (%), Factor IX (%), Factor X (%), Factor XI (%), Factor XIII Activity (%), Factor XIII Antigen (%), Protein C Activity (%), Protein S Activity (%), Fibrinogen (mg/dL), Plasminogen (%), Plasmin Inhibitor (%), Antithrombin III (%), von Willebrand Factor Antigen (% or IU/dL), von Willebrand Factor Ristocetin Cofactor (% or IU/dL), C5a (ng/ml), Prothrombin Fragment F 1+2 (pmol/L), Thrombin-Antithrombin Complex (TAT) (μg/L), and the like. Measuring such plasma characteristics and plasma proteins are known in the art. In another embodiment, the acceptable or clinical range for von Willebrand Factor Ristocetin Cofactor (VWF:RCo) is between about 50 and about 200 IU/dL, or about 50 and about 200 IU/dL, and von Willebrand Factor Antigen (VWF:Ag) value is between about 50 and 200 IU/dL.

In an embodiment, the clinical reference range for In-Use stability is as follows:

TABLE 3

| Plasma protein/Plasma Characteristic | Clinical Reference range |
|---|---|
| Activated Partial Thromboplastin Time aPTT (s) | (22-35) |
| Prothrombin time PT (s) | (10-14) |
| International Normalized Ratio INR | (0.9-1.1) |
| Thrombin Time TT (s) | (14.5-20.5) |
| Fibrinogen Fib (mg/dL) | (150-400) |
| Factor V Activity FV Act (%) | (50-200) |
| Factor VII Activity FVII Act (%) | (50-200) |
| Factor VIII Activity FVIII Act (%) | (50-200) |
| Factor IX Activity FIX Act (%) | (50-200) |
| Factor X Activity FX Act (%) | (50-200) |
| Factor XI Activity FXI Act (%) | (50-200) |
| Factor XIII Activity FXIII Act (%) | (57-192) |
| Factor XIII Antigen FXIII Ant (%) | (75.2-154.8) |
| Protein C Activity PC Act (%) | (75-150) |
| Protein S PS Act (%) | (60-150) |
| Antithrombin III Activity AT III Act (%) | (80-120) |
| Plasminogen PLG (%) | (70-150) |
| Plasmin Inhibitor PI (%) | (85-156) |
| von Willebrand factor ristocetin cofactor assay VWF:RCo (% or IU/dL) | (50-200) |
| von Willebrand factor antigen vWF Ant (% or IU/dL) | (50-200) |
| Thrombin-Antithrombin TAT (μg/L) | (0-4) |
| Prothrombin Fragment 1 + 2 PF1 + 2 (pmol/L) | (91-137) |
| Complement component 5a C5a (ng/mL) | (4.7-74)* |

TABLE 3-continued

| Plasma protein/Plasma Characteristic | Clinical Reference range |
|---|---|
| pH | (7.35-7.45) |
| Protein (mg/ml) | (6-8.3) |
| Osmolality (mOsm/kg) | (>240) |

*Clinical reference range reported for apheresed plasma.

The data shows that the dried plasma when reconstituted is stable for transfusion after being stored as a reconstituted plasma for a time period ranging between about 1 hours to about 26 hours. Example 4 describes experiments performed that verified that the reconstituted previously spray dried plasma unit remained stable during storage and prior to transfusion.

The reconstituted spray dried plasma of the present invention can be stored for transfusion at room temperature or be refrigerated. In certain aspects, reconstituted previously spray dried plasma is refrigerated to enable storage prior to transfusion for longer periods of time.

The reconstituted previously dried plasma of the present invention can be stored for transfusion between a temperature of 1° C. and 45° C. Room temperature is considered between about 20° C. and 30° C. In an aspect, refrigerated temperatures are between about 1° C. and about 6° C. terms "cooling," "cold temperature," "temperature below room temperature," and "temperature below ambient temperature," interchangeably refer to any temperature between 1° C. and 20° C. In any of the embodiments of the invention described herein, the temperature is selected from the group of temperatures consisting of 45° C., 44° C., 43° C., 42° C., 41° C., 40° C., 39° C., 38° C., 37° C., 36° C., 35° C., 34° C., 33° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., and 1° C. In some embodiments, the reconstituted previously spray dried plasma of the present invention is stored at a temperature of less than about 15° C., preferably less than 10° C., and more preferably less than 5° C. In some other embodiments, the reconstituted previously spray dried plasma of the present invention is stored at room temperature. In other embodiments, the reconstituted previously spray dried plasma of the present invention is stored at warm temperatures, e.g., above 23° C. In yet other embodiments, the dried plasma is stored at a combination of these temperatures.

As used in all of the aspects and embodiments of the invention herein, the term "period of time" or "time period" refers to a duration of time during which reconstituted previously spray dried plasma of the present invention are stored prior to transfusion at any given temperature. The term "period of time" can range from seconds to minutes to hours to days to weeks to months. In an embodiment, the term "period of time" refers a number of hours including about 3 to about 30 hours, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 hours.

In various other embodiments, the reconstituted previously spray dried plasma of the present invention is stored prior to transfusion at room temperature. The reconstituted previously spray dried plasma of the present invention is stable and preserves the functionality of plasma proteins and/or plasma characteristics during the time period, when compared to corresponding clinical reference ranges or that prior to storage, or compared to thawed previously frozen plasma over the same period of time. Reconstituted previously spray dried plasma samples stored at or below room temperature are thus suitable for transfusion after extended periods of storage time, in an embodiment, for at least about 1 hour, at least about 2 hours, at least about 3 hours, at least about 4 hours, at least about 5 hours, at least about 6 hours, at least about 7 hours, or at least about 8 hours and up to about 26 hours.

The invention, in certain aspects, provides a novel method of storing a reconstituted spray dried plasma in which the steps include obtaining plasma from a donor and drying the plasma using the methods and systems described herein, and reconstituting the plasma and storing the reconstituted plasma for a period of time without a substantial loss (e.g., about 25% or less) or without a subclinical loss of one or more plasma protein amounts and/or plasma characteristics. The method further includes transfusing the stored reconstituted plasma into a recipient.

The Spray Dried Plasma of the Present Invention Exhibits Functionality of the Most Fragile of Proteins, Including Von Willebrand's Factor, and Other Active Proteins, Absence of Complement Activation (C5a, C3a) and a pH which is Near Normal without Buffering or Treatment with $CO_2$ The spray dried plasma of the present inventions is able to preserve the most fragile proteins and functions of the donor plasma, reduce complement activation and having a pH upon reconstitution that is near normal without additional buffering or treatment with $CO_2$. This is accomplished with pretreating the liquid plasma with pretreatment solution (e.g., spray dry stable acidic substance (SDSAS) and one or more amino acids).

The present invention provides efficacy preservation and includes the preservation of the function of clotting factors in the plasma in a manner that does not otherwise harm the plasma or the transfused patient. During spray drying, some blood plasma proteins degrade to some extent, due to shear stress, surface stress (e.g., air-liquid interfacial stress), exposure to extreme pH, thermal stress, dehydration stress, and other environmental stresses.

The methods and compositions of the present invention recognize that pH and associated stresses can be reduced or the effects of which can be ameliorated by the use of formulations of the liquid plasma prior to or contemporaneously with spray drying. Formulation of the liquid plasma by glycine HCl or a similar spray dry stable acidic substance (SDSAS), and one or more amino acids (e.g., glycine), at novel concentrations, maintains the pH of the plasma at a non-alkaline level during the spray drying process. Adding an amino acid to the pretreatment solution results in higher recovery and better subsequent storage stability of plasma protein functions when compared to unformulated plasma In a particular embodiment, the pretreatment solution is added to the donor plasma, wherein the pretreatment solution when added to the plasma has glycine in an amount ranging between about 10 μmole/mL of plasma and about 110 μmole/mL of plasma (e.g., about 20, 30, 40, 50, 60, 70, 80, 90, 100, 110 μmole/mL of plasma), and hydrochloric acid (HCl) in an amount ranging between about 10 μmole/mL of plasma and about 30 μmole/mL of plasma (e.g., about 10, 15, 20, 25, and 30 μmole/mL of plasma), to thereby obtain formulated plasma. The formulated plasma has a pH in a range between about 6.0 and about 6.6 which offsets spray drying impacts on pH to yield a final rehydrated product that is at normal physiologic pH, a pH range between about 6.5 to about 7.8. In an embodiment, pretreatment of the plasma is optional.

In an embodiment, the amounts of an SDSAS and amino acid for the pretreatment step ranges as follows:

TABLE 4

| | Glycine (μmol/mL) mM | | HCl (μmol/mL) mM | |
|---|---|---|---|---|
| | low | high | low | high |
| Pretreatment | 43 | 473 | 43 | 129 |
| Formulated plasma | 6.8 | 75.1 | 6.8 | 20.5 |
| Rehydrated plasma | 10 | 110 | 10 | 30 |

Proteins and their functionality are also protected in part because mass transfer occurs at lower temperatures, as described herein. As described, the drying rate is constant and as the liquid particle evaporates and loses moisture, the moisture transfers from the liquid plasma droplet to the drying gas, and the heat from the drying gas transfers to the plasma droplet making it into a dried particle. The plasma droplet enters the drying chamber essentially at room temperature and the temperature stays constant the majority of the evaporation period. See FIG. 43S. Once most all of the moisture leaves the particle, the temperature of the particle increases to equilibrate with the dryer chamber exit temperature of 65° C. During evaporation, the droplet is maintained at a lower temperature thereby protecting heat sensitive proteins such as vWF. See FIG. 43S. During the evaporation process, the temperature of the liquid droplet and the proteins therein experience a lower temperature, the thermodynamic wet bulb temperature, compared to the inlet drying gas temperature, thereby protecting the proteins. See FIG. 43R. Evaporation reduces protein temperature to near the thermodynamic wet bulb value and when the evaporation slows the particle temperature rises. See FIG. 43Sa.

The term "recovery" is defined herein as referring to the percentage of an analyte preserved after spray drying compared with the analyte in a sample of the same native plasma that may have been frozen (the same sample before spray drying); the analyte is analyzed on native plasma and/or rehydrated plasma at the same protein concentrations. The analyte can be any known plasma substance such as a plasma protein (e.g., vWF antigen or fibrinogen), as described herein, and can be measured by concentration or activity of the analyte (e.g., vWF:RCo activity), also as described herein. The amount of the analyte can be compared to its corresponding clinical reference range.

A spray dry stable acidic substance (SDSAS) as used herein is any substance such as an acid or acidic salt or other substance that effectuates pH and is physiologically suitable for addition to the plasma being spray dried and physiologically suitable to the subjects (human or otherwise) to which the reconstituted plasma is to be administered (transfused). The SDSAS remains sufficiently stable (e.g., does not materially evaporate or chemically breakdown) during the spray drying process. The SDSAS effectuates the pH adjustment described herein which results, for example, a maintained or an improved von Willebrand's factor recovery or functionality in the reconstituted plasma described herein, as compared to non-pretreated spray dried plasma. Specific examples of spray dry stable acidic substances include glycine HCl, HCl, citric acid, lactic acid, monosodium citrate and other SDSAS's described herein. Other SDSAS's may be known in the art or may be determinable by straightforward experimentation.

In an embodiment, pretreatment solution of the present invention used to obtain the spray dry formulation includes one or more SDSAS and one or more amino acids. Addition of the amino acid allows for protection of the plasma proteins during spray drying without lowering the pH of the pre-treatment solution. The addition of an amino acid increases the pH of the pretreatment solution, but surprisingly does not affect the pH of pretreated spray dried plasma or the rehydrated spray dried plasma. Further, in an embodiment, using an amino acid along with a SDSAS provides a spray dried plasma, once rehydrated, with reduced levels of C5a, an anaphylatoxin, or levels of C5a that are similar to never frozen plasma (NFP) or FDA approved apheresed plasma products. In an embodiment, complement activation is associated with inflammation and should be kept low within a clinically acceptable range. In particular, the pH of the pretreatment solution is in a range between about 2.0 and about 4.0 (e.g., 2.0, 2.2, 2.4, 2.6, 2.8, 3.0, 3.2, 3.4, 3.6, 3.8, 4.0) and when combined with plasma results in a pretreated plasma having a pH of between about 6.0 and about 6.6 (e.g., 6.0, 6.1, 6.2, 6.3, 6.4, 6.5, 6.6), and once the previously spray dried plasma is reconstituted, results in a reconstituted plasma having a pH of between about 6.5 to about 7.8 (e.g., 6.5, 6.6, 6.7, 6.8, 6.9, 7.0, 7.1, 7.2, 7.3, 7.4, 7.5, 7.6, 7.8). The total concentration of the one or more amino acid(s) in the reconstituted plasma is present in an amount between about 1 mM and about 150 mM. Examples of amino acids that can be combined with the SDSAS for the pretreatment solution include glycine, alanine, asparagine, glutamine, isoleucine, leucine, methionine, phenylalanine, proline, serine, threonine, tryptophan, tyrosine, and valine. In a particular embodiment, glycine is an amino acid added to the SDSAS composition.

Accordingly, spray drying formulation, i.e., treatment of feed plasma prior to or contemporaneously with spray drying, preserves and allows recovery or functionality of active clotting factors of rehydrated plasma that has undergone the spray drying process as well as long term stability during storage after drying. As further discussed below, these improvements to certain embodiments of spray drying of blood plasma involving formulation with a SDSAS and/or an amino acid, also improve the ease and lower the cost of rehydration of the plasma product by allowing the spray dried plasma to be rehydrated with sterile water (e.g., water for injection: WFI or sterile water for injection: SWFI). The spray dried plasma of the present invention may be reconstituted with sterile water for injection without the need for a buffered rehydration solution or treatment or storage with CO2 or other treatment to control the pH of the reconstituted plasma.

The spray dried plasma of the present invention, in an embodiment, has improved functionality or recovery of active plasma proteins, long term stability of plasma proteins and a reduction in anaphylatoxins. In an embodiment, the method to obtain the dried plasma of the present invention includes combining donor plasma with a pretreatment solution having a SDSAS and an amino acid, and a spray drying system. The invention further contemplates adjusting the pH of the donor plasma with the SDSAS by bringing the concentration of the SDSAS to about 1 mM to about 50 mM, which lowers the pH of the plasma to about 5.0 to about 6.5 to create formulated plasma. In another embodiment, the invention further contemplates adjusting the pH of the plasma to be spray dried with a pretreatment solution having a SDSAS and an amino acid by bringing the concentration of the SDSAS in the formulated plasma to about 1 mM to about 50 mM and the amino acid compound to about 1 mM and about 150 mM, which lowers the pH of the plasma to about 6.0 to about 6.6 to create formulated plasma.

In an embodiment, to obtain the dried plasma of the present invention, the methods include methods for producing spray dried plasma by combining plasma with a pretreatment solution, wherein the pretreatment solution comprises an amino acid (e.g., glycine) in an amount ranging between about 10 μmole/mL of plasma and about 110 μmole/mL of rehydrated plasma (e.g., about 10, 20, 30, 40, 50, 60, 70, 80. 90. 100 110 μmole/mL of plasma), and SDSAS (e.g., hydrochloric acid (HCl)) in an amount ranging between about 10 μmole/mL of plasma and about 30 μmole/mL of rehydrated plasma (e.g., about 10, 15, 20, 25, and 30 μmole/mL of plasma), to thereby obtain formulated plasma. The method also includes drying the formulated plasma with a spray drying system to create spray dried formulated plasma, as described herein. In an embodiment, the pretreatment solution has glycine in an amount of about 84 μmole/mL of plasma and HCl in an amount of about 20 μmole/mL of plasma.

The pretreatment solution, in an embodiment, has glycine in an amount ranging between about 15 mmol and about 30 mmol (e.g., about 15, 20, 25, and 30 mmol) or between about 43 μmol/mL and about 473 μmol/mL, and HCl in an amount ranging between about 3 mmol and about 7 mmol (e.g., about 3, 4, 5, 6, and 7 mmol) or between about 43 μmol/mL and 129 μmol/mL, to thereby obtain formulated plasma; and drying the formulated plasma with a spray drying system to create spray dried formulated plasma. In a certain embodiment, the pretreatment solution has glycine in an amount of about 22 mmol and HCl in an amount of about 5.3 mmol.

After drying the formulated plasma with the spray drying system to create spray dried formulated plasma, the spray dried formulated plasma had a recovery of functional von Willebrand factor (vWF) of at least 10 to at least 100 percentage points greater than the recovery of functional von Willebrand factor obtained from an otherwise identical spray dried plasma that has not undergone acid formulation with the pretreatment solution of the present invention. In another embodiment, the spray dried formulated plasma has a recovery of functional von Willebrand factor (vWF) that are similar to or within about 20% (e.g., about 15%, 10%, 5%) of never frozen plasma or FDA approved plasma products to fresh frozen plasma. The SDSAS may be selected from any known in the art, however, glycine HCl, HCl, citric acid and lactic acid are preferred substances for use in the present invention. When adding an amino acid to the SDSAS to form the pretreatment solution, in an embodiment, glycine is a preferred substance of the present invention (e.g., HCl/glycine or citric acid/glycine combinations). The physiologically compatible pretreatment solution is added to the plasma before spray drying and preferably shortly before spray drying or contemporaneously with spray drying. Additionally, the pH of the plasma may be determined before the addition of a SDSAS and an amino acid to the plasma to determine an appropriate amount of acid to add. In an embodiment, about 7.4 mM of citric acid is added to the CPD plasma or WB plasma. In an embodiment, the pH of the formulated plasma is about 5.5 to about 6.5. The present invention further contemplates that the recovery of functional vWF may be from about 10 to about 100 percentage points to about 40 percentage points (e.g., about 10, 15, 20, 25, 30, 35, 40, 50, 60, 70, 80, 90, 100 percentage points) greater than the recovery of functional von Willebrand factor obtained from an otherwise identical spray dried plasma that has not undergone pretreatment with a SDSAS and an amino acid. In an embodiment, the data show that levels of Ristocetin Cofactor (vWF:RCo) were non-existent or undetectable when plasma is spray dried without pretreatment. See FIGS. 17-19. In this embodiment, Ristocetin Cofactor (vWF:RCo) of pretreated spray dried plasma was 2×, 3×, 4×, 5× or greater, as compared to non-pretreated spray dried plasma.

It has been discovered that desirable C5a levels result from a pretreatment solution having an SDSAS and an amino acid addition, and optionally rapid mixture/agitation of the pretreatment components. In an embodiment, desirable C5a levels are those that are similar to C5a levels in NFP or an FDA approved apheresis plasma product. In an embodiment C5a levels are reduced, as compared to C5a levels from rehydrated plasma that underwent pretreatment only with a SDSAS, and optional rapid mixture/agitation of the pretreatment components. In particular, levels of C5a for reconstituted plasma resulting from the pretreatment solution of the present invention can be between about 0.1 ng/mL to about 74 ng/mL and in particular between 20 ng/ml and 70 ng/ml (e.g., about 30 ng/ml). C5a levels are reduced when treated with a pretreatment solution having at least one SDSAS and at least one amino acid, as compared to plasma subjected to a pretreatment solution having only an SDSAS. In an embodiment, the C5a levels are reduced by about 20% or less (e.g., 20%, 15%, 10%, 5%, 1%), as compared to plasma subjected to the pretreatment solution of the present invention with acid alone. In another embodiment, C5a levels are about the same as that of never frozen plasma, or within about 20% or less (e.g., 20%, 15%, 10%, 5%, 1%) of C5a in never frozen plasma or approved FDA apheresis plasma products.

The present invention contemplates a reconstituted spray dried plasma product for human transfusion (administration), the reconstituted spray dried plasma product having been reconstituted with, for example, sterile water for injection and the reconstituted spray dried plasma product having a pH of about 6.5 to about 7.8. The reconstituted plasma of the present invention has functional von Willebrand factor of greater than 5 percentage points as compared to the recovery of functional von Willebrand factor obtained from an otherwise identical spray dried plasma that has not undergone formulation with a SDSAS and/or an amino acid; or about 5 percentage points to about 40 percentage points (e.g., about 25 percentage points to about 35 percentage points) greater than the recovery of functional von Willebrand factor obtained from an otherwise identical spray dried plasma that has not undergone pretreatment with a SDSAS and an amino acid. Additionally, the present invention relates to reconstituted spray dried plasma having levels of C5a between about 0.1 ng/mL to about 74 ng/ml and in particular between 20 ng/ml and 40 ng/ml (e.g., about 30 ng/ml). In an embodiment, the present invention pertains to reconstituted spray dried plasma pretreated with an SDSAS and an amino acid have levels the C5a levels that are reduced e.g., by about 20% or less (e.g., 20%, 15%, 10%, 5%, 1%), as compared to plasma subjected to the pretreatment solution having an SDSAS. In another embodiment, C5a levels of reconstituted plasma of the present invention are about that approved FDA plasma products.

Autologous Uses of the Dried Plasma Unit of the Present Invention

The dried plasma of the present invention can be from a third-party donor or from the intended recipient. The latter is known as autologous plasma. Autologous refers to plasma taken from and provided to the same individual. Autologous spray dried plasma is desirable because it is compatible with recipient's plasma, e.g., there is no need to be ABO/Rh type matched before use, and it is unlikely to carry pathogens or immunogens allergenic to the recipient.

The autologous use of spray dried plasma of the present invention is characterized by at least two major components—the dried plasma unit and a reconstitution fluid. In an embodiment, the reconstitution solution is sterile water (SWFI) and the resultant reconstituted plasma has a near physiologic pH. In an embodiment, the sterile water comes as a premeasured, standard amount in a pouch.

In an embodiment, an intended recipient who may be at increased risk for a plasma transfusion (e.g., soldier, policeman, fire fighter, adventurer) can provide/donate their own plasma and one can dry the plasma using the methods described herein to obtain a dried plasma unit, having the one or more of the characteristics described herein. One or more dried plasma units dried from plasma provided by the intended recipient can be carried by or on behalf of the intended recipient so that it is readily available for their use. In this embodiment, autologous uses are encompassed by the present invention because the dried plasma units are light weight, whose packaging is rugged, and storable in various temperatures (including room temperature and/or warmer temperatures). When the intended recipient is in need of a plasma transfusion, a health care provider (e.g., doctor, nurse, first responder) carries the reconstitution solution (e.g., SWFI) and can reconstitute the intended recipient's own dried plasma for emergency transfusion. In an emergency, instant plasma with its trove of clotting factors would be available to the bleeding recipient. Early delivery of much needed plasma in a trauma situation increases the likelihood of a favorable result.

In an embodiment, the reconstitution solution (e.g. SWFI) can be carried by either the health care provider or the intended recipient. However, in situations like a battlefield, it is preferable for the health care provider to carry the reconstitution solution because it tends to be relatively heavy and SWFI is readily available to health care providers. The advantage of an autologous dried plasma unit is the elimination of compatibility issues and reduction in infectious transmission. Autologous dried plasma does not need to undergo ABO Rh matching and reduces infection transmission by a non-autologous or potentially allogeneic donor.

The manufacturing system for the dried plasma of the present invention is relatively compact and can be deployed in a very wide variety of environments. The manufacturing process for the spray dried plasma of the present invention is automated and easy to use by a person with minimal education and straight forward training.

Accordingly, the steps of providing an autologous dried plasma unit include the step of providing liquid plasma by the intended recipient (which can be obtained using methods known in the art and/or those described herein) and drying the intended recipient's liquid plasma using the spray drying system described herein. Finally, the method includes the step of reconstituting the recipient-provided dried plasma unit and, when in need, transfusing the recipient-provided reconstituted dried plasma in the recipient. The recipient provided dried plasma unit can be reconstituted by a health care provider or other qualified person.

This autologous dried plasma system can readily be adapted to other situations or available for use by any person that wants their own plasma nearby and readily available for future use. Other situations in which autologous dried plasma can be used include those who are residents of rural areas and are far from sources of plasma, or those that live anywhere but prefer to have their own plasma transfused into them in the case of an emergency. Intended recipients can store their own dried plasma units in the home, in safe rooms, vehicles, or with the health care providers, and the local health care providers can carry the reconstitution solution. In accordance with the storage data herein, such dried plasma units for autologous use can be replenished every 1-4 years. Wide deployment of the dried plasma unit of the present invention can be done as a prophylactic measure against death or permanent injury from bleeding trauma or disease.

A recipient can be human or mammal.

Pretreatment Formulation and Process-Detailed Description

Embodiments of the present disclosure are directed to methods and compositions relating to a spray dried liquid sample. In certain embodiments, the liquid sample is plasma obtained from a blood donor. In a preferred embodiment, the blood donor is human. However, it may be understood that the disclosed embodiments may be employed to spray dry any biological mixture of solid particles and/or molecules in a continuous liquid medium, including, but not limited to, colloids, suspensions and sols (a colloidal suspension of very small particles).

The control of reconstituted dried plasma pH by the invention described herein which utilizes spray drying is an improvement over the reported pH control of reconstituted plasma made by freeze drying or lyophilization. Excessively high or low pH of blood plasma is associated with increased morbidity or mortality including pH above 7.8 ("alkalosis"). In this respect the present invention is superior to the freeze-dried products and processes of the prior art. Drying processes result in loss of $CO_2$ which causes the pH of the dried product to increase unless controlled in some manner. The present invention does that with no extra processing steps, reconstitution with sterile water only and has been approved for clinical trials by the United States Food and Drug Administration. Reconstitution with sterile water only is highly desirable in dried plasma products. In the event of loss or damage to the pre-measured, pre-packaged sterile water for reconstitution provided as part of a kit for emergency, ER, OR or other urgent use of any dried plasma, a measured amount of readily available sterile water can be used for reconstitution.

"Human lyophilized plasma is . . . alkalotic with a pH near 8, . . . " Zaza M, Kalkwarf K J, Holcomb J B. Dried Plasma. Damage Control Resuscitation. 2019; 145-162. Published 2019 May 6. doi: 10.1007/978-3-030-20820-2_8, page 8, second full paragraph. Zaza, et al excuse this by saying "however, [lyophilized plasma] is well tolerated clinically in humans", citing solely the 2013 article of Saillol, et al, "The evolving role of lyophilized plasma in remote damage control resuscitation in the French Armed Forces Health Service." *Transfusion.* 2013; 53: 65S-71S. The Saillol article concerns the French Army's lyophilized dried plasma known as French LYophilized Plasma (FLYP). Saillol, et al admit that "the pH upon reconstitution [of FLYP"] is close to 8." Id. at 67S. The Saillol, et al. report is limited to combat situations of severe bleeding in which the protocol included tranexamic acid, FLYP with red blood cells in a 1:1 ratio and other actions to control the patient's blood pH. *Id.* at 66S. Salliol, et al, admit that "further research is needed to determine specific indications for FLYP in the therapeutic management of civilian patients with severe hemorrhage." *Id.* at Abstract last sentence, see p. 65S. In contrast, the lower, well-controlled pH of the present invention is expected to be suitable for use in all situations where plasma transfusion is indicated in any amount under any circumstance.

The pH of reconstituted dried plasma made by the freeze-drying process of Terumo-BCT has been reported to be high at 7.66-7.94. 7.94 is very close to 8.0. The so-called French Lyophilized Plasma (FLYP) plasma product made by the French Army is reported to also have a reconstituted pH "close to 8.0." See Flaumenhaft, et al, Retention of Coagulation Factors and Storage of Freeze-Dried Plasma, *Military Med*., Vol. 6, January/February Supplement, pp. 400-407, 403 (2021). "TFDP [Terumo Freeze Dried Plasma] units exhibited a significant elevation in pH after freeze drying, as expected based on other lyophilized plasma products . . . " Sheffield W P, et al., "Retention of hemostatic and immunological properties of frozen plasma and COVID-19 convalescent apheresis fresh-frozen plasma produced and freeze-dried in Canada" *Transfusion.* 2021 Dec. 14. doi: 10.1111/trf.16772. Epub ahead of print. PMID: 34907536.). There is no report that the Terumo freeze-dried plasma product has been approved for clinical trials in the United States or elsewhere. The FLYP plasma has not been the subject of clinical trials in the United States. The authors of Flaumenhaft dismiss the high pH of the Terumo-BCT reconstituted freeze-dried plasma material as "within the Terumo-BCT required range of 7.0-8.0" and "aligned" with the FLYP plasma pH of close to 8.0. In contrast, the pH of the spray dried plasma product of the present invention does not exceed 7.8 and in general has a pH range closer to physiological pH.

The reported pH of the reconstituted dried plasma made by the freeze-drying process of Teleflex has not been reported. However, it is evidently higher (more alkaline) than physiological pH at the end of the freeze-drying process such that, in a clinical trial investigator's contract with United States Food and Drug Administration, Teleflex described its REPLAS™ freeze dried plasma as requiring extra processing and equipment to reduce the pH of the Teleflex product when reconstituted. In particular, an acidic reconstitution fluid must be used to restore pH of the reconstituted [lyophilized plasma] to a physiological pH before infusion. Van, et al, J Trauma Injury, Infection and Critical Car Vol 71 No 1, p 22 (July 2011). In fact, according to Van, preliminary studies in our laboratory revealed that LP reconstituted without an acid has a pH of ~9 and its infusion resulted in rapid death. ID. at 20. The REPLAS™ freeze dried process is described as including the following steps: "vacuum chamber is broken with medical grade carbon dioxide (CO2) gas to correct for loss of dissolved CO2 from the starting plasma material during the freeze-drying process" and that "in addition, REPLAS™ is packaged in an outer foil pouch that is flushed with a fixed amount of CO2 gas, which results in a near neutral pH in the reconstituted . . . product." Jose A. Cancelas, Investigator's Agreement A Phase 1, Single-Center, Partial Doubleblind, Randomized, Controlled (Versus Fresh Frozen Plasma [Ffp] In Cohort 3 Only) Clinical Study Of The Safety Of Ascending Doses Of Autologous Freeze Dried Plasma (Fdp) In Healthy Volunteers, Apr. 19, 2018; pp-24.25. Date of download Dec. 6, 2021 https://clinicaltrials.gov/ProvidedDocs/26/NCT02930226/Prot_000.pdf The system of spray drying plasma of the present invention does not require elaborate, expensive use of CO2 gas treatment of the dried plasma or CO2 storage of the dried plasma to control pH in the reconstituted plasma product or the equipment needed to effect these extra, pH correction processes.

Plasma

Plasma is the fluid that remains after blood has been centrifuged (for example) to remove cellular materials such as red blood cells, white blood cells and platelets. Plasma is generally yellow-colored and clear to opaque. It contains the dissolved constituents of the blood such as proteins (6-8%; e.g., serum albumins, globulins, fibrinogen, etc.), glucose, clotting factors (clotting proteins), electrolytes ($Na^+$, $Ca^{2+}$, $Mg^{2+}$, $HCO_3$-, Cl, etc.), hormones, etc. Whole blood (WB) plasma is plasma isolated from whole blood with no added agents except anticoagulant(s). Citrate phosphate dextrose (CPD) plasma, as the name indicates, contains citrate, sodium phosphate and a sugar, usually dextrose, which are added as anticoagulants. The level of citrate in CPD plasma, derived from whole blood, is about 20-30 mM. Thus, the final citrate concentration in the whole blood derived CPD plasma formulated with 7.4 mM citric acid will be about 27.4-37.4 mM.

The plasma of the present invention may be dried after pooling or unit-by-unit. Pooling of multiple plasma units has some benefits. For example, any shortfall in factor recovery on an equal-volume basis can be made up by adding volume from the pool to the finished product. There are negative features as well. Making up volume from the pool to improve factor recovery is expensive. Importantly, pooled plasma must be constantly tested for pathogens as any pathogens entering the pool from, for example, a single donor, runs the risk of harming hundreds or thousands of patients if not detected. Even if detected, pathogen contamination of pooled plasma would render the whole pool valueless. Testing can be obviated by pathogen inactivation of the plasma by irradiation or chemically such as solvent detergent treatment; however, each such treatment adds cost and complexity to pooled plasma processing. In any event, pooled plasma processing is generally unsuitable to the blood centers and generally only really suitable to an industrial, mass production environment.

Conversely, unit-by-unit (unit) collection and processing is well-suited to the blood center environment and eliminates the risk of pooled plasma pathogen contamination by allowing for pre-processing testing for pathogens and tracking of the unit to ensure that each unit leaves the blood center site pathogen free. The inventors have discovered that efficient and effective preservation and recovery of functional clotting factors is the standard by which successful unit blood plasma processing should be measured. Such efficiency is also very helpful in the pooled plasma environment as well.

Clotting Factors

There are many blood plasma factors associated with clotting. The methods and compositions of the present invention include recovering amounts of functional fibrinogen, Factor V, Factor VII, Factor IX and vWF from rehydrated plasma that has undergone the spray drying process. Such blood plasma factors are important in-patient treatment especially after trauma injuries to promote clotting of wounds. Thus, rapid administration of plasma is an important factor contributing to positive clinical outcomes. The spray dried plasma of the present invention can be readily reconstituted in a few minutes at the location of the trauma event without moving the patient and without time delay. Further, the spray dried plasma of the present invention has high levels of functional proteins that are stable for extended periods of time without freezing.

Functional vWF has generally been difficult to recover and has become one indicator for preservation of all factors. The present invention includes recovering amounts of functional vWF, in an amount in rehydrated spray dried plasma that is at least about 5 percentage points or greater (e.g., about 5, 10, 15, 20, 25, 30, 35, 40, 45, 50, 60 or greater percentage points) as compared to amounts of functional vWF of rehydrated spray dried plasma that do not undergo the pre-treatment steps of the present invention. The present invention includes recovering amounts of functional vWF, in an amount in rehydrated spray dried plasma that is at about 5 percentage points to about 40 percentage points or about 10 percentage points to about 35 percentage points higher as compared to amounts of functional vWF of rehydrated spray dried plasma that do not undergo the pretreatment step of the present invention. vWF activity is typically assayed with an assay called the von Willebrand factor: Ristocetin cofactor (vWF:RCo) assay, as is known to those of skill in the art. The vWF:RCo assay measures the ability of a patient's plasma to agglutinate platelets in the presence of the antibiotic Ristocetin. The rate of Ristocetin induced agglutination is related to the concentration and functional activity of the plasma von Willebrand factor. Another assay, the vWF antigen assay, measures the amount of vWF protein present in a sample. Yet another assay to determine if functional clotting plasma proteins exist in reconstituted previously spray dried plasma is to perform a Bioflux study. See Example 9 and 10.

In an embodiment, one or both von Willebrand Factor Antigen (% or IU/dL), von Willebrand Factor Ristocetin Cofactor (% or IU/dL) are measured before and after spray drying to determine the recovery of vWF. In an embodiment, the acceptable or clinical range for von Willebrand Factor Ristocetin Cofactor (VWF:RCo) is between about 50 and about 200 IU/dL, and von Willebrand Factor Antigen (VWF:Ag) value is between about 50 and 200 IU/dL. In an embodiment, the present invention includes determining amounts of vWF using a VWF:RCo assay or a VWF:Ag assay in rehydrated spray dried plasma that is at least about 5 percentage points or greater (e.g., about 5, 10, 15, 20, 25 or greater percentage points) as compared to those amounts in rehydrated spray dried plasma that do not undergo the pre-treatment steps of the present invention.

Pretreatment Solution Having One or More Spray Dry Stable Acidic Substances (SDSAS) and One or More Amino Acids The present invention contemplates the use of a pretreatment solution that includes one or more physiologically compatible spray dry stable acidic substances (SDSAS) combined with one or more amino acids, as a formulation agent for plasma prior to being spray dried. As used herein, the phrase "SDSAS and amino acid" and the like refers to a pretreatment solution that has at least one SDSAS and/or at least one amino acid. Similarly, the use of "the SDSAS" or "an amino acid" refers to one or more SDSAS or one or more amino acids, respectively. The phrase "formulated plasma" or "pretreated plasma" or "PreT" refers to the mixture of the pretreatment solution (e.g., at least one SDSAS and/or at least one amino acid) and plasma prior to spray drying. Dried formulated plasma refers to spray dried plasma that was pretreated with the pretreatment solution.

While the present invention is not limited by theory, it is presumed by the inventors that the SDSAS of the present invention (e.g., citric acid, lactic acid, hydrochloric acid, etc.) exerts its effects because it prevents or alleviates the rising of the pH of the plasma during the spray drying process. Addition of an amino acid to the SDSAS still allows the pre-treatment solution to have an acidic pH, but not be so low as to harm the plasma proteins. Non-limiting examples of suitable SDSAS are hydrochloride (HCl), citric acid and lactic acid. When an SDSAS is combined with an amino acid, an example includes glycine HCl. The SDSAS (e.g., (HCl, citric acid or lactic acid) and amino acid (e.g., glycine) can be added to the plasma in a combined form (e.g., glycine HCl) or as separate compounds (e.g., glycine and HCl). Other non-limiting examples of suitable acids are ascorbic acid and gluconic acid. Because $CO_2$ is lost from plasma during spray drying, the reaction generating bicarbonate and $H^+$ from $CO_2$ and $H_2O$ is shifted away from $H^+$, thereby increasing the pH (i.e., Chatelier's principle). Human blood/plasma contains a buffer system comprised of carbonic acid ($H_2CO_3$) and bicarbonate anion ($HCO_3$-), which is important for maintaining blood pH between 7.35 and 7.45, as a value higher than 7.8 can lead to death. In this buffer, hydronium ($H_3O^+$) and bicarbonate anion are in equilibrium with carbonic acid (Equation 1). Furthermore, the carbonic acid in the first equilibrium can decompose into $CO_2$ gas and water, resulting in a second equilibrium system between carbonic acid and water (Equation 2).

In summation, the blood buffer is:

$$H_2CO_3 + H_2O \rightleftharpoons H_3O^+ + HCO_3^- \quad \text{(Equation 1)}$$

With the following simultaneous equilibrium:

$$H_2CO_3 \rightleftharpoons H_2O + CO_2 \quad \text{(Equation 2)}$$

Spray drying drives off $CO_2$ leading to the reduction of the levels of $H_2CO_3$ and $H_3O^+$, and thereby drives up the pH level of the drying plasma. Consequently, the pretreatment solution of the present invention helps to safely lowers the pH of the formulated plasma prior to spray drying to result in a spray dried plasma, that when reconstituted with Sterile Water for Injection, has a resulting physiologically compatible pH.

Glycine addition helps offset this change. Amino acid addition prevents the pH from going too low. Therefore, in an embodiment, the plasma is formulated with a pretreatment having the SDSAS and an amino acid. Because of the formulation/pretreatment step, vWF activity loss is reduced and/or the amount of undenatured vWF is increased, as compared to spray dried plasma not subjected to the formulation steps of the present invention. The SDSAS is present in the pretreatment solution in an amount between about 1 mM to about 50 mM, which lowers the pH of the formulated plasma to about 5.5 to about 6.5 or to about 7.2 to create formulated plasma. When the amino acid such as glycine is also present along with the SDSAS in the pretreatment solution in an amount between about 1 mM to about 150 mM, the pH of the formulated plasma is about 6.0 to about 6.6.

Because the physiologically compatible SDSAS and amino acid of the present invention is included in this manner, the inventors further determined that the rehydration step can be performed by water alone (e.g., SWFI). Alternatively, sodium phosphate or other agents can optionally be added to the rehydration solution. Further, any other suitable rehydration fluid as can be determined by one of ordinary skill in the art may be used.

From experiments conducted by the inventors with spray drying, it has been discovered that the von Willebrand factor activity level in plasma dried by spray drying is affected, in part, by the shear forces generated during the aerosolization process (see, Examples, below) and an increase in the pH of the plasma. The present invention shows that the utilization of a step wherein the plasma is formulated with at least one SDSAS and at least one amino acid greatly improves the recovery and stability of active vWF over conditions where the SDSAS and the amino acid is not used as formulation agents.

A SDSAS is a substance which does not evaporate easily at room temperature at atmospheric pressure. Typically, the boiling point of the SDSAS will be greater than about 150° C. at atmospheric pressure. In addition to glycine HCl, non-volatile acids that are suitable of use as the SDSAS of the present invention include phosphorus-containing acids such as, for example, ortho-phosphoric acid, pyrophosphoric acid, meta-phosphoric acid, poly phosphoric acid, alkyl- and aryl-substituted phosphonic and phosphinic acids, phosphorous acid, and the like, and mixtures thereof. Other non-volatile acids suitable for use as the SDSAS of the present invention include, but are not limited to ascorbic acid, citric acid, lactic acid, gluconic acid, oxalic acid, halogenated acetic acids, arene sulfonic acids, molybdic acid, phosphotungstic acid, tungstic acid, chromic acid, sulfamic acid, and the like.

In an embodiment, the pre-treatment solution of the present invention can include one or more SDSAS and one or more amino acids. Addition of the amino acid to the SDSAS allows for protection of the plasma proteins without allowing the pH to go too low and cause protein damage and other deleterious effects such as complement activation. The addition of an amino acid increases the pH of the pretreatment solution, but surprisingly does not affect the pH of rehydrated spray dried plasma (ODP). In particular, the pH of the pretreatment solution is in a range between about 2.0 and about 4.0 and results in a formulated plasma (e.g., prior to spray drying) having a pH of between about 6.0 and about 6.6, results in a rehydrated plasma having a pH of between about 6.5 to about 7.8. In an embodiment, the pre-treatment solution of the present invention includes the SDSAS and at least one (e.g., one or more) amino acids. The total concentration of the amino acid(s) present in the pretreatment solution is an amount between about 1 mM and about 150 mM. Examples of amino acids that can be added to the SDSAS of the pretreatment solution include alanine, asparagine, glutamine, glycine, isoleucine, leucine, methionine, phenylalanine, proline, serine, threonine, tryptophan, tyrosine, and valine. In a particular embodiment, glycine is added to the SDSAS composition as shown in the examples. The addition of an amino acid increases the pH of the pretreatment solution, but surprisingly does not affect the pH of rehydrated spray dried plasma (ODP). See Example 17. Even more surprisingly, addition of an amino acid mitigates C5a elevation. See Example 16. These amino acids have at least two pKa values, as follows:

TABLE 5

| Amino acid | $pKa_1$ | $pKa_2$ | $pKa_3$ | pI |
|---|---|---|---|---|
| Glycine | 2.34 | 9.60 | — | 5.97 |
| Alanine | 2.34 | 9.69 | — | 6.00 |
| Valine | 2.32 | 9.62 | — | 5.96 |
| Leucine | 2.36 | 9.60 | — | 5.98 |
| Isoleucine | 2.36 | 9.60 | — | 6.02 |
| Methionine | 2.28 | 9.21 | — | 5.74 |
| Proline | 1.99 | 10.60 | — | 6.30 |
| Phenylalanine | 1.83 | 9.13 | — | 5.48 |
| Tryptophan | 2.83 | 9.39 | — | 5.89 |
| Asparagine | 2.02 | 8.80 | — | 5.41 |
| Glutamine | 2.17 | 9.13 | — | 5.65 |

TABLE 5-continued

| Amino acid | $pKa_1$ | $pKa_2$ | $pKa_3$ | pI |
|---|---|---|---|---|
| Serine | 2.21 | 9.15 | — | 5.68 |
| Threonine | 2.09 | 9.10 | — | 5.60 |
| Tyrosine | 2.20 | 9.11 | — | 5.66 |

SDSAS useful in the process of the invention are capable of replacing (or compensating for) the volatile acid, i.e. $CO_2$ that escapes from the plasma during spray drying. As indicated above, examples or suitable acids include, but are not limited to, glycine HCl, ascorbic acid, citric acid, gluconic acid, and lactic acid.

A volatile acid as defined herein has a pKa less than about 3 and a boiling point less than about 150° C. at atmospheric pressure. Typically, the pKa of the volatile acid is within the range of about 1 to about 15. Non-limiting examples of volatile acids are hydrogen chloride, hydrogen bromide, hydrogen iodide, hydrogen fluoride, acetic acid, formic acid, hydrogen sulfide, hydrogen selenide, sulfur dioxide, fluorosulfonic acid, methane sulfonic acid, trifluoroacetic acid, trifluoromethanesulfonic acid, and the like.

A volatile strong acid can be fixed with an amino acid or like to render it non-volatile, making it easier to use. For example, volatile hydrogen chloride can be converted to glycine hydrogen chloride (glycine HCl, glycine hydrochloride). To distinguish this from adding an amino acid to the pretreatment solution, this describes how an SDSAS is made. The pretreatment solution includes the addition of an amino acid that is not bound to an acid with an already conjugated and stable SDSAS. Alternatively, glycine and HCL can be added to the pretreatment solution in such amounts to form the SDAS (e.g., glycine HCL) and free amino acid (e.g., glycine) in solution. Since there is a 1:1 relationship between glycine and HCl, one can add more glycine than HCl to obtain a solution with free glycine and glycine HCl. In an embodiment of the present invention, HCl and glycine are added to a solvent, such as SWFI, to create the pretreatment solution such that the final concentration in the formulated plasma is about 16.8 mM HCl and about 69.6 mM glycine. In other words, in an embodiment of the present invention, 5.2 mM HCl and 21.5 mM glycine is added to 50 mL of solvent, such as SWFI, to create the pretreatment solution. The present invention includes adding the following to a solvent, such as SWFI, to create a pretreatment solution: between about 3.0 to about 7.0 mmol (e.g., 3.0, 4.0, 4.5, 5.0, 5.5, 6.0, 6.5, and 7.0) mmole HCl and about 15 mmole and about 30 mmole glycine (e.g., about 15, 17, 20, 22, 25, 27, 30 mmoles glycine) in 50 mL of solvent to obtain 260 of formulated plasma. In yet other words, glycine in an amount of about 440 mM, and HCl in an amount of about 106 mM is present in the pretreatment solution. In an embodiment between about 290 mM to about 570 mM (e.g., about 290, 300, 350, 400, 450, 500, 550, and 570) glycine and about 70 mM to about 140 mM (e.g., 70, 80, 90, 100, 110, 120, 130, 140 mM) HCl is present in the pretreatment solution.

In this case, 16.8 mM glycine HCl and 86.4 (69.6-16.8) glycine are present in the formulated plasma of the present invention, which is within the range of a SDSAS of about 1 mM to about 50 mM and amino acid of about 1 mM and about 150 mM (e.g., 50 mM to about 100 mM). The following table shows how the calculations above were obtained.

TABLE 6

| Experiment #1 formulation - Glycine, 1.0M and glycine HCl, 0.4M; Experiment #2-440 mM glycine and 106 mM hydrochloric acid | | M = mmole/mL = mole/L | Pre-T Sol (mL) | # of mmoles in Pretreatment solution | Final con. In Formulated plasma (mM) | Plasma (mL) |
|---|---|---|---|---|---|---|
| Experiment #1 (TR-0345) formulation (0.4M) | (Glycine) HCl | 0.4 | 13 | 5.2 | 20.0* | |
| Experiment #1 (TR-0345) formulation (1.0M) | Glycine | 1 | 13 | 13 | 50.0* | 247 |
| Experiment #1 (TR-0345) formulation (1.4M) | (total glycine) | 1.4 | 13 | 18.2 | 70.0* | 247 |
| Experiment #2 (106 mM) | HCl | 0.106 | 50 | 5.3 | 17.1* | 260 |
| Experiment #2 (440 mM) | Glycine | 0.44 | 50 | 22 | 71.0* | 260 |

*obtained by # of mmoles in the pretreatment solution divided by the total volume (add the volume of pretreatment solution and plasma)

In an embodiment, the pretreatment solution of the present invention can have a formulation ratio of 405 mM glycine to 98 mM HCl. This embodiment may be advantageously used to treat approximately 266 mL of plasma to be dried with 53 mL of pretreatment solution made from 1.61 g of glycine and 0.52 g of HCl 36.5 or the equivalent amounts. This formulation results in approximately 67 mM of glycine and approximately 16 mM HCL in the approximately 319 mL of formulated plasma before that plasma is spray dried.

A study of pooled, ABO matched, never frozen plasma (NFP) derived from whole blood treated with the citrate phosphate dextrose (CPD) anticoagulation regimen and pretreated with pretreatment solution of the present invention demonstrated that dilution of the pretreatment solution of the present invention by plasma to be dried by +20%, +10%, +5%, −5%, −10%, and −20% had no meaningful impact on the characteristics of the dried plasma when reconstituted and then assayed by a 25 assay panel. In particular, the impact of the pretreatment dilution range on the sensitive vWFRCo assay showed normalized percent recovery of vWF by the assay to be within the error range displayed by the control plasma. pH was also well controlled, ranging between 7.32 and 6.84 with the pH of the control plasma being 7.11.

These results demonstrate that the pretreatment solution of the present invention reliably permits the production of spray dried plasma which displays, after reconstitution, assay panel comparable results to that of NFP, FFP and PF24 and with assay characteristics essentially the same as NFP, FFP and PF24.

The pretreatment solution of the present invention can have a ratio by weight of glycine to HCl of between approximately 5 and 3. The formulated plasma which has been treated with the pretreatment solution of the present invention can have a ratio by mmol/ml of glycine to HCl of between approximately 5 and 3.

In an embodiment, the present invention involves adding a volatile acid and an amino acid as separate compounds (e.g., not as a salt) to create the solution. The volatile acid and amino acid should be added in amounts that results in a SDSAS of about 1 mM to about 50 mM and amino acid of about 1 mM and about 150 mM. In the case where there is a 1:1 relationship between the volatile acid and the amino acid, such as is the case with HCl and glycine, each are added in equal amounts ranging between about 1 mM to about 50 mM and additional amounts of amino acid is added to achieve the free amino acid concentration of about 1 mM and about 150 mM in solution. In other embodiments, a corrosive strong acid can be converted to an acidic salt for use in pretreating plasma prior to spray-drying. Examples include $NaHSO_4$ and $NaH_2PO_4$: namely the acidic salts of sulfuric acid.

In an embodiment, the pretreatment solution has glycine in an amount ranging between about 10 μmole/mL of plasma and about 110 μmole/mL of plasma (e.g., about 10, 20, 30, 40, 50, 60, 70, 80. 90. 100 110 μmole/mL of plasma), and hydrochloric acid (HCl) in an amount ranging between about 10 μmole/mL of plasma and about 30 μmole/mL of plasma (e.g., about 10, 15, 20, 25, and 30 μmole/mL of plasma), to thereby obtain formulated plasma. In an embodiment, the pretreatment solution has glycine in an amount of about 84 μmole/mL of plasma and HCl in an amount of about 20 μmole/mL of plasma.

In another embodiment, the pretreatment solution has an amount of glycine and an amount of HCl that forms a ratio that allows for free glycine to be present in the pretreatment solution, In one aspect, the ratio of glycine to HCl is between about 1.5 and about 8.0 (e.g., 1.5, 2.0, 2.5, 3.0, 3.5, 4.0, 4.5, 5.0, 5.5, 6.5, 7.0, 7.5, 8.0). In a certain embodiment the ratio of glycine to HCl is 4.15. In yet another embodiment, the ratio of glycine to HCl effects a pH of the pretreatment solution to be between about 2.0 and about 4.0, or results in a formulated plasma of step a) has a pH of about 6.0 to about 6.6. Once reconstituted with sterile water, the formulated plasma having the above-referenced ratio of glycine to HCl results in a pH of about 6.7 to about 7.8.

The present invention further includes a method of producing spray dried plasma by combining plasma with a pretreatment solution, wherein the pretreatment solution has glycine in an amount ranging between about 15 mmol and about 30 mmol (e.g., about 15, 20, 25, and 30 mmol), and HCl in an amount ranging between about 3 mmol and about 7 mmol (e.g., about 3, 4, 5, 6, and 7 mmol). In a certain embodiment, the pretreatment solution has glycine in an amount of about 22 mmol and HCl in an amount of about 5.3 mmol.

Non-volatile acids and acidic salts are collectively defined as and included as spray dry stable acidic substance (SDSAS's) in this invention. The pretreatment solution of the present invention includes, in an embodiment, the SDSAS and one or more amino acids.

In an embodiment, the SDSAS and/or one or more amino acids of the present invention is added to the plasma within about 30 minutes, about 20 minutes, about 15 minutes, about 10 minutes, about 5 minutes, about 1 minute or time zero (0 minutes) of spray drying the plasma. In an embodiment, the SDSAS of the present invention is added contemporaneously to the plasma as the plasma is being pumped into the spray drying apparatus. The term "contemporaneously"

shall be defined herein as meaning within about 60 seconds, about 50 seconds, about 40 seconds, about 30 seconds, about 20 seconds, about 10 seconds, about 5 seconds, about 1 second and about 0 seconds. With the addition of the amino acid to the SDSAS which increases the pH of the pretreatment solution, in an embodiment, the plasma formulation (e.g., pretreatment solution and plasma to be spray dried) may be able to be stored or allowed to sit for up to about 24 hours (e.g., 1, 5, 10, 15, 20, or 24 hours) before spray drying.

In an embodiment, the present invention includes mixing the pretreatment solution and the plasma to be spray dried using a technique called rapid mixing. The rapid mixing step is optional. One of the inventive discoveries includes that rapid or instant mixing of the pretreatment composition and the plasma. It was discovered that slowly mixing the pretreatment solution with the plasma allows localized contact or pockets of unmixed acid to contact the plasma proteins, which can harm these proteins and specifically increase C5a. In contrast, when rapidly mixing and/or agitating the pretreatment solution with the plasma, in an embodiment, amounts of C5a are similar that of fresh frozen plasma or other similar FDA approved products on the market. Rapid mixture and/or agitation allows for instant, thorough and rapid mixing of the pretreatment solution (e.g., having a SDSAS and one or more amino acids) and the plasma. See Examples 17 and 18. Rapid mixture is defined as adding a large volume of plasma to a relatively small volume of a pretreatment solution, prior to spray drying the plasma. In general, when adding a large volume to a much smaller volume (e.g., a volume that is between about 10 and about 30% (about 10, 15, 20, 25, 30%) of the large volume), the mixing of the two volumes results in a rapid and thorough mixture of the two volumes. In a preferred embodiment, 260 mL of plasma is added to 50 mL of the pretreatment solution. In an embodiment, once rapid/instant mixing occurs, the operator can gently invert the bag having both the pretreatment solution and the plasma a few times (e.g., 1-5 times) to further mix the two together. By contrast, with respect to mixing the pretreatment solution with plasma, when pouring a small volume of pretreatment solution into a large volume of plasma to be spray dried, it takes longer for the small volume to be well mixed into the larger volume and pockets of the small volume can form within the larger volume. During this time it was discovered that the localized contact or pockets of unmixed acid formed within the mixture caused an increase in the amount of C5a in the resulting reconstituted plasma. Agitation is defined as a constant shaking or movement of components (e.g., SDSAS, amino acid, and plasma) of a pretreatment solution. Rapid mixture or agitation results in a uniformly mixed plasma formulation with little or no localized contact or pockets of unmixed acid.

The present inventions relate to adding SDSAS and at least one amino acid to blood plasma to be spray dried in a time period prior to spray drying short enough to obtain a formulation with the desired pH ("plasma formulation") and to prevent denaturing or damage of certain plasma protein(s) such as von Willebrand's factor due to prolonged exposure to the low pH condition or prevent the increase of C5a. In an embodiment, keeping the time delay to 30 minutes or less between formulation of the plasma with SDSAS and spray drying, as described below, results in improved recovery of plasma proteins, including von Willebrand factor, without undesirable protein damage due to prolonged exposure to the low pH condition prior to spray drying.

The time period between pretreatment formulation and spray drying will depend on the pH/acidity of the plasma formulation created by the mixing of the SDSAS, an amino acid, and the plasma. In an embodiment, the time period between contacting the SDSAS and an amino acid, with the blood plasma and spray drying the plasma is in a range between about 0 seconds (e.g., at the time aerosolization occurs: time 0) and about 30 minutes. In an embodiment, to minimize protein denaturing, the time between adding of the pretreatment solution to the plasma and spray drying should be kept to minimum. The actual maximum time between formulation and spray drying is determined empirically. This close-in-time formulation at time 0 is referred to herein as "contemporaneous formulation."

There are a number of methods by which contemporaneous formulation may be carried out. In one embodiment a formulation station is provided in association with the spray dryer. In conjunction with the formulation station, the weight or volume of the pre-spray dried plasma is determined and an SDSAS and amino acid dose measured to obtain the desired pH of the plasma formulation. The dose may be introduced into the plasma by any convenient method including by injection through a port on the plasma bag. In an embodiment, the bag containing the plasma and the bag containing the pretreatment solution are sterilely connected by tube using a tube sealer that can sterilely heat seal two ends of a tube together. In such a case, the transfer of the plasma to the pretreatment bag can be done manually or with the use of a collection monitor or scale. Gravity can be used to assist the transfer by hanging the plasma bag higher than the pretreatment bag. A formulation station may be manually, semi-automatically or automatically operated. Naturally, the timing of the dosing should be controlled as described above. Timing control may be manual, semi-automatic or automatic.

In another embodiment, an appropriate dose of SDSAS and one or more amino acids is introduced into the plasma flow channel of the spray dryer prior to the spray drying head. The pretreatment solution introduction is controlled manually, semi-automatically or automatically to result in the desired plasma formulation.

In a further embodiment, an appropriate dose of the pretreatment solution (e.g., SDSAS and one or more amino acids) is introduced into the spray drying chamber sufficiently close to the spray drying nozzle so that the pretreatment solution and plasma are mixed together to form a plasma formulation before spray drying occurs in the spray drying chamber connected to the spray drying head. Pretreatment solution (e.g., SDSAS one or more amino acids) introduction is controlled manually, semi-automatically or automatically to result in the desired plasma formulation.

In yet another embodiment, the pretreatment solution is combined with the donor plasma using a sterile connection device and a scale, as further described herein.

C5a

G protein-coupled receptors are prevalent throughout the human body, comprising approximately 60% of known cellular receptor types, and mediate signal transduction across the cell membrane for a very wide range of endogenous ligands. They participate in a diverse array of physiological and pathophysiological processes, including, but not limited to those associated with cardiovascular, central and peripheral nervous system, reproductive, metabolic, digestive, immunological, inflammatory, and growth disorders, as well as other cell-regulatory and proliferative disorders. One of the most intensively studied G protein-coupled receptors are the complement (C) system of humans and other mammals that involves more than 20 components that participate in an orderly sequence of reactions resulting in complement activation. The blood complement system has a wide array of functions associated with a broad spectrum of host defense mechanisms including anti-microbial and anti-viral actions. Products derived from the activation of C components include non-self-recognition molecules C3b, C4b and C5b, as well as the anaphylatoxins C3a, C4a and C5a that influence a variety of cellular immune responses. These anaphylatoxins molecules are involved in pro-inflammatory actions, both acute and chronic inflammation, and its accompanying pain and tissue damage.

The data reveals the surprising result that the addition of an amount of glycine to an acid pretreatment solution increases the pH of the pretreatment solution, providing additional protection to plasma proteins and mitigating C5a elevation. The addition of appropriate level of glycine does not affect the ultimate pH of the rehydrated spray dried plasma (ODP).

Figure 28:
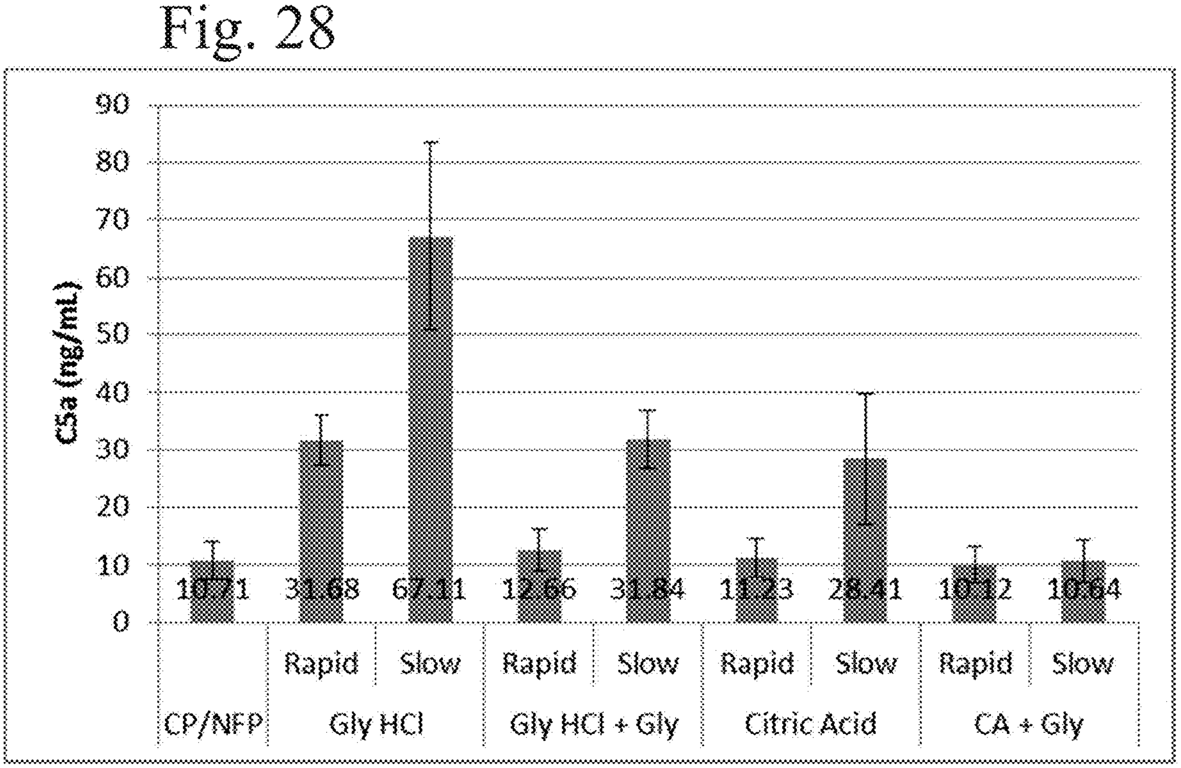
FIG. 28 is a bar graph showing C5a analysis of control plasma (CP)/Never Frozen Plasma (NFP) rapidly and slowly pretreated with 400 mM glycine HCl, 400 mM glycine HCl+1 M glycine, 148 mM citric acid, 148 mM citric acid+1 M glycine in tube (n=7) and Control Plasma/Never Frozen Plasma (CP/NFP).

It is desirable for the pretreatment solution of present invention to result in rehydrated plasma that has reduced levels of C5a or levels in FDA approved apheresed plasma products. In particular, the present invention involves a pretreatment solution that results in C5a levels similar to fresh frozen or never frozen plasma or available FDA approved apheresed plasma products. As shown in the results of FIG. 28, Example 17, if localized contact with a low pH acid can be avoided, C5a levels are similar to that of Never Frozen plasma. Localized contact with a low pH acid can be avoided by increasing the pH using an amino acid, such as glycine, or utilizing a rapid mixing technique described above, or a combination thereof. As can be seen from FIG. 28, when using Glycine HCl having a pH of 1.32 without the addition of a more basic amino acid such as glycine, the rapid mixture technique reduces the C5a levels from about 64 ng/mL to about 31 ng/ml. When lowering the pH by adding glycine to the SDSAS (e.g., the Glycine HCl/Glycine pretreatment solution), the rapid mixture technique resulted in a C5a level to about 12 ng/ml, close to the level of Never Frozen Plasma (NFP) which is about 10 ng/ml. Using citric acid, having a pH of 2.28 by itself without an amino acid addition and using the rapid mixture technique also results in C5a level similar (12.66 ng/mL) to NFP. The pH of citric acid is higher than that of glycine HCl. When pretreatment solution of citric acid is combined with an amino acid (glycine), the pH of the solution is 3.4 and the rapid mixture does not really affect the C5a level, as both are close to NFP, e.g., about 10 ng/ml. It has been discovered that desirable C5a levels result from a pretreatment solution having an SDSAS and an amino acid addition, rapid mixture/agitation of the pretreatment components, or the combination of both. In particular, levels of C5a for reconstituted plasma resulting from the pretreatment solution of the present invention can be between about 4.7 ng/ml to about 74 ng/mL and in particular between 8 ng/ml and 12 ng/ml (e.g., about 10 ng/ml). C5a levels are reduced, as compared to plasma not subjected to a pretreatment solution having at least one SDSAS and at least one amino acid. In an embodiment, the C5a levels are reduced by about 20% or less (e.g., 20%, 15%, 10%, 5%, 1%), as compared to plasma not subjected to the pretreatment solution of the present invention. In another embodiment, referring to FIG. 28, C5a levels, with rapid mixing and with certain pretreatment formulations, result in about levels the same as that of never frozen plasma, or within about 20% or less (e.g., 20%, 15%, 10%, 5%, 1%) of C5a in never frozen plasma or already approved FDA apheresed plasma products.

Similarly, in an embodiment, rapid mixture and/or agitation are not necessary for pretreatment solutions having a pH of about 3 to about 6 (e.g., 3.0, 3.5, 4.0, 4.5, 5.0, 5.5, 6.0). An important discovery is that although the pH of the pretreatment solution changes e.g., ranges from about 1 to about 4, the pH of the plasma stayed about the same e.g., about 6.2.

Protein Stability of Pre-Treated Plasma

Proteins potentially undergo physical degradation (e.g., unfolding, aggregation, insoluble particulate formation) by a number of mechanisms. Many proteins are structurally unstable in solution and are susceptible to conformational changes due to various stresses encountered during purification, processing and storage. These stresses include temperature shift, exposure to pH changes and extreme pH, shear stress, surface adsorption/interface stress, and so on. Proteins in solutions can be converted to solid formats (i.e., converted to a powder or other dry format by having the water and other volatile components of the protein solution greatly reduced or removed) for improved storage using a number of methods.

Freeze drying (also known as lyophilization) is the most common processing method for removing moisture from biopharmaceuticals, and can increase the stability, temperature tolerance, and shelf life of these products. It is a process wherein a suspension, colloid or solid is frozen and then "dried" under a vacuum by sublimation (phase transition). In this process, proteins can suffer from cold denaturation, interface stress (adsorption at the water/ice-interface), exposure to increasing alkaline pH ($CO_2$ loss), and dehydration stress. Freeze drying is well established within the industry. However, it requires expensive equipment that takes up a great deal of space within a production facility. Freeze drying also can take days to complete, and manufacturers that need a powdered product must incorporate a granulation step to the process. In an environment where budgets are tightening, and where time and facility space are at a premium, freeze drying might be a difficult option for some companies. Because of the space needed, drying plasma by freeze-drying technology is limited to plasma manufacturers, and cannot be implemented in blood centers.

Because of the difficulties inherent with freeze drying of plasma with regard to time, space and cost, the present invention is directed towards an improved spray drying process for plasma that overcomes the known difficulties related to the spray drying of plasma.

In the spray-drying process, the viscous liquid is pumped through the feeding line to the nozzle, where the exiting fluid stream is atomized into numerous droplets under aerosol gas. The liquid droplets are met with dry gas and turned into dry particles. It is a much shorter and less expensive process than the freeze drying process, allowing it to be implemented in research labs and blood centers. However, before the present invention, in this process, plasma proteins can suffer from extensive shear stress, interface stress, thermal stress, dehydration stress and exposure to extreme pH.

Aerosolization exposes the liquid sample to shear stress and produces an extremely rapid and very large expansion of the air-liquid interface. The synergistic effects of shear stress and air-liquid interfacial stress can cause severe detrimental effects on labile compounds such as proteins. Complex biological molecules are difficult to spray dry because they are very sensitive to high shear stress. Although some control relating to the amount of shear stress encountered can be obtained by, for example, choice of the type of atomizer used and the aerosolization pressure used, it is very challenging to apply spray drying technology to human plasma because it contains so many diverse proteins. The diverse proteins may be susceptible to different stresses and this can make it difficult determine processing conditions suitable for all of the types of proteins found in plasma. In particular, vWF, which is designed by nature to be shear sensitive for its biological functions, is the most shear-force sensitive human plasma protein. Most of the other plasma proteins remain largely intact after spray drying except vWF. As shown in the Examples section, spray-drying diminished vWF activity to below the level of detection (see, Example 27, FIG. 17).

Ionizable amino acid residues have been shown to play important roles in the binding of proteins to other molecules and in enzyme mechanisms. They also have a large influence on protein structure, stability and solubility. The types of interactions these side chains will have with their environment depend on their protonation state. Because of this, their pKa values and the factors that influence them are a subject of intense biochemical interest. Strongly altered pKa values are often seen in the active sites of enzymes, to enhance the ability of ionizable residues to act as nucleophiles, electrophiles or general bases and acids. As a consequence of the change in protonation of these residues, the stability of proteins is pH-dependent. Therefore, it is believed that inhibition of the alkalization of plasma during spray drying can potentially improve the processing and storage stabilities of many plasma proteins.

As mentioned above, the spray drying process subjects plasma proteins to different forces than those are found in the lyophilization process. First, spray drying exposes plasma proteins to high stress forces during the aerosolization process as the plasma is forced through the narrow orifice exposed to high rate of air flow that is necessary to create suitably sized droplets for drying. Second, the spray drying process exposes plasma proteins to high temperatures that are necessary to force the water from the aerosolized droplets. Third, the spray drying process subjects the plasma proteins to dramatic and rapid increases in pH as a result of the rapid release of $CO_2$ during drying. Since lyophilization does not subject plasma proteins to these forces, and especially to this unique combination of forces, one of ordinary skill in the art would not look to nor find suggestion or motivation in the lyophilization art with regard to improving the spray drying process for plasma.

In spite of the difficulties associated with the spray drying of plasma, a spray drying process of the present invention results in high recovery and high stability of functional plasma proteins, especially, but not limited to vWF, wherein the recovery of vWF is in an amount in rehydrated spray dried plasma that is at least about 5 percentage points or greater (e.g., about 5, 10, 20, 30, 40, 50, 60, 70, 80 percentage points or greater) as compared to amounts of active/undenatured vWF of rehydrated spray dried plasma that does not undergo the pretreatment steps of the present invention.

The compositions and steps of the present invention relate to the impact of the formulation of liquid plasma with a SDSAS, for example, glycine HCL alone or in conjunction with an amino acid on the recovery from the spray drying process and stability (during storage of dried and rehydrated plasma after spray drying) of functional vWF and other coagulation factors. This can be done by adding a SDSAS such as, for example, glycine HCl, citric acid or lactic acid alone or in conjunction with an amino acid such as glycine to the liquid plasma before spray drying begins or contemporaneously with the spray drying process. During the spray drying process, $CO_2$ loss occurs which causes the pH of the plasma composition to become more alkaline (e.g., to increase) and adding SDSAS and an amino acid thereby maintain the plasma pH in a range to prevent significant denaturing of the clotting factors, esp. vWF. Thus, the pretreatment of plasma with citric acid, glycine HCl or other SDSAS, or in conjunction with an amino acid serves at least three main purposes: 1) increases in-process recovery of plasma proteins; 2) increases stability of plasma proteins during storage; and 3) allows spray dried plasma to be rehydrated with water (e.g., sterile water, WFI), eliminating the need for a specific rehydration solution.

When liquid plasma is formulated with SDSAS and an amino acid before it is dried, the acid resides in the dried plasma product at a level consistent to improved storage lifetime and reduced degradation of clotting factors during storage. A "level consistent to improve storage lifetime" also means, herein, at a level that results in a physiological pH upon reconstitution of the spray dried plasma. The use of the SDSAS and the amino acid also permits simple rehydration by low cost, readily available sterile water for injection or, in an emergency, plain water at a physiological pH. The convenience, lowered cost and improved safety associated with direct rehydration by water is evident. Advantages include savings in being able to ship dried plasma product without the weight and bulk of rehydration fluid and savings in the cost from not having to specially formulate rehydration fluid and reduction or elimination of refrigeration or freezing during storage.

Thus, the inventors have discovered that plasma formulation by a SDSAS and an amino acid results in spray dried plasma that has high recovery or functionality of plasma proteins, especially vWF, highly improved storage properties of the dried plasma and approximately neutral pH when rehydrated with water without a buffering rehydration fluid. Thus, the present invention permits spray dried plasma to be manufactured without the additional expense and complexity of pretreatment with additional stabilizers such as polyols and others known in the art. However, the use of stabilizers is not contraindicated and may be beneficial in some instances.

In a further embodiment, a new composition of matter for blood plasma spray drying is created by dosing by any means the blood plasma prior to spray drying with added citrate (i.e., citric acid) or other suitable SDSAS and amino acids at appropriate concentrations, as disclosed herein.

In a further embodiment the newly dosed citrate formulated blood plasma before spray drying has a concentration of citrate of about 27.5 mM and about 40.4 mM, or of about 31.6 mM and 34.2 mM.

In a further embodiment a new spray dried blood plasma product is created by spray drying blood plasma formulated with appropriate levels of a suitable SDSAS (e.g., citric acid) and a suitable amino acid prior to or contemporaneously with drying and then drying the blood plasma to the desired level of moisture. The desired level of moisture is generally less than 2%.

In various embodiments, citric acid or other SDSAS and amino acids are added to the plasma as a formulation. Experiments relating to the effect of SDSAS and amino acids on protection of the activities of proteins found in plasma are explained further in the exemplification section of this specification. The concentrations at which citric acid, for example, is used are between about 1 to about 15 mM. or between about 5 mM to about 10 mM (e.g., 7.4 mM). Accordingly, plasma proteins can be preserved better when citric acid, at the indicated concentrations, is added to it prior to or contemporaneously with spray drying. The activity of vWF is provided in the exemplification because this factor is especially sensitive to denaturing and damage by spray drying (See, FIG. 17 and FIG. 18) and, thus, is a good indicator protein to show the beneficial effects of SDSAS and amino acids with regard to recovery and stability of the spray dried plasma proteins.

Examples of other physiologically compatible SDSAS and amino acids are known to those of ordinary skill in the art and described herein.

In an embodiment, single donor plasma expressed from collected whole blood or by apheresis which has never been frozen and is less than 24 hours old from collection is desirably utilized for this process. The plasma is collected from blood by standard techniques known to those of ordinary skill in the art, as described herein. Plasma is collected through a process call plasmapheresis. Plasmapheresis refers to a procedure in which the plasma is separated from the blood either by centrifugation or membrane filtration. The system process is also usable with pooled plasma if such is desired and with starting blood plasma material made with any currently available anti-coagulation system such as those known as CPD, CP2D, ACD-A and ACD-B. A sterile, non-pyrogenic, single-use container with SDSAS e.g., a 50 ml solution glycine and hydrochloric acid packaged in a 500 ml container within an overwrap pouch. In an embodiment, the process of the present invention includes converting a single donor unit of plasma which is collected by standard procedures into a single unit of spray dried plasma.

The dried plasma of the present invention can be from a third-party donor or from the potential recipient himself/herself. The latter is known as autologous plasma. Autologous plasma is highly desirable because it resolves compatibility issues, e.g., it does not need to be ABO/Rh typed before use and is unlikely to carry any foreign substance such as pathogens or immunogens to the recipient whose plasma it is.

The in vitro characterization data demonstrate that the manufacturing effects of the system are comparable between units manufactured with different starting materials. Units manufactured from apheresed plasma (ACD-A anti-coagulation treatment) showed similar percent change due to manufacturing effects on the starting material as compared to units manufactured from whole blood derived plasma (CPD anti-coagulation treatment). A statistical analysis (ANOVA) was performed on the percent change pre and post manufacturing between the two starting materials across 20 assays including clotting times, coagulation function, and activation markers. Of the 20 assays, total protein concentration, PT, TT, and Factor VIII and XIII activities were determined to be statistically significantly different, however, the mean percent change is similar, and the mean values are all within the clinical reference range. In summary, the in vitro test results support the conclusion that the manufacturing impact on both apheresed and whole blood plasma is comparable, and the coagulation profile is within ±20% of their paired control or within the normal reference range.

EXEMPLIFICATION

Abbreviations and Nomenclature

FFP-Fresh Frozen Plasma manufactured from CPD Whole Blood; plasma not filtered. Plasma is placed in −18° C. freezer within 8 hours of collection.

CP: control plasma, referring to plasma before spray drying

CP/FFP: FFP control plasma

CP/NFP—Control Plasma/Never Frozen Plasma, Control Plasma made from Never Frozen Plasma, separated from CPD whole blood within 8 hours of collection Batch—represents a unique spray drying run at Velico. SpDP/FFP-Spray dried plasma manufactured from thawed FFP SpD: spray-drying SpDP: spray-dried plasma NFP—Never Frozen Plasma, manufactured from CPD Whole Blood, plasma not filtered (leukoreduced).

ODP—On demand plasma, Applicant's spray dried plasma. Also referred to as SpDP.

Feed plasma: liquid plasma to be fed through a feeding tube to spray-drying device Fed plasma: liquid plasma having been fed to the system without being sprayed Sprayed plasma: fed plasma subjected to aerosolization vWF: von Willebrand factor vWF:RCo: vWF activity measured by vWF ristocitein assay PreT: pretreatment or pre-treated (formulation or formulated)

CA: citric acid

PreT—Control Plasma pretreated with glycine HCl solution prior to spray drying

PreT/CA: pre-treated (formulated) feed plasma with citric acid

RS-CA: citric acid rehydration solution (3.5 mM citric acid)

RS-CAP: citric acid rehydration solution, buffered with sodium phosphate (pH 3.5) WFI: water for injection SDSAS: spray dry stable acidic substance SpDP/FFP: spray dried plasma, derived from pretreated Fresh Frozen Plasma C3a: a protein formed by the cleavage of complement component 3; the other is C3b. C3a is a 77 residue anaphylatoxin that binds to the C3a receptor (C3aR), a class A G protein-coupled receptor.

C5a: a protein fragment released from cleavage of complement component C5 by protease C5-convertase into C5a and C5b fragments. C5a and C5a des-Arg forms are both referred to as C5a in this document.

CPD: Citrate Phosphate Dextrose anticoagulant

DI: Deionized

TEG: Thrombelastography Hemostasis System aPTT (activated partial thromboplastin time)

PT (prothrombin time)

TT (thrombin time)

Example 1: Lyophilized Plasma Cholesterol Crystals

In an independent study lyophilized dried plasma products when stored and prepared according to manufacturer's instructions, displayed needle-like crystals that were present in every sample studied and were not dissolvable.

These needles presented and tested as cholesterol crystals. The study found the following:

1) The crystals grew in methanol and dissolved only after prolonged incubation in ethanol or after warming them in pure ethanol to 60° C. as more fully detailed here:
2) The needles appeared similar to that of needle or arc shaped cholesterol crystals such as those found in bile from the gallbladder from mice on a lithogenic diet with gall bladder hypomotility.
3) Standard fixation fluids such as ethanol are known to dissolve cholesterol crystals.

4) The cholesterol crystals can be made in vitro with various techniques, the needle shaped cholesterol crystal can be grown in methanol.
5) It has been shown that lyophilization of patient plasma samples reduces the soluble cholesterol content of the sample. It has been shown that freezing patient plasma samples also reduces the soluble content of the sample.
6) Similar but smaller and rounder crystals have been found in lyophilized control samples.

Figure 2:
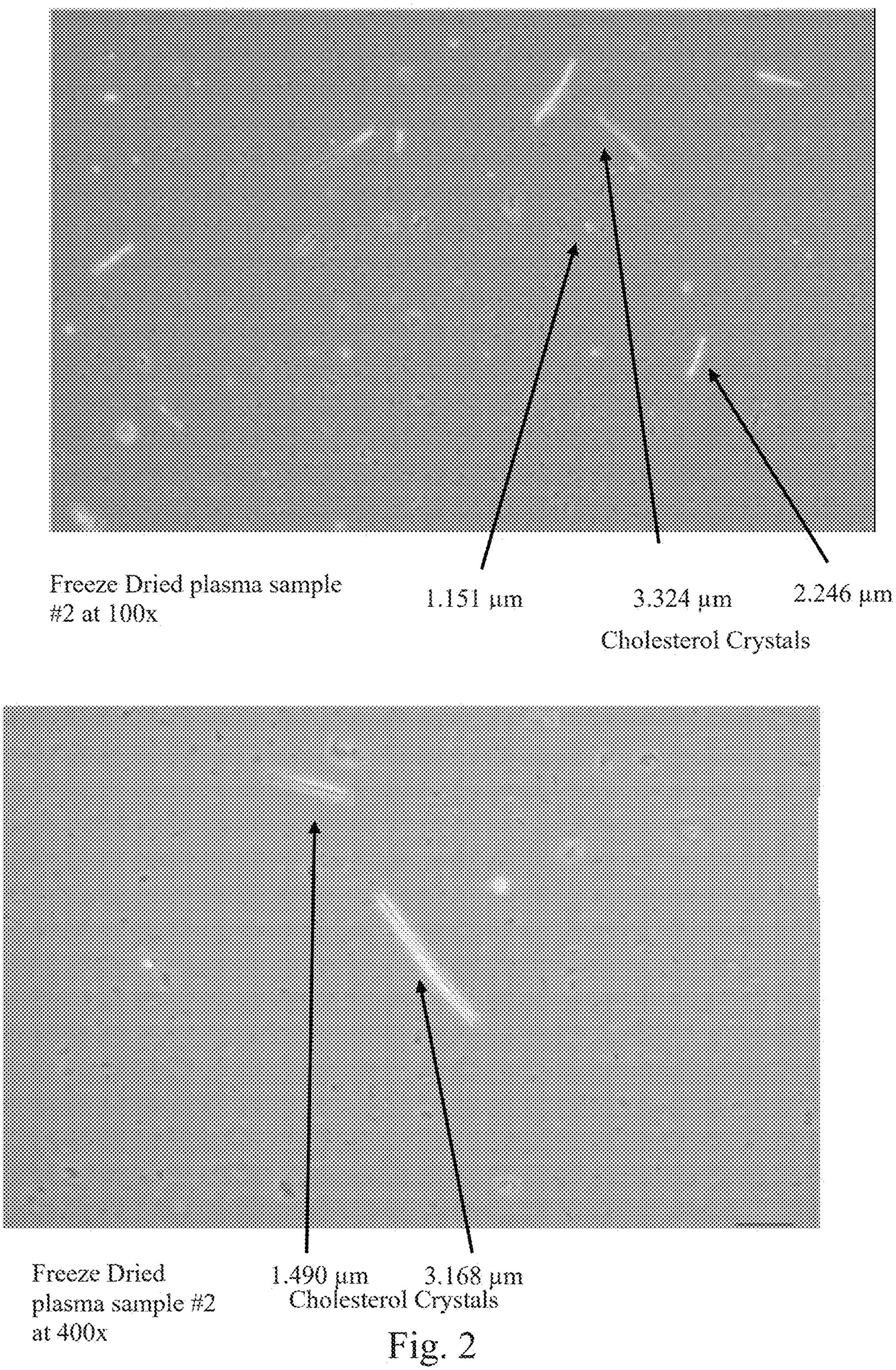
FIG. 2 is a black and white photograph showing phase contrast microscopy at 100× and 400× magnification of cholesterol crystals in freeze-dried plasma known as FLYP™ plasma.
Figure 3:
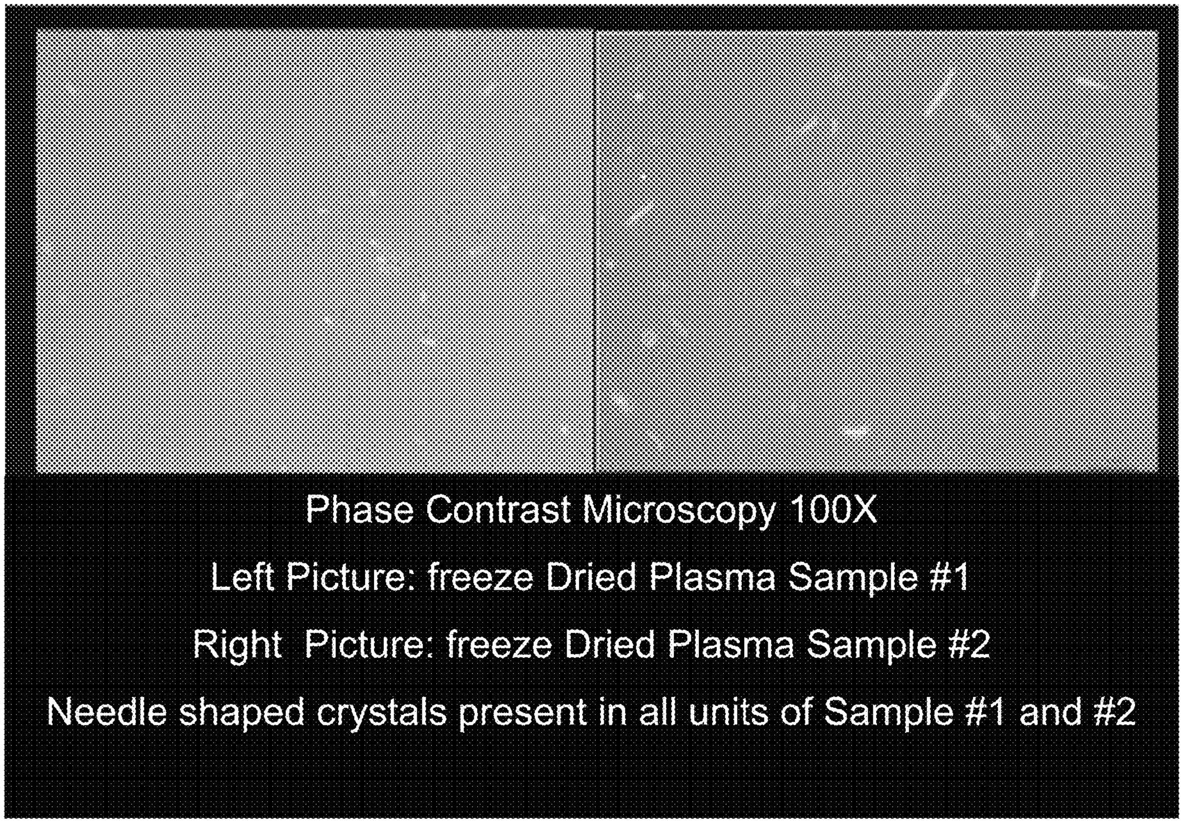
FIG. 3 is a panel of black and white photographs showing phase contrast microscopy at 100× magnification of cholesterol crystals in freeze-dried plasma with LYOPLAS™ plasma (left) and FLYP™ plasma (right).

In the photos shown in FIGS. 1 & 2, the cholesterol crystals are observed in lyophilized human blood plasma with phase contrast microscopy at 100× and 400×.

By contrast, no cholesterol crystals observed in the spray dried plasma of the present invention. See FIG. 3 and Example 2.

Example 2—Cholesterol Crystals not Observed in Spray Dried Plasma of the Present Invention Method
Pre Study Examination:
1) Visual Inspection of the Dried Product and Resuspension Kit The reconstituted spray dried plasma the present invention were at a temperature of 12-14° C., as measured with infra-red thermometer, at the beginning of the study. The reconstituted plasma was reconstituted with SWFI and the spray dried plasma was dried using disposable 100 shown in FIG. 42A and drier 200 shown in FIGS. 45 and 46 with parameters described herein.

TABLE 9

Weigh the product and the water to suspend the unit.

| Product | Weight (grams) |
|---|---|
| Dried plasma unit | 52.4 grams |
| Supplied reconstitution water | 211.9 grams |
| Supplied transfer tubing set | 12.0 grams |

The dried plasma unit of the present invention was stored in a refrigerator at 2-6° C. before reconstitution and the water was at room temperature (21-22° C.)

TABLE 10

Observations and resuspension characteristics:

| Check to be performed | Result/Observation |
|---|---|
| check if product is clear and of normal color (not lipemic, green/red) | Product is clear and of normal color |
| check if no clots/aggregates | There are no clots or aggregates visible |
| check if turbulence is seen in the bag while moving the plasma | There is visible swirling in the product |

Figure 4:
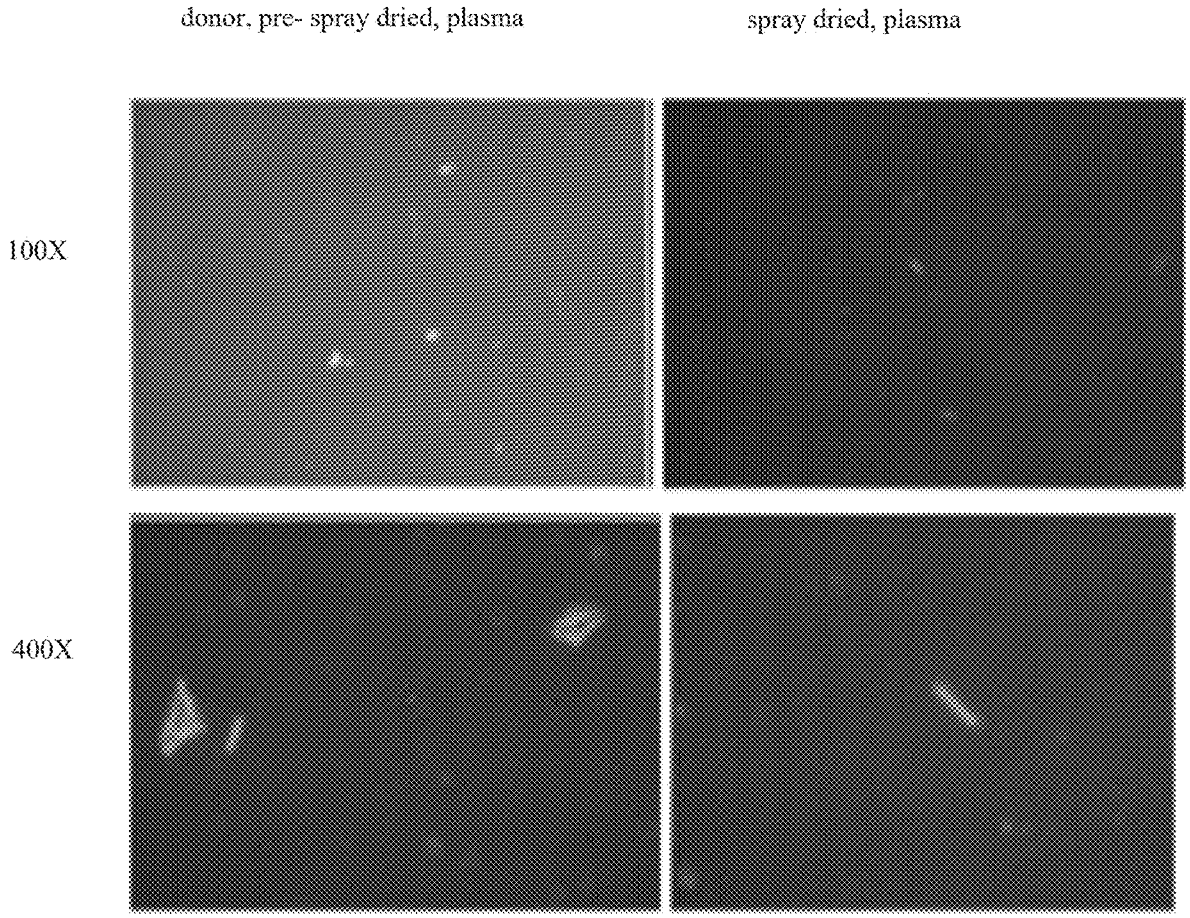
FIG. 4 is a panel of black and white photographs showing of phase contrast microscopy of spray dried plasma with no visible cholesterol crystals observed as follows: 100× magnification of donor, pre-spray dried, plasma (upper left panel), 100× magnification of spray dried, plasma (upper right panel), 400× magnification of donor, pre-spray dried, plasma (lower left panel), and 400× magnification of spray dried, plasma (lower right panel)

Two 4 ml reconstituted spray dried samples were used for microscopy.
Results
Microscopic Examination was Performed to Check for Needle Shaped Cholesterol Crystals
Sample Examination was Performed with Phase Contrast Microscopy Most fields under the lens were clear of crystals. The goal was to make a photo of any crystal-like structure. FIG. 4 shows photos as follows: 100× enlargement (upper panel) and 400× enlargement (lower panel) of donor, pre-spray dried, plasma (left) and spray dried plasma (right). As shown in FIG. 4, there are some structures that reflect light in phase contrast microscopy, the light reflecting structures were found were uric acid crystals and calcium-phosphate-like crystals, but no cholesterol crystals. The uric acid and calcium-phosphate crystals which were also found in the corresponding donor, pre-spray dried, plasma sample. Furthermore, platelets and microparticles, as shown as round dots, were less present in the spray dried plasma.

No evidence of the presence of needle shaped cholesterol crystals in reconstituted plasma that was spray dried, as compared to cholesterol crystals found in all units of reconstituted freeze-dried plasma, as described in Example 1.

When observed at 100× and 400×, needle shaped cholesterol crystals are absent from the spray dried plasma of the present invention. It is believed that similar results would be seen in blood plasma for mammals other than humans.

Example 3—Particulate Size and Distribution Characterization of the Spray Dried Plasma of the Present Invention after 7.5 Months of Room Temperature Storage, 24 Months of Refrigerated Storage and a Combined Storage (18 Months) of Refrigerated 1 Year+Room Temperature 6 Months Summary: Particle size distribution of the FrontlineODP Units was measured at initial rehydration (t=0) and 4 hours post rehydration (t=4) after storage at various temperatures and timepoints. There was no increase in particle size or distribution in rehydrated FrontlineODP Units compared to the paired Control Plasma at any storage condition after initial rehydration (t=0). Additionally, there was no increase in particle size or distribution in the rehydrated FrontlineODP Unit 4 hours after rehydration (t=4) compared to initial rehydration (t=0).

A pooled FrontlineODP Unit study using 3 different pools of PF24 was performed to evaluate particle size and distribution throughout the product shelf life and in-use shelf life after the spray-dry manufacturing process. Particle size characterization was completed on FrontlineODP Units and paired Control Plasma using the electrical sensing zone method in the range of 2-60 μm by an external laboratory.
Purpose:

The purpose of this study was to characterize particulate size and distribution of rehydrated spray dried plasma of the present invention spray dried from pooled plasma compared to (1) its paired Control Plasma stored at various environmental conditions and (2) the same rehydrated sample after t=4 hours post rehydration. This report summarizes the particulate analysis results up to 7.5 months storage at room temperature (20-25° C.), 24 months storage at refrigeration (1-6° C.) and 18 months storage of combined refrigeration (1 year) and room temperature (6 months).
Scope and Materials:

Spray dried plasma units of the plasma of the present invention were manufactured from pooled single donor plasma frozen within 24 hours (PF24) containing citrate phosphate dextrose (CPD) anticoagulant on the spray dryer of the present invention.

Particulate size analysis was completed on rehydrated plasma and paired thawed frozen control plasma at Vision Analytical (formerly CLAS Automation Miami, FL). Particulate analysis was performed in the range of 2 to 60 microns using a Beckman Coulter Multisizer 4 (electrical sensing zone method) at 0-0.5 and 4-4.5 hours after rehydration or thaw.

The particulate analysis characterization study was conducted to evaluate spray drying effects, in-use stability and product shelf-life effects on protein aggregation. A study using 3 different pools of rehydrated dried plasma of the present invention was performed to evaluate particulate size and distribution throughout the product shelf life and in use shelf life. Three separate pools each consisting of nine (9) units of plasma frozen within 24 hours of phlebotomy (PF24) were manufactured by thawing and pooling plasma that was stored at refrigeration until pretreatment and spray drying. Spray drying process of eight (8) units from each pool was completed within approximately 4.5 hours and their paired Control Plasma was frozen within approximately 5.5 hours from the spray drying of the first unit to ensure that manufacturing time of frozen and spray dried samples was similar. Units of the rehydrated plasma of the present invention were randomized to storage at various timepoints to evenly distribute the storage time of the pooled plasma prior to spray drying. Particulate size characterization was completed on the units and paired Control Plasma using the electrical sensing zone method in the range of 2-60 µm at 0, 4, 12 and 24 months refrigerated, at 5 and 7.5 months room temperature storage, and combined storage of 1 year refrigerated+6 months room temperature storage (18 months). Additionally, rehydrated units and the paired Control Plasmas were evaluated by particulate analysis at t=4 hours post rehydration/thaw to evaluate in-use stability.

timepoints (room temperature, refrigerated and combined storage) at t=0 hours and t=4 hours from rehydration or thaw (Table 11 and Table 12). See also FIGS. 5 and 6.

The particulate size distribution for the units is comparable across all timepoints at t=0 hours and t=4 hours after rehydration.

The particulate size analysis data supports that the rehydrated plasma of the present invention do not exhibit protein aggregates or other particulates after storage and rehydration (up to 4 hours) at up to 7.5 months room temperature (FIG. 5), up to 24 months refrigeration or after a combined storage temperature of 1 year refrigerated+6 months room temperature when compared to (1) its paired control and (2) after t=4 hours post rehydration. In other words, when reconstituted, the rehydrated plasma exhibits a reduced mean size of particulates when measuring with a Coulter Multisizer 4 by the electrical sensing zone method for particulates having a size between about 2 µm and 60 µm, as compared to particulates in the donor plasma.

Example 4: In Use Stability—Post-Reconstitution Storage Stability

Dried plasma products are reconstituted prior to administration, as directed on the label: post-reconstitution storage

TABLE 11

Average D-values for Control Plasma at t = 0 and t = 4 post thaw (n = 3)

| Storage Environment | Control Plasma (n = 3) | D10 (µm) t = 0 hr | D10 (µm) t = 4 hr | D50 (µm) t = 0 hr | D50 (µm) t = 4 hr | D90 (µm) t = 0 hr | D90 (µm) t = 4 hr |
|---|---|---|---|---|---|---|---|
| Initial (t = 0) | 0 months | 2.14 ± 0.02 | 2.17 ± 0.02 | 2.69 ± 0.08 | 2.84 ± 0.07 | 3.69 ± 0.18 | 4.09 ± 0.19 |
| Refrigeration | 4 months | 2.13 ± 0.00 | 2.13 ± 0.01 | 2.73 ± 0.04 | 2.77 ± 0.04 | 3.95 ± 0.07 | 4.05 ± 0.07 |
| (1-6° C.) | 12 months | 2.14 ± 0.02 | 2.16 ± 0.00 | 2.73 ± 0.07 | 2.85 ± 0.01 | 3.80 ± 0.12 | 4.05 ± 0.01 |
| | 24 months | 2.11 ± 0.01 | 2.14 ± 0.02 | 2.60 ± 0.03 | 2.73 ± 0.09 | 3.54 ± 0.04 | 3.80 ± 0.14 |
| Room Temp | 5 months | 2.13 ± 0.00 | 2.15 ± 0.00 | 2.75 ± 0.02 | 2.83 ± 0.02 | 4.03 ± 0.13 | 4.18 ± 0.08 |
| (20-25° C.) | 7.5 months | 2.16 ± 0.00 | 2.17 ± 0.00 | 2.89 ± 0.01 | 2.95 ± 0.03 | 4.31 ± 0.04 | 4.41 ± 0.03 |
| Combination (Ref 1 year + RT 6 mos) | 18 months | 2.17 ± 0.01 | 2.18 ± 0.02 | 2.82 ± 0.06 | 2.91 ± 0.07 | 4.01 ± 0.11 | 4.17 ± 0.12 |

TABLE 12

Average D-values for FrontlineODP Units at t = 0 and t = 4 post rehydration (n = 3)

| Storage Environment | FrontlineODP (n = 3) | D10 (µm) t = 0 hr | D10 (µm) t = 4 hr | D50 (µm) t = 0 hr | D50 (µm) t = 4 hr | D90 (µm) t = 0 hr | D90 (µm) t = 4 hr |
|---|---|---|---|---|---|---|---|
| Initial (t = 0) | 0 months | 2.04 ± 0.00 | 2.04 ± 0.00 | 2.26 ± 0.01 | 2.26 ± 0.01 | 2.82 ± 0.05 | 2.83 ± 0.03 |
| Refrigeration | 4 months | 2.04 ± 0.00 | 2.04 ± 0.00 | 2.24 ± 0.01 | 2.25 ± 0.02 | 2.80 ± 0.04 | 2.80 ± 0.03 |
| (1-6° C.) | 12 months | 2.04 ± 0.00 | 2.04 ± 0.00 | 2.24 ± 0.01 | 2.26 ± 0.01 | 2.78 ± 0.04 | 2.83 ± 0.05 |
| | 24 months | 2.04 ± 0.00 | 2.04 ± 0.00 | 2.25 ± 0.00 | 2.27 ± 0.01 | 2.85 ± 0.03 | 2.87 ± 0.01 |
| Room Temp | 5 months | 2.04 ± 0.00 | 2.04 ± 0.00 | 2.23 ± 0.01 | 2.24 ± 0.00 | 2.79 ± 0.02 | 2.80 ± 0.02 |
| (20-25° C.) | 7.5 months | 2.04 ± 0.00 | 2.04 ± 0.00 | 2.22 ± 0.00 | 2.22 ± 0.00 | 2.77 ± 0.00 | 2.77 ± 0.00 |
| Combination (Ref 1 year + RT 6 mos) | 18 months | 2.04 ± 0.00 | 2.04 ± 0.00 | 2.23 ± 0.01 | 2.25 ± 0.01 | 2.77 ± 0.01 | 2.79 ± 0.01 |

Average particulate size distribution results for Control Plasma and FrontlineODP units can be found in Table 11, and 12, respectively. D-values are intercepts for 10%, 50%, and 90% of cumulative mass (e.g. —D10 is the diameter at which 10% of the sample's mass is comprised of particulates with a diameter less than this value).

There is no increase in particulate size or distribution in the rehydrated units of the dried plasma of the present invention compared to its paired Control Plasma at all time was tested by in-use stability studies. The spray dried plasma unit was tested for room temperature in-use stability 0, 2, 4 and 6 hours after rehydration. The dried plasma units are to be transfused within 4 hours of rehydration when stored at room temperature per AABB Circular of Information available online from the American Association of Blood Banks. The percent difference of unit values for up to 6 hours at room temperature compared to initial values at t=0 hours after rehydration for all assays did not exceed ±15% for each timepoint (Table 13).

The percent change at each timepoint compared to t=0 was calculated with the equation below:

Mean % change at rehydration timepoints compared to ($t$ = 0) =

$$\frac{1}{6}\sum_{i=1}^{6}\frac{FrontlineODP_{Timepoint,i} - FrontlineODP_{t=0,i}}{FrontlineODP_{t=0,i}} \times 100$$

Dried plasma products are reconstituted prior to administration, as directed on the label: post-reconstitution storage time was tested by in-use stability studies. The spray dried plasma unit was tested for in-use stability 0, 5, 8, 20, 23 and 26 hours after rehydration stored at both refrigeration and room temperature. The dried plasma units to be transfused within 4 hours of rehydration when stored at room temperature or 24 hours of rehydration when stored at refrigeration per AABB Circular of Information available online from the American Association of Blood Banks. The percent difference of unit values for up to 26 hours at refrigeration and room temperature compared to initial value at t=0 hours after rehydration for all assays were comparable to t=0 or within the normal reference range. (Table 14 and Table 15).

The percent change at each timepoint compared to t=0 was calculated with the equation below:

Mean % change at rehydration timepoints compared to ($t$ = 0) =

$$\frac{1}{3}\sum_{i=1}^{3}\frac{FrontlineODP_{Timepoint,i} - FrontlineODP_{t=0,i}}{FrontlineODP_{t=0,i}} \times 100$$

TABLE 13

Unit assay results at each timepoint and compared to the t = 0 hours value.

| Assay | Clinical Reference Range | Timepoint t = 0 hours Mean | t = 2 hours Mean | t = 2 hours % change | t = 4 hours Mean | t = 4 hours % change | t = 6 hours Mean | t = 6 hours % change |
|---|---|---|---|---|---|---|---|---|
| aPTT (s) | 22-35 | 31.5 ± 4.5 | 31.5 ± 4.2 | 0% | 31.4 ± 4.1 | 0% | 31.7 ± 4.1 | 1% |
| Prothrombin Time (s) | 10-14 | 14.1 ± 1.1 | 14.0 ± 1.1 | −1% | 14.0 ± 1.2 | −1% | 14.1 ± 1.1 | −1% |
| INR (s) | 0.9-1.1 | 1.14 ± 0.10 | 1.13 ± 0.10 | −1% | 1.10 ± 0.10 | −1% | 1.10 ± 0.10 | 0% |
| Thrombin Time (s) | 14.5-20.5 | 17.0 ± 1.5 | 17.4 ± 1.6 | 2% | 17.2 ± 1.5 | 1% | 17.3 ± 1.5 | 2% |
| Factor V (%) | 50-200 | 82 ± 11 | 79 ± 11 | −4% | 79 ± 12 | −4% | 81 ± 11 | −1% |
| Factor VII (%) | 50-200 | 59 ± 14 | 59 ± 13 | 0% | 60 ± 14 | 2% | 61 ± 16 | 2% |
| Factor VIII (%) | 50-200 | 88 ± 36 | 89 ± 40 | 0% | 90 ± 40 | 2% | 87 ± 39 | −2% |
| Factor IX (%) | 50-200 | 73 ± 15 | 80 ± 23 | 8% | 74 ± 18 | 0% | 75 ± 21 | 2% |
| Factor X (%) | 50-200 | 69 ± 16 | 70 ± 15 | 2% | 71 ± 15 | 3% | 72 ± 17 | 4% |
| Factor XI (%) | 50-200 | 87 ± 19 | 90 ± 19 | 3% | 97 ± 20 | 11% | 94 ± 24 | 7% |
| Factor XIII Activity (%) | 57-192 | 96 ± 15 | 97 ± 17 | 2% | 98 ± 19 | 2% | 100 ± 20 | 4% |
| Factor XIII Antigen (%) | 75.2-154.8 | 88 ± 11 | 88 ± 12 | 0% | 89 ± 10 | 1% | 88 ± 11 | 0% |
| Fibrinogen (mg/dL) | 150-400 | 238 ± 46 | 228 ± 42 | −4% | 237 ± 33 | 1% | 231 ± 44 | −3% |
| Plasminogen (%) | 70-150 | 76 ± 7 | 77 ± 8 | 1% | 77 ± 7 | 1% | 77 ± 7 | 1% |
| Plasmin Inhibitor (%) | 85-156 | 90 ± 11 | 91 ± 11 | 2% | 91 ± 10 | 1% | 90 ± 10 | 0% |
| Protein C (%) | 75-150 | 88 ± 7 | 88 ± 6 | 0% | 89 ± 6 | 1% | 86 ± 6 | −2% |
| Protein S (%) | 60-150 | 81 ± 20 | 75 ± 19 | −8% | 71 ± 17 | −12% | 68 ± 15 | −15% |
| Antithrombin III (%) | 80-120 | 78 ± 10 | 77 ± 8 | 0% | 78 ± 8 | 0% | 78 ± 8 | 0% |
| von Willebrand Factor Antigen (%) | 50-200 | 145 ± 61 | 149 ± 72 | 2% | 150 ± 71 | 2% | 149 ± 70 | 2% |
| von Willebrand Factor Ristocetin Cofactor (%) | 50-200 | 51 ± 17 | 52 ± 16 | 2% | 50 ± 17 | −1% | 52 ± 17 | 3% |
| C5a (ng/mL) | 4.7-74* | 22.3 ± 1.9 | 22.0 ± 1.7 | 2% | 21.6 ± 2.3 | −1% | 22.4 ± 1.8 | 3% |
| Prothrombin Fragment F 1 + 2 (pmol/L) | 91-137 | 114 ± 75 | 106 ± 70 | −7% | 103 ± 66 | −9% | 99 ± 53 | −8% |
| Thrombin-Antithrombin Complex (TAT) (μg/L) | 0-4 | 3.3 ± 3.1 | 3.3 ± 3.0 | 3% | 3.1 ± 2.9 | −4% | 3.2 ± 3.0 | −1% |

*clinical reference range reported for apheresed plasma.

PT is slightly outside of the clinical reference range by 0.1 second but consistent across all timepoints.

INR is slightly outside of the clinical reference range by 0.04 and 0.03 at t=0 and t=2 hours, respectively, however INR is within the clinical reference range at all other timepoints, and percent change is within 1% and remains consistent across all timepoints.

Antithrombin III is slightly below the clinical reference range at all timepoints.

C5a is within the reference range reported for apheresed plasma of 4.9-74 ng/mL. See Thierry Burnouf "Assessment of complement activation during membrane-based plasmapheresis procedures," Journal of Clinical Apheresis 19, no. 3 (2004): 142-147

TABLE 14

Unit assay results at each timepoint stored at refrigeration and compared to the t = 0 hours value.

| Assays | Clinical Reference Range | T = 0 hours after rehydration Mean ± SD | T = 5 hours after rehydration Mean ± SD | % Change from t = 0 to t = 5 hours Mean ± SD | T = 8 hours after rehydration Mean ± SD | % Change from t = 0 to t = 8 hours Mean ± SD |
|---|---|---|---|---|---|---|
| aPTT (s) | 22-35 | 28.3 ± 1.1 | 28.9 ± 0.7 | 2% ± 2% | 29.1 ± 0.9 | 3% ± 1% |
| Prothrombin Time (s) | 10-14 | 12.1 ± 0.7 | 12.1 ± 0.7 | 0% ± 1% | 12.3 ± 0.8 | 2% ± 1% |
| INR (s) | 0.9-1.1 | 0.96 ± 0.06 | 0.96 ± 0.06 | 0% ± 0% | 0.97 ± 0.06 | 1% ± 1% |
| Thrombin Time (s) | 14.5-20.5 | 18.9 ± 2.1 | 19.1 ± 2.1 | 1% ± 1% | 19.1 ± 2.1 | 1% ± 1% |
| Factor V (%) | 50-200 | 82.2 ± 13 | 82.4 ± 14.5 | 0% ± 3% | 78 ± 12.4 | −5% ± 4% |
| Factor VII (%) | 50-200 | 88.5 ± 20.1 | 90.3 ± 18.5 | 2% ± 3% | 91.6 ± 20 | 4% ± 4% |
| Factor VIII (%) | 50-200 | 94.8 ± 15.6 | 85.3 ± 12 | −9% ± 4% | 82.8 ± 11.3 | −12% ± 3% |
| Factor IX (%) | 50-200 | 99.4 ± 15 | 97.7 ± 14.3 | −2% ± 3% | 94.3 ± 8.9 | −5% ± 6% |
| Factor X (%) | 50-200 | 100.3 ± 15.1 | 99.2 ± 15.6 | −1% ± 1% | 99.2 ± 13.2 | −1% ± 3% |
| Factor XI (%) | 50-200 | 97.6 ± 11.6 | 92.8 ± 9.8 | −5% ± 6% | 96 ± 10 | −1% ± 6% |
| Factor XIII Activity (%) | 57-192 | 89.4 ± 7.9 | 89.5 ± 6.6 | 0% ± 2% | 90 ± 6.1 | 1% ± 2% |
| Factor XIII Antigen (%) | 75.2-154.8 | 73.8 ± 3.9 | 75.5 ± 1.7 | 3% ± 3% | 76.3 ± 5.5 | 4% ± 2% |
| Fibrinogen (mg/dL) | 150-400 | 230 ± 42 | 231 ± 38 | 1% ± 8% | 234 ± 36 | 2% ± 4% |
| Plasminogen (%) | 70-150 | 105 ± 22 | 106 ± 20 | 1% ± 2% | 107 ± 21 | 2% ± 1% |
| Plasmin Inhibitor (%) | 85-156 | 89 ± 11 | 88 ± 11 | −1% ± 0% | 89 ± 10 | 0% ± 1% |
| Protein C (%) | 75-150 | 91 ± 17 | 93 ± 18 | 2% ± 3% | 94 ± 19 | 3% ± 2% |
| Protein S (%) | 60-150 | 109.2 ± 0.3 | 99.4 ± 1.3 | −9% ± 1% | 98.4 ± 0.3 | −10% ± 1% |
| Antithrombin III (%) | 80-120 | 81 ± 5 | 83 ± 6 | 2% ± 1% | 84 ± 8 | 3% ± 5% |
| von Willebrand Factor Activity | 50-200 | 54 ± 19 | 54 ± 18 | 1% ± 3% | 56 ± 19 | 5% ± 3% |
| von Willebrand Factor Antigen (%) | 50-200 | 110.3 ± 27.1 | 108.7 ± 24.7 | −1% ± 2% | 110.3 ± 27 | 0% ± 3% |
| von Willebrand Factor Ristocetin Cofactor (%) | 50-200 | 33.5 ± 10.2 | 35 ± 10.8 | 4% ± 2% | 36.6 ± 11 | 9% ± 1% |
| C5a (ng/mL) | 4.7-74* | 33.2 ± 1 | 33.9 ± 2.4 | 2% ± 5% | 33.5 ± 1.4 | 1% ± 2% |
| Prothrombin Fragment F 1 + 2 (pmol/L) | 91-137 | 100.9 ± 46.5 | 83.2 ± 12.2 | −7% ± 38% | 98.5 ± 45.1 | −2% ± 3% |
| Thrombin-Antithrombin Complex (TAT) (µg/L) | 0-4 | 1.77 ± 0.71 | 1.86 ± 0.85 | 8% ± 29% | 2.12 ± 0.6 | 27% ± 31% |

| Assays | Clinical Reference Range | T = 20 hours after rehydration Mean ± SD | % Change from t = 0 to t = 20 hours Mean ± SD | T = 23 hours after rehydration Mean ± SD | % Change from t = 0 to t = 23 hours Mean ± SD | T = 26 hours after rehydration Mean ± SD | % Change from t = 0 to t = 26 hours Mean ± SD |
|---|---|---|---|---|---|---|---|
| aPTT (s) | 22-35 | 30.6 ± 0.8 | 8% ± 2% | 29.9 ± 0.9 | 5% ± 1% | 30.4 ± 0.6 | 7% ± 2% |
| Prothrombin Time (s) | 10-14 | 12.4 ± 0.7 | 3% ± 1% | 12.3 ± 0.7 | 2% ± 0% | 12.2 ± 0.6 | 1% ± 2% |
| INR (s) | 0.9-1.1 | 0.98 ± 0.05 | 2% ± 1% | 0.98 ± 0.06 | 1% ± 1% | 0.97 ± 0.05 | 0% ± 2% |
| Thrombin Time (s) | 14.5-20.5 | 18.8 ± 2.8 | −1% ± 4% | 19.3 ± 2.2 | 2% ± 1% | 19.1 ± 2.6 | 1% ± 3% |
| Factor V (%) | 50-200 | 75.2 ± 12.9 | −9% ± 4% | 74.4 ± 10.5 | −10% ± 1% | 73 ± 7.9 | −11% ± 6% |
| Factor VII (%) | 50-200 | 89.1 ± 19.6 | 1% ± 6% | 89.7 ± 19 | 2% ± 4% | 96.7 ± 18.7 | 10% ± 8% |
| Factor VIII (%) | 50-200 | 68.5 ± 8.1 | −27% ± 4% | 66.4 ± 10.8 | −30% ± 1% | 63.5 ± 10.8 | −33% ± 3% |
| Factor IX (%) | 50-200 | 97.2 ± 12.7 | −2% ± 3% | 95.3 ± 9.1 | −4% ± 6% | 103.1 ± 20.9 | 3% ± 6% |
| Factor X (%) | 50-200 | 97.5 ± 13.9 | −3% ± 2% | 99.8 ± 14.6 | 0% ± 1% | 103.2 ± 18 | 3% ± 4% |
| Factor XI (%) | 50-200 | 88.9 ± 9.2 | −9% ± 2% | 93.4 ± 15.6 | −5% ± 6% | 97.8 ± 13.3 | 0% ± 4% |
| Factor XIII Activity (%) | 57-192 | 89.2 ± 6.2 | 0% ± 2% | 87.6 ± 5.4 | −2% ± 3% | 87.7 ± 6.6 | −2% ± 1% |
| Factor XIII Antigen (%) | 75.2-154.8 | 73.3 ± 1.9 | 0% ± 4% | 76.9 ± 2.8 | 4% ± 3% | 76.3 ± 3.1 | 4% ± 4% |
| Fibrinogen (mg/dL) | 150-400 | 227 ± 31 | −1% ± 5% | 224 ± 32 | −2% ± 4% | 243 ± 49 | 6% ± 3% |
| Plasminogen (%) | 70-150 | 106 ± 20 | 0% ± 2% | 106 ± 21 | 1% ± 1% | 104 ± 19 | −1% ± 3% |
| Plasmin Inhibitor (%) | 85-156 | 89 ± 14 | 0% ± 4% | 90 ± 12 | 1% ± 1% | 89 ± 9 | 0% ± 3% |
| Protein C (%) | 75-150 | 91 ± 19 | 0% ± 2% | 93 ± 19 | 1% ± 2% | 91 ± 18 | 0% ± 6% |
| Protein S (%) | 60-150 | 95.2 ± 0.8 | −13% ± 1% | 103.8 ± 2.8 | −5% ± 3% | 99.3 ± 5.8 | −9% ± 5% |
| Antithrombin III (%) | 80-120 | 82 ± 8 | 1% ± 4% | 83 ± 8 | 1% ± 5% | 81 ± 10 | 0% ± 6% |
| von Willebrand Factor Activity | 50-200 | 55 ± 18 | 3% ± 4% | 52 ± 18 | −2% ± 2% | 53 ± 17 | 0% ± 5% |
| von Willebrand Factor Antigen (%) | 50-200 | 110.5 ± 25 | 1% ± 4% | 111.8 ± 26 | 2% ± 3% | 112.8 ± 26.9 | 2% ± 4% |
| von Willebrand Factor Ristocetin Cofactor (%) | 50-200 | 38.4 ± 10.5 | 16% ± 6% | 37.5 ± 13.9 | 10% ± 13% | 38.1 ± 13.9 | 13% ± 12% |

TABLE 14-continued

Unit assay results at each timepoint stored at refrigeration and compared to the t = 0 hours value.

| | | | | | | | |
|---|---|---|---|---|---|---|---|
| C5a (ng/mL) | 4.7-74* | 34 ± 0.8 | 2% ± 6% | 34 ± 1.8 | 3% ± 3% | 33.7 ± 2.4 | 1% ± 5% |
| Prothrombin Fragment F 1 + 2 (pmol/L) | 91-137 | 105.6 ± 38.9 | 7% ± 9% | 92.8 ± 11.8 | 1% ± 34% | 79.6 ± 1.4 | −11% ± 32% |
| Thrombin-Antithrombin Complex (TAT) (μg/L) | 0-4 | 1.86 ± 0.96 | 2% ± 20% | 2.15 ± 0.99 | 22% ± 22% | 2.11 ± 0.66 | 26% ± 31% |

| Assays | T = 0 hours after rehydration Mean ± SD | T = 5 hours after rehydration Mean ± SD | T = 8 hours after rehydration Mean ± SD | T = 20 hours after rehydration Mean ± SD | T = 23 hours after rehydration Mean ± SD | T = 26 hours after rehydration Mean ± SD |
|---|---|---|---|---|---|---|
| pH | 7.12 ± 0.29 | 7.15 ± 0.3 | 7.15 ± 0.29 | 7.15 ± 0.32 | 7.16 ± 0.3 | 7.16 ± 0.29 |
| Total Protein | 5.12 ± 0.13 | 5.19 ± 0.11 | 5.26 ± 0.08 | 5.28 ± 0.1 | 5.34 ± 0.1 | 5.28 ± 0.11 |
| Osmo | 373 ± 6 | 371 ± 10 | 371 ± 12 | 371 ± 9 | 372 ± 10 | 373 ± 12 |

*clinical reference range reported for apheresed plasma

FXIII antigen at t=20 was slightly below the clinical reference range, but all other timepoints were within the clinical reference range and consistent across all timepoints.

vWF activity and vWF:RCo means were below the clinical reference range, but 5 vWF antigen means were within the clinical reference range. Assay values for vWF:RCO and vWF antigen were consistent across all timepoints.

C5a is within the reference range reported for apheresed plasma of 4.9-74 ng/mL.

PF1+2 is below the clinical reference range at t=5 and t=26 and is not indicative of activation.

TABLE 15

Unit assay results at each timepoint stored at room temperature and compared to the t = 0 hours value.

| Assays | Clinical Reference Range | T = 0 hours after rehydration Mean ± SD | T = 5 hours after rehydration Mean ± SD | % Change from t = 0 to t = 5 hours Mean ± SD | T = 8 hours after rehydration Mean ± SD | % Change from t = 0 to t = 8 hours Mean ± SD |
|---|---|---|---|---|---|---|
| aPTT (s) | 22-35 | 28.3 ± 1.1 | 28.1 ± 0.7 | −1% ± 2% | 28 ± 1.1 | −1% ± 1% |
| Prothrombin Time (s) | 10-14 | 12.1 ± 0.7 | 11.9 ± 0.7 | −2% ± 0% | 11.9 ± 0.8 | −2% ± 1% |
| INR (s) | 0.9-1.1 | 0.96 ± 0.06 | 0.94 ± 0.06 | −2% ± 0% | 0.95 ± 0.06 | −2% ± 1% |
| Thrombin Time (s) | 14.5-20.5 | 18.9 ± 2.1 | 19.4 ± 2.3 | 2% ± 2% | 19.2 ± 2.3 | 1% ± 2% |
| Factor V (%) | 50-200 | 82.2 ± 13 | 83.3 ± 11.7 | 2% ± 3% | 83.9 ± 11.4 | 2% ± 3% |
| Factor VII (%) | 50-200 | 88.5 ± 20.1 | 97.9 ± 21.6 | 11% ± 2960% | 98.5 ± 24.2 | 11%± |
| Factor VIII (%) | 50-200 | 94.8 ± 15.6 | 90.2 ± 16.3 | −5% ± 2% | 87.5 ± 12.2 | −7% ± 3% |
| Factor IX (%) | 50-200 | 99.4 ± 15 | 97.3 ± 14.4 | −2% ± 1% | 100.2 ± 11.3 | 1% ± 6% |
| Factor X (%) | 50-200 | 100.3 ± 15.1 | 103.3 ± 16.7 | 3% ± 2% | 101.4 ± 15.1 | 1% ± 1% |
| Factor XI (%) | 50-200 | 97.6 ± 11.6 | 94.4 ± 11.7 | −3% ± 1% | 93.3 ± 9.1 | −4% ± 2% |
| Factor XIII Activity (%) | 57-192 | 89.4 ± 7.9 | 90.2 ± 7.7 | 1% ± 715% | 91 ± 7.9 | 2%± |
| Factor XIII Antigen (%) | 75.2-154.8 | 73.8 ± 3.9 | 74.5 ± 4.2 | 1% ± 1% | 76.5 ± 3.5 | 4% ± 2% |
| Fibrinogen (mg/dL) | 150-400 | 230 ± 42 | 224 ± 28 | −2% ± 9% | 225 ± 31 | −2% ± 5% |
| Plasminogen (%) | 70-150 | 105 ± 22 | 107 ± 20 | 2% ± 3% | 104 ± 22 | −1% ± 1% |
| Plasmin Inhibitor (%) | 85-156 | 89 ± 11 | 89 ± 11 | 0% ± 0% | 90 ± 14 | 1% ± 3% |
| Protein C (%) | 75-150 | 91 ± 17 | 93 ± 18 | 1% ± 1% | 94 ± 20 | 2% ± 2% |
| Protein S (%) | 60-150 | 109.2 ± 0.3 | 95.8 ± 1.2 | −12% ± 2% | 89.5 ± 10.3 | −18% ± 9% |
| Antithrombin III (%) | 80-120 | 81 ± 5 | 81 ± 7 | −1% ± 3% | 81 ± 9 | −1% ± 5% |
| von Willebrand Factor Activity | 50-200 | 54 ± 19 | 55 ± 20 | 3% ± 3% | 56 ± 18 | 5% ± 4% |
| von Willebrand Factor Antigen (%) | 50-200 | 110.3 ± 27.1 | 111.7 ± 27.3 | 1% ± 3% | 109.6 ± 25.7 | 0% ± 2% |
| von Willebrand Factor Ristocetin Cofactor (%) | 50-200 | 33.5 ± 10.2 | 36.7 ± 11.1 | 10% ± 3% | 38.1 ± 11.1 | 14% ± 3% |
| C5a (ng/mL) | 4.7-74* | 33.2 ± 1 | 32.9 ± 1.5 | −1% ± 2% | 33.1 ± 1.9 | 0% ± 2% |
| Prothrombin Fragment F 1 + 2 (pmol/L) | 91-137 | 100.9 ± 46.5 | 89.4 ± 14.5 | −4% ± 26% | 78.8 ± 8 | −14% ± 28% |

TABLE 15-continued

Unit assay results at each timepoint stored at room temperature and compared to the t = 0 hours value.

| | | | | | | |
|---|---|---|---|---|---|---|
| Thrombin-Antithrombin Complex (TAT) (μg/L) | 0-4 | 1.77 ± 0.71 | 1.85 ± 0.94 | 0% ± 17% | 1.78 ± 1.11 | −2% ± 34% |

| Assays | Clinical Reference Range | T = 20 hours after rehydration Mean ± SD | % Change from t = 0 to t = 20 hours Mean ± SD | T = 23 hours after rehydration Mean ± SD | % Change from t = 0 to t = 23 hours Mean ± SD | T = 26 hours after rehydration Mean ± SD | % Change from t = 0 to t = 26 hours Mean ± SD |
|---|---|---|---|---|---|---|---|
| aPTT (s) | 22-35 | 28.0 ± 1.1 | −2% ± 1% | 27.8 ± 1.2 | −7% ± 8% | 28.3 ± 1.2 | 0% ± 1% |
| Prothrombin Time (s) | 10-14 | 11.9 ± 0.8 | −3% ± 3% | 11.7 ± 0.9 | −3% ± 2% | 11.9 ± 0.7 | −2% ± 0% |
| INR (s) | 0.9-1.1 | 1.0 ± 0.1 | −3% ± 2% | 0.9 ± 0.1 | −3% ± 2% | 0.9 ± 0.1 | −2% ± 1% |
| Thrombin Time (s) | 14.5-20.5 | 19.2 ± 2.5 | 1% ± 4% | 19.1 ± 2.6 | 1% ± 2% | 19.1 ± 2.4 | 1% ± 3% |
| Factor V (%) | 50-200 | 83.9 ± 11.4 | −2% ± 2% | 80.3 ± 12.4 | −4% ± 1% | 79.6 ± 11.1 | −3% ± 3% |
| Factor VII (%) | 50-200 | 98.5 ± 24.2 | 14% ± 3% | 101.3 ± 24.8 | 16% ± 6% | 109.9 ± 26.3 | 24% ± 3% |
| Factor VIII (%) | 50-200 | 87.5 ± 12.2 | −12% ± 3% | 83.5 ± 14.7 | −16% ± 8% | 73.9 ± 14.2 | −22% ± 5% |
| Factor IX (%) | 50-200 | 100.2 ± 11.3 | −1% ± 5% | 97.6 ± 9.7 | 6% ± 6% | 105.2 ± 16.3 | 6% ± 4% |
| Factor X (%) | 50-200 | 101.4 ± 15.1 | 2% ± 1% | 102.7 ± 15.7 | 6% ± 3% | 104.0 ± 16.3 | 3% ± 2% |
| Factor XI (%) | 50-200 | 93.3 ± 9.1 | −9% ± 1% | 88.7 ± 10.3 | −1% ± 2% | 94.4 ± 13.9 | −3% ± 5% |
| Factor XIII Activity (%) | 57-192 | 91.0 ± 7.9 | 0% ± 2% | 88.8 ± 7.5 | −2% ± 2% | 87.7 ± 10.2 | −2% ± 3% |
| Factor XIII Antigen (%) | 75.2-154.8 | 76.5 ± 3.5 | 0% ± 1% | 74.0 ± 3.0 | 2% ± 4% | 75.2 ± 3.9 | 2% ± 3% |
| Fibrinogen (mg/dL) | 150-400 | 225 ± 31 | −2% ± 11% | 226 ± 50 | 0% ± 9% | 225 ± 40 | −2% ± 2% |
| Plasminogen (%) | 70-150 | 104 ± 22 | 0% ± 2% | 106 ± 20 | −1% ± 2% | 104 ± 19 | −1% ± 3% |
| Plasmin Inhibitor (%) | 85-156 | 90 ± 14 | −1% ± 4% | 88 ± 13 | 0% ± 3% | 87 ± 9 | −2% ± 3% |
| Protein C (%) | 75-150 | 94 ± 20 | −2% ± 3% | 90 ± 19 | −1% ± 2% | 91 ± 19 | 0% ± 2% |
| Protein S (%) | 60-150 | 89.5 ± 10.3 | −33% ± 11% | 72.6 ± 12.2 | −39% ± 15% | 62.0 ± 15.6 | −43% ± 14% |
| Antithrombin III (%) | 80-120 | 81 ± 9 | −4% ± 7% | 78 ± 9 | −3% ± 6% | 78 ± 10 | −4% ± 6% |
| von Willebrand Factor Activity | 50-200 | 55.9 ± 18.0 | 3% ± 7% | 54.4 ± 16.8 | 3% ± 6% | 53.3 ± 18.8 | 0% ± 2% |
| von Willebrand Factor Antigen (%) | 50-200 | 109.6 ± 25.7 | 2% ± 5% | 111.7 ± 25.4 | 3% ± 5% | 111.5 ± 26.6 | 1% ± 3% |
| von Willebrand Factor Ristocetin Cofactor (%) | 50-200 | 38.1 ± 11.1 | 20% ± 2% | 40.1 ± 12.3 | 13% ± 7% | 37.3 ± 12.0 | 11% ± 2% |
| C5a (ng/mL) | 4.7-74* | 33.10 ± 1.90 | −6% ± 2% | 31.10 ± 1.80 | −9% ± 5% | 31.20 ± 2.70 | −6% ± 5% |
| Prothrombin Fragment F 1 + 2 (pmol/L) | 91-137 | 78.8 ± 8.0 | −21% ± 17% | 80.6 ± 40.5 | −13% ± 14% | 77.8 ± 22.5 | −18% ± 20% |
| Thrombin-Antithrombin Complex (TAT) (μg/L) | 0-4 | 1.78 ± 1.11 | 14% ± 30% | 1.93 ± 0.74 | 42% ± 50% | 2.60 ± 0.89 | 51% ± 15% |

| Assays | T = 0 hours after rehydration Mean ± SD | T = 5 hours after rehydration Mean ± SD | T = 8 hours after rehydration Mean ± SD | T = 20 hours after rehydration Mean ± SD | T = 23 hours after rehydration Mean ± SD | T = 26 hours after rehydration Mean ± SD |
|---|---|---|---|---|---|---|
| pH | 7.12 ± 0.29 | 7.15 ± 0.3 | 7.15 ± 0.29 | 7.15 ± 0.3 | 7.15 ± 0.3 | 7.16 ± 0.28 |
| Total Protein | 5.12 ± 0.13 | 5.24 ± 0.07 | 5.27 ± 0.09 | 5.27 ± 0.09 | 5.30 ± 0.12 | 5.28 ± 0.10 |
| Osmo | 373 ± 6 | 371 ± 10 | 370 ± 11 | 370 ± 11 | 372 ± 12 | 373 ± 9 |

*clinical reference range reported for apheresed plasma

FXIII antigen at t=0, 5, 23, and 26 was slightly below the clinical reference range, but all FXIII activity means were within the clinical reference range. Assay values for FXIII and FXIII antigen were consistent across all timepoints.

ATIII at t=23 and 26 was slightly below the clinical reference range but assay values were consistent across all timepoints.

vWF activity and vWF:RCo means were below the clinical reference range, but vWF antigen means were within the clinical reference range.

C5a is within the reference range reported for apheresed plasma of 4.9-74 ng/mL.

PF1+2 is below the clinical reference range at all timepoints other than t=0 and is not indicative of activation. Assay values are consistent across all timepoints.

Conclusion

The reconstituted dried plasma of the present invention is comparable to starting plasma (e.g. FFP, PF24, PF24RT24, NFP, thawed plasma and liquid plasma) up to 26 hours post reconstitution and at both refrigeration or room temperature and has clotting factor levels of concentration and activity that are essentially the same as FFP.

Example 5: Unit Stability

Scope:

Spray dry plasma units (also referred to herein as "Frontline ODP" Units) were manufactured from pooled plasma frozen within 24 hours (PF24) containing citrate phosphate dextrose (CPD) anticoagulant on the system of the present invention. Frontline ODP Units were compared to paired control plasma at various storage conditions and time points listed in the below table. Pooled plasma was manufactured for each storage condition. Three (3) sets of FrontlineODP Units were manufactured from pooled PF24 plasma, to obtain a total of n=3 for each time point.

Definitions:

Anticoagulant Citrate Phosphate Dextrose Solution (CPD)—a sterile solution of Citric Acid, Sodium Citrate, Monobasic Sodium Phosphate, and Dextrose in Water for Injection. It contains, in each 1000 ml, NLT 2.11 g and NMT 2.33 g of monobasic sodium phosphate ($NaH_2PO_4*H_2O$); NLT 24.22 g and NMT 26.78 g of dextrose ($C_6H_{12}O_6*H_2O$); NLT 19.16 g and NMT 21.18 g of total citrate, expressed as anhydrous citric acid ($C_6H_8O_7$); and NLT 6.21 g and NMT 6.86 g of Sodium (Na). It contains no antimicrobial preservatives.

Plasma frozen within 24 hours-plasma frozen within 24 hours after phlebotomy is prepared from a whole blood or apheresis collection. The anticoagulant solution used and the component volume are indicated on the label.

Control Plasma—an aliquot of starting plasma frozen at the time of spray drying intended to be tested in parallel with Frontline ODP Unit as a paired control.

Methods and Materials

Materials:

After storage for the prescribed times and conditions described below each dried unit was subjected to testing as described in the table below. Assays were conducted in accordance with the manufacturer's instructions.

12) 3 Additional pools of 5-6 units to obtain no less than 2400 mL of pooled plasma will be prepared as extras.
13) Assign test batch numbers to pools.
14) Store thawed PF24 at 1-6° C. until ready to pretreat.
   i. Each pool will be split into eight plasma pretreatment containers and identified with a sub-batch (A, B, C, D, E, F, G, H). The remaining PF24 from the pool will be used to prepare at least 16 aliquots of control plasma (~4 mL) in cyro-vials.
   ii. Each sub-batch is pretreated by transferring 266 mL of plasma into the plasma pretreatment container. The pretreated plasma should be processed on the Frontline Dryer within 4 hours of pretreatment.
15) Manufacture pooled Frontline ODP Units (n=8) on the Frontline Dryers.
16) Record the Frontline Dryer Number, Date, Time, and Operator's initials.
17) Store the paired control aliquots prepared in step 4a at ≤−18° C. at the end of the drying the 4$^{th}$ pooled Unit.
18) Package spray dried plasma of each Frontline ODP Unit in Frontline Sealer
19) Place a Frontline ODP Unit and desiccant into the overwrap pouch. Seal the overwrap pouch above the 1$^{st}$ tear notches with the overwrap sealer.
20) Store Frontline ODP Unit in the fridge for 7 days.
21) Open the FrontlineODP overwrap pouch, keep the desiccant in the overwrap pouch, remove the FrontlineODP Unit and leave on the bench for 5 minutes.
22) Place the FrontlineODP Unit back into the overwrap pouch containing the desiccant and reseal.

TABLE 16

Stability tests:

| Assay | Instrument/Reagent Manufacturer |
|---|---|
| pH | Accumet AAB150 Fisher Scientific Danvers Ma USA |
| Total Protein | Selectra ProM EliTech Group Paris France |
| Factor V activity (%) | ACL TOP 700 Instrumentation Laboratories Boston |
| Factor VII activity (%) | ACL TOP 700 Instrumentation Laboratories Boston |
| Factor VIII activity (%) | ACL TOP 700 Instrumentation Laboratories Boston |
| Factor IX activity (%) | ACL TOP 700 Instrumentation Laboratories Boston |
| Factor X activity (%) | ACL TOP 700 Instrumentation Laboratories Boston |
| Factor XI activity (%) | ACL TOP 700 Instrumentation Laboratories Boston |
| Factor XIII antigen (%) | ACL TOP 700 Instrumentation Laboratories Boston |
| Fibrinogen (QFA) | ACL TOP 700 Instrumentation Laboratories Boston |
| Thrombin Time (TT) (s) | ACL TOP 700 Instrumentation Laboratories Boston |
| aPTT (s) | ACL TOP 700 Instrumentation Laboratories Boston |
| Prothrombin Time PT (s) | ACL TOP 700 Instrumentation Laboratories Boston |
| Protein C activity (PC) (%) | ACL TOP 700 Instrumentation Laboratories Boston |
| Protein S activity (PS) (%) | ACL TOP 700 Instrumentation Laboratories Boston |
| Anti thrombin III activity (AT LIQ) (%) | ACL TOP 700 Instrumentation Laboratories Boston MA USA |
| vWF Ag (%) | ACL TOP 700 Instrumentation Laboratories Boston |
| Plasmin Inhibitor (%) | ACL TOP 700 Instrumentation Laboratories Boston |
| Plasminogen(%) | ACL TOP 700 Instrumentation Laboratories Boston |
| VWF: RCo (%) | BCS XP Siemens Healthineers Boston MA USA |
| FXIII activity (%) | BCS XP Siemens Healthineers Boston MA USA |
| Prothrombin Fragment 1 + 2 (PF1 + 2) (pmol/L) | ELISA Siemens Healthineers Boston MA USA |
| Thrombin Anti-Thrombin (TAT) (μg/L) | ELISA Siemens Healthineers Boston MA USA |
| C5a (ng/ml) | ELISA |

Methods:

11) Pool 8-9 units of PF24 into a 3000 mL empty container to obtain no less than 2,720 mL of pooled plasma. 12 pools in total (3 for Refrigeration, 3 total for Room Temperature, Low Excursion, and High Excursion, 3 for Combination Storage, and 3 for Intermediate Storage). N=3 at each time point.

23) From each pooled FrontlineODP Units, package FrontlineODP Units on wet ice and control plasma aliquots on dry ice to ship to for storage.
24) Note that this study is continuing for refrigerated storage at time points of 30 months, 36 months and 48 months, and for room temperature storage at Room Temperature (20-25° C.). The testing described herein will occur for these samples at these and possibly additional time points. For time points 30, 36 and 48 months in refrigeration; a total of 6 units will be used, 2 at each time point (N=2). For the 12-month time point at room temperature, 2 units will be used as well. The methods described herein will be used. In addition to the methods described herein, the age of some of the samples may be accelerated by storing the sample at 30° C.

TABLE 17

| Single Temperature Storage Condition | | |
|---|---|---|
| Storage Condition | Duration | Number of FrontlineODP Units |
| Refrigeration (2-8° C.) | 3 months | 3 |
| | 6 months | 3 |
| | 9 months | 3 |
| | 12 months | 3 |
| | 18 months | 3 |
| | 24 months | 3 |
| | 30 months | 2*results to be provided |
| | 36 months | 2*results to be provided |
| | 48 months | 2*results to be provided |
| Room Temperature (20-25° C.) | 1 month | 3 |
| | 3 months | 3 |
| | 4 months | 3 |
| | 5 months | 3 |
| | 6 months | 3 |
| | 12 months | 2*results to be provided |
| Room Temperature (30° C.) | 15 days | 3 |
| | 1 month | 3 |
| | 2 months | 3 |
| | 3 months | 3 |

TABLE 18

| Combination Storage and Excursion Storage Condition | | | | |
|---|---|---|---|---|
| Storage Condition #1 | Duration | Number of Frontline ODP Units | Storage Condition #2 | Testing at Timepoints |
| Refrigeration (1-6° C.) | 13 months | 18 | Room Temperature (20-25° C.) | 0 month<br>13 months<br>13 + 1 month<br>13 + 4 months<br>13 + 6 months |
| −80° C. | 24 hours | 3 | Room Temperature (20-25° C.) | 3 months |
| 35° C. | 24 hours | 3 | Room Temperature (20-25° C.) | 3 months |

Testing

Samples were retrieved from storage condition at the appropriate timepoint and rehydrated after the storage duration indicated had been met.

The corresponding control plasma aliquot was simultaneously thawed.

Stability testing was completed as described above. All FrontlineODP Unit testing was conducted in parallel with control plasma aliquots. Time 0 for each pool was tested.

Results

The results of the above-described testing of shelf life of the dried plasma of the present invention are described in the tables below.

TABLE 19

Pooled Stability at refrigeration 1-6° C., n = 3, % change compared to t = 0 Refrigeration (1-6° C.) at 0, 3, 6, 9, 12, 19 and 24 months.

| Pooled refrigeration (1-6° C.) | Clinical Reference Range | t = 0 CP Mean ± SD | t = 0 ODP Mean ± SD | 3 month CP Mean ± SD | 3 month ODP Mean ± SD | 3 month % Change compared to t = 0 |
|---|---|---|---|---|---|---|
| aPTT (s) | (22-35) | 26.3 ± 1.1 | 28.0 ± 2.6 | 27.2 ± 1.2 | 28.6 ± 1.5 | 2% |
| Prothrombin Time (s) | (10-14) | 11.3 ± 0.1 | 12.5 ± 0.4 | 11.6 ± 0.2 | 13.2 ± 0.2 | 5% |
| INR | (0.9-1.1) | 0.90 ± 0.01 | 1.00 ± 0.03 | 0.92 ± 0.02 | 1.06 ± 0.02 | 5% |
| Thrombin Time (s) | (14.5-20.5) | 13.5 ± 0.4 | 17.8 ± 0.5 | 12.6 ± 0.3 | 17.2 ± 0.2 | −3% |
| Fibrinogen (mg/dL) | (150-400) | 279 ± 23 | 256 ± 3 | 290 ± 9 | 259 ± 12 | 1% |
| Factor V Act (%) | (50-200) | 118 ± 3 | 108 ± 4 | 97 ± 1 | 86 ± 6 | −20% |
| Factor VII Act (%) | (50-200) | 101 ± 7 | 86 ± 5 | 91 ± 6 | 75 ± 7 | −13% |
| Factor VIII Act (%) | (50-200) | 120 ± 22 | 92 ± 14 | 110 ± 8 | 77 ± 5 | −15% |
| Factor IX Act (%) | (50-200) | 93 ± 21 | 92 ± 8 | 107 ± 2 | 97 ± 5 | 6% |
| Factor X Act (%) | (50-200) | 93 ± 4 | 82 ± 5 | 86 ± 3 | 72 ± 2 | −11% |
| Factor XI Act (%) | (50-200) | 109 ± 7 | 92 ± 9 | 118 ± 12 | 107 ± 4 | 17% |
| Factor XIII Act (%) | (57-192) | 133 ± 19 | 110 ± 8 | 129 ± 16 | 116 ± 3 | 6% |
| Factor XIII Ant (%) | (75.2-154.8) | 128 ± 12 | 108 ± 5 | 134 ± 13 | 112 ± 13 | 3% |
| Protein C Act (%) | (75-150) | 107 ± 7 | 100 ± 9 | 114 ± 8 | 100 ± 6 | 0% |
| Protein S Act (%) | (60-150) | 99 ± 4 | 88 ± 7 | 96 ± 8 | 80 ± 2 | −9% |
| Antithrombin III Act (%) | (80-120) | 98 ± 3 | 91 ± 4 | 95 ± 3 | 86 ± 3 | −6% |
| Plasminogen (%) | (70-150) | 84 ± 5 | 81 ± 6 | 93 ± 4 | 88 ± 6 | 9% |
| Plasmin Inhibitor (%) | (85-156) | 97 ± 1 | 95 ± 3 | 103 ± 2 | 96 ± 3 | 0% |
| von Willebrand Factor Ristocetin Cofactor (%) | (50-200) | 136 ± 14 | 55 ± 5 | 128 ± 14 | 50 ± 2 | −9% |
| von Willebrand Factor Antigen (%) | (50-200) | 145 ± 25 | 138 ± 12 | 137 ± 7 | 141 ± 7 | 3% |
| Thrombin-Antithrombin Complex (μg/L) | (0-4) | 3.2 ± 1.9 | 3.3 ± 1.8 | 3.4 ± 1.8 | 3.3 ± 1.6 | 2% |

TABLE 19-continued

Pooled Stability at refrigeration 1-6° C., n = 3, % change compared to t = 0 Refrigeration (1-6° C.) at 0, 3, 6, 9, 12, 19 and 24 months.

| | | | | | | |
|---|---|---|---|---|---|---|
| Prothrombin Fragment F 1 + 2 (pmol/L) | (91-137) | 86 ± 20 | 93 ± 14 | 83 ± 20 | 87 ± 19 | −7% |
| C5a (ng/mL) | (4.7-74*) | 7.7 ± 0.5 | 33.4 ± 5.3 | 7.3 ± 0.7 | 37.8 ± 9.0 | 14% |

| | | 6 month | | | 9 month | | |
|---|---|---|---|---|---|---|---|
| Pooled refrigeration (1-6° C.) | Clinical Reference Range | CP Mean ± SD | ODP Mean ± SD | % Change compared to t = 0 | CP Mean ± SD | ODP Mean ± SD | % Change compared to t = 0 |
| aPTT (s) | (22-35) | 25.7 ± 0.9 | 28.8 ± 2.2 | 3% | 26.3 ± 1.1 | 29.6 ± 2.4 | 6% |
| PT (s) | (10-14) | 11.5 ± 0.2 | 12.5 ± 0.1 | 0% | 11.3 ± 0.1 | 13.3 ± 0.3 | 6% |
| INR | (0.9-1.1) | 0.91 ± 0.01 | 1.00 ± 0.01 | 0% | 0.90 ± 0.01 | 1.07 ± 0.03 | 6% |
| TT (s) | (14.5-20.5) | 13.8 ± 0.4 | 17.2 ± 0.7 | −3% | 13.5 ± 0.4 | 17.4 ± 0.4 | −2% |
| Fib (mg/dL) | (150-400) | 270 ± 7 | 226 ± 23 | −11% | 279 ± 23 | 205 ± 12 | −20% |
| FV Act (%) | (50-200) | 106 ± 3 | 94 ± 6 | −13% | 118 ± 3 | 79 ± 2 | −27% |
| FVII Act (%) | (50-200) | 93 ± 7 | 84 ± 8 | −3% | 101 ± 7 | 70 ± 3 | −19% |
| FVIII Act (%) | (50-200) | 108 ± 10 | 83 ± 5 | −9% | 120 ± 22 | 76 ± 12 | −18% |
| FIX Act (%) | (50-200) | 104 ± 1 | 88 ± 2 | −4% | 93 ± 21 | 91 ± 12 | −1% |
| FX Act (%) | (50-200) | 92 ± 2 | 80 ± 2 | −2% | 93 ± 4 | 74 ± 7 | −10% |
| FXI Act (%) | (50-200) | 117 ± 16 | 96 ± 9 | 4% | 109 ± 7 | 98 ± 12 | 7% |
| FXIII Act (%) | (57-192) | 142 ± 13 | 119 ± 8 | 8% | 133 ± 19 | 111 ± 5 | 1% |
| FXIII Ant (%) | (75.2-154.8) | 127 ± 18 | 112 ± 13 | 3% | 128 ± 12 | 108 ± 4 | −1% |
| PC Act (%) | (75-150) | 110 ± 8 | 103 ± 4 | 4% | 107 ± 7 | 101 ± 13 | 1% |
| PS Act (%) | (60-150) | 100 ± 8 | 86 ± 2 | −2% | 99 ± 4 | 77 ± 9 | −13% |
| AT III Act (%) | (80-120) | 100 ± 2 | 95 ± 3 | 4% | 98 ± 3 | 85 ± 7 | −7% |
| PLG (%) | (70-150) | 88 ± 3 | 84 ± 5 | 4% | 84 ± 5 | 86 ± 7 | 6% |
| PI (%) | (85-156) | 97 ± 3 | 96 ± 1 | 1% | 97 ± 1 | 98 ± 5 | 3% |
| vWF:RCo (% or IU/dL) | (50-200) | 113 ± 19 | 42 ± 14 | −24% | 136 ± 14 | 46 ± 4 | −17% |
| vWF Ant (% or IU/dL) | (50-200) | 167 ± 34 | 162 ± 11 | 18% | 145 ± 25 | 142 ± 21 | 3% |
| TAT (μg/L) | (0-4) | 6.4 ± 2.6 | 6.8 ± 2.4 | 122% | 3.2 ± 1.9 | 6.3 ± 3.5 | 97% |
| PF1 + 2 (pmol/L) | (91-137) | 175 ± 14 | 200 ± 7 | 116% | 86 ± 20 | 248 ± 35 | 166% |
| C5a (ng/mL) | (4.7-74*) | 7.4 ± 0.6 | 38.7 ± 10.2 | 15% | 7.7 ± 0.5 | 31.5 ± 6.3 | −4% |

| | | 12 month | | | 19 month | | |
|---|---|---|---|---|---|---|---|
| Pooled refrigeration (1-6° C.) | Clinical Reference Range | CP Mean ± SD | ODP Mean ± SD | % Change compared to t = 0 | CP Mean ± SD | ODP Mean ± SD | % Change compared to t = 0 |
| aPTT (s) | (22-35) | 26.6 ± 0.9 | 30.0 ± 2.5 | 7% | 26.2 ± 1.2 | 31.5 ± 2.3 | 13% |
| PT (s) | (10-14) | 11.5 ± 0.1 | 12.6 ± 0.4 | 1% | 11.6 ± 0.2 | 13.1 ± 0.2 | 5% |
| INR | (0.9-1.1) | 0.92 ± 0.01 | 1.00 ± 0.03 | 0% | 0.92 ± 0.01 | 1.04 ± 0.02 | 3% |
| TT (s) | (14.5-20.5) | 13.3 ± 0.3 | 16.9 ± 0.4 | −5% | 12.7 ± 0.2 | 17.4 ± 0.6 | −2% |
| Fib (mg/dL) | (150-400) | 274 ± 22 | 222 ± 13 | −13% | 292 ± 17 | 219 ± 12 | −14% |
| FV Act (%) | (50-200) | 108 ± 1 | 99 ± 3 | −9% | 94 ± 1 | 80 ± 4 | −26% |
| FVII Act (%) | (50-200) | 79 ± 6 | 70 ± 4 | −19% | 97 ± 6 | 80 ± 6 | −7% |
| FVIII Act (%) | (50-200) | 102 ± 10 | 76 ± 12 | −17% | 108 ± 11 | 73 ± 5 | −20% |
| FIX Act (%) | (50-200) | 110 ± 7 | 90 ± 5 | −1% | 111 ± 6 | 81 ± 6 | −12% |
| FX Act (%) | (50-200) | 92 ± 2 | 77 ± 8 | −6% | 92 ± 3 | 75 ± 2 | −8% |
| FXI Act (%) | (50-200) | 120 ± 8 | 107 ± 10 | 16% | 111 ± 12 | 85 ± 5 | −8% |
| FXIII Act (%) | (57-192) | 144 ± 25 | 117 ± 8 | 7% | 144 ± 18 | 111 ± 12 | 1% |
| FXIII Ant (%) | (75.2-154.8) | 127 ± 13 | 117 ± 2 | 8% | 115 ± 11 | 99 ± 11 | −9% |
| PC Act (%) | (75-150) | 110 ± 5 | 101 ± 15 | 1% | 114 ± 9 | 95 ± 9 | −4% |
| PS Act (%) | (60-150) | 94 ± 7 | 79 ± 11 | −11% | 98 ± 6 | 79 ± 4 | −10% |
| AT III Act (%) | (80-120) | 95 ± 2 | 85 ± 8 | −7% | 94 ± 3 | 79 ± 4 | −13% |
| PLG (%) | (70-150) | 87 ± 6 | 85 ± 5 | 5% | 91 ± 4 | 83 ± 5 | 2% |
| PI (%) | (85-156) | 105 ± 0 | 100 ± 5 | 5% | 98 ± 2 | 87 ± 4 | −8% |
| vWF:RCo (% or IU/dL) | (50-200) | 122 ± 21 | 48 ± 4 | −13% | 123 ± 21 | 41 ± 2 | −25% |
| vWF Ant (% or IU/dL) | (50-200) | 145 ± 24 | 152 ± 32 | 9% | 140 ± 11 | 139 ± 10 | 1% |
| TAT (μg/L) | (0-4) | 4.1 ± 2.0 | 4.1 ± 2.3 | 24% | 5.6 ± 3.2 | 5.5 ± 2.7 | 74% |
| PF1 + 2 (pmol/L) | (91-137) | 181 ± 23 | 200 ± 28 | 115% | 143 ± 21 | 155 ± 5 | 68% |
| C5a (ng/mL) | (4.7-74*) | 6.2 ± 0.6 | 30.1 ± 5.5 | −8% | 7.7 ± 0.6 | 34.9 ± 3.8 | 5% |

| | | 24 month | | |
|---|---|---|---|---|
| Pooled refrigeration (1-6° C.) | Clinical Reference Range | CP Mean ± SD | ODP Mean ± SD | % Change compared to t = 0 |
| aPTT (s) | (22-35) | 26.7 ± 1.1 | 31.4 ± 2.5 | 12% |
| PT (s) | (10-14) | 11.1 ± 0.2 | 12.5 ± 0.3 | 0% |
| INR | (0.9-1.1) | 0.88 ± 0.01 | 0.99 ± 0.02 | −1% |
| TT (s) | (14.5-20.5) | 13.2 ± 0.4 | 18.4 ± 0.4 | 4% |
| Fib (mg/dL) | (150-400) | 298 ± 14 | 217 ± 17 | −15% |
| FV Act (%) | (50-200) | 106 ± 3 | 91 ± 10 | −17% |
| FVII Act (%) | (50-200) | 109 ± 12 | 93 ± 8 | 7% |

TABLE 19-continued

Pooled Stability at refrigeration 1-6° C., n = 3, % change compared to t = 0 Refrigeration (1-6° C.) at 0, 3, 6, 9, 12, 19 and 24 months.

| | | | | |
|---|---|---|---|---|
| FVIII Act (%) | (50-200) | 125 ± 4 | 87 ± 5 | −4% |
| FIX Act (%) | (50-200) | 111 ± 1 | 88 ± 6 | −3% |
| FX Act (%) | (50-200) | 109 ± 3 | 90 ± 7 | 11% |
| FXI Act (%) | (50-200) | 115 ± 3 | 96 ± 1 | 5% |
| FXIII Act (%) | (57-192) | 140 ± 16 | 104 ± 13 | −6% |
| FXIII Ant (%) | (75.2-154.8) | 114 ± 15 | 95 ± 7 | −12% |
| PC Act (%) | (75-150) | 116 ± 9 | 99 ± 7 | −1% |
| PS Act (%) | (60-150) | 105 ± 3 | 87 ± 5 | −2% |
| AT III Act (%) | (80-120) | 97 ± 4 | 83 ± 7 | −9% |
| PLG (%) | (70-150) | 87 ± 5 | 80 ± 7 | −1% |
| PI (%) | (85-156) | 84 ± 2 | 77 ± 6 | −19% |
| vWF:RCo (% or IU/dL) | (50-200) | 138 ± 31 | 47 ± 1 | −14% |
| vWF Ant (% or IU/dL) | (50-200) | 143 ± 10 | 150 ± 8 | 9% |
| TAT (μg/L) | (0-4) | 5.1 ± 2.3 | 4.9 ± 2.7 | 44% |
| PF1 + 2 (pmol/L) | (91-137) | 182 ± 38 | 204 ± 26 | 119% |
| C5a (ng/mL) | (4.7-74*) | 9.0 ± 0.8 | 37.9 ± 2.1 | 16% |

| Pooled refrigeration (1-6° C.) | Clinical Reference range | t = 0 CP Mean ± SD | t = 0 ODP Mean ± SD | 3 month CP Mean ± SD | 3 month ODP Mean ± SD |
|---|---|---|---|---|---|
| pH | (7.35-7.45) | 7.4 ± 0.0 | 7.0 ± 0.0 | 7.5 ± 0.1 | 7.1 ± 0.0 |
| Protein (mg/mL) | (6-8.3) | 5.5 ± 0.1 | 5.4 ± 0.3 | 5.5 ± 0.1 | 5.3 ± 0.2 |
| Osmolality (mOsm/kg) | (>240) | 309 ± 1 | 384 ± 17 | 312 ± 1 | 375 ± 11 |

| Pooled refrigeration (1-6° C.) | Clinical Reference range | 6 month CP Mean ± SD | 6 month ODP Mean ± SD | 9 month CP Mean ± SD | 9 month ODP Mean ± SD | 12 month CP Mean ± SD | 12 month ODP Mean ± SD |
|---|---|---|---|---|---|---|---|
| pH | (7.35-7.45) | 7.2 ± 0.0 | 7.1 ± 0.1 | 7.4 ± 0.0 | 7.1 ± 0.1 | 7.4 ± 0.0 | 7.1 ± 0.0 |
| Protein (mg/mL) | (6-8.3) | 5.4 ± 0.1 | 5.3 ± 0.1 | 5.5 ± 0.1 | 5.2 ± 0.4 | 5.4 ± 0.1 | 5.3 ± 0.4 |
| Osmolality (mOsm/kg) | (>240) | 313 ± 4 | 389 ± 11 | 309 ± 1 | 368 ± 24 | 311 ± 3 | 373 ± 27 |

| Pooled refrigeration (1-6° C.) | Clinical Reference range | 19 month CP Mean ± SD | 19 month ODP Mean ± SD | 24 month CP Mean ± SD | 24 month ODP Mean ± SD |
|---|---|---|---|---|---|
| pH | (7.35-7.45) | 7.5 ± 0.0 | 7.1 ± 0.0 | 7.5 ± 0.0 | 7.2 ± 0.0 |
| Protein (mg/mL) | (6-8.3) | 5.6 ± 0.1 | 5.2 ± 0.2 | 5.7 ± 0.1 | 5.4 ± 0.3 |
| Osmolality (mOsm/kg) | (>240) | 310 ± 2 | 354 ± 6 | 312 ± 1 | 369 ± 23 |

*clinical reference range reported for apheresed plasma vWF:RCo is below the normal reference range. However, despite decreased levels of vWF:RCo, vWF is functional, as evidenced by the presence of clot formation. Pursuant to Examples 9 and 10, functional clot formation assays including data from Bioflux testing, Thromboelastography TEG study and a thrombin generation (calibrated automated thrombogram (CAT) study surprisingly demonstrates effective clot formation similar to that of fresh frozen plasma including measures of clot time, clot rate, and clot strength. In this example, it was demonstrated that even though the vWF multimer is sheared into smaller multimers, the clotting function of vWF remains intact. vWF:RCo assay measures higher molecular weight multimer TAT is outside of the clinical reference range but is not indicative of activation.

PF1+2 is outside of the clinical reference range but manufacturer reports that plasma stored longer than 6 months at −60° C. is not suitable for the assay.

C5a is within the reference range reported for apheresed plasma of 4.9-74 ng/mL.

The reconstituted dried plasma of the present invention is comparable to starting plasma (e.g., PF24, FFP, PF24RT24, NFP, thawed plasma and liquid plasma) and has clotting factor levels of concentration and activity that are essentially the same as FFP.

TABLE 20

Pooled Stability at room temp (20-25° C.), n = 3, % change compared to t = 0 Room Temperature (20-25° C.) at 1, 3, 4, 5 and 6 months.

| Pooled room temperature (20-25° C.) | Clinical Reference range | t = 0 CP Mean ± SD | t = 0 ODP Mean ± SD | 1 Month CP Mean ± SD | 1 Month ODP Mean ± SD | 1 Month % Change compared to t = 0 |
|---|---|---|---|---|---|---|
| aPTT (s) | (22-35) | 27.5 ± 0.5 | 29.7 ± 1.0 | 28.5 ± 0.6 | 30.8 ± 1.0 | 4% |
| PT (s) | (10-14) | 11.6 ± 0.1 | 13.0 ± 0.4 | 11.8 ± 0.2 | 13.1 ± 0.4 | 1% |

TABLE 20-continued

Pooled Stability at room temp (20-25° C.), n = 3, % change compared to t = 0 Room Temperature (20-25° C.) at 1, 3, 4, 5 and 6 months.

| | | | | | | |
|---|---|---|---|---|---|---|
| INR | (0.9-1.1) | 0.92 ± 0.01 | 1.04 ± 0.04 | 0.94 ± 0.02 | 1.05 ± 0.03 | 1% |
| TT (s) | (14.5-20.5) | 13.2 ± 0.6 | 16.9 ± 1.0 | 13.7 ± 0.6 | 18.0 ± 1.0 | 7% |
| Fib (mg/dL) | (150-400) | 266 ± 24 | 269 ± 26 | 260 ± 23 | 226 ± 17 | −16% |
| FV Act (%) | (50-200) | 100 ± 6 | 90 ± 3 | 101 ± 7 | 91 ± 3 | 1% |
| FVII Act (%) | (50-200) | 91 ± 2 | 79 ± 3 | 87 ± 3 | 78 ± 5 | −1% |
| FVIII Act (%) | (50-200) | 113 ± 16 | 81 ± 10 | 112 ± 20 | 82 ± 13 | 0% |
| FIX Act (%) | (50-200) | 104 ± 4 | 94 ± 9 | 102 ± 8 | 85 ± 7 | −9% |
| FX Act (%) | (50-200) | 94 ± 4 | 79 ± 2 | 89 ± 7 | 76 ± 4 | −3% |
| FXI Act (%) | (50-200) | 114 ± 10 | 108 ± 16 | 122 ± 7 | 106 ± 7 | 0% |
| FXIII Act (%) | (57-192) | 117 ± 20 | 110 ± 9 | 123 ± 12 | 111 ± 18 | 2% |
| FXIII Ant (%) | (75.2-154.8) | 124 ± 12 | 107 ± 8 | 117 ± 15 | 104 ± 9 | −3% |
| PC Act (%) | (75-150) | 110 ± 4 | 101 ± 2 | 110 ± 4 | 101 ± 3 | 0% |
| PS Act (%) | (60-150) | 110 ± 5 | 91 ± 5 | 110 ± 8 | 91 ± 1 | 0% |
| AT III Act (%) | (80-120) | 93 ± 3 | 86 ± 5 | 96 ± 7 | 86 ± 3 | 0% |
| PLG (%) | (70-150) | 91 ± 2 | 86 ± 5 | 87 ± 2 | 87 ± 6 | 1% |
| PI (%) | (85-156) | 104 ± 3 | 98 ± 2 | 103 ± 4 | 99 ± 3 | 1% |
| vWF:RCo (% or IU/dL) | (50-200) | 105 ± 26 | 41 ± 9 | 114 ± 28 | 45 ± 11 | 11% |
| vWF Ant (% or IU/dL) | (50-200) | 141 ± 35 | 135 ± 21 | 134 ± 34 | 141 ± 36 | 4% |
| TAT (μg/L) | (0-4) | 1.9 ± 0.2 | 2.3 ± 0.6 | 1.6 ± 0.2 | 1.5 ± 0.5 | −35% |
| PF1 + 2 (pmol/L) | (91-137) | 83 ± 11 | 87 ± 2 | 86 ± 7 | 98 ± 4 | 13% |
| C5a (ng/mL) | (4.7-74*) | 7.1 ± 0.3 | 35.8 ± 11.2 | 7.1 ± 0.5 | 33.9 ± 11.2 | −5% |

| | | 3 Months | | | 4 Months | | |
|---|---|---|---|---|---|---|---|
| Pooled room temperature (20-25° C.) | Clinical Reference range | CP Mean ± SD | ODP Mean ± SD | % Change compared to t = 0 | CP Mean ± SD | ODP Mean ± SD | % Change compared to t = 0 |
| aPTT (s) | (22-35) | 27.8 ± 0.3 | 33.9 ± 1.9 | 14% | 27.3 ± 0.7 | 33.0 ± 0.5 | 11% |
| PT (s) | (10-14) | 11.5 ± 0.1 | 13.5 ± 0.5 | 4% | 11.8 ± 0.2 | 13.6 ± 0.2 | 5% |
| INR | (0.9-1.1) | 0.91 ± 0.01 | 1.08 ± 0.05 | 4% | 0.94 ± 0.02 | 1.09 ± 0.02 | 5% |
| TT (s) | (14.5-20.5) | 13.2 ± 0.3 | 18.8 ± 1.1 | 11% | 13.5 ± 0.8 | 19.7 ± 0.9 | 17% |
| Fib (mg/dL) | (150-400) | 294 ± 28 | 183 ± 1 | −31% | 269 ± 34 | 189 ± 13 | −30% |
| FV Act (%) | (50-200) | 100 ± 6 | 82 ± 2 | −9% | 91 ± 6 | 80 ± 6 | −11% |
| FVII Act (%) | (50-200) | 91 ± 3 | 75 ± 3 | −5% | 85 ± 2 | 74 ± 3 | −6% |
| FVIII Act (%) | (50-200) | 106 ± 21 | 66 ± 14 | −19% | 119 ± 23 | 74 ± 23 | −10% |
| FIX Act (%) | (50-200) | 106 ± 4 | 75 ± 4 | −20% | 105 ± 6 | 88 ± 9 | −7% |
| FX Act (%) | (50-200) | 90 ± 5 | 70 ± 3 | −11% | 90 ± 5 | 73 ± 2 | −8% |
| FXI Act (%) | (50-200) | 110 ± 8 | 93 ± 6 | −13% | 115 ± 8 | 106 ± 12 | −1% |
| FXIII Act (%) | (57-192) | 132 ± 15 | 91 ± 16 | −17% | 133 ± 18 | 97 ± 16 | −11% |
| FXIII Ant (%) | (75.2-154.8) | 120 ± 12 | 100 ± 12 | −7% | 127 ± 18 | 116 ± 16 | 8% |
| PC Act (%) | (75-150) | 110 ± 1 | 93 ± 3 | −8% | 114 ± 3 | 102 ± 0 | 1% |
| PS Act (%) | (60-150) | 100 ± 7 | 82 ± 9 | −10% | 92 ± 4 | 79 ± 4 | −13% |
| AT III Act (%) | (80-120) | 96 ± 6 | 80 ± 4 | −8% | 98 ± 4 | 88 ± 4 | 2% |
| PLG (%) | (70-150) | 85 ± 4 | 80 ± 9 | −7% | 95 ± 3 | 92 ± 4 | 8% |
| PI (%) | (85-156) | 108 ± 3 | 95 ± 6 | −3% | 99 ± 2 | 91 ± 2 | −7% |
| vWF:RCo (% or IU/dL) | (50-200) | 116 ± 26 | 40 ± 8 | −2% | 108 ± 27 | 42 ± 9 | 3% |
| vWF Ant (% or IU/dL) | (50-200) | 153 ± 53 | 140 ± 26 | 4% | 148 ± 46 | 143 ± 24 | 6% |
| TAT (μg/L) | (0-4) | 1.8 ± 0.4 | 1.9 ± 0.1 | −16% | 1.4 ± 0.4 | 1.6 ± 0.4 | −30% |
| PF1 + 2 (pmol/L) | (91-137) | 78 ± 9 | 97 ± 18 | 12% | 75 ± 7 | 97 ± 7 | 12% |
| C5a (ng/mL) | (4.7-74*) | 8.4 ± 0.4 | 37.9 ± 10.2 | 10% | 7.1 ± 0.4 | 30.7 ± 4.7 | −9% |

| | | 5 Months | | | 6 Months | | |
|---|---|---|---|---|---|---|---|
| ooled room temperature (20-25° C.) | Clinical Reference range | CP Mean ± SD | ODP Mean ± SD | % Change compared to t = 0 | CP Mean ± SD | ODP Mean ± SD | % Change compared to t = 0 |
| aPTT (s) | (22-35) | 27.8 ± 0.2 | 34.8 ± 1.3 | 17% | 26.8 ± 0.7 | 37.7 ± 2.7 | 27% |
| PT (s) | (10-14) | 11.8 ± 0.2 | 13.8 ± 0.3 | 7% | 11.8 ± 0.1 | 14.1 ± 0.5 | 9% |
| INR | (0.9-1.1) | 0.94 ± 0.02 | 1.12 ± 0.03 | 7% | 0.94 ± 0.01 | 1.14 ± 0.04 | 9% |
| TT (s) | (14.5-20.5) | 13.3 ± 0.3 | 20.6 ± 0.8 | 22% | 13.5 ± 0.6 | 20.3 ± 0.5 | 21% |
| Fib (mg/dL) | (150-400) | 277 ± 9 | 177 ± 6 | −34% | 277 ± 28 | 181 ± 15 | −32% |
| FV Act (%) | (50-200) | 90 ± 7 | 76 ± 7 | −16% | 84 ± 6 | 69 ± 1 | −24% |
| FVII Act (%) | (50-200) | 89 ± 6 | 72 ± 4 | −8% | 88 ± 2 | 72 ± 2 | −8% |
| FVIII Act (%) | (50-200) | 105 ± 17 | 66 ± 15 | −20% | 107 ± 22 | 59 ± 8 | −28% |
| FIX Act (%) | (50-200) | 110 ± 9 | 80 ± 2 | −15% | 115 ± 8 | 81 ± 9 | −13% |
| FX Act (%) | (50-200) | 85 ± 3 | 69 ± 6 | −13% | 92 ± 5 | 70 ± 1 | −12% |
| FXI Act (%) | (50-200) | 122 ± 10 | 95 ± 8 | −11% | 120 ± 8 | 87 ± 4 | −18% |
| FXIII Act (%) | (57-192) | 135 ± 23 | 92 ± 12 | −16% | 138 ± 21 | 90 ± 15 | −18% |
| FXIII Ant (%) | (75.2-154.8) | 125 ± 20 | 109 ± 15 | 1% | 116 ± 16 | 110 ± 18 | 2% |
| PC Act (%) | (75-150) | 111 ± 3 | 99 ± 3 | −2% | 110 ± 1 | 96 ± 6 | −5% |
| PS Act (%) | (60-150) | 104 ± 7 | 93 ± 3 | 2% | 105 ± 7 | 86 ± 6 | −6% |
| AT III Act (%) | (80-120) | 99 ± 3 | 86 ± 2 | −1% | 101 ± 6 | 85 ± 11 | −1% |
| PLG (%) | (70-150) | 95 ± 4 | 91 ± 6 | 7% | 87 ± 3 | 82 ± 3 | −4% |
| PI (%) | (85-156) | 104 ± 5 | 99 ± 3 | 1% | 103 ± 2 | 93 ± 4 | −5% |
| vWF:RCo (% or IU/dL) | (50-200) | 105 ± 30 | 40 ± 10 | −3% | 105 ± 25 | 39 ± 5 | −3% |

TABLE 20-continued

Pooled Stability at room temp (20-25° C.), n = 3, % change compared to t = 0 Room Temperature (20-25° C.) at 1, 3, 4, 5 and 6 months.

| | | | | | | | |
|---|---|---|---|---|---|---|---|
| vWF Ant (% or IU/dL) | (50-200) | 157 ± 48 | 159 ± 51 | 15% | 143 ± 42 | 131 ± 19 | −3% |
| TAT (μg/L) | (0-4) | 4.5 ± 1.1 | 3.9 ± 2.9 | 66% | 2.0 ± 0.6 | 2.9 ± 0.5 | 30% |
| PF1 + 2 (pmol/L) | (91-137) | 141 ± 22 | 193 ± 42 | 124% | 137 ± 10 | 225 ± 75 | 162% |
| C5a (ng/mL) | (4.7-74*) | 7.2 ± 0.3 | 33.9 ± 7.6 | −2% | 6.9 ± 0.2 | 39.9 ± 4.5 | 17% |

| Pooled room temperature (20-25° C.) | Clinical Reference range | t = 0 CP Mean ± SD | t = 0 ODP Mean ± SD | 1 Month CP Mean ± SD | 1 Month ODP Mean ± SD |
|---|---|---|---|---|---|
| pH | (7.35-7.45) | 7.4 ± 0.1 | 7.1 ± 0.1 | 7.3 ± 0.0 | 7.2 ± 0.1 |
| Protein (mg/mL) | (6-8.3) | 5.66 ± 0.15 | 5.50 ± 0.21 | 5.53 ± 0.19 | 5.62 ± 0.28 |
| Osmolality (mOsm/kg) | (>240) | 314 ± 1 | 380 ± 18 | 320 ± 4 | 386 ± 14 |

| Pooled room temperature (20-25° C.) | Clinical Reference range | 3 Months CP Mean ± SD | 3 Months ODP Mean ± SD | 4 Months CP Mean ± SD | 4 Months ODP Mean ± SD |
|---|---|---|---|---|---|
| pH | (7.35-7.45) | 7.5 ± 0.0 | 7.2 ± 0.1 | 7.3 ± 0.0 | 7.0 ± 0.1 |
| Protein (mg/mL) | (6-8.3) | 5.62 ± 0.15 | 5.30 ± 0.25 | 5.66 ± 0.14 | 5.75 ± 0.13 |
| Osmolality (mOsm/kg) | (>240) | 312 ± 2 | 360 ± 23 | 312 ± 1 | 394 ± 2 |

| Pooled room temperature (20-25° C.) | Clinical Reference range | 5 Months CP Mean ± SD | 5 Months ODP Mean ± SD | 6 Months CP Mean ± SD | 6 Months ODP Mean ± SD |
|---|---|---|---|---|---|
| pH | (7.35-7.45) | 7.5 ± 0.0 | 7.1 ± 0.1 | 7.4 ± 0.0 | 7.1 ± 0.1 |
| Protein (mg/mL) | (6-8.3) | 5.80 ± 0.17 | 5.79 ± 0.20 | 5.31 ± 0.15 | 5.29 ± 0.17 |
| Osmolality (mOsm/kg) | (>240) | 314 ± 1 | 385 ± 16 | 314 ± 4 | 375 ± 24 |

*clinical reference range reported for apheresed plasma aPTT is slightly outside of the clinical reference range. aPTT is prolonged due to FVIII reduction.

PT is slightly outside of the clinical reference range by 0.1 second.

INR is slightly outside of the clinical reference range by 0.04 due to the slight prolongation of PT.

vWF:RCo is below the normal reference range. However, as described above, despite decreased levels of vWF:RCo, vWF is functional and results in normal clot formation.

PF1+2 is outside of the clinical reference range but manufacturer reports that plasma stored longer than 6 months at −60° C. is not suitable for the assay.

C5a is within the reference range reported for apheresed plasma of 4.9-74 ng/mL.

The reconstituted dried plasma of the present invention is comparable to starting plasma (e.g., PF24, FFP, PF24RT24, NFP, thawed plasma and liquid plasma) and has clotting factor levels of concentration and activity that are essentially the same as FFP.

TABLE 21

Pooled Stability at Combination Refrigerated and Room Temperature Storage, n = 3, % change compared to t = 013 months at refrigerated temperature followed by, 1, 4, and 6 months at room temperature.

| Combination refrigeration (1-6° C.) followed by room temp (20-25° C.) | Clinical Reference range | t = 0 CP Mean ± SD | t = 0 ODP Mean ± SD | 13 months CP Mean ± SD | 13 months ODP Mean ± SD | 13 months % Change Compared to t = 0 |
|---|---|---|---|---|---|---|
| aPTT (s) | (22-35) | 27.8 ± 1.1 | 28.1 ± 1.2 | 26.1 ± 1.1 | 30.6 ± 2.2 | 9% |
| PT (s) | (10-14) | 11.5 ± 0.3 | 12.5 ± 0.3 | 11.5 ± 0.4 | 12.6 ± 0.1 | 1% |
| INR | (0.9-1.1) | 0.92 ± 0.03 | 1.00 ± 0.03 | 0.91 ± 0.03 | 1.00 ± 0.01 | 0% |
| TT (s) | (14.5-20.5) | 12.5 ± 0.1 | 16.7 ± 0.4 | 13.9 ± 0.3 | 17.8 ± 0.6 | 7% |
| Fib (mg/dL) | (150-400) | 309 ± 15 | 264 ± 8 | 301 ± 23 | 227 ± 13 | −14% |
| FV Act (%) | (50-200) | 98 ± 5 | 95 ± 10 | 103 ± 9 | 95 ± 2 | 1% |
| FVII Act (%) | (50-200) | 101 ± 4 | 89 ± 2 | 89 ± 4 | 78 ± 3 | −13% |
| FVIII Act (%) | (50-200) | 113 ± 25 | 85 ± 21 | 100 ± 30 | 71 ± 26 | −18% |
| FIX Act (%) | (50-200) | 126 ± 7 | 101 ± 6 | 102 ± 1 | 86 ± 1 | −15% |
| FX Act (%) | (50-200) | 99 ± 5 | 87 ± 6 | 98 ± 2 | 78 ± 6 | −9% |
| FXI Act (%) | (50-200) | 122 ± 7 | 102 ± 9 | 98 ± 6 | 89 ± 7 | 13% |
| FXIII Act (%) | (57-192) | 109 ± 4 | 114 ± 6 | 115 ± 5 | 96 ± 3 | −15% |
| FXIII Ant (%) | (75.2-154.8) | 113 ± 3 | 99 ± 7 | 106 ± 0 | 97 ± 8 | −1% |
| PC Act (%) | (75-150) | 119 ± 6 | 108 ± 9 | 116 ± 3 | 102 ± 10 | −5% |
| PS Act (%) | (60-150) | 109 ± 8 | 93 ± 6 | 103 ± 9 | 86 ± 7 | −8% |
| AT III Act (%) | (80-120) | 96 ± 4 | 90 ± 11 | 97 ± 5 | 89 ± 6 | −1% |

TABLE 21-continued

Pooled Stability at Combination Refrigerated and Room Temperature Storage, n = 3, % change compared to t = 013 months at refrigerated temperature followed by, 1, 4, and 6 months at room temperature.

| | | | | | | |
|---|---|---|---|---|---|---|
| PLG (%) | (70-150) | 95 ± 6 | 92 ± 10 | 87 ± 6 | 83 ± 6 | −10% |
| PI (%) | (85-156) | 106 ± 4 | 101 ± 8 | 111 ± 4 | 102 ± 5 | 2% |
| vWF:RCo (% or IU/dL) | (50-200) | 112 ± 39 | 44 ± 5 | 118 ± 44 | 44 ± 9 | −1% |
| vWF Ant (% or IU/dL) | (50-200) | 158 ± 49 | 151 ± 42 | 156 ± 50 | 157 ± 51 | 3% |
| TAT (μg/L) | (0-4) | 3.0 ± 1.4 | 3.4 ± 1.9 | 3.4 ± 2.1 | 3.7 ± 1.9 | 12% |
| PF1 + 2 (pmol/L) | (91-137) | 87 ± 15 | 96 ± 13 | 146 ± 30 | 165 ± 33 | 74% |
| C5a (ng/ml) | (4.7-74*) | 6.3 ± 0.9 | 36.1 ± 4.7 | 6.3 ± 0.6 | 34.9 ± 11.8 | −4% |

| Combination refrigeration (1-6° C.) followed by room temp (20-25° C.) | Clinical Reference range | 13 months + 1 month CP Mean ± SD | 13 months + 1 month ODP Mean ± SD | 13 months + 1 month % Change Compared to t = 0 | 13 month + 4 months CP Mean ± SD | 13 month + 4 months ODP Mean ± SD | 13 month + 4 months % Change Compared to t = 0 |
|---|---|---|---|---|---|---|---|
| aPTT (s) | (22-35) | 26.6 ± 1.3 | 32.1 ± 2.5 | 14% | 27.2 ± 0.9 | 39.5 ± 3.6 | 40% |
| PT (s) | (10-14) | 11.5 ± 0.2 | 12.9 ± 0.1 | 3% | 11.6 ± 0.3 | 13.9 ± 0.9 | 11% |
| INR | (0.9-1.1) | 0.91 ± 0.01 | 1.02 ± 0.01 | 2% | 0.92 ± 0.03 | 1.10 ± 0.07 | 10% |
| TT (s) | (14.5-20.5) | 13.5 ± 0.1 | 18.4 ± 1.1 | 10% | 12.8 ± 0.3 | 20.9 ± 1.8 | 25% |
| Fib (mg/dL) | (150-400) | 302 ± 10 | 236 ± 15 | −10% | 294 ± 6 | 175 ± 18 | −34% |
| FV Act (%) | (50-200) | 89 ± 7 | 81 ± 3 | −14% | 88 ± 5 | 72 ± 8 | −24% |
| FVII Act (%) | (50-200) | 83 ± 2 | 73 ± 2 | −18% | 102 ± 8 | 85 ± 6 | −5% |
| FVIII Act (%) | (50-200) | 110 ± 30 | 73 ± 23 | −15% | 106 ± 25 | 60 ± 23 | −31% |
| FIX Act (%) | (50-200) | 105 ± 1 | 85 ± 9 | −16% | 113 ± 8 | 73 ± 5 | −27% |
| FX Act (%) | (50-200) | 89 ± 4 | 77 ± 2 | 11% | 99 ± 7 | 76 ± 3 | −12% |
| FXI Act (%) | (50-200) | 104 ± 5 | 93 ± 5 | −9% | 115 ± 6 | 79 ± 3 | −22% |
| FXIII Act (%) | (57-192) | 117 ± 4 | 101 ± 4 | −12% | 121 ± 5 | 76 ± 8 | −33% |
| FXIII Ant (%) | (75.2-154.8) | 109 ± 1 | 107 ± 6 | 9% | 98 ± 4 | 91 ± 4 | −7% |
| PC Act (%) | (75-150) | 117 ± 2 | 108 ± 7 | 0% | 118 ± 4 | 96 ± 4 | −11% |
| PS Act (%) | (60-150) | 105 ± 6 | 93 ± 13 | 0% | 96 ± 6 | 85 ± 2 | −8% |
| AT III Act (%) | (80-120) | 97 ± 3 | 86 ± 3 | −4% | 96 ± 6 | 77 ± 6 | −14% |
| PLG (%) | (70-150) | 96 ± 8 | 93 ± 4 | 1% | 95 ± 8 | 90 ± 7 | −2% |
| PI (%) | (85-156) | 111 ± 4 | 105 ± 9 | 4% | 101 ± 5 | 92 ± 4 | −8% |
| vWF:RCo (% or IU/dL) | (50-200) | 118 ± 44 | 45 ± 11 | 2% | 113 ± 40 | 37 ± 6 | −16% |
| vWF Ant (% or IU/dL) | (50-200) | 158 ± 51 | 163 ± 53 | 7% | 165 ± 58 | 152 ± 57 | −2% |
| TAT (μg/L) | (0-4) | 2.7 ± 2.1 | 3.4 ± 2.2 | −3% | 4.2 ± 2.3 | 4.5 ± 1.6 | 45% |
| PF1 + 2 (pmol/L) | (91-137) | 117 ± 20 | 147 ± 23 | 56% | 105 ± 11 | 144 ± 24 | 54% |
| C5a (ng/ml) | (4.7-74*) | 6.5 ± 0.9 | 35.1 ± 8.0 | −3% | 6.4 ± 0.9 | 32.9 ± 8.7 | −10% |

| Combination refrigeration (1-6° C.) followed by room temp (20-25° C.) | Clinical Reference range | 13 month + 6 months CP Mean ± SD | 13 month + 6 months ODP Mean ± SD | 13 month + 6 months % Change Compared to t = 0 |
|---|---|---|---|---|
| aPTT (s) | (22-35) | 26.2 ± 1.3 | 40.9 ± 3.1 | 46% |
| PT (s) | (10-14) | 11.6 ± 0.4 | 14.3 ± 0.9 | 14% |
| INR | (0.9-1.1) | 0.92 ± 0.03 | 1.13 ± 0.07 | 13% |
| TT (s) | (14.5-20.5) | 13.8 ± 0.2 | 23.1 ± 2.3 | 38% |
| Fib (mg/dL) | (150-400) | 294 ± 4 | 159 ± 6 | −40% |
| FV Act (%) | (50-200) | 94 ± 4 | 74 ± 9 | −22% |
| FVII Act (%) | (50-200) | 98 ± 5 | 81 ± 5 | −8% |
| FVIII Act (%) | (50-200) | 102 ± 27 | 53 ± 21 | −39% |
| FIX Act (%) | (50-200) | 102 ± 8 | 69 ± 9 | −31% |
| FX Act (%) | (50-200) | 98 ± 3 | 73 ± 2 | −16% |
| FXI Act (%) | (50-200) | 93 ± 5 | 66 ± 5 | −35% |
| FXIII Act (%) | (57-192) | 121 ± 5 | 74 ± 8 | −35% |
| FXIII Ant (%) | (75.2-154.8) | 102 ± 3 | 93 ± 1 | −5% |
| PC Act (%) | (75-150) | 111 ± 4 | 95 ± 2 | −12% |
| PS Act (%) | (60-150) | 99 ± 9 | 87 ± 1 | −6% |
| AT III Act (%) | (80-120) | 98 ± 3 | 82 ± 8 | −8% |
| PLG (%) | (70-150) | 93 ± 6 | 91 ± 5 | −1% |
| PI (%) | (85-156) | 105 ± 5 | 97 ± 2 | −3% |
| vWF:RCo (% or IU/dL) | (50-200) | 112 ± 43 | 35 ± 10 | −21% |
| vWF Ant (% or IU/dL) | (50-200) | 165 ± 59 | 150 ± 55 | −2% |
| TAT (μg/L) | (0-4) | 5.6 ± 1.4 | 5.6 ± 0.9 | 91% |
| PF1 + 2 (pmol/L) | (91-137) | 131 ± 26 | 182 ± 27 | 93% |
| C5a (ng/ml) | (4.7-74*) | 6.7 ± 0.8 | 39.0 ± 9.3 | 7% |

TABLE 21-continued

Pooled Stability at Combination Refrigerated and Room Temperature Storage, n = 3, % change compared to t = 013 months at refrigerated temperature followed by, 1, 4, and 6 months at room temperature.

| Combination refrigeration (1-6° C.) followed by room temp (20-25° C.) | Clinical Reference range | t = 0 CP Mean ± SD | t = 0 ODP Mean ± SD | 13 months CP Mean ± SD | 13 months ODP Mean ± SD |
|---|---|---|---|---|---|
| pH | (7.35-7.45) | 7.5 ± 0.0 | 7.1 ± 0.0 | 7.3 ± 0.0 | 7.1 ± 0.0 |
| Protein (mg/ml) | (6-8.3) | 5.8 ± 0.1 | 5.7 ± 0.4 | 5.6 ± 0.3 | 5.8 ± 0.1 |
| Osmolality (mOsm/kg) | ( >240) | 315 ± 2 | 385 ± 20 | 316 ± 1 | 373 ± 24 |

| Combination refrigeration (1-6° C.) followed by room temp (20-25° C.) | Clinical Reference range | 13 months + 1 month CP Mean ± SD | 13 months + 1 month ODP Mean ± SD | 13 months + 4 months CP Mean ± SD | 13 months + 4 months ODP Mean ± SD | 13 months + 6 months CP Mean ± SD | 13 months + 6 months ODP Mean ± SD |
|---|---|---|---|---|---|---|---|
| pH | (7.35-7.45) | 7.3 ± 0.1 | 7.1 ± 0.1 | 7.4 ± 0.0 | 7.1 ± 0.1 | 7.4 ± 0.0 | 7.4 ± 0.0 |
| Protein (mg/ml) | (6-8.3) | 5.7 ± 0.1 | 5.8 ± 0.3 | 5.9 ± 0.1 | 5.7 ± 0.1 | 5.7 ± 0.1 | 5.7 ± 0.1 |
| Osmolality (mOsm/kg) | ( >240) | 315 ± 1 | 394 ± 19 | 314 ± 2 | 372 ± 15 | 261 ± 91 | 261 ± 91 |

*clinical reference range reported for apheresed plasma aPTT is prolonged due to FVIII reduction.

TT is outside of the clinical reference range by 2.6 seconds and prolonged due to fibrinogen reduction. However, fibrinogen is within the clinical reference range.

vWF:RCo is below the normal reference range. However, as described above, despite decreased levels of vWF:RCo, vWF is functional and results in normal clot formation. Even at levels below 40% vWF:RCo, vWF is functional as demonstrated with Bioflux data shown in Examples 9 and 10. This is surprising.

TAT is slightly above the clinical reference range but not indicative of activation and is comparable to its paired control.

PF1+2 is outside of the clinical reference range but manufacturer reports that plasma stored longer than 6 months at −60° C. is not suitable for the assay.

C5a is within the reference range reported for apheresed plasma of 4.9-74 ng/mL.

The reconstituted dried plasma of the present invention is comparable to starting plasma (e.g., PF24, FFP, PF24RT24, NFP, thawed plasma and liquid plasma) and has clotting factor levels of concentration and activity that are essentially the same as FFP.

TABLE 22

Pooled Stability at Intermediate Room Temperature (30° C.), n = 3, % change compared to t = 0 Intermediate Room Temperature at 15 days, 1 and 3 months.

| Pooled 30° C. | Clinical Reference range | t = 0 CP Mean ± SD | t = 0 ODP Mean ± SD | 15 Days CP Mean ± SD | 15 Days ODP Mean ± SD | 15 Days % Change compared to t = 0 |
|---|---|---|---|---|---|---|
| aPTT (s) | (22-35) | 29.1 ± 1.4 | 30.8 ± 1.0 | 28.9 ± 1.3 | 32.3 ± 1.0 | 5% |
| PT (s) | (10-14) | 11.2 ± 0.3 | 11.9 ± 0.2 | 11.7 ± 0.3 | 13.1 ± 0.2 | 10% |
| INR | (0.9-1.1) | 0.89 ± 0.02 | 0.95 ± 0.02 | 0.94 ± 0.03 | 1.05 ± 0.02 | 10% |
| TT (s) | (14.5-20.5) | 13.4 ± 0.8 | 17.5 ± 0.7 | 13.5 ± 0.6 | 19.3 ± 1.0 | 10% |
| Fib (mg/dL) | (150-400) | 282 ± 26 | 254 ± 24 | 282 ± 41 | 211 ± 25 | −17% |
| FV Act (%) | (50-200) | 106 ± 7 | 104 ± 5 | 94 ± 8 | 86 ± 2 | −18% |
| FVII Act (%) | (50-200) | 100 ± 5 | 91 ± 8 | 87 ± 6 | 77 ± 4 | −16% |
| FVIII Act (%) | (50-200) | 97 ± 12 | 74 ± 12 | 91 ± 9 | 67 ± 9 | −8% |
| FIX Act (%) | (50-200) | 103 ± 9 | 92 ± 4 | 115 ± 6 | 96 ± 9 | 4% |
| FX Act (%) | (50-200) | 97 ± 6 | 89 ± 6 | 91 ± 1 | 76 ± 3 | −14% |
| FXI Act (%) | (50-200) | 111 ± 6 | 94 ± 7 | 126 ± 14 | 108 ± 9 | 14% |
| FXIII Act (%) | (57-192) | 118 ± 7 | 97 ± 5 | 116 ± 10 | 96 ± 13 | −1% |
| FXIII Ant (%) | (75.2-154.8) | 111 ± 8 | 102 ± 6 | 107 ± 8 | 103 ± 2 | 2% |
| PC Act (%) | (75-150) | 110 ± 3 | 105 ± 4 | 110 ± 3 | 100 ± 3 | −5% |
| PS Act (%) | (60-150) | 98 ± 7 | 90 ± 9 | 98 ± 4 | 87 ± 7 | −3% |
| AT III Act (%) | (80-120) | 92 ± 4 | 90 ± 4 | 2 ± 6 | 82 ± 2 | −8% |
| PLG (%) | (70-150) | 92 ± 4 | 92 ± 2 | 88 ± 3 | 87 ± 3 | −5% |
| PI (%) | (85-156) | 104 ± 2 | 102 ± 3 | 103 ± 1 | 100 ± 4 | −2% |
| vWF:RCo (% or IU/dL) | (50-200) | 97 ± 20 | 43 ± 4 | 92 ± 21 | 39 ± 1 | −9% |
| vWF Ant (% or IU/dL) | (50-200) | 123 ± 20 | 128 ± 22 | 123 ± 19 | 127 ± 20 | 0% |

TABLE 22-continued

Pooled Stability at Intermediate Room Temperature (30° C.), n = 3, % change compared to t = 0 Intermediate Room Temperature at 15 days, 1 and 3 months.

| | | | | | | |
|---|---|---|---|---|---|---|
| TAT (μg/L) | (0-4) | 3.3 ± 1.0 | 3.3 ± 1.1 | 2.4 ± 0.8 | 2.4 ± 1.0 | −28% |
| PF1 + 2 (pmol/L) | (91-137) | 98 ± 21 | 120 ± 28 | 98 ± 5 | 104 ± 13 | −9% |
| C5a (ng/ml) | (4.7-74*) | 6.8 ± 0.6 | 34.8 ± 1.9 | 6.1 ± 0.4 | 36.0 ± 2.4 | 4% |

| | | 1 months | | | 2 Months | | |
|---|---|---|---|---|---|---|---|
| Pooled 30° C. | Clinical Reference range | CP Mean ± SD | ODP Mean ± SD | % Change compared to t = 0 | CP Mean ± SD | ODP Mean ± SD | % Change compared to t = 0 |
| aPTT (s) | (22-35) | 28.5 ± 1.6 | 34.6 ± 1.6 | 12% | 28.5 ± 1.2 | 36.6 ± 2.0 | 19% |
| PT (s) | (10-14) | 11.5 ± 0.3 | 13.4 ± 0.3 | 13% | 11.6 ± 0.3 | 14.1 ± 0.3 | 18% |
| INR | (0.9-1.1) | 0.91 ± 0.03 | 1.08 ± 0.02 | 13% | 0.93 ± 0.02 | 1.14 ± 0.03 | 20% |
| TT (s) | (14.5-20.5) | 13.7 ± 0.5 | 20.2 ± 0.9 | 15% | 13.2 ± 0.5 | 22.2 ± 1.0 | 27% |
| Fib (mg/dL) | (150-400) | 278 ± 33 | 214 ± 28 | −16% | 303 ± 30 | 175 ± 10 | −31% |
| FV Act (%) | (50-200) | 96 ± 7 | 87 ± 3 | −16% | 92 ± 6 | 79 ± 2 | −24% |
| FVII Act (%) | (50-200) | 94 ± 6 | 77 ± 4 | −15% | 87 ± 6 | 73 ± 3 | −20% |
| FVIII Act (%) | (50-200) | 92 ± 14 | 61 ± 7 | −17% | 97 ± 13 | 61 ± 9 | −16% |
| FIX Act (%) | (50-200) | 110 ± 12 | 90 ± 2 | −3% | 110 ± 8 | 87 ± 7 | −6% |
| FX Act (%) | (50-200) | 87 ± 6 | 70 ± 3 | −21% | 84 ± 5 | 66 ± 5 | −26% |
| FXI Act (%) | (50-200) | 105 ± 13 | 94 ± 11 | −1% | 122 ± 11 | 96 ± 13 | 2% |
| FXIII Act (%) | (57-192) | 114 ± 8 | 90 ± 9 | −7% | 113 ± 9 | 78 ± 5 | −20% |
| FXIII Ant (%) | (75.2-154.8) | 110 ± 7 | 101 ± 2 | 0% | 107 ± 11 | 102 ± 3 | 0% |
| PC Act (%) | (75-150) | 110 ± 3 | 99 ± 4 | −5% | 113 ± 5 | 96 ± 1 | −8% |
| PS Act (%) | (60-150) | 107 ± 4 | 91 ± 8 | 1% | 107 ± 7 | 90 ± 7 | 0% |
| AT III Act (%) | (80-120) | 91 ± 6 | 80 ± 6 | −10% | 95 ± 1 | 80 ± 3 | −11% |
| PLG (%) | (70-150) | 90 ± 4 | 88 ± 5 | −4% | 84 ± 4 | 84 ± 2 | −8% |
| PI (%) | (85-156) | 108 ± 5 | 102 ± 6 | 0% | 102 ± 6 | 98 ± 3 | −4% |
| vWF:RCo (% or IU/dL) | (50-200) | 100 ± 23 | 38 ± 2 | −12% | 94 ± 22 | 34 ± 3 | −21% |
| vWF Ant (% or IU/dL) | (50-200) | 121 ± 19 | 125 ± 20 | −2% | 123 ± 16 | 125 ± 18 | −2% |
| TAT (μg/L) | (0-4) | 1.9 ± 1.4 | 2.1 ± 1.2 | −39% | 3.2 ± 1.2 | 3.3 ± 1.0 | −1% |
| PF1 + 2 (pmol/L) | (91-137) | 104 ± 9 | 113 ± 12 | −2% | 99 ± 5 | 110 ± 13 | −4% |
| C5a (ng/ml) | (4.7-74*) | 6.0 ± 0.2 | 31.8 ± 6.0 | −8% | 6.5 ± 0.5 | 33.6 ± 4.0 | −3% |

| | | 3 Months | | |
|---|---|---|---|---|
| Pooled 30° C. | Clinical Reference range | CP Mean ± SD | ODP Mean ± SD | % Change compared to t = 0 |
| aPTT (s) | (22-35) | 28.7 ± 1.2 | 39.4 ± 0.9 | 28% |
| PT (s) | (10-14) | 11.3 ± 0.2 | 14.3 ± 0.2 | 20% |
| INR | (0.9-1.1) | 0.90 ± 0.02 | 1.14 ± 0.03 | 20% |
| TT (s) | (14.5-20.5) | 13.1 ± 0.6 | 24.8 ± 1.1 | 42% |
| Fib (mg/dL) | (150-400) | 289 ± 27 | 155 ± 8 | −39% |
| FV Act (%) | (50-200) | 101 ± 8 | 81 ± 3 | −22% |
| FVII Act (%) | (50-200) | 96 ± 6 | 78 ± 7 | −15% |
| FVIII Act (%) | (50-200) | 93 ± 9 | 48 ± 5 | 34% |
| FIX Act (%) | (50-200) | 110 ± 6 | 74 ± 6 | −20% |
| FX Act (%) | (50-200) | 94 ± 4 | 71 ± 4 | −20% |
| FXI Act (%) | (50-200) | 115 ± 6 | 83 ± 6 | −12% |
| FXIII Act (%) | (57-192) | 116 ± 9 | 65 ± 10 | −33% |
| FXIII Ant (%) | (75.2-154.8) | 108 ± 5 | 101 ± 3 | 0% |
| PC Act (%) | (75-150) | 113 ± 3 | 95 ± 4 | −10% |
| PS Act (%) | (60-150) | 94 ± 4 | 83 ± 8 | −7% |
| AT III Act (%) | (80-120) | 93 ± 4 | 82 ± 6 | −9% |
| PLG (%) | (70-150) | 87 ± 3 | 86 ± 2 | −7% |
| PI (%) | (85-156) | 107 ± 3 | 99 ± 2 | −3% |
| VWF:RCo (% or IU/dL) | (50-200) | 94 ± 23 | 32 ± 5 | −27% |
| vWF Ant (% or IU/dL) | (50-200) | 130 ± 24 | 135 ± 31 | 5% |
| TAT (μg/L) | (0-4) | 2.9 ± 1.1 | 3.2 ± 0.9 | −4% |
| PF1 + 2 (pmol/L) | (91-137) | 102 ± 9 | 109 ± 7 | −6% |
| C5a (ng/ml) | (4.7-74*) | 7.4 ± 0.6 | 41.3 ± 5.5 | 19% |

TABLE 22-continued

Pooled Stability at Intermediate Room Temperature (30° C.), n = 3, % change compared to t = 0 Intermediate Room Temperature at 15 days, 1 and 3 months.

| Pooled 30° C. | Clinical Reference range | t = 0 CP Mean ± SD | t = 0 ODP Mean ± SD | 15 Days CP Mean ± SD | 15 Days ODP Mean ± SD |
|---|---|---|---|---|---|
| pH | (7.35-7.45) | 7.4 ± 0.0 | 7.0 ± 0.0 | 7.4 ± 0.0 | 6.9 ± 0.0 |
| Protein (mg/ml) | (6-8.3) | 5.56 ± 0.08 | 5.65 ± 0.09 | 5.53 ± 0.08 | 5.61 ± 0.09 |
| Osmolality (mOsm/kg) | ( >240) | 313 ± 2 | 397 ± 1 | 314 ± 2 | 395 ± 7 |

| Pooled 30° C. | Clinical Reference range | 1 months CP Mean ± SD | 1 months ODP Mean ± SD | 2 Months CP Mean ± SD | 2 Months ODP Mean ± SD | 3 Months CP Mean ± SD | 3 Months ODP Mean ± SD |
|---|---|---|---|---|---|---|---|
| pH | (7.35-7.45) | 7.4 ± 0.0 | 7.0 ± 0.1 | 7.5 ± 0.0 | 7.1 ± 0.0 | 7.5 ± 0.0 | 7.0 ± 0.1 |
| Protein (mg/mL) | (6-8.3) | 5.30 ± 0.04 | 5.37 ± 0.10 | 5.54 ± 0.05 | 5.71 ± 0.09 | 5.46 ± 0.08 | 5.64 ± 0.13 |
| Osmolality (mOsm/kg) | ( >240) | 311 ± 3 | 386 ± 7 | 312 ± 2 | 395 ± 10 | 311 ± 2 | 392 ± 10 |

*clinical reference range reported for apheresed plasma aPTT is prolonged due to FVIII reduction.

PT is slightly outside of the clinical reference range by 0.3 seconds.

INR is slightly outside of the clinical reference range by 0.04 due to prolonged PT.

TT is slightly outside of the clinical reference range.

vWF:RCo is below the normal reference range. However, as described above, despite decreased levels of vWF:RCo, vWF is functional as evidence by its contribution to clot formation.

C5a is within the reference range reported for apheresed plasma of 4.9-74 ng/mL.

The reconstituted dried plasma of the present invention is comparable to starting plasma (e.g., PF24, FFP, PF24RT24, NFP, thawed plasma and liquid plasma) and has clotting factor levels of concentration and activity that are essentially the same as FFP.

TABLE 23

Pooled Stability at Low and high excursion, n = 3, % change compared to t = 0 24 hours at 37° C. followed by 3 months room temp (20-25° C.) and 24 hours at −80° C. followed by 3 months room temp (20-25° C.).

| Pooled room temperature (20-25° C.) | Clinical Reference range | t = 0 CP Mean ± SD | t = 0 ODP Mean ± SD | High excursion + 3 months CP Mean ± SD | High excursion + 3 months ODP Mean ± SD | High excursion + 3 months % Change compared to t = 0 |
|---|---|---|---|---|---|---|
| aPTT (s) | (22-35) | 27.5 ± 0.5 | 29.7 ± 1.0 | 28.1 ± 0.6 | 32.7 ± 2.1 | 10% |
| PT (s) | (10-14) | 11.6 ± 0.1 | 13.0 ± 0.4 | 11.9 ± 0.2 | 13.4 ± 0.4 | 3% |
| INR | (0.9-1.1) | 0.92 ± 0.01 | 1.04 ± 0.04 | 0.95 ± 0.02 | 1.07 ± 0.04 | 3% |
| TT (s) | (14.5-20.5) | 13.2 ± 0.6 | 16.9 ± 1.0 | 13.8 ± 0.7 | 19.4 ± 0.6 | 15% |
| Fib (mg/dL) | (150-400) | 266 ± 24 | 269 ± 26 | 279 ± 27 | 209 ± 10 | −22% |
| FV Act (%) | (50-200) | 100 ± 6 | 90 ± 3 | 90 ± 8 | 81 ± 3 | −10% |
| FVII Act (%) | (50-200) | 91 ± 2 | 79 ± 3 | 90 ± 7 | 78 ± 1 | −1% |
| FVIII Act (%) | (50-200) | 113 ± 16 | 81 ± 10 | 94 ± 21 | 64 ± 4 | −21% |
| FIX Act (%) | (50-200) | 104 ± 4 | 94 ± 9 | 101 ± 7 | 77 ± 8 | −18% |
| FX Act (%) | (50-200) | 94 ± 4 | 79 ± 2 | 87 ± 10 | 74 ± 1 | −7% |
| FXI Act (%) | (50-200) | 114 ± 10 | 108 ± 16 | 120 ± 12 | 103 ± 4 | −2% |
| FXIII Act (%) | (57-192) | 117 ± 20 | 110 ± 9 | 122 ± 7 | 92 ± 28 | −15% |
| FXIII Ant (%) | (75.2-154.8) | 124 ± 12 | 107 ± 8 | 116 ± 12 | 107 ± 14 | −1% |
| PC Act (%) | (75-150) | 110 ± 4 | 101 ± 2 | 102 ± 4 | 98 ± 4 | −3% |
| PS Act (%) | (60-150) | 110 ± 5 | 91 ± 5 | 101 ± 7 | 90 ± 5 | −1% |
| AT III Act (%) | (80-120) | 93 ± 3 | 86 ± 5 | 93 ± 3 | 85 ± 8 | −1% |
| PLG (%) | (70-150) | 91 ± 2 | 86 ± 5 | 82 ± 7 | 82 ± 5 | −4% |
| PI (%) | (85-156) | 104 ± 3 | 98 ± 2 | 108 ± 1 | 104 ± 6 | 7% |
| vWF:RCo (% or IU/dL) | (50-200) | 105 ± 26 | 41 ± 9 | 109 ± 33 | 40 ± 4 | 1% |
| vWF Ant (% or IU/dL) | (50-200) | 141 ± 35 | 135 ± 21 | 152 ± 54 | 150 ± 18 | 10% |
| TAT (μg/L) | (0-4) | 1.9 ± 0.2 | 2.3 ± 0.6 | 1.4 ± 0.4 | 2.0 ± 0.4 | −10% |
| PF1 + 2 (pmol/L) | (91-137) | 83 ± 11 | 87 ± 2 | 73 ± 9 | 93 ± 19 | 8% |
| C5a (ng/ml) | (4.7-74*) | 7.1 ± 0.3 | 35.8 ± 11.2 | 7.3 ± 0.7 | 36.0 ± 9.7 | 2% |

TABLE 23-continued

Pooled Stability at Low and high excursion, n = 3, % change compared to t = 0 24 hours at 37° C. followed by 3 months room temp (20-25° C.) and 24 hours at −80° C. followed by 3 months room temp (20-25° C.).

| Pooled room temperature (20-25° C.) | Clinical Reference range | Low excursion + 3 months CP Mean ± SD | ODP Mean ± SD | % Change compared to t = 0 |
|---|---|---|---|---|
| aPTT (s) | (22-35) | 28.1 ± 0.6 | 32.1 ± 0.5 | 8% |
| PT (s) | (10-14) | 11.9 ± 0.2 | 13.3 ± 0.2 | 2% |
| INR | (0.9-1.1) | 0.95 ± 0.02 | 1.07 ± 0.02 | 3% |
| TT (s) | (14.5-20.5) | 13.8 ± 0.7 | 19.7 ± 0.4 | 17% |
| Fib (mg/dL) | (150-400) | 279 ± 27 | 206 ± 13 | −23% |
| FV Act (%) | (50-200) | 90 ± 8 | 85 ± 4 | −5% |
| FVII Act (%) | (50-200) | 90 ± 7 | 78 ± 2 | 0% |
| FVIII Act (%) | (50-200) | 94 ± 21 | 71 ± 6 | −12% |
| FIX Act (%) | (50-200) | 101 ± 7 | 80 ± 6 | −14% |
| FX Act (%) | (50-200) | 87 ± 10 | 78 ± 4 | −2% |
| FXI Act (%) | (50-200) | 120 ± 12 | 107 ± 14 | 0% |
| FXIII Act (%) | (57-192) | 122 ± 7 | 100 ± 23 | −8% |
| FXIII Ant (%) | (75.2-154.8) | 116 ± 12 | 108 ± 17 | 0% |
| PC Act (%) | (75-150) | 102 ± 4 | 98 ± 3 | −3% |
| PS Act (%) | (60-150) | 101 ± 7 | 94 ± 3 | 3% |
| AT III Act (%) | (80-120) | 93 ± 3 | 87 ± 6 | 1% |
| PLG (%) | (70-150) | 82 ± 7 | 84 ± 3 | −2% |
| PI (%) | (85-156) | 108 ± 1 | 109 ± 4 | 11% |
| vWF:RCo (% or IU/dL) | (50-200) | 109 ± 33 | 42 ± 6 | 5% |
| vWF Ant (% or IU/dL) | (50-200) | 152 ± 54 | 150 ± 26 | 11% |
| TAT (μg/L) | (0-4) | 1.4 ± 0.4 | 2.0 ± 0.4 | −12% |
| PF1 + 2 (pmol/L) | (91-137) | 73 ± 9 | 94 ± 17 | 9% |
| C5a (ng/ml) | (4.7-74*) | 7.3 ± 0.7 | 35.9 ± 4.6 | 6% |

| Pooled | | t = 0 | | High excursion + 3 months | | Low excursion + 3 months | |
|---|---|---|---|---|---|---|---|
| room temperature (20-25° C.) | Clinical Reference range | CP Mean ± SD | ODP Mean ± SD | CP Mean ± SD | ODP Mean ± SD | CP Mean ± SD | ODP Mean ± SD |
| pH | (7.35-7.45) | 7.4 ± 0.1 | 7.1 ± 0.1 | 7.5 ± 0.0 | 7.1 ± 0.1 | 7.5 ± 0.0 | 7.1 ± 0.1 |
| Protein (mg/mL) | (6-8.3) | 5.66 ± 0.15 | 5.50 ± 0.21 | 5.35 ± 0.33 | 5.49 ± 0.18 | 5.35 ± 0.33 | 5.59 ± 0.04 |
| Osmolality (mOsm/kg) | ( >240) | 314 ± 1 | 380 ± 18 | 303 ± 18 | 384 ± 25 | 303 ± 18 | 393 ± 4 |

*clinical reference range reported for apheresed plasma vWF:RCo is below the normal reference range. However, as described above, despite decreased levels of vWF:RCo, vWF is functional and results in normal clot formation.

C5a is within the reference range reported for apheresed plasma of 4.9-74 ng/mL.

The reconstituted dried plasma of the present invention is comparable to FFP and has clotting factor levels of concentration and activity that are essentially the same as FFP.

Conclusion

The reconstituted dried plasma of the present invention is comparable to starting plasma (e.g., PF24, FFP, PF24RT24, NFP, thawed plasma and liquid plasma) and has clotting factor levels of concentration and activity that are essentially the same as FFP.

Residual Moisture Stability Testing

During this study the residual moisture content of the dried plasma of the present invention was measured as follows. Residual moisture in dried plasma was determined with Karl Fischer titrator, Model No. C30S Compact KF Coulometer (Mettler Toledo Billerica Massachusetts USA). In this approach, the reagent and solvent were combined in the titration cell. When a sample was introduced into the titration cell and dissolved, reagent was released by the induction of an electrical current. The amount of current required to convert the water was the determinant of the amount of moisture.

Results

TABLE 24

Moisture Content Stability Study-Data

| Storage Condition | Timepoint (months) | Sample Size | Standard Deviation | Min | Max | Mean Moisture Content (%) |
|---|---|---|---|---|---|---|
| N/A | 0 | 20 | 0.14 | 1.16 | 1.7 | 1.46 |
| 1-6° C. | 3 | 3 | 0.43 | 1.32 | 2.08 | 1.58 |
| | 12 | 3 | 0.02 | 1.32 | 1.35 | 1.33 |
| | 24 | 3 | 0.18 | 1.22 | 1.57 | 1.36 |
| 20-25° C. | 3 | 3 | 0.01 | 1.2 | 1.22 | 1.21 |
| | 6 | 3 | 0.07 | 1.13 | 1.27 | 1.21 |
| | 12 (extra) | 3 | 0.08 | 1.19 | 1.34 | 1.24 |
| 1-6° C. + 20-25° C. | 12 + 6 | 3 | 0.03 | 1.19 | 1.24 | 1.21 |

Mean t=0 data was 1.46%, with a maximum of 1.70%. This meets the design requirement of mean moisture content <2%.

Shelf-life samples maintained a mean moisture content of <2%.

Conclusion

The dried plasma of the present invention maintains a low residual moisture between 1% and 2% in storage for a variety of time periods at a variety of conditions.

Example 6 ACD-A and CP2D Comparability

The in vitro characterization data demonstrate that the manufacturing effects of the system are comparable between units spray dried with different starting materials. Units spray dried from apheresed plasma (ACD-A anti-coagulation treatment) showed similar percent change due to manufacturing effects on the starting material as compared to units spray dried from whole blood derived plasma (CPD anti-coagulation treatment). A statistical analysis (ANOVA) was performed on the percent change pre and post spray drying between the two starting materials across 20 assays including clotting times, coagulation function, and activation markers. Of the 20 assays, total protein concentration, PT, TT, and Factor VIII and XIII activities were determined to be statistically significantly different, however, the mean percent change is similar, and the mean values are all within the clinical reference range.

The manufacturing/spray drying effect of the system on the starting material was determined by calculating the change between the unit and its paired control plasma (CP) for each of the assay.

$$\text{Mean \% change} = \frac{1}{13}\sum_{i=1}^{13}\frac{FrontlineODP_i - \text{Control Plasma}_i}{\text{Control Plasma}_i}\times 100$$

Total protein concentration was 5.34 g/dL for apheresed plasma (−2% change) compared to 5.42 g/dL for whole blood plasma (−4% change). Although the ANOVA indicated a statistical significance, the total protein concentration is comparable and percent change for spray dried units spray dried from both starting materials are within 4%.

The percent change for clotting times PT and TT showed a statistically significant difference between units spray dried from apheresed plasma and whole blood plasma. However, the mean PT is similar for apheresed plasma (13.1 seconds) and whole blood plasma (12.5 seconds). These values are well within the normal reference range. The mean TT is similar for apheresed plasma (19.6 seconds) and whole blood plasma (17.2 seconds). Both values are within the normal reference range.

A statistically significant difference in percent change was observed for coagulation factors Factor VIII and Factor XIII activities. The percent change for Factor VIII activity was 24% and 18% for apheresed and whole blood plasma, respectively, and the mean values are within the normal reference range. The percent change for Factor XIII activity for apheresed plasma is 21% and 15% for whole blood plasma and mean values are also within the normal reference range.

In summary, the in vitro test results support the conclusion that the manufacturing/spray drying impact on both apheresed and whole blood plasma is comparable, and the coagulation profile is within ±20% of their paired control or within the normal reference range. This data also supports that plasma having CP2D anticoagulation treatment will be comparably impacted by spray drying manufacturing.

TABLE 25

Summary of characterization data for ACD-A and CPD plasma

| Assay | Clinical Range Reference | Unit Value (Mean ± 1 SD) Apheresed ACD-A Plasma | Unit Value (Mean ± 1 SD) Whole Blood CPD Plasma | Percent Change compared to Control (Mean ± 1 SD) Apheresed ACD-A Plasma | Percent Change compared to Control (Mean ± 1 SD) Whole Blood CPD Plasma | p-value |
|---|---|---|---|---|---|---|
| pH | (7.35-7.45) | 7.11 ± 0.18 | 7.04 ± 0.14 | NA | NA | NA |
| Total Protein (g/dl) | (6-8.3) | 5.34 ± 0.42 | 5.42 ± 0.38 | −2% ± 4% | −4% ± 4% | 0.026 |
| Osmolality (mOsm/kg) | (280-296) | 366 ± 13 | 377 ± 17 | 366 ± 13 | 377 ± 17 | NS |
| aPTT (s) | (22-35) | 29.1 ± 4.2 | 30.8 ± 4.0 | 2% ± 7% | 2% ± 8% | NS |
| Prothrombin Time (s) | (10-14) | 13.1 ± 0.6 | 12.5 ± 0.8 | 11% ± 3% | 7% ± 3% | 0.000 |
| Thrombin Time (s) | (14.5-20.5) | 19.6 ± 0.9 | 17.2 ± 1.3 | 25% ± 7% | 34% ± 9% | 0.003 |
| Factor V (%) | (50-200) | 102.9 ± 11.4 | 92.6 ± 15.9 | −6% ± 6% | −2% ± 7% | NS |
| Factor VII (%) | (50-200) | 84.8 ± 16.0 | 80.6 ± 16.2 | −14% ± 5% | −11% ± 6% | NS |
| Factor VIII (%) | (50-200) | 89.4 ± 26.9 | 78.1 ± 28.9 | −24% ± 5% | −18% ± 11% | 0.043 |
| Factor XIII Activity (%) | (57-192) | 84.3 ± 13.3 | 103.9 ± 20.9 | −21% ± 9% | −15% ± 8% | 0.014 |
| Factor XIII Antigen (%) | (75.2-154.8) | 87.5 ± 9.7 | 94.0 ± 17.1 | −12% ± 4% | −11% ± 6% | NS |
| Fibrinogen (mg/dL) | (150-400) | 233 ± 32 | 241 ± 48 | −12% ± 6% | −10% ± 8% | NS |
| Protein C (%) | (75-150) | 100 ± 14 | 100 ± 17 | −7% ± 5% | −9% ± 4% | NS |
| Protein S (%) | (57-155) | 86.3 ± 6.2 | 85.6 ± 14.7 | −13% ± 4% | −14% ± 6% | NS |
| Antithrombin III (%) | (80-120) | 93 ± 4 | 91 ± 10 | −7% ± 5% | −9% ± 5% | NS |
| von Willebrand Factor Antigen (% or IU/dL) | (50-200) | 120.4 ± 37.3 | 125.9 ± 35.4 | −4% ± 8% | −2% ± 8% | NS |

TABLE 25-continued

| Summary of characterization data for ACD-A and CPD plasma | | | | | | |
|---|---|---|---|---|---|---|
| | | Unit Value (Mean ± 1 SD) | | Percent Change compared to Control (Mean ± 1 SD) | | |
| Assay | Clinical Range Reference | Apheresed ACD-A Plasma | Whole Blood CPD Plasma | Apheresed ACD-A Plasma | Whole Blood CPD Plasma | p-value |
| vWF:RCo (% or IU/dL) | (50-200) | 42.4 ± 16.0 | 41.8 ± 14.5 | −58% ± 4% | −55% ± 7% | NS |

NS—not significant
NA—not applicable

Example 7: Analytical Characterization of Spray Dried Plasma Samples

Introduction

Six samples of spray-dried blood product were provided for analytical characterization. All six samples were tested by scanning electron microscopy (SEM) analyses. The information for the samples provided is shown in Table 26.

TABLE 26

| Blood Product Sample Information | |
|---|---|
| Sample Description | Sample Number |
| Solubility Study | TCL5324 |
| Test Batch 2165, Run | TCL5325 |
| Test Batch 2165, Run | TCL5326 |
| Test Batch 2165, Run | TCL5327 |
| Test Batch 2165, Run | TCL5328 |
| Test Batch 2165, Run | TCL5329 |
| Test Batch 2165, Run | TCL5330 |

Experimental

Sample Handling

The samples were stored in the glove box, which was controlled such that the relative humidity remained between 3 and 15%. All sample preparation and the KF analyses were performed in the glove box to prevent exposure of the samples to ambient humidity in the laboratory.

Scanning Electron Microscopy (SEM)

Samples were prepared in a glove box to exclude moisture. Samples were mounted using carbon tabs and kept in sealed foil envelopes until they were quickly inserted into the SEM and again put under vacuum.

Figure 8A:
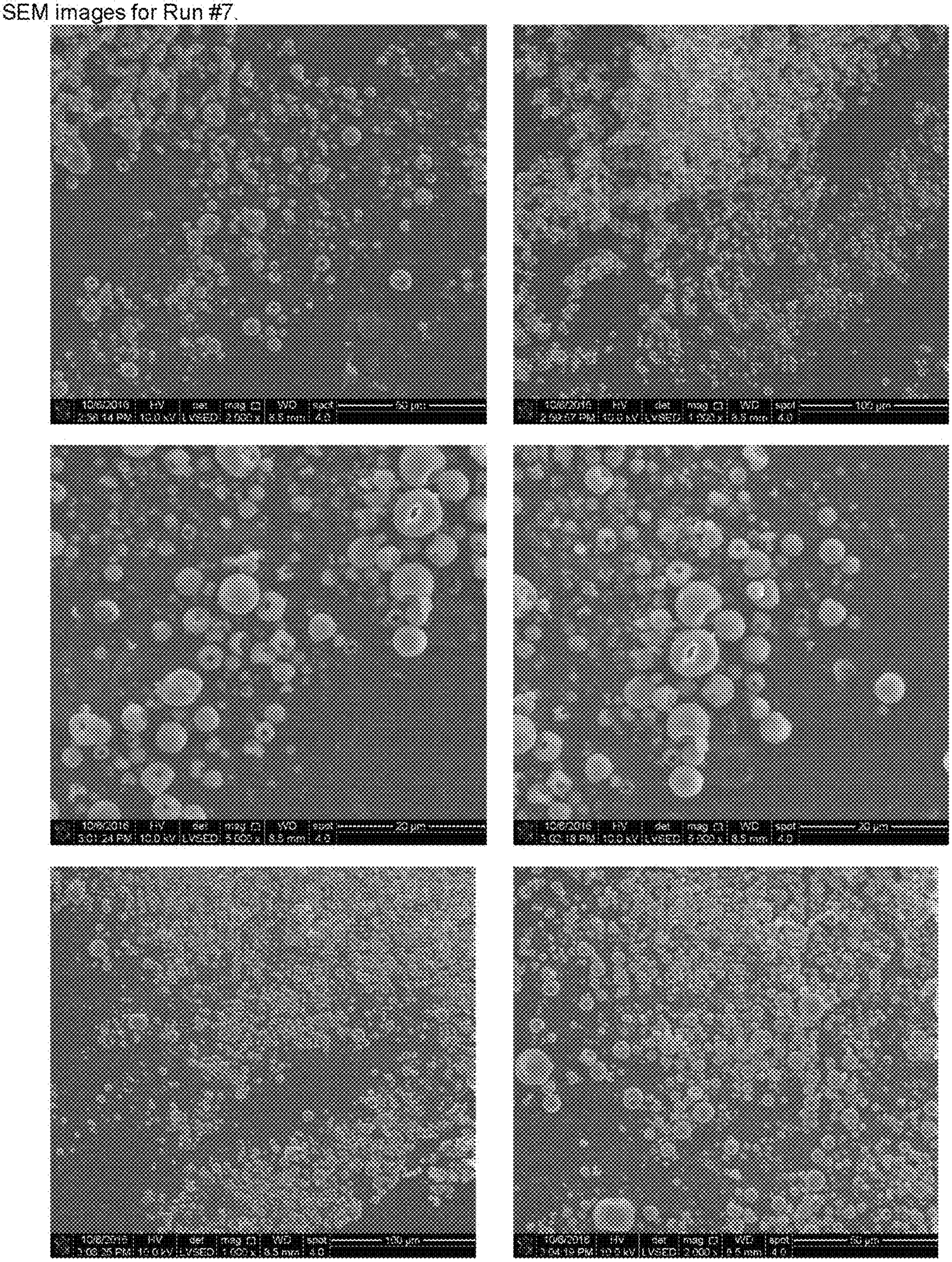
FIG. 8A is a panel of black and white photos of Scanning Electron Microscopy (SEM) of spray dried plasma particles of Run #7, upper left panel at 2000×, upper right panel at 1000×, middle left panel at 5000×, middle right panel at 5000×, lower left panel at 1000× and lower right panel at 2000×.
Figure 8B:
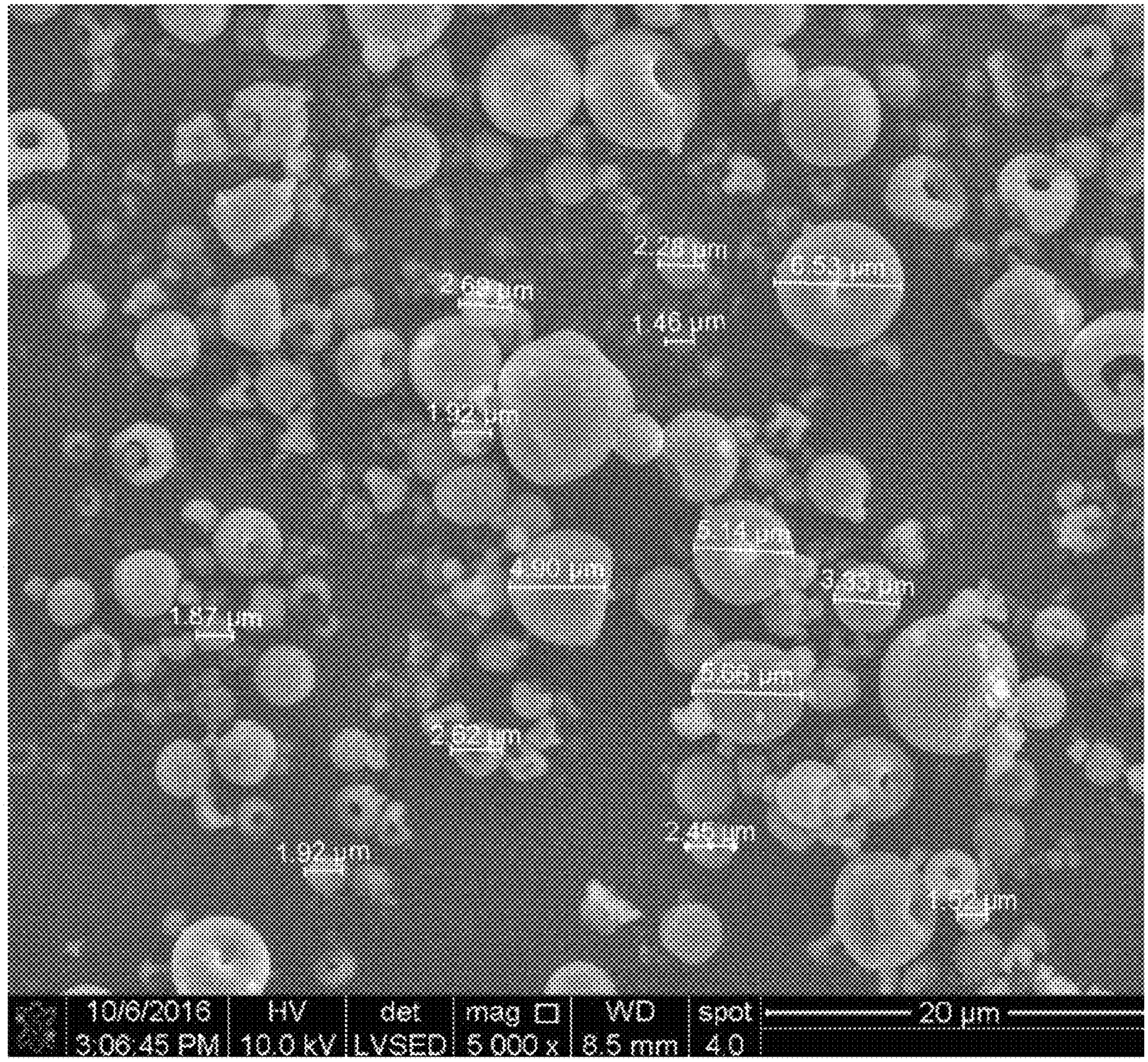
FIG. 8B is a panel of black and white photos of Scanning Electron Microscopy (SEM) of spray dried plasma particles of Run #7 at 5000× with measurements overlaid thereon showing sizes between 1.46 μm and 6.53 μm.

Samples were imaged using an FEI Quanta 3D FEG field emission scanning electron microscope (FESEM, FEI Company, Hillsboro, OR) operated in low vacuum mode. Parameters were 0.75 torr, 10 kV, Spot 4, ~8.5 mm working distance, 30 μm objective aperture, and magnifications of 1K, 2 k and 5 k in full-screen mode. Magnifications are only accurate if images are viewed at a display size of 30 cm×26 cm. Please note that the magnification bar should be used to determine feature size as it reflects correct size regardless of the viewed size of the image. Horizontal field width (HFW) also can be used to determine total image area (5 k=59.7 μm HFW). The data collection procedure used was not validated Results and Discussion The samples from Run #3 and Run #7 were also analyzed by SEM to determine if there were any visual differences between the samples. The images for Run #3 and Run #7 are displayed in FIGS. 7 and 8, respectively. The particles in both samples were observed to be hollow spheres with diameters between 1 and 8 μm. There were no clear differences in the physical appearance of the particles in the two samples.

Example 8: Bacterial Filtration Efficiency (BFE) Performance of Baffle Filter and Capture Filters in the Disposable Purpose:

This was a study for the Bacterial Filtration Efficiency (BFE) of the baffle filter 94 and capture filter 36 used in disposable 100 to confirm these filters maintain their integrity after being subjected to the stress of the spray drying process. One of the purposes was to determine the log reduction value (LRV) for the tapered ribbed baffle plate of the present invention. The results determined that there is improved LRV resulting from the use of the tapered ribbed baffle plate, as compared to similar testing using non-tapered ribbed baffle plate which resulted in a lower LRV. Another purpose of this study was to ensure that the baffle filter and capture filter maintain their integrity to prevent or reduce pathogens from entering the system during spray drying.

Scope:

The BFE test used for this study was modified from the standardized procedure listed in ASTM 2101-14 to increase the bacterial challenge density to greater than 106 colony forming units (CFU) to demonstrate a log 6 reduction value (LRV). Testing was conducted by Nelson Laboratories, LLC in Salt Lake City Utah USA.

The study was limited to a sample size of n=40 (20 baffle filters/20 capture filters).

The single use filters were prepared after exposure to spray drying cumulative stresses of temperature and pressure and then tested.

Figure 5:
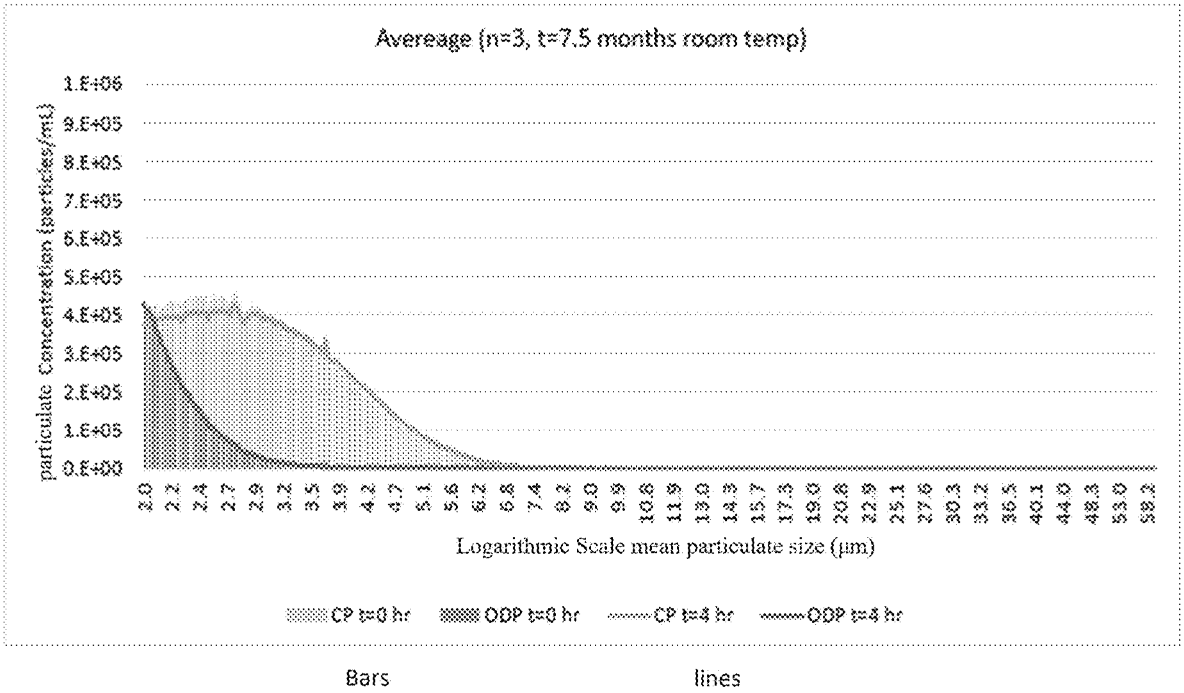
FIG. 5 is a composite bar/line graph showing particulate concentration (particulates/mL) and particulate size (logarithmic scale (μm)) of single unit dried plasma after 7.5 months of room temperature storage at initial rehydration and 4 hours post rehydration compared to its paired thawed frozen control plasma as follows: control plasma (CP) at time zero (T=0), spray dried plasma of the present invention (ODP) at time zero (T=0), control plasma (CP) at time of 4 hours (T=4), spray dried plasma of the present invention (ODP) at time of 4 hours (T=4).
Figure 6:
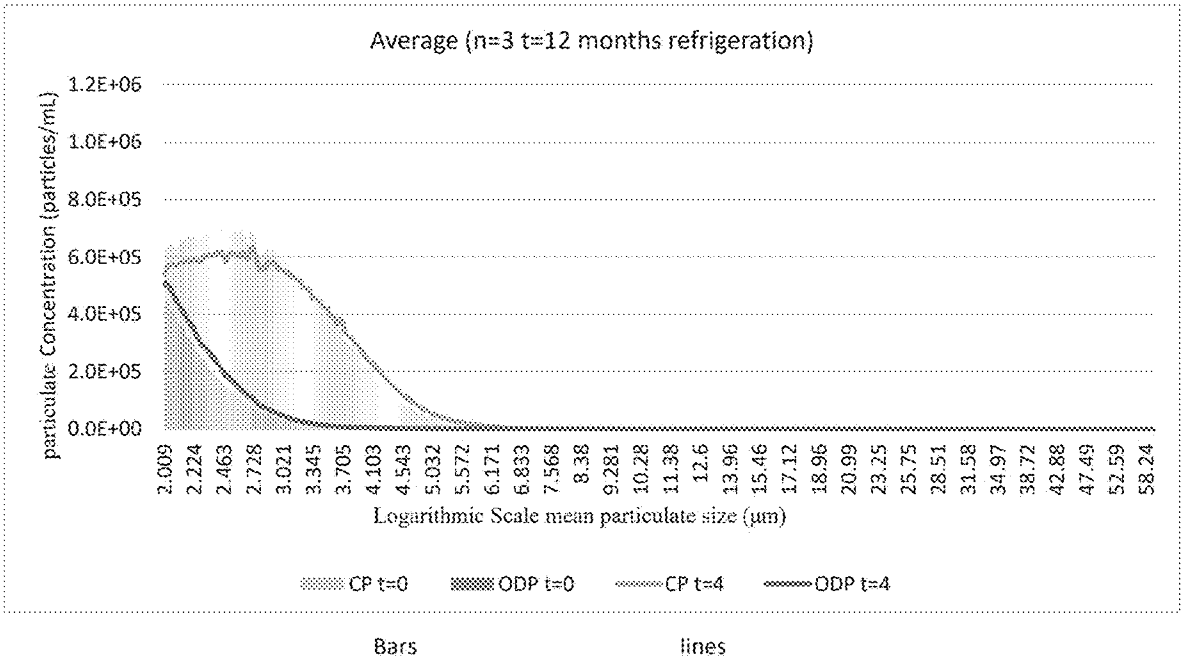
FIG. 6 is a composite bar/line graph showing particulate concentration (particulates/mL) and particulate size (logarithmic scale (μm)) of single unit dried plasma after 12 months of refrigerated storage at initial rehydration and 4 hours post rehydration compared to its paired thawed frozen control plasma as follows: control plasma (CP) at time zero (T=0), spray dried plasma of the present invention (ODP) at time zero (T=0), control plasma (CP) at time of 4 hours (T=4), spray dried plasma of the present invention (ODP) at time of 4 hours (T=4).

Equipment:

- Clean Dry Air (CDA) System VMI EQ #0503, 0504, 0505 and 0506
- Spray Dryer described herein and shown in FIGS. 4 and 5, model VEL7000
- Sealer, ASY-300005
- Sterile Connection Device (SCD) VMI EQ #0261
- Tubing Heat Sealer VMI EQ #0035 or equivalent
- Overwrap Sealer, VMI EQ #0541
- A-Z Hot Knife, TC-20, S/N: 54691
- Elix Water Purification, VMI EQ #0311

Supplies:

- Disposable 100, VEL9100; the disposable has baffle plate plasma drying chamber upper sections with tapered ribs as shown in FIG. 2L and FIG. 2La.
- 600 mL transfer pack, P/N 10016

Tyvek overwrap, P/N 10459

Microtome Blade

Steel hole punch, 2⅞" diameter

Procedure:

Test unit numbers for this study are the following: 3362, 3364 through 3371, and 3373 through 3383.

Preparation of Filters

Filled a 600 mL transfer pack with 310 mL of Type II water, assigned a test batch number to each bag of water, recorded on the 'Introduction sheet' and saved the file description.

Connected each water filled transfer pack to a disposable by SCD and spray dried on a Dryer to expose the filters to spray drying process.

Baffle Filter Extraction Process:

Cut the disposable bag from the plenum below the baffle plate ring and cut off the tubing just above the strain relief.

Flipped the Plenum upside down and used a hot knife to cut around the Plenum.

Put the top cap on the plenum/baffle plate outer rim and used the hot knife to cut around the aerosol reservoir. Removed the cut section to expose the baffle filter 94.

Used a microtome blade to cut around the Inner and outer filter ring.

Inspected the cut around the Inner Filter Ring and Outer Filter Ring for sections of tearing. Sections with a tear were used as a location to cut from the inner filter ring to the outer filter ring.

Removed the baffle filter 94 from the top cap and used a 2⅞" hole punch to outline the two sample areas. Selected an area large enough to fit the 2⅞" BFE Filter test fixture and with no visible damage/tearing.

Used a microtome blade to cut around the outlines to create two samples, one for testing and one backup in case of shipping damage.

Sealed the samples into separate compartments of a TYVEK™ Pouch and labeled with filter location, batch number, date of extraction, and test protocol number. Kept the remaining baffle filter section for posterity.

Capture Filter Extraction Process

Used scissors to cut the lower portion of the disposable to expose the outside of the capture filter 36.

Used scissors to cut along the top weld, removed the capture filter 36, and cut along the length of the side welds.

Unfolded the capture filter 36 and used the 2⅞" hole punch to outline two sample areas at the middle crease of the filter.

Used the microtome blade to cut around the outlines to create the two samples, one for testing and one backup in case of shipping damage.

Sealed the samples into separate compartments of a TYVEK™ pouch and labeled with filter location, batch number, date of extraction, and test protocol number. Kept the remaining capture filter sections for posterity.

The 20 test articles, and their 20 backups, from the baffle filter and the capture filter of the disposable were sent for testing.

Testing

The samples prepared as described above were submitted for BFE testing by Nelson Laboratories of Salt Lake City Utah USA protocol modified to meet in use conditions for the filters.

The test procedure was performed to evaluate the BFE of test articles at an increased challenge level. A suspension of *Staphylococcus aureus*, ATCC #6538, was delivered at a challenge level of greater than $10^6$ colony forming units (CFU). The challenge was aerosolized using a nebulizer and delivered to the test article at a fixed air pressure and flow rate of 30 liters per minute (LPM). The aerosol droplets were generated in a glass aerosol chamber and drawn through the test article into all glass impingers (AGIs) for collection. The challenge was delivered for a three-minute interval and sampling through the AGIs was conducted for four minutes to clear the aerosol chamber. The mean particle size (MPS) control was performed at a flow rate of 28.3 LPM using a six-stage, viable particle, ANDERSEN™ sampler for collection.

This test procedure was modified. Standard BFE procedure was modified in order to employ a more severe challenge than would be experienced in normal use. This method was adapted from ASTM F2101. The ASTM F2101 acceptance criterion of LRV greater than or equal to 3.0 was met. Testing was performed in compliance with US FDA good manufacturing practice (GMP) regulations 21 CFR Parts 210, 211 and 820.

Results:

TABLE 27

BFE Results for Baffle filter

| Test Article Number | Total CFU Recovered | Filtration Efficiency (%) | LRV Acceptance criteria (LRV ≥ 3.0) |
|---|---|---|---|
| 3364U | $1.8 \times 10^1$ | 99.99976 | 5.6 |
| 3365U | <1[a] | >99.999986 | 6.9 |
| 3366U | <1[a] | >99.999986 | 6.9 |
| 3367U | <1[a] | >99.999986 | 6.9 |
| 3368U | <1[a] | >99.999986 | 6.9 |
| 3369U | <1[a] | >99.999986 | 6.9 |
| 3370U | 1 | 99.999986 | 6.9 |
| 3371U | <1[a] | >99.999986 | 6.9 |
| 3373U | <1[a] | >99.999986 | 6.9 |
| 3374U | $5.3 \times 10^1$ | 99.99928 | 5.1 |
| 3375U | <1[a] | >99.9999901 | 7 |
| 3376U | <1[a] | >99.9999901 | 7 |
| 3377U | <1[a] | >99.9999901 | 7 |
| 3378U | $1.3 \times 10^2$ | 99.9988 | 4.9 |
| 3379U | <1[a] | >99.9999901 | 7 |
| 3380U | $1.9 \times 10^1$ | 99.99981 | 5.7 |
| 3381U | <1[a] | >99.9999901 | 7 |
| 3382U | <1[a] | >99.9999901 | 7 |
| 3383U | $9.5 \times 10^1$ | 99.99906 | 5 |
| 3395U | 1 | 99.9999901 | 7 |

LRV = Log Reduction Value

[a]There were no detected colonies on any of the assay plates for this test article.

Results from the capture filter samples are shown in Table 28. All 20 samples prepared from the crease of the capture filter (highest stress) had an LRV above 3.0.

TABLE 28

BFE Results for capture filter

| Test Article Number | Total CFU Recovered | Filtration Efficiency (%) | LRV Acceptance criteria (LRV ≥ 3.0) |
|---|---|---|---|
| 3364L | <1[a] | >99.999986 | 6.9 |
| 3365L | <1[a] | >99.999986 | 6.9 |
| 3366L | <1[a] | >99.999986 | 6.9 |
| 3367L | <1[a] | >99.999986 | 6.9 |
| 3368L | <1[a] | >99.999986 | 6.9 |
| 3369L | <1[a] | >99.999986 | 6.9 |
| 3370L | <1[a] | >99.999986 | 6.9 |
| 3371L | <1[a] | >99.999986 | 6.9 |
| 3373L | 5 | 99.999932 | 6.2 |
| 3374L | <1[a] | >99.999986 | 6.9 |

TABLE 28-continued

| BFE Results for capture filter | | | |
|---|---|---|---|
| Test Article Number | Total CFU Recovered | Filtration Efficiency (%) | LRV Acceptance criteria (LRV ≥ 3.0) |
| 3375L | 1 | 99.9999901 | 7 |
| 3376L | <1[a] | >99.9999901 | 7 |
| 3377L | <1[a] | >99.9999901 | 7 |
| 3378L | 4 | 99.99996 | 6.4 |
| 3379L | <1[a] | >99.9999901 | 7 |
| 3380L | <1[a] | >99.9999901 | 7 |
| 3381L | <1[a] | >99.9999901 | 7 |
| 3382L | <1[a] | >99.9999901 | 7 |
| 3383L | 3 | 99.99997 | 6.5 |
| 3395L | <1[a] | >99.9999901 | 7 |

LRV = Log Reduction Value

There were no detected colonies on any of the assay plates for this test article.

All 20 baffle filter had an LRV greater than 3.0 meeting the ASTM F2101-14 acceptance criteria. No baffle filter tearing was noted. The tapered rib baffle plate of the present invention successfully enables LRV's of 3.0 or greater when tested under ASTM 2102-14 and does not tear the filter.

Capture filter samples were excised from the creased area where the most stress is expected to be applied. All 20 of the capture filter samples tested for a modified BFE test showed LRV greater than 3.0.

The Bacterial Filtration Efficiency (BFE) Study demonstrates that the baffle filters and capture filters in disposable maintain their integrity during and after exposure to the cumulative stresses of temperature and pressure of the spray drying process.

Example 9: Assay and Functional Study of Clotting Performance of Dried Plasma of the Present Invention (Bioflux Study I An independent laboratory at the United States Army Institute of Surgical Research (USAISR) in Houston Texas performed a range of assay studies and functional studies using its facilities including its in-house Bioflux instrument (Fluxion Biosciences of Alameda California USA) on the dried plasma of the present invention to determine its assay and functional performance in vitro under realistic normal (arterial shear) and traumatic (pathological shear) blood flow.

The study confirmed that the dried plasma of the present invention when reconstituted and assayed solely or in conjunction with whole blood or in a resuscitation setting is comparable to Fresh Frozen plasma and performs essentially the same as Fresh Frozen Plasma, that the vWF function is normal under arterial shear or pathological shear conditions and that the Endogenous Thrombin Potential is higher than that of Fresh Frozen Plasma.

Methods and Materials

Five units of the dried plasma of the present invention (ODP) was shipped to USAISR.

The five ODP units were rehydrated at USAISR with 200 ml of SWFI.

Fresh Frozen Plasma (FFP) for comparison was thawed at 37° C. for 5 minutes.

For whole blood (WB) study WB was collected from the USAISR Research Blood Bank and centrifuge to separate platelets (plt) and red blood cells (RBC) which were washed to remove excess plasma.

Rebuilt WB was made to meet 40% hematocrit, 200 plt/nL and FFP or reconstituted ODP.

For resuscitation simulation WB was combined with a two unit dose of FFP or reconstituted ODP.

Abbreviations:

FFP=Fresh Frozen Plasma (FFP);

ODP—Spray dried plasma of the present invention (ODP);

WBCs—White Blood Cells;

RBCs—Red Blood Cells)

WB:FFP=whole blood (WB) rebuilt with Fresh Frozen Plasma (FFP);

WB:ODP_whole blood rebuilt with spray dried plasma of the present invention (ODP);

WB+10% FFP=whole blood resuscitated with 2 units of FFP;

WB+10% ODP=whole blood resuscitated with 2 units of ODP

Studies were conducted on USAISR's Bioflux analyzer using USAISR's protocols and procedures. Thromboelastography (TEG) studies were performed.

Coagulation Function

Hemostasis was measured using thromboelastography (TEG) in a TEG device (TEG 5000, Haemonetics, USA) using the kaolin contact pathway activation assay (Haemonetics) according to manufacturer's instructions. Both reconstructed whole blood samples and plasma-only samples were analyzed. Parameters of interest included reaction time (time until clot formation begins), angle (corresponding to rate of clot formation), maximum amplitude (MA, a measure of clot strength), and degree of lysis (LY30 and LY60, lysis at 30 and 60 min after reaching MA). Coagulation function of plasmas was also measured by turbidimetry for fibrin polymerization kinetics. Briefly, 96.5 μL plasma was mixed with 1.5 μL of calcium chloride (15 mM final concentration) and 2 μL of pre-HEPESbuffered saline-diluted reagent (Innovin Siemens Healthcare), for a final dilution of 1:5000. Using a 96-well plate, multiple samples were tested simultaneously using a plate reader (SpectraMax M5e, Molecular Devices) set to measure absorbance at 405 nm in kinetic mode (measurement taken every 15 s for a period of 1 h) at 37° C. Polymerization initiation and maximum turbidity were obtained from the absorbance curve associated with fibrin crosslinking following plasma exposure to the tissue factor and phospholipid contained in Innovin.

Thrombin Generation

The calibrated automated thrombogram (CAT) assay was used to measure thrombin generation in plasma using PPP low reagent (1 pM tissue factor with 4 μM phospholipid; Diagnostica Stago). A sample (80 μL) was mixed with reagent (20 μL), incubated for 10 minutes at 37° C., and mixed by autoinjector with 20 μL FluCa buffer (Z-Gly-Gly-Arg-AMC fluorogenic substrate and calcium chloride; Diagnostica Stago). Thrombograms were collected with a microplate fluorometer (Fluoroskan Ascent FL, ThermoFisher Scientific) with computer software (Thrombinoscope, Thrombinoscope BV). Samples were run in triplicate, and an additional triplicate set of plasma samples was run in parallel using a thrombin calibrator in place of reagent (to account for inner filter effect and substrate consumption rate). Lag time to initiation, peak, time-to-peak, and endogenous thrombin potential (the area under the thrombogram curve) were parameters of interest.

Flow Cytometry/Residual Cellular Material

Plasmas were examined for residual particulates by flow cytometry. Using mouse antihuman antibodies (BD Biosciences), platelet (phycoerytherin-labeled CD41a), WBC (fluorescein isothiocyanate-labeled CD45), and RBC (allophycocyaninlabeled CD235) derived microparticles were labeled and quantified on a fluidics system (FACSCanto II, BD Biosciences) with forward scatter detector for small-sized particles (less than 1 μm diameter).

Blood Chemistry

Plasma samples were evaluated using a handheld blood analyzer (i-STAT, Abbott Point of Care Inc.) with test cartridges (CG4+, Abbott). Automated cartridges were loaded with plasma (100 μL), and primary parameters of interest were pH, lactate, base excess, and bicarbonate.

Statistical Analysis

Data collection, aggregation, and statistical analyses were performed with computer software (Excel 2010, Microsoft; and Prism 7.01, GraphPad). Replicates were averaged prior to statistical analysis. In the preliminary studies comparing pretreatment, reconstitution, and FFP groups, since each plasma type was collected from the same donor, repeated measures one-way analysis of variance was used to determine intergroup differences. For the final comparison of donor-matched spray dried samples and FFP control samples, paired t tests were used to determine significant differences. Data are displayed as means_standard deviations.

Results

FIGS. 9A through 9E show TEG results of rebuilt whole blood and simulated resuscitation. R-time (clot reaction time) of WB:ODP were significantly longer than for WB:FF but were within normal range.

Only one sample showed in non-zero lysis measurement. The range for WB:ODP for 30 minutes was within the reference range. There is no reference range for lysis at 60 minutes. The lysis indices for all resuscitation samples were zero.

Figure 10A:
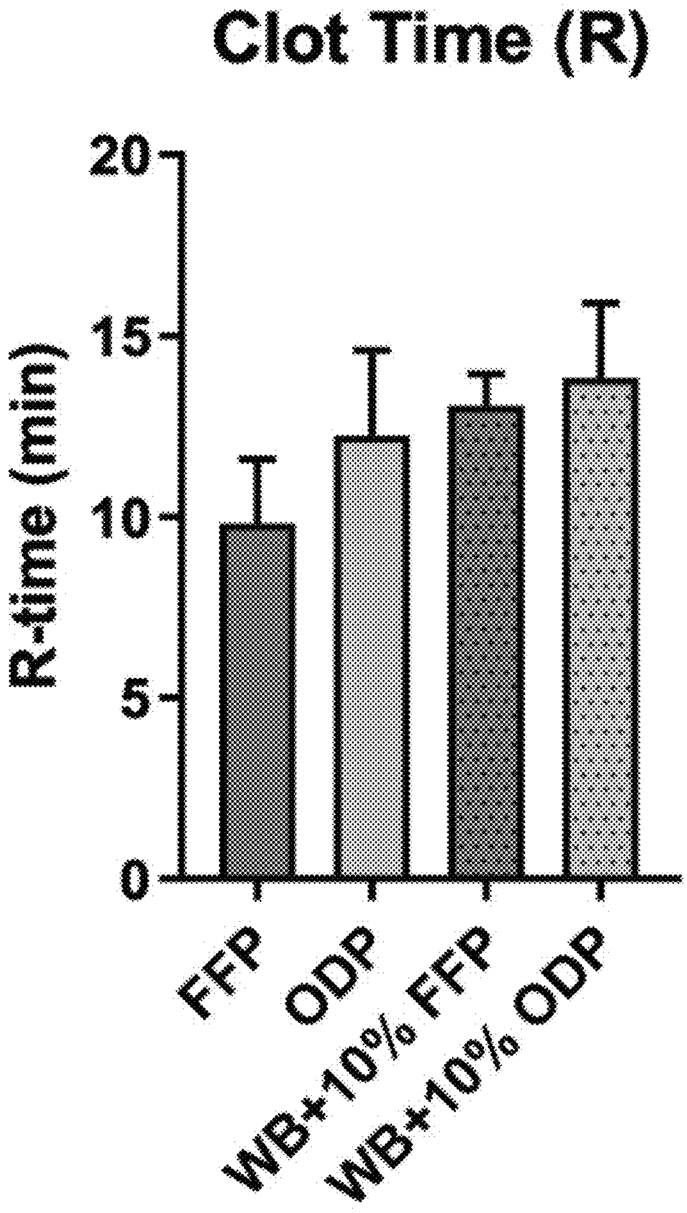
FIG. 10A is a bar graph showing results of Clot Time (R) in minutes from a Thromboelastography TEG study with plasma only (abbreviations: FFP=Fresh Frozen Plasma (FFP); ODP—spray dried plasma of the present invention (ODP); WB+10% FFP=whole blood resuscitated with 2 units of FFP; WB+10% ODP=whole blood resuscitated with 2 units of ODP). Reference ranges are shown by dotted lines.
Figure 10B:
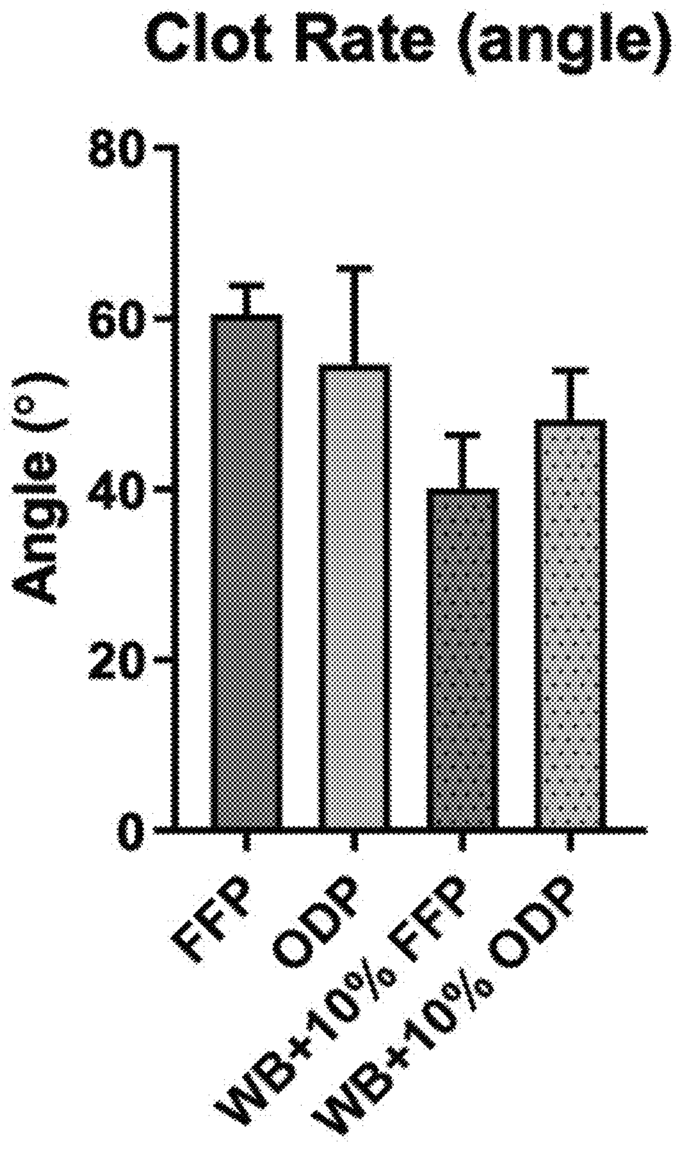
FIG. 10B is a bar graph showing results of Clot Rate (angle) in degrees from a Thromboelastography TEG study with plasma only (abbreviations: FFP=Fresh Frozen Plasma (FFP); ODP—spray dried plasma of the present invention (ODP); WB+10% FFP=whole blood resuscitated with 2 units of FFP; WB+10% ODP=whole blood resuscitated with 2 units of ODP). Reference ranges are shown by dotted lines.
Figure 10C:
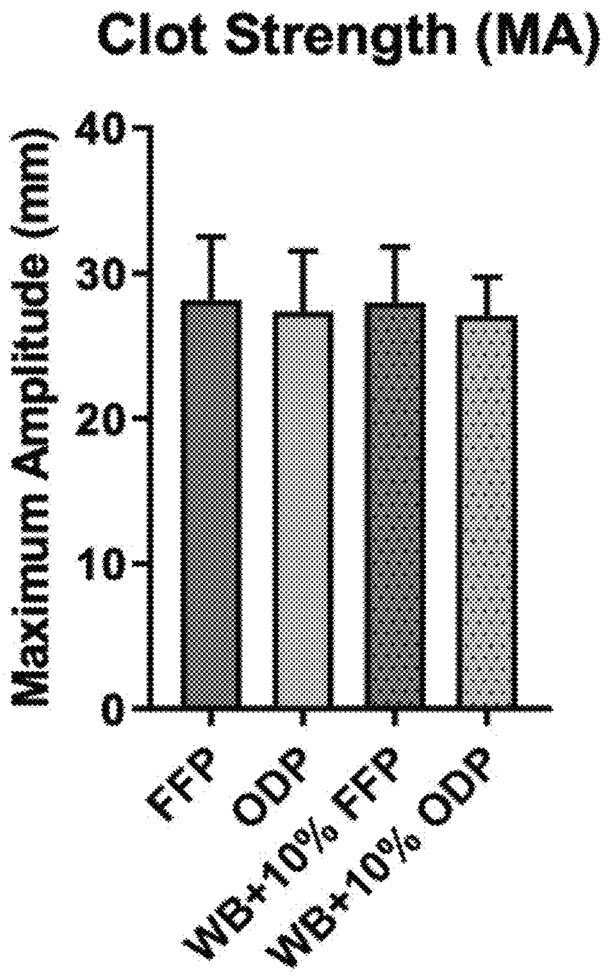
FIG. 10C is a bar graph showing results of Clot Strength in Maximum Amplitude (MA) (mm) from a Thromboelastography TEG study with plasma only (abbreviations: FFP=Fresh Frozen Plasma (FFP); ODP—spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

No reference ranges exist for TEG of plasma only. The data and FIGS. 10A-10C show comparability of WB:ODP to WB:FFP both alone and in a resuscitation setting. In particular, clot time (FIG. 10A), clot rate (angle) (FIG. 10B) clot strength (and maximum amplitude) (FIG. 10C) for reconstituted spray dried plasma was similar to FFP. Regardless of plasma proteins levels, the reconstituted previously spray dried plasma was able to form a clot in a time period and at a rate and strength that is similar to FFP.

Figure 11:
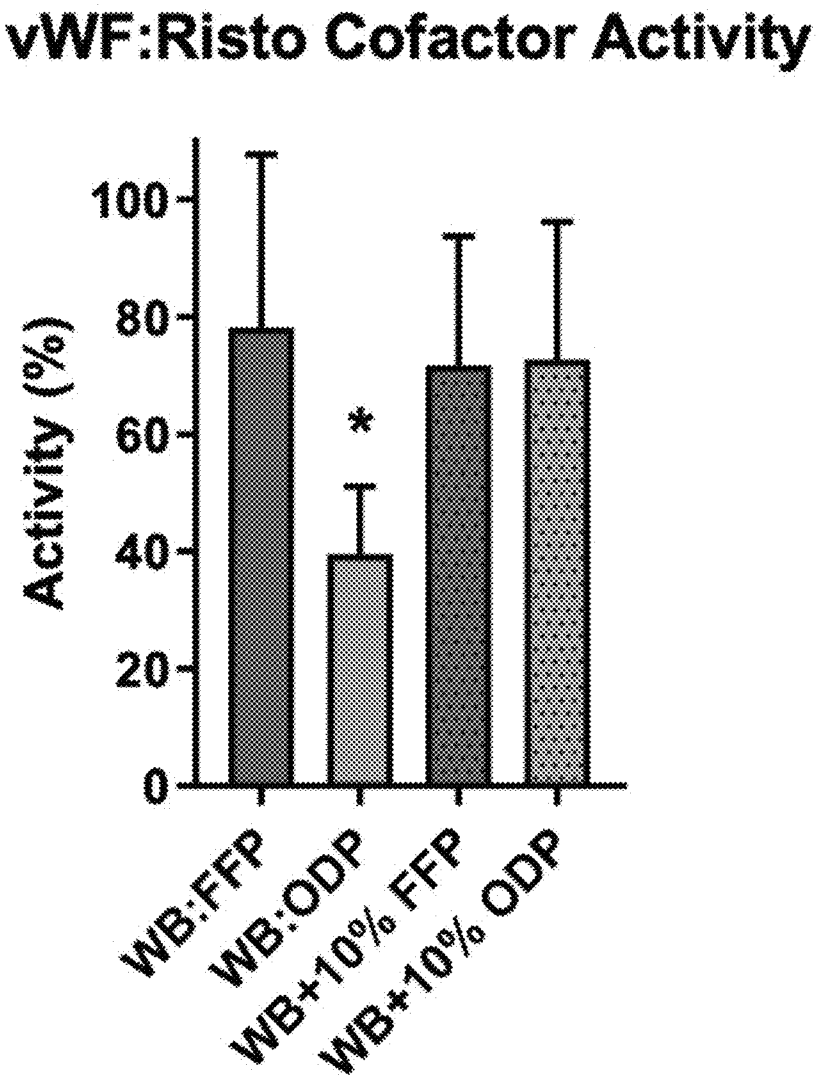
FIG. 11 is a bar graph showing results of vWF (von Willebrand Factor): ristocetin (Rist) Cofactor Activity in percent (5) from a ristocetin cofactor assay. (abbreviations: WB:FFP=whole blood (WB) rebuilt with Fresh Frozen Plasma (FFP); WB:ODP_whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

FIG. 11 shows ristocetin cofactor vWF Activity in the samples. vWF activity in the WB:ODP sample was significantly lower than the resuscitated samples. However, the p-value for differences between WB:FFP and WB:ODP was not significant (p=0.15) No differences were noted between reconstituted samples. Despite significantly lower level of vWF activity, as shown in FIG. 10, the reconstituted previously spray dried plasma enables clot formation similar to fresh frozen plasma.

Figure 12:
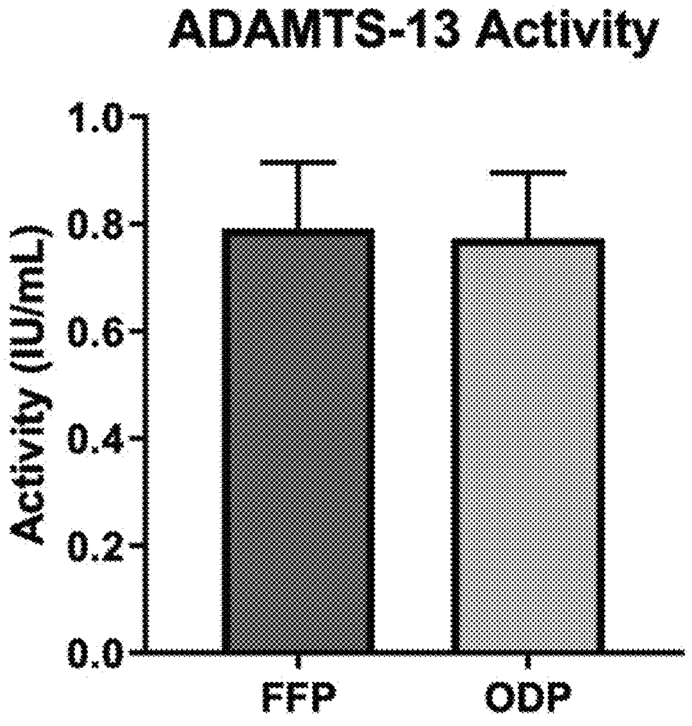
FIG. 12 is a bar graph showing results of ADAMTS-13 (von Willebrand factor-cleaving protease) activity from ADAMTS-13 assay. (abbreviations: FFP=Fresh Frozen Plasma (FFP); ODP—Spray dried plasma of the present invention (ODP).

FIG. 12 shows that no significant difference was noted between the ADAMTS-13 activity of samples of FFP and ODP alone.

FIGS. 13A-13B show Platelet Adhesion Bioflux Study results demonstrating that no significant differences were observed between rebuilt samples or between reconstituted samples at either shear condition, indicating that vWF function was normal. FIG. 13 show that vwF is clearly working to play its role in clot formation. Coagulation factors account for approximately only 20% of the clot strength whereas platelets and vWF, a platelet facilitator, account for most of the rest of the clot strength. The results from the Bioflux study shown in FIG. 13 indicate that reconstituted, previously spray dried plasma provides for clot formation, as measured by arterial shear and pathological shear. The spray drying process of the present invention provides functional, clot forming plasma. vWF is a multimer protein, regardless if sheared during the spray drying into smaller proteins, the spray dry methodology described herein provides for a functional vWF protein that participates in clot formation, in a similar fashion as it counterpart in FFP. The inventive spray drying process does not damage vWF in a way that interferes with clotting. The measure of intensity of clot and the size (area) of the clot substantiates that spray dried plasma of the present invention functions at least the same as FFP. Bioflux data is further supported by the thrombin generation data shown in FIG. 14 and TEG data shown in FIG. 9.

Interpretation: The fluorescence intensity and the area covered by clot was not significantly different with reconstituted previously spray dried in the base case or when whole blood was reconstituted with FFP. This means that the adhesive, clotting qualities of the platelets were not impaired in the inventive reconstituted spray dried plasma. This was true in the "low" arterial sheer or "high" pathological sheer conditions.

Figure 14A:
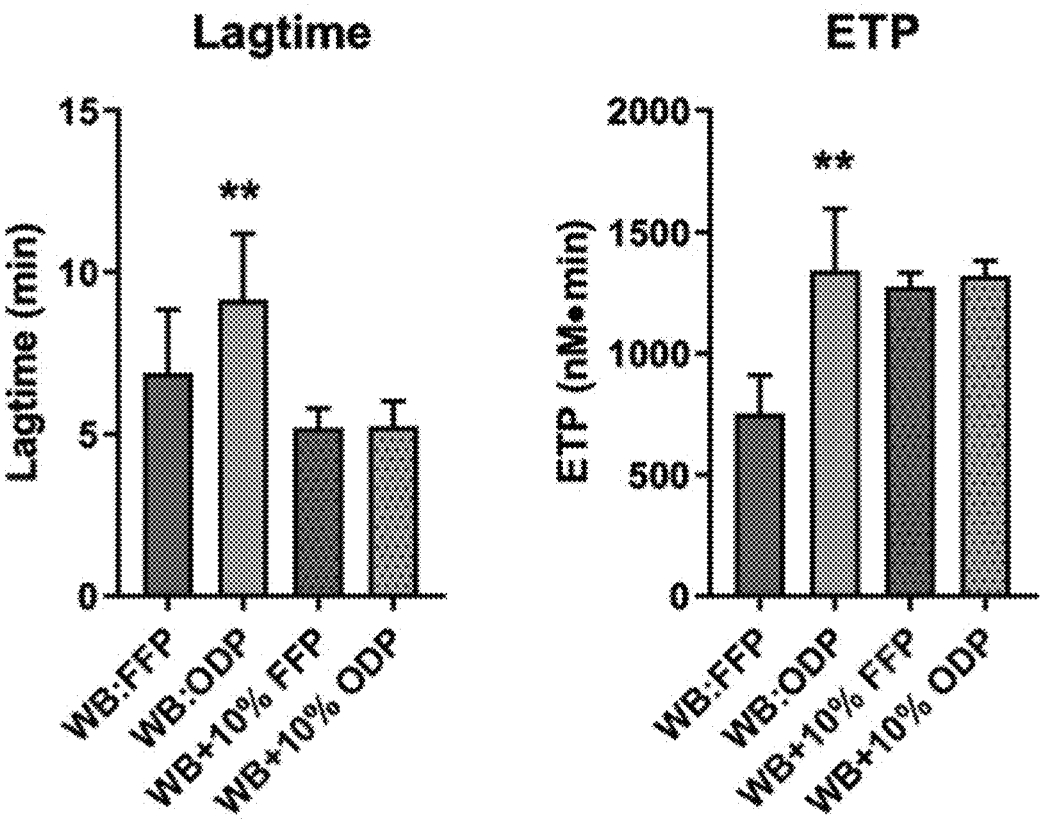
FIG. 14A includes two bar graphs showing results of from a CAT (Calibrated Automated Thrombogram) Thrombin Generation Assay showing lag time in minutes and Endogenous Thrombin Potential (ETP) (nM. Min). (abbreviations: WB:FFP=whole blood (WB) rebuilt with Fresh Frozen Plasma (FFP); WB:ODP—whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines. ETP is a measurement that reflects coagulation status and if someone is prone to bleeding (reduced ETP) or clotting (elevated ETP).
Figure 14B:
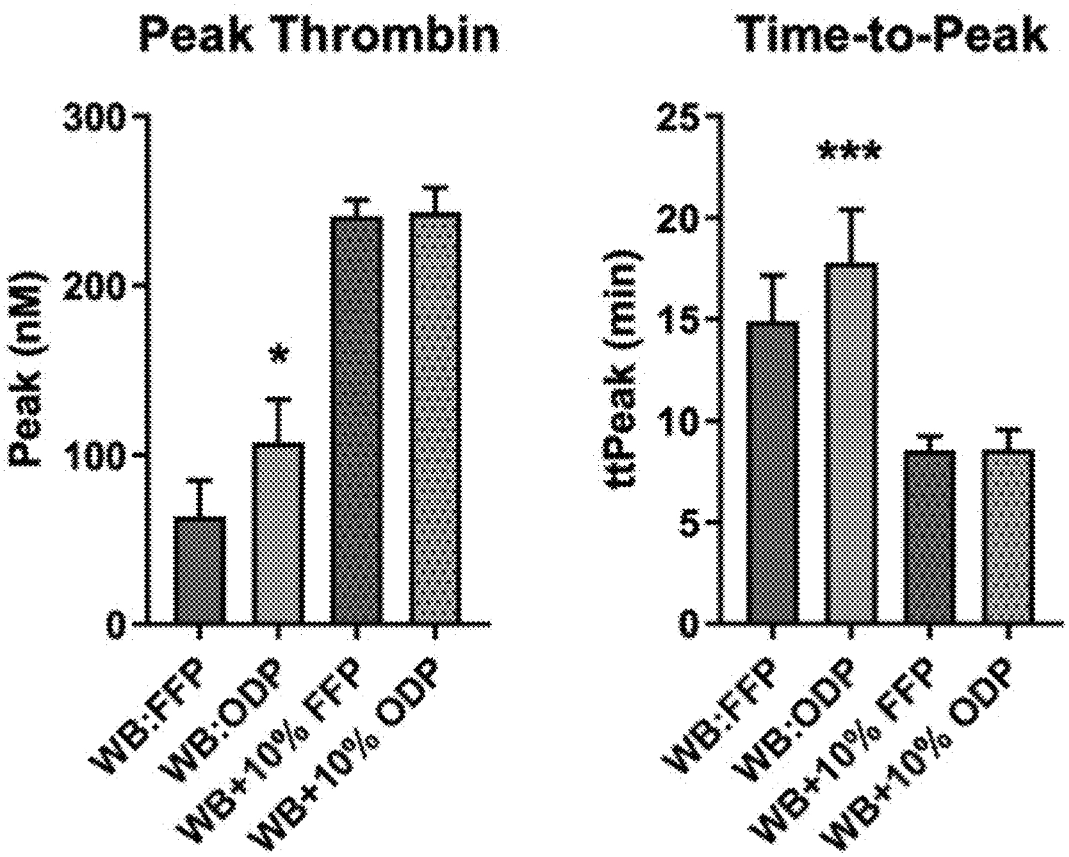
FIG. 14B includes two bar graphs showing results of from a CAT (Calibrated Automated Thrombogram) Thrombin Generation Assay showing peak thrombin (nM) and time to peak (minutes). (abbreviations: WB:FFP=whole blood (WB) rebuilt with Fresh Frozen Plasma (FFP); WB:ODP—whole blood rebuilt with spray dried plasma of the present invention (ODP); WB+10% FFP=whole blood resuscitated with 2 units of FFP; WB+10% ODP=whole blood resuscitated with 2 units of ODP). Reference ranges are shown by dotted lines.

ETP is a measurement that reflects coagulation status and if someone is prone to bleeding (reduced ETP) or clotting (elevated ETP). FIGS. 14A-14B show CAT Thrombin Generation Assay demonstrating that WB:ODP has significantly longer lag time but a higher Endogenous Thrombin Potential (ETP) than WB:FFP, indicating that the amount of thrombin which could be generated after activation of coagulation of ODP was higher than FFP when measured in vitro. Resuscitation samples showed no significant differences between FFP and ODP. Put another way, the resuscitation samples in the ETP test were informative and demonstrated no difference in the ETP measure for FFP versus ODP. The ETP of the rebuilt WB:ODP looked similar to both the FFP and ODP resuscitation samples, so it further strengthens the observation that ODP behaves similarly to FFP even though the ETP comparison for the rebuilt samples is statistically significantly different between FFP and ODP. Taken together, the Thrombin generation assay shows that reconstituted previously spray dried plasma works as well as FFP. See FIG. 14A-B.

Figure 15A:
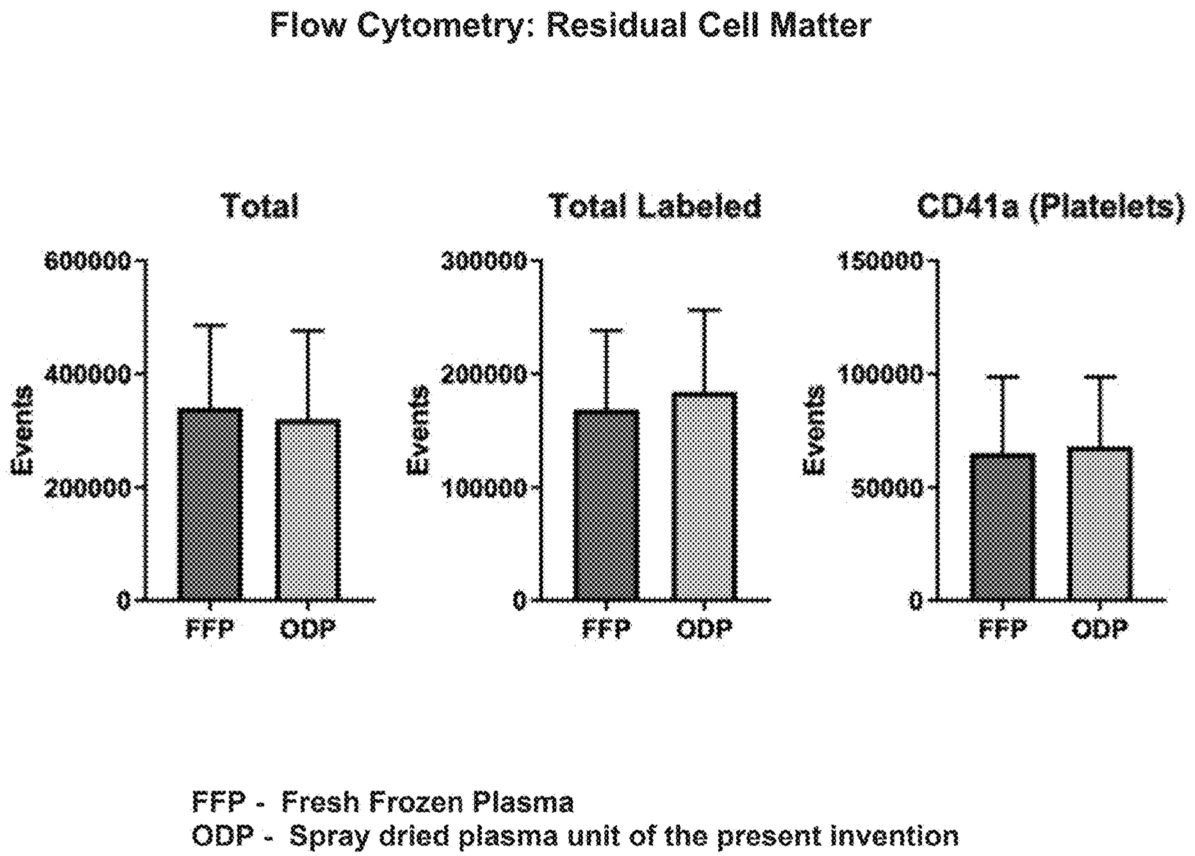
FIG. 15A includes three bar graphs showing results of Flow Cytometry of Residual Cell Matter in total events, Total labeled events and CD41A (platelet) events. (abbreviations: FFP=Fresh Frozen Plasma (FFP); ODP—Spray dried plasma of the present invention (ODP).
Figure 15B:
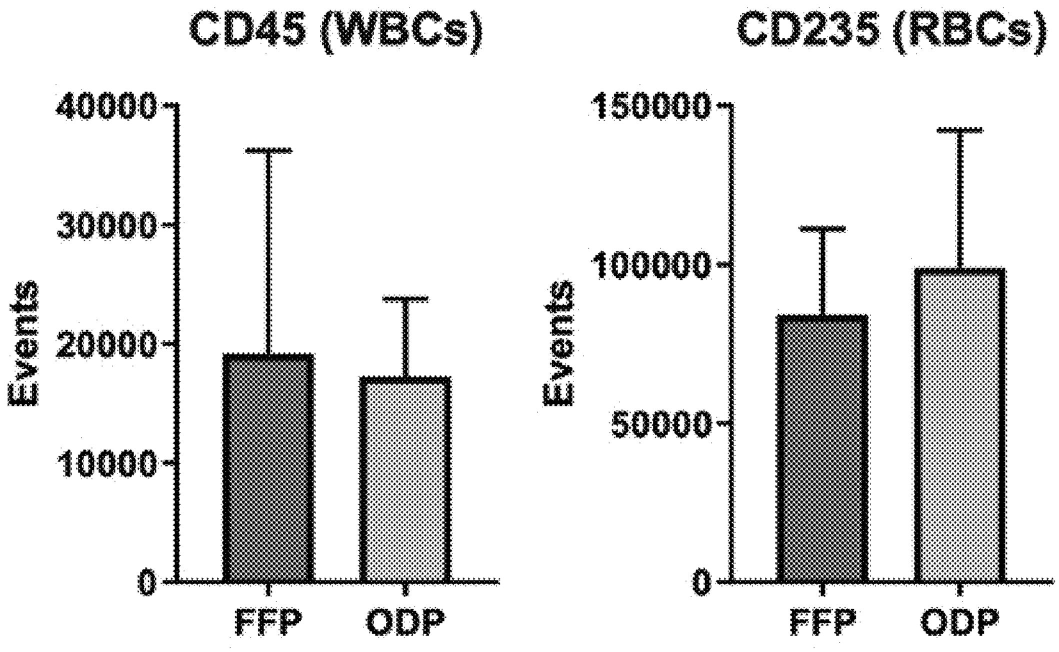
FIG. 15B includes three bar graphs showing results of Flow Cytometry of Residual Cell Matter in CD45 (WBCs) and CD235 (RBCs). (abbreviations: FFP=Fresh Frozen Plasma (FFP); ODP—Spray dried plasma of the present invention (ODP); WBCs—White Blood Cells; RBCs—Red Blood Cells)

FIGS. 15A-15B show flow cytometry results for residual cell matter. No significant differences were observed between samples of FFP and ODP of platelets (CD41+), leukocytes (CD45+) and red blood cell (CD235+) fragments.

Conclusion

The dried plasma of the present invention when reconstituted and assayed solely or in conjunction with whole blood or in a resuscitation setting is comparable as well as Fresh Frozen Plasma and performs essentially the same as Fresh Frozen Plasma, that the vWF function is normal under arterial shear or pathological shear conditions and that the Endogenous Thrombin Potential is higher than that of Fresh Frozen Plasma.

This testing will be repeated for aged and stored samples, as described in Examples 5 and 37. It is expected that the dried plasma stored in various conditions, as described in Examples 5 and 37 will allow for clot formation and that the vWF function is normal under arterial shear or pathological shear conditions.

Example 10 Bioflux Study II

An independent laboratory at the United States Army Institute of Surgical Research (USAISR) in Houston Texas performed a range of assay studies and functional studies using its facilities including its in-house Bioflux instrument (Fluxion Biosciences of Alameda California USA) on the dried plasma of the present invention to determine its assay and functional performance in vitro under realistic normal (arterial shear) and traumatic (pathological shear) blood flow.

An additional four units of the dried plasma of the present invention (ODP) was shipped to USAISR. Two of the ODP units had known vWF:RCo levels below the FDA target of 40% (37% and 33%) and 2 samples had vWF:RCo levels above 40% (60% and 42%). The purpose of this smaller study was to evaluate functionality of samples that had vWF:RCo levels below the target 40%.

The four ODP units were rehydrated at USAISR with 200 ml of SWFI.

Fresh Frozen Plasma (FFP) for comparison was thawed at 37° C. for 5 minutes.

Results

TEG measurement for plasma only showed no difference between FFP and ODP. TEG measurement for the whole blood reassembled samples showed a slight statistically significant deficiency in clotting time (R) and clot rate (angle) and a minor drop in clot strength (MA) that was statistically significantly different. The lysis was statistically significantly higher in the ODP samples at 30 and 60 minutes but it was unclear why this would be the case and noted that further investigation was required.

Thrombin generation assay results showed the lag time for ODP was statistically significantly longer than FFP, similar to the R-time in the TEG measurement, however the other parameters of ETP, Peak thrombin and Time-to-peak were not statically significantly different. The large variance in EPT could be attributed to donor variability.

Bioflux under normal arterial shear rates demonstrated that there were no differences in the overall binding of platelets to the collagen over a 10-minute period (intensity and area), but the rate of binding was slower with ODP. This finding may not have any clinical significance.

Bioflux under high pathologic arterial shear rates demonstrated that again there were no differences in the overall binding of platelets to the collagen over a 10-minute period (intensity and area) and no difference in the rate of binding.

Evaluation of residual cellular material demonstrated no statistically significant difference in cellular material as measured by particulate analysis of CD41a (Platelets), CD45 (WBCs) and CD235 (RBCs).

The study concluded that the dried plasma of the present invention when reconstituted and assayed solely or in conjunction with whole blood or in a resuscitation setting is comparable to Fresh Frozen plasma and performs essentially the same as Fresh Frozen Plasma, and that the vWF function, even in samples with vWF:RCo levels below 40%, is normal under arterial shear or pathological shear conditions and that the Endogenous Thrombin Potential, with the exception of lag time, is not statistically significantly different from that of Fresh Frozen Plasma.

Figure 16:
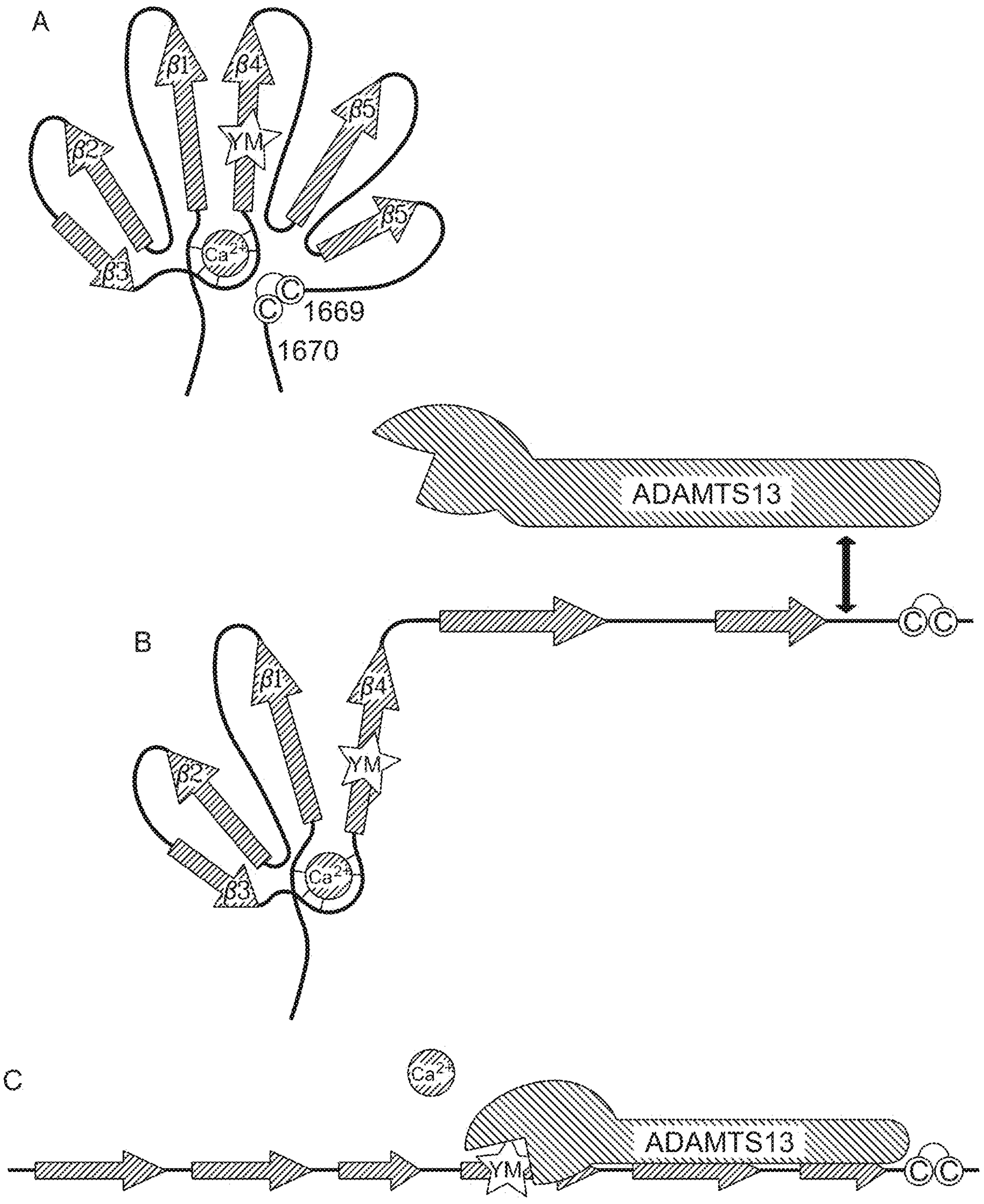
FIG. 16 panels A-C are schematic illustrations depicting unfolding/refolding model of the vWF A2 domain and protelolysis by ADAMTS13. (A) Cartoon of the vWF A2 domain in its native folded state. (B) The first step of unfolding occurs from the C-terminal end of the vWF A2 domain, influenced by the presence of the vicinal disulfide bond (cysteines depicted by C). Initial unfolding occurs up to, or including, the central b4 sheet in which the scissile bond (YM) is contained. This unfolding intermediate step exposes the high-affinity ADAMTS13 spacer-binding site. (C) Once the stabilizing effect of the calcium-binding site (CBS) is overcome this results in the complete unfolding of the vWF A2 domain and the positioning of the ADAMTS13 active site for nucleophilic attack of the Y1605-M1606 scissile bond.

Example 11: Enhancing in-Process (Spray-Drying) Stability of vWF Factor and Storage Stability of Multiple Plasma Proteins by Treating the Feed Plasma with Citric Acid Prior to Spray Drying Introduction von Willebrand factor (vWF) is a large adhesive glycoprotein with established functions in hemostasis. It serves as a carrier for factor VIII and acts as a vascular damage sensor by attracting platelets to sites of vessel injury. The size of vWF is important for this latter function, with larger multimers being more hemostatically active. Functional imbalance in multimer size can variously cause microvascular thrombosis or bleeding. The regulation of vWF multimeric size and platelet-tethering function is carried out by ADAMTS13, a plasma metalloprotease that is constitutively active. It is secreted into blood and degrades large vWF multimers, decreasing their activity. Unusually, protease activity of ADAMTS13 is controlled not by natural inhibitors but by conformational changes in its substrate, which are induced when vWF is subject to elevated rheological shear forces. This transforms vWF from a globular to an elongated protein. This conformational transformation unfolds the vWF A2 domain and reveals cryptic exosites as well as the scissile bond. To enable vWF proteolysis, ADAMTS13 makes multiple interactions that bring the protease to the substrate and position it to engage with the cleavage site as this becomes exposed by shear forces (FIG. 16). ADAMTS 13 (a disintegrin and metalloproteinase with a thrombospondin type 1 motif, member 13), also known as von Willebrand factor-cleaving protease (vWFCP), is a zinc-containing metalloprotease enzyme.

During spray drying (SpD), the plasma proteins are subject to considerable shear forces due to the spraying mechanism as the solutions are fluidized through a fine nozzle to form the droplets in contact with drying air. The process of unfurling multimeric vWF is expected to be triggered by the hydrodynamic forces of elevated shear stress during SpD in combination with air-liquid interface stress. The shear-induced structural change of vWF, when combined with other physical factors associated with SpD, such as high temperature and/or unfavorable pH as well as the air-liquid interface stress, may lead to protein denaturation (if unfolded vWF fails to refold properly post-SpD) and proteolytic degradation (unfolded vWF exposes proteolytic sites for ADMATS13), impairing the vWF activity in the spray dried plasma (SpDP), as well as other proteins.

Spray drying can be optimized to reduce the protein damage caused by shear force and temperature through mechanical engineering. However, the pH rise is inevitable during SpD due to the loss of $CO_2$, driven by both spraying and drying sub-processes. Further, the elevated pH is particularly undesirable for SpDP during storage. SpDP contains a residual amount of water and an alkaline pH will accelerate protein degradation during storage. Therefore, it is highly desirable to maintain the physiological pH during and post SpD. This can be done by adding a non-volatile spray dry stable acidic substance (SDSAS), preferably a physiologically compatible weak acid such as citric acid or lactic acid, to the liquid plasma to counterbalance the $CO_2$ loss by inhibiting pH rise during SpD and thereby allow SpDP to be stored at a non-alkaline pH. In summary, pretreatment or contemporaneous treatment of plasma with citric acid serves three main purposes: 1) it increases in-process stability of plasma proteins; 2) it increases stability of plasma proteins during storage; and 3) it allows SpDP to be rehydrated with water, eliminating the need for a rehydration solution.

Objectives

The object of this study is to evaluate the impact of a SDSAS formulation of plasma with citric acid on the recovery from SpD and stability during storage of SpDP of vWF and other coagulation factors in SpDP.

Study Design and Methods

Plasma samples were formulated by the addition of citric acid from a 20% stock solution prior to spray drying. Plasma samples were spray dried using a drying gas inlet temperature of 125° C., plasma fluid rate of 10 mL/min, aerosol gas rate of 20 L/min and the exhaust temperature was maintained at 55° C. The clotting factors fibrinogen, Factors V, VII, VIII and IX, von Willebrand factor (vWF), prothrombin time (PT) and activated partial prothromboblastin time (aPTI) were determined after spray drying and after storage at 37° C., room temperature and refrigeration. vWF multimer analysis was carried out at the BloodCenter of Wisconsin (BCW) as follows. Plasma samples, loaded at equal vWF:Ag levels (0.2 mU), were analyzed by 0.65% LiDS-agarose gel electrophoresis and western blotting with chemiluminescent detection using the Fujifilm LAS-300 luminescent image analyzer. Densitometry was performed and area-under-the curve calculated. The percentage of low (L), intermediate (I) and high (H) molecular weight (MW) multimers (M) were calculated. Formulated SpDP samples were rehydrated with water for injection (WFI), standard SpDP samples (i.e., control samples without added pretreatment agents as listed here) were rehydrated in Citrate-Phosphate Buffer (CPB).

Results

Figure 17:
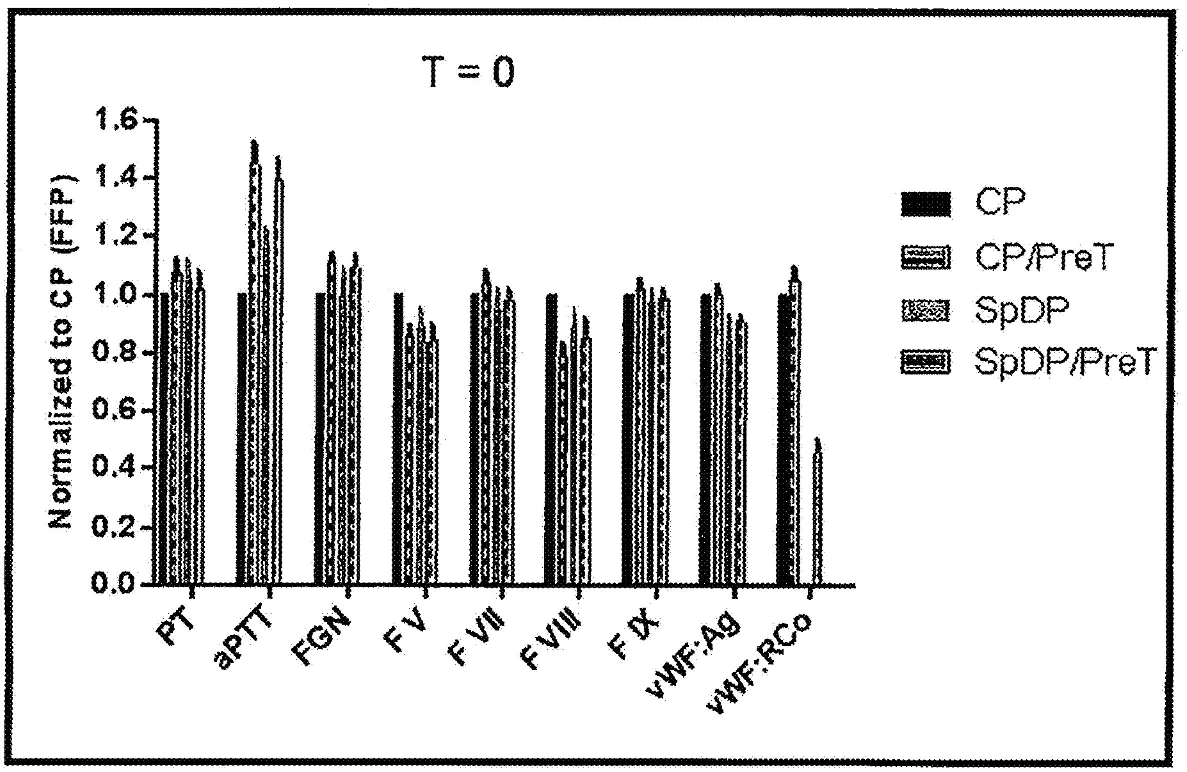
FIG. 17 is a bar graph showing that formulation of plasma with citric acid stabilizes during spray drying ~50% von Willebrand Factor: Ristocetin Cofactor (vWF:RCo) activity without any impact of other coagulation factors (Prothrombin (PT), Activated Partial Thromboplastin Time (aPTT), Fibrinogen (FGN), Factor V (FV), Factor VII (FVII), Factor VIII (FVIII), Factor IX (FIX), vWF antigen (vWF-Ag), % von Willebrand Factor: Ristocetin Cofactor (vWF:RCo)). This is done at time zero, time upon completion of spray drying, normalized to Control Plasma (Fresh Frozen Plasma (FFP)). CP indicates Control Plasma; SpDP indicates Spray-Dried Plasma; PreT indicates plasma formulation with SDSAS.

As shown in FIG. 17, SpD resulted in a loss of coagulation factor activity between 0% and up to 20% (FV, FVII, FVIII and FIX), but had no impact on fibrinogen and vWF antigen levels. However, it lowered the vWF:RCo activity below detection, which, remarkably, increased recovery by 50% by formulation. Consistent with the excellent recoveries of the coagulation factors and fibrinogen, SpD had no adverse effect on PT. SpD slightly prolonged aPTT (comparing Bar 1 and 3 in the aPTT cluster). Citric acid formulation prolonged aPTT of the plasma even before SpD, suggesting that interference of added citric acid in the assay, likely by taking some free calcium required by multi-steps in the intrinsic pathway, collectively measured as aPTT when combined with the common pathway. However, SpD had no impact on aPTT of the formulated plasma (comparing Bar 2 and 4 in aPTT cluster).

Figure 18:
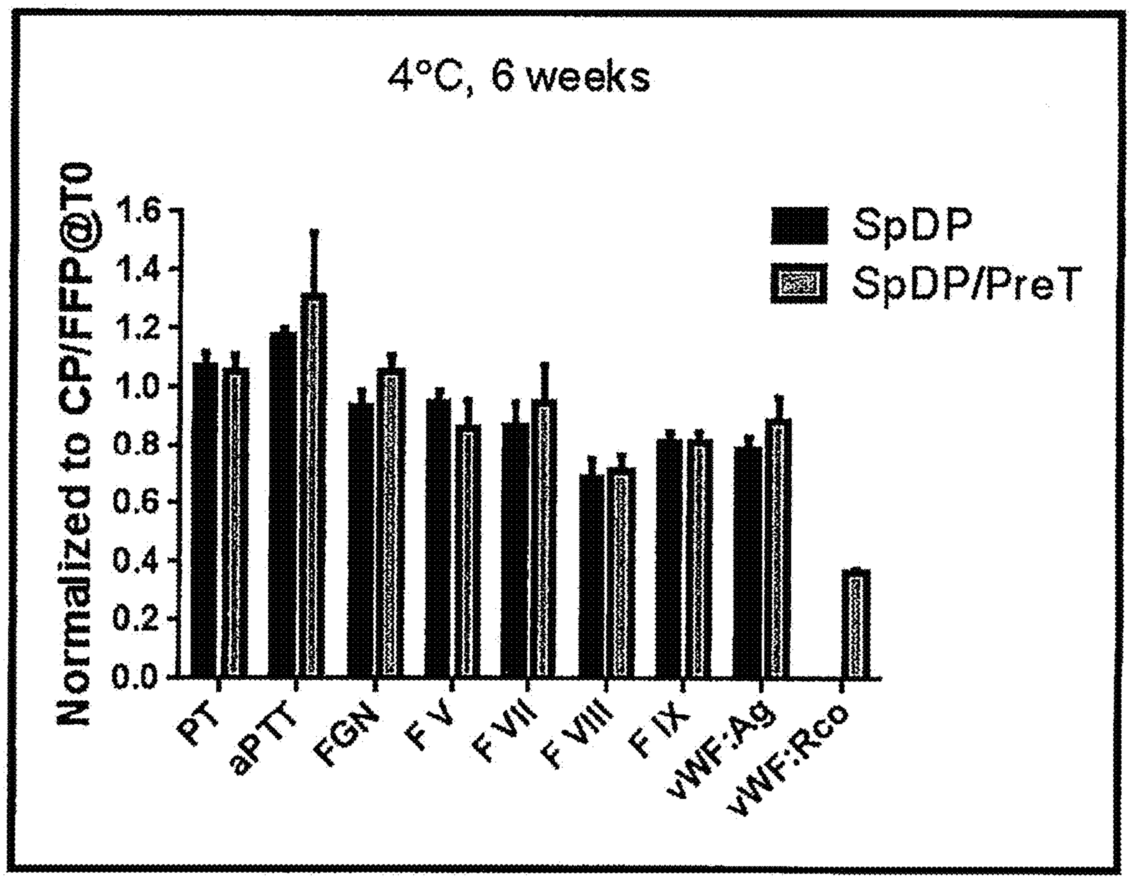
FIG. 18 is a bar graph showing that formulation of plasma with citric acid confers stability to vWF and all other coagulation factors (Prothrombin (PT), Activated Partial Thromboplastin Time (aPTT), Fibrinogen (FGN), Factor V (FV), Factor VII (FVII), Factor VIII (FVIII), Factor IX (FIX), vWF antigen (vWF-Ag), % von Willebrand Factor: Ristocetin Cofactor (vWF:RCo)). This is done at during storage at 6 weeks at 4° C. SpDP indicates Spray-Dried Plasma; PreT indicates plasma formulation with SDSAS. CP indicates Control Plasma and FFP is Fresh Frozen Plasma.
Figure 19:
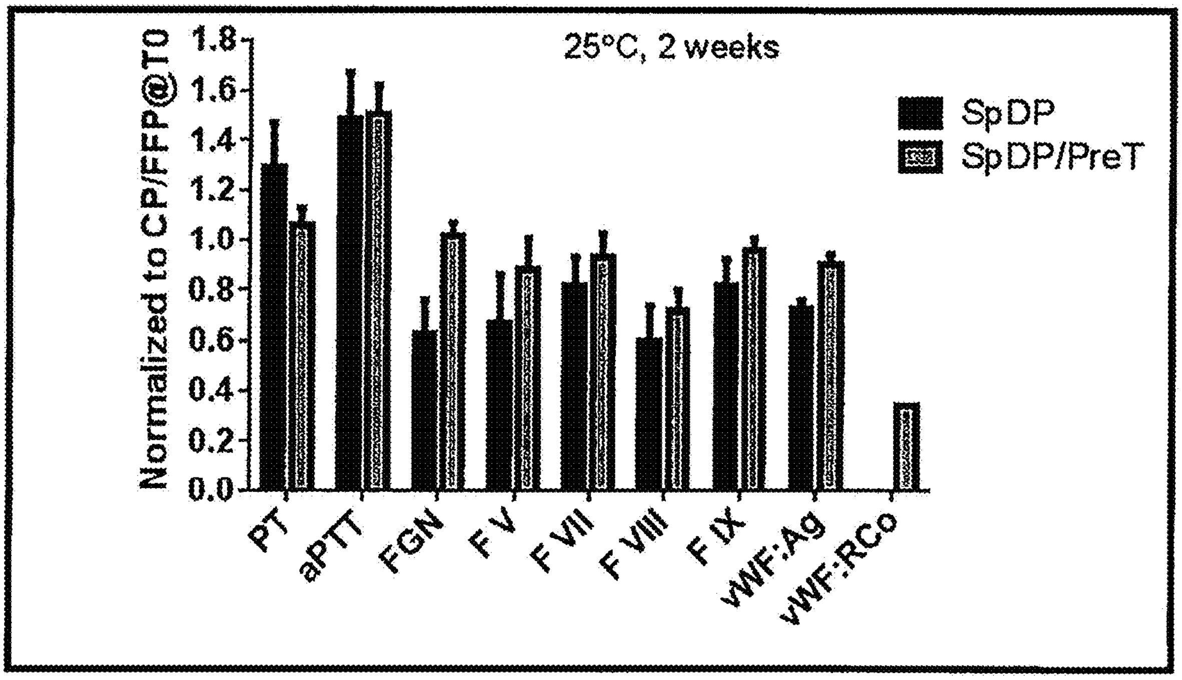
FIG. 19 is a bar graph showing that pre-treatment of plasma with citric acid confers stability to vWF and all other coagulation factors (Prothrombin (PT), Activated Partial Thromboplastin Time (aPTT), Fibrinogen (FGN), Factor V (FV), Factor VII (FVII), Factor VIII (FVIII), Factor IX (FIX), vWF antigen (vWF-Ag), % von Willebrand Factor: Ristocetin Cofactor (vWF:RCo)). This is done during storage after 2 weeks at 25° C. SpDP indicates Spray-Dried Plasma; PreT indicates plasma formulation with SDSAS. CP indicates Control Plasma and FFP is Fresh Frozen Plasma.
Figure 20:
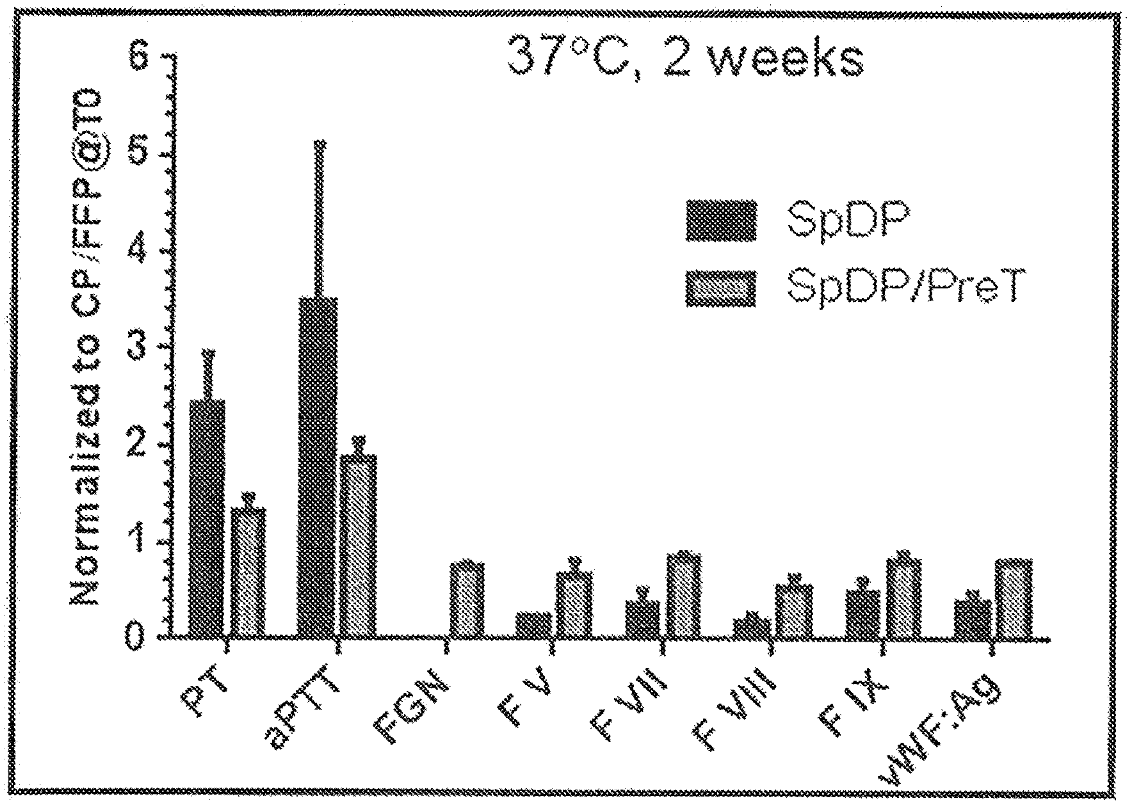
FIG. 20 is a bar graph showing that formulation of plasma with citric acid confers stability to coagulation factors (Prothrombin (PT), Activated Partial Thromboplastin Time (aPTT), Fibrinogen (FGN), Factor V (FV), Factor VII (FVII), Factor VIII (FVIII), Factor IX (FIX), vWF antige (vWF-Ag)). This is done during storage at 2 weeks at 37° C. SpDP indicates Spray-Dried Plasma; PreT indicates plasma formulation with SDSAS. CP indicates Control Plasma and FFP is Fresh Frozen Plasma.

When stored refrigerated for 6 weeks, coagulation factors in the plasma samples did not lose more than 10% of their activities (FIG. 18.). However, the benefits of Pre-T/CA were highlighted after 2 weeks at 25° C. (FIG. 19) and even more so at 37° C. (FIG. 20). All characterized parameters performed better for Pre-T/CA SpDP than standard SpDP.

Figure 21:
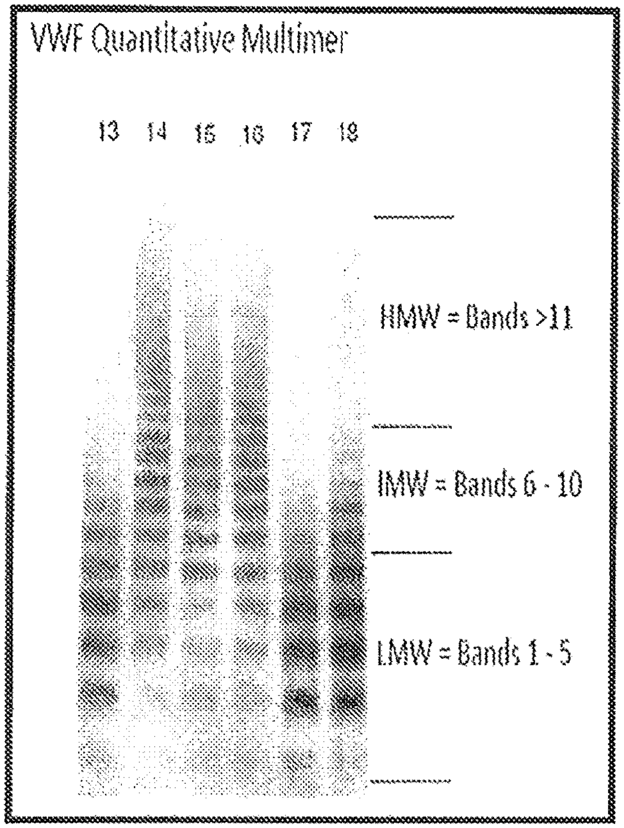
FIG. 21 is a photographic image showing that formulation of plasma with citric acid stabilizes vWF during SpD (spray drying). CP indicates Control Plasma; SpDP indicates Spray-Dried Plasma; PreT indicates plasma formulation with SDSAS; FFP indicates Fresh Frozen Plasma.

To gain insight into steep decline, and dramatic salvage of vWF:RCo activity by plasma formulation, vWF multimer quantifications were performed by the inventors on plasma samples pre and post-SpD, with or without pretreatment. The results are shown in FIG. 21. Positive and negative controls were also included. As rationalized in the introduction to the example, SpD took a heavy toll on vWF multimers, almost completely depleted high molecular weight vWF multimers (HMWM), which was paralleled by an increase in low molecular weight multimers (LMWM). However, Pre-T/CA greatly increased recovery of HMWM multimers, consistent with vWF:RCo data. Lane 13: Type 2B vWF Control=Type 2B von Willebrand disease. Lane 14: Healthy Control. Lane 15: CP=Control plasma. Lane 16: CP/PreT=control plasma plus citric acid. Lane 17: SpDP=reconstituted spray dried plasma. Lane 18: SpDP/PreT=reconstituted spray dried plasma power formulated with citric acid.

Conclusions

Surprisingly, SpD exerts a heavy toll on vWF multimer formation and activity. The results show that vWF is sensitive to shear stress which adversely affects its size and biological function. Shear stress enhances the proteolysis of vWF in normal plasma. Presumably, and while not limiting the present invention to theory, the synergistic effects of shear force during aerosolization, pH change and thermal stress, causes unfolding of vWF. Formulation of plasma with a SDSAS greatly improves the recovery of shear force labile vWF, increases the stability of multiple plasma proteins during storage and simplifies rehydration. SpDP subjected to formulation showed improved profiles of PT, fibrinogen, FV, FVII, FVIII, FIX and vWF antigen (Ag) levels when stored 2 weeks and 4° C. and 25° C.

Example 12: Characterization of the Effect of Aerosol Flow Rate on vWF Factor Background The spray-drying process can be divided into feeding, spraying, and drying stages. Each sub-process can potentially cause damage to plasma proteins, especially vWF. Identification of the critical step(s) to vWF degradation can aid in process development minimizing processing damage to plasma proteins. In this example, the impact of spraying on vWF recovery was evaluated.

Study Design and Methods

Thawed FFP samples were fed at 10 mL/minute under variable aerosol gas flow (0, 5, 10, 15 or 20 L/minute) without drying gas on. These settings, allowing the plasma to be fed into the system, with or without aerosolization in the absence of heating, allowed study of the impact of plasma feeding and spray/aerosol gas flow rate in the spray-drying process. The sprayed liquid plasma samples were analyzed for pH and vWF:RCo.

Results

Figure 22A:
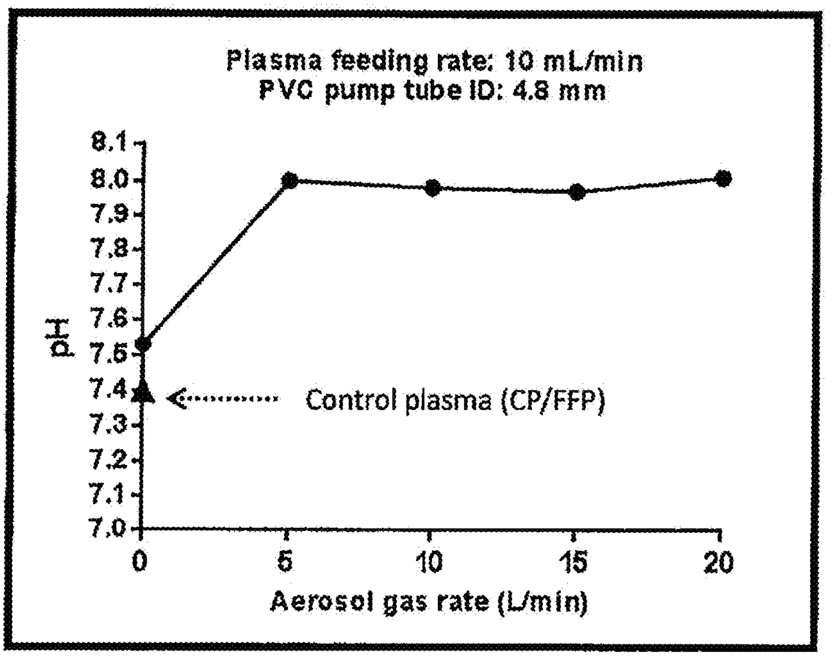
FIG. 22A is a line graph showing pH for CP/FFP and the fed plasma under constant plasma feeding rate of 10 mL/min, but variable aerosol gas flow rates (0, 5, 10, 15, and 20 L/min). CP indicates Control Plasma; FFP indicates Fresh Frozen Plasma; vWF indicates von Willebrand Factor.
Figure 22B:
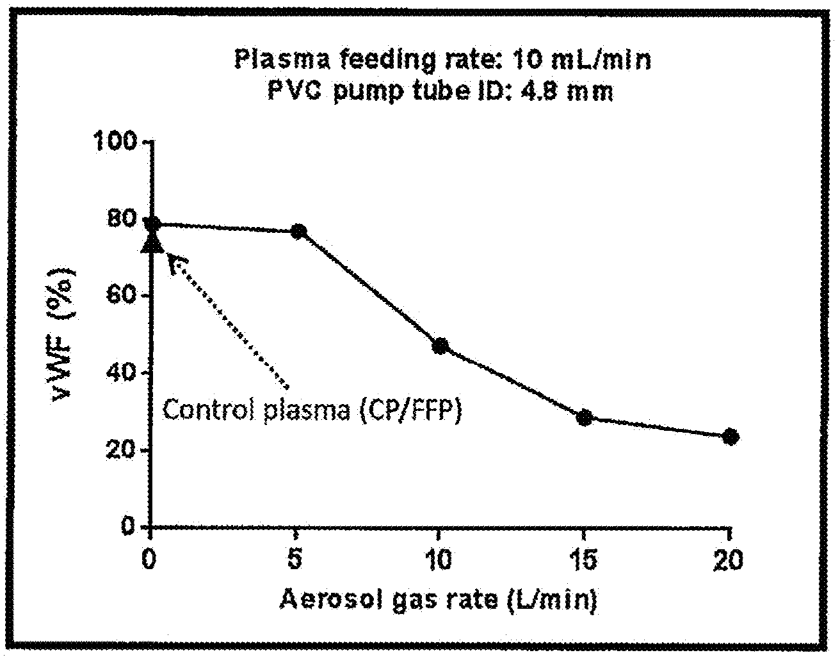
FIG. 22B is a line graph showing the results activity (%, IU/dL) of vWF:RCo activity for CP/FFP and Fed Plasma under constant plasma feeding rate of 10 mL/min, but variable aerosol gas flow rates (0, 5, 10, 15, and 20 L/min). CP indicates Control Plasma; FFP indicates Fresh Frozen Plasma.

The results are shown in FIGS. 22A and 22B. Plasma feeding at 10 mL/min without aerosol gas flow (0 L/min) allowed the evaluation of the impact of feeding alone on vWF recovery. Plasma feeding alone had no significant impact on either pH or vWF.

vWF still remained intact at 5 L/min of aerosol gas flow, but the pH was sharply elevated to approximately 8.0 (FIG. 22B). However, increase of the aerosol gas flow to 10 L/min eliminated 50% vWF:RCo activity, and suffered more damage as aerosol gas flow increased to 15 and 20 L/min (FIG. 22A). The pH remained at about 8 as the aerosol gas flow was increased from 5 to 20 L/min, indicating near complete loss of $CO_2$ in the plasma upon aerosolization. The lack of correlation between pH rise and vWF:RCo activity at 5 L/min suggests that transient exposure to slight alkaline pH (8.0) alone did not cause detectible damage to vWF.

Escalation of aerosol gas flow downsizes the plasma droplets, which has multiple consequences. The reduced droplet size increased exposure of plasma proteins to air/liquid interfacial stress. The combination of elevated aerosol gas flow and reduced droplet size increased speed of the droplet motion in the gas, thereby aggravating the shear stress to proteins on the droplet surface, which have already been stressed from interaction with the air/liquid interface.

Conclusion

This study firmly established the correlation between aerosolization and vWF factor deterioration.

Example 13: Characterization of the Effect of Plasma Feeding Rate on vWF

Background

Example 12 identified the spray sub-process as a major stress factor responsible for vWF degradation during spray drying. This indicates that the critical negative contribution of the combined shear and air/liquid interfacial stresses was exerted on the plasma droplets (and, consequently, on the plasma proteins) while traveling at a high rate of speed upon aerosolization. It also suggested that the impact of the combined shear and air/liquid interfacial stresses on plasma proteins upon aerosolization can be further modified by altering the droplet size. Droplet size can be modified by varying the plasma feed rate under a constant aerosol flow rate. In this example, plasma was fed into the system at different rates under constant aerosol flow rate. Larger droplets at a higher plasma feeding rate would have Jess air-liquid interface exposure for plasma proteins and have slower motion rate and lower shear stress for plasma proteins. Thus, the plasma proteins will sustain less stress attributed to air-liquid interface force and shear force.

Study Design and Method

Thawed FFP samples were fed at 2, 4, 6, 8 or 10 m L/min under a constant aerosol gas flow of 10 L/min without drying gas on. The sprayed liquid plasma samples were analyzed for vWF:RCo activity and pH.

Results

Figure 23A:
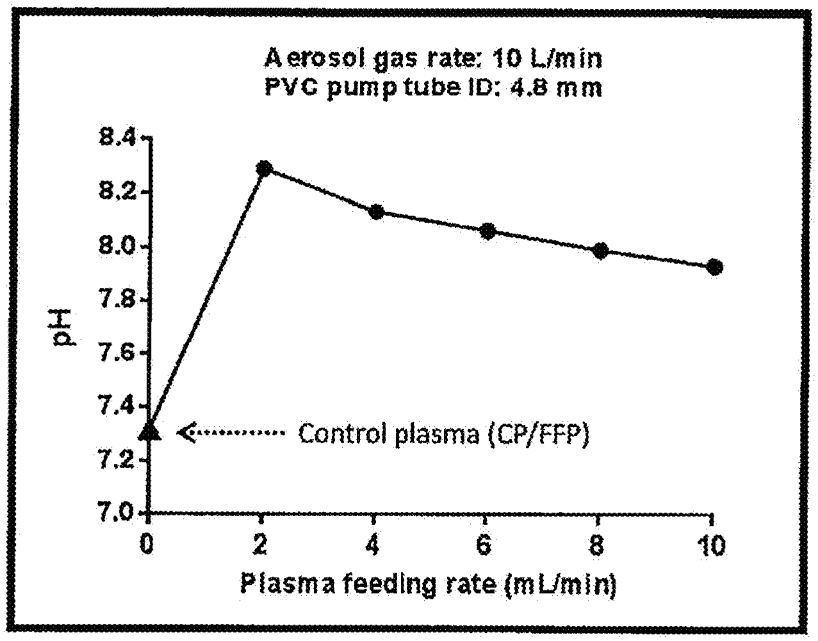
FIG. 23A is a line graph showing pH for CP/FFP and Fed Plasma at Aerosol gas flow rates of 10 L/min; fluid=2 mL/min, 10 L/min; fluid=4 mL/min, 10 L/min; fluid=6 mL/min, 10 L/min; fluid=8 mL/min, and 10 L/min; fluid=10 mL/min. CP indicates Control Plasma; FFP indicates Fresh Frozen Plasma; vWF indicates von Willebrand Factor; vWF:RCo (vWF activity measured by vWF ristocitein assay).
Figure 23B:
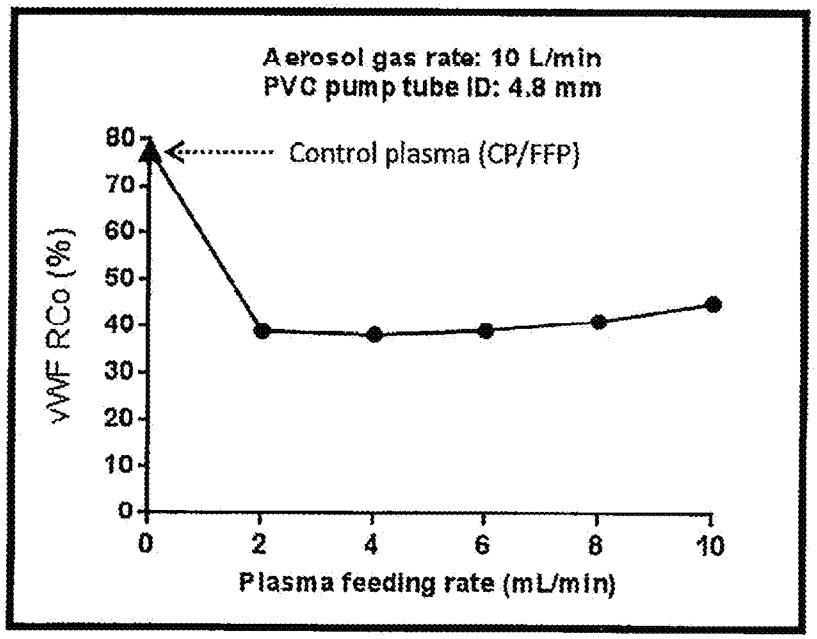
FIG. 23B is a line graph showing the results activity (%, IU/dl) of vWF:RCo for CP/FFP and Fed Plasma at Aerosol gas flow rates of 10 L/min; fluid=2 mL/min, 10 L/min; fluid=4 mL/min, 10 L/min; fluid=6 mL/min, 10 L/min; fluid=8 mL/min, and 10 L/min; fluid=10 mL/min. CP indicates Control Plasma; FFP indicates Fresh Frozen Plasma.

Consistent the observations in Example 12, at 10 L/min of aerosol gas flow, vWF:RCo activity dramatically declined after spraying between 2 and 10 mL/min of plasma input (FIG. 23). vWF:RCo recovery trended slightly higher as plasma input rate increased from 2 to 10 mL/min. pH was significantly increased under all conditions, trending lower from pH 8.3 at 2 mL/min to 7.9 at 10 mL/min as the plasma feed rate increased (FIG. 23B). The opposite trends for pH and vWF:RCo with respect to plasma feeding rate are consistent with the increase of droplet sizes as the result of the increase plasma feeding rate. This reduced the air/liquid-interface to mass ratio and, consequently, the shear and air/liquid-interface stresses as well as $CO_2$ loss.

Conclusion

The results further established the inverse relationship between vWF recovery and spray stresses.

Example 14. The Effect of Formulation of Plasma with Different Spray Dry Stable Acidic Substance (SDSAS's) on vWF Recovery During Spray Background Example 11 highlighted the importance of controlling the pH of the feed plasma in reducing the detrimental effect of spray-drying on vWF. Examples 12 and 13 identified the spray sub-process as a critical step leading to the degradation of vWF. Taken together, these data suggest that reducing the destructive effect of spray on vWF by lowering the pH of feed plasma is critical for improving the overall quality of SpDP. In this example, the impact of pretreatment on the preservation of vWF factor during spray was explored using a diverse panel of SDSAS's.

Study Design and Methods

Aliquots of thawed FFP were formulated separately with a wide range of SDSAS's including ascorbic acid, citric acid, gluconic acid, glycine hydrogen chloride (glycine-HCl), lactic acid and monosodium citrate. The amount of the treating chemical was pre-determined by titrating the unformulated SpDP rehydrated with WFI to ~pH 7.3. Control plasmas include formulated and hyper-formulated (7.4 mM citric acid in Example 11) plasma samples.

Results

Figure 24:
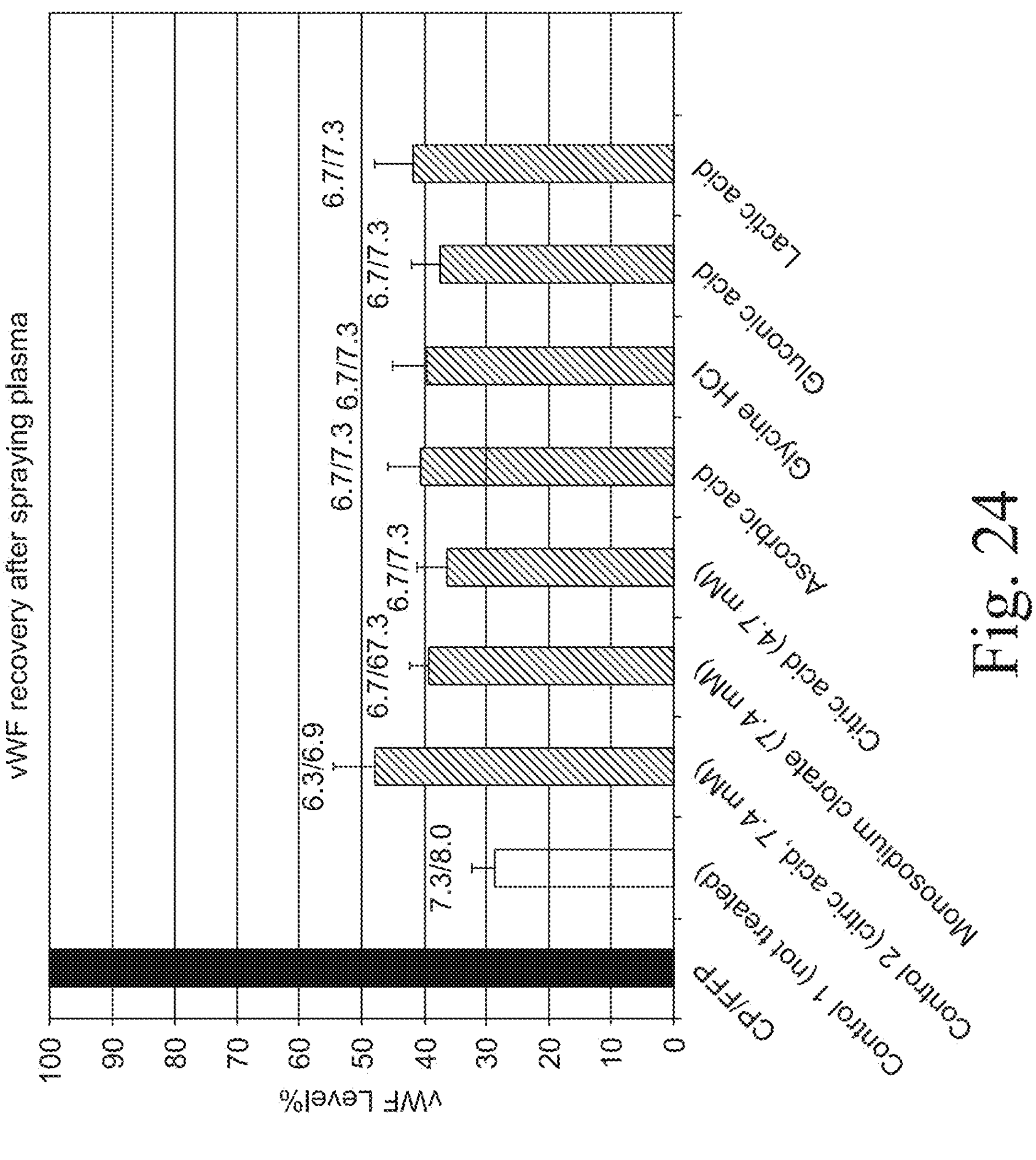
FIG. 24 is a bar graph showing the effect of different SDSAS-formulations on the vWF:RCo recovery and pH during spray. The pH levels prior to and post spray were shown on the top of the bar graph. CP indicates Control Plasma; FFP indicates Fresh Frozen Plasma; vWF indicates von Willebrand Factor.

The results are shown in FIG. 24. Spraying of the naive plasma led to a sharp rise in pH (pH 7.3 and 8.0 before and after spraying, respectively; 7.3/8.0, Bar 2) and reduced vWF:RCo activity by about 70% (30% recovery) (Bar 2). Formulation of the plasma with 7.4 mM citric acid, which lowered the pH to 6.3 in the feed plasma and resulted in a lower than the physiological pH after spraying (6.9), reduced by about 50% vWF:RCo activity during spraying (50% recovery) (Bar 3). Formulation with 7.4 mM monosodium citrate, which lowered the pH to 6.7 in the feed plasma and resulted in a physiological pH after spraying lowered vWF:RCo activity recovery by about 40% (Bar 4), which was higher than naive plasma (Bar 2). Formulation with other SDSAS's, citric acid (4.7 mM, Bar 5), ascorbic acid (Bar 6), glycine HCl (Bar 7), gluconic acid (Bar 8) and lactic acid (Bar 9), all of which lowered the plasma pH to ~6.7 and resulted in a physiological pH (~7.3) after spraying, led to similar vWF:RCo activity recovery of about 40% after spray. Taken together, these results indicated that lowering the pH of feed plasma is critical for preserving vWF during spray.

Conclusion

Enhanced vWF preservation can be achieved by formulating the feed plasma with a wide array of SDSAS's—not only citric acid, but monosodium citrate, ascorbic acid, glycine HCl, gluconic acid and lactic acid, and probably many others meeting the criteria given in the present specification. However, the most important consideration in choosing the proper SDSAS is the suitability for transfusion. Other important factors include availability of USP grade formulation, tolerance for terminal sterilization and interference with standard assays, to name a few. As plasma already contains citric acid (as an anticoagulant), addition of more citric acid to bring the concentration identified in the present invention as being suitable for enhanced plasma protein recovery and stability has the advantage of not introducing a new component to serve as a pH adjuster. Further, citrate is usually rapidly metabolized by the liver. However, rapid administration of large quantities of stored blood may cause hypocalcaemia and hypomagnesaemia when citrate binds calcium and magnesium. This can result in myocardial depression or coagulopathy. Patients most at risk are those with liver dysfunction or neonates with immature liver function having rapid large volume transfusion. Slowing or temporarily stopping the transfusion allows citrate to be metabolized. Administration of calcium chloride or calcium gluconate intravenously into another vein can be used in order to minimize citrate toxicity. Nevertheless, the elevation of citrate in SpDP can be avoided by using alternative SDSAS's such as lactic acid and glycine-HCl. Lactic acid is an important constituent in Ringer's Lactate solution, which is often used for fluid resuscitation after a blood loss due to trauma, surgery, or a burn injury. Glycine-HCl is referenced in the US Pharmacopeia.

Example 15: Enhanced vWF Factor Protection During Spray is Inversely Correlated with the pH Levels of the Feed Plasma Background Results from Example 14, evaluating different chemicals for lowering the pH of the feed plasma, confirmed the generality of the inhibition of pH rise during spray improves vWF:RCo activity recovery. However, it is still striking that vWF factor is better preserved at an acidic pH lower than the physiological pH (7.2-7.4) during the spraying process. Nevertheless, the surprising observation suggested the potential of pH manipulation for further improving vWF factor recovery. In this example, we further evaluated pH of the feed plasma with regard to vWF:RCo activity recovery after spraying. Citric acid and lactic acid were chosen for use in the study.

Study Design and Method

Aliquots of thawed FFP were formulated with different concentrations of citric acid or lactic acid from 20× stock solutions. The amount of the formulation chemicals was pre-determined ensuing a physiological or lower pH level of SpDP when rehydrated with WFI. The formulated samples were determined for pH, sprayed, and the recovered liquid samples were analyzed for pH and vWF:RCo activity.

Results

Figure 25A:
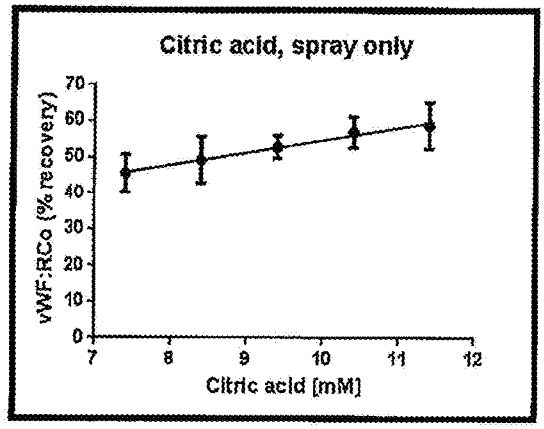
FIG. 25A-C are bar graphs showing the effect of different SDSAS-formulations on the vWF:RCo recovery and pH during spray drying. {A) citric acid, (B) lactic acid, and (C) pH. The pH levels prior to and post spray were shown on the top of the bar graph. vWF indicates von Willebrand Factor; vWF:RCo (vWF activity measured by vWF ristocitein assay).
Figure 25B:
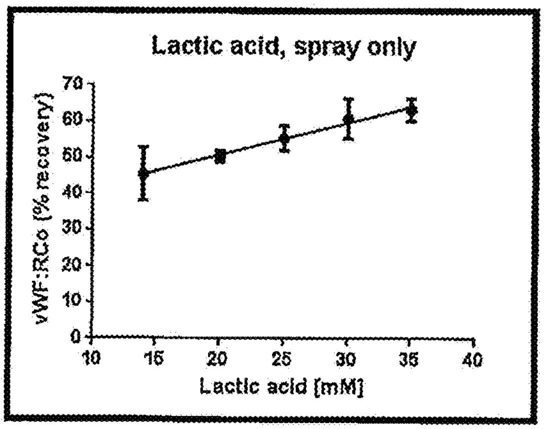
Figure 25C:
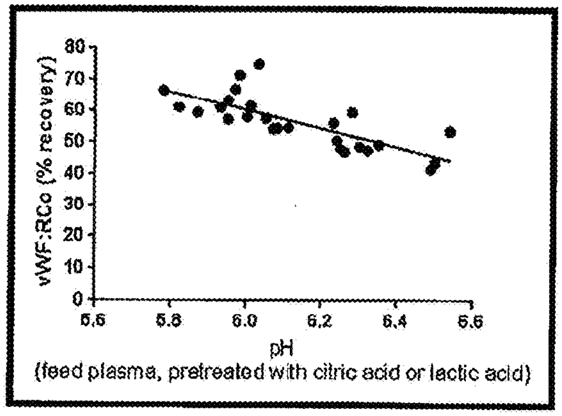

The results are shown in FIG. 25A for citric acid and FIG. 25B for lactic acid. Consistent with earlier observations, spraying alone led to a rise in pH (not shown) and vWF:RCo deterioration under all conditions. Remarkably, vWF:RCo recovery trended higher as the concentration of citric acid or lactic acid increased or pH declined. The inverse correlation between pH of the feed plasma and vWF:RCo activity recovery was clearly shown in FIG. 25C, which was generated by pooling data of both citric acid and lactic acid studies.

Conclusion

Feed plasma pH can be further exploited to increase vWF recovery in conjunction with recovery of other plasma proteins.

Example 16: pH Effect on C3A and C5A

Purpose:

This study investigated the effect of the pH on the complement activation (C3a and C5a) in spray dried plasma, derived from pretreated Fresh Frozen Plasma (SpDP/FFP).

SpDP/FFP was used for this study, where each pretreatment solution was a 20× solution so that the total concentration of glycine present in each pretreated fresh frozen plasma (FFP) was always 23 mM while the amount of HCl (introduced as glycine HCl) for pH adjustment varied. The pretreatment solutions were:

0.46 M Glycine HCl 0.40 M Glycine HCl and 0.06 M Glycine 0.34 M Glycine HCl and 0.12 M Glycine 0.28 M Glycine HCl and 0.18 M Glycine Scope:

Investigation of C3a and C5a complement elevation observed with spray dried plasma manufactured from non-leukoreduced FFP with CPD anticoagulant pretreated with 23, 20, 17, and 14 mM glycine HCl.

Experimental Overview:

All pretreatment solutions were prepared at 20× concentration, where 13 mL of pretreatment solution was added to 247 mL of FFP.

Pretreated FFP was spray dried on Alpha 3 instrument using disposable bags P/N 01082-4 with nozzle P/N 01229-1 and 19 gauge cannula P/N 01301 with following process parameters:

Plasma fluid rate: 10 mL/minute

Aerosol gas flow rate: 25 L/minute

Drying gas initial temperature: 125° C.

Drying gas flow rate: 550-750 L/min

Drying gas exhaust temperature: 50° C.

The same nozzle (01229-1) was used for all the spray drying process.

The formulations and concentrations of pretreatment solutions and pretreated FFP were as follows:

TABLE 29

Pretreatment solution overview

| Pretreatment Solution | Pretreated FFP |
|---|---|
| 0.46M Glycine HCl | 23 mM Glycine HCl |
| 0.40M Glycine HCl + 0.06M Glycine | 20 mM Glycine HCl + 3 mM Glycine |
| 0.34M Glycine HCl + 0.12M Glycine | 17 mM Glycine HCl + 6 mM Glycine |
| 0.28M Glycine HCl + 0.18M Glycine | 14 mM Glycine HCl + 9 mM Glycine |

Samples were rehydrated with deionized water produced.

Samples were stored at 4° C. for 110-112 days.

Summary:

Four (4) pretreatment solutions with a combination of glycine and glycine HCl were evaluated for SpDP in this study such that the total glycine concentration was kept constant at 23 mM for all pretreated plasma samples and the acidity was varied. SpDP was tested 110-112 days after storage at 2-8° C.

Complement activation analysis showed a direct correlation of C3a and C5a with the pH of the rehydrated SpDP. The rehydrated SpDP/FFP had a pH range of 6.6-7.8 depending on the glycine HCl concentration. C3a was more elevated at higher pH, while C5a was more elevated at low pH.

Equipment and Supplies:

Equipment:

- Alpha 3 spray drying instrument
- Analytical balance, any calibrated unit
- BCS XP hemostasis analyzer
- Freezer, any unit capable of maintaining −20° C., monitored by data logger
- Helmer Plasma Thawer,
- IL ACL TOP 700,
- Karl Fischer Titrator,
- Milli-Q Water Purification System
- NanoDrop 1000,
- Osmometer,
- pH meter, any unit calibrated before use
- Refrigerator, any unit capable of maintaining 4° C., monitored by data logger
- TEG Supplies:

- 50 mL conical tubes
- 60 mL syringe
- 250 mL volumetric cylinder
- 250 mL volumetric flask
- 300 mL transfer pack
- 800 mL disposable beaker, Fisher Scientific
- 1 L transfer pack
- Deionized (DI) water,
- Disposable Assy (210 mm Layflat, short chamber)
- Disposable spatula
- Dri-Shield Moisture Barrier Bag,
- FFP, 0119715 mL conical tubes
- Glycine, Sigma Aldrich, G8898-1 KG, lot #056K0074
- Glycine Hydrochloride, Fisher Scientific, AC411011000, lot #A0341276
- Hydrochloric acid, 0.02 N, Fisher Scientific, SA60-1, lot #152795
- Nozzle Assy, P/N 01229-1 and 19 gauge cannula P/N 01301
- Nozzle Assy
- Parafilm Disposable Assy (210 mm Layflat, 35" long chamber)
Weigh boat Procedure:

SpDP samples were prepared. SpDP/FFP was stored at 4° C., CP aliquots were frozen and stored at −20° C., and samples remained in storage for 110-112 days. Batch 1541 was prepared on Dec. 8, 2015. Batch 1542 was prepared on Dec. 9, 2015. Batch 1543 was prepared on Dec. 10, 2015. SpDP samples were prepared for analysis using by:

An aliquot of frozen CP/FFP was defrosted and the protein concentration measured.

All SpDP were rehydrated to match CP protein concentration with DI water

Rehydrated SpDP and rethawed CP/FFP was tested for: pH, C3a, C5a.

Figure 26:
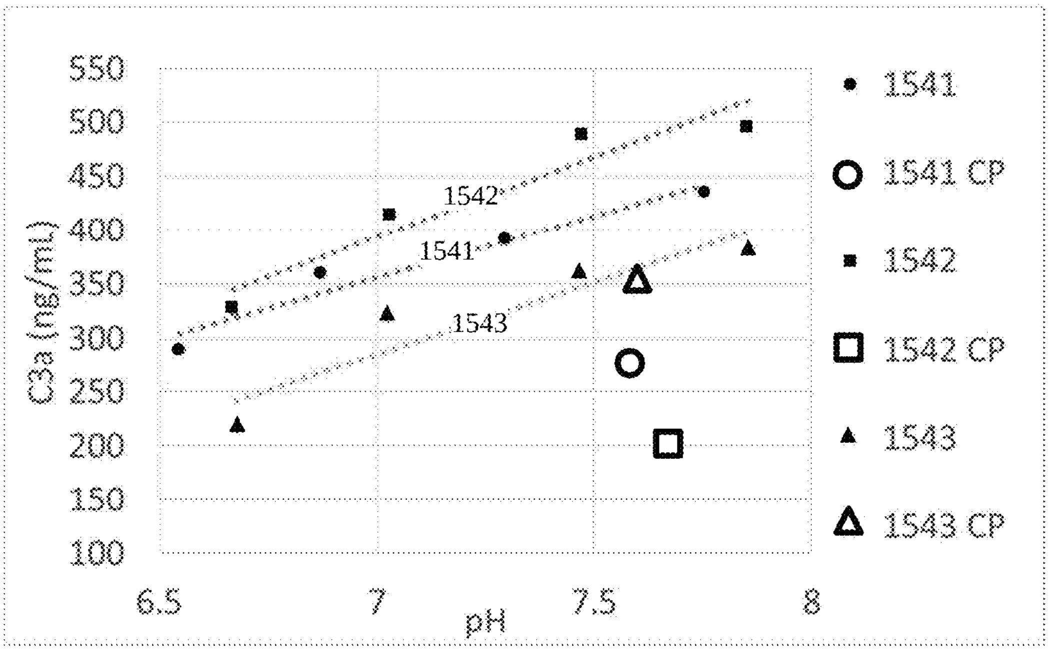
FIG. 26 is a line graph, in color, showing the amount of C3a ng/ml and pH for batches 1543, 1542, 1541 and the respective control plasma (CP) for experiments performed in Example 16.

Results:

i. C3a: Referring to FIG. 26, there is a positive correlation between the pH of the rehydrated SpDP and its C3a concentration.

TABLE 30

Equations for C3a vs. pH (See FIG. 26)

| Batch | 1541 | 1542 | 1543 |
|---|---|---|---|
| Slope | 133.61 | 147.28 | 132.75 |
| Intercept | −438.82 | −637.07 | −643.84 |
| R-Squared | 0.95 | 0.90 | 0.87 |

C5a: There is a negative correlation between the pH of the rehydrated SpDP and its C5a concentration. See FIG. 27.

TABLE 31

Equations for pH vs. C5a

| Batch | 1541 | 1542 | 1543 |
|---|---|---|---|
| Slope | −2.70 | −2.83 | −3.21 |
| Intercept | 28.50 | 30.41 | 34.26 |
| R-Squared | 0.95 | 0.65 | 0.88 |

Conclusion:

There is an upward trend between the C3a level and pH of the rehydrated SpDP, thereby the pH of the pretreatment solution as well as the pretreated plasma.

There is a downward trend between the C5a level and pH of the rehydrated SpDP, thereby the pH of the pretreatment solution.

Example 17: Pretreatment Solution pH Effect on C5A (TR-00344)

Purpose:

This study investigated the effect of the pretreatment solution pH on the complement activation (C5a) in pretreated never frozen plasma (NFP).

Scope:

The effect of 20× pretreatment solution pH on C5a of never frozen plasma (NFP) samples.

Summary:

Low pH pretreatment solution causes C5a elevation. A higher pH pretreatment solution mitigates the C5a elevation.

The addition of glycine to a pretreatment solution increases the pH of the pretreatment solution, mitigating C5a elevation. The addition of glycine does not affect the pH of the rehydrated spray dried plasma (ODP).

Rapid dispersion of the pretreatment solution and minimizing localized contact of pretreatment solution to the plasma also mitigates C5a elevation.

A 0.4 M glycine HCl+1 M glycine pretreatment solution (Gly HCl+Gly) combined with rapid mixing mitigates C5a levels to values comparable to other blood products on the market, such as apheresis plasma and Octaplasma.

Background:

pH Effect on C3a and C5a from Example 16 using samples prepared for this study.

The effect of pretreatment solution pH was initially investigated in Example 16, pH Effect on C3a and C5a. Spray dried plasma derived from pretreated Fresh Frozen Plasma (ODP/FFP) prepared and stored at 4° C. was used.

The formulations and concentrations of pretreatment solutions and pretreated FFP as well as the average pH of the rehydrated plasma were as follows:

TABLE 32

Pretreatment solution overview

| Pretreatment Solution | Pretreated FFP | pH Rehydrated Plasma |
|---|---|---|
| 0.46M Glycine HCl | 23 mM Glycine HCl | 6.55 |
| 0.40M Glycine HCl + 0.06M Glycine | 20 mM Glycine HCl + 3 mM Glycine | 6.89 |
| 0.34M Glycine HCl + 0.12M Glycine | 17 mM Glycine HCl + 6 mM Glycine | 7.22 |
| 0.28M Glycine HCl + 0.18M Glycine | 14 mM Glycine HCl + 9 mM Glycine | 7.59 |

Figure 27:
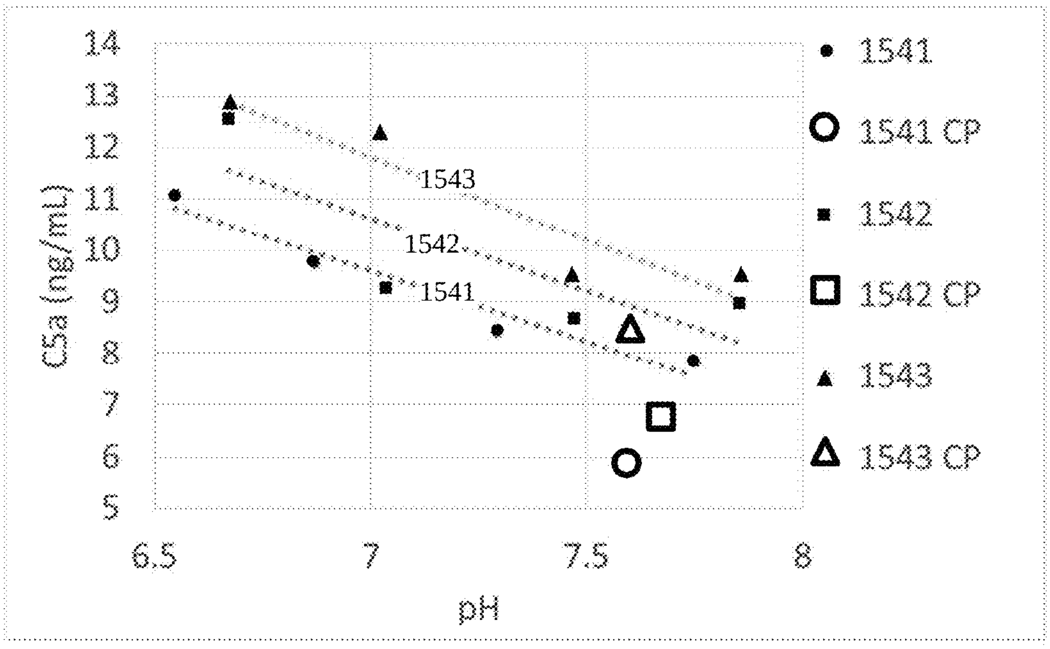
FIG. 27 is a line graph showing the amount of C5a ng/mL and pH for batches 1543, 1542, 1541 and the respective control plasma (CP) for experiments performed in Example 16.

ODP/FFP aliquots stored at 4° C. was rehydrated and tested for C5a. The results in Example 16 showed that there was a negative correlation between the pH of the rehydrated ODP/FFP and the C5a measurement as shown in FIG. 27.

REFERENCE DOCUMENTS

Larry J. Dumont, et al, "The bioequivalence of frozen plasma prepared from whole blood held overnight at room temperature compared to fresh-frozen plasma prepared within eight hours of collection," *Transfusion* 55:480 (2015).

S. Suessner, et al., "Comparison of several complement and coagulation factor concentrations in different plasma products." *Transfusion Medicine and Hemotherapy,* 41 (supplement 1): pg. 36 (2014).

Equipment and Supplies:

Equipment:
pH meter
Analytical Balance

Supplies:
15 mL conical tubes
50 ml conical tubes
250 mL volumetric flask
Citric Acid, JT Baker, 0122-01, lot #K31605
Glycine, Sigma Aldrich, G8898-1 KG, lot #056K0074
Glycine Hydrochloride, Sigma Aldrich, G2879, lot #SLMB2147V
MICROVUE C5a EIA kit, VMS-A021, lot #068724
NFP, Test Batch 1947, 1948, 1954, 1958, 1959, 1961, and 1968

Procedure:

400 Mm Glycine HCl Pretreatment Solution:

2.23 g of glycine HCl was dissolved with 50 mL of DI water in a 50 mL conical tube.

The pH of the pretreatment solution was measured. The pH of the pretreatment solution was 1.32.

400 Mm Glycine HCl+1 M Glycine Pretreatment Solution:

11.15 g of glycine HCl and 18.77 g of glycine was dissolved in DI water in a 250 mL volumetric flask. The pH of the pretreatment solution was measured. The pH of the pretreatment solution was 2.66.

148 Mm Citric Acid Pretreatment Solution:

1.42 g of citric acid was dissolved in 50 mL of DI water in a 50 mL conical tube. The pH of the pretreatment solution was measured. The pH of the pretreatment solution was 2.28.

148 Mm Citric Acid+1 M Pretreatment Solution:

1.42 g of citric acid and 3.75 g of glycine were dissolved in 50 mL of DI water. The pH of the pretreatment solution was measured. The pH of the pretreatment solution was 3.40.

Never frozen plasma with CPD anticoagulant (NFP/CPD) was procured from Research Blood Component (RBC), Test Batch 1947, 1948, 1954, 1958, 1959, 1961, and 1968. Three (3) samples were prepared from each unit of NPF/CPD: control plasma (CP), rapid mixing sample, and slow mixing sample. Set aside a minimum of 3 mL of CP in a 15 mL conical tube.

Rapid Mixing:

Prepare four (4) 15 mL conical tubes with 0.5 mL of each pretreatment solution placed in the tube. 9.5 mL of NFP was rapidly injected on to the pretreatment solution using a 10 mL pipette. The tube was capped and mixed by inverting gently a couple of times.

Slow Mixing:

Prepare four (4) 15 mL conical tubes with 9.5 mL of NFP/CPD in each tube. 0.5 mL of each pretreatment solution was slowly added on top of the plasma and allowed to sit for one (1) minute. The tube was capped and mixed by inverting gently a couple of times. The pH of the CP and Rapid Mixing and Slow Mixing sample with each of the pretreatment solutions was measured. The C5a of the CP and Rapid Mixing and Slow Mixing sample with each of the pretreatment solutions was measured.

Results:

pH of the Pretreatment Solution and Pretreated Plasma:

i. The addition of 1 M glycine increased both glycine HCl and citric acid pretreatment solution by one (1) pH unit. Although the pH of the pretreatment solutions varied significantly in the range of 1.3 to 3.4, the pH of the pretreated plasma was constant at approximately 6.1-6.2. See Table 33 for the pH measurements.

TABLE 33 pH of pretreatment solution and pretreated NFP

| Pretreatment solution (20X) | pH of pretreatment solution | Pretreated plasma | pH of pretreated plasma |
|---|---|---|---|
| 400 mM glycine HCl | 1.32 | 20 mM glycine HCl | 6.18 ± 0.05 |
| 400 mM glycine HCl + 1M glycine | 2.66 | 20 mM glycine HCl + 50 mM glycine | 6.17 ± 0.06 |
| 148 mM citric acid | 2.28 | 7.4 mM citric acid | 6.19 ± 0.05 |
| 148 mM citric acid + 1M glycine | 3.40 | 7.4 mM citric acid + 50 mM glycine | 6.17 ± 0.06 |

Effect of Pretreatment Solution pH on C5a Measurement

Pretreated NFP results showed that rapid mixing and increasing pH of pretreatment solution by adding glycine minimizes the C5a elevation. Rapid mixing disperses the pretreatment solution into the plasma, minimizing the localized contact of the acidic pretreatment solution and plasma. The addition of glycine to the glycine HCl pretreatment solution with rapid mixing resulted in C5a measurements slightly higher than CP/NFP and comparable to citric acid. The addition of glycine to the citric acid pretreatment solution resulted in C5a measurements comparable to CP/NFP regardless of mixing speed.

FIG. 28 shows C5a analysis of NFP rapidly and slowly pretreated with 400 mM glycine HCl, 400 mM glycine HCl+1 M glycine, 148 mM citric acid, and 148 mM citric acid+1 M glycine in tube (n=7). C5a levels of NFP/CPD rapidly pretreated with 400 mM glycine HCl+1 M glycine compared to apheresis plasma and Octaplasma. C5a levels of NFP/CPD rapidly pretreated with 400 mM glycine HCl+1 M glycine pretreatment solution is comparable to C5a measurements for plasma products already approved and on the market. C5a measurements in Table 34 show that plasma pretreated with glycine HCl+glycine of 11.30 ng/mL (9.22-20.01 ng/mL) is comparable to Octaplas measurement of 17.1 ng/mL (14.3-26.2 ng/ml) and apheresis plasma measurement of 16.1 ng/ml (14.7-17.8 ng/ml).

The data also clearly show that regardless of the acid used in the pre-treatment solution or mixing technique the addition of extra glycine results in a significant decline of C5a measured in the resulting reconstituted plasma. The data particularly show that the formulation of glycineHCL with extra glycine (Gly HCL+GLY in the FIG. 28) of the present invention results in a greater that 50% reduction in C5a compared to glycineHCL alone without implicating the potential negative effects of increased citric acid in the reconstituted plasma when transfused to a recipient.

TABLE 34

C5a measurements for NFP/CPD pretreated with 400 mM glycine HCl + 1M glycine pretreatment solution, Octaplas, and Apheresis plasma

| | Reference | Gly HCl + Gly Rapid Mix (n = 7) | | | Suessner (n = 30) | |
|---|---|---|---|---|---|---|
| Assay | Range | Average | Min | Max | Octaplas | Apheresis |
| C5a (ng/ml) | 4.7-9.5 | 11.30 ± 5.42 | 9.22 | 20.01 | 17.1 (14.3-26.2) | 16.1 (14.7-17.8) |

Conclusion:

The data indicate that the lower the pH of the pretreatment solution, the higher the C5a elevation.

The addition of glycine to pretreatment solution increases the pH of the pretreatment solution and decreasing C5a elevation, while not affecting the pH of the pretreated plasma. This is the key rationale for introducing glycine for the development of the pretreatment solution. Rapid mixing also decreases C5a elevation by dispersing the pretreatment solution quickly into the plasma and minimizing localized contact of acidic solution and plasma. 400 mM glycine HCl+1 M glycine pretreatment solution with rapid mixing results in C5a levels in NFP/CPD comparable to products on the market such as Octaplas and apheresis plasma.

Example 18 Glycine HCl and Glycine Pretreatment Solution Manual Pretreatment Method Purpose:

The purpose of this test report is to describe the results for evaluating a manual pretreatment method using a 20× glycine HCl+glycine pretreatment solution (0.4 M glycine HCl and 1 M glycine) to manufacture spray dried never frozen plasma (ODP/NFP).

The glycine HCl+glycine pretreatment solution was selected as the pretreatment solution. The previous pretreatment solution was a 20× 0.4 M glycine HCl solution. There was no statistical difference between the rehydrated spray dried fresh frozen plasma (ODP/FFP) pretreated with glycine HCl pretreatment solution, and glycine HCl+glycine pretreatment solution.

20 units of NFP were pretreated with the new pretreatment solution of 0.4 M glycine HCl+1 M glycine, with a manual pretreatment method, spray dried on the Alpha instrument, and full panel in-house testing was completed to characterize the resulting ODP/NFP.

Scope:

Evaluated the 20× pretreatment solution (Glycine HCl (400 mM)/Glycine (1000 mM) Pretreatment Solution, Lab Use, P/N 01516), using a manual pretreatment method by characterizing ODP/NFP, manufactured at Medic Regional Blood Center in Knoxville, TN.

Disposable bag P/N 01082-3, Rev 7, nozzle P/N 01376, Rev 1, and spray dryer Alpha 1 and 4 were used to manufacture ODP/NFP.

SUMMARY

ODP/NFP/PreT manually pretreated with a shaker was characterized to have coagulation and plasma profile similar to CP/FFP and as previously characterized ODP/NFP/PreT and ODP/FFP/PreT. The manual pretreatment method minimized C5a elevation of ODP/NFP/PreT to levels slightly above the normal reference range, similar to apheresis plasma, and significantly below Octaplas.

Deviations:

Due to plasma availability at Medic, ODP was prepared from 12 units of O and eight (8) units of A instead of nine (9) units of A, nine (9) units of O, and two (2) units of B.

TEG supplies were not available for batches 2058-2061, 2064-2065, 2070-2075, and 2077.

Equipment and Supplies:

Equipment:

- Alpha 1 spray drying instrument
- Alpha 4 spray drying instrument
- Analytical balance, any calibrated unit
- Scale, any calibrated unit
- Freezer, any unit capable of maintaining <−18° C., monitored by data logger
- Refrigerator, any unit capable of maintaining 2-6° C., monitored by data logger
- Milli-Q Academic Water Purification System
- NanoDrop 1000
- pH meter, any unit calibrated before use
- Osmometer
- BCS XP
- IL ACL TOP 700
- Selectra Pro M
- TEG
- Tubing Heat Sealer
- Vortex, any unit Supplies:

- 1 L volumetric flask
- 5 mL cryogenic vial
- 50 mL conical tubes
- DI water
- Disposable Assembly P/N 01082-3, Rev 7
- Disposable spatula
- Dri-Shield Moisture Barrier Bag, VMS S-6498
- Glycine Hydrochloride, 01429, lot #V10185
- Glycine, 01515, lot #SLBQ1160V
- Glycine HCl (400 mM)/Glycine (1000 mM) Pretreatment Solution, Lab Use, 01516, lot #10014
- NFP
- Nozzle Assembly P/N 01376, Rev 1
- One-Time Humidity-Indicating Strips, 01517
- Test batches 2058-2065, 2070-2083, and 2090

Procedure:

Preparation of Pretreatment Solution:

Pretreatment solution lot #10014 was prepared by dissolving 44.61 g of glycine HCl (lot #V10185) and 75.07 g of glycine (lot #SLBQ1160V), and dissolved with DI water in a 1 L volumetric flask.

Test batches 2058-2065, 2070-2083, and 2090 (12 units of O and eight (8) units of A) were pretreated using glycine HCl+glycine 20× pretreatment solution prepared.

Pretreated NFP was spray dried on the Alpha 1 and Alpha 4 instruments, using Disposable Assembly Bags (P/N 01082-3, Rev 7), with Nozzle Assembly (P/N 01376, Rev 1), using the following process conditions:

- Plasma fluid flow rate: 10 mL/minute
- Aerosol gas flow rate: 15 L/minute
- Drying gas initial temperature: 125° C.
- Drying gas flow rate: 550-750 L/min
- Drying gas exhaust temperature: 52° C.

Results:

C3a and C5a Analysis OF CP/FFP, CP/FFP/PreT, and ODP/NFP/PreT

Figure 29:
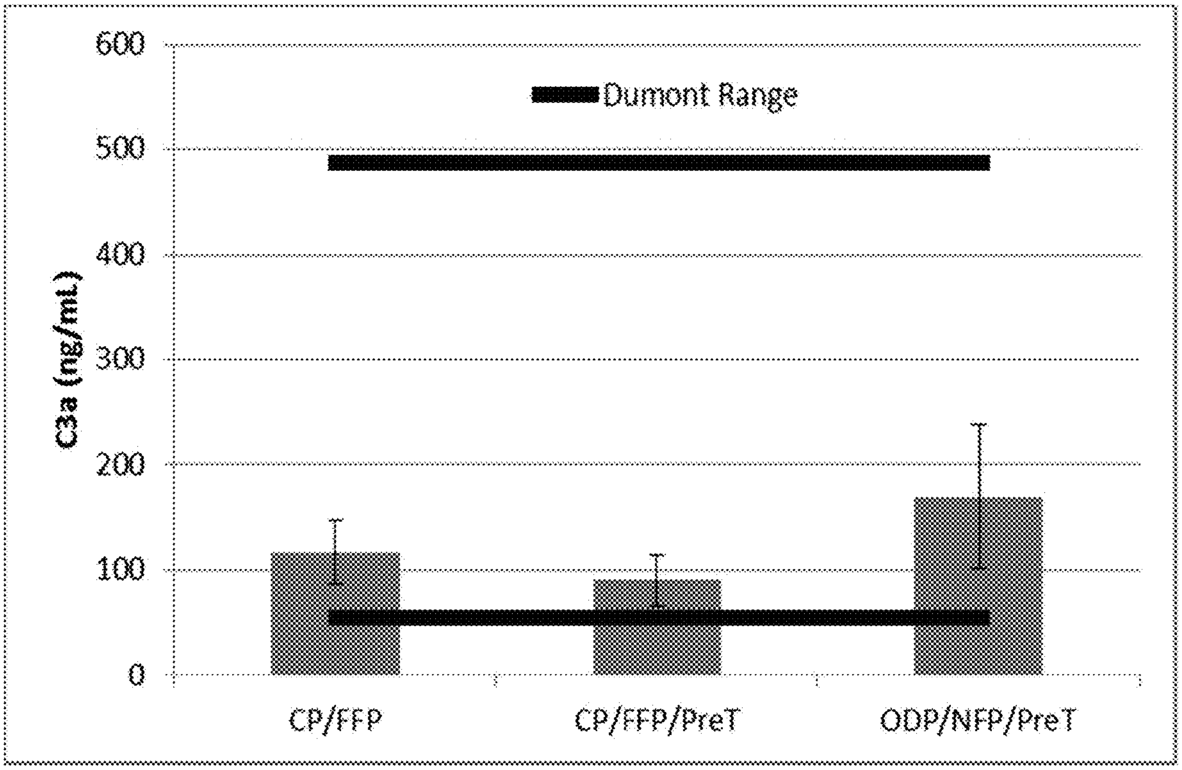
FIG. 29 is a bar graph showing C3a measurement in ng/mL of CP/FFP (control plasma/fresh frozen plasma), CP/FFP/PreT (Control plasma/Fresh Frozen Plasma/Pretreated), and ODP/NFP/PreT (On demand plasma (Applicant's inventive spray dried plasma) never frozen, pretreated) average of n=20±1 SD.

FIG. 29 shows C3a measurement of CP/FFP, CP/FFP/PreT, and ODP/NFP/PreT average of n=20±1 SD. The C3a measurements of CP/FFP, CP/FFP/PreT, and ODP/NFP/PreT were within the reference range published in Dumont's paper. Spray drying plasma resulted in an elevation of C3a compared to the CP/FFP, however the values obtained were within the lower range of the reference range and below values obtained for products available on the market such as Octaplas and apheresis plasma.

Figure 30:
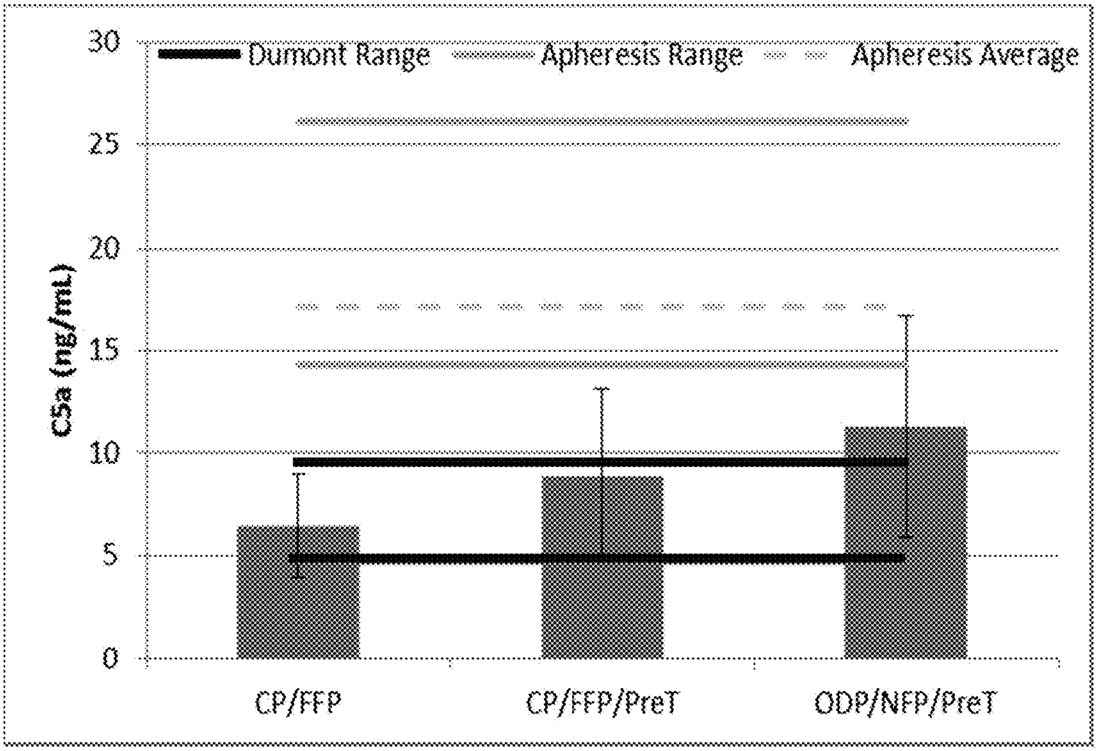
FIG. 30 is a bar graph showing C5a measurement in ng/ml of CP/FFP, CP/FFP/PreT, and ODP/NFP/PreT average of n=20±1 SD.

The C5a measurements of CP/FFP, CP/FFP/PreT, and ODP/NFP/PreT can be found in FIG. 30 and Table 35. FIG. 30 shows C5a measurement of CP/FFP, CP/FFP/PreT, and ODP/NFP/PreT average of n=20±1 SD. The C5a measurements of CP/FFP were similar to the reference range published in Dumont's paper as shown in FIG. 30 and Table 35. C5a measurements increased after pretreatment and spray drying. Although the C5a measurements of CP/FFP/PreT and ODP/NFP/PreT were higher than CP/FFP, the C5a values were comparable to Octaplas and significantly lower than apheresis plasma, which are both products available on the market.

TABLE 35

C3a and C5a measurements of Reference Range, ODP/NFP/PreT, Octaplas, and Apheresis plasma

| | Reference | ODP/NFP/PreT n = 20 | | | n = 30 | |
|---|---|---|---|---|---|---|
| Assay | Range | Average | Min | Max | Octaplas | Apheresis |
| C3a (ng/mL) | 55-486 | 170.21 ± 68.99 | 98.9 | 384.9 | 669.1 (563.9-867.2) | 980.4 (728.2-1154.3) |
| C5a (ng/ml) | 4.7-9.5 | 11.30 ± 5.42 | 4.6 | 25.5 | 16.1 (14.7-17.8) | 17.1 (14.3-26.2) |

Additional Assay Analysis of CP/FFP and ODP/NFP/PreT

Figure 31:
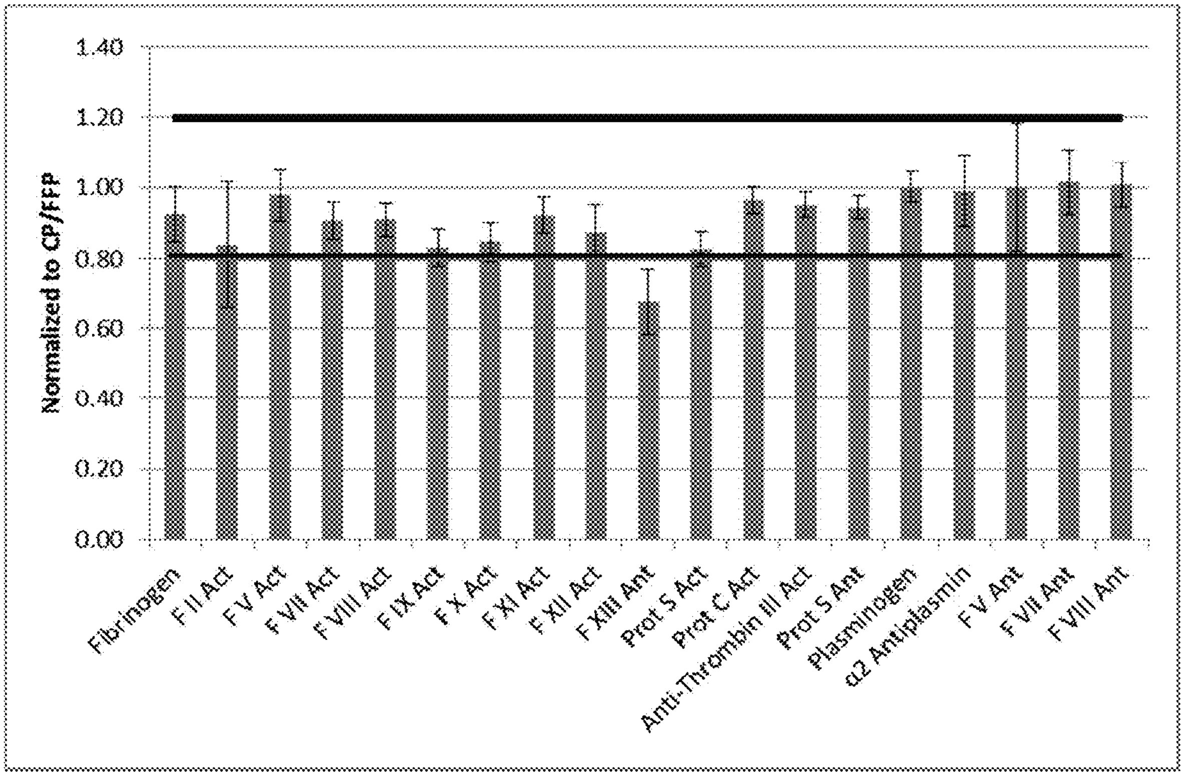
FIG. 31 is a bar graph showing ODP/NFP/PreT activity and antigen measurements normalized to CP/FFP.
Figure 32:
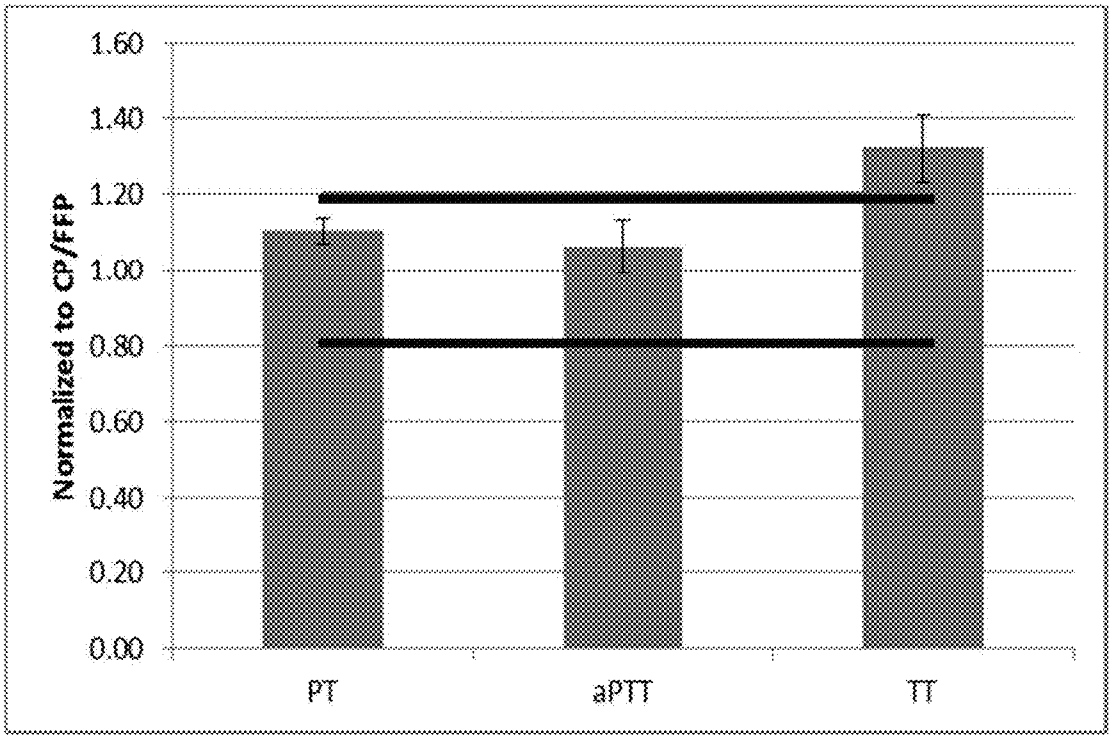
FIG. 32 is a bar graph showing aPTT (activated partial thromboplastin time), PT (prothrombin time), and TT (thrombin time) of ODP/NFP/PreT normalized to CP/FFP.

All ODP/NFP/PreT activities and antigens were within CP/FFP±20% except for Factor XIII Antigen, where Factor XIII Antigen was approximately 70% of CP/FFP. Typically, antigens are close to CP/FFP regardless of the activity. The effect of manufacturing spray dried plasma on Factor XIII Antigen assay will be further evaluated. See FIG. 31 for ODP/NFP/PreT data normalized to CP/FFP. FIG. 31 shows ODP/NFP/PreT activity and antigen measurements normalized to CP/FFP.

aPTT (activated partial thromboplastin time), PT (prothrombin time), and TT (thrombin time) of ODP/NFP/PreT were comparable to CP/FFP. There was a slight prolongation of TT of 17.5 seconds compared to 13.2 seconds for CP/FFP. TT is sensitive to pH and lower pH prolongs TT. Since ODP is rehydrated to a lower pH than CP with the current pretreatment solution formulation, it was expected to see a prolonged TT due to pH effect. See Table 36 for pH measurements. FIG. 32 shows results for aPTT, PT, and TT of ODP/NFP/PreT normalized to CP/FFP.

TABLE 36 pH of CP/FFP, CP/FFP/PreT, and ODP/NFP/PreT

Figure 33:
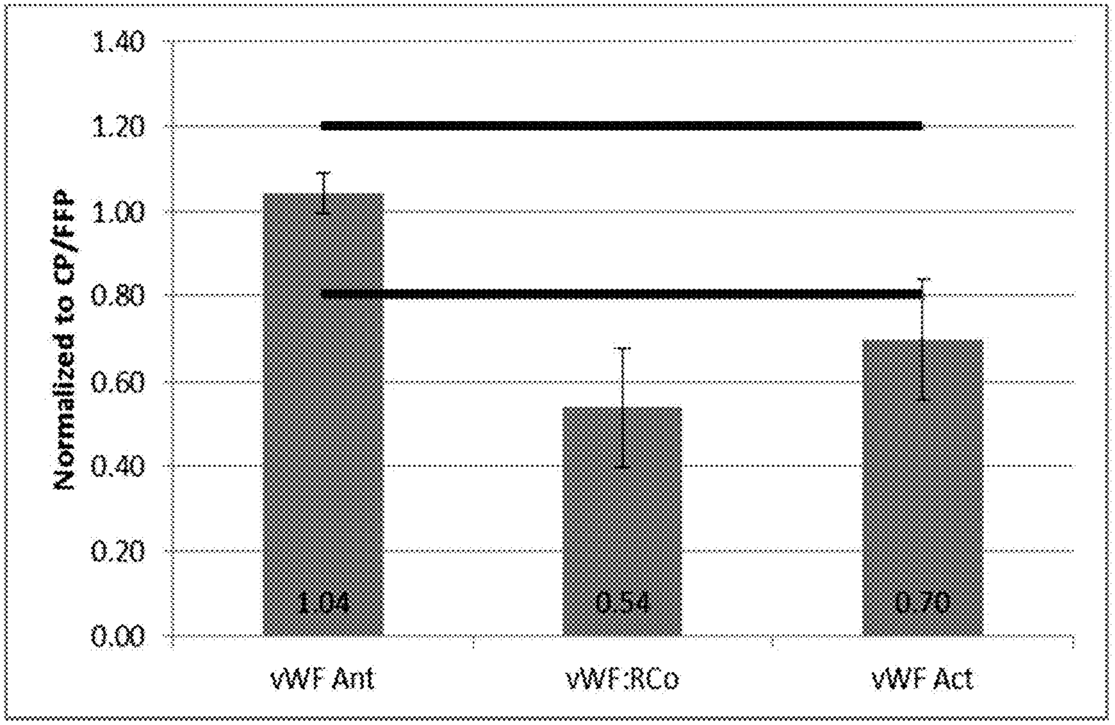
FIG. 33 is a bar graph showing vWF Antigen (von Willebrand Factor), vWF:RCo (vWF activity measured by vWF ristocitein assay), and vWF Activity of ODP/NFP/PreT (On demand plasma (Applicant's inventive spray dried plasma) never frozen, pretreated) normalized to CP/FFP (Control plasma/Fresh Frozen Plasma).

| | CP/FFP | CP/FFP/PreT | ODP/NFP/PreT |
|---|---|---|---|
| Average | 7.73 | 6.40 | 7.21 |
| Std Dev | 0.15 | 0.11 | 0.28 |

vWF antigen, vWF:RCo, and vWF activity were measured for ODP/NFP/PreT and normalized to CP/FFP. vWF antigen remained similar to CP/FFP. vWF:RCo measured significantly less compared to CP/FFP and vWF activity measured higher than vWF:RCo as observed previously. The manual addition of pretreatment solution effectively delivered pretreatment solution to plasma and protected vWF during the spray drying process. FIG. 33 shows the results of vWF Antigen, vWF:RCo, and vWF Activity of ODP/NFP/PreT normalized to CP/FFP.

Figure 34:
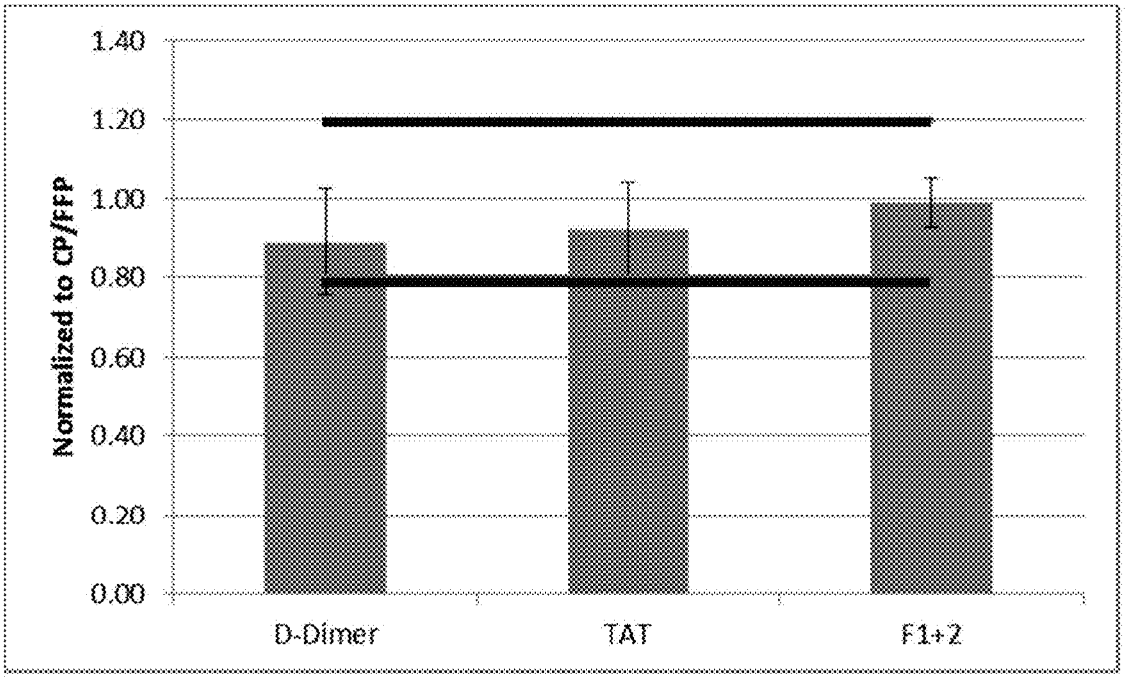
FIG. 34 is a bar graph showing activation marks D-Dimer, TAT, and F1+2 of ODP/NFP/PreT (On demand plasma (Applicant's inventive spray dried plasma) never frozen, pretreated) normalized to CP/FFP (Control plasma/Fresh Frozen Plasma).

The activation markers D-Dimer, TAT, and F1+2 of ODP/NFP/PreT were similar to CP/FFP, indicating the manual pretreatment method and spray drying process did not activate the coagulation system. FIG. 34 shows results for D-Dimer, TAT, and F1+2 of ODP/NFP/PreT normalized to CP/FFP.

Figure 35:
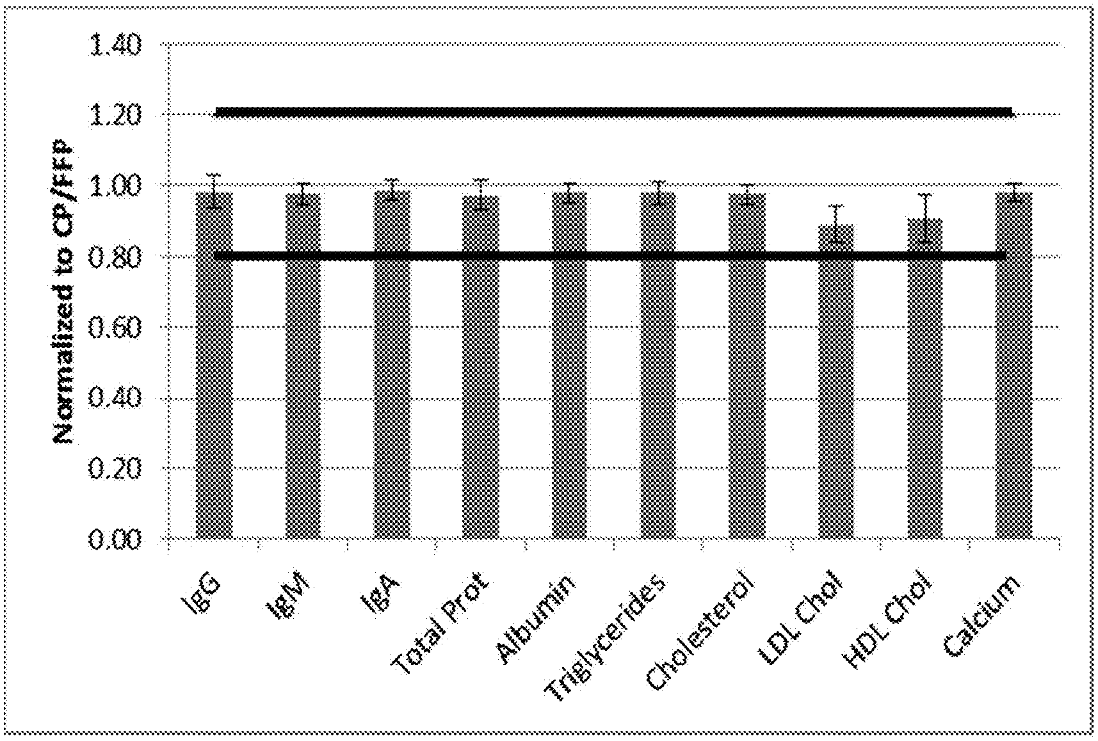
FIG. 35 is a bar graph showing chemistry analyzer results of ODP/NFP/PreT (On demand plasma (Applicant's inventive spray dried plasma) never frozen, pretreated) for IgG, IgM, IgA, total protein, albumin, Triglycerides, Cholesterol, LDL Cholesterol, HDL Cholesterol and Calcium, normalized to CP/FFP (Control plasma/Fresh Frozen Plasma).

The assays completed on chemistry analyzer showed that ODP/NFP/PreT were similar to CP/FFP, See FIG. 35.

Figure 36:
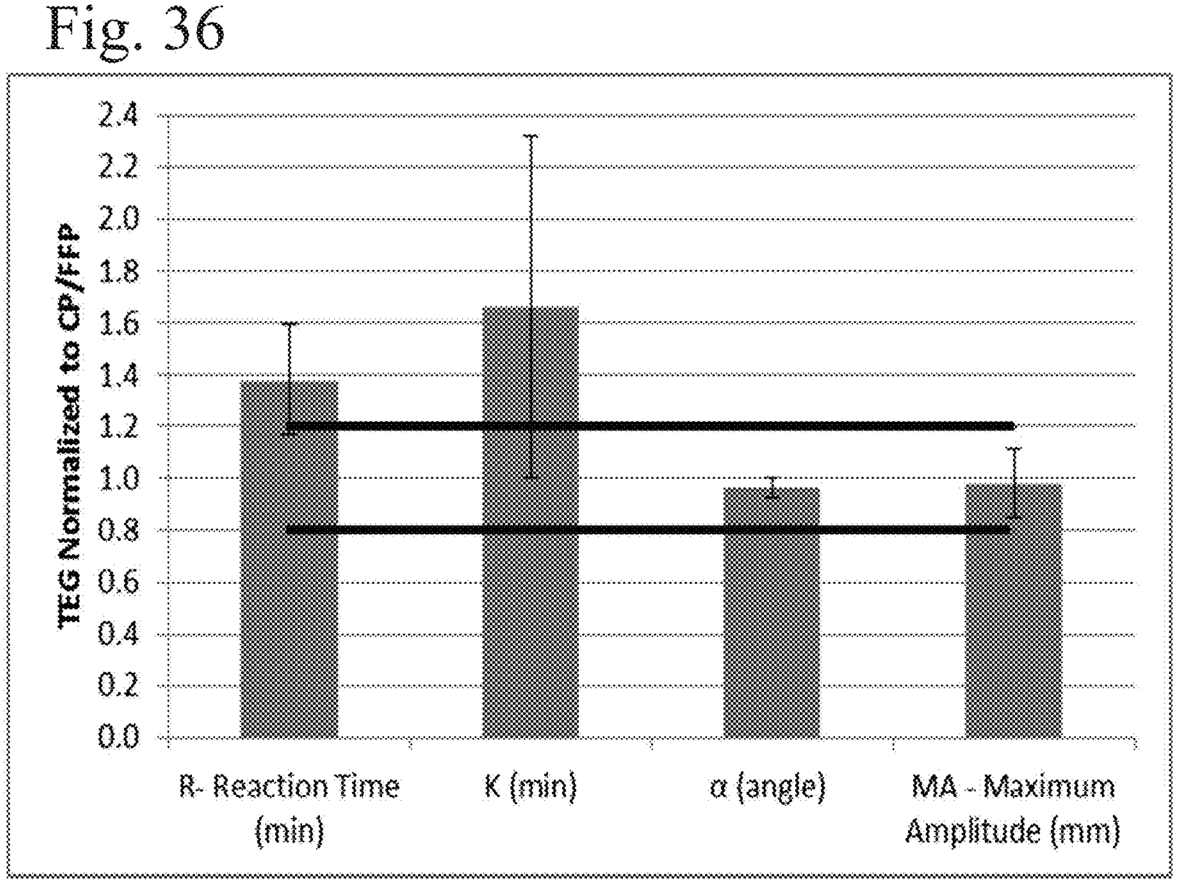
FIG. 36 is a bar graph showing Thrombelastography Hemostasis System (TEG) results for R-Reaction Time (min) K (min), a (angle) and MA (Maximum Amplitude (mm)) of ODP/NFP normalized to CP/FFP (Control plasma/Fresh Frozen Plasma).

The TEG results showed that the strength of the clot (Maximum Amplitude, MA) and the rate of the clot formation (a) of ODP/NFP were similar to CP/FFP. FIG. 36 shows TEG results of ODP/NFP normalized to CP/FFP. A prolongation was observed in the reaction time (R) and time to reach maximum amplitude (K). The TEG was developed to be a whole blood assay. The aPTT assay for plasma in FIG. 32 does not show the significant prolongation in clotting time as the TEG results show.

Conclusion:

The manual pretreatment method executed on ODP/NFP/PreT resulted in coagulation parameters similar to CP/FFP. The manual pretreatment method delivered pretreatment solution to the NFP such that C5a elevation was minimized in ODP/NFP/PreT to a level slightly above normal reference range of FFP, similar to apheresis plasma, and significantly less than Octaplas.

Example 19: An Increase in C5a Levels was Observed in Spray Dried Plasma Treated with Low pH Pretreatment Solution"

Objective: To determine the quality of spray dried plasma (SpDP or ODP-On Demand Plasma) manufactured from never frozen plasma (NFP) in the production intent disposables.

Method: Four ABO-identical units of NFP were pooled and split into a 15-mL aliquot for producing FFP control, and 4×250 mL units for producing ODPs. The 4 NFP units were pretreated with 400 mM glycine HCl (20×, 20 mM in pretreated plasma) using a pretreatment station. The pretreated plasma units were spray dried with 49, 50, 51, and 52° C. exhaust gas temperatures, stored for 3 days, rehydrated in 150 mL of water, protein matched to paired FFP, and analyzed.

Figure 37A:
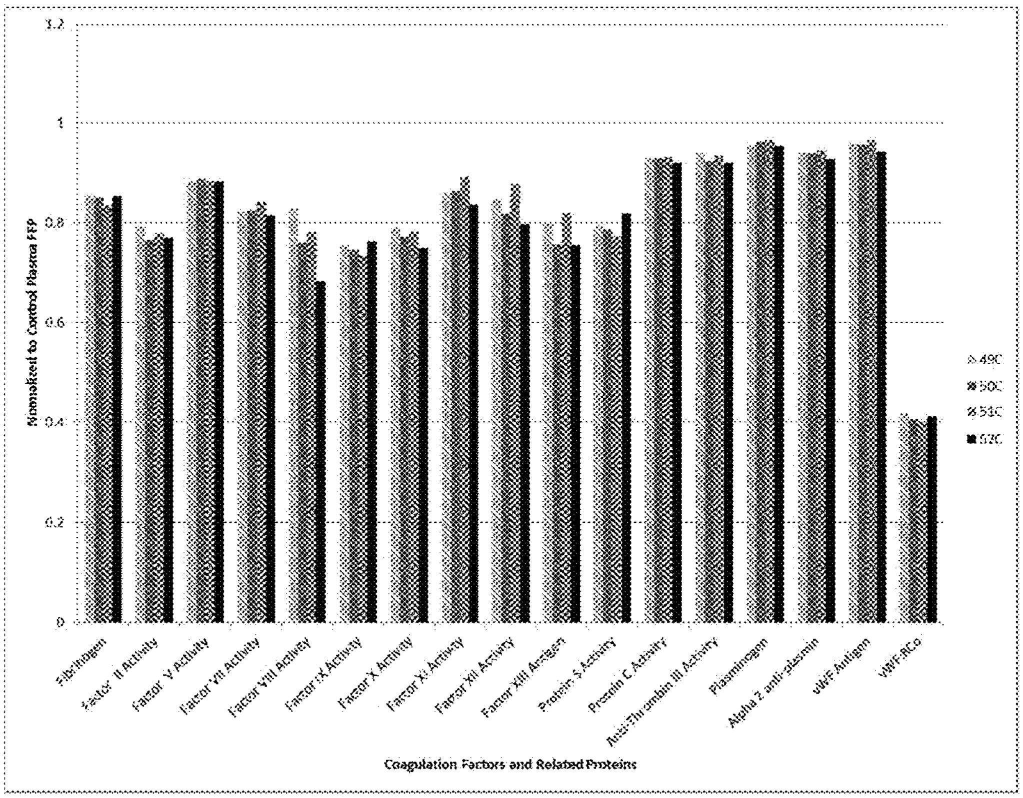
FIG. 37A is a bar graph showing shows coagulation profile results and ELISA assay results for various clotting factors and compliment activation for never frozen plasma pretreated with 400 mM glycine HCl and spray dried at 49, 50, 51, and 52° C. exhaust gas temperatures.
Figure 37B:
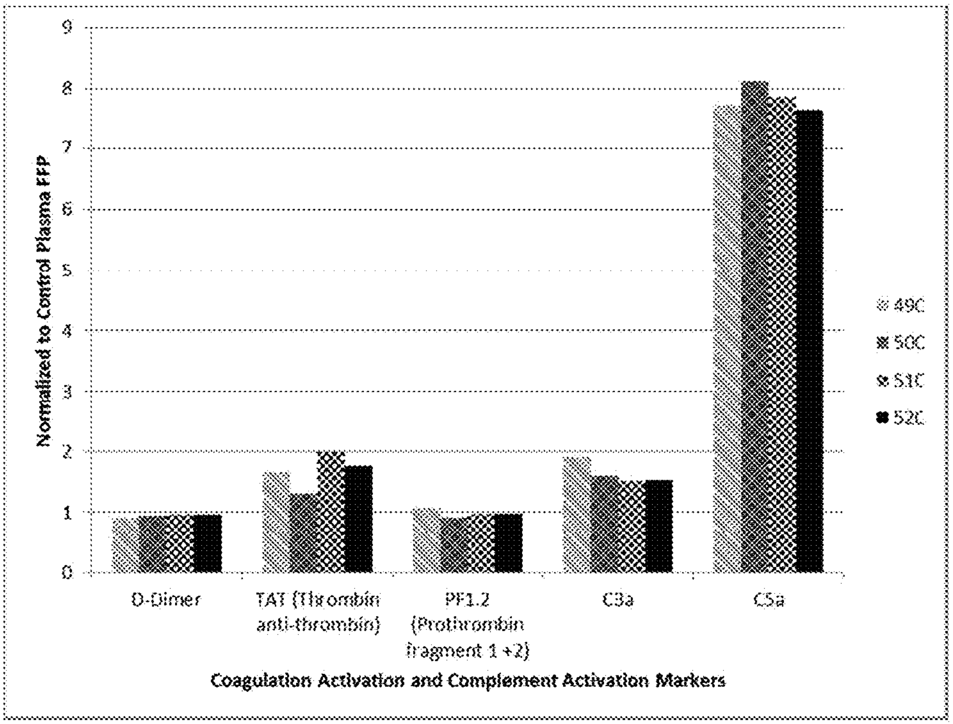
FIG. 37B is a bar graph showing shows coagulation activation and complement activation marks (D-Dimer, TAT, PF1.2, C3a and C5a) for fresh frozen plasma normalized to control plasma pretreated with 400 mM glycine HCl and spray dried at 49, 50, 51, and 52° C. exhaust gas temperatures.

Result: The results are shown in FIG. 37A. Nearly all coagulation and related proteins had a recovery of >70% after spray drying except for vWF, which had >90% antigen recovery but ~40% recovery by vWF:RCo assay. The data showed that the spray drying process only had a mild impact on the plasma proteins. FIG. 37B showed the levels of markers for coagulation activation (D-dimer, TAT, PF1.2) and complement activation (C3a and C5a). The spray drying process did not cause significant coagulation activation or complement activation as evaluated by C3a. However, the levels of C5a were greatly elevated in the ODP.

C5a is an anaphylatoxin, causing increased expression of adhesion molecules on endothelium, contraction of smooth muscle, and increased vascular permeability. C5a des-Arg is a much less potent anaphylatoxin. Both C5a and C5a des-Arg can trigger mast cell degranulation, releasing proinflammatory molecules histamine and TNF-α. C5a is also an effective chemoattractant, initiating accumulation of complement and phagocytic cells at sites of infection or recruitment of antigen-presenting cells to lymph nodes. C5a plays a key role in increasing migration and adherence of neutrophils and monocytes to vessel walls. White blood cells are activated by upregulation of integrin avidity, the lipoxygenase pathway and arachidonic acid metabolism. C5a also modulates the balance between activating versus inhibitory IgG Fc receptors on leukocytes, thereby enhancing the autoimmune response. Due to the strong biological functions of C5a, elevated levels of C5a are not desirable in plasma products.

Conclusion: The process of producing ODP needs to be optimized to mediate the C5a elevation.

Example 20: C5a Elevation Occurs Upon Mixing of the Plasma with Pretreatment Solution, and the Extent of C5a Elevation Depends on Specific Pretreatment Solution and its pH The production of ODP involves multiple sub-processes: pre-treatment, spraying, and drying. C5a elevation can occur in one or multiple steps. Plasma pretreatment is required to improve vWF recovery during the spray drying process and the overall quality of ODP. This step was typically completed by adding a highly acidic pretreatment solution into the plasma bag, followed by inverting the bags. This process exposes plasma proteins to a low pH environment during pretreatment (400 mM glycine HCl: pH 1.3) and post pretreatment (pretreated plasma: pH 6.2-6.5) prior to spray drying. The following study was conducted to determine the possible contribution of the pretreatment to the C5a elevation in ODP. Citric acid has been used successfully to pretreat plasma and was used herein as a control.

Objective: To determine the impact of the pretreatment condition on the C5a elevation.

Method: Stock solutions (20×) of glycine HCl (400 mM, 280 mM and 140 mM) and citric acid (148 mM, 100 mM and 50 mM) were prepared. One mL of the stock solution was added to 19 mL of plasma in a conical tube, the tube was then capped and inverted to homogenize the solution. The pretreated plasma samples were analyzed for the pH and C5a at 10 min, 1, 2 and 21 hr intervals.

Figure 38A:
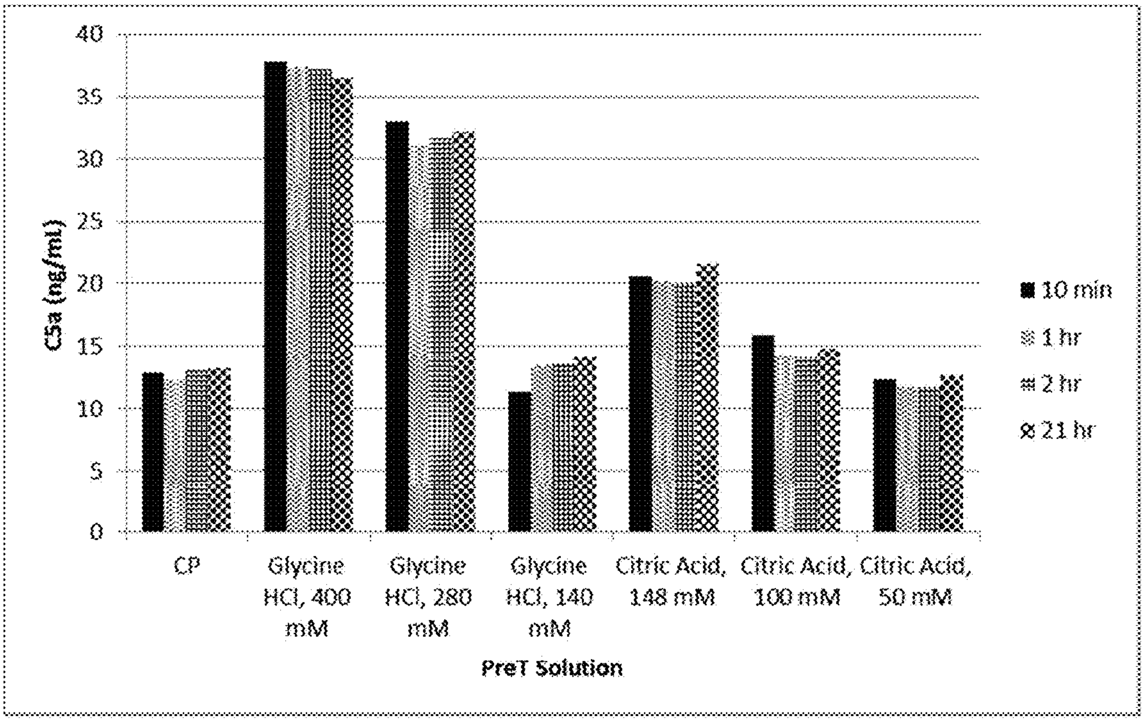
FIG. 38A is a bar graph showing C5a levels in ng/ml at 10 min, 1 hour, 2 hours, and 21 hours, of rehydrated plasma pretreated with Glycine HCl (GlyHCl) at 400 mM, 280 mM, 140 mM and Citric Acid (CA) at 148 mM, 100 mM and 50 mM.
Figure 38B:
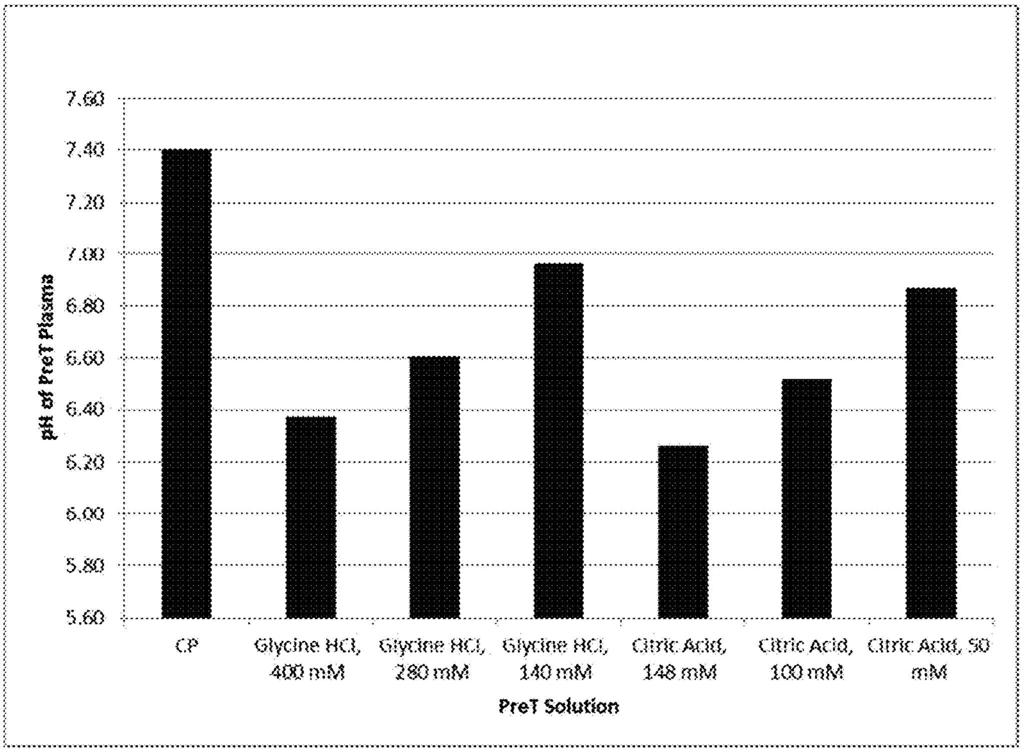
FIG. 38B is a bar graph showing the pH of plasma pretreated with Glycine HCl (GlyHCl) at 400 mM, 280 mM, 140 mM and Citric Acid (CA) at 148 mM, 100 mM and 50 mM.

Results: The results are shown in FIG. 38. Pretreatment of the plasma with 400 mM glycine HCl led to a steep elevation in C5a levels in comparison to the control plasma (CP). The extent of C5a elevation decreased as the glycine HCl concentration was decreased (FIG. 38A). C5a levels increased when the pH of the pretreated plasma (PreT plasma) (FIG. 38B) increased. Similar trends held true for citric acid, the C5a elevation was much lower under similar pH conditions to glycine HCl treated plasma samples. Other than the initial elevation of C5a resulting from the pretreatment, the levels of C5a remained constant up to 21 hr. This data clearly suggested that C5a elevation occurred during mixing of the plasma with the pretreatment solution. The difference in pH between citric acid (148 mM, pH 2.0) and 400 mM glycine HCl (pH 1.3) may account for the differential C5a elevation in the pretreated plasma samples.

Conclusion: C5a elevation is a transient event, occurring during the mixing of the plasma with the acidic pretreatment solution. Optimization of the mixing and/or raising the pH of the pretreatment solution may mitigate the C5a elevation.

Example 21: Re-Formulation of the PreT Solution to have a Higher Initial pH without Impacting the pH of Pretreated Plasma Data from Example 20 clearly suggested that raising the pH of the pretreatment solution can potentially reduce or even eliminate C5a elevation incurred from pretreatment. However, an important objective of pretreatment is to improve vWF recovery during spray drying by lowering the pH of the plasma. The dual requirements apparently possess a formulation dilemma: on one hand, the pH of pretreatment solution needs to be raised; on the other hand, the pH of pretreated plasma using this solution cannot be elevated. Fortunately, amino acids such as glycine, a zwitterionic compound being neutrally charged around pH 6.0 (approximately the pH of pretreated plasma), but positively charged at pH<6, may fulfill the requirements.

Methods: Stock solutions (20×) of 400 mM glycine HCl containing increasing concentrations of glycine (400, 600, 800, 1000, 1200, 1400 and 1600 mM) were prepared and used to pretreat plasma. The pH levels of the pretreatment solutions and pre-treated plasma samples were measured.

Figure 39:
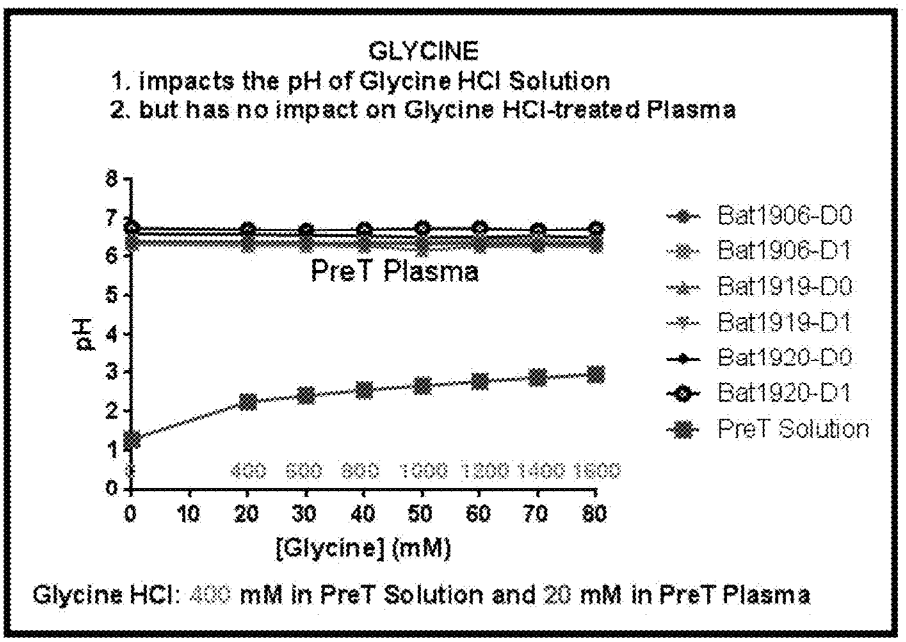
FIG. 39 is a line graph showing the pH levels of the pretreatment solutions and pre-treated plasma samples when plotted against the glycine concentration (mM).

Results: The pH levels of the pretreatment solutions and pre-treated plasma samples were plotted against the glycine concentration in FIG. 39. The pH of the pretreatment solution increased with the increase of glycine concentration, but the pH levels of the pretreated plasma remained unchanged. The data confirms that glycine raises the pH of glycine HCl solution but has no impact on glycine HCl-treated plasma.

Conclusion: A combination of glycine HCl with glycine may inhibit C5a elevation without compromising vWF recovery.

Example 22: Re-Formulation of the PreT with Glycine Mediates C5a Elevation

Methods: Stock solutions (20×) of 400 mM glycine HCl, supplemented with increasing concentrations of glycine (0, 400, 600, 800, 1000, 1200, 1400 and 1600 mM), were prepared and used to pretreat plasma. The pretreatment was conducted by rapidly adding 19 mL of plasma to 1 mL of pretreatment solution in a conical tube. In addition, pretreatment using 400 mM glycine HCl was also performed by conventional procedure, i.e. adding 1 mL pretreatment solution to 19 mL plasma (slow mix). The pretreated samples were analyzed in 10 min and 60 min.

Results: The results were shown in FIG. 40. The levels of C5a decreased as the glycine concentrations increased in the pretreatment solution, and 1000 mM glycine eliminated C5a elevation. FIG. 43O also highlighted the importance of rapid mixing the plasma with pretreatment solution to reduce C5a elevation.

Conclusion: Inclusion of 1000 mM glycine in 400 mM glycine HCl combined with rapid mixing of the plasma with pretreatment solution can reduce or even eliminate C5a elevation.

Example 23: Production and Evaluation of ODP Derived from NFP Pretreated with 400 mM Glycine HCl+1000 mM Glycine Under Agitation Test tube studies described in Examples 20 and 21 led to the reformulation of 400 mM glycine HCl to include 1000 mM glycine and an agitating pretreatment process for mediating C5a elevation associated with the pretreatment step.

This study was to evaluate the feasibility for pretreating a unit of NFP using a manual pretreatment method involving shaking the plasma, assessment of C5a levels, and the impact of spray drying process on C5a.

Method: 20 units of NFP were pretreated with the new pretreatment solution containing 400 mM glycine HCl+1000 mM glycine, with a manual pretreatment method, spray dried on the Alpha instrument, and full panel in-house testing including C5a was conducted to characterize the resulting ODP.

Result: The manual pretreatment method executed on ODP/NFP/PreT resulted in coagulation parameters similar to CP/FFP. The C5a measurements of CP/FFP, CP/FFP/PreT, and ODP/NFP/PreT can be found in FIG. 30 and Table 37. The C5a measurements of CP/FFP were similar to the reference range published in Dumont's paper as shown in FIG. 30 and Table 37. C5a measurements increased after pretreatment and spray drying. Although the C5a measurements of CP/FFP/PreT and ODP/NFP/PreT were higher than CP/FFP, the C5a values were comparable to Octaplas and significantly lower than apheresis plasma, which are both products available on the market.

TABLE 37

| Larry Dumont Paper | | Suessner | | | | |
|---|---|---|---|---|---|---|
| | Reference | n = 20 | | | n = 30 | |
| Assay | Range | Average | Min | Max | Octaplas | Apheresis |
| C3a (ng/ml) | 55-486 | 170.21 ± 68.99 | 98.9 | 384.9 | 669.1 (563.9-867.2 | 980.4 (728.2-1154.3) |
| C5a (ng/ml) | 4.7-9.5 | 11.30 ± 5.42 | 4.6 | 25.5 | 16.1 (14.7-17.8) | 17.1 (14.3-26.2) |

Larry J. Dumont et al, "The bioequivalence of frozen plasma prepared from whole blood held overnight at room temperature compared to fresh-frozen plasma prepared within eight hours of collection," Transfusion 55 (2015): 480.

S. Suessner, S. Kaltenberger, K. Augner, C. Gabriel. "Comparison of several complement and coagulation factor concentrations in different plasma products." Transfusion Medicine and Hemotherapy 2014; 41 (supplement 1): pg. 36.

Conclusion: Combined use of glycine and agitation is effective for mediating C5a elevation without sacrificing vWF.

Example 24: Evaluation of Alternative Acidic Substance for Mediating Pretreatment Related C5a Elevation In addition to glycine HCl, other acids such as lactic acid and gluconic acid can be used to pretreat plasma prior to spray drying. The pretreatment solutions made of these chemicals have higher pH (400 mM lactic acid: pH 2.1; 400 mM gluconic acid: pH 2.2) than glycine HCl pretreatment solution (400 mM glycine HCl: pH 1.3), and, consequently, may cause less C5a elevation during pretreatment. Lactic acid was used in the following proof-of-concept study.

Methods: Stock solutions (20×) of 400 mM lactic acid, supplemented with increasing concentrations of glycine (0, 400, 600, 800, 1000, 1200, 1400 and 1600 mM) were prepared and used to pretreat plasma. All pretreatments were conducted by adding 1 mL of PreT solution to 19 mL of plasma in a conical tube and inverting the tube several times. The pH levels of the PreT solution and PreT plasma, and C5a levels of PreT plasma and untreated control plasma were measured.

Figure 41A:
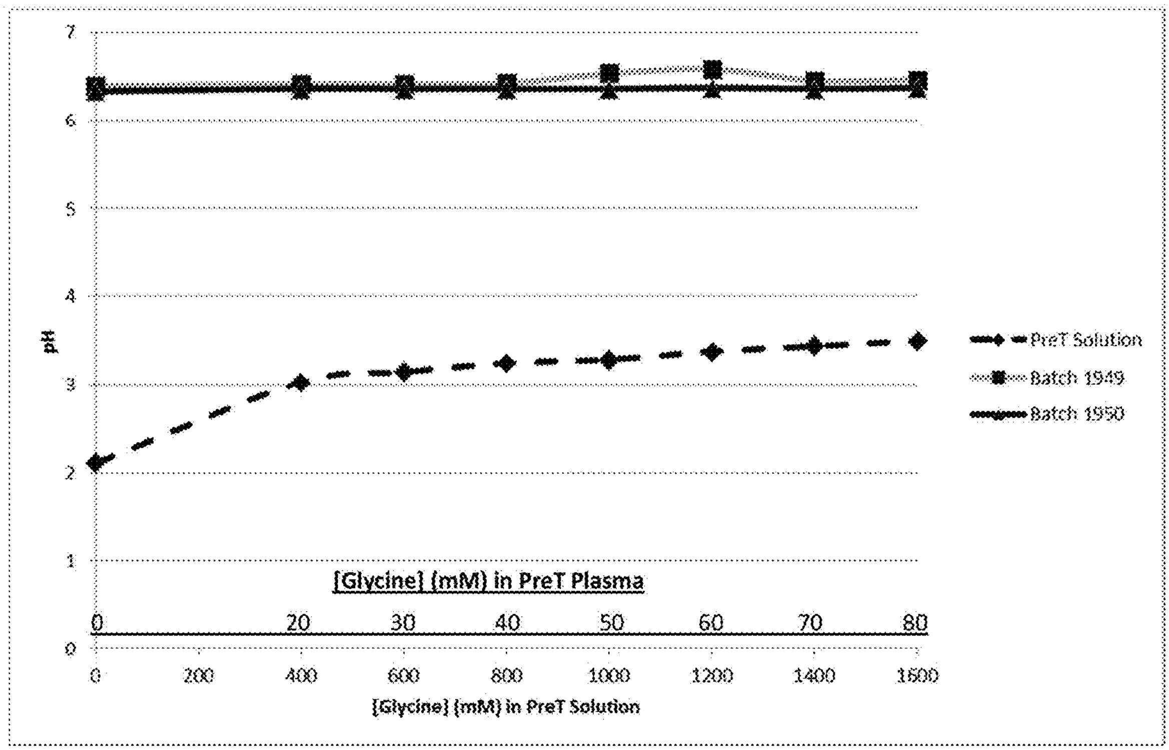
FIG. 41A is a line graph showing the pH of pretreatment solution and plasma (batches 1949 & 1950) pretreated with 400 mM lactic acid, and supplemented with increasing concentrations of glycine (0, 400, 600, 800, 1000, 1200, 1400 and 1600 mM).
Figure 41B:
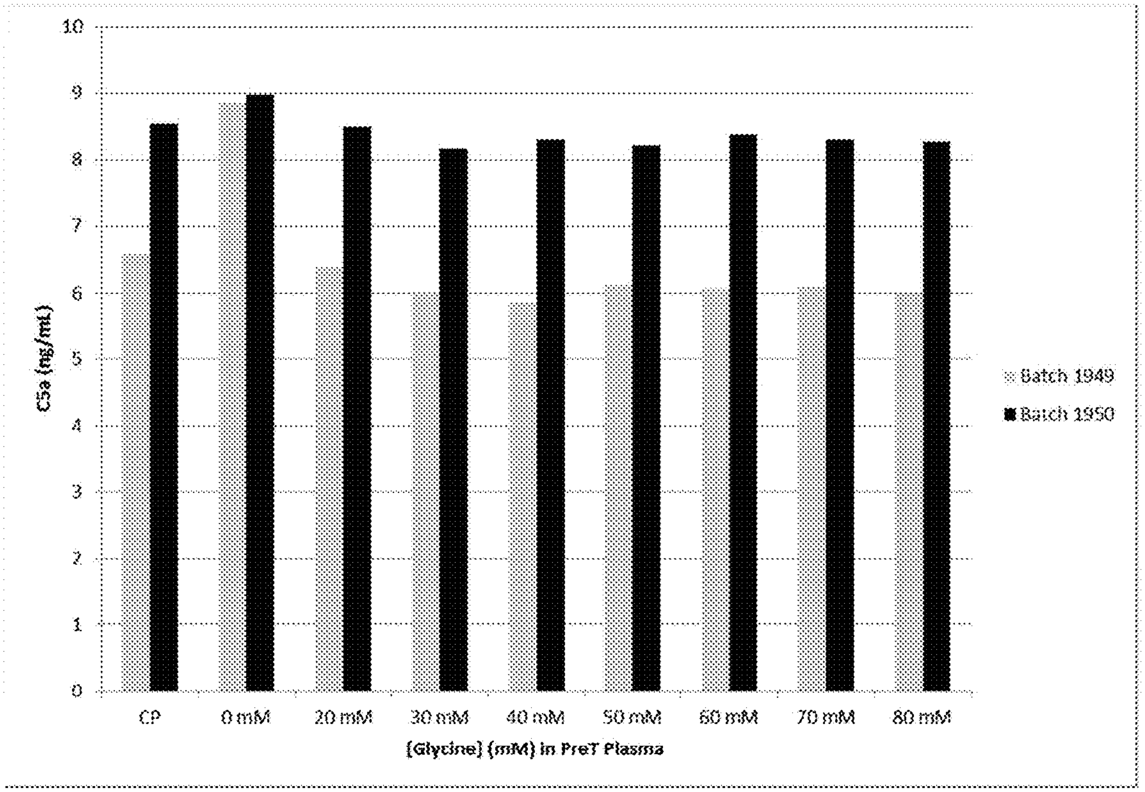
FIG. 41B is a bar graph showing the C5a levels in ng/ml of plasma (batches 1949 & 1950) pretreated with 400 mM lactic acid and supplemented with increasing concentrations of glycine wherein the pretreated plasma had concentrations of 0, 20, 30, 40, 50, 60, 70, and 80 mM glycine.

Results: The results were shown in FIGS. 41A and B. Consistent with observations for glycine HCl, addition of glycine to 400 mM lactic acid raised the pH of the pretreatment solution, but had no impact on the pH of pretreated plasma (FIG. 41A). On the contrary, treatment of plasma with 400 mM lactic acid only slightly elevated the levels of C5a, and the elevation was completely abolished by including 400 mM glycine in the pretreatment solution.

Conclusion: This study proved the generality of using glycine in the pretreatment solution for inhibiting C5a elevation during pretreatment and demonstrated the potential of abolishing the agitation step when used with a weak acid for the pretreatment.

Example 25. Reconstituted Plasma pH of Spray-Dried Plasma Pretreated with Glycine and HCl (Three Instrument Study—TR-00563

Summary:

The in vitro characterization of pooled spray dried plasma manufactured on the three (3) different spray dryer of the present invention, as described herein and referred to as FRONTLINE™ spray drier system from Velico Medical Inc's (Beverly, MA USA). FRONTLINE™ Dryers demonstrated that there is no statistically significant difference in percent change between the paired controls and the spray dried plasma unites manufactured on three (3) FRONTLINE™ Dryers in support of a lack of inter-instrument variability. The results also demonstrate minimal impact of the manufacturing process on spray dried plasma units, as compared to the starting plasma (prior to drying). Spray dried plasma processed by the FRONTLINE™ spray drier is referred to herein as FRONTLINEODP™. The plasma was dried using the disposable of the present invention, as described herein and shown in FIG. 42A.

The same 20 pooled plasma units were spray dried on three (3) FRONTLINE™ Dryers. The resulting 60 spray dried plasma units were characterized across 20 assays. A one-way analysis of variance (ANOVA) was completed for spray dried plasma units manufactured by the three (3) FRONTLINE™ Dryers for the characterization assays comparing the percent change from pre-(paired control plasma) and post-manufacture spray dried plasma unit. All p-values were greater than 0.05, indicating that there was no statistically significant difference between the percent change of spray dried plasma units manufactured across the three (3) FRONTLINE™ Dryers. The study demonstrated the robustness of the spray drying process and that there is no statistically significant variability in percent change of units manufactured between the different FRONTLINE™ Dryers.

TABLE 38

| ANOVA Results for mean comparison of percent changes across three (3) Frontline Dryers | | | | | |
|---|---|---|---|---|---|
| | | Percent Change | | | |
| | Assay | Dryer 1 | Dryer 2 | Dryer 3 | p-value |
| General Properties | Total Protein g/dL | −2% ± 3% | −2% ± 3% | −2% ± 3% | 0.897 |
| | Osmolality (mOsm/kg) | 24% ± 5% | 24% ± 3% | 24% ± 5% | 0.893 |
| Global Tests | aPTT (s) | 11% ± 6% | 12% ± 6% | 11% ± 6% | 0.77 |
| | Prothrombin Time (s) | 11% ± 3% | 10% ± 2% | 11% ± 4% | 0.939 |
| | Thrombin Time (s) | 29% ± 6% | 32% ± 7% | 29% ± 5% | 0.053 |
| Coagulation Factors | Factor V (%) | −10% ± 5% | −11% ± 5% | −9% ± 6% | 0.689 |
| | Factor VII (%) | −12% ± 6% | −13% ± 5% | −13% ± 6% | 0.678 |
| | Factor VIII (%) | −21% ± 8% | −19% ± 8% | −22% ± 7% | 0.259 |
| | Factor XIII Activity (%) | −11% ± 7% | −11% ± 7% | −10% ± 8% | 0.965 |
| | Factor XIII Antigen (%) | −12% ± 4% | −12% ± 3% | −11% ± 4% | 0.735 |
| | Fibrinogen (mg/dL) | −11% ± 6% | −10% ± 6% | −12% ± 7% | 0.333 |
| Anticoagulant Proteins | Protein C (%) | −6% ± 4% | −6% ± 3% | −6% ± 3% | 0.941 |
| | Protein S (%) | −13% ± 4% | −15% ± 3% | −12% ± 4% | 0.185 |
| | Antithrombin III (%) | −9% ± 4% | −9% ± 3% | −9% ± 4% | 0.917 |
| vWF | von Willebrand Factor Antigen (%) | 1% ± 5% | 1% ± 5% | 1% ± 5% | 0.967 |
| | von Willebrand Factor Ristocetin Cofactor (%) | −58% ± 5% | −59% ± 4% | 59% ± 5% | 0.572 |
| Complement Protein | C5a (ng/ml) | 397% ± 145% | 434% ± 149% | 354% ± 117% | 0.215 |
| Activation Markers | Prothrombin Fragment F 1 + 2 (pmol/L) | 8% ± 16% | 7% ± 13% | 10% ± 22% | 0.77 |
| | Thrombin-Antithrombin Complex (TAT) (μg/L) | 11% ± 25% | 18% ± 33% | 5% ± 14% | 0.244 |

Method:

Spray dried plasma, obtained using the methods of the present invention, were manufactured from pooled single donor plasma pre-treated with a solution containing 440 mM glycine and 106 mM hydrochloric acid which were added to SWFI. Plasma combined with the pre-treatment solution is referred to as formulated plasma. The pretreatment solution was made using the following table:

TABLE 39

| Pretreatment formulation | | | | | | |
|---|---|---|---|---|---|---|
| | Conc. (mM) | 250 mL | 500 mL | 1000 mL | 2000 mL | 4000 mL |
| HCl (mL) | 106 | 2.18 ± 0.11 | 4.36 ± 0.22 | 8.72 ± 0.44 | 17.44 ± 0.87 | 34.88 ± 1.74 |
| Glycine (g) | 440 | 8.26 ± 0.41 | 16.52 ± 0.83 | 33.08 ± 1.65 | 66.16 ± 3.31 | 132.32 ± 6.62 |

The spray drier used in processing spray dried plasma is described herein and is FRONTLINE™ spray drier system from Velico Medical Inc's (Beverly, MA USA). The study was limited to a sample size of n=60. Plasma units are produced from 20 pooled plasma samples processed on three different spray driers. Each pool is equally divided, treated with the pre-treatment solution and spray dried using one of the three instruments.

Sixty (60) units of blood plasma blood type A (27 units), blood type O (27 units), and blood type B (6 units) were pre-treated with the pre-treatment solution, pooled and spray dried on spray dried on three separate spray drying systems (i.e., FRONTLINE™ Systems (Velico Medical Inc, Beverly MA USA)) (n=20 pooled samples each) and tested.

The manufacturing effect of these spray drying system on the starting material was determined by calculating the change between the plasma unit having the pretreatment solution described herein and its paired control plasma (CP) for each of the assays.

$$\% \text{ Change} = \frac{FrontlineODP - CP}{CP} \times 100$$

Inter-instrument variability will be assessed across 20 assays outlined in the FDA panel including pH Materials:

ACCUMET® Benchtop pH Meter

Blood Collection Monitor

Calibrated timer

Clean Dry Air (CDA) System

Freezer

FRONTLINE™ System VEL 7000×3 and 1 Sealer ASY 30000S (Velico Medical Inc, Beverly MA, USA)
HELMER® Plasma Thawer
Instrumentation Laboratories ACL TOP 700 coagulation analyzer
Osmometer
Plate Reader
Plate Washer
Refrigerator
SELECTRA PRO M® Chemistry Analyzer
SIEMENS BCS XP® coagulation analyzer
Sterile Connection Device
Tubing Heat Sealer
Overwrap Sealer
Plasma Pretreatment Container having pretreatment solution having 16.8 mM HCl and 69.6 mM glycine and SWFI
Plasma Drying Chamber
Sterile Water for Injection (SWFI)
Never Frozen Plasma (NFP)
Fresh Frozen Plasma (FFP)
Plasma frozen within 24 hours (PF24)
3000 mL transfer pack
Reagents to complete panel per work instructions
5 mL Cryo-vials, P/N 01379

Results:

Statistical analysis was performed using MINITAB® statistical software to determine if there was a statistically significant difference between the percent change of pre-treated spray dried plasma units including pH as compared to its paired control plasma made across the three (3) FRONTLINE™ Dryers. Method of analysis was one-way ANOVA with a two-sided confidence interval.

All ANOVA values were greater than 0.05 indicating that the null hypothesis was correct for each assay. There was no statistically significant difference between the three (3) FRONTLINE™ Dryer's performance including the PH value across the three instruments of the resulting reconstituted spray dried plasma being in the range of 6.93 to 7.21 with a mean of 7.06.

TABLE 40

ANOVA Results for mean comparison of percent changes across three (3) Frontline Dryers

| | | Percent Change | | | |
|---|---|---|---|---|---|
| | Assay | Dryer 1 | Dryer 2 | Dryer 3 | p-value |
| General Properties | Total Protein g/dL | −2% ± 3% | −2% ± 3% | −2% ± 3% | 0.897 |
| | Osmolality (mOsm/kg) | 24% ± 5% | 24% ± 3% | 24% ± 5% | 0.893 |
| Global Tests | aPTT (s) | 11% ± 6% | 12% ± 6% | 11% ± 6% | 0.77 |
| | Prothrombin Time (s) | 11% ± 3% | 10% ± 2% | 11% ± 4% | 0.939 |
| | Thrombin Time (s) | 29% ± 6% | 32% ± 7% | 29% ± 5% | 0.053 |
| Coagulation Factors | Factor V (%) | −10% ± 5% | −11% ± 5% | −9% ± 6% | 0.689 |
| | Factor VII (%) | −12% ± 6% | −13% ± 5% | −13% ± 6% | 0.678 |
| | Factor VIII (%) | −21% ± 8% | −19% ± 8% | −22% ± 7% | 0.259 |
| | Factor XIII Activity (%) | −11% ± 7% | −11% ± 7% | −10% ± 8% | 0.965 |
| | Factor XIII Antigen (%) | −12% ± 4% | −12% ± 3% | −11% ± 4% | 0.735 |
| | Fibrinogen (mg/dL) | −11% ± 6% | −10% ± 6% | −12% ± 7% | 0.333 |
| Anticoagulant Proteins | Protein C (%) | −6% ± 4% | −6% ± 3% | −6% ± 3% | 0.941 |
| | Protein S (%) | −13% ± 4% | −15% ± 3% | −12% ± 4% | 0.185 |
| | Antithrombin III (%) | −9% ± 4% | −9% ± 3% | −9% ± 4% | 0.917 |
| vWF | vWF Antigen (%) | 1% ± 5% | 1% ± 5% | 1% ± 5% | 0.967 |
| | vWF:RCo (%) | −58% ± 5% | −59% ± 4% | −59% ± 5% | 0.572 |
| Complement Protein | C5a (ng/ml) | 397% ± 145% | 434% ± 149% | 354% ± 117% | 0.215 |
| Activation Markers | Prothrombin Fragment F 1 + 2 (pmol/L) | 8% ± 16% | 7% ± 13% | 10% ± 22% | 0.77 |
| | Thrombin-Antithrombin Complex (TAT) (μg/L) | 11% ± 25% | 18% ± 33% | 5% ± 14% | 0.244 |

The average characterization results are shown in Table 41. The characterization results for each instrument are shown in Tables 42-44.

TABLE 41

Summary of Results (Average of 20 FrontlineODP Units spray dried on three Frontline Dryer for a total of n = 60)
Average of 3 Instruments

| | | FrontlineODP | | Change compared to Control | |
|---|---|---|---|---|---|
| | Assays | Mean ± SD | Range (min-max) | Mean ± SD | Range (min-max) |
| General Properties | pH | 7.06 ± 0.07 | (6.93-7.21) | −5% ± 1% | (−8%--3%) |
| | Total Protein g/dL | 5.44 ± 0.23 | (4.95-5.89) | −2% ± 3% | (−10%-4%) |
| | Osmolality (mOsm/kg) | 382 ± 14 | (343-404) | 24% ± 5% | (9%-31%) |
| Global Factors | aPTT (s) | 30.6 ± 2.1 | (27.0-34.7) | 11% ± 6% | (−1%-22%) |
| | Prothrombin Time (s) | 12.7 ± 0.5 | (11.8-13.8) | 11% ± 3% | (4%-19%) |
| | Thrombin Time (s) | 17.2 ± 1.2 | (14.9-21.8) | 29% ± 6% | (21%-47%) |
| Coagulation Factors | Factor V (%) | 94.0 ± 12.2 | (74.6-121.2) | −10% ± 5% | (−19%-5%) |
| | Factor VII (%) | 84.4 ± 9.9 | (63.1-105.2) | −12% ± 6% | (−25%-2%) |
| | Factor VIII (%) | 79.4 ± 14.7 | (51.0-126.2) | −21% ± 8% | (−32%-2%) |
| | Factor XIII Activity (%) | 112.7 ± 12.6 | (88.9-153.6) | −11% ± 7% | (−23%-6%) |
| | Factor XIII Antigen (%) | 101.6 ± 13.4 | (81.7-140.1) | −12% ± 4% | (−21%--3%) |
| | Fibrinogen (mg/dL) | 253 ± 25 | (213-314) | −11% ± 6% | (−27%-3%) |
| Anticoagulant Proteins | Protein C (%) | 100 ± 6 | (86-111) | −6% ± 4% | (−17%-2%) |
| | Protein S (%) | 93.5 ± 7.4 | (81.7-111.9) | −13% ± 4% | (−23%--3%) |
| | Antithrombin III (%) | 89 ± 6 | (75-101) | −9% ± 4% | (−17%-0%) |
| vWF | von Willebrand Factor Antigen (%) | 123.3 ± 22.0 | (94.3-187.8) | 1% ± 5% | (−14%-9%) |
| | von Willebrand Factor Ristocetin Cofactor (%) | 41.2 ± 8.8 | (27.2-61.9) | −58% ± 5% | (−67%--45%) |
| Complement Protein | C5a (ng/ml) | 33.45 ± 7.72 | (21.11-53.58) | 397% ± 145% | (197%-846%) |
| Activation Markers | Prothrombin Fragment F 1 + 2 (pmol/L) | 91.4 ± 23.7 | (51.3-171.8) | 8% ± 16% | (−47%-53%) |
| | Thrombin-Antithrombin Complex (TAT) (μg/L) | 2.04 ± 1.20 | (0.32-5.56) | 11% ± 25% | (−45%-137%) |

TABLE 42

Summary of Results for Frontline Dryer 1 (n = 20)
Instrument 1

| | | FrontlineODP | | Change compared to Control | |
|---|---|---|---|---|---|
| | Assays | Mean ± SD | Range (min-max) | Mean ± SD | Range (min-max) |
| General Properties | pH | 7.07 ± 0.06 | (6.98-7.21) | −5% ± 1% | (−6%--3%) |
| | Total Protein g/dL | 5.44 ± 0.22 | (5.07-5.89) | −2% ± 3% | (−10%-1%) |
| | Osmolality (mOsm/kg) | 383.36 ± 10.16 | (357-398) | 24% ± 3% | (16%-29%) |
| Global Factors | aPTT (s) | 30.77 ± 2.19 | (27-34.7) | 12% ± 6% | (1%-22%) |
| | Prothrombin Time (s) | 12.7 ± 0.47 | (11.8-13.3) | 10% ± 2% | (8%-15%) |
| | Thrombin Time (s) | 17.51 ± 1.48 | (15-21.8) | 32% ± 7% | (24%-47%) |
| Coagulation Factors | Factor V (%) | 93.31 ± 12.5 | (74.6-118.5) | −11% ± 5% | (−19%--2%) |
| | Factor VII (%) | 84.02 ± 9.99 | (63.1-105.2) | −13% ± 5% | (−25%--3%) |
| | Factor VIII (%) | 81.8 ± 16.65 | (51.25-126.2) | −19% ± 8% | (−32%-2%) |
| | Factor XIII Activity (%) | 112.7 ± 13.36 | (91-147) | −11% ± 7% | (−22%-1%) |
| | Factor XIII Antigen (%) | 101.81 ± 14.17 | (84.8-140.1) | −12% ± 3% | (−21%--7%) |
| | Fibrinogen (mg/dL) | 258.25 ± 27.54 | (213-314) | −10% ± 6% | (−19%-1%) |
| Anticoagulant Proteins | Protein C (%) | 99.7 ± 5.95 | (87-107) | −6% ± 3% | (−12%-2%) |
| | Protein S (%) | 92.22 ± 7.56 | (81.7-106.4) | −15% ± 3% | (−23%--9%) |
| | Antithrombin III (%) | 89.2 ± 6.07 | (75-101) | −9% ± 3% | (−15%--1%) |

TABLE 42-continued

Summary of Results for Frontline Dryer 1 (n = 20)
Instrument 1

| | Assays | FrontlineODP Mean ± SD | FrontlineODP Range (min-max) | Change compared to Control Mean ± SD | Change compared to Control Range (min-max) |
|---|---|---|---|---|---|
| vWF | von Willebrand Factor Antigen (%) | 123.1 ± 22.59 | (99.4-187.8) | 1% ± 5% | (−14%-9%) |
| | von Willebrand Factor Ristocetin Cofactor (%) | 40.52 ± 8.07 | (28.1-56.6) | −59% ± 4% | (−67%-−52%) |
| Complement Protein | C5a (ng/mL) | 35.89 ± 7.66 | (25-52.99) | 434% ± 149% | (200%-719%) |
| Activation Markers | Prothrombin Fragment F 1 + 2 (pmol/L) | 89.61 ± 19.54 | (58.37-122.76) | 7% ± 13% | (−17%-32%) |
| | Thrombin-Antithrombin Complex (TAT) (μg/L) | 2.1 ± 1.18 | (0.5-5.36) | 18% ± 33% | (−27%-137%) |

TABLE 43

Summary of Results for Frontline Dryer 2 (n = 20)
Instrument 2

| | Assays | FrontlineODP Mean ± SD | FrontlineODP Range (min-max) | Change compared to Control Mean ± SD | Change compared to Control Range (min-max) |
|---|---|---|---|---|---|
| General Properties | pH | 7.05 ± 0.07 | (6.93-7.16) | −5% ± 1% | (−7%-−4%) |
| | Total Protein g/dL | 5.45 ± 0.2 | (4.95-5.85) | −2% ± 3% | (−8%-4%) |
| | Osmolality (mOsm/kg) | 382.51 ± 14.22 | (352.5-403.67) | 24% ± 5% | (14%-31%) |
| Global Factors | aPTT (s) | 30.37 ± 2.05 | (27.2-33.9) | 11% ± 6% | (1%-22%) |
| | Prothrombin Time (s) | 12.73 ± 0.55 | (11.9-13.8) | 11% ± 4% | (5%-19%) |
| | Thrombin Time (s) | 17.19 ± 0.92 | (14.9-18.8) | 29% ± 5% | (21%-39%) |
| Coagulation Factors | Factor V (%) | 94.69 ± 13 | (77.8-121.2) | −9% ± 6% | (−18%-5%) |
| | Factor VII (%) | 83.82 ± 10 | (67.6-101.5) | −13% ± 6% | (−24%-2%) |
| | Factor VIII (%) | 78.81 ± 12.75 | (58.65-106.9) | −22% ± 7% | (−31%-−2%) |
| | Factor XIII Activity (%) | 112.95 ± 12.01 | (88.9-136.6) | −10% ± 8% | (−22%-6%) |
| | Factor XIII Antigen (%) | 102.12 ± 13.32 | (81.7-133.8) | −11% ± 4% | (−18%-−4%) |
| | Fibrinogen (mg/dL) | 250.25 ± 25.36 | (220-306) | −12% ± 7% | (−27%-3%) |
| Anticoagulant Proteins | Protein C (%) | 99.65 ± 6.34 | (87-110) | −6% ± 3% | (−11%-1%) |
| | Protein S (%) | 94.85 ± 7.07 | (83.6-111.9) | −12% ± 4% | (−21%-−3%) |
| | Antithrombin III (%) | 89.2 ± 6.47 | (80-100) | −9% ± 4% | (−15%-0%) |
| vWF | von Willebrand Factor Antigen (%) | 123.56 ± 22 | (94.5-181.8) | 1% ± 5% | (−14%-7%) |
| | von Willebrand Factor Ristocetin Cofactor (%) | 40.8 ± 8.85 | (27.2-61.8) | −59% ± 5% | (−67%-−50%) |
| Complement Protein | C5a (ng/ml) | 30.83 ± 7.15 | (21.11-47.49) | 354% ± 117% | (204%-671%) |
| Activation Markers | Prothrombin Fragment F 1 + 2 (pmol/L) | 92.14 ± 23.38 | (57.18-134.34) | 10% ± 22% | (−47%-53%) |
| | Thrombin-Antithrombin Complex (TAT) (μg/L) | 2.01 ± 1.3 | (0.36-5.56) | 5% ± 14% | (−27%-30%) |

TABLE 44

| Summary of Results for Frontline Dryer 3 (n = 20) Instrument 3 | | | | | | |
|---|---|---|---|---|---|---|
| | | FrontlineODP | | Change compared to Control | | |
| | Assays | Mean ± SD | Range (min-max) | Mean ± SD | Range (min-max) |
| General Properties | pH | 7.08 ± 0.08 | (6.93-7.2) | −5% ± 1% | (−8%--4%) |
| | Total Protein g/dL | 5.42 ± 0.26 | (4.99-5.81) | −3% ± 4% | (−10%-3%) |
| | Osmolality (mOsm/kg) | 381.12 ± 18.31 | (342.5-400.5) | 23% ± 6% | (9%-30%) |
| Global Factors | aPTT (s) | 30.55 ± 2.29 | (27-34.2) | 11% ± 7% | (−1%-22%) |
| | Prothrombin Time (s) | 12.74 ± 0.51 | (11.9-13.6) | 11% ± 3% | (4%-16%) |
| | Thrombin Time (s) | 16.9 ± 0.97 | (15-19.1) | 27% ± 5% | (21%-38%) |
| Coagulation Factors | Factor V (%) | 93.88 ± 11.55 | (79.5-118.5) | −10% ± 4% | (−18%--2%) |
| | Factor VII (%) | 85.25 ± 10.01 | (66.9-99.1) | −11% ± 8% | (−23%-2%) |
| | Factor VIII (%) | 77.6 ± 14.78 | (50.95-122.1) | −23% ± 7% | (−32%--4%) |
| | Factor XIII Activity (%) | 112.35 ± 13.12 | (96.5-153.6) | −11% ± 7% | (−23%-3%) |
| | Factor XIII Antigen (%) | 100.93 ± 13.36 | (83.8-138.7) | −13% ± 5% | (−18%--3%) |
| | Fibrinogen (mg/dL) | 250.43 ± 21.24 | (213-302) | −12% ± 6% | (−23%--2%) |
| Anticoagulant Proteins | Protein C (%) | 99.3 ± 6.71 | (86-111) | −6% ± 4% | (−17%-0%) |
| | Protein S (%) | 93.43 ± 7.57 | (83.3-111.8) | −13% ± 5% | (−22%--3%) |
| | Antithrombin III (%) | 88.73 ± 6.5 | (78-99) | −9% ± 5% | (−17%--3%) |
| vWF | von Willebrand Factor Antigen (%) | 123.35 ± 22.63 | (94.3-182.7) | 1% ± 5% | (−12%-8%) |
| | von Willebrand Factor Ristocetin Cofactor (%) | 42.18 ± 9.74 | (28.4-61.9) | −57% ± 5% | (−65%--45%) |
| Complement Protein | C5a (ng/mL) | 33.63 ± 7.85 | (24.68-53.58) | 402% ± 162% | (197%-846%) |
| Activation Markers | Prothrombin Fragment F 1 + 2 (pmol/L) | 92.46 ± 28.35 | (51.32-171.79) | 8% ± 10% | (−9%-25%) |
| | Thrombin-Antithrombin Complex (TAT) (μg/L) | 2.02 ± 1.17 | (0.32-4.98) | 9% ± 23% | (−45%-72%) |

The percent change between the spray dried plasma units and its paired control on average is within ±20% for pH, aPTT, PT, Factor V activity, Factor VIII activity, Factor XIII activity, Factor XIII antigen, fibrinogen, Protein C, Protein S, Antithrombin III, von Willebrand Factor (vWF) antigen, Prothrombin Fragment 1+2 (PF1+2), Thrombin Anti-Thrombin (TAT), total protein. The mean von Willebrand ristocetin cofactor (vWF:RCo) levels of spray dried plasma units of 41.2% is ≥40%, meeting FDA's recommendation per Meeting ID #BQ150234 (Mar. 14, 2018). Decreased recovery of vWF:RCo activity was observed and is due to the shearing during the spray drying process. There was a 23% and 27% change with osmolality and thrombin time (TT), respectively, for spray dried plasma units compared to its paired control. The increase in osmolality in the spray dried plasma units is attributed to the hydrochloric acid and glycine in the Plasma Pretreatment Container. The European Pharmacopoeia specifies the pH as 6.5-7.6 and minimum osmolality of 240 mOsm/kg for Human Plasma (pooled and treated for virus inactivation). A previous internal study demonstrated that decreasing the pH of plasma induced a prolonged TT. The observed changes compared to the control for osmolality and TT are not clinically significant because the mean osmolality and pH are still within the acceptable ranges as indicated by the above-mentioned standard and the prolonged TT is an effect of the sample pH on the assay. The C5a in spray dried plasma unit is elevated compared to control plasma but the average of 33.45 ng/ml is acceptable because clinically acceptable values have been reported for apheresis plasma in the range of 4.9-74 ng/mL. The increase in levels for C5a are not considered clinically significant. Factor VIII had a mean change of −21% from spray dried plasma unit to control plasma across the three (3) instruments. This is acceptable however, because the average spray dried plasma characterization value of 79.4% is within the acceptable test ranges of 50%-200%. All spray drying manufacturing processes were within the stated acceptance criteria:

The starting mass recorded on Frontline Dryer was 348 g±32 g.

Total mass spray dried recorded on Frontline Dryer was 325 g±30 g

Drying gas inlet temperature: 115±3° C.

Drying gas flow rate: 750±10 L/min

Drying gas exhaust temperature: 65±2° C.

Aerosol gas flow rate: 40±1 L/min

Mean rehydrated ODP were within the acceptance criteria of:

pH within 6.69-7.37, where the actual value was 7.06.

Osmolality within 338-450 mOsm/kg, where the actual value was 382 mOsm/kg.

Protein concentration ODP normalized to control was within 0.88-1.17 on the Chemistry analyzer, where the actual value was 0.98.

Conclusion:

The in vitro characterization of pooled spray dried plasma dried on the three (3) FRONTLINE™ Dryers demonstrated that there was no statistically significant difference between the performance of the three (3) FRONTLINE™ Dyers as determined by % change of the pretreated spray dried plasma units from their paired control across 20 characterization assays. This supports the lack of inter-instrument variability of the FRONTLINE™ Dryers including the PH value across the three instruments of the resulting reconstituted spray dried plasma being in the range of 6.93 to 7.21, with a mean of 7.06.

The characterization data show that reconstituted spray dried plasma units treated with a pre-treatment solution containing 16.8 mM HCl and 69.6 mM glycine, intended for transfusion are comparable to the paired control plasma.

Example 26. pH of Reconstituted Plasma Pretreated with Glycine and HCl

[TR-562 Engineering Verification Study]
Method:

This study compared spray dried plasma unit with paired control plasma to evaluate manufacturing effects of Velico Medical Inc's (Beverly, MA USA) the FRONTLINE™ spray drier system on the starting plasma, when using a pre-treatment solution to treat the starting plasma. The FRONTLINE™ spray drier system used in processing spray dried plasma is described herein. Spray dried plasma processed by the FRONTLINE™ spray drier is referred to herein as FRONTLINEODP™. Plasma combined with the pre-treatment solution is referred to as formulated plasma. The pre-treatment solution has 440 mM glycine and 106 mM hydrochloric acid which were added to SWFI. The pretreatment solution was made using the following table:

TABLE 45

| Pretreatment formulation | | | | | | |
|---|---|---|---|---|---|---|
| | Conc. (mM) | 250 mL | 500 mL | 1000 mL | 2000 mL | 4000 mL |
| HCl (mL) | 106 | 2.18 ± 0.11 | 4.36 ± 0.22 | 8.72 ± 0.44 | 17.44 ± 0.87 | 34.88 ± 1.74 |
| Glycine (g) | 440 | 8.26 ± 0.41 | 16.52 ± 0.83 | 33.08 ± 1.65 | 66.16 ± 3.31 | 132.32 ± 6.62 |

Summary:

The in vitro characterization of spray dried plasma manufactured on the FRONTLINE™ System demonstrated that reconstituted formulated spray dried plasma units are comparable to the paired control plasma, including with regard to pH. Comparability of the in vitro tests supports that the manufacturing impact is acceptable resulting in formulated spray dried plasma units that meets the acceptance criteria for pH and coagulation factor activities profile within the normal reference range (n=60 pairs). The manufacturing effects of the FRONTLINE™ System on the starting material are comparable across blood type A, B, and O. The overall results demonstrate preservation of coagulation factors and analytes as evidence of comparability of reconstituted formulated spray dried plasma units to FFP and a resultant rehydrated plasma range of pH of 6.69-7.37 with a mean of 7.04.

The global assays aPTT and PT had a minimal change with the mean percent change of 2% and 7% respectively, between the reconstituted formulated spray dried plasma units and its paired control. TT was slightly prolonged and with a mean of 34% change for reconstituted formulated spray dried plasma units compared to paired controls. A previous study demonstrated that decreasing the pH of plasma induced a prolonged TT, therefore, the prolonged TT is due to the lowered sample pH from the pretreatment solution on the assay.

The intrinsic and extrinsic coagulation Factors II, V, VII, VIII, IX, X, XI, XII, XIII and fibrinogen activities had mean percent changes between the reconstituted formulated spray dried plasma units and paired controls within ±20%. The most labile factors, Factors V and VIII, had ≤5% and <20% change, respectively. Factors II, XI and fibrinogen were all within 10% change and Factors VII, IX, X and XIII activity had ≤15% change between reconstituted formulated spray dried plasma units and paired controls. All mean assay values were well within the clinical reference ranges.

Protease inhibitors C1 Esterase Inhibitor and Alpha 1 Proteinase Inhibitor have a change of ≤5% demonstrating minimal loss due to the FRONTLINE™ manufacturing process. The balance of pro- and anticoagulant activities is maintained following manufacture of reconstituted formulated spray dried plasma units. Of the anticoagulant protein assays, the mean percent change between the reconstituted formulated spray dried plasma unit and paired control for both Protein C and Antithrombin III is 9%, 14% for Protein S and 7% for Free Protein S. The mean change for procoagulant factors Plasminogen and Plasmin Inhibitor are 5% and 4%, respectively. All mean values are well within the clinical reference ranges.

The mean percent change in von Willebrand Factor (vWF) antigen assay is within ±20%. There is a 55% and 33% change with von Willebrand ristocetin cofactor (vWF:RCo) and vWF activity, respectively. Mean vWF:RCo of FrontlineODP Units is 41.8% meeting the FDA's recommendation of ≥40% per Meeting ID #BQ150234 (Mar. 14, 2018). vWF activity of 73.0±20.3% is within the normal reference range of 38.0-169.7%. Decreased recovery of vWF activity and vWF:RCo activity observed is thought to be due to the shearing during the spray drying process.

Figure 40:
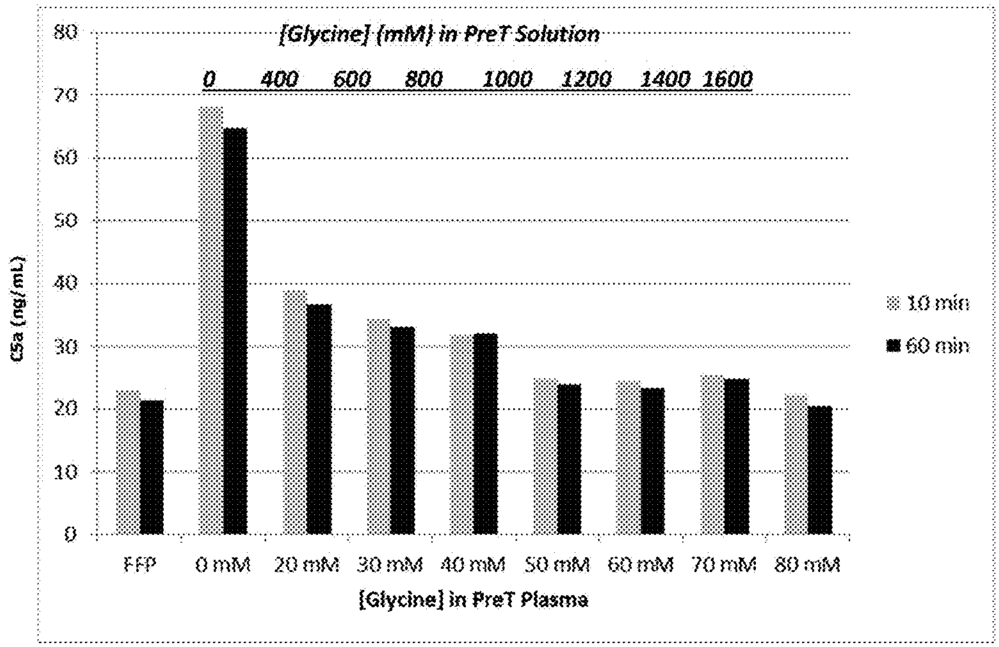
FIG. 40 is a bar graph showing C5a levels (ng/ml) for 400 mM glycine HCl, supplemented with increasing concentrations of glycine (0, 400, 600, 800, 1000, 1200, 1400 and 1600 mM) at 10 minutes and 60 minutes using rapid mixing (e.g., when larger volume of plasma is rapidly added to a relatively smaller volume of the pretreatment solution).

Complement protein assays have mean percent changes between the reconstituted formulated spray dried plasma units and paired controls of 31% and 659% for C3a and C5a, respectively. The C3a is slightly increased compared to control plasma, but the mean value of 300.2 ng/ml is within the clinical reference range of 55-486 ng/ml. Acid alone treatment resulted in improved recovery of vWF and the storage stability of spray dried plasma, but high levels of C5a (compared to NFP). Dual treatment with both acid and glycine brought down the C5a level (FIG. 40). The C5a level is not necessarily lower than NFP, but comparable to or not exceeding other FDA approved plasma products. C5a mean value is slightly increased in reconstituted formulated spray dried plasma units (33.9 ng/mL) compared to its paired control (7.6 ng/mL). The higher percent change pre- and post-manufacture occurs during the pretreatment process. This C5a value is within the reference range reported for apheresed plasma of 4.9-74 ng/mL and therefore does not reflect complement activation.

The activation marker assays, D-Dimer, Prothrombin Fragment 1+2 (PF1+2), and Thrombin Anti-Thrombin (TAT) all had mean percent changes between the reconstituted formulated spray dried plasma units and paired controls within ±20%.

For all chemistry assays, the mean percent change between reconstituted formulated spray dried plasma units and paired controls are within ±20% for total protein, cholesterol, LDL, HDL, Triglyceride, Albumin, Calcium, IgA, IgG, and IgM. There was a 22% change with osmolality for reconstituted formulated spray dried plasma unit compared to its paired control. The increase in osmolality in the reconstituted formulated spray dried plasma unit is attributed to the hydrochloric acid and glycine in the Plasma Pretreatment Container. The pH of reconstituted formulated spray dried plasma units (7.04) did not increase with uncorrected drying and was decreased compared to its paired control (7.44). The European Pharmacopoeia specifies the pH as 6.5-7.6 and minimum osmolality of 240 mOsm/kg for Human Plasma (pooled and treated for virus inactivation). The observed changes compared to the control for pH and osmolality are within the acceptable ranges as indicated by the above-referenced standard. The average moisture content is 1.46% (n=20).

The in vitro characterization results of 60 reconstituted formulated spray dried plasma units and paired controls demonstrate that the manufacturing impact of the FRONTLINE™ System on the starting material is acceptable and the characterization data is within the normal reference range, demonstrating preservation of coagulation factors, proteins, analytes and pH.

Materials:

- ACCUMET® Benchtop pH Meter
- Blood Collection Monitor
- Calibrated timer
- Clean Dry Air (CDA) System
- Freezer
- FRONTLINE™ System VEL 7000×3 and 1 Sealer ASY 30000S (Velico Medical Inc, Beverly MA, USA)
- HELMER® Plasma Thawer
- Instrumentation Laboratories ACL TOP 700 coagulation analyzer
- Osmometer
- Plate Reader
- Plate Washer
- Refrigerator
- SELECTRA PRO M® Chemistry Analyzer
- SIEMENS BCS XP® coagulation analyzer
- Sterile Connection Device
- Tubing Heat Sealer
- Overwrap Sealer
- Plasma Pretreatment Container having pretreatment solution having 16.8 mM HCl and 69.6 mM glycine and SWFI
- Plasma Drying Chamber
- Sterile Water for Injection (SWFI)
- Never Frozen Plasma (NFP)
- Fresh Frozen Plasma (FFP)
- Plasma frozen within 24 hours (PF24)
- 3000 mL transfer pack
- Reagents to complete panel per work instructions
- 5 mL Cryo-vials, P/N 01379

Procedure:

27 blood type A (45%), 27 blood type O (45%), and 6 blood type B (10%) units of plasma were spray dried by the FRONTLINE™ system to represent the American blood type distribution of approximately 36% blood type A, 48% blood type O, 11% blood type B, and 5% blood type AB. "FAQs about Blood and Blood Donation," AABB, accessed Dec. 15, 2020. https://www.aabb.org/for-donors-patients/faqs-about-blood-and-blood-donation The spray dried plasma units obtained from FRONTLINE™ spray drier system were manufactured from thawed PF24. The paired control was refrozen at the time the spray dried plasma unit was manufactured and thawed prior to testing. Each was pre-treated with a pre-treatment solution described above.

The dried plasma units were spray dried and tested after a minimum of 7-day storage at refrigeration. The manufacturing effect of the FRONTLINE™ System on the starting material was determined by calculating the change difference between the dried plasma units and its paired control plasma (CP) for each of the assay.

$$\%\ \text{Change} = \frac{FrontlineODP - CP}{CP} \times 100$$

Results:

Dried plasma unit characterization results (n=60) are shown in Table 46.

TABLE 46

Summary of Results (n = 60, unless otherwise specified)

| Assays | Clinical Reference Range | Control Plasma Mean ± SD | Frontline ODP Mean ± SD | Percent Change compared to Control Mean ± SD | 95% Confidence Interval (Percent Change) |
|---|---|---|---|---|---|
| pH | (7.35-7.45) ① | 7.44 ± 0.08 | 7.04 ± 0.14 | | |
| Osmolality (mOsm/kg) | (280-296) ① | 309 ± 7 | 377 ± 17 | 22% ± 6% | (21%, 24%) |
| aPTT (s) | (22-35) ① | 30.0 ± 2.9 | 30.8 ± 4.0 | 2% ± 8% | (0%, 5%) |
| Prothrombin Time (s) | (10-14) ① | 11.7 ± 0.7 | 12.5 ± 0.8 | 7% ± 3% | (6%, 8%) |
| Thrombin Time (s) | (14.5-20.5) ① | 12.9 ± 1.2 | 17.2 ± 1.3 | 34% ± 9% | (31%, 36%) |
| Factor II Activity (%) | (70-120) ② | 98.1 ± 10.7 | 88.5 ± 10.3 | −10% ± 5% | (−11%, −9%) |
| Factor V Activity (%) | (50-200) ③ | 95.0 ± 16.6 | 92.6 ± 15.9 | −2% ± 7% | (−4%, −1%) |
| Factor V Antigen (%) | (50-175) ④ | 71 ± 14 | 66 ± 14 | −8% ± 9% | (−11%, −6%) |
| Factor VII Activity (%) | (50-200) ③ | 90.1 ± 17.6 | 80.6 ± 16.2 | −11% ± 6% | (−12%, −9%) |
| Factor VII Antigen (IU/mL) | (0.7-1.46) ⑤ | 1.01 ± 0.14 | 0.96 ± 0.15 | −4% ± 6% | (−6%, −3%) |
| Factor VIII Activity (%) | (50-200) ③ | 95.3 ± 34.2 | 78.1 ± 28.9 | −18% ± 11% | (−21%, −15%) |
| Factor VIII Antigen (IU/mL) | (0.5-1.8) ⑥ | 1.24 ± 0.30 | 1.18 ± 0.28 | −5% ± 5% | (−7%, −4%) |

TABLE 46-continued

Summary of Results (n = 60, unless otherwise specified)

| Assays | Clinical Reference Range | Control Plasma Mean ± SD | Frontline ODP Mean ± SD | Percent Change compared to Control Mean ± SD | 95% Confidence Interval (Percent Change) |
|---|---|---|---|---|---|
| Factor IX Activity (%) | (50-200) ③ | 104.1 ± 12.9 | 91.6 ± 12.2 | −12% ± 7% | (−14%, −10%) |
| Factor X Activity (%) | (50-200) ③ | 91.4 ± 13.3 | 81.0 ± 13.7 | −12% ± 4% | (−13%, −10%) |
| Factor XI Activity (%) | (50-200) ③ | 108.1 ± 18.2 | 98.3 ± 18.1 | −9% ± 9% | (−11%, −7%) |
| Factor XII Activity (%) | (50-200) ③ | 124.0 ± 21.3 | 104.6 ± 18.7 | −16% ± 5% | (−17%, −14%) |
| Factor XIII Activity (%) | (57-192) ⑦ | 122.1 ± 23.4 | 103.9 ± 20.9 | −15% ± 8% | (−17%, −13%) |
| Factor XIII Antigen (%) | (75.2-154.8) ⑧ | 106.3 ± 21.8 | 94.0 ± 17.1 | −11% ± 6% | (−13%, −10%) |
| Fibrinogen (mg/dL) | (150-400) ③ | 270 ± 57 | 241 ± 48 | −10% ± 8% | (−12%, −8%) |
| Plasminogen (%) | (70-150) ① | 92 ± 11 | 87 ± 12 | −5% ± 4% | (−6%, −4%) |
| Plasmin Inhibitor (%) | (85-156) ⑨ | 103 ± 10 | 99 ± 12 | −4% ± 4% | (−5%, −3%) |
| C1 Esterase Inhibitor (%) | (70-130) ③ | 104 ± 13 | 99 ± 14 | −5% ± 4% | (−6%, −4%) |
| Alpha 1-Proteinase Inhibitor (mg/dL) | (90-200) ① | 109.2 ± 11.2 | 104.8 ± 11.2 | −4% ± 4% | (−5%, −3%) |
| Protein C Activity (%) | (75-150) ⑩ | 109 ± 17 | 100 ± 17 | −9% ± 4% | (−10%, −8%) |
| Protein S Activity (%) | (60-150) ⑪ | 99.7 ± 14.5 | 85.6 ± 14.7 | −14% ± 6% | (−16%, −13%) |
| Free Protein S (%) | (57-155) ⑩ | 100.8 ± 15.9 | 93.5 ± 16.6 | −7% ± 4% | (−9%, −6%) |
| Antithrombin III (%) | (80-120) ③ | 100 ± 10 | 91 ± 10 | −9% ± 5% | (−10%, −8%) |
| von Willebrand Factor Activity (%)[a] | (50-200) ③ | 112.5 ± 36.0 | 73.6 ± 20.1 | −33% ± 9% | (−36%, −31%) |
| von Willebrand Factor Antigen (%)[a] | (50-200) ③ | 130.6 ± 40.2 | 125.9 ± 35.4 | −2% ± 8% | (−4%, 0%) |
| von Willebrand Factor Ristocetin Cofactor (%) | (50-200) ③ | 95.6 ± 36.3 | 41.8 ± 14.5 | −55% ± 7% | (−57%, −53%) |
| C3a (ng/ml) | (55-486) ⑫ | 233.0 ± 82.2 | 300.2 ± 114.9 | 31% ± 28% | (23%, 38%) |
| C5a (ng/ml) | (4.7-9.5) ⑬ | 7.6 ± 6.3 | 33.9 ± 8.9 | 659% ± 992% | (408%, 910%) |
| D-Dimer (mg/L)[b,c] | (0-0.5) ① | 0.54 ± 0.64 | 0.55 ± 0.56 | 17% ± 26% | (10%, 24%) |
| Prothrombin Fragment PF 1 + 2 (pmol/L) | (91-137) ③ | 153.2 ± 124.5 | 159.5 ± 144.0 | 14% ± 53% | (1%, 28%) |
| Thrombin-Antithrombin Complex (TAT) (μg/L)[d] | (0-4) ⑭ | 5.07 ± 11.93 | 5.12 ± 12.18 | 10% ± 53% | (−4%, 23%) |
| Total Protein (g/dL) | (6-8.3) ① | 5.65 ± 0.37 | 5.42 ± 0.38 | −4% ± 4% | (−5%, −3%) |
| Cholesterol (mg/dL) | (0-200) ① | 150 ± 38 | 141 ± 35 | −6% ± 4% | (−7%, −5%) |
| LDL (mg/dL) | (0-100) ① | 93 ± 34 | 81 ± 27 | −13% ± 5% | (−14%, −12%) |
| HDL (mg/dL) | (35-100) ① | 41 ± 15 | 34 ± 10 | −14% ± 6% | (−16%, −13%) |
| Triglycerides (mg/dL) | (0-150) ① | 114 ± 65 | 111 ± 64 | −3% ± 4% | (−4%, −2%) |
| Albumin (g/dL) | (3.3-5) ① | 3.84 ± 0.22 | 3.62 ± 0.24 | −5% ± 3% | (−6%, −4%) |
| Calcium (mg/dL) | (8.6-10.3) ① | 6.40 ± 0.26 | 6.07 ± 0.29 | −5% ± 4% | (−6%, −4%) |
| IgA (mg/dL) | (69-309) ① | 186 ± 81 | 175 ± 76 | −6% ± 5% | (−7%, −5%) |
| IgG (mg/dL) | (614-1295) ① | 870 ± 235 | 829 ± 222 | −5% ± 5% | (−6%, −3%) |
| IgM (mg/dL) | (53-334) ① | 69 ± 42 | 64 ± 39 | −7% ± 4% | (−8%, −6%) |

The global assays aPTT and PT percent change between the FRONTLINEODP™ Unit and its paired control on average is within ±20%. There was a 34% change with TT for FRONTLINEODP™ Unit compared to its paired control. A previous study demonstrated that decreasing the pH of plasma induced a prolonged TT, therefore the prolonged TT is an effect of the sample pH on the assay. Of the coagulation factor assays, the percent change between the FRONTLINEODP™ Unit and its paired control on average is within ±20% for Factor II activity, Factor V activity, Factor V antigen, Factor VII activity, Factor VII antigen, Factor VIII activity, Factor VIII antigen, Factor IX activity, Factor X activity, Factor XI activity, Factor XII activity, Factor XIII activity, Factor XIII antigen, and fibrinogen. Protease inhibitors C1 Esterase Inhibitor and Alpha 1 Proteinase Inhibitor have a change of ≤5% demonstrating minimal loss due to the FRONTLINEODP™ manufacturing process. Of the anticoagulant protein assays, the mean percent change between the FRONTLINEODP™ Unit and paired control for both Protein C and Antithrombin III is 9%, 14% for Protein S and 7% for Free Protein S. The mean change for procoagulant factors Plasminogen and Plasmin Inhibitor are 5% and 4%, respectively. All mean values are well within the clinical reference ranges. The mean activation marker assays D-Dimer, Prothrombin Fragment 1+2 (PF1+2), and Thrombin Anti-Thrombin (TAT) for FRONTLINEODP™ Units and paired control was above the normal reference range, however the percent change for all assays are between the FRONTLINEODP™ Unit and its paired control within ±20%. The mean percent change in von Willebrand Factor (vWF) antigen assay is within ±20%. There is a 55% and 33% change with von Willebrand ristocetin cofactor (vWF:RCo) and vWF Activity, respectively. The mean vWF:RCo levels of FRONTLINEODP™ units of 41.8% is ≥40%, meeting FDA's recommendation per Meeting ID #BQ150234 (Mar. 14, 2018). vWF activity of 73.0±20.3% is within the normal reference range of 38.0-169.7%. Decreased recovery of vWF activity and vWF:RCo activity was observed and is thought to be due to the shearing during the spray drying process. Complement protein assays have mean percent changes between the FRONTLINEODP™ Unit and its paired control of 31% and 659% for C3a and C5a, respectively. The C3a in FRONTLINEODP™ Units is slightly increased compared to control plasma, but the average of 300.2 ng/mL is within the clinical reference range of 55-486 ng/mL. C5a is elevated in FRONTLINEODP™ Units (33.9 ng/ml) compared to its paired control value (7.6 ng/mL) and is due to the pretreatment process. This value is within the range reported for apheresed plasma of 4.9-74 ng/ml and does not demonstrate complement activation. For all chemistry assays, the percent change between the FRONTLINEODP™ Unit and its paired control on average is within ±20% for total protein, cholesterol, LDL, HDL, Triglyceride, Albumin, Calcium, IgA, IgG, and IgM. There was a 22% change with osmolality, for FRONTLINEODP™ Unit compared to its paired control. The increase in osmolality in the FRONTLINEODP™ Unit is attributed to the hydrochloric acid and glycine in the Plasma Pretreatment Container. The pH of FRONTLINEODP™ Units (7.04) was decreased compared to its paired control (7.44). There was a 22% change with osmolality for FRONTLINEODP™ Unit compared to its paired control. The European Pharmacopoeia specifies the pH as 6.5-7.6 and minimum osmolality of 240 mOsm/kg for Human Plasma (pooled and treated for virus inactivation). The observed changes compared to the control for pH and osmolality are within the acceptable ranges as indicated by the above-mentioned standard.

Mean FRONTLINEODP™ Unit characterization results by blood type are shown in Table 47.

TABLE 47

Mean FRONTLINEODP ™ Unit characterization results by blood type (A, B, and O)

| Assays | Clinical Reference Range | Type A (n = 27) | Type B (n = 6) | Type O (n = 27) |
|---|---|---|---|---|
| pH | (7.35-7.45) | 7.05 ± 0.12 | 7.10 ± 0.10 | 7.03 ± 0.17 |
| Osmolality (mOsm/kg) | (280-296) | 376 ± 19 | 368 ± 9 | 379 ± 16 |
| aPTT (s) | (22-35) | 30.5 ± 5.0 | 28.4 ± 2.2 | 31.6 ± 2.9 |
| Prothrombin Time (s) | (10-14) | 12.5 ± 1.0 | 13.0 ± 0.5 | 12.4 ± 0.7 |
| Thrombin Time (s) | (14.5-20.5) | 17.4 ± 1.3 | 17.5 ± 1.4 | 17.0 ± 1.2 |
| Factor II Activity (%) | (70-120) | 89.2 ± 10.0 | 92.0 ± 8.7 | 87.0 ± 10.9 |
| Factor V Activity (%) | (50-200) | 92.4 ± 16.1 | 86.6 ± 6.2 | 94.1 ± 17.1 |
| Factor V Antigen (%) | (50-175) | 66 ± 14 | 62 ± 15 | 66 ± 14 |
| Factor VII Activity (%) | (50-200) | 80.9 ± 17.0 | 72.9 ± 14.6 | 81.9 ± 15.7 |
| Factor VII Antigen (IU/mL) | (0.7-1.46) | 0.98 ± 0.16 | 0.91 ± 0.15 | 0.96 ± 0.14 |
| Factor VIII Activity (%) | (50-200) | 84.3 ± 32.2 | 96.8 ± 29.8 | 67.7 ± 21.3 |
| Factor VIII Antigen (IU/mL) | (0.5-1.8) | 1.23 ± 0.30 | 1.47 ± 0.40 | 1.06 ± 0.16 |
| Factor IX Activity (%) | (50-200) | 91.2 ± 12.6 | 88.1 ± 9.2 | 92.7 ± 12.5 |
| Factor X Activity (%) | (50-200) | 81.9 ± 14.9 | 81.5 ± 13.9 | 80.0 ± 12.8 |
| Factor XI Activity (%) | (50-200) | 101.2 ± 16.9 | 104.3 ± 17.9 | 94.0 ± 18.9 |
| Factor XII Activity (%) | (50-200) | 109.5 ± 16.8 | 111.3 ± 13.2 | 98.1 ± 19.9 |
| Factor XIII Activity (%) | (57-192) | 102.7 ± 25.9 | 106.0 ± 15.0 | 104.5 ± 16.6 |
| Factor XIII Antigen (%) | (75.2-154.8) | 94.5 ± 21.2 | 93.6 ± 10.4 | 93.5 ± 13.9 |
| Fibrinogen (mg/dL) | (150-400) | 230 ± 49 | 210 ± 18 | 258 ± 46 |
| Plasminogen (%) | (70-150) | 88 ± 11 | 92 ± 9 | 86 ± 13 |
| Plasmin Inhibitor (%) | (85-156) | 100 ± 13 | 100 ± 10 | 98 ± 11 |
| C1 Esterase Inhibitor (%) | (70-130) | 98 ± 15 | 97 ± 13 | 100 ± 13 |
| Alpha 1-Proteinase Inhibitor (mg/dL) | (90-200) | 102.9 ± 12.8 | 104.8 ± 7.9 | 106.8 ± 10.1 |
| Protein C Activity (%) | (75-150) | 99 ± 15 | 101 ± 16 | 100 ± 19 |
| Protein S Activity (%) | (60-150) | 88.6 ± 16.1 | 83.6 ± 9.2 | 83.0 ± 14.0 |
| Free Protein S (%) | (57-155) | 97.4 ± 18.9 | 88.6 ± 11.1 | 90.7 ± 14.7 |
| Antithrombin III (%) | (80-120) | 92 ± 9 | 91 ± 9 | 89 ± 12 |
| von Willebrand Factor Activity (%) | (50-200) | 70.4 ± 29.8 | 81.2 ± 28.5 | 66.8 ± 19.6 |
| von Willebrand Factor Antigen (%) | (50-200) | 128.5 ± 46.6 | 150.1 ± 39.8 | 108.6 ± 32.1 |
| von Willebrand Factor Ristocetin Cofactor (%) | (50-200) | 45.7 ± 15.9 | 44.9 ± 15.8 | 37.1 ± 11.6 |
| C3a (ng/mL) | (55-486) | 306.1 ± 133.6 | 293.3 ± 34.8 | 295.7 ± 108.7 |
| C5a (ng/mL) | (4.7-9.5) | 33.5 ± 8.5 | 28.6 ± 5.7 | 35.5 ± 9.7 |
| D-Dimer (mg/L) | (0-0.5) | 0.46 ± 0.72 | 0.43 ± 0.21 | 0.49 ± 0.41 |
| Prothrombin Fragment F 1 + 2 (pmol/L) | (91-137) | 122.7 ± 52.4 | 121.8 ± 61.8 | 204.6 ± 199.3 |
| Thrombin-Antithrombin Complex (TAT) (μg/L) | (0-4) | 2.81 ± 4.56 | 2.88 ± 2.59 | 7.75 ± 17.21 |
| Total Protein (g/dL) | (6-8.3) | 5.45 ± 0.38 | 5.45 ± 0.34 | 5.39 ± 0.40 |
| Cholesterol (mg/dL) | (0-200) | 145 ± 30 | 157 ± 77 | 134 ± 23 |

TABLE 47-continued

Mean FRONTLINEODP ™ Unit characterization results by blood type (A, B, and O)

| Assays | Clinical Reference Range | Type A (n = 27) | Type B (n = 6) | Type O (n = 27) |
|---|---|---|---|---|
| LDL (mg/dL) | (0-100) | 83 ± 24 | 94 ± 60 | 75 ± 19 |
| HDL (mg/dL) | (35-100) | 35 ± 9 | 29 ± 13 | 35 ± 10 |
| Triglycerides (mg/dL) | (0-150) | 114 ± 72 | 133 ± 67 | 103 ± 56 |
| Albumin (g/dL) | (3.3-5) | 3.67 ± 0.24 | 3.64 ± 0.31 | 3.57 ± 0.21 |
| Calcium (mg/dL) | (8.6-10.3) | 6.04 ± 0.29 | 6.12 ± 0.20 | 6.09 ± 0.31 |
| IgA (mg/dL) | (69-309) | 196 ± 67 | 156 ± 68 | 159 ± 83 |
| IgG (mg/dL) | (614-1295) | 800 ± 154 | 865 ± 169 | 850 ± 285 |
| IgM (mg/dL) | (53-334) | 69 ± 36 | 86 ± 47 | 54 ± 38 |

The manufacturing effects of the FrontlineODP System on the starting material are comparable across blood type A, B, and O.

All spray drying manufacturing process were within the acceptance criteria listed below.

Drying gas inlet temperature: 115±3° C.

Drying gas flow rate: 750±10 L/min

Drying gas exhaust temperature: 65±2° C.

Aerosol gas flow rate: 40±1 L/min

Mean rehydrated ODP were within the acceptance criteria of:

pH within 6.69-7.37, where the average value was 7.04 SD+−0.14.

Osmolality within 338-450 mOsm/kg, where the average value was 377 mOsm/kg.

Protein concentration dried plasma units normalized to control was within 0.88-1.17 on a Chemistry analyzer, where the average value was 0.96.

Conclusion:

The characterization data of 60 samples show that reconstituted plasma units made from the FRONTLINE™ system which are intended for transfusion are comparable to the paired control plasma, including with regard to pH in the range of 6.69-7.37 with an average of 1.04 SD+−0.14.

Comparability of the in vitro tests supports that the manufacturing impact of the FRONTLINE™ process is acceptable resulting in spray dried plasma units that meet the acceptance criteria with coagulation factor profile within the normal reference range and a pH range of 6.69-7.37 and a pH mean of 7.04 SD+−0.14.

Example 27: Impact of Nozzle Annulus Radial Distance $D^d$ on Plasma Yield and Quality Purpose: Compare plasma protein concentration yield and residual moisture of recovered dried plasma obtained by the composite nozzle assembly of the present invention with an annulus diameter of $D^o$ of 0.091" and that of 0.082", a cannula outside diameter $D^c$ of 0.050" and a resulting annulus radial distances, $D^d$, of 0.021" and 0.015" at an aerosol flow rate of 40 L/min and 114° C. drying gas inlet temperature.

Methods and Materials:

Pre-production spray dryer (Model No. Wall-E3) by Velico Medical Inc. (Beverly Massachusetts USA)

9 Pre-production disposable devices (Model: V2.0 from Velico Medical Inc.) with a nozzle annulus radial distance of 0.021"

8 Pre-production disposable devices (Model V3.0 from Velico Medical Inc.) with a nozzle radial distance width of 0.015"

17 units for PF24 (Plasma frozen within 24 hours after phlebotomy) human blood plasma Laboratory balance scale Model No. AB204 from Mettler-Toledo, LLC in Columbus Ohio, United States of America Protein meter Model no. 1000 from ThermoFisher Scientific Inc. in Waltham, Massachusetts, United States of America Total protein measurement was determined with NanoDrop 1000. Utilizing the absorbance at 280 nm (A280), protein concentration (c) was calculated by the instrumentation using the Beer-Lambert equation A280=c*ε*b (ε is the wavelength-dependent protein extinction coefficient, b is the pathlength). Total protein measurement was done according to the NanoDrop 1000 specification.

Residual moisture in dried plasma was determined according to specification of Karl Fischer moisture sensor, Model No. C30S Compact KF Coulometer (Mettler Toledo Billerica Massachusetts USA). In this approach, the reagent and solvent were combined in the titration cell. When a sample was introduced into the titration cell and dissolved, reagent was released by the induction of an electrical current. The amount of current required to convert the water was the determinant of the amount of moisture.

vWFrco assays (model no. 23044717) from Siemens Healthineers, ThermoFisher Scientific Inc. in Waltham, Massachusetts, United States of America.

von Willebrand Factor ristocetin cofactor (vWF:RCo) activity assay was performed by determining the amount of reagents and samples required by using the information in the subsequent sections. The dead volume of each of the reagents for the BCS XP is as listed below.

TABLE 48

| Item | Volume μL |
|---|---|
| GW 5 Reagent Bottle | 150-200 |
| GW 5 Reagent Bottle | 2000 |
| GW 15 Reagent Bottle | 300-350 |
| Behring Coagulation Cup | 250-300 |

One vWF:RCo assay requires the amounts of sample and reagents listed below.

TABLE 49

| Item | Volume Required μL | Volume/ Bottle (mL) | Container |
|---|---|---|---|
| Sample | 20 | N/A | Behring Coagulation Cup |

TABLE 49-continued

| Item | Volume Required µL | Volume/ Bottle (mL) | Container |
|---|---|---|---|
| Sodium Chloride | 40 | N/A | GW 15 |
| BC vWF Reagent | 300 | 4 | GW 5 |

Reagent Preparation:

Always initial and date (including time) a vial when opened or reconstituted. Always write the expiration date on the label.

BC vWF Reagent: Reconstitute BC vWF Reagent with 4.0 mL of DI water. Mix on high with a vortex mixer twice for five seconds. Drop a small Teflon magnetic stir bar into the BC vWF Reagent Bottle. Once prepared, the BC vWF Reagent can be stored on board for 8 hours in a position with stirring marked with yellow in rack lanes 1-5 or for 2 days at 2-8° C. Swirl gently before use.

Control Plasma N and Control Plasma P: Obtain a vial of Control Plasma N and Control Plasma P and reconstitute each vial with 1.0 mL of DI water. Swirl gently without causing any foam formation to dissolve lyophilized powder. Let stand at 15-25° C. for at least fifteen minutes. Once reconstituted, Control Plasma N and Control Plasma P can be stored on board for eight hours in rack lanes 5-14. Swirl gently without causing any foam formation before use.

0.9% Sodium Chloride Solution: Obtain a GW15 bottle from the BC vial kit with a sodium chloride barcode. Pour approximately 10 mL of sodium chloride solution into the vial. At the end of the day, throw out any unused sodium chloride solution and rinse the vial with DI water.

SHP (Only if Calibration is Required): Obtain a vial of SHP and reconstitute with 1.0 mL of DI water. Swirl gently without causing any foam formation to dissolve lyophilized powder. Let stand at 15-25° C. for at least 15 minutes. Once reconstituted, SHP can be stored on board for 4 hours in rack lanes 5-14. Swirl gently without causing any foam formation before use.

Loading Reagents into the BCS XP: Load reagents into the BCS XP by following: Load the BC vWF Reagent in any of the stirring positions in rack lanes 1-5. Load the SHP, Control Plasma N, and Control Plasma P in any position in rack lanes 5-14. Load Sodium Chloride Solution in any position in rack lanes 3-14.

Calibration for each assay is required every 6 months, when a new reagent lot is used, or at laboratory discretion as described in WI-00125. If calibration is required, prepare SHP. Select the assay vWF to calibrate. Run controls immediately after calibration has completed to verify the curve. If the controls are out of range, rerun the control and if it is still out of range, recalibrate.

Controls: Print reagent overview sheet, add the 0.9% Sodium Chloride Solution lot number, Run Control N and Control P before running assays on test samples. Check all controls are within range before running test samples.

Running Assays: Use the same reagent lot number when testing comparative samples. Load test samples in Behring Coagulation Cup into a sample rack and load in any rack lanes 5-14. Request the assay vWF. Samples with a measurement greater than 150% must be diluted in half using the 0.9% sodium chloride solution by adding 200 µL of the test sample to 200 µL of the 0.9% sodium chloride solution in a new sample cup. Mix thoroughly by pipetting up and down five to ten times. Any test result less than approximately 17% is below the measurement range and is not acceptable.

(The lower limit may change slightly depending on the SHP used to generate the calibration curve for the assay.

Note: The ABO blood group has been known to exert a major quantitative effect on circulating vWF levels. Studies have consistently reported that blood group type O subjects have significantly lower plasma vWF levels than non-O individuals.

Note: VIII/vWF appears as a series of aggregates with different molecular weights therefore subjects with higher VIII levels tend to have higher vWF.

Characterization Studies: if either the dried plasma of the present invention or CP has a raw value of <40% then confirmation/rerun analysis was at the discretion of the reviewer/operator.

Exploration/Stability/Method Development Studies: Characterization study guidelines can be used to evaluate if any trends are present and/or establish the quality of the sample. Any deviation outside the characterization study guidelines would not be an indication for confirmation/rerun analysis due to the varying nature of exploratory studies.

17 units of plasma was spray dried using the pre-production spray dryer at 114° C. inlet temperature and aerosol gas flow rate of 40 L/min. with 9 disposable devices having a nozzle annulus radial distance of 0.021" and 8 disposable devices having a nozzle radial distance width of 0.015". Total plasma mass recovered was measured and compared. Inside of disposable devices were inspected for residual plasma deposits (loss) and weighed.

The protein concentration ratio (PCR) was determined as follows $$PCR = \text{Rehydrated dried plasma protein concentration/control protein concentration}$$

Yield was determined as follows:

$$\text{Yield} = ((\text{dried plasma mass grams} + 200\,\text{g rehydration water}) \times PCR)/\text{starting plasma mass in grams}$$

Residual moisture in dried plasma was determined according to specification of Karl Fischer moisture sensor, Model No. C30S Compact KF Coulometer (Mettler Toledo Billerica Massachusetts USA).

vWFrco recovery assay result was determined by Siemens BCS XP System Model No. 23044717 from Siemens Healthineers, ThermoFisher Scientific Inc. in Waltham, Massachusetts, United States of America. von Willebrand Factor ristocetin cofactor (vWF:RCo) activity assay was performed. The amount of reagents and samples was determined by using the information in the subsequent section. The dead volume of each of the reagents for the BCS XP is as listed below.

TABLE 50

| Item | Volume µL |
|---|---|
| GW 5 Reagent Bottle | 150-200 |
| GW 5 Reagent Bottle | 2000 |
| GW 15 Reagent Bottle | 300-350 |
| Behring Coagulation Cup | 250-300 |

One vWF:RCo assay requires the amounts of sample and reagents listed below.

TABLE 51

| Item | Volume Required μL | Volume/ Bottle (mL) | Container |
|---|---|---|---|
| Sample | 20 | N/A | Behring Coagulation Cup |
| Sodium Chloride | 40 | N/A | GW 15 |
| BC vWF Reagent | 300 | 4 | GW 5 |

Reagent Preparation:

Always initial and date (including time) a vial when opened or reconstituted. Always write the expiration date on the label.

BC vWF Reagent: Reconstitute BC vWF Reagent with 4.0 mL of DI water. Mix on high with a vortex mizer twice for five seconds. Drop a small Teflon magnetic stir bar into the BC vWF Reagent Bottle. Once prepared, the BC vWF Reagent can be stored on board for 8 hours in a position with stirring marked with yellow in rack lanes 1-5 or for 2 days at 2-8° C. Swirl gently before use.

Control Plasma N and Control Plasma P: Obtain a vial of Control Plasma N and Control Plasma P and reconstitute each vial with 1.0 mL of DI water. Swirl gently without causing any foam formation to dissolve lyophilized powder. Let stand at 15-25° C. for at least fifteen minutes. Once reconstituted, Control Plasma N and Control Plasma P can be stored on board for eight hours in rack lanes 5-14. Swirl gently without causing any foam formation before use.

0.9% Sodium Chloride Solution: Obtain a GW15 bottle from the BC vial kit with a sodium chloride barcode. Pour approximately 10 mL of sodium chloride solution into the vial. At the end of the day, throw out any unused sodium chloride solution and rinse the vial with DI water.

SHP (Only if Calibration is Required): Obtain a vial of SHP and reconstitute with 1.0 mL of DI water. Swirl gently without causing any foam formation to dissolve lyophilized powder. Let stand at 15-25° C. for at least 15 minutes. Once reconstituted, SHP can be stored on board for 4 hours in rack lanes 5-14. Swirl gently without causing any foam formation before use.

Loading Reagents into the BCS XP: Load reagents into the BCS XP by following WI-00125 Section 8.12. Load the BC vWF Reagent in any of the stirring positions in rack lanes 1-5. Load the SHP, Control Plasma N, and Control Plasma P in any position in rack lanes 5-14. Load Sodium Chloride Solution in any position in rack lanes 3-14.

Calibration for each assay is required every 6 months, when a new reagent lot is used, or at laboratory discretion as described in WI-00125. If calibration is required, prepare SHP. Select the assay vWF to calibrate. Run controls immediately after calibration has completed to verify the curve. If the controls are out of range, rerun the control and if it is still out of range, recalibrate.

Controls: Print reagent overview sheet, add the 0.9% Sodium Chloride Solution lot number, Run Control N and Control P before running assays on test samples. Check all controls are within range before running test samples.

Running Assays: Use the same reagent lot number when testing comparative samples. Load test samples in Behring Coagulation Cup into a sample rack and load in any rack lanes 5-14. Request the assay vWF. Samples with a measurement greater than 150% must be diluted in half using the 0.9% sodium chloride solution by adding 200 μL of the test sample to 200 μL of the 0.9% sodium chloride solution in a new sample cup. Mix thoroughly by pipetting up and down five to ten times. Any test result less than approximately 17% is below the measurement range and is not acceptable. (The lower limit may change slightly depending on the SHP used to generate the calibration curve for the assay.

Note: The ABO blood group has been known to exert a major quantitative effect on circulating vWF levels. Studies have consistently reported that blood group type O subjects have significantly lower plasma vWF levels than non-O individuals.

Note: VIII/vWF appears as a series of aggregates with different molecular weights therefore subjects with higher VIII levels tend to have higher vWF.

Characterization Studies: if either the dried plasma of the present invention or CP has a raw value of <40% then confirmation/rerun analysis was at the discretion of the reviewer/operator.

Exploration/Stability/Method Development Studies: the reviewer/operator will have discretion to request a confirmation/rerun analysis at any time. Characterization study guidelines can be used to evaluate if any trends are present and/or establish the quality of the sample. Any deviation outside the characterization study guidelines would not be an indication for confirmation/rerun analysis due to the varying nature of exploratory studies.

Results

| | Data | |
|---|---|---|
| | 0.021 Dd | 0.015 Dd |
| Yield | 76.2% | 77.9% |
| vWFrco | 49.0% | 50.0% |
| Moisture | 1.8% | 1.0% |

The pre-production disposable drying chambers (V3.0) with nozzle annulus distance $D^d$ of 0.015" provided a 2.2% greater yield percentage improvement as compared to those with nozzle $D^d$ of 0.021". Both yields are sufficient for purposes of spray drying human blood plasma.

The disposable drying chambers with 0.015" annulus radial distance $D^d$ yielded 1.0% residual moisture as compared to 1.8% residual moisture for disposable drying chambers with 0.021 annulus radial distance $D^d$. Again, for purposes of use for spray drying purposes, a residual moisture of less than 2% is sufficient.

vWF recovery of the 0.015" annulus radial distance nozzle compared to the 0.021" annulus radial distance nozzle was improved by 1 percentage point. While 49% or 50% vWF recovery as measured by the vWFrco assay is acceptable per FDA guidance per Meeting ID #BQ150234 (Mar. 14, 2018), the importance of VWF to clotting performance in vivo is so great that optimizing vWF recovery is of paramount importance.

Conclusion

Reduction of annulus radial distance improves dried plasma and VWFrco yield and reduces residual moisture in the dried plasma.

Example 28: Impact of Chamfered Cannula on vWFrco Recovery

Purpose: To study vWF recovery ratio by vWFrco assay of plasma dried with a composite nozzle assembly having a chamfered cannula, as compared to one with an unchamfered cannula. Specifically, an expensive Buchi stainless-steel nozzle assembly with unchamfered cannula (no chamfered cannula nozzle is known to be available commercially) used during development to produce regulatorily acceptable dried plasma was used a benchmark against which to judge the performance of a significantly less expensive composite nozzle of the present invention suitable for use in a disposable drying chamber for spray drying human blood plasma. The study also determined vWF recovery of less expensive chamfered and unchamfered plastic nozzle assemblies as compared to stainless steel nozzle benchmark.

Methods and Materials

- Spray dryer test bed (Beta model, Velico Medical Inc, Beverly Massachusetts US)
- 8 plasma drying disposables
- 1 control Buchi Model No. 4244 stainless steel spray drying nozzle
- 1 pre-production composite nozzle with an unchamfered cannula (Velico Medical Inc, Beverly Massachusetts USA)
- 1 pre-production composite nozzle with chamfered cannula of 45 Degrees and 0.003" length, as shown in FIG. 43F (Velico Medical Inc, Beverly Massachusetts USA)
- 8 units of PF24 plasma
- vWF rco assays as needed ((model no. 23044717) from Siemens Healthineers, ThermoFisher Scientific Inc. in Waltham, Massachusetts, United States of America) for control plasma and test samples The units were grouped to three studies. Groups I and II used stainless steel and an unchamfered composite nozzle assembly and Group III used a chamfered composite nozzle assembly. The unchamfered stainless steel cannula was made with a polycarbonate plastic assembly (i.e., nozzle cap, nozzle insert, nozzle reservoir and the like), the chamfered stainless-steel cannula was made with a polycarbonate plastic assembly (i.e., nozzle cap, nozzle insert, nozzle reservoir and the like), and the stainless-steel nozzle assembly was made from stainless-steel (i.e., cannula, nozzle cap, pressurized air outlet and the like).

The control for each group was obtained by mixing each unit prior to spray drying. The control liquid plasma was not spray dried.

One unit from each of the (units 2795, 2800 and 2815) was spray dried with the control stainless steel nozzle. One unit from Group I (unit 2796) and two units from Group II (units 2801 and 2802) were spray dried with pre-production composite nozzle with an unchamfered cannula. Two units (2816 and 2817) from Group III were spray dried with pre-production composite plastic nozzle with a chamfered cannula.

The spray dried plasma was reconstituted with 200 ml Sterile Water for Injection. vWF rco assays were performed on the control samples and the reconstituted plasma dried as described above.

Results

TABLE 52

CP is control plasma that is pumped thru the cannula but not dried

| Group | Nozzle Assembly | Batch | Nozzle Type | Chamfer | vWF (%) | vWF (%) dried plasma/CP Ratio |
|---|---|---|---|---|---|---|
| Group I | N/A | 2795/2796 CP | N/A | N/A | 97.4% | N/A |
| | | 2795 | Steel | No | 51.1% | 52.5% |
| | Steel | 2795 | Steel | No | 52.5% | 53.9% |
| | | 2796 | Plastic Nozzle #1 | No | 42.4% | 43.5% |
| | Unchamfered Plastic | 2796 | Plastic Nozzle #1 | No | 44.8% | 46.0% |
| Group II | N/A | 2800/2801/2802 CP | N/A | N/A | 149.4% | N/A |
| | Steel | 2800 | Steel | No | 67.3% | 45.0% |
| | Unchamfered Plastic | 2801 | Plastic Nozzle B01 | No | 55.9% | 37.4% |
| | Unchamfered Plastic | 2802 | Plastic Nozzle B02 | No | 56.1% | 37.6% |
| Group III | N/A | 2815/2816/2817 CP | N/A | N/A | 73.1% | N/A |
| | Steel | 2815 | Steel | No | 39.9% | 54.6% |
| | Chamfered Plastic | 2816 | Plastic Nozzle B6 | Yes | 41.4% | 56.6% |
| | Chamfered Plastic | 2817 | Plastic Nozzle A1 | Yes | 40.5% | 55.4% |

The Results are Shown Below:

Table 52

CP is control plasma that is pumped thru the cannula but not dried

As shown in FIG. 50, vWF recovery ratio of the chamfered cannula composite nozzle of the present invention was 3.7% greater as compared to the stainless-steel control nozzle. It is surprising to have any increase in vWF recovery ratio over the expensive stainless steel benchmark nozzle. The chamfered cannula used in the composite nozzle assembly of the present invention is less expensive and performs just as well or better than the expensive stainless-steel version or the unchamfered composite nozzle.

Conclusion

The chamfered cannula results in improved vWF recovery in spray drying of human blood plasma.

Example 29: Increasing Aerosol Flow Rate Increases Yield

Purpose: It was determined that aerosol flow rate of 40 L/min increased yield by 7.5%

Methods and Materials

Plasma yield by weight was compared using aerosol flow rates of 35 L/min and 40 L/min. Two liquid plasma units were spray dried using the dryer of the present invention at an aerosol flow rate of 35 L/min and two at 40 L/min. Dried plasma units were weighed in the disposables and compared.

pre-production spray dryer of the present invention 4 late pre-production drying chambers of the present invention 4 units PF24 human plasma laboratory balance scale Result Yield percentage by weight at 35 L/min. was 82.75%.

Yield percentage by weight at 40 L/min was 86.4%.

Conclusion

Increased aerosol flow rate to 40 L/min increases plasma yield.

Example 30: Human Factors Study I

Method: observation/interview usability, human factors and heuristic evaluation compliant with FDA Guidance for Industry and Food and Drug Administration Staff, section 6.4.2 "Empirical Approaches to Identifying Critical Tasks" and section 6.3.2 "Heuristic Analysis" (2016), IEC 62366-1:2015, sections 5.1-5.6 "Usability Engineering Process" and section 5.7 "Establish User Interface Evaluation Plan" and IEC TR 62366-2:2016, sections 8.4 "Recommend Methods for Developing the Use Specification" and section 3.27 and section 16.2.2 "Conduct Heuristic Analysis" of IEC TR 62366-2 (2016)." Unpublished report from Ximedica Providence Rhode Island (USA).

Materials:

1 VELICO® Alpha spray dryer (Velico Medical Inc, Beverly MA USA), the developmental version;

10 VELICO® Alpha disposables measuring about 66 inches in length;

7 participants selected as representative of end users and end user managers from blood centers in the United States;

3 trained observers;

2,163 photographs;

Multiple interviews and observations of each participant.

Methodology: Participants received training on the use of the VELICO® Alpha system consistent with that expectable in a blood center in the United States. Following that Alpha system was operated under observation followed up by interviews over a period of hours.

Results:

Touch points on system outside of comfortable range of motion: bending required is too low; reaching required is too great; control screen too high for shorter users and too close to other controls, placement and directionality of disposable loading unintuitive.

Insufficient feedback provided to user: audible feedback expected; need confirmation that a given task has been performed properly in a noisy environment, too few clues that system preparation had been done properly.

Difficulty in feeding disposable tubing.

Emergency cut-off too close to other controls but still needed to be readily locatable.

Some disposable loading steps required too much force for smaller or weaker operators.

Disposable is too long.

Disposable slides out of place during loading.

Disposable must be tucked into place in processing chamber.

Insufficient information where to connect aerosol gas tubing.

Address physical abilities of 5% female to 95% male user

Example 31: Human Factors Study II

Human Factors Study 2 2019 ("Velico OnDemand Drying System Formative #2")

Method: Loring observation/interview usability, human factors and heuristic evaluation consistent with ISO 14971:2007 "Application of Risk Management to Medical Devices"; IE 62366-1:2015 "Medical Devices: Part 1—Application of Usability Engineering to Medical Devices"; ANSI HE75:2009: Human Factors Engineering—Design of Medical Devices "; Applying Human Factors and Usability Engineering to Medical Devices: Guidance for Industry and Food and Drug Administration Staff." Unpublished report from Loring Human Factors, Inc. Westwood MA (USA).

Materials:

4 VELICO® Beta Development Spray Dryer functional mockups (Velico Medical, Inc. Beverly MA USA). This beta disposable measured 34.2 inches in length.

Beta disposables as need.

12 blood center managers, and technicians selected to be representative of employees of US blood center. The participants ranged in height from 5'2" (female) to 5'10" (male)

A moderator, trained observers and a notetaker from Loring.

Three video cameras.

Multiple interviews and observations of each participant.

Methodology: Participants received training on the use of the then current Velico Beta development system mockups consistent with that expectable in a blood center in the United States including overhead guidance signage. Following that they operated the Beta system mockups under observation with interviews and discussion over a period of approximately 2 hours at intervals over 2 days.

Results:

The disposable tubing length and threading was confusing;

The disposable too long for the space available in spray dryer apparatus chamber;

The disposable plenum would not slide into place easily;

None of the other concerns voiced in Human Factors Study 1 directed to the Velico Alpha spray dryer and disposable were repeated in Human Factors Study 2 directed to the Velico Beta spray dryer and disposable incorporating the instances of the present invention.

Example 32: Human Factors Study III (2021)

Method: See methodology from Example 31. Additionally, participants received training on the use of the VELICO® prototype commercial intent system consistent with that expectable in a blood center in the United States. Following that they each processed two units of plasma from start to finish 13 the first unit with coaching as needed and the second without assistance. The entire activity was conducted under observation with follow up interviews and discussion.

Materials:

VELICO® prototype commercial intent spray dryers (Velico Medical, Inc. Beverly MA USA).

VELICO® prototype commercial intent disposables as needed.

4 Participants, two managers and two blood center technicians of height 5'2" to 5'9"

Loring trained moderator and videographer.

Results:

The resultant report stated: "All the issues that arose during Formative #1 (i.e., Examples 30-31) appear to be sufficiently mitigated." The issues referred to in Formative #1 were rectified by the present inventions incorporated into the Velico commercial intent spray dryer and disposable.

Example 33 Human Factors Study IV (2022)

Purpose: To determine ease of use for users of the spray drying machine and disposable.

Methods and Materials: The subjects were provided with a 10 minute instruction on how to install the disposable device of FIG. 42A into the spray drying machine shown in FIG. 45A-C. The subjects were timed and observed. Three subjects, female, two having a height of 5'0" height and one of height 4'11" at a separate time. One subject, male, having a height of 6'9" which fell in the $99^{th}$ percentile, respectively, according to Height calculator at "Height Percentile Calculator for Men and Women in the United States" https://dqydj.com/height-percentile-calculator-for-men-and-women/Don't Quit Your Day Job (2022). Subjects were interviewed as to ease of use.

Two guided training sessions (<5 minutes each) were provided for loading and unloading the disposable of the present invention into the spray dryer.

Disposable Device of FIG. 42

Spray drying machine shown in FIG. 45A-C.

2 subjects, female, 5'0" height, no observable or reported physical challenges or disabilities, no prior training or experience with spray dried plasma equipment 1 subject, female, 4'11" height, no observable or reported physical challenges or disabilities, prior experience with spray dried plasma equipment 1 subject, male, 6'9" height, no observable or reported physical challenges or disabilities, no prior training or experience with spray dried plasma equipment The same trainer was used as that in Example 32.

Results

Each subject was observed to be able to successfully load and unload the plasma drying chamber from the spray dryer without limitations or difficulty due to their stature or strength.

Conclusion

The disposable drying chamber of the present invention of about 34" in length can be readily loaded and unloaded into the spray dryer of the present invention without limitation or difficulty by subjects in the $5^{th}$ percentile to the $99^{th}$ percentile of height as reported by the CDC NHANES 2015-2016 survey. See Height calculator at "Height Percentile Calculator for Men and Women in the United States" https://dqydj.com/height-percentile-calculator-for-men-and-women/Don't Quit Your Day Job (2022).

Example 34 Computer Flow Modeling of Liquid Plasma Flow Exiting the Cannula of the Nozzle Assembly of the Present Invention A computer simulation of the liquid plasma as it exits the cannula was used to calculate the difference in shear rate experienced by the plasma for different cannula end geometries. A transient simulation technique known as the 'Volume of Fluid' approach was implemented using a two dimensional, axi-symmetric flow domain mesh. This is a feature available on the commercial computer code; Ansys-Fluent, version 2019-R1, and was run on a dedicated HPZ840 multi-processor workstation.

This approach captured the physics across the air to liquid interface and effectively tracked the shape of liquid surface as it was being drawn out for the cannula.

Various different inner cannula edge geometries as shown in FIG. 52 was simulated: 90/60/45/15 degrees with respect to cannula axis and the maximum shear rate in the liquid phase was calculated. The 45 degree angled edge was simulated with and without a flat edge. FIG. 52.

It has been determined that the maximum weighted wall shear for the 60/45/15 degrees angles of the cannula was less, as compared to that for a 90 degree cannula, as shown in Table 53 below. The maximum weighted shear was 225 Pa for the 90 degree cannula, as compared to 40-70 Pa obtained for 60/45/15 degree angles. As can be seen from the table below, all of the values were significantly less than the value for the 90 degree cannula.

TABLE 53

| Cannula Geometries | Max wall area weighted shear stress, Pa |
|---|---|
| No Chamfer (90 deg) | 225 |
| 45 deg chamfer (equal inlet/outlet angles) | 65 |
| 45 deg sharp edge | 67 |
| 15 deg inlet angle | 46 |
| 60 deg inlet angle | 56 |

As can be seen in FIGS. 53A and 53B, the maximum wall shear in Pa (pascal) of the cannula is shown. The no-chamfer (90 degree angle) cannula wall is compared against the 45 degree chamfer angle in FIG. 53A and the 60 degree angle with a flat edge in FIG. 53B. In both figures, at about 0.007 seconds, as the plasma exits the cannula of the no chamfered (90 degree angle) cannula, a spike in wall shear is seen at around 225 Pa. By comparison, the 45 degree chamfer exhibits a maximum shear of 65 Pa and the 60 degree with a flat edge exhibits a maximum shear of 56 Pa.

Since the maximum average wall shear is less, vWF recovery is expected to be improved, as compared to the non-chamfered cannula. Example 28 provides data showing that the chamfered edge improves vWF recovery. Based on the modeling done in this example showing reduced maximum shear, vWF recovery for chamfers with an angled edge, with and without a flat edge, is expected to be improved as well.

Example 35: Process Simulation and Bioburden

The results for the dried plasma units in this Example support that the plasma spray drying process in a routine (unclassified) blood center component or similar manufacturing environment. The bioburden results demonstrate consistency of the spray drying process across different dryers in maintaining product integrity.

Methods/Procedure:

The system used in this example is the spray drying system of the present invention that spray dries a measured unit of plasma with a drying gas inlet temperature of 114° C.

Three (3) different dryers were used to spray dry 7 (seven) units each for a total of 21 samples. After spray drying a unit of plasma, the dried plasma unit was rehydrated with 200 mL of SWFI. Each test article was aseptically transferred to a sterile bag. The inside of the test article bag was rinsed with 50 ml of sterile Fluid D and transferred to the same sterile bag, mixed for 30 seconds and two equal aliquots were made for t=0 and t=4 time point testing. From the t=0 time point, four (4) equal aliquots were made from the 120 ml recovered. One (1) aliquot was heat shocked at 80±2° C.

for 15±1 minutes, then allowed to cool down. Following membrane filtration (4×24 ml) and rinse with 10 ml of Phosphate Buffered Saline (PBS), the filters (one per plate) were aseptically placed onto Trypticase Soy Agar (TSA) plates and incubated aerobically and anaerobically at 30-35° C. for 5 days, and onto Sabouraud Dextrose Agar (SDA) plates and incubated aerobically at 20-25° C. for 5 days. Each control article, frozen plasma (21 units) was thawed prior to testing. 15 ml from each control article was transferred aseptically to a sterile bag and 85 ml of sterile Fluid D was added to the bag and mixed for 30 seconds to be tested for t=O time point. Four (4) equal aliquots were made from 96 ml recovered. One (1) aliquot was heat shocked at 80±2° C. for 15±1 minutes, then allowed to cool down. Following membrane filtration (4×24 ml) and rinse with 10 mL of Phosphate Buffered Saline (PBS), the filters (one per plate) were aseptically placed onto Trypticase Soy Agar (TSA) plates and incubated aerobically and anaerobically at 30-35° C. for 5 days, and onto Sabouraud Dextrose Agar (SDA) plates and incubated aerobically at 20-25° C. for 5 days. Samples of PBS and Fluid D, which served as negative controls, were similarly filtered and incubated. Colony Forming Units (CFU) were determined for each filter. The remaining control articles were stored at room temperature for 4 hours and refrozen to be stored as retain samples. The study and its design employed methodology to minimize uncertainty of measurement and control of bias for data collection and analysis.

During this study the upper (inlet) and lower (exhaust) ports of the disposable were open to the atmosphere of an unclassified environment in which BSL2 controls were utilized for 17-30 minutes. The 21 reconstituted previously spray dried samples were tested at time 0 to 30 minutes (t=0) and time 4 to 4.5 hours (t=4) for the following: Aerobic bacteria, Anaerobic bacteria, Heat Shocked bacterial and Yeast and Mold.

Bioburden was evaluated on the units rehydrated by aseptically spiking and rehydrating with SWFI, in a routine (unclassified) lab environment. The inlet port and the exhaust port of the disposable were open for 17-30 minutes during this study, replicating (approximating) normal use conditions. The rehydrated units were stored at room temperature for 4 hours to assess product integrity and safety during the rehydrated unit's shelf life of 4 hours per AABB Circular of Information. The same rehydrated unit was tested at t=0 (Table 54) and t=4 hours (Table 55) with seven (7) samples spray dried on three (3) different dryers (n=21).

TABLE 54

Bioburden Results (Frozen Control Plasma, t = 0)

| | CFU/Plate | | | |
|---|---|---|---|---|
| Sample | TSA (Aerobic) | TSA (Anaerobic) | TSA (Heat Shocked) | SDA (Yeast and Mold) |
| 3397 | NOC | NOC | NOC | NOC |
| 3398 | NOC | NOC | NOC | NOC |
| 3399 | NOC | NOC | NOC | NOC |
| 3400 | NOC | NOC | NOC | NOC |
| 3401 | NOC | NOC | NOC | NOC |
| 3402 | NOC | NOC | NOC | NOC |
| 3403 | NOC | NOC | NOC | NOC |
| 3404 | NOC | NOC | NOC | NOC |
| 3405 | NOC | NOC | NOC | NOC |
| 3406 | NOC | NOC | NOC | NOC |
| 3407 | NOC | NOC | NOC | NOC |
| 3408 | NOC | NOC | NOC | NOC |
| 3409 | NOC | NOC | NOC | NOC |
| 3410 | NOC | NOC | NOC | NOC |
| 3412 | NOC | NOC | NOC | NOC |
| 3411 | 1 Yellow CI RA | NOC | NOC | NOC |
| 3413 | 1 Cream CI FL | NOC | NOC | NOC |
| 3414 | NOC | NOC | NOC | NOC |
| 3415 | NOC | NOC | NOC | NOC |
| 3416 | NOC | NOC | NOC | NOC |
| 3417 | NOC | NOC | NOC | NOC |
| Average CFU/Plate | 0 | 0 | 0 | 0 |
| CFU/Device | <1 | <1 | <1 | <1 |
| CFU/ml | <1 | <1 | <1 | <1 |

CFU = Colony Forming Units
CI = Circular,
FL = Flat,
RA = Raised
NOC: No Observable Colonies = 0 = < 1 for calculations
Average CFU/Plate = Sum of CFU/Plate + Number of Plates
CFU/Device = Average CFU/Plate × Total Volume (100 ml)/Volume filtered (24 ml)
CFU/ml = Average CFU/Plate + Volume Filtered (24 ml)

TABLE 55

Bioburden results for Units Immediately after rehydration (t = 0)
Bioburden Results (Rehydrated Plasma, t = 0)

| | CFU/Plate | | | |
|---|---|---|---|---|
| Sample | TSA (Aerobic) | TSA (Anaerobic) | TSA (Heat Shocked) | SDA (Yeast and Mold) |
| 3397 | NOC | NOC | NOC | NOC |
| 3398 | NOC | NOC | NOC | NOC |
| 3399 | NOC | NOC | NOC | NOC |

TABLE 55-continued

Bioburden results for Units Immediately after rehydration (t = 0)
Bioburden Results (Rehydrated Plasma, t = 0)

| Sample | CFU/Plate | | | |
|---|---|---|---|---|
| | TSA (Aerobic) | TSA (Anaerobic) | TSA (Heat Shocked) | SDA (Yeast and Mold) |
| 3400 | NOC | NOC | NOC | NOC |
| 3401 | NOC | NOC | NOC | NOC |
| 3402 | NOC | NOC | NOC | NOC |
| 3403 | NOC | NOC | NOC | NOC |
| 3404 | NOC | NOC | NOC | NOC |
| 3405 | NOC | NOC | NOC | NOC |
| 3406 | NOC | NOC | NOC | NOC |
| 3407 | NOC | NOC | NOC | NOC |
| 3408 | NOC | NOC | NOC | NOC |
| 3409 | NOC | NOC | NOC | NOC |
| 3410 | NOC | NOC | NOC | NOC |
| 3412 | NOC | NOC | NOC | NOC |
| 3411 | NOC | NOC | NOC | NOC |
| 3413 | NOC | NOC | NOC | NOC |
| 3414 | NOC | NOC | NOC | NOC |
| 3415 | NOC | NOC | NOC | NOC |
| 3416 | NOC | NOC | NOC | NOC |
| 3417 | NOC | NOC | NOC | NOC |
| Average CFU/Plate | 0 | 0 | 0 | 0 |
| CFU/Device | <1 | <1 | <1 | <1 |
| CFU/ml | <1 | <1 | <1 | <1 |

CFU = Colony Forming Units
NOC: No Observable Colonies = 0 = < 1 for calculations
Average CFU/Plate = Sum of CFU/Plate + Number of Plates
CFU/Device = Average CFU/Plate × Total Volume (125 ml) Volume filtered (30 ml)
CFU/ml = Average CFU/Plate + Volume Filtered (30 ml)

TABLE 56

Bioburden Results for FrontlineODP Units 4 hours after Rehydration (t = 4 hours)
Bioburden Results (Rehydrated Plasma, t = 4)

| Sample | CFU/Plate | | | |
|---|---|---|---|---|
| | TSA (Aerobic) | TSA (Anaerobic) | TSA (Heat Shocked) | SDA (Yeast and Mold) |
| 3397 | NOC | NOC | NOC | NOC |
| 3398 | NOC | NOC | NOC | NOC |
| 3399 | NOC | NOC | NOC | NOC |
| 3400 | NOC | NOC | NOC | NOC |
| 3401 | NOC | NOC | NOC | NOC |
| 3402 | NOC | NOC | NOC | NOC |
| 3403 | NOC | NOC | NOC | NOC |
| 3404 | NOC | NOC | NOC | NOC |
| 3405 | NOC | NOC | NOC | NOC |
| 3406 | NOC | NOC | NOC | NOC |
| 3407 | NOC | NOC | NOC | NOC |
| 3408 | NOC | NOC | NOC | NOC |
| 3409 | NOC | NOC | NOC | NOC |
| 3410 | NOC | NOC | NOC | NOC |
| 3411 | NOC | NOC | NOC | NOC |
| 3412 | NOC | NOC | NOC | NOC |
| 3413 | NOC | NOC | NOC | NOC |
| 3414 | NOC | NOC | NOC | NOC |
| 3415 | NOC | NOC | NOC | NOC |
| 3416 | NOC | NOC | NOC | NOC |
| 3417 | NOC | NOC | NOC | NOC |
| Average CFU/Plate | 0 | 0 | 0 | 0 |

TABLE 56-continued

Bioburden Results for FrontlineODP Units 4 hours after Rehydration (t = 4 hours)
Bioburden Results (Rehydrated Plasma, t = 4)

| Sample | CFU/Plate | | | |
|---|---|---|---|---|
| | TSA (Aerobic) | TSA (Anaerobic) | TSA (Heat Shocked) | SDA (Yeast and Mold) |
| CFU/Device | <1 | <1 | <1 | <1 |
| CFU/ml | <1 | <1 | <1 | <1 |

CFU = Colony Forming Units
NOC: No Observable Colonies = 0 = <1 for calculations
Average CFU/Plate = Sum of CFU/Plate + Number of Plates
CFU/Device = Average CFU/Plate × Total Volume (125 ml) Volume filtered (30 ml)
CFU/ml = Average CFU/Plate + Volume Filtered (30 ml)

Conclusion:

The average number of CFU/Plate for rehydrated plasma was 0 (Aerobic), 0 (Anaerobic), 0 (Heat Shocked), and 0 (Yeast and Mold). The total CFU/Device was <1. The total CFU/ml was <1. The average number of CFU/Plate for frozen plasma was 0.1 (Aerobic), 0 (Anaerobic), 0 (Heat Shocked), and 0 (Yeast and Mold). The CFU/Device was <1. The total CFU/Device was <1. The total CFU/ml was <1. The PBS and Fluid D plates (negative controls) showed no growth.

As can be seen from the tables above, no colony forming units of bacteria were found in rehydrated plasma after use of the spray drying system of the present invention in an unclassified environment. Notably, rehydrated previously spray dried samples 3411 and 3412 showed no observable colonies of any of the four groups of pathogens tested. However, prior to spray drying, the control for sample 3411 showed one colony of aerobic pathogen identified as "yellow, circular, raised" and sample 3412 showed one colony of aerobic pathogen identified as "cream, circular, flat." The spray dried system and process of the present invention inhibited the growth of these pathogens.

The bioburden results of units tested 4 hours after rehydration are comparable to the same samples tested immediately after rehydration. The results support the product integrity and safety when rehydrated in an unclassified lab or similar environment are similar to the rehydration and administration environment for the product and also demonstrates consistency of the manufacturing process across three (3) different Frontline Dryers in maintaining product integrity.

Example 36: Rapid Spray Drying Time Duration 375 samples were spray dried using the methods and spray drying system described herein. Below is a summary of spray dry run times performed for 375 runs.

n=375 runs

TABLE 57 n = 375 runs

| | Run duration [minutes] | Drying duration [minutes] | Total mass processed [grams] |
|---|---|---|---|
| Ave | 37.09 | 24.91 | 324 |
| Min | 32.64 | 22.61 | 298 |
| Max | 41.86 | 27.72 | 340 |
| Std Dev | 2.67 | 1.21 | 4.08 |

TABLE 57-continued

| n = 375 runs | Run duration [minutes] | Drying duration [minutes] | Total mass processed [grams] |
|---|---|---|---|
| Ave − 2SD | 31.75 | 22.48 | 316 |
| Ave + 2SD | 42.42 | 27.33 | 332 |

The FrontlineODP Unit manufacturing process includes a pre and post spray dry integrity check of the Plasma Drying Chamber (PDC) and the spray drying of the plasma. The Drying Duration is defined as the time taken to spray dry a unit of plasma. The Run Duration is defined as the total time for the pre and post integrity check including the Drying Duration. The inlet temperature of drying gas was at 114° C. for these runs and averages 65-70° C. in the plasma drying chamber of the disposable. The average Run Duration run is 37.09 minutes. The interior of disposable including the plenum interior, the upper or baffle filter, the interior of the drying chamber and the capture filter receive a continuous flow for drying gas at temperatures (approximately 65-85° C.) and time e.g., for 30-45 minutes (e.g., 32-41 minutes. For droplets that are dried during spray drying process, the dried particles are subjected to heated drying gas for a time period ranging from 15 seconds to about 31 minutes. Accordingly, the plasma droplets are exposed to drying gas at temperatures (approximately 65-85° C.) and time (approximately 15 seconds-28 minutes) and such conditions are expected to reduce pathogens since they are pasteurizing conditions for salmonella. The time and temperatures of the spray drying process of the present invention provides time and temperatures to inhibit the growth and/or proliferation of pathogens that may enter or be present in the interior of the disposable or onto either the baffle filter or capture filter.

The current invention described demonstrates rapid drying of plasma units (298-340 mL) within 22-28 minutes.

Example 37: Rough Storage

Scope:

Shelf life study of spray dry plasma units (also referred to herein as “Frontline ODP” Units) is to be performed. This study is to assess 6 months of storage in various “emergency response” type environments (e.g., ambulances stored in bay with and without air condition) and in emergency response bags (e.g., back packs and medical bags (e.g., PELICAN™ bags).

ODP units were manufactured from pooled plasma frozen within 24 hours (PF24) containing citrate phosphate dextrose (CPD) anticoagulant on the system of the present invention. Frontline ODP Units were compared to paired control plasma at various storage conditions and time points listed in the below table. Control ODP plasma is OPD stored for the same length of time at refrigeration. Pooled plasma was manufactured for each storage condition. Five (5) FrontlineODP Units were manufactured from pooled PF24 plasma. Evaluate 2 pools are separated as follows. 1 unit for control, 2 units (N=2) for trucks stored in a controlled temperature, and 2 units (N=2) for trucks stored in an uncontrolled temperature. One unit from the controlled group and one unit from the uncontrolled group will be stored in a backpack with a data logger, and one unit from the controlled group and one unit from the uncontrolled group will be stored in a PELICAN™/medical bag with a data logger. FrontlineODP Units will be stored for 6 months and will span through summer and winter seasons.

Definitions:

Anticoagulant Citrate Phosphate Dextrose Solution (CPD)—a sterile solution of Citric Acid, Sodium Citrate, Monobasic Sodium Phosphate, and Dextrose in Water for Injection. It contains, in each 1000 ml, NLT 2.11 g and NMT 2.33 g of monobasic sodium phosphate ($NaH_2PO_4*H_2O$); NLT 24.22 g and NMT 26.78 g of dextrose ($C_6H_{12}O_6*H_2O$); NLT 19.16 g and NMT 21.18 g of total citrate, expressed as anhydrous citric acid ($C_6H_8O_7$); and NLT 6.21 g and NMT 6.86 g of Sodium (Na). It contains no antimicrobial preservatives.

Plasma frozen within 24 hours—is plasma frozen within 24 hours after phlebotomy is prepared from a whole blood or apheresis collection. The anticoagulant solution used and the component volume are indicated on the label.

Control Plasma—an aliquot of starting plasma frozen at the time of spray drying intended to be tested in parallel with Frontline ODP Unit as a paired control.

Control ODP Plasma—ODP stored for the same length of time at refrigeration.

Methods and Materials

Materials:

After storage for the prescribed times and conditions described below each dried unit was subjected to testing as described in the table below. Assays were conducted in accordance with the manufacturer’s instructions.

TABLE 58

Stability tests:

| Assay | Instrument/Reagent Manufacturer |
|---|---|
| pH | Accumet AAB150 Fisher Scientific Danvers Ma USA |
| Total Protein | Selectra ProM EliTech Group Paris France |
| FV activity | ACL TOP 700 Instrumentation Laboratories Boston |
| FVII activity | ACL TOP 700 Instrumentation Laboratories Boston |
| FVIII activity | ACL TOP 700 Instrumentation Laboratories Boston |
| FIX activity | ACL TOP 700 Instrumentation Laboratories Boston |
| FX activity | ACL TOP 700 Instrumentation Laboratories Boston |
| FXI activity | ACL TOP 700 Instrumentation Laboratories Boston |
| FXIII antigen | ACL TOP 700 Instrumentation Laboratories Boston |
| Fibrinogen (QFA) | ACL TOP 700 Instrumentation Laboratories Boston |
| Thrombin Time (TT) | ACL TOP 700 Instrumentation Laboratories Boston |
| aPTT | ACL TOP 700 Instrumentation Laboratories Boston |
| PT | ACL TOP 700 Instrumentation Laboratories Boston |
| Protein C activity (PC) | ACL TOP 700 Instrumentation Laboratories Boston |
| Protein S activity (PS) | ACL TOP 700 Instrumentation Laboratories Boston |
| Anti thrombin III activity (AT LIQ) | ACL TOP 700 Instrumentation Laboratories Boston MA USA |

TABLE 58-continued

| Stability tests: | |
|---|---|
| Assay | Instrument/Reagent Manufacturer |
| vWF Ag | ACL TOP 700 Instrumentation Laboratories Boston |
| Plasmin Inhibitor | ACL TOP 700 Instrumentation Laboratories Boston |
| Plasminogen | ACL TOP 700 Instrumentation Laboratories Boston |
| VWF: RCo | BCS XP Siemens Healthineers Boston MA USA |
| FXIII activity | BCS XP Siemens Healthineers Boston MA USA |
| Prothrombin Fragment 1+2 (PF1+2) | ELISA Siemens Healthineers Boston MA USA |
| Thrombin Anti-Thrombin (TAT) | ELISA Siemens Healthineers Boston MA USA |
| C5a | ELISA |

Methods:

25) Pool 5 units of PF24 into a 3000 mL empty container to obtain no less than 1,500 mL of pooled plasma. 2 pools in total (1 for controlled temperature, 1 for uncontrolled temperature). N=2 at each time point.

26) Assign test batch numbers to pools.

27) Store thawed PF24 at 1-6° C. until ready to pretreat.

i. Each pool will be split into five plasma pretreatment containers and identified with a sub-batch (A, B, C, D, E). The remaining PF24 from the pool will be used to prepare at least 2 aliquots of control plasma (~4 mL) in cyro-vials.

ii. Each sub-batch is pretreated by transferring 266 mL of plasma into the plasma pretreatment container. The pretreated plasma should be processed on the Frontline Dryer within 4 hours of pretreatment.

28) Manufacture pooled Frontline ODP Units (n=5) on the Frontline Dryers.

29) Record the Frontline Dryer Number, Date, Time, and Operator's initials.

30) Store the paired control aliquots prepared in step 3 are frozen at the same approximate time as ODP manufacture.

31) Package spray dried plasma of each Frontline ODP Unit in Frontline Sealer

32) Place a Frontline ODP Unit and desiccant into the overwrap pouch. Seal the overwrap pouch above the 1$^{st}$ tear notches with the overwrap sealer.

33) Ship FrontlineODP Units to storage site at ambient conditions.

34) Each unit includes a temperature data logger (Model No EL-USB-1-LCD_to collect temperature readings every 30 minutes during the duration of the study.

Two pools of plasma were divided into three groups 1) a control (ODP Unit #1), t=0, (units P1-1, P2-1), 2) plasma stored in trucks having controlled temperature (units P1-2, P2-2 (backpack), P1-3, P2-3 (PELICAN™ bags)); and 3) plasma stored in trucks having uncontrolled temperatures (units P1-4, P2-4 (backpack), P1-5, P2-5 (PELICAN™ bags)). Group 2 and 3 each will have 4 units each, two stored in backpacks and two stored in PELICAN™ bags. All units stored in backpacks or PELICAN™ bags have a data logger. See table below.

TABLE 59

Pooled Spray Dried Units Storage - (P1 and P2 indicate Pool 1 or 2. −1 through −5 indicate the 5 FrontlineODP Units in each pool.) Units

| | | | |
|---|---|---|---|
| Pool Plasma (2 pools) | Control" ODP Unit #1 Test at Velico at t = 0 (P1-1, P2-1) | | |
| | Trucks stored in controlled temperature | ODP Unit #2 (P1-2, P2-2) | Backpack + data logger |
| | | ODP Unit #3 (P1-3, P2-3 | Pelican Bag + data logger |
| | Trucks stored in uncontrolled temperature | ODP Unit #4 (P1--4, P2-4) | Backpack + data logger |
| | | ODP Unit #5 (P1-5, P2-5) | Backpack + data logger |

TABLE 60

| A: Pooled FrontlineODP Storage Condition | | |
|---|---|---|
| Storage Condition | Duration | Number of FrontlineODP Units |
| ODP Control | 6 months | 2 |
| In backpack, in trucks stored in a controlled temperature environment (with Air Condition) | 6 months | 2 |
| In PELICAN ™ M case, in trucks stored in a controlled temperature environment (with Air Condition) | 6 months | 2 |
| In backpack, in trucks stored in an uncontrolled temperature environment | 6 months | 2 |

TABLE 60-continued

| A: Pooled FrontlineODP Storage Condition | | |
|---|---|---|
| Storage Condition | Duration | Number of FrontlineODP Units |
| In PELICAN ™ M case, in trucks stored in an uncontrolled temperature environment | 6 months | 2 |

Testing

Data from the data logger was recorded every 30 minutes throughout the duration of the time points. Samples were retrieved from storage condition at the appropriate timepoint and rehydrated after the storage duration indicated had been met.

The corresponding control plasma aliquot was simultaneously thawed with the rehydration of 5 pooled FrontlineODP units.

Stability testing was completed as described above. All FrontlineODP Unit testing was conducted in parallel with control plasma aliquots.

Results

When obtained, the results of the above-described testing of shelf life of the dried plasma of the present invention will be described in the tables below.

TABLE 61

Stability for pooled FrontlineODP Units stored at various storage conditions for 6 months.

| | | ODP Control | | Backpack (Air Condition) | | |
|---|---|---|---|---|---|---|
| | Clinical Reference Range | CP Mean ± SD | ODP Mean ± SD | CP Mean ± SD | ODP Mean ± SD | % Change compared to t = 0 |
| aPTT (s) | (22-35) | | | | | |
| PT (s) | (10-14) | | | | | |
| INR | (0.9-1.1) | | | | | |
| TT (s) | (14.5-20.5) | | | | | |
| Fib (mg/dL) | (150-400) | | | | | |
| FV Act (%) | (50-200) | | | | | |
| FVII Act (%) | (50-200) | | | | | |
| FVIII Act (%) | (50-200) | | | | | |
| FIX Act (%) | (50-200) | | | | | |
| FX Act (%) | (50-200) | | | | | |
| FXI Act (%) | (50-200) | | | | | |
| FXIII Act (%) | (57-192) | | | | | |
| FXIII Ant (%) | (75.2-154.8) | | | | | |
| PC Act (%) | (75-150) | | | | | |
| PS Act (%) | (60-150) | | | | | |
| AT III Act (%) | (80-120) | | | | | |
| PLG (%) | (70-150) | | | | | |
| PI (%) | (85-156) | | | | | |
| vWF:RCo (% or IU/dL) | (50-200) | | | | | |
| vWF Ant (% or IU/dL) | (50-200) | | | | | |
| TAT (μg/L) | (0-4) | | | | | |
| PF1 + 2 (pmol/L) | (91-137) | | | | | |
| C5a (ng/ml) | (4.7-9.5) | | | | | |

| | | PELICAN ™ Case (Air Condition) | | | Backpack (Uncontrolled) | | |
|---|---|---|---|---|---|---|---|
| | Clinical Reference Range | CP Mean ± SD | ODP Mean ± SD | % Change compared to t = 0 | CP Mean ± SD | ODP Mean ± SD | % Change compared to t = 0 |
| aPTT (s) | (22-35) | | | | | | |
| PT (s) | (10-14) | | | | | | |
| INR | (0.9-1.1) | | | | | | |
| TT (s) | (14.5-20.5) | | | | | | |
| Fib (mg/dL) | (150-400) | | | | | | |
| FV Act (%) | (50-200) | | | | | | |
| FVII Act (%) | (50-200) | | | | | | |
| FVIII Act (%) | (50-200) | | | | | | |
| FIX Act (%) | (50-200) | | | | | | |
| FX Act (%) | (50-200) | | | | | | |
| FXI Act (%) | (50-200) | | | | | | |
| FXIII Act (%) | (57-192) | | | | | | |
| FXIII Ant (%) | (75.2-154.8) | | | | | | |
| PC Act (%) | (75-150) | | | | | | |
| PS Act (%) | (60-150) | | | | | | |
| AT III Act (%) | (80-120) | | | | | | |

TABLE 61-continued

Stability for pooled FrontlineODP Units stored at various storage conditions for 6 months.

| | |
|---|---|
| PLG (%) | (70-150) |
| PI (%) | (85-156) |
| vWF:RCo (% or IU/dL) | (50-200) |
| vWF Ant (% or IU/dL) | (50-200) |
| TAT (μg/L) | (0-4) |
| PF1 + 2 (pmol/L) | (91-137) |
| C5a (ng/mL) | (4.7-9.5) |

| | | PELICAN ™ (Uncontrolled) | | |
|---|---|---|---|---|
| | Clinical Reference Range | CP Mean ± SD | ODP Mean ± SD | % Change compared to t = 0 |
| aPTT (s) | (22-35) | | | |
| PT (s) | (10-14) | | | |
| INR | (0.9-1.1) | | | |
| TT (s) | (14.5-20.5) | | | |
| Fib (mg/dL) | (150-400) | | | |
| FV Act (%) | (50-200) | | | |
| FVII Act (%) | (50-200) | | | |
| FVIII Act (%) | (50-200) | | | |
| FIX Act (%) | (50-200) | | | |
| FX Act (%) | (50-200) | | | |
| FXI Act (%) | (50-200) | | | |
| FXIII Act (%) | (57-192) | | | |
| FXIII Ant (%) | (75.2-154.8) | | | |
| PC Act (%) | (75-150) | | | |
| PS Act (%) | (60-150) | | | |
| AT III Act (%) | (80-120) | | | |
| PLG (%) | (70-150) | | | |
| PI (%) | (85-156) | | | |
| vWF:RCo (% or IU/dL) | (50-200) | | | |
| vWF Ant (% or IU/dL) | (50-200) | | | |
| TAT (μg/L) | (0-4) | | | |
| PF1 + 2 (pmol/L) | (91-137) | | | |
| C5a (ng/ml) | (4.7-9.5) | | | |

| | Clinical | ODP Control | | Backpack (Air Condition) | | PELICAN ™ Case (Air Condition) | |
|---|---|---|---|---|---|---|---|
| | Reference range | CP Mean ± SD | ODP Mean ± SD | CP Mean ± SD | ODP Mean ± SD | CP Mean ± SD | ODP Mean ± SD |
| pH | (7.35-7.45) | | | | | | |
| Protein (mg/ml) | (6-8.3) | | | | | | |
| Osmolality (mOsm/kg) | ( >240) | | | | | | |

| | Clinical | Backpack (Uncontrolled | | PELICAN ™ Case (Uncontrolled) | |
|---|---|---|---|---|---|
| | Reference range | CP Mean ± SD | ODP Mean ± SD | CP Mean ± SD | ODP Mean ± SD |
| pH | (7.35-7.45) | | | | |
| Protein (mg/ml) | (6-8.3) | | | | |
| Osmolality (mOsm/kg) | ( >240) | | | | |

vWF:RCo is expected to be below the normal reference range. However, despite decreased levels of vWF:RCo, it is expected that vWF will be functional and perform well in clot formation. It is expected that functional clot formation assays including data from Bioflux testing, Thromboelastography TEG study and a thrombin generation (calibrated automated thrombogram (CAT) study will demonstrate effective clot formation similar to that of fresh frozen plasma including measures of clot time, clot rate, clot strength, etc. It is expected that even though the multimer vWF may be sheared into smaller polypeptides, the clotting function of vWF will remain intact. vWF:RCo assay measures higher molecular weight multimer TAT is expected to be outside of the clinical reference range but is not indicative of activation.

PF1+2 is expected to be outside of the clinical reference range but manufacturer reports that plasma stored longer than 6 months at −60° C. is not suitable for the assay.

C5a is expected to be within the reference range reported for apheresed plasma of 4.9-74 ng/mL. The reconstituted dried plasma of the present invention from this experiment is expected to be comparable to starting plasma (e.g., PF24, FFP, PF24RT24, NFP, thawed plasma and liquid plasma) and have clotting factor levels of concentration and activity that are essentially the same as FFP.

Example 38: Evaluation for the Safety of Spray Dried Plasma in a Multidose Randomized Cohort Study Compared with Plasma Frozen within 24 Hours of Collection (PF24)

Scope: The primary objective of this study was to assess the safety of autologous single infusions of reconstituted previously spray dried plasma or Frontline ODP (on demand plasma) units at increasing doses of 1 unit (approximately 200 mL; Cohort 1), 2 units (approximately 400 mL; Cohort 2), and 4 units (approximately 800 mL; Cohort 3) in healthy subjects.

The plasma was spray dried using the spray dry system and disposable described and shown herein.

Additionally, the study was designed:

a. To assess the safety of 4 FrontlineODP unit infusions (approximately 800 mL) compared with infusion of the same dose of autologous plasma refrigerated within 8 hours of collection and frozen within 24 hours of collection (PF24)
b. Changes in coagulation factors after infusion of 4 units of FrontlineODP compared with infusion of the same dose of PF24

This clinical study is currently underway with Cohort 1 completed and Cohort 2 and Cohort 3 in progress. Due to confidentiality concerns, data is not being disclosed until the study is completed. Accordingly, this example describes the results that we expect to obtain.

Methods a. Clinical research sites that are being used:
    i. Hoxworth Blood Center, University of Cincinnati
    ii. Versiti Blood Center of Wisconsin
    iii. Spaulding Clinical Research, LLC
b. The appropriate number of subjects will be screened to accrue 24 subjects. Subjects were chosen according to the following inclusion and exclusion criteria:

TABLE 62

| Males and nonpregnant/nonbreastfeeding females | | |
|---|---|---|
| Inclusion criteria: | 1. | Males and nonpregnant/nonbreastfeeding females |
| | 2. | For females, a minimum weight of 140 pounds and maximum weight of 220 pounds; for males, a minimum weight of 140 pounds and a maximum weight of 250 pounds |
| | 3. | Subject is 18 to 65 years of age, inclusive. |
| | 4. | Subject self-reports that he or she feels well and healthy. |
| | 5. | Subject scores ≥35 on the Duke Activity Status Index |
| | 6. | Subject is able to donate a unit of plasma by plasmapheresis based on the Association for the Advancement of Blood & Biotherapies (AABB) Donor History Questionnaire with modifications indicated: subjects with history of travel, which puts them at risk for Creutzfeldt-Jakob Disease ormalaria, are eligible to participate. |
| | 7. | Subject has read the educational materials on donating blood and has had his or her questions answered. |
| | 8. | Subject is able and willing to provide written informed consent. |
| | 9. | Females of childbearing potential should either be surgically sterile (hysterectomy or tubal ligation) or should use a highly effective medically accepted contraceptive regimen. Highly effective methods of birth control are defined as those which result in a low failure rate (ie, less than 1% per year) when used consistently and correctly such as implants, injectables, combined oral contraceptives, some intrauterine devices, sexual abstinence, condoms with spermicide, or vasectomized partner. |
| | Note: | Subjects should not become pregnant for at least 3 months after the last infusion of study product. |
| | 10. | All females must have a negative urine or serum pregnancy test. |
| | 11. | Subject understands the English language |
| Exclusion criteria: | 1. | Subject has known liver, kidney, cardiovascular, neurologic, gastrointestinal, blood, endocrine/metabolic, autoimmune, or pulmonary disease, or treated or untreated hypertension. |
| | 2. | Subject has cancer of any kind, under treatment or resolved. |
| | 3. | Subject has known or past coagulopathy conditions. |
| | 4. | Subject has any conditions, uses medications, etc. on the AABB medical deferral list. |
| | 5. | Subject has a history of asthma (defined as use of a prescribed daily asthma controller medication or required asthma medication in the past 2 weeks) |
| | 6. | Subject has a previous diagnosis of stroke, deep vein thrombosis (DVT), venous or arterial thrombosis, blood clots, or transient ischemic attack. |
| | 7. | Subject has a family history of venous or arterial thrombosis before the age of 50 years in first degree relatives (ie, biological parents, full siblings, or children) |
| | 8. | Subject has a D-dimer test result ≥0.5 FEU/mL. |
| | 9. | Subject has a recent (within 1 year of Screening) history of an abnormal electrocardiogram of clinical significance as determined by the site principal investigator (PI). |
| | 10. | Subject has known HIV or AIDS-related illness or received a positive test result for HIV infection. |

TABLE 62-continued

| Males and nonpregnant/nonbreastfeeding females |
|---|
| 11. Subject has a positive test result for hepatitis B virus, hepatitis C virus, or human T-cell lymphotropic virus. |
| 12. Subject has a history of significant treated or untreated mental health issues. |
| 13. Subject is currently taking an antibiotic or another medication for an infection. |
| 14. Subject has received aspirin or other platelet-inhibiting agents within 14 days of study donation and infusion visits. Prior and concomitant medication information will be recorded beginning 30 days before enrollment through the final follow-up visit. |
| 15. Subject is currently using any medications for anticoagulant therapy. |
| 16. Subject has used clotting factor concentrates(s) (eg, FVIIa) |
| 17. Subject has received blood or blood products within the past 12 months. |
| 18. Subject has had concurrent headache and fever in the past week |
| 19. Subject has systolic blood pressure (current) greater than 140 mm Hg. |
| 20. Subject has diastolic blood pressure (current) greater than 90 mm Hg. |
| 21. Subject has an oral temperature greater than 100° F. |
| 22. Subject has known hematocrit ≤39% for male donors and ≤38% for female donors. |
| 23. Subject has a positive DAT result. |
| 24. Subject has received any investigational agent within 1 month before treatment infusion for this study. |
| 25. Subject is participating in any phase of any other investigational studies while participating in this study. |
| 26. Subject is unwilling or unable to comply with the requirements of this protocol, including the presence of any condition (physical, mental, or social) that is likely to affect the subject's return for follow-up visits as scheduled. |
| 27. Subject has other unspecified reasons that, in the opinion of the site PI, make the subject unsuitable for enrollment. |
| 28. Subject is institutionalized because of legal or regulatory order. |
| 29. Subject has a positive urine drug screen. |

This study in healthy volunteers was designed to assess the safety of infusing ascending doses of reconstituted autologous FrontlineODP in 1, 2, and 4 fixed-dose units. Subjects in Cohort 1 (n=6) received 1 unit of FrontlineODP (Arm 1), which is approximately 200 mL. Subjects in Cohort 2 (n=6) received 2 FrontlineODP units (Arm 2) (total volume of approximately 400 mL). Subjects in Cohort 3 (n=12) were assigned to receive 4 FrontlineODP units and 4 units of PF24 (Arms 3 and 4), each of which has a total volume of approximately 800 mL, in random order. Subjects were assigned to these cohorts beginning with the lowest dose in Cohort 1.

In the absence of Treatment emergent adverse events (TEAEs), Serious Adverse Event (SAEs), or the implementation of protocol stopping rules in Cohort 1, and with site PI documentation and independent medical monitor (IMM) review, data monitoring committee recommendation, and sponsor approval, subjects assigned to Cohort 2 will receive an infusion with an increased dose of 2 units. The IMM is a recognized transfusion expert who is independent of the clinical research sites and Applicant.

In the absence of TEAEs, SAEs, or the implementation of protocol stopping rules in Cohort 2 subjects, and with site PI documentation and IMM review, data monitoring committee recommendation, and sponsor approval, infusions will proceed in Cohort 3. Cohort 3 is designed as a randomized, controlled, crossover infusion of 4 units of FrontlineODP (approximately 800 mL) and 4 units of PF24 (approximately 800 mL) at separate visits. Subjects will be randomly assigned to a specific infusion schedule of either 4 units of FrontlineODP or 4 units of PF24 at the first infusion followed by infusion with the alternate study product at the second visit. Crossover of FrontlineODP and PF24 enables comparison of infusion safety and select coagulation factor recoveries within the same subject between FrontlineODP and PF24 at this higher dose. The FrontlineODP and PF24 study products in all cohorts were obtained solely from plasmapheresis donations. In Cohort 3, a 2-week period (maximum of 6 weeks) between infusions is required regardless of study arm.

Concurrent infusions will not take place across cohorts, ensuring infusions at the next higher dose do not begin until all subject infusions at the previous dose have been completed.

The dosage and route of administration for the study was FrontlineODP, 1 to 4 units (200 mL each), administered intravenously. Reference product, dosage and route of administration PF24, 4 units (200 mL each), administered intravenously.

In Cohorts 1 and 2, the infusion occurs on Day 1 and the duration of study participation for each subject was approximately 3 months, including Screening. In Cohort 3, the infusions will occur on Days 1 and 15 and the duration of study participation for each subject is approximately 4 months, including Screening.

Criteria for Evaluation is as Follows:

Safety: If any of the following events occur, administration of the study product will be paused until a thorough review of the events is undertaken by the site Principal Investigator (PI), local institutional review board, IMM, and the sponsor's safety office. The study will be resumed upon agreement by the site PI, IMM, and sponsor's representative. The following circumstances will be considered for all subjects throughout the study to assess continuation of the study:

a. An SAE that is determined to be possibly, probably, or definitely related to the study product
b. An adverse event (AE) related to the study product that the site PI, sponsor representative, and the IMM agree jeopardizes the subject's health or safety c. An AE related to the study product that requires medical or surgical intervention to prevent occurrence of an SAE d. A postinfusion, abnormal coagulation function assay result, and/or Postinfusion development of hemolysis or Deep Vein Thrombosis (DVT), cardiac ischemia, or pulmonary embolism. DVT will be determined according to the Institute for Clinical Systems Improvement Health Care Guideline: Venous Thromboembolism Diagnosis and Treatment (includes assessment of D-dimer results and Wells Criteria ≥2).

If any of these conditions occur, the study will be paused. The decisions made by the site PI and IMM regarding the review of data from the subjects in each cohort will be documented. As of the filing date of this patent application, no adverse events have been reported.

The statistical methodology used for this study is as follows. Safety was be assessed by evaluating vital signs, clinical laboratory tests during and after infusion, and TEAEs. No formal statistical hypotheses were tested. Demographics, medical history, and safety data was summarized using standard descriptive statistics. For quantitative variables, summaries included the sample size, mean, median, standard deviation, minimum, and maximum. For categorical variables, summaries included the frequency (eg, number and percentage) of subjects for each outcome.

Additionally, for Cohort 3 data, descriptive statistics will be presented by treatment for the change between Baseline and each time point after the start of the infusion, where appropriate, of the safety endpoint measured. Additional summaries (such as by period or sequence) will be included if deemed necessary. Plots of the mean and SD values for particular assessments by time point and treatment, will be included. Color coded spaghetti plots displaying the respective individual subject data by time point and treatment will also be provided.

Definitions for secondary objectives:

a. Change from Baseline: Postbaseline value—baseline value b. Body mass index (kg/$m^2$): weight (kg)/height (m)2

Safety: All safety data will be presented in data listings. Treatment emergent AEs will be summarized by treatment and overall, as follows: summary of TEAEs, TEAEs by relationship, TEAEs by severity, and TEAEs leading to study product withdrawal or study discontinuation by relationship to study product. Additional summaries (such as by period) may be included if deemed necessary. Serious TEAEs will be provided in a data listing. Clinical laboratory test results and vital sign measurements will be provided in data listings and summarized for each treatment.

Sample Size. The sample size for this study was 24. The sample size was selected to reasonably balance the ability to address the study's primary objective while minimizing the number of subjects potentially at risk. Precision estimates were calculated using different safety outcome incidence rates and different samples sizes as presented in the following table. For example, in 25 subjects, a safety outcome with incidence rate of 10% would have a 95% CI of 1.6% to 29.2% and a corresponding width of 27.6 at a 2-sided alpha of 0.05. To account for subject attrition and for comparison purposes, sample sizes of 20 and 28 are included in the table.

TABLE 63

Precision Estimates Based on Safety Outcome Incidence Rates and Sample Size

| Sample | Incidence | | |
|---|---|---|---|
| Size | 10% | 25% | 50% |
| 20 | (1.2-3.17)<br>d = 30.5 | (8.7-9.1)<br>d = 40.4 | (27.2-72.8)<br>d = 45.6 |
| 24 | (1.6-29.2)<br>d = 27.6 | (9.8-46.7)<br>d = 36.9 | (29.1-70.9)<br>d = 41.8 |
| 28 | (2.0-27.3)<br>d = 25.4 | (10.7-44.9)<br>d = 34.2 | (30.6-69.4)<br>d = 38.7 |

Endpoints/Results:

a. The primary endpoints to assess safety are treatment-emergent adverse events (TEAEs); serious adverse events (SAEs); suspected, unexpected, serious adverse reactions (SUSARs); and death. The reconstituted spray dried plasma is expected to be safe for human transfusion and TEAEs, SAEs and SUSARs and death are not expected.

b. The following secondary endpoints to be evaluated in Cohorts 1 and 2, given that there is a theoretical concern about hypercoagulability: Hypercoagulability is not expected or expected to be present within acceptable clinical ranges.

c. Change in pre and postinfusion values for prothrombin time (PT), international normalized ratio (INR), activated partial thromboplastin time (aPTT), D-dimer, protein S activity; protein C activity, prothrombin fragments 1+2 (PF 1+2); thrombin-antithrombin complex (TAT); antithrombin III (AT-III); alpha-2 antiplasmin after infusion of 1 and 2 units of FrontlineODP in Cohorts 1 and 2, respectively. The change in pre and postinfusion values for these blood factors are expected to be within acceptable clinical ranges.

d. Change in pre and postinfusion vital signs and in values for hematology, urinalysis, direct antiglobulin test (DAT), and serum chemistry tests after infusion of 1 and 2 units of FrontlineODP in Cohorts 1 and 2, respectively. The change in pre and postinfusion values for these tests are expected to be within acceptable clinical ranges.

e. The following secondary endpoints will be evaluated in Cohort 3, given that there is a theoretical concern about hypercoagulability that will be increased with a larger dose: Hypercoagulability is not expected or expected to be present within acceptable clinical ranges.

f. Change in pre and postinfusion values for PT; INR; aPTT; Factors I, II, V, VII, VIII, IX, X, XI; D-dimer; von Willebrand Factor activity; protein S activity; protein C activity; prothrombin fragments 1+2 (PF 1+2); thrombin-antithrombin complex (TAT); antithrombin III (AT-III); alpha-2 antiplasmin; and C3a des Arg activity after infusion of 4 units of FrontlineODP compared with 4 units of PF24. The change in pre and postinfusion values for these blood factors are expected to be within acceptable clinical ranges.

g. Determine if changes in vital signs or in specific hematology, urinalysis, DAT, and serum chemistry values are similar after infusion of either 4 units of autologous FrontlineODP or PF24. The change in pre and postinfusion values for these tests are expected to be within acceptable clinical ranges.

All 24 subjects enrolled completed evaluations out to the study endpoints with no subjects lost to follow up. The primary safety endpoint was met, as no serious adverse events (SAEs) were reported or stopping rules invoked due to safety concerns during the study. The DMC held an interim meeting between Cohorts 1 and 2 and will hold another between Cohorts 2 and 3 to review data. Since there was a lack of safety concerns per protocol, it was recommended to proceed with subject infusion in the next Cohort, Cohort 2. The rehydrated FrontlineODP plasma transfused in patients in Cohort 1 was considered safe and therefore the study proceeded to Cohort 2.

Hypercoagulability was not observed in Cohort 1 (n=6) and not expected to be observed in Cohort 2 (n=6) with the infusion of one and two units of investigational product, respectively, as assessed by factor levels preinfusion (baseline) and postinfusion measures. For Cohort 1, values for pre- and postinfusion values for global measures of coagulation (PT, INR, aPTT, or INR), D-dimer, protein S, protein C, PF 1+2, TAT, AT-III, alpha-2-antiplasmin were the same for both FrontlineODP or PF24 infusions and were within acceptable clinical ranges and the same is expected for Cohort 2. In Cohort 1, changes in pre- and postinfusion vitals, hematology, urinalysis, DAT and serum chemistry with either product infused were comparable and were within acceptable clinical ranges and the same is expected in Cohort 2.

Cohort 3 (n=12) will include intra-subject comparisons of infusion of autologous FrontlineODP and PF24, with a 14-day washout period between infusions and with order of infusion randomized between arms 3 (ODP x PF24) and 4 (PF24×ODP). Hypercoagulability is not expected to be observed in Cohort 3 irrespective of study arm. To date, no SAEs or safety signals were observed in either study arm and none are expected for Cohorts 2 and 3. For TEAEs, no differences were observed in Cohort 1 and no differences are expected to be observed in Cohorts 2 and 3 between infusions of FrontlineODP and PF24, regardless of order of infusion. In Cohort 1, values for pre- and postinfusion values for PT, INR, aPTT, INR, Factors I, II, V, VII, VIII, IX, X, XI, D-dimer, von Willibrand Factor activity, protein S, protein C, PF 1+2, TAT, AT-III, alpha-2-antiplasmin and C3a des Arg activity, after infusion of 4 units of FrontlineODP compared with 4 units of PF24, were comparable and within acceptable clinical ranges. The same results are expected in Cohorts 2 and 3. Changes in pre- and postinfusion vital signs, hematology, urinalysis, DAT and serum chemistry with either product infused were similar in Cohort 1 and all were within acceptable clinical ranges. Similar results are expected in Cohorts 2 and 3.

This study demonstrates safety of infusion of up to 4 units of autologous FrontlineODP and comparability to infusion of 4 units of conventional PF24, with respect to pre- and postinfusion values for all secondary endpoints.

Example 39 Pathogen Reduction with Heat

The prophetic study described in this Example will support whether plasma spray drying process reduces low concentrations of most commonly identified microorganisms in the starting plasma.

The contamination frequency for platelets is 1:1,000 to 1:2,500. The most common contamination is via *Escherichia coli, Staphylococcus epidermidis* and *Klebsiella pneumoniae* in low concentrations of 1 to 2 colony forming units (CFU) per mL.

Methods/Procedure:

The system used in this example is the spray drying system of the present invention that spray dries a measured unit of plasma with a drying gas inlet temperature of 114° C. and the temperature in the plasma drying chamber of the disposable is between 65° C. and 70° C. Plasma is subjected to rapid mixing and shear as it travels through the nozzle, as described herein.

The starting plasma will be inoculated with approximately 5 CFU/mL prior to spray drying. After spray drying a unit of plasma, the dried plasma unit will be rehydrated with 200 mL of SWFI. Each test article will be aseptically transferred to a sterile bag. The inside of the test article bag will be rinsed with 50 ml of sterile Fluid D and transferred to the same sterile bag and mixed for 30 seconds. Four (4) equal aliquots will be made. One (1) aliquot will be heat shocked at 80±2° C. for 15±1 minutes, then allowed to cool down. Following membrane filtration (4×24 ml) and rinse with 10 ml of Phosphate Buffered Saline (PBS), the filters (one per plate) will be aseptically placed onto Trypticase Soy Agar (TSA) plates and incubated aerobically and anaerobically at 30-35° C. for 5-14 days, and onto Sabouraud Dextrose Agar (SDA) plates and incubated aerobically at 20-25° C. for 5-14 days. Each control article (spiked frozen plasma) will be thawed prior to testing. 15 ml from each control article will be transferred aseptically to a sterile bag and 85 ml of sterile Fluid D will be added to the bag and mixed for 30 seconds to be tested. Samples of PBS and Fluid D, which served as negative controls, will be similarly filtered and incubated. Colony Forming Units (CFU) will be determined for each filter. The study and its design employed methodology to minimize uncertainty of measurement and control of bias for data collection and analysis.

More specifically, using aseptic technique, 15 mL of the reconstituted plasma will be removed using a sterile syringe.

5-10 mL will be inoculated into an aerobic blood culture (BC) bottle, which is then placed onto the laboratories BACTEC blood culture incubation/monitoring system

- when BC bottles are flagged positive by the system, BC bottles will be removed from the system, a Gram stain will be performed, and a 1 L aliquot from the BC bottles will be planted onto a sheep blood agar plate. Organism identification will be performed by standard lab methods to assure that the orinism ID is identicat to that of the organism originally used to spike the ODP product.

The remaining 5 mL of the reconstituted ODP fluid will be plated onto a sheep blood agar plate and a chocolate agar plate. Those inoculated plates will then be incubated in 5% $CO_2$ incubators, overnight.

All testing will be performed in duplicate.

All control agar plates from time of spiking the human plasma bag will be evaluated and colony counts (as baseline) will be obtained.

After reconstituting the ODP product, and respectively corresponding agar plates are assessed, colony counts will be obtained, and ultimately compared against the baseline colony counts.

The use of BC bottles serves as a form of quality control to assure that the respective spiked ODP product indeed contained a bacterium. Results: It is expected that there will be reduced pathogen amounts or non-detectable pathogen amounts in the rehydrated previously spray dried plasma.

Example 40: Pathogen Reduction with No Heat

The prophetic study described in this Example will support whether the shear that occurs to the plasma during the plasma spray drying process reduces low concentrations of most commonly identified microorganisms in the starting plasma.

The contamination frequency for platelets is 1:1,000 to 1:2,500. The most common contamination is via *Escherichia coli, Staphylococcus epidermidis* and *Klebsiella pneumoniae* in low concentrations of 1 to 2 colony forming units (CFU) per mL.

Methods/Procedure:

The system used in this example is the spray drying system of the present invention described herein. The donor plasma goes through the spray drying system but is not subjected to heat. For this experiment, the heater in the spray drying system will remain off during spray drying. Plasma is subjected to atomization and shear as it travels through the nozzle, as described herein.

The starting plasma will be inoculated with approximately 5 CFU/mL prior to spray drying. After spray drying a unit of plasma, the dried plasma unit will be rehydrated with 200 mL of SWFI. Each test article will be aseptically transferred to a sterile bag. The inside of the test article bag will be rinsed with 50 ml of sterile Fluid D and transferred to the same sterile bag and mixed for 30 seconds. Four (4) equal aliquots will be made. One (1) aliquot will be heat shocked at 80±2° C. for 15±1 minutes, then allowed to cool down. Following membrane filtration (4×24 ml) and rinse with 10 ml of Phosphate Buffered Saline (PBS), the filters (one per plate) will be aseptically placed onto Trypticase Soy Agar (TSA) plates and incubated aerobically and anaerobically at 30-35° C. for 5-14 days, and onto Sabouraud Dextrose Agar (SDA) plates and incubated aerobically at 20-25° C. for 5-14 days. Each control article (spiked frozen plasma) will be thawed prior to testing. 15 ml from each control article will be transferred aseptically to a sterile bag and 85 ml of sterile Fluid D will be added to the bag and mixed for 30 seconds to be tested. Samples of PBS and Fluid D, which served as negative controls, will be similarly filtered and incubated. Colony Forming Units (CFU) will be determined for each filter. The study and its design employed methodology to minimize uncertainty of measurement and control of bias for data collection and analysis.

More specifically, using aseptic technique, 15 mL of the reconstituted plasma will be removed using a sterile syringe.

5-10 mL will be inoculated into an aerobic blood culture (BC) bottle, which is then placed onto the laboratories BACTEC blood culture incubation/monitoring system when BC bottles are flagged positive by the system, BC bottles will be removed from the system, a Gram stain will be performed, and a 1 L aliquot from the BC bottles will be planted onto a sheep blood agar plate. Organism identification will be performed by standard lab methods to assure that the orinism ID is identicat to that of the organism originally used to spike the ODP product.

The remaining 5 mL of the reconstituted ODP fluid will be plated onto a sheep blood agar plate and a chocolate agar plate. Those inoculated plates will then be incubated in 5% CO2 incubators, overnight.

All testing will be performed in duplicate.

All control agar plates from time of spiking the human plasma bag will be evaluated and colony counts (as baseline) will be obtained.

After reconstituting the ODP product, and respectively corresponding agar plates are assessed, colony counts will be obtained, and ultimately compared against the baseline colony counts.

The use of BC bottles serves as a form of quality control to assure that the respective spiked ODP product indeed contained a bacterium.

Results: It is expected that there will be reduced pathogen amounts or non-detectable pathogen amounts in the rehydrated previously spray dried plasma.

The relevant teachings of all the references, patents and/or patent applications cited herein are incorporated herein by reference in their entirety. Citation of the above documents and studies is not intended as an admission that any of the foregoing is pertinent prior art. All statements as to the contents of these documents are based on the information available to the applicants and do not constitute any admission as to the correctness of the contents of these documents. The entire teachings of all applications, patents and references cited herein are incorporated herein by reference. Specifically, the entire teachings of U.S. Pat. Nos. 7,993,310, 8,469,202, 8,533,971, 8,407,912, 8,595,950, 8,601,712, 8,533,972, 8,434,242, 10,843,100, 9,561,184, 9,545,379, 11,052,045; US Patent Publication Nos. 2010/0108183, 2011/0142885, 2013/0000774, 2013/0126101, 2014/0083627, 2014/0083628, 2014/0088768, and U.S. patent application Ser. No. 14/670,127 are incorporated herein by reference and are instructive of what one of ordinary skill in the art would know and understand at the time of the present invention. Additionally, entire teachings of applications filed on even date herewith are hereby incorporated herein by reference: U.S. Application No. 63/406,747, entitled "A Spray Drying Process That Reduces Pathogens"; U.S. application Ser. No. 17/945,132, entitled "Methods For Making Spray Dried Plasma"; U.S. application Ser. No. 17/945,130, entitled "Alignment of A Disposable For A Spray Drying Plasma System"; U.S. application Ser. No. 18/097,352, entitled "Nozzle For A Disposable For Use With Spray Drying System"; U.S. application Ser. No. 18/096,945, entitled "Baffle Plate Used In A Disposable For A Spray Drying System"; U.S. application Ser. No. 17/945,126, entitled "Pretreatment Of Plasma For Spray Drying And Storage"; U.S. application Ser. No. 17/945,129, entitled "Usability Of A Disposable For A Spray Drying Plasma System"; U.S. application Ser. No. 17/945,125, entitled "Blood Plasma Product"; U.S. application Ser. No. 17/945,124, entitled "Disposable For A Spray Drying System"; U.S. application Ser. No. 18/096,645, entitled "Rapid Spray Drying System"; U.S. application Ser. No. 18/097,822, entitled "Blood Plasma Product"; and U.S. application Ser. No. 18/097,958, entitled "Two-Phase Delivery Of Plasma".

The terms about, approximately, substantially, and their equivalents may be understood to include their ordinary or customary meaning. In addition, if not defined throughout the specification for the specific usage, these terms can be generally understood to represent values about but not equal to a specified value. For example, 1%, 0.9%, 0.8%, 0.7%, 0.6%, 0.5%, 0.4%, 0.3%, 0.2%, 0.1%, 0.09% of a specified value.

The terms, comprise, include, and/or plural forms of each are open ended and include the listed items and can include additional items that are not listed. The phrase "And/or" is open ended and includes one or more of the listed items and combinations of the listed items.

The relevant teachings of all the references, patents and/or patent applications cited herein are incorporated herein by reference in their entirety. Citation of the above documents and studies is not intended as an admission that any of the foregoing is pertinent prior art. All statements as to the contents of these documents are based on the information available to the applicants and do not constitute any admission as to the correctness of the contents of these documents.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spray drying nozzle assembly that comprises:

A) a nozzle opening defined by a nozzle inner wall;

B) a cannula adapted to receive a plasma source providing a plasma, said cannula having a cannula opening and a cannula outer wall; and C) an annulus defined by a space between the nozzle inner wall and the cannula outer wall;

wherein the cannula is configured to emit plasma through said cannula opening and said annulus is configured to emit a vortex pattern of a pressurized aerosol gas to atomize plasma.

2. The spray drying nozzle assembly of claim 1, further comprising a vortex generator in communication with a pressurized aerosol gas source wherein the vortex generator provides the vortex pattern of the pressurized aerosol gas.

3. The spray drying nozzle assembly of claim 2, wherein the vortex generator comprises a plurality of channels and a plurality of pads to create the vortex pattern of the pressurized aerosol gas.

4. The spray drying nozzle assembly of claim 3, wherein the plurality of channels and the plurality of pads are curved.

5. The spray drying nozzle assembly of claim 3, wherein the plurality of channels is curved and the plurality of pads have one or more curved edges.

6. The spray drying nozzle assembly of claim 1, wherein the cannula of the spray dry nozzle assembly has an inner diameter in a range between about 0.010 inches and about 0.040 inches and an outer diameter between about 0.030 inches and about 0.060 inches.

7. The spray drying nozzle assembly of claim 1, wherein the cannula has a bottom surface and a wall with an inner surface and an outer surface.

8. The spray drying nozzle assembly of claim 7, wherein the bottom surface has an angled plane that has at least a portion that is angled in relation to an inner surface plane of the inner surface of the wall to thereby obtain an angled edge cannula.

9. The spray drying nozzle assembly of claim 7, wherein the bottom surface has a first portion having an angled plane and a second portion having a flat plane that forms a substantially flat edge, wherein the angled plane of the bottom surface is angled in relation to an inner surface plane of the inner surface of the wall to thereby obtain an angled edge cannula.

10. The spray drying nozzle assembly of claim 9, wherein the angled plane is disposed at an angle in a range between about 120 degrees and about 150 degrees relative to the inner surface plane, and wherein the flat plane is disposed at an angle of about 90 degrees relative to inner surface plane.

11. The spray drying nozzle assembly of claim 8, wherein the angled plane is disposed at an angle in a range between about 120 degrees and about 150 degrees relative to the inner surface plane.

12. The spray drying nozzle assembly of claim 8, wherein the angled edge cannula, when used in spray drying plasma, results in an amount of one or more functional proteins from reconstituted previously dried plasma dried, said amount is within about 1% and 25% of an amount of the one or more functional proteins from reconstituted previously dried plasma dried with a spray drying nozzle assembly without an angled edge cannula.

13. The spray drying nozzle assembly of claim 12, wherein the one or more functional proteins from reconstituted previously dried plasma dried comprises von Willebrand factor (vWF).

14. The spray drying nozzle assembly of claim 12, wherein an amount of vWF is measured by von Willebrand Factor Ristocetin Cofactor, or wherein an amount of vWF is measured by von Willebrand Factor Ristocetin Cofactor, and the amount of vWF is within about 20% of an amount of vWF in donor plasma.

15. The spray drying nozzle assembly of claim 14, wherein the amount of vWF is within about 10% of an amount of vWF in donor plasma.

* * * * *